United States Patent
Harkin et al.

(10) Patent No.: US 10,196,691 B2
(45) Date of Patent: Feb. 5, 2019

(54) COLON CANCER GENE EXPRESSION SIGNATURES AND METHODS OF USE

(75) Inventors: Denis Paul Harkin, Dromore (GB); Vitali Proutski, Oxford (GB); Julie Clarke, Dromore (GB); Peter Kerr, Belfast (GB); Richard Kennedy, Belfast (GB); Andreas Winter, Gersthofen (DE); Timothy Davison, Hillsborough (GB); Max Bylesjo, Glasgow (GB); Vadim Farztdinov, Franfurt am Main (DE); Claire Trinder, Statford-upon-Avon (GB); Robert James Holt, Knutsford (GB)

(73) Assignee: ALMAC DIAGNOSTICS LIMITED (GB)

( * ) Notice: Subject to any disclaimer, the term of this patent is extended or adjusted under 35 U.S.C. 154(b) by 0 days.

(21) Appl. No.: 13/981,601

(22) PCT Filed: Jan. 25, 2012

(86) PCT No.: PCT/US2012/022594
§ 371 (c)(1),
(2), (4) Date: Oct. 10, 2013

(87) PCT Pub. No.: WO2012/103250
PCT Pub. Date: Aug. 2, 2012

(65) Prior Publication Data
US 2014/0094379 A1 Apr. 3, 2014

Related U.S. Application Data

(60) Provisional application No. 61/435,922, filed on Jan. 25, 2011.

(51) Int. Cl.
*C12Q 1/6886* (2018.01)
(52) U.S. Cl.
CPC ...... *C12Q 1/6886* (2013.01); *C12Q 2600/112* (2013.01); *C12Q 2600/118* (2013.01); *C12Q 2600/158* (2013.01)
(58) Field of Classification Search
None
See application file for complete search history.

(56) References Cited

U.S. PATENT DOCUMENTS

| | | | |
|---|---|---|---|
| 5,427,930 A | 6/1995 | Birkenmeyer et al. | |
| 5,554,501 A | 9/1996 | Coassin et al. | |
| 5,744,311 A | 4/1998 | Fraiser et al. | |
| 5,981,185 A | 11/1999 | Matson et al. | |
| 5,985,567 A | 11/1999 | Rampal | |
| 6,013,789 A | 1/2000 | Rampal | |
| 6,025,134 A | 2/2000 | Sooknanan | |
| 6,027,889 A | 2/2000 | Barany et al. | |
| 6,033,881 A | 3/2000 | Himmler et al. | |
| 7,695,913 B2 | 4/2010 | Cowens et al. | |
| 2001/0055596 A1 | 12/2001 | Meagher et al. | |
| 2004/0146921 A1 | 7/2004 | Eveleigh et al. | |
| 2005/0287544 A1 | 12/2005 | Bertucci et al. | |
| 2006/0003359 A1 | 1/2006 | Feinberg et al. | |
| 2006/0292572 A1 | 12/2006 | Stuart et al. | |
| 2007/0134655 A1 | 6/2007 | Bentwich | |
| 2007/0166704 A1 | 7/2007 | Huang et al. | |
| 2009/0291434 A1* | 11/2009 | Cowens et al. | 435/6 |
| 2010/0261169 A1 | 10/2010 | Wallach et al. | |

FOREIGN PATENT DOCUMENTS

| | | |
|---|---|---|
| EP | 0320308 A2 | 6/1989 |
| EP | 2213738 A2 | 11/2010 |
| JP | 2009/512440 | 3/2009 |
| WO | WO 85/01051 | 3/1985 |
| WO | WO 89/10977 | 11/1989 |
| WO | WO 90/01069 | 2/1990 |
| WO | WO 2005/054508 A2 | 6/2005 |
| WO | WO 2005/083128 A2 | 9/2005 |
| WO | WO 2006/048291 A2 | 5/2006 |
| WO | WO 2006/093507 A2 | 9/2006 |
| WO | WO 2007/048074 A1 | 4/2007 |
| WO | WO 2007/112330 A2 | 10/2007 |
| WO | WO 2009/045115 A1 | 4/2009 |
| WO | WO 2009/147537 A2 | 12/2009 |
| WO | WO 2010/0060055 A1 | 5/2010 |
| WO | WO 2010/060055 A1 | 5/2010 |

OTHER PUBLICATIONS

Coyle et al.( Journal of Clinical Oncology, 2009 ASCO Annual Meeting Proceedings (Post-Meeting Edition); vol. 27, No. 15S (May 20 Supplement), 2009: e14558(Abstract)).*
Kerr et al.( Clin Cancer Res Oct. 1, 2007 13; A39(Abstract)).*
Simon et al. Journal of Clinical Oncology. 2005. 23(29):7332-7341.*
Bertucci et al. Oncogene. 2004. 23:1377-1391.*
Perez-Villamil et al. BMC Cancer. 2012. 12:260.*
Singapore Search Report and Written Opinion dated Jun. 30, 2014 for co-pending Singapore Application No. 201305625-4, pp. 1-13.
Chinese Office Action and Search Report dated May 16, 2014 for co-pending Chinese Application No. 2012800101232, pp. 1-8.
New Zealand Office Action dated Jan. 27, 2014 for co-pending New Zealand Application No. 612471, pp. 1-3.

(Continued)

*Primary Examiner* — Joseph G. Dauner
(74) *Attorney, Agent, or Firm* — Finnegan, Henderson, Farabow, Garrett & Dunner LLP

(57) ABSTRACT

A gene expression signature of colon cancer, microarrays including them and methods of using the colon gene expression signature are provided. The gene expression signature is especially useful for determining the prognosis of a patient diagnosed with colon cancer, such as stage II colon cancer. The gene signature described herein is also useful for determining effectiveness of surgical resection with or without adjuvant chemotherapy, and determining possibility of cancer recurrence in patients with colon cancer.

14 Claims, 176 Drawing Sheets
Specification includes a Sequence Listing.

(56) References Cited

OTHER PUBLICATIONS

Lee et al., "Differential Expression in Normal-Adenoma-Carcinoma Sequence Suggests Complex Molecular Carcinogenesis in Colon," Oncology Reports, 2006, vol. 16, pp. 747-754.
International Search Report and Written Opinion dated Jul. 11, 2012 for PCT/US2012/022594, pp. 1-17.
GENBANK, Accession No. AW168079, Nov. 12, 1999, 2 pages.
GENBANK, Accession No. AW369343, Feb. 4, 2000, 2 pages.
GENBANK, Accession No. BM847988, Mar. 6, 2002, 2 pages.
GENBANK, Accession No. BE178335, Jun. 22, 2000, 2 pages.
Unwala, New Zealand Office Action for co-pending New Zealand Application No. 612471, Dec. 5, 2014, 3 pages.
Abramovitz, et al., A systems approach to clinical oncology: Focus on breast cancer, Proteome Science 2006, Apr. 4, 2006, pp. 1-15, BioMed Central, Montreal, Quebec, Canada.
Altschul, et al., Basic Local Alignment Search Tool, J. Mol. Biol. (1990) 215, pp. 403-410, National Center for Biotechnology Information, Bethesda, MD.
Benson, et al., American Society of Clinical Oncology Recommendations on Adjuvant Chemotherapy for State II Colon Cancer, Journal of Clinical Oncology, Aug. 15, 2004, pp. 3408-3419, vol. 22, No. 16, Alexandria, VA.
Benson, et al., New Approaches to the Adjuvant Therapy of Colon Cancer, The Oncologist, 2006;11:973-980, Robert H. Lurie Comprehensive Cancer Center, Northwestern University, Chicago, Illinois.
Bhattacharjee, et al., Classification of human lung carcinomas by mRNA expression profiling reveals distinct adenocarcinoma subclasses, PNAS, Nov. 20, 2001, vol. 98, No. 24, pp. 13790-13795.
Bishop, et al., Neural Networks for Pattern Recognition, Department of Computer Science and Applied Mathematics, 1995, pp. 1-498, Clarendon Press, Oxford.
Breiman, Random forests, Statistics Department, University of California, Jan. 2001, pp. 1-33, Berkley, California.
Carney, et al., A colorectal cancer patient focus group develops an information package, Surgical Oncology, Ann R. Coll Surg Eng 2006; 88; 447-449, Bristol BS16 1LE, UK.
Colorectal Cancer DSA™ Technical Note; Jan. 2007, pp. 1-5; http://www.almacgroup.com/wp-content/uploads/Colorectal_Cancer_DSA_techsheet3.pdf (retrieved Jul. 13, 2015).
Corpet, Multiple sequence alignment with hierarchical clustering, Nucleic Acids Research, Laboratoire de Génétique Cellulaire, Oct. 14, 1998, vol. 16 No. 22 1988, Tolosan, France.
Cui, et al, Statistical tests for differential expression in cDNA microarray experiments, Genome Biology, Mar. 17, 2003, pp. 1-10, 4:210, BioMed Central Ltd, Bar Harbor, Maine.
Díaz-Rubio Garcia, A panel discussion of controversies and challenges in the adjuvant treatment of colon cancer, Clin. Transl. Oncol. 2005; 7(1):3-11, Hospital Clinico San Carlos, Madrid, Spain.
Dooley, et al. "Expression Profiling of Human Sultotransferase and Sulfatase Gene Superfamilies in Epithelial Tissues and Cultured Cells", Biochemical and Biophysical Research Communications, 277 (1):236-245; 2000.
Dudoit, Comparison of Discrimination Methods for the Classification of Tumors Using Gene Expression Data, Journal of the American Statistical Association, Mar. 2002; vol. 97, No. 457, American Statistical Association.
Ferguson, et al., High-Density Fiber-Optic DNA Random Microsphere Array, Anal. Chem., Nov. 15, 2000, vol. 22, pp. 5618-5624, American Chemical Society, Medford, Massachusetts.
Fukumura, et al., A sensitive transcriptome analysis method that can detect unknown transcripts, Nucleic Acids Research, 2003, vol. 13, No. 16, Oxford University Press.
Gill, et al., Pooled Analysis of Fluorouracil-Based Adjuvant Therapy for Stage II and III Colon Cancer: Who Benefits and by How Much?, Journal of Clinical Oncology, May 15, 2004, pp. 1797-1806, vol. 22, No. 10, American Society of Clinical Oncology, Chicago, IL.

Godfrey, et al., Quantitative mRNA Expression Analysis from Formalin-Fixed, Paraffin-Embedded Tissues Using 5' Nuclease Quantitative Reverse Transcription-Polymerase Chain Reaction, Journal of Molecular Diagnostics, May 2000, p. 84-91, vol. 2, No. 2, American Society for Investigative Pathology.
Golub, et al., Molecular Classification of Cancer: Class Discovery and Class Prediction by Gene Expression Monitoring, www.sciencemag.org, Science, Oct. 15, 1999, pp. 531-537, vol. 286.
Heid, et al., Real Time Quantitative PCR, Genome Methods, 2006, pp. 986-994, ISSN 1054-9803/96, Cold Spring Harbor Laboratory Press.
Higgins, et al., CLUSTAL: a package for performing multiple sequence alignment on a microcomputer, Gene, pp. 237-244, 73 (1988), Elsevier, Science Publishers B.V.
Higgins, et al., Fast and sensitive multiple sequence alignments on a microcomputer, Cabios Communications, pp. 151-153, vol. 5 No. 2. 1989, IRL Press.
Jemal, et al., Cancer Statistics, 2004, A Cancer Journal for Clinicians, Jan./Feb. 2004, pp. 8-29, vol. 54, No. 1, American Cancer Society.
Johnston, et al., A genetic signature of relapse in stage II colorectal cancer derived from formalin fixed paraffin embedded tissue (FFPE) tissue using a unique disease specific colorectal array, Journal of Clinical Oncology, Jun. 2006, pp. 1-3, vol. 24, No. 18S, American Society of Clinical Oncology.
Kawamoto, et al., Expression Profiling by iAFLP: A PCR-Based Method for Genome-Wide Gene Expression Profiling, Genome Research, 1999, pp. 1305-1312, ISSN 1054-9803/99, Cold Spring Harbor Laboratory Press.
Kennedy, et al., Development and Independent Validation of a Prognostic Assay for Stage II Colon Cancer Using Formalin-Fixed Paraffin-Embedded Tissue, Journal of Clinical Oncology, Dec. 10, 2011, pp. 4620-4626, vol. 29, No. 25, American Society of Clinical Oncology.
Kinney, et al., Genetic Testing for Colorectal Carcinoma Susceptibility, Focus Group Responses of Individuals with Colorectal Carcinoma and First-Degree Relatives, Cancer, Jan. 1, 2001, pp. 57-65; vol. 91, No. 1, American Cancer Society.
Nguyen, et al., Genetic Testing for Colorectal Carcinoma Susceptibility Focus Group Responses of Individuals with Colorectal Carcinoma and First-Degree Relatives, Bioinformatics, 2002, pp. 39-50, vol. 18 No. 1, Oxford University Press.
O'Connell, et al., Relationship Between Tumor Gene Expression and Recurrence in Four Independent Studies of Patients With Stage II/III Colon Cancer Treated With Surgery Alone or Surgery Plus Adjuvant Fluorouracil Plus Leucovorin, Journal of Clinical Oncology, Sep. 1, 2010, pp. 3937-3944, vol. 28, No. 25, American Society of Clinical Oncology.
Oeth, et al., iPLEX™ Assay: Increased Plexing Efficiency and Flexibility for MassARRAY⊔ System Through Single Base Primer Extension with Mass-Modified Terminators, Sequenom Application Note, Apr. 28, 2005, pp. 1-12.
Oliphant, et al., BeadArray™ Technology: Enabling an Accurate, Cost-Effective Approach to High-Throughput Genotyping, BioTechniques, Jun. 2002, pp. 56-61, 32, San Diego, CA.
Pearson, et al., Improved tools for biological sequence comparison, Proc. Natl. Acad. Sci. USA, Apr. 1988, pp. 2444-2448, vol. 85.
Pruitt, NCBI Reference Sequence (RefSeq): a curated non-redundant sequence database of genomes, transcripts and proteins, Nucleic Acids Research, 2005, pp. 501-504, vol. 33, Oxford University Press.
Ramaswamy, et al., Multiclass cancer diagnosis using tumor gene expression signatures, PNAS, Dec. 18, 2001, pp. 15149-15154, vol. 98, No. 26.
Rupp, et al., Purification and Analysis of RNA from Paraffin-Embedded Tissues, Research Report, BioTechniques, 1988, pp. 56-60, vol. 6, No. 1, University of Pittsburgh School of Medicine.
Salazar, et al., Gene Expression Signature to Improve Prognosis Prediction of Stage II and III Colorectal Cancer, Journal of Clinical Oncology, Jan. 1, 2011, pp. 17-24; vol. 29, No. 1, American Society of Clinical Oncology.
Salkeld, et al., A matter of trust—patient's views on decision-making in colorectal cancer, Health Expectations, pp. 104-114, 7, Blackwell Publishing Ltd., Australia. Sep. 18, 2003.

(56) References Cited

OTHER PUBLICATIONS

Schena, et al., Parallel human genome analysis: Microarray-based expression monitoring of 1000 genes, Proc. Natl. Acad. Sci. USA, Oct. 1996, pp. 10614-10619, vol. 93, Biochemistry.

Smyth, Linear Models and Empirical Bayes Methods for Assessing Differential Expression in Microarray Experiments, Statistical Applications in Genetics and Molecular Biology, Jan. 2004, pp. 1-26, vol. 3, Issue 1, Article 3, Walter and Eliza Hall Institute of Medical Research, Melbourne, Australia.

Sobrero, Should adjuvant chemotherapy become standard treatment for patients with stage II colon cancer?, http://oncology.thelancet.com Jun. 2006, pp. 515-517, vol. 7, Department of Medical Oncology, Ospedale San Martino, Genoa, Italy.

Specht, et al., Technical Advance: Quantitative Gene Expression Analysis in Microdissected Archival Formalin-Fixed and Paraffin-Embedded Tumor Tissue, American Journal of Pathology, Feb. 2001, pp. 419-429, vol. 158, No. 2, American Society for Investigative Pathology.

Tibshirani, et al., Diagnosis of multiple cancer types by shrunken centroids of gene expression, PNAS, May 14, 2002, pp. 6567-6572, vol. 99, No. 10.

Tusher, et al., Significance analysis of microarrays applied to the ionizing radiation response, PNAS, Apr. 24, 2001, pp. 5116-5121, vol. 98, No. 9.

Van'T Veer, et al., Gene expression profiling predicts clinical outcome of breast cancer, Nature, Jan. 31, 2002, pp. 530-536, vol. 415, Macmillan Magazines Ltd.

Velculescu, et al., Characterization of the Yeast Transcriptome, Jan. 2, 1997, pp. 243-251, vol. 88, Cell Press.

Yang, et al., BADGE, BeadsArray for the Detection of Gene Expression, a High-Throughput Diagnostic Bioassay, Genome Research, 2001, pp. 1888-1898, ISSN 1088-9051, Cold Spring Harbor Laboratory Press.

Yeang, et al., BADGE, BeadsArray for the Detection of Gene Expression, a High-Throughput Diagnostic Bioassay, Bioinformatics, Center for Genome Research, 2001, pp. S316-S322, vol. 17 Suppl. 1, Oxford University Press.

Youden, Index for Rating Diagnostic Tests, Cancer, Jan. 1950, pp. 32-35, National Bureau of Standards, Washington D.C.

International Preliminary Report on Patentability for International Patent Application No. PCT/US2012/022594, dated Jul. 30, 2013 (11 pages).

Supplementary Partial European Search of European Patent Application No. EP 12 73 9742, dated Mar. 24, 2015, (7 pages).

Supplementary European Search of European Patent Application No. EP 12 73 9742, dated Jul. 20, 2015 (17 pages).

First Examination Report in European Patent Application No. EP 12 73 9742, dated Jun. 28, 2016 (6 pages).

Patent Examination Report No. 1 in Australian Patent Application No. 2012209074, dated Jan. 8, 2016 (3 pages).

Substantive Examination Report Stage 1, Indonesian Patent Application No. W00 2013 03123, dated Feb. 4, 2016, (4 pages).

Office Action for Eurasian Patent Application No. 201391074/28, dated Apr. 22, 2015, (7 pages).

Written Opinion for Singapore Patent Application No. 2013056254, dated Apr. 15, 2015 (7 pages).

Third Official Action for Mexico Patent Application No. MX/a/2013/008367, dated Sep. 22, 2016, along with letter from foreign counsel dated Oct. 18, 2016 summarizing the office action, (8 pages).

Notification of Reasons for Refusal for Japanese Patent Application No. 2013-551314, dated Nov. 19, 2015, (11 pages).

Allen et al., "The colorectal cancer disease-specific transcriptome may facilitate the discovery of more biologically and clinically relevant information," BMC Cancer (2010) 10:687.

Lee, SK et al., Differential Expression in Normal-Adenoma-Carcinoma Sequence Suggests Complex Molecular Carcinogenesis in Colon. Oncology reports, 16;747-54, 2006.

Smith et al., Comparison of Biosequences, Advances in Applied Mathematics, (1981), pp. 482-489, Academic Press, Inc.

\* cited by examiner

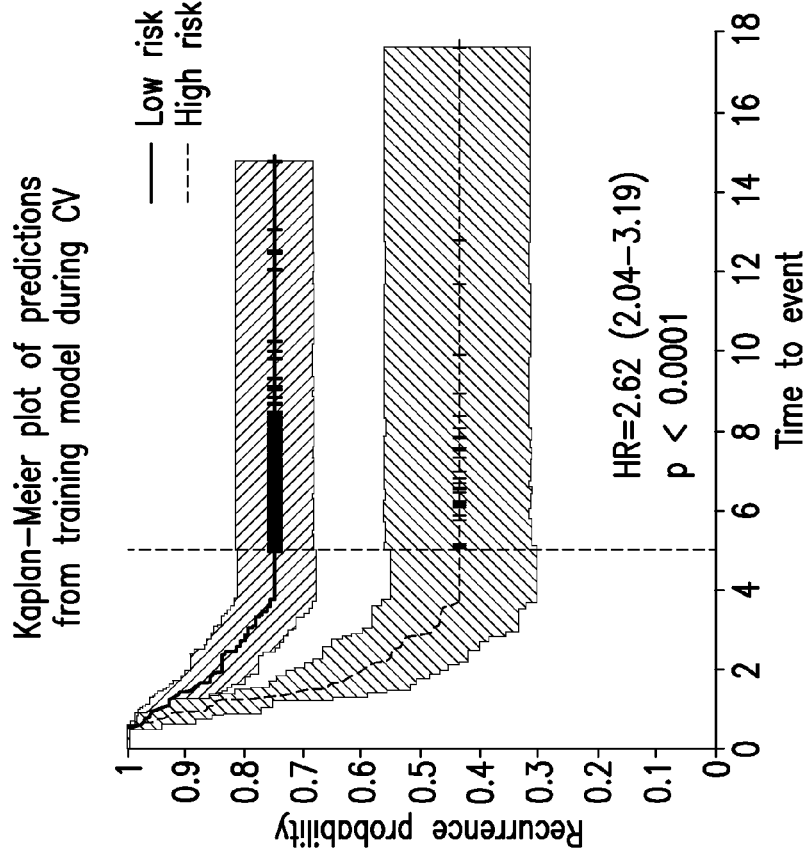
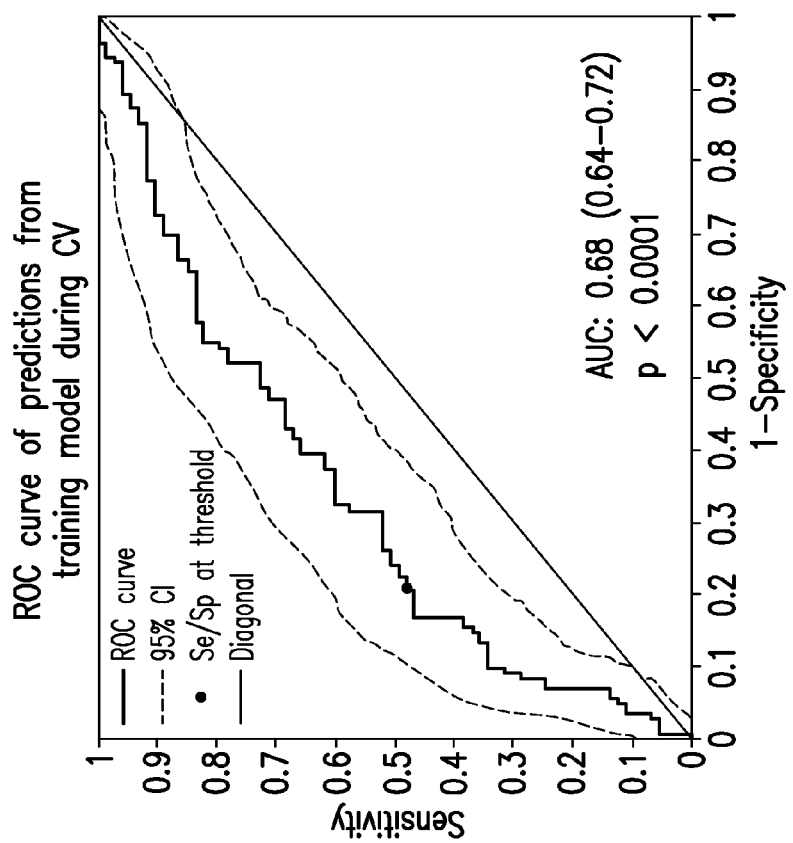
FIG. 3B
FIG. 3A

Table 3: Key Patient and Tumor Characteristics

| | TRAINING SET | % OF TOTAL (215) | | VALIDATION SET | % OF TOTAL (144) |
|---|---|---|---|---|---|
| Prognosis | | | Prognosis | | |
| Good | 142 | 66 | Good | 85 | 59 |
| Poor | 73 | 34 | Poor | 59 | 41 |
| Age at Diagnosis (Years) | | | Age at Diagnosis (Years) | | |
| Mean (SD) | 71 (9.9) | | Mean (SD) | 70 (10.1) | |
| Median | 72 | | Median | 70 | |
| Range | 45 to 95 | | Range | 45 to 90 | |
| FFPE Block 'Age' (Years) | | | FFPE Block 'Age' (Years) | | |
| Mean (SD) | 9.9 (3.2) | | Mean (SD) | 7.48 (3.1) | |
| Median | 9.0 | | Median | 8.2 | |
| Range | 5.2 to 18.3 | | Range | 1.38 to 15.8 | |
| Contributing Centre | | | Contributing Centre | | |
| Alabama | 33 | 15 | Alabama | 9 | 6 |
| Bethesda | 13 | 6 | Bethesda | 2 | 1 |
| Georgetown | 0 | 0 | Georgetown | 6 | 4 |
| MGH | 12 | 6 | MGH | 11 | 8 |
| UPMC | 46 | 21 | UPMC | 11 | 8 |
| Calgary | 34 | 16 | Calgary | 11 | 8 |
| Karolinska | 15 | 7 | Karolinska | 29 | 20 |
| NI240 | 11 | 5 | NI240 | 2 | 1 |
| St Vincents | 51 | 24 | St Vincents | 28 | 19 |
| Asterand | 0 | 0 | Asterand | 5 | 3 |
| BioServe | 0 | 0 | BioServe | 11 | 8 |
| Cureline | 0 | 0 | Cureline | 19 | 13 |
| Country of Origin | | | Country of Origin | | |
| Europe | 77 | 36 | Europe | 89 | 62 |
| USA | 104 | 48 | USA | 44 | 31 |
| Canada | 34 | 16 | Canada | 11 | 8 |
| Ethnicity | | | Ethnicity | | |
| African American | 20 | 9 | African American | 6 | 4 |
| Asian | 5 | 2 | Asian | 0 | 0 |
| White | 190 | 89 | White | 137 | 95 |
| Unknown | 0 | 0 | Unknown | 1 | 1 |
| Sex | | | Sex | | |
| M | 106 | 49 | M | 69 | 48 |
| F | 109 | 51 | F | 75 | 52 |
| T Stage | | | T Stage | | |
| 3 | 188 | 87 | 3 | 119 | 83 |
| 4 | 27 | 13 | 4 | 25 | 17 |
| T Grade | | | T Grade | | |
| Well | 9 | 4 | Well | 12 | 8 |
| Moderate | 174 | 81 | Moderate | 114 | 79 |
| Poor | 31 | 14 | Poor | 18 | 13 |
| Undifferentiated | 1 | 0.5 | Undifferentiated | 0 | 0 |
| Number of Nodes Assessed | | | Number of Nodes Assessed | | |
| Mean (SD) | 14 (7.5) | | Mean (SD) | 13.1 (10.0) | |
| Median | 13 | | Median | 10 | |
| Range | 6 to 40 | | Range | 6 to 98 | |
| T Location | | | T Location | | |
| Caecum | 60 | 28 | Caecum | 33 | 23 |
| Ascending Colon | 46 | 21 | Ascending Colon | 31 | 22 |

FIG.6

| Signature rank | Probe Set ID | Gene Symbol | Orientation | Gene Description | SEQ ID NO: | Target sequence |
|---|---|---|---|---|---|---|
| 1 | ADXCRPD.5128.C1_at | MUM1 | Sense | melanoma associated antigen (mutated) 1 [Source:HGNC Symbol;Acc:29641] | 1 | CTGTTTTTCCCGTGTAGATTTCTGATACTTCAATCCCCT ACTCCCCCAAAACAGTTGAAGCCCAGCCCACTCTTA |
| 2 | ADXCRAD_BG481316_s_at | SIGMAR1 | Sense | sigma non-opioid intracellular receptor 1 [Source:HGNC Symbol;Acc:8157] | 2 | CCGGTATACCAAGGGAGCCAGTTGTGTTCAGACACACA CATCACAGCTTGACTCACTAACTGAGGCCTTTCCATAGC TCCACAGCTT |
| 3 | ADXCRIH.3975.C1_at | ARSD | Sense | arylsulfatase D [Source:HGNC Symbol;Acc:717] | 3 | TTGGCCAGTGTGTTTCTAAGTCAATTCTAGTGTGTTTC ATCCTCACCTCTTCCCTCTGTGGCTTTGATGATGGA |
| 4 | ADXCRAD_NM_176825_s_at | SULT1C2 | Sense | sulfotransferase family, cytosolic, 1C, member 2 [Source:HGNC Symbol;Acc:11456] | 4 | AGGCTGGTCTTAACTGACTGCTTTTATTATTACCATGC ACTGGCAATTCCAAACAATGTCAGTGTTAAAATGCTCT CCCTGAAAAGAGAAAAAAGGAAAAAAGAAAAAGAAAAGA AAAGTGAAAAGAAAAACTCTTATTGGCCTAAGTTCTAAA TAATAGCTAGTTACCACTGAGTTTTAACTATATGTATAT GAGCTTCAAATAAGCACCTTTTA |
| 5 | ADXCRAG_AB049149_s_at | PPFIBP1 | Sense | PTPRF interacting protein, binding protein 1 (liprin beta 1) [Source:HGNC Symbol;Acc:9249] | 5 | AAATGCTGCAGCAGGTATGTGCAGAGGCCAGAACCAAG ATGGGATTTCCCTGCTGAACTATGTGAGATGCTGCATTT CTATGTTGTGTTGCTCTGATGCAGCAGTAAGTTTTTG ATTCACTTAGACCAGCACATTA |

FIG.7-1

| | | | | |
|---|---|---|---|---|
| 6 | ADXCRP D.15673.C 1_at | N/A | No Transcript match | N/A | 6 | GAAGGTCAGGACTTTGTGAACATATAAACTGCAGATG GCTATTAGATATCCAAGTAGAGATGCTGAAGAGATGAAT GTATATAGAAGTCTGAATTTGGGAGAGAGATCTGGATAG GAGATACTTACCTGGTGTTTAACAGCTTACAGATTGTGT AAAGTCATGAAACGGATAAGAAACCTTAAAGAGAGAAAA GGGAATAGAGAGGTTACCAAATGAATTGCAGTTTCCAAATT GCAGAG |
| 7 | ADXCRP D.7289.C1 _s_at | INO80 | Sense | INO80 homolog (S. cerevisiae) [Source:HGNC Symbol;Acc:26956] | 7 | CTCTGATTTGCACACCTGAAAATCGCGGAATTGAGTTTC GATAGATTGATTTTTAAAACTTTTTGGAGTAGGGGGTAT AGGGGAATCATTTAATTTAAATCATTAAGATTCCCCTGCT CAAACCCAGATTCCTGTGTACAGATGCTATTTAGAGGGA ATCAGAAAAATGCCAAGCCTTTTCTCTTTGAATGTGCTA TTTTTATAACTGAACTTGTACATATGTATAAAGAGAGACA CATCTTCCTTTTACTA |
| 8 | ADXCRA G_BC011 901_at | KRT17 | Sense | keratin 17 [Source:HGNC Symbol;Acc:6427] | 8 | GCTTCCTTGCCTGATGACAATAAAGCTTGTTGACTCAGC TAA |
| 9 | ADXCRA D_BE2959 38_at | RBBP4 | Sense | retinoblastoma binding protein 4 [Source:HGNC Symbol;Acc:9887] | 9 | GGGTCAGAAAGATGCCTTCAGTTTTGGTCAGTGTCTAAA AGTTAAGTCTGTTTAGGCCAAGCATGGTGGCTCACGCC TGAAATCCCAGCACTTGGGAGGCCGAGGCAAGTGGA TCACAAGGTCAGGAGATGAGACCATCTTAGCCAACATG GTGAAACCCCGTCTCTACTAAAATACAAAAAATTAGCC AGGCGTGGGGGTGCGTGCCTATAATCCCAGCTACTTGG GAGGCTGAGGCAGGGAATCGCTTGAACNCGGGAGGC AGAGGTCACGCCATGGACTCCAG |

FIG. 7-2

| 10 | ADXCRA D_NM_00 2260_s_at | KLRC1 /// KLRC2 | Sense | killer cell lectin-like receptor subfamily C, member 1 [Source:HGNC Symbol;Acc:6374] /// killer cell lectin-like receptor subfamily C, member 2 [Source:HGNC Symbol;Acc:6375] | 10 | CTTTCTAAAAGTTGCATGTTATGTGAGTCAGCTTATAGG AAGTACCAAGAACAGTCAAACCATGGAGACAGAAAGT AGAATAGTGGTTGCCAATGTCTCAGGAGGAGGTGAAATA GGAGATGACCACTACTTGATAGAACGTTTCTTTGTGTCG TGATGAAAACTTTCTAAATTTCAGTAATGGTGATGGTTGT AACTTTGCGAATATACTAAACATCATTGATTTTTAATCAT TTTAAGTGCATGAAATGTATGCTTTGTACATGACACTTCA ATAAAGCTATCCAGAAAAA |
|---|---|---|---|---|---|---|
| 11 | ADXCRA D_AF1438 66_s_at | ZC3HAV1 | Sense | zinc finger CCCH-type, antiviral 1 [Source:HGNC Symbol;Acc:23721] | 11 | AGCAAGCTTACTAAAAACTGCACTTCACACTTAGCTTAA TGTTTGAGGGAATTAACTTCATAAA |
| 12 | ADXCRP D.14126.C 1_at | FNDC3B | Sense | fibronectin type III domain containing 3B [Source:HGNC Symbol;Acc:24670] | 12 | ACCATGGCAACGAGGTAGTCTGTTCTATTTTTGGAGTAT GAAAGTAGTGCCTTCTTAAATCTAATATAAATGAGAGTT CCAGAAAACCAGTGCTTCAAACAAATTTGATTTA |
| 13 | ADXCRSS .Hs#S192 6324_at | AC018359.1 (Clone_based_ vega_gene) /// AC123023.1 (Clone_based_ vega_gene) | AntiSense | Novel processed transcript /// Putative processed transcript. | 13 | TGGGCTTAAAACTCAGCTCTGCCACTTACATTCCTCATT TCTTTCTATCCTGGGTCTGCCAAATGTAAGAAAAGTTT TCACATTTTTTTACCAGTTTTCTCACCCATGACCACCCT GTCTCAAAATGATTATGCAACAGCCCAGAGTCCCCCATT CCAAATTCTTTGCAAAGAGCAAGATTTCCCTCGCTATT TCTGAATTCATCCACACCTCTATTTCTCT |

FIG. 7-3

| 14 | ADXCRA D_BX0911 64_s_at | RNF39 | AntiSense | RING finger protein 39 isoform 2 [Source:RefSeq peptide;Acc:NP_73957 5] | 14 | ACTCCCCAAGGGTTCTCAATTCTCTTTTCCCAGGCTCGT CCATGACTGTTTCTTGTCCTCAGAGCCCTTGCCTTCCTT GCTGCCTCCTCAGTCCCATTCTGTCTCTTTCAGCGG CCCCATCCTTATCTACCTTCCCCAGTGCATCCCAGAAAA ACATCTGTCCCTTCC |
| 15 | ADXCRA D_BX6412 59_at | NHLRC3 | Sense | NHL repeat containing 3 [Source:HGNC Symbol;Acc:33751] | 15 | CCTGAGCTTGGGTGACTCATTGTGTGCTAAGAAAAAAAA TCAAATTTCAGAACATGCGAGACCTCGACCCAGGTAAAT |
| 16 | ADXCRA D_AA6012 08_x_at | AC004878.3 (Clone_based_ vega_gene) | AntiSense | Known pseudogene. | 16 | GACTGGAGAAAGAAGAGGTGGCATAGGATTGACTAAGA TGAAGGAGGGGGCCAGGCGTGTGGCTCACCCCTGT AACCCCAACACTTTGGGAGGCTGAGGCGGGCAGATCA CCTGAGGTCAGGAATTCAAGACCAGCCTGGCCAACATG GTGAAACCCCATCTCTACTAAAAGTACAAAAATTAGCCA GGGCGGTAGTGGTGTGTGCCTAT |
| 17 | ADXCRP D.10016.C 1_at | SATB2 | AntiSense | SATB homeobox 2 [Source:HGNC Symbol;Acc:21637] | 17 | ATCCTCAACAGCTAATCACTCTTTAACTCCTGAATTCTG GCTCCTGTCCCCACTACTTTAATGAAATTATACTCTAAA CTTCGCCAGTCTTCTCCCAACCAACTGCCAAATCTCATG ACATGGTTTTAAGCCTCTCTCTCTCTTAACTTCTCAGCTTTC CACAAGTAGAACAAGTCTTCTTCTGGAAACTCTCCACGCA TGTCCTCTATACTCTCACTACTGTCTCCCTCTTCTTCCTT CTCCACCTGCCCCCATCCTCCTGGCATTTCTACTCTCTTT |

FIG.7-4

| 18 | ADXCRA G_BC072 004_at | CLCN2 | Sense | chloride channel 2 [Source:HGNC Symbol;Acc:2020] | 18 | TTCTCCCAGTTCATCCTACCTGGAATCTGACCCACTACC CACCTGCAACAAGTCTTCCAGAGGCAGGAAGATAGGCC CTGCCCTGGCAGGATGGGTGGGGTCACTTGACCCCT GCTCCCCCTTTGAGGGGAAAGGGGTGGAACTAAGATG GGTTTATAACTGGAACCTCCAATGACCAGATGTATAG AGATTTACAAAGATTTTTATATTAATTAATAAAACAAATT CTTAAATAGAACAAAATAAACACCTAATGAGCCACTTAT ATAT |
| 19 | ADXCRA D_BF8807 25_at | AC079781.1 (Clone_based_ ensembl_gene) | Sense | Known long non-coding RNA | 19 | ATGGTGGATAAATGGGACTTAGGACTAAAACTCATGCCT TGGTGTGTTTTGCAGTGATGTTTTGTTCTGGGGTGCAT CACAA |
| 20 | ADXCRA G_NM_00 3234_s_at | TFRC | Sense | transferrin receptor (p90, CD71) [Source:HGNC Symbol;Acc:11763] | 20 | GCGTAGCTAAGTGAAAAGGTCATAGCTGAGATTCCTGG TTCGGGTGTTACGCACACGTACTTAAATGAAAGCATGTG GCATGTTCATCGTATAAC |
| 21 | ADXCRA D_AL8320 68_at | SIK3 | Sense | SIK family kinase 3 [Source:HGNC Symbol;Acc:29165] | 21 | ACTCTCAAGAACAGTAGAGAGGGAAAAGAAAAAGAAAAA GAACAGTGGAGGTTGTGTAAGGACATTTGAGAAGAG ATTCATGAAACAGGCCAAATGGTAGGTTTGCTAGTTCGC AGGGGGAGAACCAATGAATTAATTTAGAAAGAGCTTCTC TGGGATTAGAATGAAAATAAATCACTGGCTGGGTGCAC ACCTGTAATTCTAGCTATTCAGGCAGGAGGA |

FIG. 7-5

| 22 | ADXCRA D_NM_02 1777_at | ADAM28 | Sense | ADAM metallopeptidase domain 28 [Source:HGNC Symbol;Acc:206] | 22 | TTGTCTCAGCATCAGTATATCCCATGCAATATTTGAGGT GTGCTCATACTAAAATTATTTGTGTATCTGAAATTCAAAT TAAACTGGGTGTCTTTTCTTTTCATCTGGCAACCCTACT AAGATCATAAACCCTTGGA |
| --- | --- | --- | --- | --- | --- | --- |
| 23 | ADXCRA D_BP3934 43_at | SLC2A3 | Sense | solute carrier family 2 (facilitated glucose transporter), member 3 [Source:HGNC Symbol;Acc:11007] | 23 | ACTTGGGAGGAAATACACAGTAGTTAGAAAAAGCCTCCT AGGTGATTTTGATGAATCCCAGTCTCAAATTTCTTCATTT GGAAATGATAATGTAGGCCACACGTATTACTGGAGAAAA ATGTGCTCCCGAGACTTTCCAGAGCAGCAGAGAGCTGGGA CTAGGCAGGTGAGGCAGCTACGTGCAAGTGTAGCCCT GAGAATGAGCACCTCTCTTTAAAGAATGTACCTTG |
| 24 | ADXCRA D_AA1315 06_at | CXCL9 | Sense | chemokine (C-X-C motif) ligand 9 [Source:HGNC Symbol;Acc:7098] | 24 | GAGAGGTTGTCTGTGGCCAGAATTTAAACCTATACTCAC TTTCCCAAATTGAATCACTGCTCACAC |
| 25 | ADXCRP DRC.1543 2.C1_s_at | ZNF770 | Sense | zinc finger protein 770 [Source:HGNC Symbol;Acc:26061] | 25 | TTGCATTAGGTATTAGTCTAGGGATAAAGTATACAGGCG GATGTGCGTTGGTTGTTATATACAAATATGTCATTTTATGTAA GGGACTTGAGTATACTTGGATTTTTGGT |

FIG.7-6

| 26 | ADXCRA G_BC004 542_s_at | PLXNB2 | Sense | plexin B2 [Source:HGNC Symbol;Acc:9104] | 26 | GAAAAAGCGGTACGATGCCTTCCTGACCTCACGGCCT CCCAAGGGTGCCGGCACTCTGGGTGGACTCACGGCT GCTGGGCCCCACGTCAAAGTCAAGTGAGACGTAGGT CAAGTCCTACGTCGGGGCCCAGACATCCTGGGTCCT GGTCTGTCAGACAGGCTGCCCTAGAGCCCACCCAGT CCGGGGGACTGGGAGCAGTTCCAAGACCACCCACC CCTTTTTGTAAATCTTGTTCATTGTAAATCAAATACAGCG TCTTTTTC |
| 27 | ADXCRP D.4449.C1 _at | ARHGAP8 | Sense | Rho GTPase activating protein 8 [Source:HGNC Symbol;Acc:677] | 27 | TGCCTCTGGTCCTTGGACTCTTGTCCATGGTTCCTGAG CTGTGG |
| 28 | ADXCRP DRC.1402 9.C1_at | B4GALT5 | Sense | UDP-Gal:betaGlcNAc beta 1,4-galactosyltransferase, polypeptide 5 [Source:HGNC Symbol;Acc:928] | 28 | GCCCAGCCTTGAAGTCATGTTCTAAATTGTATTTGAATTT GTGCCTCTTTGTTTTCCCCAAACCAAAGCCCTCAAATT GTAGTCTCTGTCGGCTTCTGCAGAATTCTGGAAAATGCC AGTTTTCCTCCCCGCCCTTGTTTTCCATAAAACATATTT ATATATTGTGATGAGGAGTACTTTCTGAAGAGTACTTCG TANNNNNNNNNAATTGCCTTGTTTGCCTTCAACTTCCTT GATTTTCA |
| 29 | ADXCRA G_BC005 352_s_at | TNFAIP8 | Sense | tumor necrosis factor, alpha-induced protein 8 [Source:HGNC Symbol;Acc:17260] | 29 | AAAAGTCTAGATTGGTCTTGATATTGAGATAATAAAAGT AAGTAGCATTAAGAAAAGTAACAATCTTCATTCTACAGA TGAACTCATTGAAACAATTTAGGGAATGAGGGCAAA AGGGGAGAAATACTGCTAAAGAACATGAGCATAAAAAC GCGTGCGTTTCAGTGTTTAAGAAGGCTTGATAAA |

FIG. 7-7

| | | | | |
|---|---|---|---|---|
| 30 | ADXCRAD_BG619847_at | EWSR1 | Sense | Ewing sarcoma breakpoint region 1 [Source:HGNC Symbol;Acc:3508] | 30 | ATAATTATGGGCTCACTTCCTACTGGAGATGTTGAAAGTCTAAATCGGTTTGACCATTTGATTGATGGCACAATCTGGTTTAGAAACTTTGTTTAGATCAATGACATAACCCTGCTGCCTCTGCCTGCCCTTCCCCTCCCCCTTCCCATCCCTTTTCCCTATCTGTGTCTGTACTTTGATGAAGGTGAGCTATAATATTGGTGGTTAATATAATCCAGAAGGCTTAGTTCTGTGTGT |
| 31 | ADXCRAD_N86095_at | FLCN | Sense | folliculin [Source:HGNC Symbol;Acc:27310] | 31 | GAGGAAGGGCTGAAATGCTTTCTATTGGATACTATCTGGGCATATTACTTCCTGTGGTTCACTGTCTGGGTGACAGGATTCATAGAAGCCCAAACTTTAGCACCACGCAGCATACCCTTGTAACAAAGCCGCACACGTACGCCCTCAAGCTAAACAAAAGTGGACCGGGAGCCGAGGTGGGGATCATGAGGGTCAGGAGTTTGAGACCAGCCTGGCAGATAACGGTGAAACCCCGTCTCTACTAAAATACCAAAAAGGTTAGCCGACATGGTGCAGGTCCTTT |
| 32 | ADXCRAD_CX785794_s_at | GUF1 | Sense | GUF1 GTPase homolog (S. cerevisiae) [Source:HGNC Symbol;Acc:25799] | 32 | CTTTCTCTCTTACCTGCTATGCTTGAAGCCCCCGCCCCTCTTCAAGTTGTCCTGCCTTTCAAGACCAATGTACA |
| 33 | ADXCRIH.2688.C1_s_at | ARSE | Sense | arylsulfatase E (chondrodysplasia punctata 1) [Source:HGNC Symbol;Acc:719] | 33 | GAAAAAGTAGTCCACCACGATCCACCTTTGCTCTTTGACCTCTCAAGAGACCCTTCTGAGACCCACATCCTCACACCAGCCTCAGAGCCCGTGTTCTATCAGGTGATGGAACGAGTCCAGCAGGCGGTGTGGGAACACCAGCGGACACTCAGCCCAGTTCCTCTGCAGCTGGACAGGCTGGGCAATATCTGGAGACCGTGCTGCAGCCCTGCTGTGCCCGTTCCCCTCTGCTGGTGCCTTAGGGAAGATGACCCACAATAAATGTCTGCAGTGAA |

FIG. 7-8

| | | | | |
|---|---|---|---|---|
| 34 | ADXCRPD.6725.C1_s_at | EFNA3 | Sense | ephrin-A3 [Source:HGNC Symbol;Acc:3223] | 34 | TCTTCTGTGAAGACAGGACCTATGCAACGCACAGACAC TTTTGGAGACCGTAAAACAACAGCGCCCCCTCCCTTCC AGTCCTGAGCCGGAACCATCTCCCAGGACCTTGCCCT GCTCACCCTATGTGGTCCCACCTATCTCCTGGCCTT TTTCAAGTGCTTTGGCTGTGACTTTCATACTCTGCTCTTA GT |
| 35 | ADXCRPD.16070.C1_at | TMEM87A | Sense | transmembrane protein 87A [Source:HGNC Symbol;Acc:24522] | 35 | GTCATGAGACGGGATTTGGTCACCAAGGAAGTGAGTAT ATATAGAGAAGAGAGGTCCAAGGGCTGGGCCTTGAATAT TTAATATAATTTAGAAGTCTGTAACGATGAAGTAGTTAGC AGAAGAAACTTGAGGAGAGACCAGTGAGGTGGGTAGCA AAAC |
| 36 | ADXCRPD.2228.C2_s_at | KIAA0141 | Sense | KIAA0141 [Source:HGNC Symbol;Acc:28969] | 36 | CCACTGGAAAGGAGTGTTGTAAGACTAGGTTTTGGCTA AGAACTTCTCACCTCAGCCCTANAGAGGGAGCCTGTGG GTTCTCAGAGAGATATCACAATTTGAGTCCCAAGAAGA GGCCAGATACCCACCCACCTTCCCCCAAATCTTAAGCA CCTGCGCCAGTACAGTCAAGAAGAGG |
| 37 | ADXCRAD_AW604939_x_at | CD177 | Sense | CD177 molecule [Source:HGNC Symbol;Acc:30072] | 37 | TTTGCCCTTCCTGCTAACTCTATTACCCCCACGATTCTT CACCGATGATGACCACCCACCTCAACCTCCCTCTGAC CTCATAACCTAATGGCCTTGGACACCAGATTCTTACCCA TTTGTCCATGAATCATCTTCCCCACACACAATCATTCA TATCTACTCACCTAACAGCAACACTGGGGAGGAGCCTGG AGCATCCGGACTTGCCCTATGGGAGAGGG |

FIG.7-9

| | | | | |
|---|---|---|---|---|
| 38 | ADXCRAD_AK024864_at | RP11-294O2.2 (Clone_based_vega_gene) | Sense | Novel processed transcript. | 38 | GGAAGAGCTCGGTGAGCATGATCATGGCTCAGGTCTC CATCCACATGCCTAAGACAGCAGGGTGAGTGTGAAGATGG GAACTGACTCAGAATTAACTGTGTGATCATGGGCAAGTT GCCAAGTTAACCCTCATATCTAAATTCAGGTATCCTTGA ACAAACATAGAACAGATACTGATGATCCGCCATGTTTACT ATAACCATAAACTCTTTGTGAATTAAAAATGGCCCTCTCAA CCTGGA |
| 39 | ADXCRPD.10763.C1_s_at | AC027612.6 (Clone_based_vega_gene) | Sense | lymphocyte-specific protein 1 pseudogene (LOC654342), non-coding RNA [Source:RefSeq DNA;Acc:NR_027238] | 39 | CAGGGCCATACAGGGTGTGTACATCACAGATAGGG |
| 40 | ADXCRAD_AL832068_x_at | SIK3 | Sense | SIK family kinase 3 [Source:HGNC Symbol;Acc:29165] | 40 | GTACTCTCAAGAACAGTAGAGGGAAAAGAAAAAGAAA AAGAACAGTGGAGGTTGTGGTAAGGACATTTGAGAAG AGATTCATGAAACAGGCCAAATGGTAGGTTTGCTAGTTC GCAGGGGGAGAACCAATGAATTAATTTAGAAAGAGCTT CTCTGGGATTAGAATGAAAATAAATCACTGGCTGGGTG CACACCTGTAATTCTAGCTATTCAGGCAGGAGGATGGC TCGAGCCTAGGAGTTGGAGGTCAGCATAGCCAACATAG GGA |
| 41 | ADXCRAG_BX648499_s_at | C4orf41 | Sense | UPF0636 protein C4orf41 [Source:UniProtKB/Swiss-Prot;Acc:Q7Z392] | 41 | CAAGACCGGCCCTTGGCTGTTGTTACAGAGATGTTGGG CAGAGCTATGCAGGTGTTTCATTGTGAACTCTAGCTTTG ATCATGGTAAAAAGTTAACCTTTTCTATTTTTTAATGGAT GTTATACC |

FIG.7-10

| 42 | ADXCRP D.4415.C1 _s_at | TCOF1 | Sense | Treacher Collins-Franceschetti syndrome 1 [Source:HGNC Symbol;Acc:11654] | 42 | GAGAGACAAAGCAAGTGGTGATGTCAAGGAGAAGAAAG GGAAGGGGTCTCTTGGCTCCCAAGGGGCCAAGGACGA GCCA |
|---|---|---|---|---|---|---|
| 43 | ADXCRA D_CX7521 89_s_at | GTF2F1 | Sense | general transcription factor IIF, polypeptide 1, 74kDa [Source:HGNC Symbol;Acc:4652] | 43 | AGCGGCGGCTCAAGGATCAGGACCAGGACGAGGATGA GGAGGAAGGAGAAACGTGGCCGCAGGAAGGCCGAGC GAGCTGCGCATCCACGACCTGGAGGACGACCTGGAGA TGTCGTCCGATGCCAGTGATGCCAGTGCCAGTGAGGAGGG GGGCAGAGTCTCCGAGGCAAGAAGAGAAGACGCGCTG GCTCATGGCGCGGGGCGGAGAAGAAGAAGAAGAAGGTT CAGACGACGAGGCCTTCGA |
| 44 | ADXCRP D_AW265 514_at | TRPS1 | AntiSense | trichorhinophalangeal syndrome I [Source:HGNC Symbol;Acc:12340] | 44 | GGGAGTCCAGGATTAAGGTTTTGCAGGGTTTGGTTTCTA GTGAGGGCTTTCTTCCTGGCTTGCAGATGGCCATCTTC TCTCCATAGGCTAACATGGCCTCTACTTTGTGTGTGGGA GAGTCAGAGATAGAGCAAGCCCTCTTGTCTCTCTTCATA TAAGCCTACTAATCCCCATCAGACCAGGTCCCTTATGAT CTTAAAC |
| 45 | ADXCRP D.2546.C1 _s_at | MED1 | Sense | mediator complex subunit 1 [Source:HGNC Symbol;Acc:9234] | 45 | AGCAAGGTGTCTCAGAACCCAATTCTTACCAGTTTGTTG CAAATCACAGGGAACGGGGGGTCTACCATTGGCTCGAG TCCAACCCCCTCCTCATCACAACGCGCCACCTGTCTCTT CGATGGCCGGC |
| 46 | ADXCRA D_CN427 849_at | PLXNA3 | Sense | plexin A3 [Source:HGNC Symbol;Acc:9101] | 46 | CAGGTGTTGGGACAGTCCCACCCTCCCTGCTATTTATAT CCCTCTGCCTATTTATTGAATCGAACTTCGCCCTCTGTCT CCATCTGTAAATATGTG |

FIG. 7-11

| 47 | ADXCRP D.6189.C1 _s_at | CHD3 | Sense | chromodomain helicase DNA binding protein 3 [Source:HGNC Symbol;Acc:1918] | 47 | AGAGTGGCAGTTTGCATGGCGAACCCCCACTTCCTCT TTGCTGCCCCTTCACTTTCTTGCTGCCCCTTTCCCAGTC TCTCTTCACACCCACTCCTGGTCTGTCCTGATCCCCTCT TCTGTATCCAGGTTTATTGGTTGTTGTACATAT |
|---|---|---|---|---|---|---|
| 48 | ADXCRP D.4446.C3 _at | B3GNT3 | Sense | UDP-GlcNAc:betaGal beta-1,3-N-acetylglucosaminyltransferase 3 [Source:HGNC Symbol;Acc:13528] | 48 | GAATATTCTGGCTGGCGAACTCCTACACATCCTTCAAAA CCCACCTGGTACTGTTCCAGCATCTTCCCTGGATGGCT GGAGGAACTCCAGAAAATATCCATCTTCTTTTTGTGGCT GCTAATGGCAGAGAAGTGCCTGTGTCTAGAGTTCCAACTGT GGATGCATCCGTCCCGTTTGAGTCAAAGTCTTACTTCCC TGCTCTCACCTACTCACAGACGGGGATGCTAAGCCGTG CACCTGCTGTGGGT |
| 49 | ADXCRP D.8017.C1 _at | GSTO2 | Sense | glutathione S-transferase omega 2 [Source:HGNC Symbol;Acc:23064] | 49 | TAAGACCTACTACTCTGATAGCCCCACATGGTGACTATAG TAAATAATAACTTAATTGCACATTTAAAATAACTTAAAC AGTGTAATTGGGTTGTTTGTAATTGAAAGGATAAATGCT TGGGGAGTGGATACCCCATTCTCCATGATGTGCTTATT GCATACTGCATGCCTGGACCAAAATATGTACCCCAT |

FIG. 7-12

| | | | | |
|---|---|---|---|---|
| 50 | ADXCRSS.Hs#S300 6539_at | AC010522.1 (Clone-based (Ensembl) /// ZNF418 /// ZNF814 | AntiSense | cDNA FLJ52732, moderately similar to Zinc finger protein 418 [Source:UniProtKB/TrEMBL;Acc:B4DR41] /// zinc finger protein 418 [Source:HGNC Symbol;Acc:20647] /// zinc finger protein 814 [Source:HGNC Symbol;Acc:33258] | 50 | ATTTACTACCTTATTATGAAGTGTGCCCTCCAAAAT |
| 51 | ADXCRA G_NM_00 3890_at | FCGBP | Sense | Fc fragment of IgG binding protein [Source:HGNC Symbol;Acc:13572] | 51 | CTTTTCTGGGTCACAGAGGCCAAATGTGAGAGCATTGA ATAAA |
| 52 | ADXCRP DRC.1112 6.C1_at | KDELR3 | Sense | KDEL (Lys-Asp-Glu-Leu) endoplasmic reticulum protein retention receptor 3 [Source:HGNC Symbol;Acc:6306] | 52 | GACCTTTTCATCATCAATAGATCGCCCTTAAAGACCCATTGT AAGGTCATAAAAAACCTCGGCCAACTGCACAAAGATGG TGCCTCACTGCAACAAGAAACCTTAAGGTGTCTTACCGA CGAAATAAAAAACATAAATGATTGTTCTCCAAGGCCTGA GGGCAAGACTCATGATGGGCAAGTCAACCCAATCTGG AACAATGTCCCTCCTCTTAG |
| 53 | ADXCRA G_AL3899 51_s_at | NUP50 | Sense | nucleoporin 50kDa [Source:HGNC Symbol;Acc:8065] | 53 | GATTATGTTTTCCATGGAAGGACAAGTCTGACTGTTCAT AGGCTGATTTTCTTAAGAGGATTATTCTGTTTTACAATT TCAATTCTAGATCACATTTTATATGCTGCATGCCAAAA AAA |

FIG.7-13

| | | | | |
|---|---|---|---|---|
| 54 | ADXCRAG_BC062348_s_at | AL136419.1 (Clone_based_ensembl_gene) | Sense | Full-length cDNA clone CS0DF029YN24 of Fetal brain of Homo sapiens (human) Fragment [Source:UniProtKB/TrEMBL;Acc:Q86U40] | 54 | ACCTGTCCCTGTCCTACCTTAACTGATCAATGACCTTGTGACAGTCTCTTCTGGACAATGGGTCTTATCATCTCCCCACCATGTACCTTGTGAC |
| 55 | ADXCRPD.2239.C1_s_at | SLC2A14 /// SLC2A3 | Sense | solute carrier family 2 (facilitated glucose transporter), member 14 [Source:HGNC Symbol;Acc:18301] /// solute carrier family 2 (facilitated glucose transporter), member 3 [Source:HGNC Symbol;Acc:11007] | 55 | TAGACAGTATGAGTCAATGTGCAGTGTAGCCCACACTTGAGAGGATGAATGTATGTGCACTTGCTCTGGGTGGAAGTACGTTATTGTTGACTATTTCTCTGTGTTGTTCCTACAGCCCCTTTTCATATGTTGCTCAGTCTCCCTTTCCCTTCTTGGTGCTTACACATCTCAGACCCTTTAGCCAAACCCTTG |
| 56 | ADXCRPD.8017.C1_x_at | GSTO2 | Sense | glutathione S-transferase omega 2 [Source:HGNC Symbol;Acc:23064] | 56 | AAGACCTACTATCTGATAGCCCCACATGGTGACTATAGTAATAATAACTTAATTGCACATTTAAAAATAACTTAAACAGTGTAATTGGGTTGTTGTTTGTAATTGAAAGGATAAATGCTTGGGGGAGTGGATACCCCATTCTCCATGATGTGCTTATTGCATACTGCATGCCTGGACCAAAATATGTACCCCATAAATATATACACCTACTATGTGCCCCGAAA |

FIG.7-14

| | | | | | |
|---|---|---|---|---|---|
| 57 | ADXCRAD_BF197118_at | N/A | No Transcript match | N/A | 57 | GAATTTGGTTTTGATCTCCCTATTGAGAGACTGGTGTACAGTATTTGTCTATCCCTGCACAAATTATTAAAGCAAGTTTTGCCATTCTGTTATCTTCCTCATGAATATCTTGATTACTTTTGGCCCTAACTACATCAAGTTCCACAGAAATCCCAATTGGAATCTTAGTTAAAATTGTGTTGTCTATGGACCAGTTGAAGAAAACTGACACATTTATAATACTGACTCTGTTCCATAAAG |
| 58 | ADXCRPD.1045.C1_s_at | FBXO45 | Sense | F-box protein 45 [Source:HGNC Symbol;Acc:29148] | 58 | CCAGCTTTAAAGGTGAGATTGTAGAGATGCTGTCAAAGGGATAAGGAAATAGCAAGAGATTTTAAGTAGTGTGTTGTGAAGACTGATCCCCATTTTACAACTGCCTGTTCTTCTCCAGTCCNNNNNNNNNCAGCCAGCTTGACTATTAGAAAAGTATGAAACTGGTTGGGGTTTATTTTAATATTTTTAATATATTTGAGAAGCATGGTCTG |
| 59 | ADXCRAD_BF961733_s_at | ST7L | AntiSense | suppression of tumorigenicity 7 like [Source:HGNC Symbol;Acc:18441] | 59 | AAATTCAATATGGAACTTGAGGCCAAAAAAACAGAAGGTTACTCTCAATGCCATCC |
| 60 | ADXCRAD_CX872171_at | C12orf47 | Sense | N/A | 60 | TATGTGCCAAATCTACTAGACATTGGAGAAACAGTAGGAACAACACATGGTACCGGCACATGGATCTTTCAGG |

FIG.7-15

| | | | | |
|---|---|---|---|---|
| 61 | ADXCRIH.283.C1_at | OLFM4 | AntiSense | olfactomedin 4 [Source:HGNC Symbol;Acc:17190] | 61 | AGTCTGGTTCTAATCTTCTGAGCTGCCTTTGGAAGGAAGTTATGAGGTAGAAGATTCTACTGACTTTTAGTAAGGTGGACAATGAGAGAAGAAAAGCAGGTGCCTCATCTACAGATCCTTCTGGGATTTATTTGCCATGTACAATTTAATGCATAAAAGGCCTCTCTCCATAAAACTCAGCACTTTACAGATGTAGAATATATAAGCATGCCAAATTTACTTATCTGTCACATACAAAGCATCATTCCAGGTGCTAGTGAGG |
| 62 | ADXCRPD.15298.C1_at | GRHL2 | Sense | grainyhead-like 2 (Drosophila) [Source:HGNC Symbol;Acc:2799] | 62 | GTAGGACAGTAGGACAGTACACAGTAGAACAGTCTAGGACAGTTCAGATGACAGTACACAGTAGGACAGTTCACAGTAAGACAGTTCACGTACGGTACCCAGTAGGACAGTACACAGTAGAACAGTTCACAGTGCANNNNNNNNNNNNNNNNNNNNNNNNNNNNNNNNNNNNNNNNNNNNNNNNNNNNNNNNNNNNNNNNNNNNNNNNNNNNNNNNNNNNNNNNNNATAGGACAGTTCACAGTAAGACAGT |
| 63 | ADXCRSS.Hs#S1918752_at | DEDD | Sense | death effector domain containing [Source:HGNC Symbol;Acc:2755] | 63 | GAAGCTGCCAGAGGGTAATTGGTTTCCCAGAAGTTCTTAAATTTGGGAGCTGTCTTGCCGCAAGCCATTGAGACTGGAAATTCTTGGAGTTGGTATTGTTTTGTAAATTGACTAATAGAGAGTTAGGGAAGCCTGGAGACTTGTTGGGGGTGAGTTCTCTAAATGGTTTAGGCTTGTCTGTGTACTTTTGCAACGAGATTGTCTAATTCTATGGGCCTCTGAGGT |
| 64 | ADXCRAD_BC035661_at | SMC5 | Sense | structural maintenance of chromosomes 5 [Source:HGNC Symbol;Acc:20465] | 64 | TTCTTGTGCATTATTACATTTACTCATCCTCCAGGACAATGTTGAAGAGAAATGATGTATTAGTCCATTTTCACACTGCTATAAAGAACTGCCTGTATTAGCCTAGCATGGTGGCGGACACCTGTAATCCCAGCTATGCAAGAGGCTGAGACGAGAA |

FIG. 7-16

| | | | | |
|---|---|---|---|---|
| 65 | ADXCRAD_BX0966 75_s_at | HKR1 | Sense | HKR1, GLI-Kruppel zinc finger family member [Source:HGNC Symbol;Acc:4928] | 65 | AACCCAACCTTAAAGCTGAAGAACAGTCCCGGCTAAATC CTCATACTGAATTGAGAACCTGTCTTCCCATTGGTGTG CTTTCCTCCGATTGATCCCAACCCTTCACCTATTTACG TATACCTGCCCTTTCCTAATTGGTTTTACACTGCTGTG CCCACCTTTGAGTGGTGCCTTTGCATA |
| 66 | ADXCRPDRC.6154.C1_at | N/A | No Genome match | N/A | 66 | TGGTGAAATTTTGTACCCCGGATGCAGTTGGCACTTT |
| 67 | ADXCRPD.80.C1_s_at | PLK4 | Sense | polo-like kinase 4 (Drosophila) [Source:HGNC Symbol;Acc:11397] | 67 | AAAAATGTTGGTTGGCTACACAGTTAACTAGTGGAGCT GTGTGGGTTCAGTTAATGATGGGTCCCAGTTGGTTGT GCAGGCAGGAGTGTCTTCTATCAGTTATACCTCACCAAA TGGTCAAACAACTAGGTATGGA |
| 68 | ADXCRAG_BC027 959_at | LOC80054 | Sense | Homo sapiens hypothetical LOC80054 (LOC80054), non-coding RNA. | 68 | TTGGAGATAAGGCTTTTAGGAAGTCATTAAAGTGAGATG |
| 69 | ADXCRAD_BQ440 009_s_at | FBXO45 | Sense | F-box protein 45 [Source:HGNC Symbol;Acc:29148] | 69 | CAGGTTGTTTGTTCTAGTTCTAATTTCTTAAAAACCACT ACATGGTTACAAAATTGGAATAACATTTGGGACAACTG GGTTAACTACAAAGAGAGAGGATTTTAAGAGGAGATGTGT TGTATTGACTCATTTGTATTATTTTGGCTTACAGTTCC CATAGCTGTTAGAGTCTGG |

FIG.7-17

| | | | | |
|---|---|---|---|---|
| 70 | ADXCRPD.14045.C1_at | AntiSense | AL031666.1 (Clone_based_ensembl_gene) /// ZMYND8 | Known long non-coding RNA /// zinc finger, MYND-type containing 8 [Source:HGNC Symbol;Acc:9397] | 70 | GGCCAATGAGAACCCAGCCTTCAAATAAACAAGCTTCTCATTGTTAACACAGGGTTCAAAGGCAGGAGGTTGGAGGTGTTTTGCAGGGTATCCAGAATTCTGATCGCTGAATACTTTAGGGCAAAGAGTAAGATTTCCCACACCTCCCCCTAAATCTTACAATTCCCTGATGAGGCAGGAACATGGGAAAAAAAGATACAGGTTAAATTACAAAGCAGAAAAATATGCCCAGCTAGAAGCTAAAGACCTGGTCTCAAAACACTGAACCGAGGAGCACTGATT |
| 71 | ADXCRAG_NM_002146_s_at | Sense | HOXB3 | homeobox B3 [Source:HGNC Symbol;Acc:5114] | 71 | CCCTGGCCTGAGAGGTTGCTTTTAAGTCTTCCACCCTTGTTCCATCTGCCTGCCAACCCATCGGAAAGGAATCCACATCATATTGGAGATGACCCCATCAACCCCAGGGCTCAGCACTACCAAGTTGGAATTCCACGCCCGGAGTGGGGTAGAGGAAGACGAGACAGGAGGAGCAGAAAAGCACATTTAAAAACCAGAACAAGATGGCTAGGCCATCACCAACCAACGGACTTACCTTACATCTTTGTAG |
| 72 | ADXCRAG_BC058002_at | Sense | MORC3 | MORC family CW-type zinc finger 3 [Source:HGNC Symbol;Acc:23572] | 72 | TTTTTTCTATCCCTGCCATTCAGTCTCCATTAGCACTCTATTCTCTCTCATTTATTCCACCCCGTCTTCC |
| 73 | ADXCRPD.14007.C1_s_at | AntiSense | APBB2 | amyloid beta (A4) precursor protein-binding, family B, member 2 [Source:HGNC Symbol;Acc:582] | 73 | GAAACACGTGTATTATGGGAACAACTGAAAGGTCAGCCTGAAGACTTTTGCCCTGTTGCTTCTGAGAGTGCTGGATATGAGTCCCTGTCTGTCTCTGAAACTTCTAAAATATGCACCCTTAACCAGCTTTCCACGGAGGGATAAGCCTTTGTCAATACAAATGGTACAGTGAGCAGAGA |

FIG.7-18

| 74 | ADXCRA G_BC012 165_s_at | RMND5A | Sense | required for meiotic nuclear division 5 homolog A (S. cerevisiae) [Source:HGNC Symbol;Acc:25850] | 74 | AGTCTGGCCCCATAGTGACTTTTGCCCCATGATTCTGCT TCACTGTTGGAATCCTCTTTGAAGTTCCCCTCTCTTG CTAAAGCAGTGAAGAAGAGAACAGAGACAAACTCTTT GGACTGTGAAAGAGAAGGTAGAGAATTCCAGGCAACAG TCTGACCAAGGGTGTAAACCAG |
|---|---|---|---|---|---|---|
| 75 | ADXCRA G_AF1099 07_at | NUMB | AntiSense | numb homolog (Drosophila) [Source:HGNC Symbol;Acc:8060] | 75 | GGGAGGGGGAGATACACATATATAATATTAAAAAATGT CATCTTCCACAGAAAACACTGACTCTGCCTTCCAAAGT CACAAGTACAGATGGAGTCCAAGTTCAGGAGTGGTGCC CAAACCCAGATACTCAAACCAAACTGCAGAAACATTCAG GAAAAACAAGCCAAGCCATTATTTTAGAAACACAACG CAAAACAATAAGATAAAATTAAGTAAAGGGAAGTAACA GATGGAATAAAAACCAAGATATCACATTCCATAAAGGGC AA |
| 76 | ADXCRP D.9554.C1 _at | ZHX2 | AntiSense | zinc fingers and homeoboxes 2 [Source:HGNC Symbol;Acc:18513] | 76 | GTGGTGGTTATCGACAGGAATCTGTCAGAGAGCATACC CATGGAGCATTTATAATTGGGAGCCATTCCAGAATTCTG GTTTGCATACAACTCTTTAAAAGCCAGCTACCCTGAAA TGTACACTATCTGAGCTCTGCCTTTGCCTGTGATGAGTG ATGTTGGTCCTGCCTCTTAGTTCTGCTCTCCAGTCTCCAC CATCGGCTTCTCCAGATTTTCCTTCCAGGACCAGCAGGC AGGTGGGGTGTGGTGACTTTGTGGCAGACACTGTGGCAG ATTAAAGGTGGTTGCAAATT |

FIG.7-19

| | | | | |
|---|---|---|---|---|
| 77 | ADXCRP DRC.1009 0.C1_at | ELOVL5 | Sense | ELOVL family member 5, elongation of long chain fatty acids (FEN1/Elo2, SUR4/Elo3-like, yeast) [Source:HGNC Symbol;Acc:21308] | 77 | ACCACCTGAAGGACCACCAGAATGGGTCATGGCTGCT GTGAATGGACCACCAAGACAGCTTTCACCCCTGGAAAA CAATGTGAAGCCAAGGAAGCTGCGGAAGGATGGAAGTC AAAGAATTGAAACCCTCCAAACCACGTCATCTGATTGTA AGCACAATATGAGTTGTGCCCAATGCTCGTTAACAGCT GCTGTAACTAGTCTGCCTACAATAGTGTGATTCATGTA GGACTTCTTTC |
| 78 | ADXCRA G_AF3502 51_s_at | USP32 | Sense | ubiquitin specific peptidase 32 [Source:HGNC Symbol;Acc:19143] | 78 | CTTGTAGCTGACATTTGGCAAAAGCGTCACTGAAAGGC AAGCTAAATGTAGTTATTTTATCCTGTGGCCCTGAAGCA CAAAATAAAAAT |
| 79 | ADXCRIH RC.3651. C1_s_at | TRIM31 | Sense | Tripartite motif-containing 31 [Source:HGNC Symbol;Acc:16289] | 79 | GTTTACCGAAGGCACCAGTTCAGCCAGAGTGAAATCC GGAGAGGAGCAACGCCAGCCTGGGTCACAGTCCATCA AACCCCATGAGCCGGACCACTCTCGCTCTTCCTTACATT CCCACGTCCCCCTTCTCTCCCAACCCTCATATCAGCA AGGGAAATTAATTAATGAGATTTGATAAATCAGTAGATA GAATGAGGTCCCCCTTTTGAAATATTTAGCAGACTGGAA CCCCCCGCAAGCTCTGTAGGGGGTGGATGGGAGACA CTTCTAACTTTAATAAA |

FIG. 7-20

| 80 | ADXCRIH.1405.C1_s_at | CFB | Sense | Complement factor B Precursor (EC 3.4.21.47)(C3/C5 convertase)(Properdin factor B)(Glycine-rich beta glycoprotein)(GBG)(PB F2) [Contains Complement factor B Ba fragment;Complement factor B Bb fragment] [Source:UniProtKB/Swiss-Prot;Acc:P00751] | 80 | CTGGAGGAGTGAGTCCCTATGCTGACCCCAATACTTGCAGAGGTGA |
|---|---|---|---|---|---|---|
| 81 | ADXCRPD.17657.C1_at | ARHGEF1 | AntiSense | Rho guanine nucleotide exchange factor (GEF) 1 [Source:HGNC Symbol;Acc:681] | 81 | GCATTCACACATGTGCATGCTCACACAGAGACGGTTCTGGAGTTGTGGAGGGAAGCCTGCCCCGCCTTCCGCCCCACTCCCTGAACCTACAGCTCTCTCCATGGCCCCCTCACCTGCTCGGGCTGGGCCGGGGCTTAGGGCGAGAGGCAGGGGCAGGGACTTTCAGGGATCCGGCAGTCTCAGTGATGAGACACCAGCTGGGAGAAAGGCCAAATCCCTGGGCA |

FIG.7-21

| 82 | ADXCRP D.2812.C1 _x_at | CCND2 | AntiSense | cyclin D2 [Source:HGNC Symbol;Acc:1583] | 82 | AGGATTCCTTCTTGTGTTTAAGCAGGAGCAGGCAGAAA AGCCTAACAACCCCGTCTTTCCCATGGCAGCCCCAC GCCCATCATCACACAAGGCCCAAGGATGGGAAAGAGA AAAGCTAGAAGGACCCAGGGCCTCGGGACTACAGGA AGAGTGGAAAGTTACAGACTGTAAATAGAGTCGGGTAG GCTTGTGCCCTTCCTTATTGTCCGGTCTTTCATTTGCT GCTTCTGTTTAAGCTCAAGGGTCAGTCACCATGAAATGA ATTTGCACCTCGGTTTCTCTTTAGGCTCCA |
| 83 | ADXCRA G_X56774 _x_at | IGF1 | Sense | insulin-like growth factor 1 (somatomedin C) [Source:HGNC Symbol;Acc:5464] | 83 | CTCAGAGAAGGAAAGGTTGGCCAAAGACACATCCAGGA GGGGAACAGAAGAGAGGGACAGAAGAAGCAAGTCTGCAGA TCAGAGGAAAGAAGAAAGAGCAGAGAGGAGAGATTGG AAGTAGAAAATGCTGAATGCAGAGGCAAAAAGGAAAAT GAAGGACAGGAGGAGCAGCAGAGGATTAAACAGACAGAGGATGA TGAGAGAGGAGCAGCAGACAAGAATGAAAAGCAGAAA TACAATAGAGGAAATGAAGAAAAGTAGGCCTGCTGGAG CTAGATGATGATGT |
| 84 | ADXCRIH. 1727.C1_s _at | FLNB | Sense | filamin B, beta [Source:HGNC Symbol;Acc:3755] | 84 | GGGCCCATGGATTAACGCCCTCATCCCAAGGTCCGTCC CATGACATAACACTCCACACCCGCCCCAGCCAACTTCA TGGGTCACTTTTTCTGGAAAATAATGATCTGTACAGACA GGACAGAATGAAACTCCTGCGGCTCTTTGGCCTGAAAG TTGGGAATGGTTGGGGAGAGAAGGCAGCAGCTTATTGG TGGTCTTTTCACCATTGGCAGAAACAG |

FIG. 7-22

| 85 | ADXCRA D_BC0178 96_x_at | ARL17A /// ARL17B | AntiSense | ADP-ribosylation factor-like 17A [Source:HGNC Symbol;Acc:24096] /// ADP-ribosylation factor-like 17B [Source:HGNC Symbol;Acc:32387] | 85 | GGGAAACTCTGTCACTACTGAAAATACAAAAGTACAAAA AAAAAAAAAATTAGCTGGGCATGGTGGTGCAAGCCT ATACTCCCAGCTACTCAGGAGGCTGAATTTGGAGGATC CCTTGAGCCCAGGGGGGTTGAGGCTGCATTGAGGTATA ATTTTGCCACTGTATTTCAGCCTGGG |
| 86 | ADXCRA D_BP2959 13_s_at | CTSD | Sense | cathepsin D [Source:HGNC Symbol;Acc:2529] | 86 | GGCTCTGCCACCCTACCTGTTCAGTGTCCCGGCCCGT TGAGGATGAGGCCGCTAGAGGCCTGAGGATGAGCTGG AAGGAGTGAGAGGGGACAAAACCCACCTTGTTGGAGCC TGCAGGGTGGTGCTGGGACTGAGCCAGTCCCAG |
| 87 | ADXCRP D.2812.C1 _at | CCND2 | AntiSense | cyclin D2 [Source:HGNC Symbol;Acc:1583] | 87 | GGGCCTCGGGACTACAGAGGAAGAGTGGAAAGTTACAGA CTGTAAATAGAGTCGGGTAGGCTTGTGCCCTTCCTTATT TGTCCGGTTCTTTCATTTGCTGCTTCTGTTTAAGCTCAA GGGTCAGTCAGTACCATGAAATGAAATTGCACCTCGGTTTCT CTTTAGGCTCCA |
| 88 | ADXCRA D_NM_01 4630_s_at | ZNF592 | Sense | zinc finger protein 592 [Source:HGNC Symbol;Acc:28986] | 88 | GAGAGCTCTGCCTAGTCTGTTGGCGAGGGCCCTGA TCACCTTGCCCCTCCTCCCTGTCTCTCTGATTCTTTTC CCTCAAAATAGTCCTGAGAACTAATTGTCACAGACATTG GAATATTTGTACTGCTCTCGTGCCATTTGAGAGGCTGCT GCCCAGGCAGGCCAGCCCTACTCCTCTTGGCTACAC TCATGTTGCTCAGATATATTCA |

FIG. 7-23

| 89 | ADXCRP DRC.3108 .C1_s_at | APOE | Sense | apolipoprotein E [Source:HGNC Symbol;Acc:613] | 89 | CTGGGAACTGGGCACTGGGTCGCTTTTGGGATTACCTGC GCTGGGTGCAGACACTGTCTGAGCAGGTGCAGGAGGA GCTGCTCAGCTCCCAGGTCACCCAGGAACTGAGGGCG CTGATGGACAGAGACCATGAAGGAGTTGAAGGCCTACAA ATCGGAACTGGAGGAACAACTGACCCCGGTGGCGGAG GAGACGCGGGCACGGCTGTCCAAG |
|---|---|---|---|---|---|---|
| 90 | ADXCRA G_BC062 632_s_at | LRRC37B2 /// AC005562.3 (Clone_based_ vega_gene) | AntiSense | leucine rich repeat containing 37, member B2 [Source:HGNC Symbol;Acc:25390] /// Known pseudogene. | 90 | GATGAAGAGGGCTGATTGTATCTAACTTAGGTCTTGCA TGCAGCTGGCACTTAATGCATTTTATTGACTGTTTTAGC TAACATTCAATGGACA |
| 91 | ADXCRA G_BC016 467_s_at | FKBP10 | Sense | FK506 binding protein 10, 65 kDa [Source:HGNC Symbol;Acc:18169] | 91 | GCCAGACTGGGCTGTAGTTAGCTTTCATCCCTAAAGAA GGCTTTCCCTAAGGAACCATAGAAGAGAGGAAGAAAAC AAAGGGCATGTGTGAGGAAGCTGCTTGGGTGGGTGTT AGGGCTATGAAATCTTGGATTTGGGGCTGAGGGCTGGG AGGGAGGGCAGAGCTCTGCACACTCAAAGGCTAAACTG GTGTCA |
| 92 | ADXCRP D.10820.C 1_at | NOL8 | Sense | nucleolar protein 8 [Source:HGNC Symbol;Acc:23387] | 92 | AAGCTGAGAAACTACCTGAGGTGTCTAAAGAAATGTATT |

FIG.7-24

| | | | | |
|---|---|---|---|---|
| 93 | ADXCRAD_AI862559_x_at | ANGPTL6 | Sense | angiopoietin-like 6 [Source:HGNC Symbol;Acc:23140] | 93 | GGAATTAAGGCTATTACTCTGAAGAAAGTTGGGGGCCAGGGCTCCTATTTTTTGCTGAGGAGATGGAAGATCAGGGCTTGTATTCAATAAGAATGGGAGGGCCAGGGATGCCTGGCAAAGCCTTGCACTGTGAGGTGCAGGTAGAGGCTTTTATTCTGGTGAGAGGACATGACTCTCTCTCCCCTCAGGTAACTGTGCCCTGTA |
| 94 | ADXCRPD.3248.C1_at | SLCO4A1 | Sense | solute carrier organic anion transporter family, member 4A1 [Source:HGNC Symbol;Acc:10953] | 94 | ACTCCGCAGGGGCTGTGAATCCCACTGGGAGGGCGGCGGGCCTGCAGCCCGAGGAAGGCTTGTGTGTCCTCAGTTAAAACTGTGCATATCGAAATATATTTTGT |
| 95 | ADXCRSS.Hs#S3002165_at | SAMD4B | AntiSense | sterile alpha motif domain containing 4B [Source:HGNC Symbol;Acc:25492] | 95 | GGAGTTCTACGGGATCTGAGAGAAAACCATGAGGAAAGTTTTCAGGATCCTTAAACAATTTTTGGAGCGTGTGATGTGGGGACTGGAAAAGATGTGGAGTATGTAAAGGGATTTTGGAAGAAGCTTTTGGAATATGATGCTGAGAGTCCTCTGGAGATTTCAGGCAATTGCTGGAGATTTTAGAATGAGTGGGGTGGGGAAGGGGATCCCGGTGAAGATCACTGGGCTACATGAGGGTGATCTCTA |
| 96 | ADXCRAD_CN408490_x_at | CHAF1A | Sense | chromatin assembly factor 1, subunit A (p150) [Source:HGNC Symbol;Acc:1910] | 96 | GGAGCGGCGCAAGGAGAGACAGGAAGCCCTGGAGGCTAAACTTGAGGAAAAAGGAAAAGGAAGAAGAGAAACGGTTAAGAGAAGAGAGAGCGCATTAAAGCAGAGAAGGCCGAAATCACGAGGTTCTTCCAGAAACCAAAGACTCCACAGG |

FIG. 7-25

| | | | | |
|---|---|---|---|---|
| 97 | ADXCRAD_CX867137_s_at | Sense | TMEM97 | transmembrane protein 97 [Source:HGNC Symbol;Acc:28106] | 97 | TTAATTTTCATGTTGCGGAGCCCCTACTACAAGTATGAAGAGAAAAGAAAAATGAAGGAAACAACCACTGGCCCAGGGTAGAGATGCCTACAGGGTGGTTGCTTGTTGGATACAATACAAGGAAACACTGCTCAGAACCCACGTCTTCAGCAGCATTTGAAACACTGGCAGCAATGCACAAGAGCAAGATGGTGTCAGGAACCATGTCAAACCCTC |
| 98 | ADXCRAD_CX784758_s_at | Sense | PTK2 | PTK2 protein tyrosine kinase 2 [Source:HGNC Symbol;Acc:9611] | 98 | TAAGCTTTTAAGCATCATGAGAAGAACAATTTATGTTCACATTAAGATACGTTCTAAAGGGGATGGCCAAGGGGTGACATCTTAATTCCTAAACTACCTTAGTCGCATAGTGGAAGAGGA |
| 99 | ADXCRPD.6429.C1_s_at | Sense | SULT2B1 | sulfotransferase family, cytosolic, 2B, member 1 [Source:HGNC Symbol;Acc:11459] | 99 | GCCTGGAGCGTGAGCCCAGACCCAACTCCAGCCCCAGCCCCAGCCCCGGCCCAGGCCTCTGAGACCCCGCACCCACGACCCCTCATAATAAACACGTGATTCTG |
| 100 | ADXCRAD_CX872171_x_at | Sense | C12orf47 | N/A | 100 | TATGTGCCAAATCTACTAGACATTGGAGAAACAGTAGGAACAACACATGGTACCGGCACATGGATCTTTCAGGAAAACGAAGTAGGTAATAAACAGGAAAAAGCCCGAGTCTGATGCTAAGA |
| 101 | ADXCRAD_NM_022064_s_at | Sense | RNF123 | ring finger protein 123 [Source:HGNC Symbol;Acc:21148] | 101 | CTGCCTGTATCCTCATTGGTGGGAGCCCAGCCATGGCCCTAATTGTGCCTGAGCTTGACTTTCAGTCAGGGCCACAGTGAGCATTAAATTATT |
| 102 | ADXCRIH.3995.C1_s_at | Sense | TRIM5 | tripartite motif-containing 5 [Source:HGNC Symbol;Acc:16276] | 102 | GGAGTTAAATGTAGTGCTTTCCAGGATAGTTCCTTCCATACTCCTTCTGTTCCTTTCATTGTGCCCCTCT |

FIG.7-26

| 103 | ADXCRA G_U91543 _s_at | CHD3 | Sense | chromodomain helicase DNA binding protein 3 [Source:HGNC Symbol;Acc:1918] | 103 | CAGCCGTTTCCCTGCAGAATCAGCTCTGTCTCATGTGG AAGTGGAGAATCAGCCTTGCCTGGCCTTTAGGAACTTTT GTGGGGAAGAGAGCTTTGAAGAGAGGAGGGGACTTT AGAGAGGGATGAAAATGAGCCCTGGGAGGAGGAAGG GACGAGGAGGGGTGGCTGCATGTTACCGTTCCCCTACCT CTCCCCACGTGGAGGGTGGGAGCAGTTATGAGGGAGGA AGTCAACTGCTG |
|---|---|---|---|---|---|---|
| 104 | ADXCRP D.4213.C1 _x_at | APOL6 | Sense | apolipoprotein L, 6 [Source:HGNC Symbol;Acc:14870] | 104 | CAGGCATTCCTTTCTATCGATAATTACTCTTTCAACCAAT TGCCAATCAGAAAATTGTTATATCTACTATAATCTAGAA GCCCCCACATCAAGTTGTTTTGCCTTTCTGGACAGGAC CAATGTATATCTTAAATGTATTTGATTGATCTCTCATGTC TCCCTAAAATGTATAAAACCACGCTGTTCCCGACCACC TGGAGCACATGTGTTCTCAGGTGTCTCCTGAGGGCTGTGTC ACAGGCCATGTTCACTTACATTTGGCTCAGAATA |
| 105 | ADXCRA D_BE2959 38_x_at | RBBP4 | Sense | retinoblastoma binding protein 4 [Source:HGNC Symbol;Acc:9887] | 105 | GGGTCAGAAAGATGCCTTCAGTTTTGGTCAGTGTCTAAA AGTTAAGTCTGTTTAGGCCAAGCATGGTGGCTCACGCC TGAAATCCCAGCACTTGGGGAGGCCGAGGCAAGTGGA TCACAGGTCAGGAGATGAGACCATCTTAGCCAACATG GTGAAACCCCGTCTCTACTAAAATACAAAAAATTAGCC AGGCGTGGGGTGCGTGCCTATAATCCCAGCTACTTGG GAGGCTGAGGCAGGGGAATCGCTTGAACNCGGGAGGC AGAGGTCACGCCATGGACTCCAGCC |

FIG.7-27

| | | | | |
|---|---|---|---|---|
| 106 | ADXCRAD_NM_021651_at | EIF3K | Sense | eukaryotic translation initiation factor 3, subunit K [Source:HGNC Symbol;Acc:24656] | 106 | CGCACCATTGCACTAGTGATAAGATCGAAACTCCAT |
| 107 | ADXCRAG_AJ420536_at | TPBG | Sense | trophoblast glycoprotein [Source:HGNC Symbol;Acc:12004] | 107 | TTTGAAATCACCATGTCTGATAAAAACATGCAATTGCTTTGGTGAATTGTTTGTTTATTGTTGTTGCTTTGAGTGAATGCTTCAGTTTGCTCTAGATTTTCACTTTGTTTGTTAAAAATTACCATGTTTTAACCCCGAAAACATTTAATGTTTTGAAATGATTTTTTCATAACAATCTTATGAGTCTATTATATAATAGGAAGTATTTTGGAAATTTAATGGTGATATTTCTTTGGAAAA |
| 108 | ADXCRSS.Hs#S1918491_at | AXIN2 | AntiSense | axin 2 [Source:HGNC Symbol;Acc:904] | 108 | TGTGCACAGGAGACTCAGGACAGTGGGGGAAAGTCACTTCTCCACATAAGAGGCTCAAATCCCAACGCCACCCTCCGTCAGACCCCTTTGGCCCAGTCCGACCCCTCCAGGGTTACCAAGTTGGGCTTTCACAGCATGTCTGAGCAAACACGGCAGCGACCTTTTACATAATTGCAACCTCCTCCAGAGAGAGAGAGGCCACATTCTCTCGGCCC |
| 109 | ADXCRAD_BM702062_at | TSKU | Sense | tsukushi small leucine rich proteoglycan homolog (Xenopus laevis) [Source:HGNC Symbol;Acc:28850] | 109 | TAACGGAGTGTCACTTTCAACCGGCCTCCCCTACCCCTGCTGGCCGGGATGGAGACATGTCATTTGTAAAAGCAGAAAAAGGTTGCATTTGTTCACTTTGTAATATTGTCCTGNGCCTGTGTTGGGGTGTTGGGGAAGCTGGGCATCAGTGGCCACATGGGCATCAGGGGCTGGCCCCACAGAGACCCCACAGGGCAGTGAGCTCTGTCTTCCCCACCTGCCTAGCCCATCATCTATCTAACCGGTCCTTGATTTAATA |

FIG. 7-28

| 110 | ADXCRSS.Hs#S3730315_at | MUC6 | Sense | mucin 6, oligomeric mucus/gel-forming [Source:HGNC Symbol;Acc:7517] | 110 | CATGCACAGATGGCCACATTCTGCCTCCATCCACTCAAT GCCAACAGGCACGATTCCTCCACCGACAACGCTCAAGG CCACAGGGTCCACCCACACAGCGCCAACAATGACGCT GACCACCAGCGGGACCAGCCAAGCCTGAGCTCATTAA ACACAGCCAAAACCTCTACATCCTACATTCACACACTT CCTCCACACACCATGCTGAAGCCACCTCAACTTCTACC ACCAACATCACCCCCAAACCCACCAGTACAGGAACCCC ACCAATGACAG |
|---|---|---|---|---|---|---|
| 111 | ADXCRAD_BM142126_s_at | SAMD4B | Sense | sterile alpha motif domain containing 4B [Source:HGNC Symbol;Acc:25492] | 111 | CCCCATTATGTCATGACCTCACTTAAGTGGAACACTATA TCATAACCCAGAGATTCGTCCCAGCCCAGAGTCCGAC AGACTGTCTGGTCCCTATTCCTAATGAGGG |
| 112 | ADXCRAD.9207.C1_s_at | MUC3A | AntiSense | mucin 3A, cell surface associated [Source:HGNC Symbol;Acc:13384] | 112 | CACATCTGGCCTGACGTTCTCGTTGCATCAAGCCATCAT CCACCGGGCGCCCCTGGACGCGGCGTNNNNNNNNNNNN NNNNNNNNNNNNNNNNNNNNNAATGCTGACCACT CAGTAGAGCAGGGCCAGCCAGCCAGAGGGGACGAAGTCA CCAATCCAGGCACCACCTTCCCACATGTCCCTGCAACT TCTCTCTTTCCAGTGTGCTGAAGAAGGAGGAGGTGCCACC CCTCCTCCAGATAAATGGCCCAGAAAACGATCCAAAA AAATACCCAGGGAGCGGATTCCTTATGTA |
| 113 | ADXCRAD_BM691081_s_at | ARRB2 | Sense | arrestin, beta 2 [Source:HGNC Symbol;Acc:712] | 113 | GATGATCAACTCTGCTAGGAAGCGGGTGGGAAGAAG GGAGGGGATGGGGTTGGGAGAGGTGANGGCANGATTA AGATCCCACTGTCAATGGGGATTGTCTCAGCCCCTC TTCCCTTCCCCTCCACCTGGAAGCTTCTTCAACCAATCCC TTCACA |

FIG.7-29

| | | | | |
|---|---|---|---|---|
| 114 | ADXCRSS.Hs#S1923930_s_at | IGLL5 | Sense | immunoglobulin lambda-like polypeptide 5 [Source:HGNC Symbol;Acc:38476] | 114 | GCAGTCTCAGAGACACCAAGGAGGGAGAGTGACTAGAAA GAAAACCTTCTTGCAGAGACATAGGGATGGGGAAGAA CTGCAGACTGAACTGGGGCAAAGGACTGTAGGACTTAA CCAGAGAGATTTGAGGGAGGAGATGAGGCTGAGAGCCA GGGGATCCTGCCATGTCCCAGCATAAAAACAGTACCTG ACACAGATAGGTGCTTGGGAAGCTGTTGTCGGATGAAT GAGTGGACA |
| 115 | ADXCRAG_AF395751_s_at | DCLRE1C | Sense | DNA cross-link repair 1C (PSO2 homolog, S. cerevisiae) [Source:HGNC Symbol;Acc:17642] | 115 | AAGCTGCAACTGGTGAGAGTATAGCAGTCAAAAAAAG AAAATGCTCACTCTTAGATACCTAAGAATTCAAAGCGTT TCAACCTAGAGCAACCACTAAAAAACCTGCACAGAGAT GACAGTCAATATTACAATAGAG |
| 116 | ADXCRAG_AF004231_s_at | LILRB2 | Sense | leukocyte immunoglobulin-like receptor, subfamily B (with TM and ITIM domains), member 2 [Source:HGNC Symbol;Acc:6606] | 116 | AGCCCAGCAGATCCTACACACATTTTCACAAACTAACCC CAGAACAGGCTGCAAACCTATACCAA |
| 117 | ADXCRPDRC.14528.C1_s_at | GALNT4 | Sense | UDP-N-acetyl-alpha-D-galactosamine:polypeptide N-acetylgalactosaminyltransferase 4 (GalNAc-T4) [Source:HGNC Symbol;Acc:4126] | 117 | TCACTTTCCTGGATTGTCACTGTGAGTGTAATTCCGGTT GGCTGGAACCGCTTTTGGAAAGGATTGGGAGAGATGAA ACAGCAGTTGTGTGTCCTGTTATAGACACAATTGATTGG AATACTTTTGAATTCTATATGCAGATAGGGGAGCCCATG ATTGGTGGGTTTGACTGGCGTTTAGCATTTCAGTGGCAT TCTGTCCCCAAAACAGGAAAGGGACAGGCGGATATCAAG AATTGACCCCATCAGATCACCTACCATGGCTGGAGGA |

FIG. 7-30

| 118 | ADXCRP D.16974.C 1_s_at | WWC2 | Sense | WW and C2 domain containing 2 [Source:HGNC Symbol;Acc:24148] | 118 | TAGTGTTTTGCCCTAAATCTAAGGATGGTGGCCTAGTGGT GGCCCTGTGTTCTGAGGACAGAGAGAGCTGGAGGGGT GGAGGGGAATGCATCGGCACTCATTGTGTAACCAAG AAGAGGGGAAAGATGTCTTGATAGAATCAAAGTTGCC AAAACAAGAAGAGAGTCTATCAAGCAGATTTCTAACATT TAGCTAGAAAACTACTTCATAGCTCTCATTTTTAG |
|---|---|---|---|---|---|---|
| 119 | ADXCRA D_AK0927 50_s_at | EHBP1L1 | Sense | EH domain binding protein 1-like 1 [Source:HGNC Symbol;Acc:30682] | 119 | CACTACCGCGCCCCGCGCTGGCTTGCCCTCCTGTTCTCCA GAGCAATAAAGTTGGACGAGACT |
| 120 | ADXCRA D_CF2721 04_at | HIST1H2AJ | Sense | histone cluster 1, H2aj [Source:HGNC Symbol;Acc:4727] | 120 | GAGAGCCACCACAAGACTAAGTAAAGACCGAGTTGA |
| 121 | ADXCRP D.1493.C1 _at | TNPO1 | Sense | transportin 1 [Source:HGNC Symbol;Acc:6401] | 121 | GAATAAATGGGGTTGGGCATATCAAACTAAAGATG |
| 122 | ADXCRA D_BX1071 09_s_at | IGKJ3 /// IGKJ4 | Sense | immunoglobulin kappa joining 3 [Source:HGNC Symbol;Acc:5721] /// immunoglobulin kappa joining 4 [Source:HGNC Symbol;Acc:5722] | 122 | TTCTCTGCATCGGTCAGGTTAGTGATATTAACAGCGAAA AGAGATTTTGTTAGGGGAAAGTAATTAAGTTAACACT GTGGATCACCTTCGGCCAAGGACACGACTGGAGATTA AACGTAAGTAATTTTCACTATTGTCTTCTGAAATTTGGG TCTGATGGCCAGTATTGACTTTTAGAGGCTTAAATAGGA GTTTGGTAAAGATTGGTAAATGAGGGCATTTAAGATTTG CCATGGGTTGCAAAAGTTAAACTCAG |

FIG.7-31

| 123 | ADXCRA D_AA7747 60_at | EIF4G3 | Sense | eukaryotic translation initiation factor 4 gamma, 3 [Source:HGNC Symbol;Acc:3298] | 123 | CAAATATACAAAATGCCTCCAAGCTCAAATAGCTATAAC TGTACCAAAGACATGGAAGAAACCAAAAGATCGGACCC GAACCACTGAAGAGATGTTAGAGGCAGAATTGGAGCTT AAAGCTGAAGAGGAGCTTTCATTGACAAGTACTTGAA TCTGAACAAGATAAAATGAGCCAGGGTTTCATCCTGAA AGAGACCCCTCTGACCTAAAAAAAGTGAAAGCTGTGGA AGAAAATGGAAGAAGCTGAGCCAGTACGTAATGGTG CTGAGAGTGTTTCTGA |
|---|---|---|---|---|---|---|
| 124 | ADXCRA G_BC010 540_at | C11orf2 | Sense | Protein fat-free homolog (Another new gene 2 protein) [Source:UniProtKB/Swi ss-Prot;Acc:Q9UID3] | 124 | CCGCAGGCAGGTGTCAGGACCGGCCTAATAAACATGTG T |
| 125 | ADXCRSS Hs#S809 218_at | N/A | No Transcript match | N/A | 125 | AAATGTGACTGCTTTGTAAAACTCCAGAGTCAAGGACTC ATAGGCAGGAGGATGTCATAAATTAACAGGAAAGGATG AGAAATCTCCACTCCACTCCCTCCTCCCTCCCTTGATCA CTCATTCCCTCTCTTCCATTCATTAACCACCCACTACAT GCCATGCCCTAAGGAAGCAGCTATCTAAGAAGTCCCTG CCTGCAGGGGCTTTACAGACCAGGAGGAGGAAGGCAACCC ATAGAGCCAGGATCCTGATAACCACTGCTGACTGCC |
| 126 | ADXCRA D_AL0394 47_x_at | KIF24 | Sense | kinesin family member 24 [Source:HGNC Symbol;Acc:19916] | 126 | AAACCCTGGAAGAATCTTTCACTTGAACTCAACTTGACT GGNGTTCAGTCAACCANTCTCAGGGAAGGGGAAG CACTATCTCCACANCANCACTNANTCTGGGCCTCCCGC CCCATCTCCCCCAGCCCCTCTCAGCAACAACTAGGCAGGC TTCAGCT |

FIG.7-32

| 127 | ADXCRP D.8954.C1 _at | Sense | CDK11A /// CDC2L1 | cyclin-dependent kinase 11A [Source:HGNC Symbol;Acc:1729] | 127 | GCAGGGCTGCCGGAGCGTCGAGGAGTTCCAGTGCCTG AACAGGATCGAGGAGGGCACCTATGGAGTGGTCTACAG AGCAAAAGACAAGAGAAAACAGATGAAATTGTGGCTCTAAA GCGGCTGAAGATGGAGAAGGAGAAGGAGGGCTTCCCG ATCACGTCGCTGAGGGAGATCAACACCATCCTCAAGGC CCAGCATCCCAACATCGTCACCGTTAGAGAGATTGTGG TGGGCACACATTATGGAGGCGCAGTCGCCTACGCA |
| --- | --- | --- | --- | --- | --- | --- |
| 128 | ADXCRSS .Hs#S301 0175_at | Sense | CDS2 | CDP-diacylglycerol synthase (phosphatidate cytidylyltransferase) 2 [Source:HGNC Symbol;Acc:1801] | 128 | AGGAGTCAGGAGAACAAGTCAGGGATTAGGAGACAGC GGTTTGGTTTATTGTTATCCAG |
| 129 | ADXCRA D_AW297 731_at | AntiSense | PARP14 | poly (ADP-ribose) polymerase family, member 14 [Source:HGNC Symbol;Acc:29232] | 129 | AATAAATTCTCAATTTCTTAGTCTCTTAATTCTTAAATTTAA AAAGGTTGTTCTTACCTTTTAAAATTTTTAAAAATAATTA TGTCAAGTAATTTTTGAATATAGTAACCTGATTCTACATT TCTCATGGGATAAATTCTAAGGTAAAAAAATTGCAAATA AATCTTAAACTTTATTTAGTAGGTTTATTATTAGCAGCAG ATGTCTAGCCAGGTAGATTACTTTTATCAGAGAAGAGCTA CTCACCAACAACTACTAGAAGAGCTA |

FIG. 7-33

| 130 | ADXCRA D_AU1464 90_at | TAF15 | Sense | TAF15 RNA polymerase II, TATA box binding protein (TBP)-associated factor, 68kDa [Source:HGNC Symbol;Acc:11547] | 130 | CTGGGAAATCCAGTGTTTGTATGTAAAAATAAAAGGTAA GTTAATTCTAGATTGAGGGCAGAGGCTATTCTTAATC TCCAATCTCCTTGGGAAGGGAAGTATTAGGAGGCAGT AATGGAGTAGAAA |
|---|---|---|---|---|---|---|
| 131 | ADXCRSS .Hs#S298 1341_at | N/A | No Genome match | N/A | 131 | GGTACACTGGGCACGCAATGCGCGTGTTAGTAGCCAAA TAGTAAAAGGGCCGTATTTCAACAGCGACTCCAAGACA ACTGGCGTTGCCCATTCTCAGTCTCCGGCCTATCCTAC ACATCTAATACCCGGCTACAATATAAAGCTATAGTAAAG GTTCACGGGGTCTTTTCGTCCCGTTGCGGGTAATCGGC ATCTTCACGGATACTACAATTTCACGAGCTCGCGGTTG AGACAGTGCCCAGATGCTTACACCATTCGTGTATGGAC GGGCTCTG |
| 132 | ADXCRA G_NM_00 1988_at | EVPL | Sense | envoplakin [Source:HGNC Symbol;Acc:3503] | 132 | GGACAGCAGCACTCAGTTCTTCCTCCACCTCCACCCA GTGATCCCAATAAACGAATTCTGTCTCCCCGTG |
| 133 | ADXCRSS .Hs#S373 0315_x_at | MUC6 | Sense | mucin 6, oligomeric mucus/gel-forming [Source:HGNC Symbol;Acc:7517] | 133 | ACAGATGGCCACATTCTGCCTCCATCCACTCAATGCCA ACAGGCACGATTCCTCCACCGACAACGCTCAAGGCCAC AGGGTCCACCCACACAGGCCAACAATGACGCTGACCA CCAGCGGGACCAGCCAAGCCCTGAGCTCATTAAACACA GCCAAAACCTCTACATCCCTACATTCACACACTTCCTC ACACACCATGCTGAAGCACCTCAACTTCTACCACCAA CATCACCCCAAACCCACCAGTACAGAGAACCCCACCAA TGACAGTGACCA |

FIG. 7-34

| 134 | ADXCRA D_CN312 224_s_at | RPL32P3 | Sense | ribosomal protein L32 pseudogene 3 [Source:HGNC Symbol;Acc:27024] | 134 | TAGTACCTGCCTCATTCAGTCAACGTGAGGATCTAGAG CAGCATTTGCATAAATGACGCGTGGGGCACAGAGCAGA CTCAACACAGAGCAGCTTACGTTATGAGGCTTGGCAGG CTGGGAGCTCCTGTCGGCCTCTCTCCTCCAGCTCTGTGC CCACTGAGCTCGGCACAAGGGTTGGCCCATGACAGGT GTTTATTATGTGAAATAAATGAGAGGACAAGACATTT GCTGATTTC |
| 135 | ADXCRP DRC.1404 5.C1_s_at | AL031666.1 (Clone-based (Ensembl) /// ZMYND8 | Sense | Known long non-coding RNA /// zinc finger, MYND-type containing 8 [Source:HGNC Symbol;Acc:9397] | 135 | GCCTCATCAGGGAATTGTAAGATTTAGGGGAGGTGTG GGAAATCTTACTCTTTGCCCTAAAGTATTCAGCGATCAG AATTCTGGATACCCTGCAAAACACCTCCAACCTCCCTGC CTTTGAACCCTGTGTTAACAATGAGAAGCTTGTTTATTT GAAGGCTGGGTTCTC |
| 136 | ADXCRIH. 2111.C1_a t | SNHG12 | Sense | small nucleolar RNA, H/ACA box 44 [Source:HGNC Symbol;Acc:32637] | 136 | GGACAGATGAAGACTCTTAAGATGACAGAAGGTGATTTT TCTGGTGATCGAGGACTTCCGGGTAATGACAGTGATG AAATGCAGGGGACCTGGTTGCCCCAAGTTTCCTGGCA GTGTGTGATACTGAGGAGGTGAGCTTGTTTCTGGAGCT GTGCTTTAAGATTCATGTTACATGTAAAGCTGTCCTCATT TGTGACTATGACCTATGGAGTTGGGACAATCTCTATG GGAAGCAGAAGCAGGAACCCCGGTCATTTTAGGTAGA AACAACAGCATGCTAATGCAAAA |
| 137 | ADXCRIH. 3648.C2_a t | NCAPD2 | Sense | non-SMC condensin I complex, subunit D2 [Source:HGNC Symbol;Acc:24305] | 137 | AAGAGAGAAGCTTCTGCACGCACCAGAGGCACCCAGTCC CACAGGCGCCTACCTGCCCCGCCGGATAAGAGGTTCCCTG CCATTTCTCTAGTCTCCCCCCTTCAACAGCACACACAAAT AAGCCCAAGAAGATGACAGGAACCGTCCCGCCAACTT CACACGAGTGCTAAGGCGGAAGACAGCAGCCATCTTGGGCCT TCGGA |

FIG. 7-35

| 138 | ADXCRA G_BC015 816_s_at | MAST2 | Sense | microtubule associated serine/threonine kinase 2 [Source:HGNC Symbol;Acc:19035] | 138 | TGCCTGATGCCTCAGGTGACAGAAGGCAGGACGTTCCA TGCCGAGGCTGCCCCCTCACCAGAAGTCTGAGCCCA GCCTCAGGAGGGGCCAAGAACCAGGGGGCCATCAAAA GCATCGGGATTTGGCATTGGTTCCAGATGAGCTTTTAAA GCAAACATAGACAGTTGTTTGCCATTTCTTGCACTCAGAC CTGTGTAATATA |
| --- | --- | --- | --- | --- | --- | --- |
| 139 | ADXCRA D_BP2850 69_x_at | IFIT3 | Sense | interferon-induced protein with tetratricopeptide repeats 3 [Source:HGNC Symbol;Acc:5411] | 139 | GCCCCAACCTGGGATTGCTGAGCAGGAAGCTTTGCAT GTTGCTCTAAGGTACATTTTTAAAGAGTTGTTTTTTGGCC GGGCGCAG |
| 140 | ADXCRA G_AF2740 48_s_at | UHRF1 | Sense | ubiquitin-like with PHD and ring finger domains 1 [Source:HGNC Symbol;Acc:12556] | 140 | ACCAAAGTTTGCAGCCTATACCTCAATAAAACAGGATA TTTTAAATCACATACCTGCAGACAAACTGGAGCAATGTT ATTTTTAAAGGGTTTTTTCACCTCCTTATTCTTAGATTAT TAATGTATTAGGGAAGAATGAGACAATTTTGTGTAGGCT TTTTCTAAAGTCCAGTACTTGTCCAGATTTTAGATTCTC A |
| 141 | ADXCRA D_CN291 160_at | SRGAP1 | Sense | SLIT-ROBO Rho GTPase activating protein 1 [Source:HGNC Symbol;Acc:17382] | 141 | ATTGATTCCTGACCATAGCAGTGAGAGGCCATTTTTGT GCAGGAAATGTGCTTAGGACTCAGTCTTGTTTTCGATTA TCCACCACAGAAACCCTGAGACACAGAGCAGCTTAGAA GTCTCTACCCAGGCGTAAATAGAGCTCCCTACTCCAGA CCACCTGCCACCACCTCCCAAGTTGAGAACACAAGCT CCAGCTGGGCTGGAGAGTCAGGCTTGGTGCAGGGTGA CTTTGGGCGAAGTTTGTCAGATCCATAAAGCAAACTGGA ATTTGAGCTTTCACTTACCCTAGTATACG |

FIG. 7-36

| | | | | |
|---|---|---|---|---|
| 142 | ADXCRIH.1654.C3_s_at | Sense | CFTR | cystic fibrosis transmembrane conductance regulator (ATP-binding cassette sub-family C, member 7) [Source:HGNC Symbol;Acc:1884] | 142 | TTCTTTTCCACAGAGAGCTCCAGGTAGAGGGTGTGTAAGT AGATAGGCCATGGGCACTGTGGGTAGACACACATGAAG TCCAAGCATTTAGATGTATAGGTTGATGGTGGTA |
| 143 | ADXCRPD.10513.C1_s_at | Sense | NR3C2 | nuclear receptor subfamily 3, group C, member 2 [Source:HGNC Symbol;Acc:7979] | 143 | TGAGTTGTTTGTTCACCAGTGATGCTATGTTATGCATTT GTTTACATCTCATAACATGTGGTAAATATTTATGCAAGAT GGCTAGCCAGACNNNNNNNNNNNNNNNNNNNNNNNC ANCCGTGAAATAGAGAATGCAGGGTGACCCATGTAAAC AGGCTAGAAGATACATTTGAAAAGATGAGGGTTAAAGA GTGTGTACATGTTGGGCAGGTAAAGAGATAGCATCCTCTA GGGAGGATATTATCAGGAGTCAGAGTAATCTTGGTAAA |
| 144 | ADXCRIH.1055.C1_s_at | Sense | AC090937.2 (Clone_based_vega_gene) | Novel processed transcript. | 144 | AATCATTGATTGACTTGCTGTCTGTGAACTTGCAGGAACTGT TTCATAGTTTCATTACACAGAGTAAACTGTTTGCCATGC AAGGTTATTTTGCATCTGCATTTAAGTG |
| 145 | ADXCRPD.3033.C1_x_at | Sense | CTGF | connective tissue growth factor [Source:HGNC Symbol;Acc:2500] | 145 | GACATTAACTCATTAGACTGGAACTTGAACTGATTCACA TCTCATTTTCCGTAAAAATGATTTCAGTAGCACAAGTTA TTTAAATCTGTTTTTCTAACTGTGGGGAAAAGATTCCAC CCAATTCAAAACATTGTGCCATGTCAAACAAATAGTCTA TCAACCCCAGACACTGGTTTGAAGAAT |

FIG.7-37

| 146 | ADXCRA D_BI4946 81_at | C11orf35 | Sense | collagen, type XXVII, alpha 1 [Source:HGNC Symbol;Acc:22986] | 146 | GTATGTGAAAGTCTCTATTTGTGTATTTCTCTCCTAAAGT TGTGTCTCTTTGGGAATTGGATTTGATTTTATTATTTAA TACCTCACTTTGGCCCGTCCCCCTCCCAACACTTCTGT ATCCTCGCCCTGCCGCCCCAGCCTGGACGCTCTGCGT GGAAGTGCGTGTTTGTAGCAGCTCGGGCCTCATCTCAG CGCTCGGATCCCTCCTGCTGCCAGAATCCACTGGCCTC TGTCTCATTCTTGGG |
| 147 | ADXCRA G_NM_17 3542_s_at | PLBD2 | Sense | phospholipase B domain containing 2 [Source:HGNC Symbol;Acc:27283] | 147 | TCCCTCAGGAAGCAGTCCCCTGTCTCCCTTTCTGGGC AGCTTCCTTGAGGACAGAAACTTGAAAACAAACACAAAC CAAAGTTTCTGGCCATCTGTGGCTGGAGGGTTCTGAAT GTCCTCTCTCCATGTCAGGCAGCAGAGGGTCAGCCCCATG CTTCTGCCCTCAGGCCCCACCCCAGCCACCCCAGGCC TGCCCCTCACCTCAGGGCCCATACCCACCACAGCCCTGAT GGAGGAACCAGACCGCAGGCTGTGCCACCATTAAACAA GAGCGGCTGTG |
| 148 | ADXCRA D_AW020 871_at | SVIL | Sense | supervillin [Source:HGNC Symbol;Acc:11480] | 148 | AAGGAGGCAGATGAGATTTCATATCAAAAGA |
| 149 | ADXCRA G_AL1174 66_s_at | LIMK2 | Sense | LIM domain kinase 2 [Source:HGNC Symbol;Acc:6614] | 149 | TGACTTCTACCTCCCATGTTTGCTCTCCAACTCATTAG CTCCTGGGCAGCATCCTCCTGAGCCACATGTGCAGGTA CTGGAAAACCTCCATCTTGGCTCCCAGAGCTCTAGGAA CTCTTCATCACAACTAGATTTGCCTCTTCTTAAGTGTCTAT GAGCTTGCACCATATTTAA |

FIG.7-38

| 150 | ADXCRA D_CN309 527_s_at | HIST1H4J /// HIST1H4K | Sense | histone cluster 1, H4j [Source:HGNC Symbol;Acc:4785] /// histone cluster 1, H4k [Source:HGNC Symbol;Acc:4784] | 150 | CCACCGTAAAGTACTGCGCGACAATATCCAGGGCATC |
|---|---|---|---|---|---|---|
| 151 | ADXCRA D_W6818 0_at | EEF2K | AntiSense | eukaryotic elongation factor-2 kinase [Source:HGNC Symbol;Acc:24615] | 151 | GTGGAATAAGTTCTCCTAGCTCAGAAGGATCTCAACCTC TTGCAAGTTACTTTTCACTTTTAAGGGCCCTTAAAGAAG CATTTGCTTAGCTCTGTATCCAGGCAACTGACATTAAGGTCACA CGAAGAGCAACAGACCAGCAACTGACATTAAGGTCACA TGGGTGGGTGGGGAGTAGAATTGCGGGGTGACAGTT CCAGCCAATCCAGACACGAATCATGTTTGANGGACCCG AGCCTCAAGGGTGATTCC |
| 152 | ADXCRA D_BI7535 34_at | KIAA0467 | Sense | KIAA0467 [Source:HGNC Symbol;Acc:29040] | 152 | AGACATATGACAATGTTCAGCAGGTCATCTTTAATGCAG |
| 153 | ADXCRA G_NM_00 3376_at | VEGFA | Sense | vascular endothelial growth factor A [Source:HGNC Symbol;Acc:12680] | 153 | ACGAAAGCGCAAGAAATCCCGGTATAAGTCCTGGAGCG TTCCCTGTGGGCCTT |

FIG.7-39

| | | | | |
|---|---|---|---|---|
| 154 | ADXCRAD_BU5218 45_x_at | SMARCA4 | Sense | SWI/SNF related, matrix associated, actin dependent regulator of chromatin, subfamily a, member 4 [Source:HGNC Symbol;Acc:11100] | 154 | CCTCGTGGATCATCAAGGACGACGCGGAGGTGGAGCG GCTGACCTGTGAGGAGGAGGAGGAGAAGATGTTCGGC CGTGACCTCCCGCCACCGCAAGGAGGTGGACTACAGCG ACTCACTGACGGAGAAGCAGTGGCTCAAGGCCATCGAG GAGGGCACGCTGGAGGAGATCGAAGAGAGGTCCGGC AGAAGAGAAATCATCACGGAAGCGCAAGCGA |
| 155 | ADXCRSS.Hs#S301 7684_x_at | RP11-460N11.2 (Clone_based_vega_gene) | AntiSense | Known pseudogene. | 155 | TAGGGTTTCTCTCCACTATGAATGATCTGATGTATAGTA AGGTTCGAAGACCACTTAAAAATTTTGCCACAATCTTTG CATTTGTAGGGTTTGTCTCCAGTATGAACTATGTTATGTT GAGTAAGGCTGAGGAATAGTAAAAAGCTTTGCCACATT CTTCACATTATAGGGTTTCTCTCAAGTATGAATTCTTT ATGTTCTTTCAGTTTTGAGGATTTTCTAAAGGCTTTGCCA CATTCATCACATTTGTAGGGTTTCTCTCCCATATGAATAA |
| 156 | ADXCRAG_XM_29 0516_x_at | CDC42BPG | Sense | CDC42 binding protein kinase gamma (DMPK-like) [Source:HGNC Symbol;Acc:29829] | 156 | ACTGGAGGGTCTCCGGGCACACTCTGGCCCTTCCCAGA AAGGGGGTCGTTTTCTCGAATCTTCAACCAGTTGTGTA TTGGAAACTAGGGCGCCATTTTACTATTGATCACAGTCAT TATATTGTT |
| 157 | ADXCRPD.15527.C 1_at | SLC6A6 | Sense | solute carrier family 6 (neurotransmitter transporter, taurine), member 6 [Source:HGNC Symbol;Acc:11052] | 157 | TTCGGAAATAGGGAAGACTGTCTCTGAAGAAGGAGGAA GTGTAGCTTATGGGAGGCTGAGGAGTTTGGAGTTTCTC CTTGTGGGAAGGTGGGAGCCATGGAGGCTGAAGACAG TTGTCCAACTCAGGGCATACAAATTGATGAGGAACTCA |

FIG.7-40

| 158 | ADXCRIH.895.C1_s_at | LRRC59 | Sense | leucine rich repeat containing 59 [Source:HGNC Symbol;Acc:28817] | 158 | AGGACCTCAGAGATGTAAGCATTTTAGCAGCCACACAAA ATCTCTGGCTATGAAAGGGACTTCATGACCATCCAGTCC AATATAACACTTGCAGACAGAGAAACTGAGGTCTTCCAT GACTTGCCTAGTCTCCCAGCTAGTTGAGGCAAAACTG GATTCCCCACTCTGGTATTCTTCCTTTACATCATTT TCCCTCCTTTAAAATGTCCTGAGAGACCAGAACTCACA |
|---|---|---|---|---|---|---|
| 159 | ADXCRAD_AA709148_s_at | CHD2 | AntiSense | chromodomain helicase DNA binding protein 2 [Source:HGNC Symbol;Acc:1917] | 159 | ACTAAAGACATTAAGCATTTGCACTTAATTGGGTACTTC GGGAAAGAAGTGTGTAGGTTGGCATTAAAGGTACTTCTT ACACTGCATGTTCTGTAAGGACAGCAAAATACATCTATA TAGGTTCACTGTTAAATTCTCGAGGACTAATGGATCCGC ATGTGAAAAGTAA |
| 160 | ADXCRPD.15720.C1_x_at | CHID1 | Sense | chitinase domain containing 1 [Source:HGNC Symbol;Acc:28474] | 160 | TGAGCCCCGTGCCTGGCCTGGTCATTTCTCTTGCTGTG CCCAACCTGCCATTAATCCATCCATCCTGAGCCCGAC GTGGTCATTTCTCTCACCACCCAGCATACCGCCCAACG TGGTCCTTT |
| 161 | ADXCRAD_AA829635_at | ZNF75A | AntiSense | zinc finger protein 75a [Source:HGNC Symbol;Acc:13146] | 161 | TAAGTACTTAAGTCCTGCTCGTCTCTTGGCCAAGCCAGACTA GGCCCAACACCCTGCAATTCACCCTGGCTCCAAAGAGGG CAAAAGCAACTCTCTTTCTCTAAGGCCAGGGAAGTATCT ACCACAATCTCTGAAACCTGTGAACTTTTCTGTGGGCCT GTAGTTTCAAGTCCCACCTTAACTGTCCTTAAAAAAAAA CCAAACAATGACCATCTACCTAATCCATCCATTCTCAACTA ACTGCCACCATCTCTACTATATCCACCTGCATCCTATTT |
| 162 | ADXCRAG_BC007608_at | HMGB3 | Sense | high-mobility group box 3 [Source:HGNC Symbol;Acc:5004] | 162 | TAGGCTTAGCTTGATTTCTGGGCCCACTGTCTGTGTTCT TAAGATGCCAACCT |

FIG.7-41

| | | | | |
|---|---|---|---|---|
| 163 | ADXCRP DRC.1680 7.C1_s_at | LYPLA1 | Sense | lysophospholipase I [Source:HGNC Symbol;Acc:6737] | 163 | TATGATGCACAGTTCGTGTCAACAGGAAATGATGGATGT CAAGCAATTCATTGGTAAACTCCTACCTCCAATTGATTG ACGTCACTAAGAGAGCCCTTGTGTAGAAGTACACCAGCAT CATTGTAGTAGAGTGTAAACCTTTTCCCATGCCCAGTCT TCAAATTTCTAATG |
| 164 | ADXCRP D.5568.C1 _at | DDX27 | Sense | DEAD (Asp-Glu-Ala-Asp) box polypeptide 27 [Source:HGNC Symbol;Acc:15837] | 164 | CAGCTGGGCCCTGGCTGATGTCATGAGCCAACTCAAGA AGAAGAGGGCAGCCACTACATTAGATGAGAAGATTGAG AAAGTTCGAAAGAAAAGGAGAAAACAGAGGATAAAGAAGC CAAGTCTGGGAAGTTGGAAAAGGTAGAAAAGAAGCAAAG GAAGGCTCTGAACCAAAGGAGCAGGAAGACCTTCAAGA GAATGATGAGGAAGGCTCAGAAGATGAAGCCTCGGAGA CTGACTACTCATCAGCTGATGAGAACATCCTC |
| 165 | ADXCRP D.16185.C 1_at | ITGA6 | AntiSense | integrin, alpha 6 [Source:HGNC Symbol;Acc:6142] | 165 | AACCCACCACTCCAATTAGGCATTGCTCCCACTCCTCCCAT CAGTGCTCTCACAAGGTCACCAGTGCTTCTACATTGC CAATCTAGCAGGATCAAATCTCAGTAAGTGTCATTTGATAT AACTGATCTTTCACTTCCTCTTTGAAACCCCATCATGTG GTTCCAGGACCACACACTCCCTCCCTCCTCCTGCC ATGGGTGTCAGTCTCCAGGGCTCTCCCTAACCTCCATG TGTAAGAA |
| 166 | ADXCRSS .Hs#S192 7899_at | ITGA6 | AntiSense | integrin, alpha 6 [Source:HGNC Symbol;Acc:6142] | 166 | TGCCCATTCTCCAAAAAGCACGTGCCCAGCCCCCAATC CCCTCTATATCTCAGCTGAAGCATCACCTCCATTAATGA AGCCTAGTCCTTTCCTGCCTCGTGTGTTGCTTGTTGCT GCTCACACCCTTTAGACAAGACTTGCTGCCACTGACTCC CACCAGTCCCTGTTCCCTGGAAGAAATCAAGGAAGCCC ACCTTGATCTCATTTGAGCTCCTAATTTTACAGAAATAG GGACAAAGGTTCAAAGGGAGCCTCACAGGTCGCATGGT GAACCAAGC |

FIG. 7-42

| 167 | ADXCRPD.14605.C1_s_at | NPIPL3 | Sense | nuclear pore complex interacting protein-like 3 [Source:HGNC Symbol;Acc:28989] | 167 | AGCATCTGAAACTATATCCAGAATGACACTGGATTTTCATAAAAGTGTTGATCCTCACACCTCTTTATAGTCTTGCACCTAGCACAGTGGAGTGAAACACTTTAAATAGCACTGTTCCTTGAGTATATGGAAAAAGTGAAGTATTGATAAGTGCTCAGCTAATATGAGCAGCATCTCAGGAGTCTCCAATTCTTGAATTACCAGGGAGTA |
| 168 | ADXCRAD_CA440361_at | ROBO1 | Sense | roundabout, axon guidance receptor, homolog 1 (Drosophila) [Source:HGNC Symbol;Acc:10249] | 168 | GGAGTTGGAGCCCACTCTGGGAAAACATGTTGAGATCTTGCCTCTGCAAAATAAAGTAAAATAAAATTTAAAAAAGTAAAAAATAAAATCAGCTGAGCATGGTGACATGCACCTGTGGTACCAGCTACTTTGGAGGCTAAGTTGAGAGGCACTGATGGGAGGATCATTTGACGGCCCAGAGGTTGAGGC |
| 169 | ADXCRIH.1552.C1_s_at | ATP2C2 | Sense | ATPase, Ca++ transporting, type 2C, member 2 [Source:HGNC Symbol;Acc:29103] | 169 | GGCAGCTGGCGGTCATTTACATCCCCGCTGCAGAGGGTCTTCCAGACGGAGAACCTGGAGCGCTTGATTGCTGTTTTTAACTGGATTGGCCTCATCCGTCTCTCATTTGTCAGAGCTCCTCAAACTATGTGAAAAATACTGTTGCAGCCCCAAGAGAGTCCAGATGCACCCTGAAGATGTGTAGTGGACCGCACTCCGCGGCACCTTCCCTAATCATCTCGATCTGGTTGTGACTG |
| 170 | ADXCRAD_BM796805_s_at | SLC39A7 | Sense | solute carrier family 39 (zinc transporter), member 7 [Source:HGNC Symbol;Acc:4927] | 170 | ATAGTGTTGGGCACTGTCTGACCATGTTGCATTTGGAAGGCTAAATGGGGCCATGAAGAAGGCTGGAAGGACAGGTGGTGATGGCAGCCTACCTGGTGTCCCTACCCCACCTGTTCTCGGAGAACCAAGTTGCTACACAGGAAGTTCTCCAAGGTCCAGTTTCCTTTCTCCACCAGTTGGTGGAGGCTTCAGGGAAGACCAGAGTCCTGNACAGAGAGGTAACAGGAGGAGTCGGGGATAAACATCAAACATCAATCGTGTGTCCTGATTTTGGGAGTGAT |

FIG.7-43

| | | | | |
|---|---|---|---|---|
| 171 | ADXCRP D.11457.C 1_at | RNF43 | Sense | ring finger protein 43 [Source:HGNC Symbol;Acc:18505] | 171 | GGGCCTTCCGTGTGCTGGCAGAACAAAGAAATGAATGGAT GCATGGACAGATAGAGACTAATGCAGCTTGTTGAGA CAGGGGCTACAGCTTCACTGATGTAAGAACAACTCCAC CCTCATGCCCCAGCCTTTTCTTGGGGCAGGGCACAT GATAACCTTTCTCCCACACTAAACCTTGCTCACTACCAG ACTAGTAGGCCTTAAACTCTGGGAGCAAGAATGGAACT CCTTCCTATCTCAACA |
| 172 | ADXCRSS .Hs#S301 7684_at | RP11- 460N11.2 (Clone_based_ vega_gene) | AntiSense | Known pseudogene. | 172 | CTCCACTATGAATGATCTGATGTATAGTAAGGTTCGAAG ACCACTTAAAAATTTTGCCACAATCTTTGCATTTGTAGG GTTTGTCTCCAGTATGAACTATGTTATGTTGAGTAAGGC CTGAGGAATAGTAAAAAGCTTTGCC |
| 173 | ADXCRP D.14252.C 1_s_at | LMTK2 | AntiSense | lemur tyrosine kinase 2 [Source:HGNC Symbol;Acc:17880] | 173 | AACTAGTGGCTAGCATGGCTTGACCTGCCTCATTCCC CTCGAATAACTGAAGATCCTGTACAACATGGAGACTCT CGGAACACATTTATCCACAGTGCAATTACAGAAAGCAGTTC GTGATTTCTCTAGAAATAATAATATGGCTCACTGGTGA CCATTCCCCTCACGTGTCCTCTGTGGTGCCCACACGTG CGCCGGGATGTGCAGGCGTGGACGCGGAGAGAGCCCCT GTGGAAAGCACACATGCGGGTGCACAC |
| 174 | ADXCRP D.17881.C 1_s_at | C17orf88 | AntiSense | chromosome 17 open reading frame 88 [Source:HGNC Symbol;Acc: 17505] | 174 | TGGAGGTGCCACAAAAATCATCTGGTAAATTGTTTAAAG TAATCCCAAATGCAACTCAAATCTACAGAATCCCAGGTG AAGCTCAGTAATCTGTATTTT |

FIG.7-44

| | | | | | |
|---|---|---|---|---|---|
| 175 | ADXCRAD_BM931578_s_at | BCL9L | Sense | B-cell CLL/lymphoma 9-like [Source:HGNC Symbol;Acc:23688] | 175 | TGTCTCCTCGTGTCCGCATTGCTGGAGCTCCACCTCCC TCTTGGTTTCTCCGCACCCGCCATTTTCCTTCTGTCTT TACCTGCTTCGTATCCTTTCCCTGCTGATGTGGCTGACC CCTCTCCCACCCCTCCCTGCAGGCGGCTGGCCAGGTG GGCAGGTGCCAGCCGGAGCTGTAAATAGAGCGCTGCG CTTTTGTGCTGGTTTGTGCGTGTGCTGTATTTCTGTG |
| 176 | ADXCRAD_BE251606_s_at | ERF | Sense | Ets2 repressor factor [Source:HGNC Symbol;Acc:3444] | 176 | CCATGGGCCACAAATCTCTACAAGTGCCTGCTATCCCT CTC |
| 177 | ADXCRSS.Hs#S1913861_at | ACTN4 | AntiSense | actinin, alpha 4 [Source:HGNC Symbol;Acc:166] | 177 | GTATCTGCTCAAGTAGAAGCTTCCGTCTCTCTTGTAACA GGTCAGTGCTTCAGTTACCACTGCCATTGAATTACCCAC TCGCTATCACTTGCCTCTTATTCCATAAAAAAGAAAC GGAGGAAAAAACTGTTAAGTTTTACCTTGTTTAAAGTA ACACGAGTGCTTTTTGTTATTCTGTAAACTAAATACATAAA TGAAGGCAAAGGAAGGAAACTGAGGGAAGGAACAAAA TGTGAGTGATGAAAACACGGAGTTCATTAAATGAA |
| 178 | ADXCRPDRC.10450.C1_s_at | NCOR1 | Sense | nuclear receptor corepressor 1 [Source:HGNC Symbol;Acc:7672] | 178 | GCAGGTCAAAAACCTGCCCTCCTGTGACTTATTCCCTG AGACTTTTCAGGAGAGCCAGCCACAGATGATGAAGAA ATGATGGAAGTTCATTTGGAGAGTCAAATGGGNNNNNN NNNNNNNNNNNNNCTGCCTTTGATACAGGCAATTCAGTG GACTATATAATAGTGGAGGGTTGAGATGTAGAGTTTTT |

FIG.7-45

| | | | | |
|---|---|---|---|---|
| 179 | ADXCRPD.16001.C1_x_at | KCNK1 | AntiSense | potassium channel, subfamily K, member 1 [Source:HGNC Symbol;Acc:6272] | 179 | GTGCTATGGGAACCAGGTGCCAGGTGAGGCCAGGTGA AGACAGGTGAGGCCAGGTGAAGATAGGTGAGGCCAGG TGAAGACAGATGTTACGGAACCAGCAGGTAGAAAGCT AAGTGCTGTGGAGAAAGAGCGGGAAGAGAAATGGAGGAG GTGTCTGGGACAACAGAAGAACTTGAAAAGAACCTGCTTCT CAGTAGCCCCAAGTCCTCTGTGTG |
| 180 | ADXCRAD_BP395790_at | CMIP (Entrez) | Sense | C-Maf-inducing protein (c-Mip)(Truncated c-Maf-inducing protein)(Tc-Mip) [Source:UniProtKB/Swiss-Prot;Acc:Q8IY22] | 180 | TGAAGAGCCTTCTGGGTACCTAGAGGTGCTGGGAAGGA GTTTGGATTTAATCTTGGCTGTCCTGTGACAGGGATTCG GAGGCCATGGGGGAGGGTTGAGCAGGGAGACAGGAGA CAGGCAAGAGGCGCTGTGAGAAGCGTGGGCTGAGTGA CCTGCTCCTTGGTGAGTGAGAAGTCCTAGAACTGAGCA CCATGGCATGCACCTG |
| 181 | ADXCRPD.1872.C1_at | AL008582.1 (Clone_based_ensembl_gene) | Sense | Known long non-coding RNA | 181 | ATCCTTCCACAGTCTGCAAACCAGTTCCTTCTGCAGTGT TTTCCTCTGGGAGTGTCTTGGGCTAAGCCACAGCGGTG TCACCCCACCACACACTGCCCTGCAAAGGACTGCC AATACCCCCAGCCCATTCCCCAGCCTCACATATAAATAA GGACTTGCGACCCAGAATCACATCCAGAAGGGAAGTTT CACATGGCTTGGAATCCTTTAAAAAGGACAGCAAACCA AATNNNNNNNNNNNCCCTCCCTACCCACAACATCC AGCCTGATCCCGGGAATT |

FIG.7-46

| | | | | |
|---|---|---|---|---|
| 182 | ADXCRPD.6804.C1_s_at | SLC26A6 | Sense | solute carrier family 26, member 6 [Source:HGNC Symbol;Acc:14472] | 182 | CGACAGCCCTGTTTCGGTCACCAGACTCTGAACATGCTACATCCTGCCCAAGACTGCACCTCTGGAGGTGCAGGGCACCCTTGAGAGCCCCTCACCCTAGGCCGCCTCCAGGTGCTACCCAGGAGTCCCCTCCATGTACACACAACTCAGGAAGGAGGTCCTGGGACTCCAAGTTCAGCGCTCCAGGTCTGGGACAGGGCTGCATGCAGTCAGGCTGGCAGTGGCGCGGTACAGGGAGGAACTGGTGCATATTTAGCCTCAGGAATAAAGATTTGTCTGCTCAA |
| 183 | ADXCRSS.Hs#S1917662_at | GCC2 | Sense | GRIP and coiled-coil domain containing 2 [Source:HGNC Symbol;Acc:23218] | 183 | ATGAGTACTGAGACTGCGTTAAGCAACATAGAGGTCAGTGTCCATGACATGCTGGAACCAGAGCTTGATTGCAGTTGGTTCTAGAAAAAATGGGGAGGCAATGTTTGAGAGCATATATAGACAACTCTTTTCAAGGGATTTGCTATAGGGAGAGAAAAAGCGATGGGACAAAACTAGAGGGAC |
| 184 | ADXCRAD_BC017975_x_at | OSBP | Sense | oxysterol binding protein [Source:HGNC Symbol;Acc:8503] | 184 | GACCAGTTTAGGCAACATAGTGGAACCCTGTGTCTACAAAAAATAAAAAAATTTAGCTGGGCATTTGGCATATGCCTATAGTCCCAGCTACTTGGGAGGCTGAGGAGGAGGATCACTTGAGCCCAGGAGGTCAAGTTTGCAGTGAACTACGATTGCACCATTGCAT |
| 185 | ADXCRPD.13916.C1_s_at | DLG3 | Sense | discs, large homolog 3 (Drosophila) [Source:HGNC Symbol;Acc:2902] | 185 | GGGCACTCGCGATTTGGTCATTCTCTTGAGAGCTAGGAGGGGTCAGCCTGAGGCCGGAGAGGAAGGGCTTTTGCCTGGGGTGAGAGGGTGAGAGACTTGACCTGAAAGCAGCTCCTGCCCCTGAGGTGCAANCCAGAGTCCTGTGTGCGGACAGAGA |

FIG. 7-47

| | | | | |
|---|---|---|---|---|
| 186 | ADXCRIH.2384.C1_s_at | PHF3 | Sense | PHD finger protein 3 [Source:HGNC Symbol;Acc:8921] | 186 | AATTTTTACTATTGGTCATTTGCAGAACAGTAAATTCTGTGTGTTGGTACAGAGTGCTCTGTACCAGTGCTCATCATCCCTTCTTCATACCAACGGTCCCTAGTTATAG |
| 187 | ADXCRAD_BX3960 33_s_at | DNAJC16 | Sense | DnaJ (Hsp40) homolog, subfamily C, member 16 [Source:HGNC Symbol;Acc:29157] | 187 | TAGAGATGGGTTCTTCTGGTTGATACAGACTATGCATTGCGTCTAGCAGATGGGGTAAACTGGCCTAAACACAAGTCTTTGCAGAATACATGCCAATTTCCAAAAAA |
| 188 | ADXCRAD_BI8560 32_s_at | SMARCD1 | Sense | SWI/SNF related, matrix associated, actin dependent regulator of chromatin, subfamily d, member 1 [Source:HGNC Symbol;Acc:11106] | 188 | TCTCCCTGCCTCACAGGATTGTGACTCCCAGCCCCTGCCCTCAAAGCTTCAGACCCCTCAGGTAGCAGCAGGACCTTGTGATCTTGGCCCCCTTGGATCTGAGATGGTTTTGCATCTTTCCAGGAGAGCCTCACATTCTTCTTCCAGGTTGTATCACCCCCGAGTTAGCATATCCCAGGCTCGCAGAC |
| 189 | ADXCRAD_BQ016 677_x_at | POLR3A | Sense | polymerase (RNA) III (DNA directed) polypeptide A, 155kDa [Source:HGNC Symbol;Acc:30074] | 189 | GGTAGCCATTGGTTCTTGGATCTGTGTTAGAATGAGTGCTTTCCCTTCCTACTGATGTGATTGTGGATTAGGAATTCGTGACCGAGTGATTTTGGCCAGTGGTTGGGTTGGGTTTAAAATTCTATTAAAATTTGTAGTTTGGGGTGCT |
| 190 | ADXCRAD_BC0405 27_at | CEP120 | Sense | centrosomal protein 120kDa [Source:HGNC Symbol;Acc:26690] | 190 | GAAGGTTTGGACGATTATTTGACTCGCCTGATAGAAGAAAGGGATACTTTGATGAGAACGGGTGTGTATAATCACGAGGATCGAATAATAAGTGAACTCGACCGACAGATCAGAGAGATTTTGGCAAAAGCAATGCCAGTAATTAATAACATTTGGAAAAGCTTTATAGAGACTCTAAGTCTA |

FIG. 7-48

| | | | | |
|---|---|---|---|---|
| 191 | ADXCRAD_CF146855_x_at | VPS53 | Sense | vacuolar protein sorting 53 homolog (S. cerevisiae) [Source:HGNC Symbol;Acc:25608] | 191 | TTGCCAGGCACGGCGGCTCATGCCTGTAGTCGCAACAC TTTGGGAGACCAAGGCAGGAGGAGATCACTTGAGTCCAGG AGTTTGAGACCAGCCTGGCAACATACAGATGTCTACA AAAATAAAA |
| 192 | ADXCRPD.1793.C1_at | FAM60A | AntiSense | family with sequence similarity 60, member A [Source:HGNC Symbol;Acc:30702] | 192 | TCATACAACAAATCCCATCTCTGTCCCCTGAAATTCCCC TAGTTTCATTCATTAGAAGGGGATTNNNNNNNNNNNG ACTTAAAGAGCACTTTACAGCAGCATTCAGCTTTCCTAT GAAATACTCAGCATCTTAAATATTATATACAACTCTTTT TTAGTAAGCTAGACACTGGCTTCAGAGTTCGTGGGAGT GGGGAAATCAACCCATTCAAAACTACTCTAGAAATTGT CTTTTGGCAGAATAGCAGGTATCCAAGTTA |
| 193 | ADXCRAG_AL832008_at | FNIP1 | Sense | folliculin interacting protein 1 [Source:HGNC Symbol;Acc:29418] | 193 | AGTTCTAGGGGATATTTGTGCAATAAATACACATGTCAA CTTGAA |
| 194 | ADXCRPD.10387.C1_at | RBM47 | Sense | RNA binding motif protein 47 [Source:HGNC Symbol;Acc:30358] | 194 | AAAGCAGGTAGTTAGTTACCATTTGGAGAGGGATTCCG GAACCTAGAGAGAGATGAGGCTGAAGAGGCGGGAAGA AACCAGATGGCAAGGACTTTGTCTCATGCGCAAAGCAT ATAATTTATAGA |

FIG.7-49

| | | | | |
|---|---|---|---|---|
| 195 | ADXCRPD.10174.C1_at | PEA15 | Sense | phosphoprotein enriched in astrocytes 15 [Source:HGNC Symbol;Acc:8822] | 195 | AGAGGTAATATCCTTCCTATTCTTCCTTCACTTCTGCCCC TCCTCCCACCTCTTCCCCAGCCTCCCTCCCTCACCTGACCTATT TAGGGGTGATGGGATGAAAAGAAGAGAGTGAAGGATA TGTAATCAAGTGCAAAATACTGTGGTAAGTACAGAGAAT GAATAAGGTGGAAAGGAAAGTGAAAGTGTGGGATGGT TAGGGGCTTTAAGGACTTCCCAGGAAAATAGGATTCTGG |
| 196 | ADXCRAD_CF1267 72_s_at | TTYH3 | Sense | tweety homolog 3 (Drosophila) [Source:HGNC Symbol;Acc:22222] | 196 | GACCAGGGCCTCCTCTGTGGGATCTTTGTTTTGTGTTTA ACCATAATGGTTGTGTACTGAACCACTTCATATTTGTAT ATATAATATATATATATATATCTCCTTAAGACTCAGCCT CCTGGTTTACCCCCCGGCCTGNGCATCTGACCTCCCC CACCCCAGTGTGATTTAACATCCAGGAACTGAGGCCTG AA |
| 197 | ADXCRAD_CN272 025_at | PABPN1 | Sense | poly(A) binding protein, nuclear 1 [Source:HGNC Symbol;Acc:8565] | 197 | TAAGAGCTGTGGAGGACTGAAAACTGGATAAAAGGGG GTCCTTTCCTTGCCCCTGTCTCTCACTCAGATGCGCTT CTTTTTCGCCACTGTTTGGCAAAGTTTTCTGTTAAGCCC CCCTCCCCCTGCCCAGTTCTCCAGGTGCGTTACTATTT CTGGGATCATGGGGTCAGTTTTAGGACACTTGAACACTT CTTTTCCCCCTTCCCTTCACGTAACTGGGCAGGGG CCTACGGGGAGGGGCTTGTACTGAACTATCTAGTGATC ACGTTAACACCTAACTCTC |
| 198 | ADXCRIH RC.2093.C1_s_at | HSPD1 | Sense | heat shock 60kDa protein 1 (chaperonin) [Source:HGNC Symbol;Acc:5261] | 198 | GGACTGCAGCTAAGTGTCCACTCCCCAAAGTCTTCCTAT TCCTAACTCCATGACAGCTCCTCAGTAGAGCTTTCCTCC TCAGAAGCAACTAGAACAATGCAGTTAACATTATTTGGC CCCAACGGCGTTACTGTTGTATTTGGCTGAGATCTTTA GAAGCCCGAGGCCTAAACAATTAACTGAGGAACATCTAA |

FIG. 7-50

| 199 | RDCR243_E10_s_at | GOSR1 | Sense | golgi SNAP receptor complex member 1 [Source:HGNC Symbol;Acc:4430] | 199 | TTACTGAACTACAGCCTGGTTTGTAGACTTCCTGTTTCT ACACTGCTGCTCTTCACCATTGGAATTCACTGTGTATT TATATTACTGGCTTCAGTGCCGAGCCACAGTAATAAAAG GATATCATCTGTATTTCTCAACCATATCATGGTGTATAGA TGCTGTTATTCAGGCGAACTTGCTCATGGGGTGGACTAA CACCTGGTTTGGTACAGA |
|---|---|---|---|---|---|---|
| 200 | ADXCRAD_AL8330 17_x_at | MACROD1 | Sense | MACRO domain containing 1 [Source:HGNC Symbol;Acc:29598] | 200 | GAGCCATGATTGTGTTACTGCCTTCCAGCCTGGGCAAC AGAGTGAGACTCCATCTCAAAAAAAAAAAGAAAAGAA AGAAAATCAGACTCTGAGGCTGCAGGCGGTGGCTCACT CTTGTAATCCCAGCACTTTGAGAGGCTGAGGCAGGAAG ATTGCTTGAGCCCAGGAGTTTGAGACCAACTTGAGCAA CACAGTGGCACCCTATCTCTACCTAAAAAA |
| 201 | ADXCRAG_XM_04 0265_s_at | LARP4B | Sense | La ribonucleoprotein domain family, member 4B [Source:HGNC Symbol;Acc:28987] | 201 | GGAGCCGGCCACGGAATTGCGAAAGCCCAGCTACGCAG AGATTTGTCAGAGAACGAGTAAAGAGCCTCCTTCTTCCC CATTGCAACCCCAAAAAGAACAAAAGCCAAACACTGTTG GTTGTGGGAAGGAGGAAAAGAAGCTGGCAGAGCCCGC AGAGAGATACCGGGAGCCCCAGACCAGAGGGCGGGGG CCTGGAGCCCCAGAGACCAGAGGGCGGGGG GGCCGGCCCCTCGCCCTCGGCCATGGGGAAGCGTCTCA GCCGAGAGCAGAGCAC |

FIG. 7-51

| | | | | |
|---|---|---|---|---|
| 202 | RDCR489_A06_x_at | C17orf88 /// LRRC37A /// LRRC37A2 | AntiSense | chromosome 17 open reading frame 88 [Source:HGNC Symbol;Acc:17505] /// leucine rich repeat containing 37A [Source:HGNC Symbol;Acc:29069] /// leucine rich repeat containing 37, member A2 [Source:HGNC Symbol;Acc:32404] | 202 | CGTGCTACCATCACAGCTGAATGCAATGAAAGGCGGTC CTCTGAGAGGAGCAGGGTGGAGATGCTAAGTGGAGG CCCCGTCCCATTGCTGATAGATCCTCATCTGGCATGCG CTCCACCCTCCCCATTCTCTGCTCCCACGTATCGTAGC CCCATCACAGAAGATGCGACATGGAAAAACGCACTGTG TCCACCCTA |
| 203 | ADXCRPD.15720.C5_1_s_at | CHID1 | Sense | chitinase domain containing 1 [Source:HGNC Symbol;Acc:28474] | 203 | GCTGTGCCCAACCTGCCATTAATCCCATCCATCCTGAG CCCGACGTGGTC |
| 204 | ADXCRPD.252.C5_s_at | WHSC1L1 | Sense | Wolf-Hirschhorn syndrome candidate 1-like 1 [Source:HGNC Symbol;Acc:12767] | 204 | TTTTAGCAACCAGCCAGAGAGGGCGTGGGTTCATGAAA AACGGGTACGAGAGTATAAAGGTCATAAACAGTATGAA GAATTACTGGCTGAGGCAACCAAACAAGCCAGCAATCA CTCTGAGAAACAAAAGATTCGGAAACCCCGACCTCAGA GAGAACGTGCTCAGTGGGATATTGGCATTGCCCATGCA GAGAAAGCATTGAAAATGACTCGAGAA |
| 205 | ADXCRAG_BC026694_s_at | TMEM184A | Sense | transmembrane protein 184A [Source:HGNC Symbol;Acc:28797] | 205 | CCTCGTGGGCACGTGGAGAAGGGCCCACGTGTCTCCA CACGCCAGCCACAGGGGAGCCCTGGCCAGGCGCCCA GCCAGGGGAGCGTGTGCCTGGGATGGGTCACAGAACC AGCGGGCACCTGTGAGGCTGGCCAGCACCGTGGGGCT GTGGGAATCGCTCTTATTTATATTTAAA |

FIG. 7-52

| | | | | |
|---|---|---|---|---|
| 206 | ADXCRP D.8832.C1 _at | AntiSense | GPT2 | glutamic pyruvate transaminase (alanine aminotransferase) 2 [Source:HGNC Symbol;Acc:18062] | 206 | TTCCAAGTGCGACCTCAAATGACAACTTTCTCAGGTGGT GCCTGGATAGGAAAGGCACGGAACAGAATCTGTAGAA AACCAAACCTATCATGATCAGCATTCCTACCGACGTTA ACCTCCTAGACTGACTGACCTTATTTTGAAAGCAA ATCAAGTGTATACAGTCTCTCTTTTTAAAAAACTGTAAAC GTTGTAAAGTTTTTAGGGGCTGTTTATAATCTGAAGATTT ATAAAAAATTACTGGACTTGTTAGGACTAT |
| 207 | ADXCRP D.10116.C 1_s_at | Sense | OXSR1 | oxidative-stress responsive 1 [Source:HGNC Symbol;Acc:8508] | 207 | TGAGATGATCAGACACCGGAGTTCAACGTCCCAGCAGT CTTGGTAAAAGGAGGGAGCCTACTGAGCCAGGAGGGA GAAAGAAGATTGACCAGCTTGCTAGAAAAATACTTAGC NNNNNNNNNNNNNNNNNNGTGGAGGGGGACGGAGA GGAACAAGGATGGGGAGGGAGGAATGAGGTATAGAAAA GAGATAGCATCTCTTTGGCACAAGACTAGTGGCT |
| 208 | ADXCRA D_BU1809 46_s_at | Sense | DOT1L | DOT1-like, histone H3 methyltransferase (S. cerevisiae) [Source:HGNC Symbol;Acc:24948] | 208 | CCCAGGATGCGTCAGTCGTCTGTTCAGTCGTCAGCAGCCC CCACCCCCCGCGCAGCTGCCCTCGCCATCGTGGTCAG ACCCCCTCCCAACACAACACGCTGCTGGTCTGTGTCA GCCTTTGTAACGTGGGAGGCTCTGCCGTGTCTTCCGGG TGAACTGTATTTGGATTGCGCGCATTGCCAGGTCCG |
| 209 | ADXCRP D.11636.C 1_at | AntiSense | RUNX1 | runt-related transcription factor 1 [Source:HGNC Symbol;Acc:10471] | 209 | ATAGGTAGCAAAGTAAGGCCCAGAAAGGTTAAGTAATT TTCCCAAAGTCACACAGCTTTGATATACAGCAAAACTCA TATCCCTGAGCTTTCTACTCACTGTTCTTCCGGTTATAT CCCTGAGGTCATAAATCTCCACCCGCAAACCAATAGC ACCAGTACAAGAAATCTGGACTGGAGATACTTTATCCAC ACCTACCACTGCCCAAAAAGTAAAATCTGACTCTGTGA TTCTAATGTACCAATGGTAC |

FIG.7-53

| | | | | | |
|---|---|---|---|---|---|
| 210 | ADXCRAD_AL5562 40_s_at | NMD3 | Sense | NMD3 homolog (S. cerevisiae) [Source:HGNC Symbol;Acc:24250] | 210 | ATTTTTATTGCAGTAGGAGGAGAAATATATTTAAAATATTTG TAGATTTATAGCAAATAGAGACTCGTTATTTAAAGGTTAA ATAACAATTGTTCTTTTGTGTTTTGCCAGTTTAGGGC AGTAGCTGCTTTTGTCATAAATATCTTCCTACCACATC |
| 211 | ADXCRAD_BX1129 07_s_at | TICAM2 /// TMED7 /// TMED7-TICAM2 | Sense | toll-like receptor adaptor molecule 2 [Source:HGNC Symbol;Acc:21354] /// transmembrane emp24 protein transport domain containing 7 [Source:HGNC Symbol;Acc:24253] /// TMED7-TICAM2 readthrough [Source:HGNC Symbol;Acc:33945] | 211 | CTTGAGTAAAGACATTTGCTTAATTTCTTTTCTTATTC CCCACTTGTATATCCCCTACCAGTACCGGGATCTGCAC ACATCTTTTTGCAGNTACCTCTTCATAGCCATGAACCAA AACGTTCTATGAGGAGC |
| 212 | ADXCRAD_BQ670 114_s_at | IGF2R | Sense | insulin-like growth factor 2 receptor [Source:HGNC Symbol;Acc:5467] | 212 | CCTTCCTGATTGTTTACAGTCATTGGAATAAGGCATGGC TCAGATCGGCCACAGGGCGGTACCTTGTGCCCAGGGTT TTGCCCCAAGTCCTCATTTAAAAGCATAAGGCCGGACG CATCTCAAAACAGAGGGCTGCATTCGAAGAAACCCTTG CTGCTTTAGTCCCGATAGGGTATTTGACCCCGATATATT TTAGCATTTTAATTCTCTCCCCCTATTTATTGACTTTGAC AATTACTCAGGTTTGA |

FIG. 7-54

| | | | | | |
|---|---|---|---|---|---|
| 213 | ADXCRA D_CN264 940_at | ID2 | Sense | inhibitor of DNA binding 2, dominant negative helix-loop-helix protein [Source:HGNC Symbol;Acc:5361] | 213 | TCCTGTCCTTGCAGGTAAGACCTGCTCCGGGGTCCCCG CCCCGCCGCCGCACACTCCCGCGGTCGTCTGGGCTGT CACTAGGAGATCCGTAGCCCAGACGGTGACTTTCGTAT GAGCTATTTAACTTTATTTCTTCAGAATCTGCTGTAGAT TGAGCTGTGCGTGAAATTGCTAGTAAGTTCTGACATGTT AATGCGTCTGTCTTTAAATCTGAATTGTTACCATAAACGT GTTTAATGGAACTTGCTGGTCTGTGTGGA |
| 214 | ADXCRSS .Hs#S122 8858_x_at | AC004968.2 (Clone_based_ ensembl_gene) | Sense | Known long non-coding RNA | 214 | ACCTCATCCCCGAATAATAACTAAGCACTAGAGTGATGC TGGGGATGCTGGGGCTTGGTTTAGGTGGCTGGGGAAG TTATCTTGGAGGTGAGACTCCAGTGGACTCTGCGGATG GGTAAGGTCTCAGAGAGAGGTTGGGGAAGTTATCTTGGAG GTGAGACTCCAGTGGACTCTGCGGATTGGTAAGGTCTC AGAGAGGTTGAGGTTAAGAAGAGAGCATTCCAGACCAT TCCAAAATCAGCACATAACACACATGGCTTGAAA |
| 215 | ADXCRP D.6228.C1 _at | PTP4A1 | AntiSense | protein tyrosine phosphatase type IVA, member 1 [Source:HGNC Symbol;Acc:9634] | 215 | GTTTCTACAGTTCACTTGTCTGCTGCATAGAGGTCGTGCTGT GCCTGGCAGTAATCTCCACTGCCCTTCAGAAACTCCAT AAATGTGTGACCAAGAACACCACAGAATTGAGGAATATG TTTACTCATTGAAGATTGTGGCCTAATCATACAGCCGGT CCCGAG |
| 216 | ADXCRA D_AW963 267_s_at | NFIX | Sense | nuclear factor I/X (CCAAT-binding transcription factor) [Source:HGNC Symbol;Acc:7788] | 216 | ATGCAAGTAGGCAGCCAGCCCGTCTGTTCCCTCTCCGC CCCGCCCCCGCCCCCGCCCCCGTCACTGCGCTTCTGTTAT ACCATCTTTGCCTGACTCTCTACGGCTTCTCCATTGAAT GGCTAATGTGTATGTGAAAT |

FIG. 7-55

| | | | | |
|---|---|---|---|---|
| 217 | ADXCRP D.17288.C 1_at | BIRC6 | Sense | baculoviral IAP repeat-containing 6 [Source:HGNC Symbol;Acc:13516] | 217 | TACACAAACTTTATTACAGGCACAAAATTATCAAAAATAC GGTATAAAATTACCTTAAGGCTATGTGTATATAAGGGATGT GTGTATGTGTATACACAAAATAAATTTTGTGTTTC CACTTGGATCCCCTCCCTAAGATAACTCATTGTGTACAT GCAAATATTAGAAAATGCNNNNNNNNNNNNNNNNNNNNNN NNNNNNNNNNNNNNNNNNNNNNNNNNNNNNNNNNNNNNNN NNNNNNNNNNNNCTATTTTATCCACCATTTTCATGCTG TATTAA |
| 218 | ADXCRP D.10737.C 1_s_at | ABR | Sense | active BCR-related gene [Source:HGNC Symbol;Acc:81] | 218 | AACTGCGATGATGCACCTGCTCCGTCCCGTCCCTGCCCGACCC CAACCTCATCACCTTCCTCTTCCTGCTGGAACACTTGAA AAGGGTTGCCGAGAAGGAGCCCATCAACAACAAATGTCAC TTCACAACCTGGCTACCGTGTTTGGACCCACGTAACTG AGACCCTCAGAAGTGGAGAGCAAAGCACACAACTCACCTC GGCTGCGGACATCTGGCCCCATGACGTCATGGGCCAG GTCCAGGTCCTCCT |
| 219 | ADXCRA G_BC015 928_s_at | ARRDC3 | Sense | arrestin domain containing 3 [Source:HGNC Symbol;Acc:29263] | 219 | GCTCATAACAAATATACCAGCATTCATGATAGCATTTCA GCATTTTCCAAGGTACCAAGTGTACTTATTTGTTGTTGT TGTTGTTGTTGTATTTTTAGAAGGAATTCAGCTCTGATGTT TTTAAAGAAAACCAGCATCTCTGATGTTGCAACATACGT GTAAAATGGGTGTTACATCTATCCTGCCATTTAACCCCA CAGTTAAT |
| 220 | ADXCRA G_AF1366 31_at | NRN1 | Sense | neuritin 1 [Source:HGNC Symbol;Acc:17972] | 220 | TATCCAACGGTATAGATCACAAGGGGGGATGTTAAAT GTTAATCTAAAATATAGCTAAAAAAGATTTTGACATAAA AGAGCCTTGATTTTAA |

FIG. 7-56

| 221 | ADXCRP D.8313.C1 _at | TSPAN1 | Sense | tetraspanin 1 [Source:HGNC Symbol;Acc:20657] | 221 | GACAAAGCTCTAGGATGATGGCTGAGGGGTAGAAGAAG GGGCAAGGAGACAGAGAGGTCTTGGAGATGACGCCCAT ATCTCTGGCATGACAACCCAGATGGCAGGGGGTGGG GCCTGGTTTGTGGGAAGGGGTGTCCCACTAGACAGATGT GTACCCAGTGGAGGTGCAGCTCAGATTGGAGCTGGCC ATGGGTATTTGAAAATCATGTGCGCACAGGTAGCCACT GAAGCCATGGGAGTGAAAGAGAACACTTGGAAAGTGAA CTCTGGGAAA |
|---|---|---|---|---|---|---|
| 222 | ADXCRP D.8891.C1 _at | RNF213 | Sense | ring finger protein 213 [Source:HGNC Symbol;Acc:14539] | 222 | TGGACCGTCCAAGAAGGAGTACATCAGAGGTTTTGGT AGATGCTGCTGTAGACCTCTCATATCCGATGAATGGGAAG CTGCTAATGCCATACCCAGACAGAGAAGAAGCAGGA TGCAGCCCCGCTTGAGGCCGCCAGCGTGCCTTCTGCA GACTGTGAGCAGAGCAA |
| 223 | ADXCRA D_BG709 217_s_at | FRYL | Sense | FRY-like [Source:HGNC Symbol;Acc:29127] | 223 | AGCTTTGCAGTTATAGGCTCTAACCTGGACATGTCAGAA GCCAACTACAAACTGATGAACTTAATCTGGAAATAAGA GAGTCTCTACGCATGGTGCAATCATACCAACTTCTAGCA CAGGCCAAACCAATGGGAAATATGGTGAGCACTGGATT CTGAGACACTTCAGGCTTTAGGAAAGAAACTAAACTG AAGATGATGAAGAATATTAACCAAGCACCTTTTAATGGA CCCTTGCTTCACTGATAACTTTCTGGCAGCATCTACTTT TTAGT |

FIG.7-57

| 224 | ADXCRP D.17672.C 1_at | BLCAP /// RP11-425M5.5 (Clone_based_vega_gene) | AntiSense | bladder cancer associated protein [Source:HGNC Symbol;Acc:1055] /// Putative processed transcript. | 224 | AGGTCTAGGAGAGATGCCTGAGCCTCCACTGACCTCTGTG CATGTGGCCCACCAGTGCCACTGGCCACTCTGTCCTTTTGGAAA CTGTCCTCTGGCTTTCTAGGAACCCCATGTTTTTGGTCT TCTCCTCTGCCCCCTCCTTCTCCAGTCTCCTCAGCAGGA CTCTATTCCTGTACCCATTCCTAAAATGTCACGAACTCG TTTCTGGCCTTGTCCTTCTTTGAGTGCATCTCTGGTTCT TCATCTATCCCTGTTGAGATGCTCACCCTTCTTTTGGTGA GCTCCCAACCGGTACAGGTA |
| 225 | ADXCRP D.14904.C 1_at | RBM19 | Sense | RNA binding motif protein 19 [Source:HGNC Symbol;Acc:29098] | 225 | AATTGTGCCTACCTCAGATAGACAGTGCCAGAATTAAGT GAGTCAAGCCAAGTAAAGCCCAGAGAAGA |
| 226 | ADXCRP D.12875.C 1_at | KANK1 | AntiSense | KN motif and ankyrin repeat domains 1 [Source:HGNC Symbol;Acc:19309] | 226 | TCTTCACAGAGACAATTCGATCAGTCCTTCAGGTCTTAA GTCACTTCTCAAGAATGCCGTACTTGCCTAGGCTAGATT AGATCCTACTGTTACATGCTCCCTTA |
| 227 | ADXCRIH. 157.C4_s_at | HMGB1 | Sense | high-mobility group box 1 [Source:HGNC Symbol;Acc:4983] | 227 | TTTTAGTAGGTACGTCATGACAACTACCATTTTTTAAGAT GTTGAGAATGGGAACAGTTTTTTAGGGTTTATTCTTGA CCACAGATCTTAAGAAAAT |
| 228 | ADXCRIH. 278.C1_s_at | MRPL23 | Sense | mitochondrial ribosomal protein L23 [Source:HGNC Symbol;Acc:10322] | 228 | GGCGGCGCGTCCCCAGCTGGTTCGGGCTGTGACGGGGTG GCCAGCAGGGAGCGCGCCCCAGGTGGGCAGCTGTGGCA GAGCAGCAGCCGCGGCGGCGGCCATCCCCAGCTG GTTCGGGGCCGTGACGGGCGGCCAGCAGGGACGCGC CCCAGGTGGGCAGCTGTGGCAGAGAGCAGTCCCGACACC TAAATAAAAGTCTTGCTGCAGGA |

FIG.7-58

| | | | | |
|---|---|---|---|---|
| 229 | ADXCRP D.14739.C 1_s_at | FANCD2 | Sense | Fanconi anemia, complementation group D2 [Source:HGNC Symbol;Acc:3585] | 229 | AGATAAATTGTTGCCTGCTTCTGTGTCTCTGCCAGCCTG TGATCATATTGGGTTAGAGTTAGAAATCCGCTGTTTGCC TTTCTTACTGGTAGGATCCTT |
| 230 | ADXCRIH. 481.CB1_ at | RP11-122C9.1 (Clone_based_ vega_gene) | AntiSense | Known pseudogene. | 230 | ATCCTCGCCATTCGAATTTCAGTTCTGTACATCTGCCTA TATTCCTTGTGATAGTGCTTTGCTTTTCATAGATAAGCT TCCTCCTTGCCTTTCGAAGCATCTTTTGGGCAAACTTCT TTCTCAGGCGCTTGATCTTCAGCTCTGCG |
| 231 | ADXCRP D.5372.C1 _at | MGEA5 | Sense | meningioma expressed antigen 5 (hyaluronidase) [Source:HGNC Symbol;Acc:7056] | 231 | AAACGAACTGTAAAAGACCATGCAAGAGGCAAAATAAAA CTTGAAGTGAATGCTTAA |
| 232 | ADXCRP D.14347.C 1_x_at | TYRO3 | Sense | TYRO3 protein tyrosine kinase [Source:HGNC Symbol;Acc:12446] | 232 | AGCACGCTACCAAATCTCAAAATATCCTAAGACTAACAC AAGGCAGCTGTGTCTGAGCCCAACCCTTCTAAACGGTG ACCTTTAGTGCCAACTTCCCCTCTAACTGGACAGCCTCT TCTGTCCCACAGTCTCCACGAGAGAAATCAGGCCTGAT GAGGGGGAATTCCTGGAACCTGACCCCAGCCTTGGT GGGGGAGCCCTCTGGAATGCATGGGCGGGTCCTAGC TGTTAGGGACATTTCCAAGCTGTTAGTTGCTGTTTAAAA TA |

FIG.7-59

| 233 | ADXCRA D_BX5094 55_s_at | DECR1 | Sense | 2,4-dienoyl CoA reductase 1, mitochondrial [Source:HGNC Symbol;Acc:2753] | 233 | CATCATGTTTTTGTGGGCAAATACAAGTTGTTATAATTAA AACCCCTAATTTGAATATTTTGTACCAAGAACCAAGG CAAATGTTTAATTTGTTATAAAACCTGTTTGTGAAGTGCT GTGTTAAATTGTGCTGCTGGCTAATAGGCCTCATTTCAA TTTAATAAATATTTATTGAGGACTGGCTTTATGTCTGGCC CTGTGC |
|---|---|---|---|---|---|---|
| 234 | ADXCRP D.15787.C 1_s_at | SAPS2 | Sense | SAPS domain family, member 2 [Source:HGNC Symbol;Acc:19253] | 234 | AGTATCTGATATGTGTGTGGAGGCAGCCATCTTTTCCTG AAAGTCCTTTTAGGAATCATTATTTCTGGTCCTCTGAAGT TGCCGCTACCACTCATAAATATCTATCCACACCCCTTA CAAGAAGAATAAGGAAGATCTTAAGACCTAGAAGGAA |
| 235 | ADXCRSS .Hs#S298 4711_at | SH3GLB1 | AntiSense | SH3-domain GRB2-like endophilin B1 [Source:HGNC Symbol;Acc:10833] | 235 | ACTTGACCTAGGCAGTGACCATTCTCTCCCACTTTCACA CATGTTCACTTGACTTCCAGGCCATACTCTTAGTTTCCA TTTTACCTCACTGCCTCACTCGTTATCATCTTCCTTGCCT CGTTCCTCCAACTCTCTATGCTAGAGTACTTCAGGGATCA GTCCTTGATCCTCCTCCTCTTTCTCTATACTTACTCCTTGA GGGTTTATCTAGTCTCACAGATTTAAATATCTTTGATATG CTGACAACTCTCTAATTATCTAATTCACCCTGCCC |
| 236 | ADXCRP D.9852.C1 _at | DNAJC10 | AntiSense | DnaJ (Hsp40) homolog, subfamily C, member 10 [Source:HGNC Symbol;Acc:24637] | 236 | AAAATTTCTCTTTGCTCTTTCGTAGAAATAAAACTTAACA GTTGGATAGGCCCTGATCCCAGCTTTCTGGCATGTCTG AGCATAAGCCTGACAGTCTACTTTTCCAGCTTTCACTTT TCCTTTAATCATCCTAGCCAAGAGCTCAAATTCTGGAGC AAAATTCTGGCAAGGTCCACACCAAGGAGCATAGAAAT CAATCACCCAATGATTTTTCCCTTGTAGAACTTTTCACT GAAAGTCTGAGGTGTTAGATCTGTGGATACTTGATCCC GGGAA |

FIG.7-60

| 237 | ADXCRP D.7174.C1 _at | LRRC37B | AntiSense | leucine rich repeat containing 37B [Source:HGNC Symbol;Acc:29070] | 237 | GGCACAACATTTTGAGGACAATTAAAATTTATATCTAC ATAGTCTTCACCCAACTCTTCCATTTCTAGATATCTATG CTACAGGAATACTTGCCCACTAAGCNNNNNNNNNNNNN NNNNNNNNNNNNNNNNNNNNNNNNNNNNNNNNNNNNNN NNNNNNNNNNNNNNNNNNNNNNNNNNNNNNNNNNNNTGG GGTGACCCTCTAAGTCCTAGGAAGGAAGAAATTATGA AGTGAAAGAATATCATATAAGTGATACCATGAAGTGAAA GAA |
| --- | --- | --- | --- | --- | --- | --- |
| 238 | ADXCRP D.2593.C1 _x_at | MAVS | AntiSense | mitochondrial antiviral signaling protein [Source:HGNC Symbol;Acc:29233] | 238 | GGAGTAGCCAAGACTCCTGTTTCTCTGCATTTTTCNNNN NNNNNNNNNNNNNNNNNNNNNNNNNNNNNNNNNNNNNN NNNNNNNNNNNNNNNNNNNNNNNNNNNNNNNNNNNNNN NNNNNNNNNNNNNNNNNNNNNNNNNNNNNNNNNNNNNN NNNNNNNNNNNNNNNNNNNNNNNNNNNTGGGGTCCCTG TTGCCCAGCATGCCTGGACCCTCCAACACTTAGTGAT AATAACATATATCCAACCCTTGGTAAATGCCAGGACT |
| 239 | ADXCRP D.10843.C 1_s_at | TSR2 | Sense | TSR2, 20S rRNA accumulation, homolog (S. cerevisiae) [Source:HGNC Symbol;Acc:25455] | 239 | GGCCTTTAGTTAACATCCGAGTGACGAAGCCGGTTCC CCAGTACAGCTGTCTTTTGGGTGCGGTCATTGTGAGGA AGGGGATGAGTGAGTGTGGTGTGGCTGGAGGAGGAG CTAGATGCCGGTGGACAGTGGGCAGTGGGCAGGTGGATTTGGGG AGGAGAGGATCAGCAGCAGCAGAAGTACTCAGTGATAG GGGGCTGGCTGGGTCAGGAATGGTGAGATGAACATGC AAGT |

FIG. 7-61

| 240 | ADXCRA D_AL8322 50_s_at | SNRPN /// SNURF | Sense | small nuclear ribonucleoprotein polypeptide N [Source:HGNC Symbol;Acc:11164] /// SNRPN upstream reading frame [Source:HGNC Symbol;Acc:11171] | 240 | ACTTGAACCCCGAAGGCAGTGTTTGTGTGAGCAGAAA TTGCTTCATTGCA |
|---|---|---|---|---|---|---|
| 241 | ADXCRA D_BQ187 449_s_at | SLC37A1 | Sense | solute carrier family 37 (glycerol-3-phosphate transporter), member 1 [Source:HGNC Symbol;Acc:11024] | 241 | GGGCCATGGCACTGCTGTTCAGCTCAGGCACAGGGGC ACAGCAGAGGTTTGGGAAGCGGTCTCCCCACCGGCAC TGGGATTGGCGGGTCCAAGCCCAGCAACCGGCTTCGC TCCACAACACACACACCACCTGGACTGTTTTAATACA TAGCAACAGACTGGGTTATTTATTTAAGATGTGTATTGT GTCATATGAAGTTNAAGAGACATAAATGGCATTTTGTTA TTTATTAAGACAAACTCCAATTGTTCTCTGGCTGTTTTT TCAGTTGTGTCTAGCAAATACTTATCTGCCCT |
| 242 | ADXCRP D.12485.C 1_at | AC130352.2 (Clone_based_ ensembl_gene) | AntiSense | Novel miRNA. | 242 | AGACTGACTGCTAAACTGTATGAATGATGAGGGATTTG CACGTATAATCTTAACTGTACATCAAATGTTAATTTTTA TTTTATCCACTGTCTCTTTGAAACCTAACTCTTGACTAAGA ACTGACTTTCCTGTACTTGTTGTTGACTCAAGTAAACTT CCAATTCCACATAGTCAAAGATGATGTGCTGAGAAATC TCTCAAAGGAAAAATGCTAAGAATACAGGCAGAGTTATG CGGCAAATTTTGCAGAATTAACACAATTGCACTGTGAG TATGAAGCAC |

FIG.7-62

| | | | | | |
|---|---|---|---|---|---|
| 243 | ADXCRPD.15952.C1_s_at | SPDYE2 | AntiSense | speedy homolog E2 (Xenopus laevis) [Source:HGNC Symbol;Acc:33841] | 243 | ATGGACAGAACGGAGACTAGTTCCGTAAGAGGGACAGATTACGGGAAAGATCACGACCAGCCGTCAACCCACCCCCAGAATGAGCAGAGTCCCAGCGGAGCACCT |
| 244 | ADXCRPD.3305.C1_at | SMURF1 | Sense | SMAD specific E3 ubiquitin protein ligase 1 [Source:HGNC Symbol;Acc:16807] | 244 | TTTGTTACATATGCAATAAACTCACGACTTTACATTT |
| 245 | ADXCRPD.5066.C1_at | N/A | No Genome match | N/A | 245 | GGAAGTGGACGCAAAGTGGATGCGGCAGCAGAAA |
| 246 | ADXCRAD_AL833174_x_at | C1orf21 | Sense | Uncharacterized protein C1orf21 (Cell proliferation-inducing gene 13 protein) [Source:UniProtKB/Swiss-Prot;Acc:Q9H246] | 246 | TGGCCATGCATGATGGCTTACACCTGTAATTCCAACACTTTGGGAGTCTGAGGTGGGAGGATTGCTTGGGTCCAGGAGTTTAAGACCAGCCTGCCAACATGGTGAAACCCTGCCTCTACAAAAAATACAAAAATTAGGCAGGCATGATGGTGTGCACCTGTGGTCCCAGCTACTCAGGATGCTGAGGTGGGAGGATCACTTGAGCCTGGGAGGATGGAGGTTGCAGTGAGCCGTGATCATGCCATTGCACTCCAGCCTGGGTGACAGGGTAAGAAACTGTCTCAAAA |
| 247 | ADXCRPD.11335.C1_at | RP11-706O15.1 (Clone_based_vega_gene) | AntiSense | HCG1981372, isoform CRA_cNovel protein ; [Source:UniProtKB/TrEMBL;Acc:B1B108] | 247 | TGGAGTGCATAGGTAGCAGTGCTTCTCCCCCAAGGCTGGGGCGATGGAATCAGTAGACTATTGAGGGCATCTGAAAGGGCATCTGTGTCAGGGTTAGTCCTCAGGTATGGTGGCCAATGGGTTCTTTGTTGGTTGACTGTTGACAATGCGTTTGTTGAATGGCAGCCTGCACTAGGTGACGCTGAAGCCACAGAA |

FIG.7-63

| | | | | |
|---|---|---|---|---|
| 248 | ADXCRAD_DN602385_s_at | MAPK1IP1L | Sense | mitogen-activated protein kinase 1 interacting protein 1-like [Source:HGNC Symbol;Acc:19840] | 248 | TTCATTCCCACAAAAACCTGAGGCAGTCTTTTGCCCAGAGCGTTCCCTGTAGCCACCCCACCCCACTTGCCCTTGGTTCTTTAGAAGGAGCACACACATCCCTTGATTCCTCCCTGATGTGGTAAACTGGCACACTCCAGGGTCTAAAACATAAAACAGTTGTGTTTAGGAACCTTAAGTCATGC |
| 249 | ADXCRAG_BC033465_at | VDR | Sense | vitamin D (1,25-dihydroxyvitamin D3) receptor [Source:HGNC Symbol;Acc:12679] | 249 | ACAGAGGGCTTCTTCAGATCAGTGCTTGAGTTTGGG |
| 250 | ADXCRPD.11659.C1_at | ARHGAP26 | AntiSense | Rho GTPase activating protein 26 [Source:HGNC Symbol;Acc:17073] | 250 | ATTCTGCATGATTCACGGACTAGGAGTCCCTGGTCAAAACTTCAAAAACTAAGTGATGGGTCCCAAGTTACTCAGTGGCAGAAACTTGATTCAGTAACATGTCAGTCTGTGGGCTTGAAAGTCTTAAGTGTCTCTACTTCTTCTATCCTTGTGCTTTCCCGGGACTTTACACAATCCCACCTCCCACTGGACAATTGTCAAATCCCAGAGAGTATGGGAAGTCTGTTCATCTCTGATCACCATAA |
| 251 | ADXCRAD_AA601031_at | RP11-761E20.1 (Clone_based_vega_gene) | Sense | Novel processed transcript. | 251 | GACGGTCCGCCGTGCCAAGAGAACGGGATGACATTCAACTGGGACTTGCCTCACCTTGGCTTGGGGACCTCGAGAGCGGTCCCGTCCCGTGGGGCAGTGTTACTCGTGGTGGTAGAAGTGGAGGGCGTGTCCGGGTACTTGAGTTCATGGGCATCTCTCCCGCGCCTCTCAGCTCTTACCGTTTCCATGTCTCACACGTTCAGTTGCAGTCTTCTTACCGTTTTGAAGGCGACGTGGGCAAGAAGTCCTGGGCAGCACAAGAAAGTCAATCACGTTGAGACAGAG |

FIG.7-64

| 252 | ADXCRAG_BC015773_s_at | PPP1R14C | Sense | protein phosphatase 1, regulatory (inhibitor) subunit 14C [Source:HGNC Symbol;Acc:14952] | 252 | GACTCTAGCCACAGCCTAACCAAGGATTATCAAAGGAG GTGGACACTCAAGGAAGGGCCACGCCAGGCTGCGTTT CCTGCAAGGACTCAGATGTTCAGTACCTTATGATACAGG GAAGATAGTTTCTTACAAGTAGTTGGTAATATTTTTT TCTTAAGTTGTACATTTGACTCAGCTGTCAAATTTCTCAC ACTTGTATATATCTACACACAACTAAGTTAAA |
| 253 | RDCR178_E08_s_at | INSR | Sense | insulin receptor [Source:HGNC Symbol;Acc:6091] | 253 | GGGAACACAGGGAATGCCGATTTTATATACATGGTACACA GAGAGGGGTGTCACTTCACAAAATCTTCCAGCATGTTCT TCAGAATATATTAATTTATATGCGAGGTGAGGTTGGGAATG AAAAGAACAGGTCAGCACNNNNNNNNNNCCTATAACAT ACAAAAGAACACATGGTGGACTTTCAGGGAGTGCAA |
| 254 | ADXCRPDRC.14444.C1_s_at | PRKDC | Sense | protein kinase, DNA-activated, catalytic polypeptide [Source:HGNC Symbol;Acc:9413] | 254 | GAGATTTTTGTGGTCGGTGTATTCGAGAATTCCTTAAAT GGTCCATTAAGCAAATAACACCACAGCAGCAGGAGAAG AGTCCAGTAAACACCAAATCGCTTTTCAAGCGACTTTAT AGCCTTGCGCTTCACCCACCCAATGCTTTCAAGAGGCTGGG AGCATCACTTGCCTTTAATAATATCTACAGGGAATTCAG GGAAGAAGAGTCTCTGGTGGAACAGTTTGTGTTTGAAG CCTTGGTGATATACATGGAGAGTCTGGCCTTAGCACAT |
| 255 | ADXCRPD.1547.C1_x_at | HCN3 | Sense | hyperpolarization activated cyclic nucleotide-gated potassium channel 3 [Source:HGNC Symbol;Acc:19183] | 255 | TTCCTTCTGAGTTTGCTGTTGGTGGTGCAGGAATAAGGGAAA GGCCCAAGGTATCCAAGCCTGGGAAGGGCAGGCCAG CCAGCACCTCTGCCTTCTCAGGGACAAGAGAGTAGTCCTT TACCACCCTCACTCTGCCTGTCCCCTCCTCCTACTCTACA GCATTAAAGACTGTGGGACCAGGACCCTAAGTCTCCTT TCCTTCTGGGTGGGGAGTTCTGGGGTTCTTGGTGTGTG GGAGAAGTTTTATAATTGCTTCCAAACAGCTGGGTTTAA ATATA |

FIG. 7-65

| 256 | ADXCRSS.Hs#S297 8040_at | CAMK1D | Sense | calcium/calmodulin-dependent protein kinase ID [Source:HGNC Symbol;Acc:19341] | 256 | TTCTGGATGTATCTTCAGGAGCATTAGCATTCCCTGGTA GGTTGAAGATGGGCCAGTAAGGGAAACAGAAGGGTCAA AGGTGATGCCAAGATTTTTGCCCAAGCACCTGAAAGAT GGAGTTGCCCATGACTAAGATGGGAAGCACGGGGTC AGCACCGATTTGGGGGAAGATCAGGATTTCATTCTTG GATGTGCTGAGTTTGAAACATCTGAGTCATATCCAAGTG AAGAGTTTGAATAGGCCGTTGGATATATTTAGGATAAAA GCCTGGGCTA |
| 257 | ADXCRAD_CX8722 80_s_at | P4HB | Sense | prolyl 4-hydroxylase, beta polypeptide [Source:HGNC Symbol;Acc:8548] | 257 | ACCAGGCGCATCCTCGAGTTCTTTGGCCTGAAGAAGGAA GAGTGCCCGGCCGTGCGCCTCATCACCCTGGAGGAGG AGATGACCAAGTACAAGCCCGAATCGGAGGAGCTGACG GCAGAGAGGATCACAGAGTTCTGCCACCGCTTCCTGGA GGGCAAAATCAAGCCCCACCTGA |
| 258 | RDCR489_A06_at | C17orf88 /// LRRC37A /// LRRC37A2 | AntiSense | chromosome 17 open reading frame 88 [Source:HGNC Symbol;Acc: 17505]/// leucine rich repeat containing 37A [Source:HGNC Symbol;Acc:29069] /// leucine rich repeat containing 37, member A2 [Source:HGNC Symbol;Acc:32404] | 258 | CGTGCTACCATCACAGCTGAATGCAATGAAAGGCGGTC CTCTGAGAGGAGCAGGGTGGGAGATGCTAAGTGGAGG CCCCGTCCCATTGCTGATAGATCCTCATCTGGCA |

FIG. 7-66

| 259 | ADXCRP D.15527.C 1_x_at | Sense | SLC6A6 | solute carrier family 6 (neurotransmitter transporter, taurine), member 6 [Source:HGNC Symbol;Acc:11052] | 259 | TGATCTAGAGGTCCCCCTTCGGAAATAGGGAAGACTGT CTCTGAAGAAGGAGGAAGTGTAGCTTATGGGAGGCTGA GGAGTTTGGAGTTTCTCCTTGTGGAAGGTGGGAGCCA TGGAGGCTGAAGACAGTTGTCCAACTCAGGGCATACAA ATTGATGAGGAACTC |
|---|---|---|---|---|---|---|
| 260 | ADXCRP DRC.2992 .C1_s_at | Sense | TAPBP | TAP binding protein (tapasin) [Source:HGNC Symbol;Acc:11566] | 260 | CTGCCCCTCGAGTGAGACTGGGACAAGATGCTCTGCTG GACTTGAGCTTTGCTACATGCCCCCCACCTCCGAGGC CGCCTCATCTCTGGCTCCGGGTCCCGGTCCCCTTTGGGC TAGAGTGGGCGACGCCAGCACCTGGGTAAGGGACATCT GCTC |
| 261 | ADXCRA D_AB0331 02_s_at | Sense | FAM184B | family with sequence similarity 184, member B [Source:HGNC Symbol;Acc:29235] | 261 | GTGAGCCAAGTTCGAACTCCTGCATTCCAACCAGCCT |
| 262 | ADXCRA D_BM264 147_s_at | Sense | CDK12 | cyclin-dependent kinase 12 [Source:HGNC Symbol;Acc:24224] | 262 | GATGGGATAATTTGGGAGGCTTCTCATTCTGGCTTCTAT TTCTATGTGAGTACCAGCATATAGAGTGTTTTAAAAACA GATACATGTCATATAATTTATCTGCACAGACT |
| 263 | ADXCRA G_AK1603 79_at | Sense | SP100 | SP100 nuclear antigen [Source:HGNC Symbol;Acc:11206] | 263 | ACCAAATACCACAGGTTCTCAGTTGTGAGTGGGAGCTA AATGATGAGAACTCATGAACACAATGAAGGAACAGAC ACTAGGGTCTACTTGAGGGTGGAAGATGGGAAGAGGGA GAGGAGCAGAAAAAGTACCTATTGGTGATGAAGTACTC TGTACAACAAACCCGTGACAAGAGTTTCCCTATATAAC |

FIG.7-67

| 264 | ADXCRIH.3937.C1_at | SH3D19 | AntiSense | SH3 domain containing 19 [Source:HGNC Symbol;Acc:30418] | 264 | AACAGCTGCTTTTGGTATCAATACCCTGTTGGTTATTAG TTTAAAATTTAGTCAATGATGCTTTTTGGGTGGGTGTGA AGGGGGAAGAAAATCTTGAGCATGTAATGACTTAAATTG TTTCCCAAATCAAATTAAATTCTGGGCCAGTATAAGACC TACACACTCACATTTCACAAGTGAGGGCATGATGGGG GTAGGGCAGGCAGGGGAGGAGAAAAGAGAGACAATC AGCACCCCTGAGGGGCTGAACATAGGGGCATCCAAA ACGTGCTTGCTGTGGGAAGAAT |
|---|---|---|---|---|---|---|
| 265 | ADXCRP DRC.1366 3.C1_s_at | DYNC1H1 | Sense | dynein, cytoplasmic 1, heavy chain 1 [Source:HGNC Symbol;Acc:2961] | 265 | CATTTTGGATGACGACGATCATAACCACTCTGGAGAA CCTGAAGAGAGAGGCTGCAGAGGTCACCAGGAAAGTT GAGGAGACGGACATTGTCATGCAGAGGTGGAGACCG TGTCCCAGCAGTACCTCCCGCTCTCCACCGCCTGCAGC AGCATCTACTTCACCATGGAGTCCCTCAAGCAGATACA CTTCTTGTACCAGTACTCCCTCCAGTTTTTCCTGGACAT TTATCACAACGTCCTATACGAGAACCCGAACCTGA |
| 266 | ADXCRP D.15326.C 1_s_at | ZNF69 | Sense | zinc finger protein 69 [Source:HGNC Symbol;Acc:13138] | 266 | ATGACATACAGTGCATGGCTCACAATCCCAGGAGATGA GGGCAGCACAGCTGCAGAGCAACAACAGAGTGGGGAGA ACATCCAGGATGCACATTCAACCAGCAGTGGGGAGCA AGACAGACAGGGACCTGTGGGCCAAAGCGTT |
| 267 | ADXCRA G_BC007 608_x_at | HMGB3 | Sense | high-mobility group box 3 [Source:HGNC Symbol;Acc:5004] | 267 | TAGGCTTAGCTTGATTTCTGGGCCCACTGTCTGTGTTCT TAAGATGCCAACCTGTTGCTTTTTTTTTTTCCCCC ATTTAAAAGGATAGTACCTACTCCCTCTAACCACCTCAC CCCATTCTTGAATGACATTTTATCCTTCGGAAAGAACAA GGCTGTGATGTAGTGACTATTGTCTGTCTCCTGTGTG TGTCTGTTCTTGTCACAAATGTATTTGGGGACGTTGGAT GCATTCATTTTCT |

FIG.7-68

| 268 | ADXCRA D_CR747 486_s_at | PPPDE2 | Sense | PPPDE peptidase domain containing 2 [Source:HGNC Symbol;Acc:24577] | 268 | GCCCCACTGTCACTAACTGTAAACTCAGGCTCAGGCTT CAACTGC |
|---|---|---|---|---|---|---|
| 269 | ADXCRA D_BE8322 79_s_at | PARP6 | Sense | poly (ADP-ribose) polymerase family, member 6 [Source:HGNC Symbol;Acc:26921] | 269 | AAGATTCTTCTTTGTATATGAGGATGGTCAGGTGGGCGA TGCCAACATTAATACTCAGGACCCCAAGATACAGAAGG AAATCATGCGTGTGATCGGAACTCAGGTTTACACAAACT GAGGGGGCCCCAGCCCTCGTACCACCCCTGTTACCCC AGGATCCATCTGCCCTCATAAAAGTGTTCAGGTACAGCA GCTGAGGCTGCCCTGAGGAATCAAGGGCCATTACCAA GGGGCAGGAAAGGATATGTAAGAGGTGGCCTTCA |
| 270 | ADXCRA D_CV5731 77_s_at | AC138866.2 (Clone_based_ ensembl_gene) /// AC146949.1 (Clone_based_ ensembl_gene) /// AC146944.2 (Clone_based_ ensembl_gene) | Sense | Novel long non-coding RNA /// Known non-coding long RNA /// Novel long non-coding RNA | 270 | TTGCAGCGAGTCAGGATCGCAGCACTACACTCC |

FIG. 7-69

| | | | |
|---|---|---|---|
| 271 | ADXCRAD_BX0983 87_at | EFR3A | Sense | EFR3 homolog A (S. cerevisiae) [Source:HGNC Symbol;Acc:28970] | 271 | TTCACAGGAAGTAGGTAAACACCGAAATTTAGTCAGTGTCATTATTAGAGTTGTGCTTTCATAAAAGAATCTCTCAAGTGTGACAAGGCTAAATTAGAAGAAGAGACTGGAGGTAGAGGCCAGTTAGGAGATCCTTGTAATAATCCACAGTTGATGGAATGAGGATCTATAGTAGCCAGGCTGGAGGTAACAAAGAGGGACAGGAGGGCAGGAGTACTCTACTTTAAAGTAG |
| 272 | ADXCRAD_XM_37 4484_at | PCLO | Sense | piccolo (presynaptic cytomatrix protein) [Source:HGNC Symbol;Acc:13406] | 272 | AGTTGTTAAGTGTATCAGATGTGTTGGGCATGTGAATCTCCAAGTGCCTGTGTAATAAATA |
| 273 | ADXCRAD_AW957 273_s_at | APOL1 | Sense | apolipoprotein L, 1 [Source:HGNC Symbol;Acc:618] | 273 | GTGGTTGTCATGTGATGGGTCCCCTCCAGGTTACTAAAGGGTGCATGTCCCCTGCTTGAACACTGAAGGGCAGGTGGTGGGCCATGGCCATGGTCCCCAGCTGAGGAGCAGGTGTCCCTGAGAACCCAAACTTCCCAGAGAGTATGTGAGAACCAAC |
| 274 | ADXCRPD.15551.C 1_at | EPHB4 | AntiSense | EPH receptor B4 [Source:HGNC Symbol;Acc:3395] | 274 | GGAGACATCGATCTCTTTTGCAAATTCCCTCACAGCCTCATTAGGGTCTTCATAAGTGAAGGGGTCGATGTAGACCTTAGTACCATGTCCGATGAGAGATACTGTCCGTGTTTGTCCGAATATTCTGCTTCTCTCCCATTGCTGCTCTGCTTCCTGAGGCAGAGAACTGCGACCACACAATGACCACCAGGACCAGGACCACACCCACGACTGCCGTGCCCGCCAATCAGGGCCAGCTGCTCCCGCCAGCCCTGCTCTCGTCATCCAGTTGGGTCCGGCTGTGATGTTCCTGGGCCGAAGGGCC |

FIG.7-70

| | | | | |
|---|---|---|---|---|
| 275 | ADXCRAD_BX11171 9_at | TAF15 | Sense | TAF15 RNA polymerase II, TATA box binding protein (TBP)-associated factor, 68kDa [Source:HGNC Symbol;Acc:11547] | 275 | GGAGTTTGTGACTAGATGGGCAATATAGTAAGATGTCAT CTTTTAAAAATGAAAAAATTAGCTGGCCACTGTGCACA CGCCTGTAGTCCCAGCTACTTGGGAAGCTGAGGTAGGA GGATTGCTTGAGCCCAGGAGTTCAAGGCTGCAGTGAGC TATGATTGTGCTTATGAATAGCACTGCACTCCAGTCTG GGCAATAGTGAGTCGGTCAAATTCCATTTCCCCCTCCGC CCCATACCCTCTTCAAATGTTT |
| 276 | ADXCRPD .14035.C1 _s_at | KCNE3 | Sense | potassium voltage-gated channel, Isk-related family, member 3 [Source:HGNC Symbol;Acc:6243] | 276 | ACTGCATCAGGTCTCAGTGTCCCTATCTGTAAGATCAAC AAGAAACACGGTTAAGGGAGGTCGTCACTGGGGTGGGA GAAGAGGGGCTGGTAGACCGAAGCCTTGTGCATAAGGA TTTTTTCCAGGAAAAGATAGACTTTATAAACAGTGGGA GCCCATGAACAAACATATAAAAGTAGCAACAGATAATGA CC |
| 277 | ADXCRPD .8986.C1_ at | HOXB8 | AntiSense | homeobox B8 [Source:HGNC Symbol;Acc:5119] | 277 | TATTGTAACTCTTCCGCCCTTTTCAGGCGCAGACAACAG AACAAAGTATAGAGGAACAACAACAAAATATAATTAGCCC TCCCTCCCCCCATAAAGCAATTCACGGATACAGAATAC ATTCTCTTCACAGTAACCTAAGAACACTTGTAACAATTG CCCACAGCGCGCATGCTAACTAACTAAAGTAACCTCTTTGA |
| 278 | ADXCRPD .10916.C1 _at | KLRAQ1 | AntiSense | KLRAQ motif containing 1 [Source:HGNC Symbol;Acc:30595] | 278 | TACTGCTTGCATATCCTTTCCTCAGCTAACCGTCCTCCT GGGCCCTTCTGCTTCTGACCCCCTCAGGACCTTAGGAC ATAATCACTCCCTGCTTCTATCTTCAGTATCTCCTCATTA CAAATAAAGCATTTGCTGCAGCTCATTTAACTCTTGTGTC CACAGTGAGTCTCTTCCATTACTTACTCACACTTAATTCT CTGTCCTGACTCCTGCTGTCCCCAGCCTTTTCTTTCACTTTG CCCGTCTGTCAGGCTCTCATGCTTCCATTTGGCAACT TCAGGAAGGTACGCGGAGCTCCC |

FIG. 7-71

| | | | | |
|---|---|---|---|---|
| 279 | ADXCRA G_AY2067 18_s_at | PPARA | Sense | peroxisome proliferator-activated receptor alpha [Source:HGNC Symbol;Acc:9232] | 279 | GCCAGTCACCCTGCGGATCGAGAGAGAGGGGGTAGAGTC TTCTTCAAATGGCAGTTTTACTTCAAATGGCAGATTTCAC AAGAGTTGGTTATTTTTACAATGGTTAGGTTGTTAAGT CTCCTTTGTATGTAAGGTAGTTTTTCAACATCTAAAATT TTTGTTTTAGCCTTCAAAACCAACTTACCAACCTCAGTC CAGCTGGGAAGGCAGCGTTGATTATGGTAGTTTGTCAA GAATATATGGACCTGGAAACAC |
| 280 | ADXCRP D.9565.C1 _at | PKM2 | Sense | pyruvate kinase, muscle [Source:HGNC Symbol;Acc:9021] | 280 | CACTGCTCAGGGTTGGAGGCTCAGTCCCTTTGCCCTGT CTGTTCCAGCTCTGGAGCTAACTCAGGATCCCTGATC AGGGTTACATAGGTTTGGTAAAATGAGTGCTGGAAATTA ACTTTCTCCCAGTAGTCTTAGGTCATGCTCAGTGAACTT AAACTTTATCCAGATATGTTTTCCTTCAGCCTTTCTATT CCCTTTCTAGCCAGTGAAAGACCCGCTGC |
| 281 | ADXCRP D.12822.C 1_x_at | CDC42SE2 | AntiSense | CDC42 small effector 2 [Source:HGNC Symbol;Acc:18547] | 281 | CGAGAGTATATCAGTTAAAGGGTAAGAAATGTAGACCC CATATTTTAATTCAGTAGCACCAGTTCAAATCCAGTTATT CAGAATTAACAAAGCAACTGTTGCTCAAAAAATGCCAA TAAACTCCCGAGCCAACTGAGAT |
| 282 | ADXCRP D.4113.C1 _s_at | FA2H | Sense | fatty acid 2-hydroxylase [Source:HGNC Symbol;Acc:21197] | 282 | ACCAAGGAGCTGGTCAGACGCCCTTTCTAATCCTACA TGTTGAGCTTATGTAAAAAATGTTGTTTCCTCCTGTTTTT GGTTCCTTTCTTACCCACAAACCATTACTACTTG |
| 283 | ADXCRA G_BC000 004_x_at | HSCB | Sense | HscB iron-sulfur cluster co-chaperone homolog (E. coli) [Source:HGNC Symbol;Acc:28913] | 283 | CAACAGAGTGAGACTTAATCTTGAAAAATAAATA |

FIG.7-72

| | | | | |
|---|---|---|---|---|
| 284 | ADXCRP D.7428.C1 _at | EIF2S2 | Sense | eukaryotic translation initiation factor 2, subunit 2 beta, 38kDa [Source:HGNC Symbol;Acc:3266] | 284 | AGTAGAGGGCCCTCAACCCACACACTGGCTGAAACTGC CACCAACTGCCACGATGAACCCAACTGCTGTTTATGCC CCCATTTTCCTTTTTTGTATCTACACCCACACGATTCCC AATGTTGGATATTTCTACATGAATAAAGCAAGGATCAGT GCCTCTTATGT |
| 285 | ADXCRP D.240.C1_ s_at | TCEAL4 | Sense | transcription elongation factor A (SII)-like 4 [Source:HGNC Symbol;Acc:26121] | 285 | AGGGCAAAACAGGAGATGAGGAAATGTTAAAGGATAAA GGAAAGCCAGAGAGTGAGGGAGAGGCAAAAGAAGGAA AGNNNNNNNNNNNNNNNNNNNNNNNNNNNNNNNNN NNNNNNNNNNNNNNNNNNNNNNNNNNNNNNNNNNN NNNNNNNNTGAAGGAGAGCCAGGAGTGAAACAAGGG CTGCAGGAAAGCGCCCAGCTGAGGATGATGTACCCAG GAAAGCCAAAAGAAAAACTAATAAGGGGCTGGCTCATT ACCTCAAGGAGTATAAAGAGGCCATAC |
| 286 | ADXCRIH. 3436.C1_s _at | USP12 | Sense | ubiquitin specific peptidase 12 [Source:HGNC Symbol;Acc:20485] | 286 | TGTGGGGTGACAGTTTACATTTACTTTTCTTCTTAATG CAGCTGGATCTAAGTAAAATGTTTGAAGTTTATCAGAA ACTAAATGTACTTTAAAACGTATAGGTCAGGGTTGGG GGAAAAATACAGGTATAGTAAGTAAGAAAAGTGACCAT GAAGAAAGCATCGTGAGGTTGTATGTTGGTTGACTGTG ATTAAAATGCGGGGCTGGTGGTATACATGTAAGTGTGGCC TGATTGCCGTGTACTATGTACATGATTGTTGGGATGGCT GTCC |
| 287 | ADXCRP D.10809.C 1_at | KANK1 | AntiSense | KN motif and ankyrin repeat domains 1 [Source:HGNC Symbol;Acc:19309] | 287 | GAAAACCTATAACATGATGAGTAAGAGTTCTATGGTAGA GAGGTAGGAGGAGAAAGGTGAAAACTGCCACAAGCCAA ATGAGACTGCAGCAAGTATGTAAGGAGCCTGTTCTCA GGTCCACCCACATCCAGCTATCACCCTCTGACCGCC TTTTCCCATGAGCCTGAAAGGGTCACAGAC |

FIG. 7-73

| | | | | |
|---|---|---|---|---|
| 288 | ADXCRPD.8357.C1_at | WSB1 | AntiSense | WD repeat and SOCS box-containing 1 [Source:HGNC Symbol;Acc:192221] | 288 | GACGCACAACCTTCAACACTAATTGCCCTTTACTAAGCC GACCAGGGCTAGACACTAAGCCAGAAAAGCCTTTTCCA GAGTTTCCTCTTCCGCACAAAGCTTTCCTTCTGTCACT CCACCCAACCACCCAGCTCCTCCCCCTTAAGTGTTTGAAA GATAATTCTAAAAGTCTCCTCCCCCGAACCGCTGCGTTT CTTAAGGCCACACCATTTTAAAAATACTGTATTGCTTTTG CCAGGCTGTTGGGACCTCTTCCATCTCATTTCTATCTAA GAGTGGTGGTACACACGAGGAC |
| 289 | ADXCRSS.Hs#S833047_at | CD200 | Sense | CD200 molecule [Source:HGNC Symbol;Acc:7203] | 289 | AAAGCAGATGGGTGTGTTCAGACAAGATCTGGAAGCTG TGGCATGGCAGAGACAAGGGAGATGGGACCCCTTTGGC ACTGGAGGAAGAGAGGCTTGAATCTTCTTGGAGCACTAAA AGTTCCAAAAGACCTAAGCAGCAGAAAATGCTTCCGAAGAG GAGGATCTGTATGGCAAGATGACTGTAATCAGGCTCAT AAAAGTAAGACCTTACATAGGAGGAATGGCTCAAGCAAGTGAGGGGAAG ACATTTCATGTAGGAGGAATGGCTCAAGCAAAATACCA AGGCGGGAAATTGCGTGGT |
| 290 | ADXCRAD_AW134504_at | AL604028.2 (Clone_based_ensembl_gene) | Sense | Known protein coding. | 290 | AGAAGTTTTGAGAAGCAGTTTTGTTGGGTCAAGGGGTA CTTTCAAATTACACTTATGAGTCAGTATCTATAAAAGTT TCAGAAGTACCTACACATTTAGCCCTCTACATCCAAGCAG TAGCTTTTGCAG |
| 291 | ADXCRAD_BC033251_at | RHOQ | Sense | ras homolog gene family, member Q [Source:HGNC Symbol;Acc:17736] | 291 | CAGTGAGCTATAATACAAGGCTTCATTGCACTCCAGCCT AGGCATTAGAGAGCGAGACCGTGTTTATTTAAA |

FIG.7-74

| | | | | | |
|---|---|---|---|---|---|
| 292 | ADXCRAD_CN297218_at | CUL9 | Sense | cullin 9 [Source:HGNC Symbol;Acc:15982] | 292 | GCAGATGCAGGAAACACCTAGAGAGCAGCCCAGAGTCACGGGGCTGAGGGGCGGGAGCTGCCCCTGTCATAGGGAGGGGGATTCCCAGCGTCTGTAGTGCTTCCTGTTTGCTGAATAAAGGTCTCTTTCTCACAC |
| 293 | ADXCRPD.9433.C1_s_at | PAG1 | Sense | phosphoprotein associated with glycosphingolipid microdomains 1 [Source:HGNC Symbol;Acc:30043] | 293 | CAGAAATGTTAGTGCCGTGCTCTAACCAAGTAAGCTTAGTGTTCCCACAGTATCTGTATCTGGCTGAGTCTCTCAAGCAGCAACCCCACTGTCCAGCATGTGGAAGGTAGATCCTTATGACAACACCAGACCCATAGTTACCAGGAAAGAA |
| 294 | ADXCRAD_BE043858_x_at | QPRT | AntiSense | quinolinate phosphoribosyltransferase [Source:HGNC Symbol;Acc:9755] | 294 | GTGTTTAAGGGCATTTCACAGATGGGAAATAAGGTGCAGAGGGCTAGAGAGATGGGCTCAAGGCTGTGGTGCCAGTGACACTGGCTTCCCCTGTGTTGTCTTGCTCTTGAACATCACGCCAACGCAGCAGCAGAACAAAGATAAAGAACCAATTCCAAAACCAGGCGTGGTGGC |
| 295 | ADXCRAD_CN423589_s_at | VPS26B | Sense | vacuolar protein sorting 26 homolog B (S. pombe) [Source:HGNC Symbol;Acc:28119] | 295 | GGCCGAGAAGATGCTGGGCACCCACCCAGCACCCCATCTACCAACACCAGGGCTGGGGGCGGGGGGGGACCTTGTGAGGCTCAGTTGACCCGTTACTTGCAACCTGAAAA |
| 296 | ADXCRPD.17323.C1_at | ANKS4B | Sense | ankyrin repeat and sterile alpha motif domain containing 4B [Source:HGNC Symbol;Acc:26795] | 296 | CAAGAATCTGGCATTTCTCTTCAGTTATCTTATATGTACATATAANNNNNNNNNNNNNNNNNNNNNNNNNNNNNNNNNNNNNGGAGATGAAGGTCTCAGTCTCTTACCCACTGCACTCTAGCCCAGGCGGGTAAGAGACTCCAT |

FIG. 7-75

| 297 | ADXCRP D.8537.C1 _at | NCRNA00262 | No Transcript match | non-protein coding RNA 262 [Source:HGNC Symbol;Acc: 26785] | 297 | CCTCTACGCCAGAGAAGGGAATGGAGAGGTCAGGCTG GCTAGAGAGTGGGGTTGAGTCGTCCATGCCCTTGAATG CCAGGATGAGGGCTAAAGAGTCAAATGGAATGGGTGAC TTCATATGCAGAAGTTTTACAAGAGAGAGAACTCAGT TGGGCCAAGAGAAGTGGGGTCGTCATGTGGGTAATCAC GTAACAGTGATCGTTCAGTCAGTCATGCGGAATGCTTTCAAG GTGTTGGACAC |
| 298 | ADXCRSS .Hs#S298 6790_at | RABGAP1 | AntiSense | RAB GTPase activating protein 1 [Source:HGNC Symbol;Acc:17155] | 298 | CCTCTACGAGGTGTGCTATTCTCATCTCATCTTATAGG CAAGTTAACTGAGGTATAAGGAGGTTGGTTATGTAACTT GACCAAAGTCACACAATAAGGGACTGGGAGATCTGGGA TTTGAGCCCTGGCAGATGGACTCCATCCAAAGTCCTCA CTATCCTAGCACCTCTCTATCCCCTCCCTTTCCTCTC CTACCTTCTTCTGTGCTTCAAACAGACAGTTATCT CTACCCTTAAAAACACAGCTGTGCTGACTACTCTGCTTA GATGCCC |
| 299 | ADXCRIH. 2921.C1_s _at | CALM3 | Sense | calmodulin 3 (phosphorylase kinase, delta) [Source:HGNC Symbol;Acc:1449] | 299 | CCTCTGGGACAAGTAAGTCAATGTGGGCAGTTCAGTCG TCTGGGTTTTTCCCCTTTTCTGTTCATTTCATCTGGCTC NNNNNNNNNNNNNNNNNNNNNNNNNNNNNNNNNTGC TTCCCCTCACTGCCCAGGTCGATCAAGTGG |
| 300 | ADXCRP D.15035.C 1_at | DLG5 | Sense | discs, large homolog 5 (Drosophila) [Source:HGNC Symbol;Acc:2904] | 300 | TGGTCAAGAAGGACTATGACGCCCTTCGGAAGAGGTAC AGTG |

FIG.7-76

| | | | | |
|---|---|---|---|---|
| 301 | ADXCRPD.15234.C1_at | MACF1 | AntiSense | microtubule-actin crosslinking factor 1 [Source:HGNC Symbol;Acc:13664] | 301 | AGAATAGCAACTGGCTCAGTCCTTTAGGTGTCTACACTAATATCAAAGGAACAGGCCAGGCCCAAGGAGAGAGAGGGAATATGTTTCTGTGCCTGATCCTTTCTCTAGATTTTATCTCAGTTGTATGACATTGAAGCACCTGACTGAGCAATTGAGCATGATGTGTTCTCCTGACCATCCTCTAAAACCATTTTCCACCAGTTTCTACCTTCTGATGGCGCTTTAGTCACCTGCACTTACAAACAGGTGCCCAAA |
| 302 | ADXCRAD_CN337685_s_at | ZNF609 | Sense | zinc finger protein 609 [Source:HGNC Symbol;Acc:29003] | 302 | GGCTCTGATGATGGACCCTCAGTGATGGATGAAACAAGCAATGATGCCTTTGATTCTTTAGAAGGAGTGTATGGAAAAGAAAAATGTAAAAACCTCTAGTTTAAAACCTGAAAAGATTCCTTCCAAGAGCCTAAAGTCAGCCCGTCCCATTGCCCCTGCCATCCCCCCACAGCAGCAGCAAATCTACACCTTCCAGACAGCCACCTTCACAGACAGCCCAGCCATGGCACAGTGGCACAAGCCATGCCCAACAGTC |
| 303 | ADXCRAD_AV706878_s_at | DDX17 | Sense | DEAD (Asp-Glu-Ala-Asp) box polypeptide 17 [Source:HGNC Symbol;Acc:2740] | 303 | TTTTCATGCAGATTAGTTAGAATTCACTGCCAGGTTTCTTCTGCCCACCAAAATGATCCAGTCTGGAATAACATTTTG |

FIG.7-77

| | | | | |
|---|---|---|---|---|
| 304 | ADXCRAD_BQ325790_s_at | MICA /// HCP5 | Sense | MHC class I polypeptide-related sequence A [Source:HGNC Symbol;Acc:7090] /// HLA complex P5 (HCP5), mRNA [Source:RefSeq DNA;Acc:NM_006674] | 304 | GTAGGCTAGGGATCATGGGGAATAGTTAGTAATGACAGGGATAGTTGAACTTAAAAAAAAGTTTGTGAGGCTGACAAAGATGAAACGGACACATTTCCTGATCTTGGAGGGTCATAGGGTAGAAGATGGTAGAT |
| 305 | ADXCRIH.1351.C1_s_at | SDC4 | Sense | syndecan 4 [Source:HGNC Symbol;Acc:10661] | 305 | GATGGGTGGGATATTTGTGTCTGTGTTCTTATATATATTATTATTCTTCCTTGGTTCTGTTCTAGAAAATAGATAAATATATTTTTTCAGGAAATAGTGTGGTGTTTCCAGTTTGATGTTGCTGGGTGGTTGAGTGAGTGAATTTTCATGTGGCTGGGTGGGTT |
| 306 | ADXCRPDRC.3995.C1_s_at | IQSEC1 | Sense | IQ motif and Sec7 domain 1 [Source:HGNC Symbol;Acc:29112] | 306 | GAAACAGCATGGGACCGTGTGATTGGGTCCAGGCTGGGCTGTCAGGGAAGCGCCCTGGTGTCTCCGACTCATCAATTCTCGGGTCTTTTTTAAAAGCCAGGCTCCCCAAAGCACTCTTTGTCTCGCAATTTGAGGAGGTTGTTCCGACCTGGAAGCGTTAAACTGCTGCATGTCATCTGGCGTCAGCTGTGAGGCGCGCTCTGCGTCTGTGCGTTTGCAAAATGTATTGGCGTGACTGTAAACACATCGTT |

FIG. 7-78

| 307 | ADXCRP D.10961.C 1_at | RP11-86H7.1 (Clone_based_ vega_gene) | Sense | Novel processed transcript. | 307 | GTCAAGCTCAGTTGAGGGTTAATGATGAGGCAGGCTGA TGCGGGTTCTTTGCCCAGTCCCAGGGTTCCAAGAAGCC TTCCTGGGAGAGGGGCCTGAGTTGAATGGTGCAAGAT GAACAAGAAATGGCAAGAGAGAGAGCATGGCTAAGGGCTAG GGGCATGAAGCAGCAGGGGACCCCCAGCCATGTAGTA TCACTGAGGATGAGAATAAGGGGAGAAGGAGGAGGAG GGAGAGAAGGTATACTTCTGAGGGCA |
|---|---|---|---|---|---|---|
| 308 | ADXCRSS .Hs#S192 3995_at | N/A | No Transcript match | N/A | 308 | AGTTCAGGGCTACTAGTGCGCTATGTTGATCTGGTGTTCA TGCTAAGTTCCGCATCAATATGGTGACTTCTAGGGAGTG GGGGACCACCAGGTTGCCTAAGGAGGGGTGAACCTGC CTACGTTGGAAATAGAGCTGGTCAAAACTCCTGTGCTCA TCAGTAGTAGAATAGCACCTGTGAATA |
| 309 | ADXCRSS .Hs#S374 4180_at | CHD2 | Sense | chromodomain helicase DNA binding protein 2 [Source:HGNC Symbol;Acc:1917] | 309 | GACAGCTTGGAAGGAAGGATTGACCATGGGTTGATTCC ATGGAGGTAGAGAAGCAAGAGAGACCTGATGATTACAA TGATGGCTAAGTGTAGTATGCCCATTAGGATTGAATTGA ATTAGGGGAAATTGTGTGAAGTGTTTGGAAGGAAGCAAT ATTGTGTGATTAGCTCCAAAGCTGGCCACTGGTAGAAG TTGTTTCAATGGAAGAACAAGGATGGAATTGAGTGGGC CAGAGAGCCCTAGATTAATGGGT |
| 310 | ADXCRP D.1981.C1 _s_at | MRPS10 | Sense | mitochondrial ribosomal protein S10 [Source:HGNC Symbol;Acc:14502] | 310 | TATTCAGCGAAACTTACCTGAAGGGGTTGCCATGGAAG TAACAAAGACACAATTAGAACAGTTACCAGAACACATCA AGGAGCCAATCTGGGAAAACACTATCAGAAGAAAAAGA AGAAAGCTAGTCATAAAGCCTCAGGGAGGCCATTTTTG CCTAAA |

FIG. 7-79

| 311 | ADXCRP D.10195.C 1_at | SLK | Sense | STE20-like kinase (yeast) [Source:HGNC Symbol;Acc:11088] | 311 | CAAATGCGAGATCTTCAGTTGCAGTGTGAAGCCAATGT CCGCGAACTGCATCAGTCTGCAGAATGCAGAAATGCCACT TGTTGGTTGAGCATGATGAGACTCAGAAACTGAAGGAGTTA GATGAGAACATAGCCAAGAATTAAAGGAGTGGAGAGA GAAATTGAGACCTAGGAGAGAAAGGCACTGGAAGAAGAGT TTGCCAGGAAACTACAGGAACACAGGAAGTATTATATAAAA TGACTGGGGAGTCTGAATGCCTTAACACATCAACCCCG GA |
| 312 | ADXCRA G_AF1321 97_x_at | CYFIP2 | Sense | cytoplasmic FMR1 interacting protein 2 [Source:HGNC Symbol;Acc:13760] | 312 | TTTCAGAAACTGTCAAATGTACCATATTTGTATTAAGAGT TGTTGGGAATTTTTGTACAATGAATTTACATTTATTTATG GTGACATATTTACGCTTGTGATCAAATAATGATGTTAAAT TCTTAAATCATATTTGCTATGCAGCTGAAGATGATATTT GATTTGTATTTTGGGGTACCTGTGTTGAGTTGATAAAC ATTTCCATCTTCATTAAAACTGCTTCCAAACTAAA |
| 313 | ADXCRA D_CR749 083_at | SSR1 | Sense | signal sequence receptor, alpha [Source:HGNC Symbol;Acc:11323] | 313 | TAAAGCATGGATCTCGCTTTGGTTGTAAAAA |
| 314 | ADXCRA G_BC051 650_s_at | TOM1L2 | Sense | target of myb1-like 2 (chicken) [Source:HGNC Symbol;Acc:11984] | 314 | ATGGTGGGGTCTCTCACCTTCTTGACCCTCTCTCCATC ATTCAGTCGCCAGCCCAGGCTTCACCACCCAAGCTGGCT CAGCAGCCGAGCCTGCACCGAGGGTCCCTGCAGGCT CCCTGGGCAGGGAGAGGGCCAAGGACAATTGGGAGGG CAGCAGGCAGCCCGAGACTACCGAGATGGTGGCCATGTGGCACGC TGCTGAGACGACGACACTACCAATAAACCAAACTGC |

FIG. 7-80

| | | | | |
|---|---|---|---|---|
| 315 | ADXCRAD_CN256682_s_at | TRAPPC6A | Sense | trafficking protein particle complex 6A [Source:HGNC Symbol;Acc:23069] | 315 | CTGCCCGTCTGTAAGTTCCAGGTGGTGATTCCGAAATC CTAAGCCTGCCTCGCACCTGCTGCTGAGCCGCACTGCTGCC CCTGGCCTCACCGGCCTGCTCAGGAGACGGTGGGGCCGCT GCATTTCGGGGTGGTCTTGGGAATCCCAGGCCCTAGG GGTCACATTTGCTCAGGAAGTGGGTATCAAATTGAGGT GGGGGTGTCAGAGGAGGCAAAGGGGTCCCAGCTGCGG TCAGGACTGTGGT |
| 316 | ADXCRAD_BC040647_x_at | OAF | Sense | OAF homolog (Drosophila) [Source:HGNC Symbol;Acc:28752] | 316 | CCTGGGGTGACGGAATAAGACTCGGTCTCCAAAGAA |
| 317 | ADXCRAD_BX421336_s_at | PPIF | Sense | peptidylprolyl isomerase F [Source:HGNC Symbol;Acc:9259] | 317 | AAGGCTGCTAGGGATGTTAGACCTCGGCCAGGACCAC CACATTGCTTCCTAATACCCACCCTTCCTCACGACCTCA TTTCTGGGCA |
| 318 | ADXCRAD_NM_145809_x_at | AC107983.1 (Clone_based_vega_gene) | Sense | TL132 protein (LOC220594), non-coding RNA [Source:RefSeq DNA;Acc:NR_003554] | 318 | TACCTGTTTATCTGTAACTGTTATCCAAACAAATTAAATA CTGTGGATGCCTTTAAAAA |

FIG.7-81

| | | | | |
|---|---|---|---|---|
| 319 | ADXCRP D.11050.C 1_at | GALNT5 | Sense | UDP-N-acetyl-alpha-D-galactosamine:polypeptide N-acetylgalactosaminyltransferase 5 (GalNAc-T5) [Source:HGNC Symbol;Acc:4127] | 319 | GACAGTGGATAACTTTCAAAGAGGCATCTTTGTGTGGC CCATGAACTTTGTTGGAGAACAATTCCTCCAGATGTCA CTGCAAAAAACAGAATTAAAGAAACTGATACAATAAGG TGCCCTGTCATGCCTGGTGGTGGATTGTTTCTACTGACAAA AGTTACTTTTTGAACTTGGAACATACGACCCTGGCCTT GATGTTTGGGGTGGGGAAAATATGGAGCTCTCATTCAA GGTGTGGATGTGTGGTGGTGAAATTGAGATCATTCCCT GCTCCCGAGTGGGCCATATATTCAGAAAT |
| 320 | ADXCRP D.15212.C 1_s_at | CHD3 | Sense | chromodomain helicase DNA binding protein 3 [Source:HGNC Symbol;Acc:1918] | 320 | ATGAGTATCTCAGCTCCTTCAAGGTGGCACAGTACGTC GTGCGGGAAGAAGACAAGATTGAGGAAATTGAGCGAGA GATCATCAAGCAGGAGGAGAATGTGGACCCTGACTACT GGGAGAAGCTGCTGAGGCATCACTATGAGCAACAGCAG GAAGACCTAGCCCGGAATCTAGGCAAGGCAAGGCGGGG TTCGCAAGCAAGTTAACTACAATGATGCTGCTCAGGAAG ACCAAGACAACCAGTCAGAGTACTCGGTGGGT |
| 321 | ADXCRA G_AF1722 69_s_at | TNIK | Sense | TRAF2 and NCK interacting kinase [Source:HGNC Symbol;Acc:30765] | 321 | CTATGGCCGATAACTAAGGATGTGGTCTCCAATGGG GAGAAATGCCACGTCTGTGGCCTACATTCATTCCAATC AGATAATGGGCTGGGGCGGAGAAAGCTATTGAGATCCGG TCAGTGGAAACAGGAC |
| 322 | ADXCRP D.17448.C 1_at | CAPS | Sense | calcyphosine [Source:HGNC Symbol;Acc:1487] | 322 | CCACCATTGCGGGTCCCCCAGGAAGCCAGGTGACCCC AGGTGGGAGGCTGTGTGTGGAGGCCATCCTGGAAGGA AGTTTTAGACCTGCCCAGGTGTGGAGCGAGGGCACAG GGGCATCCTAACCTCCAGAAACTGAAA |

FIG.7-82

| 323 | ADXCRPD.12030.C1_at | POSTN | AntiSense | periostin, osteoblast specific factor [Source:HGNC Symbol;Acc:16953] | 323 | AGCAAAGTGTATTCTCCATCTGGCCTCAGAGCAGATGC CAAGCCTAATTGGGCCACCAGATCCGTGAAGGTGGTTT GCTGTTTTCCAGCCAGCTCAATAACTTGTTTGGCAGAAT CAGGAATTAGGACCTGATCAATCAAATGGATCACACCAT TAGTTGGTCACAATATCCTTTGTTGTTCACCATTTTGATT CCATTTACTGTTATACTGTCACCGTCACATCCTATCTCA ATTGTATTTCCTTCCAGCGTCTCAAGACTGCTACTCCCA TAATA |
|---|---|---|---|---|---|---|
| 324 | ADXCRAG_AF176912_at | CLCF1 | Sense | cardiotrophin-like cytokine factor 1 [Source:HGNC Symbol;Acc:17412] | 324 | GCTTGCCCCAGAACTTAGTCTCTTTGCCCAGCCTCACC CCTCCTGGTCTGCTCATCAGACTCTTGCCACCCTGGCTC CCACTCCCTGCTTGCCTCTGGTGGAGCTGCACAGAGCT CTGGGAAGAGGCCCTCTTCCTCCCCGCACTGGGGCGA TGGGCGCACCTCAGACTTACCACTGCTGCTGCCACCA CCAACCCCTTGATCCCTGCCTCCCACACAGCTTCT GTCCACCCAGGTTTCCCTCACCCCACCTTTGCTAAGT CTTCCT |
| 325 | ADXCRPDRC.12746.C1_at | FAT1 | Sense | FAT tumor suppressor homolog 1 (Drosophila) [Source:HGNC Symbol;Acc:3595] | 325 | GCCCTGCTGCGAAGTGGAGTCCGAGGTCATGATGAGT GACTATGAGAGCGGGGACGGAGACGGTCACTTCGAAGAGG TGACGATCCCGCCCCTGGATTCCCAGCAGCACACGGAA GTCTGACTCTCAACTCCCCCCAAAGTGCCTGACTTTAGT GAACCTAGAGGTGATGTGCGTCATCCGCGCTGTTCTTT GCAGCAGTGCTTCCAAGCTTTTTTGGGTGAGCCGAA |

FIG. 7-83

| | | | | |
|---|---|---|---|---|
| 326 | ADXCRP D.3213.C1 _at | ARHGEF2///R P11-336K24.6 (Clone_based_ vega_gene) | Sense | Rho/Rac guanine nucleotide exchange factor (GEF) 2 [Source:HGNC Symbol;Acc:682] /// Known nncoding transcript with no ORF. | 326 | AGAAGCAACACGATGATGGGCCCCAGTTTGAATTTC AGACAGTGGAGGAGGAATATTGCTAGGAG |
| 327 | ADXCRIH. 2217.C1_s _at | ADIPOR2 | Sense | adiponectin receptor 2 [Source:HGNC Symbol;Acc:24041] | 327 | TACTCTCAGCAGTCAGAGGCTTGCTGCTCTGTGCAGA TTTTTAATTTTCTTTTTTGGCCTAGGCTGGTTGGGACCT CTACAGCTTCATTCTTTCACCATTAAATAGTGGCCTTTT CAGTATTTTCCCTCTTCCCCTTTATAAATTATGCTAAAGC CACAAAGCACATTTTTGGGATCATAGAAGGTTGGGGT TCCAGAAAGGCATCTGTGTGATGGTTCCATTGATGTGG GATTTCCCTACTTGCTGTATTCTCAGTTTCTAATAAAA |
| 328 | ADXCRA D_CN390 037_s_at | C15orf42 | Sense | Treslin (TopBP1-interacting, replication-stimulating protein)(TopBP1-interacting checkpoint and replication regulator) [Source:UniProtKB/Swi ss-Prot;Acc:Q7Z2Z1] | 328 | AAGGACTGTCCAAGAGCCAGCCAGTTCAGGCTCAGG CCTCACCCATTGCCACTCCTGGGGAGACCATCACCTG GCTCATCGTTTCCACCAAGAGTGCCCCACAGGAGTGCC CCACAGACCCGCTGGACCAGCCTGCTGCGGGTCCTGG CCAGGGGTCTGGCTAACGGTGAGGGCTGACTCTGAACT GTCTCTCAGTCTCCAGAAAGTGTTCAAGCCTGTTGTT CCCAAATCTGATTCCTCCTATTGTCTTGTAAATCAAACTC TAAGTGAAAACTTCCCAT |

FIG. 7-84

| 329 | ADXCRSS.Hs#S192 3663_at | SOD2 | AntiSense | superoxide dismutase 2, mitochondrial [Source:HGNC Symbol;Acc:11180] | 329 | GAAGGTCATAACAGTTTCAAACAATAGCCAGGAAGTTAGAGTCACCTAGAGACATCCTTAACACGTGCCCCTGAGCTACTTTTCAGAAACCCAGACCCCACCAAATGGATTCACACAGACGTCAGATAAGGGGGAACACCAGGACTAAACTCTGACCTCCATTCTTTGCTCTCAGTTTCTTCCTGAGGGGCCTGGCCAGACCTTAATGTTCCTTTCTGCGGACCCCAA |
|-----|-------------------------|------|-----------|------------------------------------------------------------------|-----|---|
| 330 | ADXCRP DRC.1111 8.C1_s_at | TNS1 | Sense | tensin 1 [Source:HGNC Symbol;Acc:11973] | 330 | CACCTGCACTCTAGTGACCCTGGGTGCCGCCAGACCCTTCTCTTCTACAAAGACCCCAGCAGGAGTGGGAGGGTCTGCAATGGCATCGCCCCTGTCCTGCCCTGGCCAGAAGCCTGGAGCTTTGGTTTGAGGAGGTAGAGATAGTGTATCCATAGGAAGAGATCTGTCAGAACAGGCAGCTGTTGAGCTCGGGGTGTCTTCCTCAAGGCATGTGGCTCAGCAGCAAGAAAGGCAAGTTGCTCCTGCTGGGGCCCTGGACTCTGCCTTAGCTCC |
| 331 | ADXCRIH.3717.C1_s _at | GABARAP | Sense | GABA(A) receptor-associated protein [Source:HGNC Symbol;Acc:4067] | 331 | TCTCTCCAGCTCCTCTCTTAGGAGGGGTAATGGTGGAGTTGGCATCTTGTAACTCTCCTTTCTCCTTTCTCCCCTTTCTCTGCCCGCCTTTCCCATCCTGCTGTAGACTTCTTGATTGTCAGTCTGTGTCACAT |

FIG. 7-85

| | | | | |
|---|---|---|---|---|
| 332 | ADXCRPD.9610.C1_x_at | GMDS | Sense | GDP-mannose 4,6-dehydratase [Source:HGNC Symbol;Acc:4369] | 332 | ATCCACGGCCGCGTTAGAAAGAGGGTCGCACGCTGCC GCCGAGGTAGAGGGGTCCCGAGTCCTGGGCCTCGC ACCCCACAGCCCGAGTCCCTTCCCCGCGGAAGGACT CGTGGCTGTGGGTAGAGACGCGCGCTTGGCGCGGCCA GCCCTGCAGGCAGGAGCTGAGCGGCGCAGGACACG GGCAGCTGGGAGGGGCGCCTGGTGATTTACTCACTTCC CTCCTAGCAGAGAAGTGCAGCAATTCCAAACAGTTCT CATAGGAGCGTCCCTGACAACTTCATGTTATA |
| 333 | ADXCRPD.11405.C1_x_at | NAA50 | AntiSense | N(alpha)-acetyltransferase 50, NatE catalytic subunit [Source:HGNC Symbol;Acc:29533] | 333 | GTACCACAAACACACTCAACTTGTCTATGAATTAGAGAA CAAGATACTGCTGCTTCTTTTTGACTTTTGAAATATA CAATGTTTTGTAGGCTCTGCCCTTCAATGTGAAAGCAGG ACATTAAATTTGAAATTATTTGACAATTAAATGTTTAGGA CCATCTCAACTTCAACTGCAAAACTAAACAGATCTACCTT GTCCTTCCTTCAAA |
| 334 | ADXCRAG_AF1388 61_s_at | AL138478.1 (Clone_based_ ensembl_gene) | Sense | Known long non-coding RNA. | 334 | GGTTCATTTTAGTTTCAGATAGATGGCTTCACCAAAGAA CTCTTGAAAGAATACTGATTAGGGAGGGGCAGGAAGT AGGAGCTTATGTGTATATTATAAGGCTGGGAAAATCTAT GATGCAAACCCTTTCCACATAGTACT |
| 335 | ADXCRAD_R42604_at | SNTB2 | AntiSense | syntrophin, beta 2 (dystrophin-associated protein A1, 59kDa, basic component 2) [Source:HGNC Symbol;Acc:11169] | 335 | ACTCATTCTTAACCTAATCACCTAAATAATTCTTATCAT CTATTCTTCTTCAGGNAAAAATGGNGCCCTGGTGTTAT TTTAACGACTTGCCATCCTTCCTGTTTTGAGAGTNTCTTT GTTAACTGGGGCATACCTTCGNGACCCGGTCCTACCT TCCTCATTCAGACCTGTGCTGTTCATTGCTGTATTCCCA GTCCCTTAAAAA |

FIG. 7-86

| 336 | ADXCRSS.Hs#S2732484_at | MEF2A | Sense | myocyte enhancer factor 2A [Source:HGNC Symbol;Acc:6993] | 336 | ATATCTGACAGATGTGTAAACCAAGTTACCAGCATGGTGTGGAATCGTAGTTCCAAGTCATATAATACCAGACATTCAAGAAAACTAGTGCCCTGTTAACTGGGGAAGCAAATTTATATCCTTTTGGAAGAAAGTCACCTTATTCTGTATCAGAAATCTCTTTCAAATAACCTTTCAGAACTATAGAGCATCATACAAAGATGACCAAGCATACAAGAAAACAA |
|---|---|---|---|---|---|---|
| 337 | ADXCRPD.2240.C1_s_at | RSRC1 | Sense | arginine/serine-rich coiled-coil 1 [Source:HGNC Symbol;Acc:24152] | 337 | AACATCAAAGCTGGATTAGAACATCTGCCACCAGCTGAACAGGCCAAAGGCAGACTACAGCTGGTTCTTGAAGCTGCTGCAAAAGCTGATGAGCATTGAA |
| 338 | ADXCRPD.8064.C1_s_at | CYP3A5 | Sense | cytochrome P450, family 3, subfamily A, polypeptide 5 [Source:HGNC Symbol;Acc:2638] | 338 | AGCCTTAGCAAAATGCCTCCTCACCACTCCCAGGAGAATTTTTATAAAAAGCATAATCACTGATTCCTTCACTGACATAATGTAGGAAGCCTCTGAGGAGAAAAACAAGGGAGAACATAGAGAAGAACGGTTGCTACTGGCAGAAGCATAAGATCTTTGTACAATATTGCTGGCCCTGGTTCACCTGTTTACTGTTATCACAATAATGCTA |
| 339 | ADXCRAD_CB162448_s_at | CREBL2 | Sense | cAMP responsive element binding protein-like 2 [Source:HGNC Symbol;Acc:2350] | 339 | ACAGAGTCATTTGAGCTTTCTCCCCTCCCGCTAGTATCTTTACAGGACGGCAGGAAGCAGTAGAGGATGTATAATTTTGGGCGAAGTAAATTACAATTTATTTGAGGTTATTCCTAAACCTATTTATTTGGTGTTTTGGAGGAGATCACACACTAAGAGAACGTTGATTGCCTGGCTATTGTGCTGGCTGGACACTTTGGTCACTTTGAAGCATGTTAATAAATGTCACTG |

FIG. 7-87

| | | | | |
|---|---|---|---|---|
| 340 | ADXCRIH.1113.C1_x_at | IGFBP2 | Sense | insulin-like growth factor binding protein 2, 36kDa [Source:HGNC Symbol;Acc:5471] | 340 | TCCAAACACCGGCAGAAAACGGAGAGTGCTTGGGTGGTGGGTGCTGGAAAGAGACCAGCACCAGCTCGAGTTCTGACACACGTATTTATATTTGGAAAGAGACCAGCACCAGCTCGAGTCGGCACCTCCCCGGCCTCTCTCTTCCCAGCTGCAGATGCCACACCTGCTCCTTCTTGCTTCCCCGGGAGGAAGGGGGTTGTGGTCGGGGAGCTGGGGTACAGGTTTGGGGAGGGGAAGAGAAATTTTATTTTGAACCCTGTCCCTTTGCATAAGATT |
| 341 | ADXCRPD.6986.C1_x_at | GRB7 | Sense | growth factor receptor-bound protein 7 [Source:HGNC Symbol;Acc:4567] | 341 | TGAGGAGCGGGAGGGTTCCGCCACTCCAGTTTTCTCCTCTGCTTCTTTGCCTCCCTCAGATAGAAAACAGCCCCCACTCCAGTCCACTCCTGACCCTCTCCTCAAGGGAAGGCCTTGGGTGGCCCCCTCTCCTTCCTAGCTCTGGAGGTGCTGCTCTAGGGCAGGGAATTATGGGAGAAGTGGGGGCAGCCCAGGCGGTTTCACGCCCCACACTTTGTACAGACCGAGAGGCCAGTTGATCTGCTCTGTCTTTATACTAGTGACAATA |
| 342 | ADXCRPD.17978.C1_at | U6 (RFAM) | Sense | U6 spliceosomal RNA [Source:RFAM;Acc:RF00026] | 342 | AAAGACTCATCATAAGGGTCCTTCCTCTTTTCTATCCTCCCTCCATATTCAGTTGCTAAGTCTCAACTACTTTGCTCCCATCAAGATTCTCTTACTATTCTTCTATCCAGACCTTCCTCTTTATTCCTACTATTGTCATTGTCTTATTTTAGGTTCTCATCATCTTTCACTAAGATAACTACAACAGCTTCGTCGTGACCAGCGTAGGCAA |

FIG.7-88

| 343 | ADXCRA D_AA7747 60_s_at | EIF4G3 | Sense | eukaryotic translation initiation factor 4 gamma, 3 [Source:HGNC Symbol;Acc:3298] | 343 | GCTCAAATAGCTATAACTGTACCAAAGACATGGAAGAAA CCAAAAGATCGGACCCGAACCACTGAAGAGATGTTAGA GGCAGAATTGGAGCTTAAAGCTGAAGAGGAGCTTTCCA TTGACAAAGTACTTGAATCTGAACAAGATAAAATGAGCC AGGGGTTTCATCCTGAAAGAGACCCCTCTGACCTA |
| 344 | ADXCRP D.12198.C 1_at | DSP | AntiSense | desmoplakin [Source:HGNC Symbol;Acc:3052] | 344 | TGCGAATCTTCTGCAGCTCCATCAGCATCCATGTATCTT GCTTGTCATTTTCTCTGTTGGTTACAATTACTTTATTATG GTTGACATCTTGGCAGGTTCCATGATGAGTGATTTCAGT AGTGGTCACTGTCTGTGGTGCTGGGGATAGCCAGGAGCT GAATGACCAGGGTCTGGTAATGCTTCTGGGCATCGGTG AACTGAGACTGTATTTTCCGCTTGTCATCATCTCCAAAC ATCTCTAAGCCTTGGCTATTTCTGATGAACTCTTGGCAC TGTAACTCAAGGTCGGATAT |
| 345 | ADXCRA D_CF2721 04_x_at | HIST1H2AJ | Sense | histone cluster 1, H2aj [Source:HGNC Symbol;Acc:4727] | 345 | CAACTATGCGGAGCGGGTCGGTGCTGGAGCGCCGGTG TACCTGGGCGGCGGTGCTGGAGTACCTGACCGCCGAGA TCCTGGAGCTGGCTGGCAACGCGGCCCGCGACAACAA GAAGACTCGCATCATCCCGCGTCACCTCCAGCTGGCCA TCCGCAACGATGAGGAGCTCAACAAGCTTCTGGGCAAA GTCACCATCGCACAGGGTGGCGTCCTGCCCAACATCCA GGCCGTGCTGCTGCCCAAAGAAAACTGAGAGCCACCACA AGACTAAGTAAAGACCGAGTTGA |

FIG. 7-89

| | | | | |
|---|---|---|---|---|
| 346 | ADXCRPD.15112.C1_s_at | KIF21A | Sense | kinesin family member 21A [Source:HGNC Symbol;Acc:19349] | 346 | CATATTTCAGCGGATCATCAACTTTTCTCCTACCATACTATCCTCAGACAAAGAGAAACCATTGAAATTATAGACCTAGCNNNNNNNNNNNNNNNNNNNNNNNNNNNNNNNNNNNNNNNNNNNNNNNNNNNNNNNNNGTGGCTGGTAAAGAGGATAATACAGACACTGACCAAGAGAAGAGAAGAAGAAAGGGTGTTTCGGAAAGAGAAAACAATGAATTAGAAGTGGAAGAAAGTCAAGAAGTGAGTGATCA |
| 347 | ADXCRPD.1233.C1_s_at | MRPL52 | Sense | mitochondrial ribosomal protein L52 [Source:HGNC Symbol;Acc:16655] | 347 | TGCTCTTAAACCCAAAGGGGCTTCACTGAAGAGCCCACTTCCAAGTCAATAAAAA |
| 348 | ADXCRPDRC.462.C7_at | NCRNA00188 | AntiSense | small nucleolar RNA, C/D box 65 [Source:HGNC Symbol;Acc:32726] | 348 | CTTCTCTTGGGCTGAGATGCTGCTGCCAGTCTCTAAAACAGCACTCGTTCTCAAAACCTCAGGCAGGCTCCTGGCTCCAATACTCAGCTGCCAAACATGATGCTGATTCTTCACGAATTTGCAACCCAGTTCTCTCGGGTTTGCACACCCCCACTGTGGGCCGGGGAACCGGTCCCGGCCCTTGCGCAGACTCCAGGCTCTGGCAGATGTGGCCCTCCATAACAACGGGAATGAAAAGGTCACACCTTATGTGCGCCAGGCCCTTAAGGAGTCGGAATATCCCAATCCTCC |
| 349 | ADXCRAG_AB082533_at | SGK269 (Entrez) | Sense | Tyrosine-protein kinase SgK269 (EC 2.7.10.2)(Sugen kinase 269) [Source:UniProtKB/Swiss-Prot;Acc:Q9H792] | 349 | TGCTGTGGTACTTTGCTGTGTACTCCGTGGCATCATGTTACTGTGTA |

FIG.7-90

| | | | | |
|---|---|---|---|---|
| 350 | ADXCRAD_BX111719_x_at | TAF15 | Sense | TAF15 RNA polymerase II, TATA box binding protein (TBP)-associated factor, 68kDa [Source:HGNC Symbol;Acc:11547] | 350 | GGAGTTTGTGACTAGATGGGCAATATAGTAAGATGTCAT CTTTTAAAAATGAAAAAATTAGCTGGCCACTGTGGCACA CGCCTGTAGTCCCAGCTACTTGGGAAGCTGAGGTAGGA GGATTGCTTGAGCCCAGGAGTTCAAGGCTGCAGTGAGC TATGATTGTGCTTATGAATAGCCACTGCACTCCAGTCTG GGCAATAGTGAGTCGGTCAAATTCCATTTCCCCCTCCG CCCCATACCTCTTCAAATGTTTAA |
| 351 | ADXCRAD_BU192598_s_at | ICAM1 | Sense | intercellular adhesion molecule 1 [Source:HGNC Symbol;Acc:5344] | 351 | CACTTCCTGACGGATGCCAGCTTGGGCACTGCTGTCTA CTGACCCCAACCCTTGATGATATGTATTTATTCATTTGTT ATTTTACCAGTACTATTTATTGATGTCTTTTATGTAGGCTA AATGAACATAGGTCTCTGGCCTCACGG |
| 352 | ADXCRAG_BX647167_s_at | ANXA4 | Sense | annexin A4 [Source:HGNC Symbol;Acc:542] | 352 | AGCCTAGGCAATGCAGGAGGCCTTGTCTAGAAAATTT AAAAAAAAAAAAAAATTAGCTGGGCGTGGTGGCACG TACCTGTAGTTCCAGCTACTCGGGAGGCTGAGGCAGGA GGATCTCTTGAGCTAAGTAGTTCGAGGCTGAAGTGA |
| 353 | ADXCRAD_AK092750_x_at | EHBP1L1 | Sense | EH domain binding protein 1-like 1 [Source:HGNC Symbol;Acc:30682] | 353 | TTAGCCAAGTATGGTGGCACGCGCCTGTAATCCCAGCA ACTTGGAAGGCTGAGGCAGGAGGAATCGCTTGAACCTGG GAGGCAGAGGTTGCAGTGAGCCAAGATCAGACCACTAC CGCCCCGCGCTGGCTTGCCCTCCTGTTCTCCAGAGCAA TAAAGTTGGACGAGAGACTACCC |
| 354 | ADXCRIH.1053.C1_a_t | PIGR | Sense | polymeric immunoglobulin receptor [Source:HGNC Symbol;Acc:8968] | 354 | CACAGCTCTTCTTGGCGTATTTATACTCACTGAGTCTTA ACTTTTCACCAGGGGTGCTCACCTCTGCCCCTATTGGG AGAGGTCATAAAATGTCTCGAGTCCTAAGGCCTTAGGG GTCATGTATGATGAGCATACACACAGGTAATTATAAACC CACATTCTTACCATTTCACACATA |

FIG. 7-91

| 355 | ADXCRP D.16386.C 1_x_at | RHBDD1 | Sense | rhomboid domain containing 1 [Source:HGNC Symbol;Acc:23081] | 355 | GGATGGCACCATGTTTGAGAGGCTACAGAGAGGAGACCCA GAGCCAGTAAGCAAGACATAGAGTTTATAGAGAGGACT TACAGCATAGTCCAGTGGCAGCGGGCTAGACAGGAGAA CCGCAATGGCTTGAAAAGCACGAAGTATAAAGCGTTG AGCTCAACGGTTTATACTTCAGAGAAACTCAACAATCAA CTGAAGGCACTAACTGAGAAAACAAAGAACTTGAAATG GCTCAGGATCGCAATATGGCCATTCAGAGCCAATTTACA AGACCAAAGGAAGCATCAGAAGCTGA |
|---|---|---|---|---|---|---|
| 356 | ADXCRIH. 2179.C1_a t | NBN | AntiSense | nibrin [Source:HGNC Symbol;Acc:7652] | 356 | ATTTCTTTAGCTGACCATAGTGAGTCTTCCTTGAGTTCA CGTTTCTTCCTCCCAATTTCATTTCTTGAGATATTTTGCTAC TTTCTGGTACTGCTTCATCACTGAAAGTGTCATTTGTTTC TATATCCATCCTTGGCCTTTTCTAACATTGACATCTTCC TCCTGTTTTTGAACTTTCACATCAATTTCTAACTCTGGTT TTGTGTCCTTGAATAACTGTTCCAATACTTCATCTTCTAT GGCCACACATCATCCATT |
| 357 | ADXCRA D_CN311 761_s_at | ZNF655 | Sense | zinc finger protein 655 [Source:HGNC Symbol;Acc:30899] | 357 | GTATCAAATTCACGCCATGCAAAAAGATTATAAATGTAAT AAGCATGTATGTGTGAGGAGATTCAGTCATAACCCAA CGCTCATTCAACATCAAAGAGAATTTATACCTAAGAGAACT TATTTGGGTGTAGTAAATGGCAGATCTTTCAATAGGAGT TTAACTAGTCTTTGTCATATCAGAATATCCATAGTAGACA AGAATTTGATGTAACGCAAAATGGAAAACTCGACACCAC ATTTCAGGCTTTACCCAACATCGAAATAAT |

FIG.7-92

| | | | | |
|---|---|---|---|---|
| 358 | ADXCRAD_BE467688_s_at | CCND2 | Sense | cyclin D2 [Source:HGNC Symbol;Acc:1583] | 358 | CGTTCAGTACAAACATTTATGCGGTAGGCTCAGATGTTGTAATTTGCACTTAGGTACCAGGTGTCAGGAAACAGACTAAAAAGAATTCCACCAGGCTGTTTGGAGATCCTCATCTTGGAGCTTTTTCAAAGCGGNGCTTCATCTGCAAAGGCCCTTTCATCTTGAAGTTTTTCCCCTCCGTCTTTCCCCTCCCCTGGCATGGACACCTTGTGTTTAGGATCATCTCTGCAAGTTTCCTAGGTCTGAATCTGCGAGTAGAGATGAACCTGCA |
| 359 | ADXCRPD.11405.C1_at | NAA50 | AntiSense | N(alpha)-acetyltransferase 50, NatE catalytic subunit [Source:HGNC Symbol;Acc:29533] | 359 | GTACCACAAAACACACTCAACTTGTCTATGAATTAGAGAACAAGATACTGCTGCTGCTCTTTTTGACTTTTGAAATATACAATGTTTTGTAGGCTCTGCCCTTCAATGTGAAAGCAGGACATTAAATTTGAAATTATTTGACAATTAAATGTTTAGGACCATCTAACTTCAACTTCAAAACTAAACAGATCTACCTTGTCCTTC |
| 360 | ADXCRSS.Hs#S812597_at | RP11-1415C14.3 (Clone_based_vega_gene) | AntiSense | glucuronidase, beta pseudogene (LOC653391), non-coding RNA [Source:RefSeq DNA;Acc:NR_029426] | 360 | ATTACAGTTATAGCTCTCTCAAGCAAAAAACAGCAGAGAAAAACTTAGTTACCTTAGGGCTATTATTTACTTAGGGATTTGTTAAAAGGTCGAATGGGGTCACACAGAATACTAAGAAGAGCTGTTCACCCAGGCCTCACTAAGAACTCTTCTTCATTCAGTAGCTGTATAGTAACATGAC |
| 361 | ADXCRIH.949.C1_at | N/A | No Genome match | N/A | 361 | CTTTAGTAGTTTCTCGTCAGTCCCGCAGCCACCGCAGCCGGGTCCCCCCTCGTG |

FIG. 7-93

| | | | | |
|---|---|---|---|---|
| 362 | ADXCRPD.4532.C1_at | Sense | DUOXA2 | dual oxidase maturation factor 2 [Source:HGNC Symbol;Acc:32698] | 362 | AGAGAGGGGCTCACCTCTTATCCTCGGCGACCCACTG CACAAGCAGGCCGCTCTCCAGACTTAAATGTATCAC CACTAACCTGTGAGGGGACCCAATCTGGACTCCTTCC CCGCCCTTGGGACATCGCAGGCCGGGAAGCAGTGCCCG CCAGGCCTGGGCCAGGAGAGCTCCAGGAGGCACTG AGCGCTGCTGGCGCGAGGCCTCGGACATCCGCAGGCA CCAGGGAAAGTCTCCTGGGGCGATCTGTAAATAAAC |
| 363 | ADXCRPD.13185.C1_s_at | Sense | GNL1 | guanine nucleotide binding protein-like 1 [Source:HGNC Symbol;Acc:4413] /// Guanine nucleotide-binding protein-like 1 (GTP-binding protein HSR1) [Source:UniProtKB/Swiss-Prot;Acc:P36915] | 363 | CTGAATGGGCAGAGCTGGATTTTACAGGGTTGGGATTT TGCCAGGTGAGTAAGATAGAGGGGAGAAGTGGGACCA GGAAGTTCCAGGTCTGTGAACGGGCCTGGCTGAGGAG CTGGATCATGAAATCGAGTCAAGTAAGAAGGAAATTG AGGACACGAGTTGGGTATTGCATAGTGTTACTGTTAA GGTCAGGGGTCAAAGACTTACTGGCATGGAGTAACCAG AGTAAGTG |
| 364 | ADXCRAD_CN481679_s_at | Sense | MARS | methionyl-tRNA synthetase [Source:HGNC Symbol;Acc:6898] | 364 | CAGGCAAAAACGTCCCGAAGCCAGCAGTTGTAGAGAC TGTTACAACAGCCAAGCCACAGCAGATACAAGCGCTGA TGGATGAAGTGACAAACAAGGAAACATTGTCCGAAAA CTGAAAGCACAAAAGGCAGACAAGAACGAGGTTGCTGC GGAGGTGGCGAACTCTTGGATCTAAA |

FIG. 7-94

| | | | | | |
|---|---|---|---|---|---|
| 365 | ADXCRA D_BX1168 94_x_at | EIF2C2 | Sense | eukaryotic translation initiation factor 2C, 2 [Source:HGNC Symbol;Acc:3263] | 365 | CAGAGTCCCGTGTGTCCTAAAAATCTCCTAAAACCAGTC TATGAACTCAGGGCTTTAAAACATTTTAATTTATTTGGT CATTCAATTTACTTGTTTTAATACATGATTCTCTATGAAA TTGATGGGCTCAAACTAGCTGTGAATCTTGAGAGTGA AAGCAACA |
| 366 | ADXCRIH. 179.C1_at | NET1 | AntiSense | neuroepithelial cell transforming 1 [Source:HGNC Symbol;Acc:14592] | 366 | TATAAAGTAACCCTATGATGCTCCCCTTACGAGAAAACA AAACTGTACACATTTATAAACAACAGTCTCTCCCATCA GTTAACACACAGAGCCTTCTCTACACCAAAGTCTCTTTC CGTTTGCCACCAGAAAGGGCTTTGTCCCTCGCTCTTCG GATGCCGGGCTGTGTCTGGTGTGTCTTAAGCTCTTGC TGTCCTCTGCCATCTGCATGCCAGAGCCACATCTGTAA GCGTTTTCATCAACTTCTACCTGAGTAACACTGGAAACT GTCCTCGTGC |
| 367 | ADXCRA D_BG772 667_s_at | C11orf35 | AntiSense | Uncharacterized protein C11orf35 [Source:UniProtKB/Swi ss-Prot;Acc:Q8IXW0] | 367 | ACAGCTCCTTTGACCTCAGTGACAGGCACTCACCTACC TGACCCCCAAACTGAAGCCTCACTTTTCCCAGCCGTGT CCACACCCTCTGGGCTACCCCATTACCATGACAAGTATT CCCTCGCTCCAGGAGAAAAGCCAGGTCCCAGACCTGA CCCATTAAAACCCAATCATTCCA |
| 368 | ADXCRA D_BE1385 16_at | ATL2 | AntiSense | atlastin GTPase 2 [Source:HGNC Symbol;Acc:24047] | 368 | GACCAGGAAGTCCTATAAAGAATTATATTTCTATAGAATT AAAAATGCAGTTCTGTCAGCCTGGACAAC |

FIG. 7-95

| | | | | | | |
|---|---|---|---|---|---|---|
| 369 | ADXCRP D.14668.C 1_s_at | TBL1XR1 | AntiSense | transducin (beta)-like 1 X-linked receptor 1 [Source:HGNC Symbol;Acc:29529] | 369 | ATAAGAACTTATGGGATTTCCTACACGGAGACAAAAAA GATATTCCTTTATGTNGTTTAAAAGTGGCAGCTGCTCTT TCTTTATTCCATTTTAATCAATGAGTATTGATTCAAGTTT CCTTTCTATTTTCCTTATGATAAGTTTCTACAGTAGCT TATACAACAACAAATAGCATAGAGAAAACTACTGGATTCA AT |
| 370 | ADXCRP D.11100.C 1_x_at | N/A | Sense | non-protein coding RNA 152 (NCRNA00152), transcript variant 2, non-coding RNA [Source:RefSeq DNA;Acc:NR_024205] | 370 | ACAGGTAACCTTCTCACTAAGTGGGGTGTCTGAGGCC AGGGAGAGCTCTACTCATTCCCCTGTGTGATCCCAGCA GTGAGCATAGAGCAGGTGCCCTGCAATGTTAAGC |
| 371 | ADXCRA D_CB0552 15_at | BMP2 | Sense | bone morphogenetic protein 2 [Source:HGNC Symbol;Acc:1069] | 371 | AGAAAGAATAAAGCAGGATCCATAGAATAATTAGGAAA ACGATGAACCTGCAGGAAAGTGAATGATGGTTTGTTGTT CTTCTTTCCTAAATTAGTGATCCCTTCAAAGGGGCTGAT CTGGCCAAAGTATTCAATAAAACGTAAGATTTCTTCATT |
| 372 | ADXCRA D_BP2850 69_at | IFIT3 | Sense | interferon-induced protein with tetratricopeptide repeats 3 [Source:HGNC Symbol;Acc:5411] | 372 | GATTGCTGAGCAGGAAGCTTTGCATGTTGCTCTAAGG TACATTTTTAAA |

FIG.7-96

| | | | | |
|---|---|---|---|---|
| 373 | ADXCRAD_BE6446 66_at | BMPR1A | AntiSense | bone morphogenetic protein receptor, type IA [Source:HGNC Symbol;Acc:1076] | 373 | CACCCCATGCACTGTACAAATACTGCAAACACTATAGTT GCATTCATAGGACCATTAAAAAAAA |
| 374 | ADXCRAD_AW979 272_s_at | BICD1 | Sense | bicaudal D homolog 1 (Drosophila) [Source:HGNC Symbol;Acc:1049] | 374 | TTCTGAGGGACTGCTTCTGGAGCCGGCCCTCTTGTGTG ATTGAATTAGTCAGTGATGGTTCTCAGGACTAGATTAGA TTGTTACTCTTAAAATAA |
| 375 | ADXCRPD_2443.C1 s_at | TCEB3 | Sense | transcription elongation factor B (SIII), polypeptide 3 (110kDa, elongin A) [Source:HGNC Symbol;Acc:11620] | 375 | GGCCGCTTCAGACAACCACCTGAAAAAGCCAAAGCACA GAGACCCAGAGAAAGCCAAATTGGACAAAAGCAAGCAA GGTCTGGACAGCTTTGACACAGGAAAAAGGAGCAGGAGA CCTGTTGCCCAAGGTAAAAGAGAGAAGGGTTCTAACAACC TAAAGACTCCAGAAGGGAAGTCAAAACTAATTTGGATA GAAAGTCACTGGGCTCCTCCCTAAAGTTGAGGAGACA GATATGGAGGATGAATTCGAGCAGCCAACCATGTCTTTT GAATCCTACCTCAGCTATGACCA |
| 376 | ADXCRAD_AL1575 11_at | SNAPC3 | Sense | small nuclear RNA activating complex, polypeptide 3, 50kDa [Source:HGNC Symbol;Acc:11136] | 376 | ACAAACTGGAATTAGGATTTTCTCCTGATGAAGGAAAAA AGACATTAAGTCTGCATTATATTTTTAAACCCATGAAAAG ACTGAAACAACCAACAAACAAAGAAAAACTTGACTTGTTA TTAGAACAGTCATTCATTATTATTTTTCTTCTTCAAAACTGT TATTTTACCATGTTGTATCTTCTTCCCAAAGTAATATGCA GATGAAGCAAAATAACTCAGCAAGTGTCATGGACCAA GCCCTTTCCATCATTTCTAGCATTAAAGTGAA |

FIG.7-97

| | | | | | |
|---|---|---|---|---|---|
| 377 | ADXCRSS.Hs#S1862874_at | SND1 | Sense | staphylococcal nuclease and tudor domain containing 1 [Source:HGNC Symbol;Acc:30646] | 377 | TGGATGTGTTGCTGTTGGCCAAGAAGAATGAGAAGGAGCGAATTTGGGCAGTGGGACCTCCAGGCAGCCAGCCTTACAGTTTTCAGTTGGGGAGTGAGATGAGACCTGGAATTTAGGGGTCTGTGTAGTTAAAACCATGCGGTGTACAAGATTGCCCAGATTGAGTATGTGGAAGGTGTGATGGGAGGAGAGAGAGTGTTAGGAAGTGCTGGGGTCCTGCCATCTGAGAACAGGAGCCCAGAGGCAGCATATGCAGCCCGAAGGAGAGAATCCATGCTGAGGGTCGTGAATAC |
| 378 | ADXCRPDRC.7243.C1_x_at | ECE1 | Sense | endothelin converting enzyme 1 [Source:HGNC Symbol;Acc:3146] | 378 | GAGAAACAGCTGTCACCTCCCGCAGACCCTAATCCTCTCTCGC |
| 379 | ADXCRAG_BC039833_at | RNF44 | Sense | ring finger protein 44 [Source:HGNC Symbol;Acc:19180] | 379 | AATATTGTTGCTGATTCAGAGGGATATTCACTAATAAATGTAT |
| 380 | ADXCRPD.12441.C1_s_at | CCDC55 | Sense | coiled-coil domain containing 55 [Source:HGNC Symbol;Acc:25305] | 380 | ATTCTGAATCATCACTGGGAGCAAAACACAGACTCACAAGAGGAAGGGCAAGAGAGAAGGGTAAAGAACAAGAGAGACCACCTGAGGCAGTGAGCAAGTTTGCAAAGCGGAACAATGAAGAAACTGTAATGTCAGCTAGAGACAGTTGGCAGGCAGATGGCGCGGGTTAATGCAAAGACCTATA |
| 381 | ADXCRPDRC.10493.C1_at | PPFIBP1 | Sense | PTPRF interacting protein, binding protein 1 (liprin beta 1) [Source:HGNC Symbol;Acc:9249] | 381 | ATTGCTTGAACTGGGTAACTGATTTGATGTAAATGCCAAAGGAGAAGGAGTAAAAGGAAAATGACATAGAGTCTGAGCTAGAGTAACAGGGACAGTATTAATTAATATTAACCAAATATCAAATAAGAACATTTAAGAGACGAGCCACCATG |

FIG.7-98

| | | | | |
|---|---|---|---|---|
| 382 | ADXCRPD.14444.C1_at | PRKDC | AntiSense | protein kinase, DNA-activated, catalytic polypeptide [Source:HGNC Symbol;Acc:9413] | 382 | CTGCTGTGGTGTTATTTGCTTAATGGACCATTTAAGGAATTCTCGAATACACCGACCACACAAAATCTCTTAAAGTACTGTCAACAGGGTCCACATTCCATCCAATATAGCTTCTAGTAAGGCAACAGTATCCTGACTTTCAAATTTCTTGTTATGTGAACCAGTGAATCAGCTGCATAACTAGTGGCTCATACAGTTGCCTTGTCACCTGATCAACATCACACGCAAGTCGAAGCAGCACAGGAAACGTCCGCTTATAGAGCTGGTACA |
| 383 | ADXCRAG_NM_194428_at | DHX34 | Sense | DEAH (Asp-Glu-Ala-His) box polypeptide 34 [Source:HGNC Symbol;Acc:16719] | 383 | CTGAATTTGCCCATCCACCTGGTCACTTTGAGAGTTGTGCAGGGGGGCTGGGAGCACTGGTGTTCACGTGGGACCACAGGCTGCACCATAAGACCCACTCACAATAAAAAAATAAAAGGCCGAGCCGGGCATGGTTGCTCACTCCCGTAATAAAAAATAAAAGAACAGGCTGAGCCGGGAAA |
| 384 | ADXCRAD_BE644666_x_at | BMPR1A | AntiSense | bone morphogenetic protein receptor, type IA [Source:HGNC Symbol;Acc:1076] | 384 | CCAGAAAAAGCACCCCATGCACTGTACAAATACTGCAAACACTATAGTTGCATTCATAGGACCATTAAAAAAAAGAGCCAAATTACAAAACAATCTATATTTACAAACATTTCAGTTGGGTTCTTAAGCTAAAGATATTACTGTTTACTTTGGTACGATAACTAGAAAAACACAAACATTATGCTCCAGA |
| 385 | ADXCRSS.Hs#S3018206_at | MYO10 | Sense | myosin X [Source:HGNC Symbol;Acc:7593] | 385 | TCTTTGTCCTGGTCGTCTTGGTAAATGTGAGTCGCGTATCTGAGACATAGATTGTGCTTTATTCGGTGCTGCTGTGGAGAGTAGAACTAGCAGCAGTACCTGGAAAGGGCCCTGATCTGCGGGTGTGGATGAGTAGTAGAGACTCTTCAGTTGAGATTTAGCTCTAGTGAGGGTTGGGTGCAACAAATGTAGGAAAGAGTGAAGAGATGAGCAGCTCATGTCTGAGTTTATTCTGTTTCTGTTACTGTGTCACAGACCAGCCTCAGATCATAGTTCATGAT |

FIG. 7-99

| 386 | ADXCRA D_BF5155 92_x_at | YPEL5 | AntiSense | yippee-like 5 (Drosophila) [Source:HGNC Symbol;Acc:18329] | 386 | GCTCATTGCTGACTGTTTCCTTAAAAGCTGGGAAGCT GTGGGTCAATTCAGCTCGCCACCTGTTTCTGTACTGCC CACAAGCTGAGAATGAATTTTGTACTTTTAAATGGTTGG GGGGAGGGGAGAATATTTTCTGACACAAGATATATGAC ATTCACACTTGAGTGTCAAAGTTTTTAGGAACACAGCCA CGCCCATTTGTTTACACTTTACTCCTTCCACTTTACAATG AAGAGGTATGAGGAGCTGCTACAGAAACCTTCTGGCTT GCAAAGTTTA |
| 387 | ADXCRA G_BC015 944_s_at | TIA1 | Sense | TIA1 cytotoxic granule-associated RNA binding protein [Source:HGNC Symbol;Acc:11802] | 387 | ATTTTGGAGAAAAATACGCTAGATTTTAAATGTTAGAGCT GTTCCCGGAGACTTATTGCAGAAATAGATGAGAAGCAA ATCAAGACTACTATTC |
| 388 | ADXCRSS .Hs#S218 3619_at | SIPA1L3 | Sense | signal-induced proliferation-associated 1 like 3 [Source:HGNC Symbol;Acc:23801] | 388 | GCTGACAGTGAGTACTGATGGCCTGGATGTAGGGGTGA GAGAAAGAGAGGGGCTAGGATGACCCTGAGGTTTGG GCCTGACCACCAGCTGAGGGGTGAAGATACTGCATTGA GGGACCCCAGGGTCGGGGGTTTGCAGGGAGTGGCCAGA AGGCCTTGTGAAGAATCAGAGACGTGGCTGAGTCTGTT CGGTGCTGGGTGCCCGTCAGACAGTGCCTGAGATGG CAAGGAGACAGTTGGATACGCATACCTGAAGTTGAGAG AG |

FIG.7-100

| 389 | ADXCRP D.2761.C1 _s_at | SMARCC1 | Sense | SWI/SNF related, matrix associated, actin dependent regulator of chromatin, subfamily c, member 1 [Source:HGNC Symbol;Acc:11104] | 389 | ACTGCCTGGCAGAGAACATACCACTGAACTAGTATGTGCTA GAGGAGGGCACAAACATCCGCTCCTTCCCTAGGCCTGC TGGCTCTGGTTTCTATGCAGATGATTCATTGGATTGGG GGTGAGTGTTTTGTTTTTCTGGGGGCAGTGTGAGCTTTG AGGGTTGGAATATTGGGAGGCATTCCTTAGTTTCCTCAA CTAGCCTGGAAAGTTAGGAGTCTAGGGTAATTACCCCC CAATGAGTCTAGCCTACTATTCACTGCTT |
|---|---|---|---|---|---|---|
| 390 | ADXCRA D_BX1040 39_s_at | CYP1B1 | Sense | cytochrome P450, family 1, subfamily B, polypeptide 1 [Source:HGNC Symbol;Acc:2597] | 390 | AAAGCTGTGTTTATATGGAAGAAAGTAAGGTGCTTGGAG TTTACCTGGCTTATTTAATATGCTTATAACCTAGTTAAAG AAAGGAAAAGAAAACAAAAAACGAATGAAAATAACTGAA TTTGGAGGCTGGAGTAATCAGATTACTGCTTAATCAGA AACCCCTCATTGTGTTTCTACCGGAGAGAATGTATT |
| 391 | ADXCRP D.12476.C 1_x_at | ASPH | AntiSense | aspartate beta-hydroxylase [Source:HGNC Symbol;Acc:757] | 391 | AAAGAACTTCTATCCAGAATGCATAAAGAATTACCGCTC AGCAACAAAAAACAATAAAATTAGAAATGGGCAAAAAG AAACTTCACTAAAGATAATGGGTGTAGCCAATAAGCACA AGAAAAGTGCTTGACATCATTATTCATCAGGGAATTGC AAATGTAAACTACAGTAAGAAGCCACGGCATACCCACC AGAATGGCTAAAATTAAAAAGACTGACACCACCAAATGT TGGTACATATGTAGAACAACCAATTCCACACATAG |

FIG.7-101

| | | | | |
|---|---|---|---|---|
| 392 | ADXCRA D_AL8335 13_at | EEA1 | Sense | early endosome antigen 1 [Source:HGNC Symbol;Acc:3185] | 392 | TTTTATAGCGTGTAGTTGACCCTTGAACAATTTGAGTGC CAACCTCCTGTGCAGCTGAAATTCATGTATAACTTTGA CTCCCCAAAATTTAACTACTAATAGCCTATTGTTGACC AGAAGCCTTACCTACTATATATAAACAGTTGATTCACACAT ATTTTGCATGTTATATATATATTATATACAGTATTCTTTT TCTTTTGCACATTAAAAAAGACATTTATTCTGCATCATGA TCAGACTTACATTTAGCAATCAACA |
| 393 | ADXCRA G_BC017 424_s_at | KIAA1217 | Sense | KIAA1217 [Source:HGNC Symbol;Acc:25428] | 392 | GAGGTGCATGATATTGTTAGCCAAAAGGGAGAAGACAT ACAGACGGTTAATATCGATGCCAGAAAAGAGATGACCC CCCGACAAGAAGGGACTGACAATGAGGATCCAGTCGTG TGCCTGGACAAGAAACCAGTGATCATCATTTCGATGAG CCCATGGACATCCGGTCTGCCTATAAGAGACTTTCAACT ATCTTTGAGGA |
| 394 | ADXCRP D.6743.C1 _at | INPP4B | Sense | inositol polyphosphate-4-phosphatase, type II, 105kDa [Source:HGNC Symbol;Acc:6075] | 394 | GAGGAGTCGAACATGATCTTGAGGACTCTACTCTTGGA GGCTTAAAGGAATGTGTTGTCTGTAATTGTCACAGGGAA TCAGGAAGGAAGAGCCAGTTAGGGTCAAGCGTTAGAAT ATGTTAAGCTTAATAGGCTTTGACACTCAGATGTGCCCA TCAAGCAGTTAGGAATTGGATTATTTTGTTGGAAGAGG TCAGAACTAGTCAAGAGATTTCATAGTCCTTGGTAAA |
| 395 | RDCR342 _D10_x_at | GFPT1 | AntiSense | glutamine--fructose-6-phosphate transaminase 1 [Source:HGNC Symbol;Acc:4241] | 395 | CAGAATTCTATGCTTCTCTGGCAACAACAATAACTATTA GAAAATCTTAACCTCACCCAGAAGTTNNNNNNNNNNN NNNNNNNNNNNNNNNNNCAGCTTACTTAAATAAT TGTGCTAAATAGCTTATCTTCACAATTTAAAAGTAAAAAC CTTTGAAAAGAAGAAGGACTTCACCAAAAACAAACACTC TCCCTATAGCCCTGAAGATCTGGCCAGAAAAGCTCCAT TAA |

FIG. 7-102

| | | | | |
|---|---|---|---|---|
| 396 | ADXCRPD.8154.C1_s_at | RP11-294O2.2 (Clone_based_vega_gene) | Sense | Novel processed transcript. | 396 | GATAATAACCTTTAATGAACTCAATACTCGGGAAAGGCTTCACATTTCTGGGACTCAGCATTTATCCAAAATATCTATTAAGAGCCATACACCATTCTAGCTGCAATTGATTATACAAAAAAAANGACCAAAGTGGTTACAATAATAAAATAGAACACAGAGAAGAAGAAAACTACATGTGTTACAATTTGGTAAGATAAACAAACAAACAACAAAAATTAATCACTTTTTTGGTCCTGTGACACACATGATAATTTTGTCTTAATTCTCCTAACAAATGA |
| 397 | ADXCRAD_AI820050_at | MMP25 | Sense | matrix metallopeptidase 25 [Source:HGNC Symbol;Acc:14246] | 397 | CGGCAGGGTCCTGGATCACCAAGGACCTTGAAAGCATGTGGAAGACTTTGATCAATGGGGAATCATTAAGGGGTTTTGCATTCCGGAACTATCATCAGCTTCAGCGGGGGGCAGGGGGTAGGATAGAGGCAGGAGGCAGGAAGTTCTCGCAGGGTCCAGGCAAGAGATGGTGGAGTGTGGTCCTGGGGAAGGGGGCAGTGGACGGATCTGAGGGAGGTTCAGTTAGGATGGGCAAGGATTGAGATCTGGCTGGATCC |
| 398 | ADXCRAD_CD672976_at | ARHGEF2 | Sense | Rho/Rac guanine nucleotide exchange factor (GEF) 2 [Source:HGNC Symbol;Acc:682] | 398 | GGGACATCCGAAAGTCTACACCACCAGATGCCAGTGGTTCATGCCTTCTTCCCGCAACTTTAGGAAAATTTATTTATTTATTGTTTATTAGTTATGGGGGAGAGGGGAGATTTAAAGGACCAGGAGGACATGGAACCAAGCCATAGGGATCAGAGGGCCTTGTCCTTGAACACTACTGGGGTATATTCAGGCTCATCCACGCAG |

FIG.7-103

| 399 | ADXCRA D_BX0928 82_at | MSX1 | Sense | msh homeobox 1 [Source:HGNC Symbol;Acc:7391] | 399 | CAGGCAAGAGAAAAGCGCAGAGAAATCGGTGTCTGACGAT TTTGGAAATGAGAACAATCTCAAAAAAAAAAAAAAAA AAAAAAAAAAAAANGAAAAGAGAAAAAAAGACTAGCCAG CCAGGAAGATGAATCCTAGCTTCTTCCATTGGAAAATTT AAGACAAGNTCAACAACAAACAAAACATTTGCTCTGGGGGC AGGGAAAACACAGATGTGTTGCAAGGTAGGTTGAAGG GACCTCTCTCTTACCAGTACCAGAAA |
|---|---|---|---|---|---|---|
| 400 | ADXCRIH. 2218.C1_a t | CAPN12 | Sense | calpain 12 [Source:HGNC Symbol;Acc:13249] | 400 | AGAGCAGGAGAGACGGCAGAGATATGTTGCTAGGTGAA TATATATTTATATAATAAATCCGTAAGTTAATAAAGTAAAT AGTAATTCTCTG |
| 401 | ADXCRA G_NM_02 5168_s_at | LRRC1 | Sense | leucine rich repeat containing 1 [Source:HGNC Symbol;Acc:14307] | 401 | GTATGGACTGAGAGGCATTTAAATTCTGGCAAGGGAGG TGGAAATGCTGACAATGAGGAGGAAGCTTATAGTGGGT CAAACAAGGAGGTGTCTAGTGTGTTGTTTAAAAGAAGG CTTACAATTAGCCAGGC |
| 402 | ADXCRP DRC.1038 0.C1_s_at | WHSC1 | Sense | Wolf-Hirschhorn syndrome candidate 1 [Source:HGNC Symbol;Acc:12766] | 402 | TCCCAAGGTCGCTAGAAACTCGTCTTCGCGTTGCCCC CTTTCTGGCTCTCAGCGCCGTCGCCACTCGGGAGAGG CTGGGTGAGGCCCGTGTGAGGACTGACCCTGGATTCCT CGAAACTGCCATTGTGATCATTACTCTGCTCTTTGGAAA TGGCTG |

FIG.7-104

| 403 | ADXCRA G_BC015 714_s_at | PHF21A | Sense | PHD finger protein 21A [Source:HGNC Symbol;Acc:24156] | 403 | GTTACATGAAATAGTGCCAGCTGGAGGTTCTTTGCCAG CACCATGCCAAGTGAAGTGAAATAATATATTACTCTCTATTA TACACCAGTGTGTGCCTGCAGCAGCCTCCACAGCCACG ATGGGTTTGTTCTGTTTCTTGGGTGGGGAGCAGGGA CGGGCGGAGGGAGGAGAGCAGGTTTCAGATCCTTACTT GCCAGCCCGTTGTTTGGTTAGGTAGAGAAGACAAGTCCAAA GAGTGTGTGGGCTTTCCTGTTTCTAAACTTTCGCTACTA TA |
|---|---|---|---|---|---|---|
| 404 | ADXCRP DRC.1379 6.C1_at | SH3D19 | Sense | SH3 domain containing 19 [Source:HGNC Symbol;Acc:30418] | 404 | TGTCTGTGCCTCATGGAATTGCCAATGAAGATATTGTCT CTCAAAACCCCGGAGAACTCTCTTGTAAGCGTGTGGGAT |
| 405 | ADXCRA G_BC064 577_at | CPNE7 | Sense | copine VII [Source:HGNC Symbol;Acc:2320] | 405 | CCCTGTGCTTTTGCCGTCGGCCTCTGCACCTGGGTC CATGGGGTCTGCGGGGTCTGCGGGGTCTGCCTGGCCT GTGGGTTCTGCGCCGGTGGGGGCTTCAGGAGTAATAAAGTG TCACCCTATCCTTGTAAA |
| 406 | ADXCRP D.14989.C 1_s_at | IGF2 | Sense | insulin-like growth factor 2 (somatomedin A) [Source:HGNC Symbol;Acc:5466] | 406 | GGCCATCCGAAAATAGCAACAACCCAGACTGGCTCCTC ACTCCCTTTTCCATCACTACTAAAATCACAGAGCAGTCAGA GGGACCCAGTAAGACCAAAGGAGGGGAGGACAGAGCA TGAAAACCAAAATCCATGCAAATGAAATGAAATGTAATTGGCAC GACCCCTCACCCACCCCAAATCTTACATTCTTATGCATGCCAATCCT AAAAAGCACTCATACTTTATGCATCCCCGCAGCT |

FIG.7-105

| | | | | |
|---|---|---|---|---|
| 407 | ADXCRPD.14930.C1_at | DHRS11 | AntiSense | 407 | dehydrogenase/reductase (SDR family) member 11 [Source:HGNC Symbol;Acc:28639] | GATATTTGTCTATGAACAGTAGCACAGACCCTCTAATTCCATAGGGAATCATTTCCATGACTTCCCCCAAATACCCTACTCTTCTCTATCTCTGTGACAGTCTCTGGCCCTGCTCCCTCCTAAACTGCTCAAAATCCTTACCAAAATGGCTTACAAATCTCTCCTCCTCCGG |
| 408 | ADXCRAG_AK091465_at | LARP1 | Sense | 408 | La ribonucleoprotein domain family, member 1 [Source:HGNC Symbol;Acc:29531] | CCCTGTGGATCCCAACCAGGAAGTTCCTCCTGGGCCACCTCGGTTCCAGCAAGTTCCTACGGATGCCCTGGCCAACAAGTTGTTGGTGCTCCTGAGCCCTCCACCATCGCCCGCTCTCTACCAACCACTGTCCCAGAGTCACCAAACTACCGCAACCAGGACCCCTGCACTCCCCGGACCACCAGCTCAAAGACTCAAGCCAGACATCACGGTTTTACCCAGTGGTGAAAGAAGGACGGACACTGGATGCCAAGATGCCTC |
| 409 | ADXCRAD_AA702187_at | ZXDC | AntiSense | 409 | ZXD family zinc finger C [Source:HGNC Symbol;Acc:28160] | TATAGTTCTGTTGTAGGCTACACATGAACAGCAACCAAAAAGAGGAAAAATCTTCTTTGTCCCCATGCTTTTCCTTGAATTCTGCACTTTTCATATTAACATTAGCCCTTGCTTTGTGATTTGCCTTTGCTTTATTTTACCCTGTCTTAATCTTAACCTTCCCAAATATTTCCATACAGGGTGCACCTCTCCTAGACAACACACAGCGGAGAGTGTGCTTCCCATGTATTCAATCTTCGTCTCTTGAAAGGAGAGGTGCCCTCATTACACTTCACTGTGACACAGGATACCCTTGGTTT |

FIG.7-106

| | | | | |
|---|---|---|---|---|
| 410 | ADXCRP D.8783.C1 _at | NOTCH2 /// NOTCH2NL | Sense | Notch homolog 2 (Drosophila) [Source:HGNC Symbol;Acc:7882] /// Notch homolog 2 (Drosophila) N-terminal like [Source:HGNC Symbol;Acc:31862] | 410 | ATGGAAAAGAACACGATGAGAATTAGACACTGGAAAATA TGTATGTGGTTAATAAAGTGCTTTAA |
| 411 | ADXCRA D_CR740 197_s_at | BBS4 | Sense | Bardet-Biedl syndrome 4 [Source:HGNC Symbol;Acc:969] | 411 | TCAGGTTGTGAGGTTTATTAGTCCCCAAGGCAAACACAA ATATTAGATTAATCCAACTTAATAGTATACATTTAAA AGAAAAAAACAAAAGCCCTGGAAGTTGAGGCCAAGCC TGCTGAGTATTGCAGCTGCATTTGCCCAAAGGAATCC AGAACAAGTCCCCTGTGTATTTTGTTCTTGAGAGGGGT CAGTCTAGAAGCTAGATCCTATCAGGATGAGGAGCAGC AGCCCAGGGCTTGTCTGTCGGATCAGCACCAGATTTAA AGA |
| 412 | ADXCRA D_AL0440 78_at | HNRNPL | AntiSense | heterogeneous nuclear ribonucleoprotein L [Source:HGNC Symbol;Acc:5045] | 412 | GTGGTGTTCTTGATGTAGTGAGCTCAAGTCTGCGGCTG TTTCTGGGACGTGGTGGAGGCTGCATGTTCTGTTCTC TCCAGGAAGAGCTAGTGGTTTTCTACCCTGTGTTGGT GAGCAATGTGCAGAGGCAGAGCCGCTGAAGTATGGTTC CTGAGGGGTGGCGAAGCACCACCGCCCCTCACTCCAGTCA CCTCATCAGCCTCGTTTTTTTGGGCCCCACCTTGGG GCTTGCCAAACTGAGAGGCATTCAAACCATGGCAC |

FIG.7-107

| 413 | ADXCRA D_CF1274 03_at | TMEM53 | Sense | transmembrane protein 53 [Source:HGNC Symbol;Acc:26186] | 413 | AGGACGCGGGCTCTCGCTGGCCCGAGCTCTACCTCTA CTCGAGGGCTGACGAAGTAGTCCTGGCCAGAGACATAG AACGCATGGTGGAGGCACGCCTGGCACGCCGGGTCCT GGCGCGTT |
|---|---|---|---|---|---|---|
| 414 | ADXCRIH. 766.C1_s_ at | CLPTM1L | Sense | CLPTM1-like [Source:HGNC Symbol;Acc:24308] | 414 | GAAGCATTTGGAGGAATTCCTAGACATTGCGTTTTCTGT GTTGCCAAAATCCCTTCCGACATTTCTCAGACATCTCCC AAGTTCCCATCACGTCAGATTTGG |
| 415 | ADXCRA G_NM_19 4428_x_at | DHX34 | Sense | DEAH (Asp-Glu-Ala-His) box polypeptide 34 [Source:HGNC Symbol;Acc:16719] | 415 | ATGTCTCCAGATTCCAGGTGCAGGTTCTTAGCACCTCC GCAGCCGCTCTCTCTTGAGTCCATCCAGTCTCTCCTA CCCCTTGAAGTAGGGGGACCCTGAATTTGCCCATCCAC CTGGGTCACTTTGAGAGTTGTGCAGGGGGCTGGGAG CACTGTGTGTTCACGTGGGACCAGGCTGCACCATAAG ACCCACTCACAATAAAAAATAAAAGGCCGAGCGGGC ATGGTTGCTCACTCCCGTAATAAAAATAAAGAACAG GCTGAGCGGGAAA |
| 416 | ADXCRA D_BG696 656_s_at | FCGBP | Sense | Fc fragment of IgG binding protein [Source:HGNC Symbol;Acc:13572] | 416 | TGTGATTGTCAGCAATGACCATGCTGGGAAACTGTGTG GGGCCTGTGTGGAAACTTTGACGGGACCAGACCAATGAT TGGCATGACTCCCAGGAGAAGCCAGCGATGGAGAAATG GAGAGCGCAGGACTTCTCCCCATGTTATGCTGATCAG TCATCCACCAGGAACGAAGATTTCCTGAAGAAGACCTG GTCCCTCTGGAGGTTGCGGTGGCTGAAGGATGCATCAT GTGCTCCTCACCCTGCTCTACCGCTTTTCTGGGTCACA |

FIG.7-108

| | | | | |
|---|---|---|---|---|
| 417 | RDCR333_A08_s_at | C1orf27 | Sense | Protein odr-4 homolog (hODR-4)(Transactivated by transforming growth factor beta protein 1)(LAG1-interacting protein) [Source:UniProtKB/Swiss-Prot;Acc:Q5SWX8] | 417 | ACATTGGAAAGTTAAGAGAGTTCGAGGGAAGAATTATAA AGACTAGGAGTCCTAGAAAGAGAAAATTTAGAGAATAAA AGGAGAGGCAGTACTTGAAAGATAACACAATTTTACAA ATTTGTTGGAAAAACATGAATTCATAAATTCAGGAAGCA CAATATATACCCAACATATATTTAAATAAAATCCAGGCCT AGACTCA |
| 418 | ADXCRIH.2331.C1_x_at | G3BP2 | Sense | GTPase activating protein (SH3 domain) binding protein 2 [Source:HGNC Symbol;Acc:30291] | 418 | TTCCCCCTTTGAATGAGGTCTTCCATGTTTGAGGGAAAG TCTTGCACTATTGCATATATTTTGGGGACACAGATTTTCA TAGTTTCCATTTTTGGGGGCTTAAGGANNNNNNNNNNN NCTGTTTGAAACAGTTTTATACTTTCTGATATAGTACTTG AAATTCTTACCAGAAAATTACTTTGGAGTTTTGAAGCCTT TATTAATACTACTTTTAAAGAAGCAGTTGTTTTATTGTCA ATGTTTTTTTCCCCACGCATATTTCTTGTATTTC |
| 419 | ADXCRAD_AL5833 62_s_at | BUB3 | Sense | budding uninhibited by benzimidazoles 3 homolog (yeast) [Source:HGNC Symbol;Acc:1151] | 419 | TGAGATGGTTTGATGGTTTGCTGCATTAAAGGTATTGG GCAAACAAAATTGGAGGGCAAGTGACTGCAGT |

FIG. 7-109

| 420 | ADXCRSS.Hs#S775346_at | NR6A1 | AntiSense | nuclear receptor subfamily 6, group A, member 1 [Source:HGNC Symbol;Acc:7985] | 420 | TACTAACTTTCCTGCGACTAAACCACCAAGTCTGTCTCCT CTGCAATGTGTAGTTCCTGATGGCTCCGGTTTTCCCCC CACCTTTTTATTTTGAAGCCTGACTTGCAGGAGATACCC CTCTAACTGTATAGCTTCCTACTCCATTAAAGATTAGTCA GAGATGGTAATCAACCCACCTGAGCTCTTTCACTACCTG CTGCTGCAACTATGGTCAGGATAAGGGGAGCACACTCA CACTTCAGGCCTTCACGTCTGTTCCAGTTACTTTT |
|---|---|---|---|---|---|---|
| 421 | ADXCRAG_NM_002526_at | NT5E | Sense | 5'-nucleotidase, ecto (CD73) [Source:HGNC Symbol;Acc:8021] | 421 | CTTTTGAACCACTTTGCAATTGTAGATTCCAACAATAAA ATTGAAGA |
| 422 | ADXCRAG_NM_145754_s_at | KIFC2 | Sense | kinesin family member C2 [Source:HGNC Symbol;Acc:29530] | 422 | GGACTAGGAAGGGCTATTCCAGGCTCAGCCCTGCTCCT GCAGCTTTGCCGCTGAGTGTAGGAAAAACAGGCATGAC AGACCAGGGTGAGGGTTGTGCCCAGCTGGGCCACGGC CATGCGTGGGGTGGCCAATAAACACCGTGGACTCC |
| 423 | ADXCRPD.7912.C1_x_at | MTA2 | Sense | metastasis associated 1 family, member 2 [Source:HGNC Symbol;Acc:7411] | 423 | TTTCTCTTTCTGTCCGGTGTCCGGACTTTCCTAATTGGA GTTTGAGGCCCCTAAGCTGGCATCAACCCAGGCCACG CTCGCTCTTTCCTCCCTCCCCTCCCCTCTGCCTTTG TACGCCAGTTCTCAGAAATAAAGATCTTTTGTCCGTTTTT TTAACCTCGGATTCTGTAATTGGTTCTTA |
| 424 | ADXCRPD.11100.C1_at | AC068491.1 (Clone_based_vega_gene) | Sense | non-protein coding RNA 152 (NCRNA00152), transcript variant 2, non-coding RNA [Source:RefSeq DNA;Acc:NR_024205] | 424 | CCACAGGTAACCTTCTCACTAAGTGGGGTGTCTGAGG CCAGGGAGAGCTCTACTACTCATTCCCCTGTGTGATCCCCAG CAGTGAGCATAGAGAGCAGGTGCCCTGCAAT |

FIG.7-110

| 425 | RDCR269_G02_at | PPP2R2D | Sense | protein phosphatase 2, regulatory subunit B, delta isoform [Source:HGNC Symbol;Acc:23732] | 425 | CCCCCATGCCCTGTGGGAGATGGAGGTGTGTGCTGATCCCTCGTGCCCCTGTGGGAGATAGAGGTGTGTACTGATCCCCTGTTCCCCTATCTAGATGAAGGTGTACTGCTGATCCCCCGTCC |
|---|---|---|---|---|---|---|
| 426 | ADXCRPD.15397.C1_at | THBD | Sense | thrombomodulin [Source:HGNC Symbol;Acc:11784] | 426 | TTTTTGACAGTGTTGAAAATGTTCAGAAGGTTGCTCTAGATTGAGAGAAGAGACAAACACCTCCCAGGAGACAGTTCAAGAAAAGCTTCAAACTGCATGATTCATGCCAATTAGCAATTGACTGTCACTGTTCCTTGTCACTGGTAGACCAAATAAAACCAGCTCTACTGGTCTTGTGGAATTGGGAGCTTGGGAATGGATCCTGGAGGATGCCCAATTAGGCCTAGCCTTAATCAGTCCTCAGAGATTCTTC |
| 427 | ADXCRPD.7988.C1_s_at | AL354822.1 (Clone_based_ensembl_gene) /// AC145212.2 (Clone_based_ensembl_gene) | Sense | Putative uncharacterized protein ENSP00000383640 [Source:UniProtKB/TrEMBL;Acc:B7WNX9] /// Known protein coding. | 427 | CCCACTCTGTGTAGTCTTAACTATTTCTTCTAAACTCACCATTAACCTAAATAATAGTCAAATTTAGGGGGCTGTATTTGTCTTACTCGAGTCTTCTACCATAGTTGAAACTGTCGTACCCAAACGAGTTACAGAGAAATGCCACACTTTGAGACGAATTCAGGAGTCCTTTATTAGCTGGTGACTGAGAGACGGCTAACACAGGAAATACTCTCGGCCCTAAAGAATGGGCTA |

FIG.7-111

| 428 | ADXCRA G_X81197 _at | ARCN1 | Sense | archain 1 [Source:HGNC Symbol;Acc:649] | 428 | GAAGACGCCAATGATGGCTGAAGAGTTTTTCCCAGATTT ACAAGCCACTGGAGACCCCTTTTTCTGATACAATGCAC GATTCTCTGCGCGCAAGGACCCTCGACTCACCCCATG TTTCAGTGTCACAGAGACATTCTTTGATAAGGAAATGGC ACAAACATAAAGGGAAAGGCTGCTAATTTTCTTTGGCAG ATTGTATTGGCCAGCAGGAAAGCAAGCTCTCCAGAGAA TGCCCCAGTTAAATACCTCCTCTACCTTTACCTAAGTT GCTC |
| 429 | ADXCRIH. 2554.C1_s _at | CPEB2 | Sense | cytoplasmic polyadenylation element binding protein 2 [Source:HGNC Symbol;Acc:21745] | 429 | TGATCTGGTCAGTAGTGGAATTCGATTTTATGCAGACTG GATGTAATATTTGTAATCCCTGTGCAATTTTGTGACGTG CGGTTCTAATTCATGTGCAGTGATATAGTATAGATAAAA GAATGAGTAAAAGAAAATACAAGAATTCTAAAGAAAGTT GGTTTTAGCCCCTTTGATAGTCCATGGTTAAGACATCCT TTATAAACCAAAGATGGCCAGCACACTG |
| 430 | ADXCRP D.5.C1_at | WBP11 | Sense | WW domain binding protein 11 [Source:HGNC Symbol;Acc:16461] | 430 | CAGAAGAGGGCTCAACTTAGCCAATATTTTGATGCTGTC AAGAATGCTCAGCATGTGGAAGTGGAGAGTATTCCTTT GCCAGATATGCCACATGCTCCTTCCAACATTTTGATCCA GGACATTCCACTTCCTGGGTGCCCAGCACCACCCTCTATC CTAAAGAAAACCTCAGCTTAGCCTATGGACCTCCAACTCGGG CCAGTTTCTATCTTCCCTCCTTCTTGGACATGGGGGT TTCCACCGTTTGCCCCCCTGGCAGAAAAACCCTCCCTGG GCCT |

FIG.7-112

| | | | | |
|---|---|---|---|---|
| 431 | ADXCRP D.11028.C 1_at | MMP1 | AntiSense | matrix metallopeptidase 1 (interstitial collagenase) [Source:HGNC Symbol;Acc:7155] | GAGTCCAAGAGAATGGCCGAGTTCATGAGCTGCACACG ATGTAAGTTGTACTCTCTGAAATTGTTGGTCCACCTTTC ATCTTCATCAAATGAGCATCCCCTCCAATACCTGG |
| 432 | ADXCRA D_BG258 265_at | DOK3 | Sense | docking protein 3 [Source:HGNC Symbol;Acc:24583] | GAGTCACGAACCTTATTCTCCAAAACAAAAGCAACAAGG ACTTTGACTTCTCAGCAGCACTCAGCTCTGGTTCTTGAA ACACCCCGTTACTTGCTATTCCTCCTACCTCATAACAA TCTCCTTCCCAGCCTCCTACTGCTGCCTTCTCTGAGTCT TCCCAGGGTCCTAGGCTCAGATGTAGTGTAGCTCAACC CTGCTACACAAGAATCTTCTGAAAGCCTGTAAAAATGT CCATGCATGTTCTGTGAGTGATCTACCAA |
| 433 | ADXCRA D_BQ016 677_at | POLR3A | Sense | polymerase (RNA) III (DNA directed) polypeptide A, 155kDa [Source:HGNC Symbol;Acc:30074] | CCGGGGTAGCCATTGGTTCTTGGATCTGTGTTAGAATG AGTGCTTTCCCTTCCTACTGATGTGATTGTGATTAGGA ATTCGTGACCGAGTGATTTTTGGCCAGTGGTTGGGTTTA AAATTCTATTAAAATTTGTAGTTGGGCTGGGGTGCT |
| 434 | ADXCRA D_BP3766 05_s_at | GLUL | Sense | glutamate-ammonia ligase [Source:HGNC Symbol;Acc:4341] | GTGGAGGCCCATTACCGGCCTGCTTGTATGCTGGAGT CAAGATTGCGGGGACTAATGCCGAGGTCATGCCTGCCC AGTGGGAATTTCAGATTGGACCT |

FIG.7-113

| | | | | |
|---|---|---|---|---|
| 435 | ADXCRPD.11491.C1_at | ATP2B4 | Sense | ATPase, Ca++ transporting, plasma membrane 4 [Source:HGNC Symbol;Acc:817] | 435 | TTCATTTTCTTCCCCTCTGCTAGTTTGGAAGTTATATTA TACCAAGTTTTTAGTATTAGCCTAGAAATCTTAACATAA AGACTTCTAATAAGCAATATCTTTAATTTTTTTNCCTAC CCAATACTAGATCATGAGCATTTTCCCACATCATAAAGA ATTGGTCACAAGTCAGCCCCAAACATAGTCCAGTGGAA TCCAATGATA |
| 436 | ADXCRPD.11413.C1_s_at | C8orf38 | Sense | UPF0551 protein C8orf38, mitochondrial Precursor (Putative phytoene synthase) [Source:UniProtKB/Swiss-Prot;Acc:Q330K2] | 436 | AAGGCAACACTTCTGTCAGTAGAATTGCTTTGGATTGTA AATATGTTTACTTCAGAGGAAATCAGTCAGAGTGGATGG CTCAGCAAAACCCATCACAACTGCGGAAAAGGAAGTG ACTGGCTAGAGGTAAGGAAATAGATTTTCTCTAAGTTAA CTGGCCTACGTGTGAATCGAACCCTGCCACCCTGGCCTC ATTAGCACCAACACTGTGAAGAACAGCTGTGGCAGAGA |
| 437 | ADXCRAG_AB0825 33_x_at | SGK269 (Entrez) | Sense | Tyrosine-protein kinase SgK269 (EC 2.7.10.2)(Sugen kinase 269) [Source:UniProtKB/Swiss-Prot;Acc:Q9H792] | 437 | TTCACCCCTCTACTTACATATTGTAAAGTTGTATAAATCT ATCATTGAAAGGTCCCCTCTGCCAGCAGTGGTGCCACC CTTTGGTTTGCTGTGGTACTTTGCTGTGTACTCCGTGGC ATCATGTTACTGTGTA |
| 438 | ADXCRPD.7912.C1_at | MTA2 | Sense | metastasis associated 1 family, member 2 [Source:HGNC Symbol;Acc:7411] | 438 | TTTCTCTTTCTGTCCGGTGTCCGGACTTTCCTAATTGGA GTTTGAGGCCCCTAAGCTGGCATCAAC |

FIG.7-114

| | | | | |
|---|---|---|---|---|
| 439 | ADXCRSS.Hs#S1924022_at | N/A | No Genome match | N/A | 439 | TACAAAGAGTACCACGAGACACGAGAAACCTTGTGGGAACACAGGGGGACCACCCCCTAAGGCTAAATACTACTTGGTGACCGATAGCGAACAAGTACCGTGAGGGAAAGGTGAAAGAACCCCGAGAGGGAGTGAAAAGAATCTGAAACCTAGTGTTTACAAGCAGCGAAAATGGCACAAGCCATGAATCGTGTACTTTTTGTAGAACGGGCCAGCGAGTTATGACAAAA |
| 440 | ADXCRPD.11083.C1_at | DSP | Sense | desmoplakin [Source:HGNC Symbol;Acc:3052] | 440 | TCTCTTCCGAGGTCGAGGCCCTGAGGCGGCAGTTACTCCAGGAACAGGAAAGTGTCAAACAAGCTCACTTGAGGAATGAGCATTTCCAGAGGCGATAGAAGATAAAGCAGAAGCTTAAGTGAAAGCAAAATACGAAATTGAGAGGCTGCAGTCTCTCACAGAGAACCTGACCAAGGAGCACTTGATGTTAGAAGAGAACTGCGGAACCTGAGGCTGGAGTACGATGACCTGAGGAGAGAACGAAACGAGCCCACAGC |
| 441 | ADXCRPDRC.1676.C1_at | PER1 | Sense | period homolog 1 (Drosophila) [Source:HGNC Symbol;Acc:8845] | 441 | CATAGCCAAGGCTTCAAGCTCTCAGGACTTGGCTATGGAGGAGGACGAAGAAGGCAGGAGCTCATCCAGTCCAGCCTTACCTACAGCAGGAAACTGCACCAGCTAGACTCCATTCTGGGACCATCTCCAGGAGTCCATGAGAGGCTTTCTTCTCCTATGTCCCAATTCTCAGAACTCAGATGTGGCTAGACCAACCCCTGGGAAACTGCCCCAGCTTCTCCCACCATAGGGGCCGGACCCCATCACCAGCCTAGATCCAGGGCTGCCTC |

FIG.7-115

| | | | | |
|---|---|---|---|---|
| 442 | ADXCRP DRC.3805 .C1_s_at | JUN | Sense | jun oncogene [Source:HGNC Symbol;Acc:6204] | 442 | AACTTGTGCGCGCAGCCCAAACTAACCTCACGTGAAGT GACGGACTGTTCTATGACTGCAAAGATGGAAACGACCT TCTATGACGATGCCCTCAACGCCTCGTTCCTCCGTCC GAGAGCGGACCTTATGGCTACAGTAACCCAAGATCCT GAAA |
| 443 | ADXCRA D_BQ673 982_s_at | C9orf3 | Sense | Aminopeptidase O (AP-O)(EC 3.4.11.-) [Source:UniProtKB/Swiss-Prot;Acc:Q8N6M6] | 443 | GTTTTGAGATCATACACTGTTACAGAGAAAGAGAGGAG GCATATTATNAACGTGTGGACTTCAGTGTTATTCCTTCT CTTCAAAATGATGTTCCAGTGTCTA |
| 444 | ADXCRP D.9576.C1 _x_at | PICK1 | Sense | protein interacting with PRKCA 1 [Source:HGNC Symbol;Acc:9394] | 444 | CTCGGGCGGCCTTTATTTATTCTGTTCCCCAGCTCGGC CACTTCTCTGAAGGAGGGCTGGGTTCTGGGCCTGTATC GAATAAACACAAACCTGGATGGCGC |
| 445 | ADXCRP D.18146.C 1_s_at | SERPINE1 | Sense | serpin peptidase inhibitor, clade E (nexin, plasminogen activator inhibitor type 1), member 1 [Source:HGNC Symbol;Acc:8583] | 445 | GGAGGATGGTCAGGCGTCACCAACAACCCATCACCCA GTAACAAGAACCTTGACTCTCGTCAGTCCCTCTGCATCA AGACACTTACCCATTTCCCACCTCATGCCTCATGCTAACTTG AATGAAACAATCGCTGGGAAAGCATTAA |

FIG.7-116

| | | | | |
|---|---|---|---|---|
| 446 | ADXCRSS.Hs#S297 8758_at | FNDC3B | Sense | fibronectin type III domain containing 3B [Source:HGNC Symbol;Acc:24670] | 446 | ATGTGAGAGTGCTTTGCAGTTGGAAAGTGCTGTAGGAA CCCTGAATTCATCTGAAACTGTAGCTTAGTGTTAAATG ATGTCTGTTATTACTTTTTGAATAGTCTGGAGTGCTTGT TAAAGAAAAAATTATTCTGTGATATTTGTTGAATGAAGCA CAGTGAGGAGAGACTTTACTCAGGGCCCTGTAATAGCT ATAGGGACCACTGCAATAGGGTCTTGCAGTGGGGAGA GAGAATAGGCTCAATTCTGAATACATCATCATGGGCAAG TGGG |
| 447 | ADXCRA D_BX0942 82_at | GGCX | Sense | gamma-glutamyl carboxylase [Source:HGNC Symbol;Acc:4247] | 447 | TCTAAAGCTGTTTTTAACTCCGAGATTACAACTTAGAGG AACCAAGGA |
| 448 | ADXCRA D_AA1795 10_at | N/A | No Transcript match | N/A | 448 | AAATTGAAGGATTTGCTGTTATTCCTACCTGCATTGGAC TTGACCTGGGTGTTGGGTGGGTGAGTAGCAATCTGTTACTGTT TCTCTATGTGGACGATGAGGAAAGGGTTGAGAAATCCA GCGAAAGGACACTTCTGTTAATAGCTCAATCTGCTGCCC ATGGTTGGGAAAA |
| 449 | ADXCRA G_AJ2707 78_s_at | TCF7L2 | Sense | transcription factor 7-like 2 (T-cell specific, HMG-box) [Source:HGNC Symbol;Acc:11641] | 449 | TTTTTCTGTATGAAACCCAGATGTCACCAAATGGACATT AATAGTTGCATTAAGGATCAGTAGCATTAACAAAGTTG CTTTAAAAGCCATTATGTAAATCAAGACTTGAAAATGAGT GAGGGAATTTTAGCGACACTGTCTGAGCA |

FIG.7-117

| 450 | ADXCRA D_AW771 618_at | PRPF40A | AntiSense | PRP40 pre-mRNA processing factor 40 homolog A (S. cerevisiae) [Source:HGNC Symbol;Acc:16463] | 450 | TGAATTCCCAACTTTCCGAGATGTTGTTTAATGAGACTC ACCCTTATTTTCAATTCTTCCTTCATTCTCTCCCTCTTA ACTGGTTTCCTCTTCACCCAAGAAAAGCCTTTCTCTTAAC TGCAAGCTTATTTGAATTTTACCTTATTGAATATCTTTCA ACTATTTGGCAGACCTTTAACTTTCCCTACCATGCCAAT GGTCACTAAACACCTTAAATGCCACTCTTAACACCTTAA ATGCCACCCTTAACAGTATTCTTTCAGTCCTCATTC |
|---|---|---|---|---|---|---|
| 451 | ADXCRA D_BQ898 896_s_at | ARHGAP4 | Sense | Rho GTPase activating protein 4 [Source:HGNC Symbol;Acc:674] | 451 | TGTCCAGCAAGTGCAGGGTGCCTGCACTTCACCCTGTG CAGAGAGGTGGGATGGGGCCGTGCACACAGGGATGCC CGCTCCACATCCTGCCTGCCCCTCAGCCTGCTGGCCAG GCCCCTTTTGGAGGCAGCTGAGGAAGGATGCTGGGGA AAGCCCTCTCTGCGAGCTTTGTGGAAGGCTGATCAGTG GCTCTGGGTGGGCGGGTACCCTTGCTCAGATGCCTGG CAGGGCTGGGGTGGCGATTCATAAAGACCTCGTGTTGAT TCCCC |
| 452 | ADXCRP D.9582.C1 _s_at | SESN2 | Sense | sestrin 2 [Source:HGNC Symbol;Acc:20746] | 452 | CAGGAGAGAAGAGGCCCCGGCATGGGGATCTGGGTTC TAGAGGGCATGTGATGACTGTAAATGTTCACTGGGTGG GTAGGGAGTGGTATCCAGTGTTCAAGTGCAGAAATCTTT GGCTTTGCTACCAGTTCCATATGA |
| 453 | ADXCRA D_AW661 890_at | TFAM | AntiSense | transcription factor A, mitochondrial [Source:HGNC Symbol;Acc:11741] | 453 | GGTTAATCTTTGTTACTAGCCCTCACTACTCAGAATTGG TGAGACCTCTCCATTCTGCTTCACTCAGCTTACGTGGT TTGCTCACACTGACACAACAACACACCTGTCAATCCCTA TGTCCCTCCTGTCTTCCAAAAATACCTAGAAATTGCTGC TCTATTGACGGTAGTATTTC |

FIG.7-118

| 454 | ADXCRA D_AA8308 54_s_at | RNF145 | AntiSense | ring finger protein 145 [Source:HGNC Symbol;Acc:20853] | 454 | GCTCTAAAAGTTATGAACCTGACATTCTTGGTCTTACAC AATCTGGACCCAGTCTACTCTTCTATAACCATCTTCCAC TTAATTTACAAATCTTTATTAAGGCACAGGTACTCCTACT TATCCCCTATTGCCTCTCTCATGCTGAATCAATCATGCC AAAAGCTAAGAAAACATGAGACATGCTTGGGACTAAAGAA ACAGAACTGAGGATTTCCTACACATCCTAACTGCAAGGA CAGTCCATCAAAAGCCAGAGA |
|---|---|---|---|---|---|---|
| 455 | ADXCRA D_CB9973 64_s_at | FLT1 | Sense | fms-related tyrosine kinase 1 (vascular endothelial growth factor/vascular permeability factor receptor) [Source:HGNC Symbol;Acc:3763] | 455 | GGAAGCTTTAGCTACCAATCCAGTACCCTCCTAACTAGA ATGTATACACATCAGCCAGGACTGACTGACTACTTCATT AGAGATATACTGTACTCATTGGG |
| 456 | ADXCRA D_CX1658 54_s_at | Z83843.1 (Clone_based_ ensembl_gene) | Sense | Novel long non coding RNA. | 456 | TACCTGTGGTTCCAGGTACCTGGAGGGCTGACGTAGGA GGATTGCCTGAGCCCAGCAGCCCAAAGCTACAGTGAG CTGTGATTGTGCCACTGCACTCCAGCCTGGGCGAGGAG AGCAAGACTCTGTCTCANAAATAAATACATAAAATACAG CGTCCAAAAGTGTGTCATCTTCTCTTCTTCACAATTTTA TAATAAGGGGGTAAAATGCCTGTGAGTCTATTCATTAT |
| 457 | ADXCRA D_BM128 089_at | APOL2 | Sense | apolipoprotein L, 2 [Source:HGNC Symbol;Acc:619] | 457 | CTTTGGACTAAAGAATATATTGGGCGAAGAATAGAGGG |

FIG.7-119

| | | | | |
|---|---|---|---|---|
| 458 | ADXCRAD_BX106190_at | ZFAND3 | Sense | zinc finger, AN1-type domain 3 [Source:HGNC Symbol;Acc:18019] | 458 | TTCTGCTTTTCCTGTTCCCTATCCTTACGCAGGATTGTTTTACTGTTAGCCAGGTTAAGTTTAAGCTTCTTGAGGACTTTAGTACTGAAAGACAATGGCTCACTTGTAAGACCTAGTTGAAGAGTACAGATTTAGATTTGTTCAGTGTGCTGTG |
| 459 | ADXCRPD.2974.C1_s_at | LRRFIP2 | Sense | leucine rich repeat (in FLII) interacting protein 2 [Source:HGNC Symbol;Acc:6703] | 459 | AACATATGTGTAGTGTGCTGCAGCATAAGATGGAAGAACTTAAAGAAGGCCTGCGGCAAAGAGATGAGCTTATTGAGAAACATGGCTTAGTTATAATCCCGATGGCACTCCCAATGGTGATGTCAGTCATGAACCAGTGGCTGGGAGCCATCACTG |
| 460 | ADXCRIH.638.C2_at | CEACAM6 | AntiSense | carcinoembryonic antigen-related cell adhesion molecule 6 (non-specific cross reacting antigen) [Source:HGNC Symbol;Acc:1818] | 460 | AAGCTTTTAGAGAGAATACACTACACCAGGGAGTATGACTACTAGTATGACTATTAGGAGGGTAATACCAAGAGTTGGACTACGCACCTTAGGCAAGATAACAAACAACTAAAATAGAATAAAGAATGAGTCAGATGAGTGTAGCCATTTAACCAAGCAGCACATTTGTTAATTTCTACAACTTAGTCTCAGCGATACCCATTGTATTAGCCATGTTCAACAACAAGTGTCAGAAACTGCACAGACTCCTCCCTGTTCAGCTGGTAG |
| 461 | ADXCRPD.14645.C1_s_at | RERE | AntiSense | arginine-glutamic acid dipeptide (RE) repeats [Source:HGNC Symbol;Acc:9965] | 461 | CTTTGTCCGCTGCTGTCATGATTCGCCACGTGCCTTCTTGTCCTCTCACGGCTAGGCCTCCAGTGAAAGGTAGACAGTAAGCCTGGGCATTCAGTCTTCTGAATTTCTCACATCAATTCCAGGGAAAATCCAACCACTCCAACA |

FIG.7-120

| | | | | |
|---|---|---|---|---|
| 462 | ADXCRP D.12819.C 1_at | SMURF2 | Sense | SMAD specific E3 ubiquitin protein ligase 2 [Source:HGNC Symbol;Acc:16809] | 462 | ATCCAGCAAGGAATAGTGCAGCACCTAGGGACTAGCAA TGATAGGAAGTTGCACCATATTTGGCCCAGCAAGGGCA AAGGGAGAGAGTAGTTGTGTGGAGTCCAGAGAGACCCT GGTTGTTGCTTCTCATTTATTGAACCCGATTTAAAGCCA GAGAACAAAGAGCCCAGTTTATGTAGTACATGACGCAG CCTCCTAGGCACAGGGTAAAGGATGGAGAATAGATCTG GAGGATTAAATAGTAACAACAACGCGCGAGATCCTCTAA GTC |
| 463 | ADXCRP D.1255.C1 _s_at | CCDC90A | Sense | coiled-coil domain containing 90A [Source:HGNC Symbol;Acc:21097] | 463 | TTGAGAACAGAAATAGTGGCATTGCATGCCCAGCAAGA TCGGGCCCTTACCCAGACAGAGGAAGATCGAAACTG AGGTTGCTGGCC |
| 464 | ADXCRP D.18183.C 1_at | RAB11A | Sense | RAB11A, member RAS oncogene family [Source:HGNC Symbol;Acc:9760] | 464 | TATTTCTTATGCTGTCAGATTACATTTTCCTTTGAGTGC TTTGGGTGCAGCCGTGGAATCCTGATGTAAAGCATAG GTTCTTGCATTACTGAGTAAACAT |
| 465 | ADXCRA D_BM128 089_x_at | APOL2 | Sense | apolipoprotein L, 2 [Source:HGNC Symbol;Acc:619] | 465 | GCAGATGGCAAGTGCACCAAGGAGAAGGCAGGAACAC TGGAGCCTGCAATAAGGGAGGAGAGGGGACTGGAGAG TGTGGGGAATGGGAAGAAGTAGTTACTTTGGACTAAA GAATATATTGGGCGAAGAAGATAGAGGGGGAGCTTGCAGG AACCAGCAATGAGAAGGCCAGGAAAAGAAAAGAGCTGAA AATGGAGAAAACCAGAGTTAGAACTGTTGGATA |

FIG.7-121

| | | | | |
|---|---|---|---|---|
| 466 | ADXCRSS.Hs#S3007624_x_at | CTBP2 | AntiSense | C-terminal binding protein 2 [Source:HGNC Symbol;Acc:2495] | 466 | CACCCTTCTTGACCACAAAAAGGTGGCCATCCTGACTG GTCTCTACCTTCAGGAAAACAAATGGGGACCTGAGGGC GCTCAACCACCCAGACCACCCAGAAGTCACAGGAGCA CGGAACAGGAAGCAGGAGACAGCACACAGTAAGCAC ATGGCAAGCACACAGTAAACACACGGCAAGTACATGGC AAATACACAGCAGGTACACAGCGAGCACACAGTAAGCA CACGGTAAACACTCAGCAAGTACATGGCAAATGCACAG CAGGTACACAGCGAGC |
| 467 | ADXCRAD_AK024315_x_at | WDR45 | Sense | WD repeat domain 45 [Source:HGNC Symbol;Acc:28912] | 467 | CCCGGGCCAGGCAAGGTGGGTCACACCTGTAATCCCA GCACTTTGGGGAACAAGGTGGGAGAATCACTTGAGTCC GGCAGTTTGAGACCAGCCTGGCCAACATAATGAGACCG CATCTTCACAAAAATATGT |
| 468 | ADXCRPD.9576.C1_at | PICK1 | Sense | protein interacting with PRKCA 1 [Source:HGNC Symbol;Acc:9394] | 468 | AGCTCGGCCACTTCTCTGAAGGAGGGGCTGGGTTCTGG GCCTGTATCGAATAAACACAAACCT |
| 469 | ADXCRPD.4701.C2_s_at | GBP1 | Sense | guanylate binding protein 1, interferon-inducible, 67kDa [Source:HGNC Symbol;Acc:4182] | 469 | ACTTCAGGAACAGGAGCAACTACTAAAGAGGGATTTC AAAAAGAACAGCAGAATAATGAAAAATGAGATACAGGATC TCCAGACGCAAAATGAGACGACGAAAGGCATGTACCATA AGCTAAAGACCAGAGCCTTCCTGTCACCCCTAACCAAG GCATAATTGAAACAATTTTAGAATTTGGAACAAGCGTCA CTACATTTGATAATAATTAGATCTTGCATCATAACACCAA AAGTTTATAAAGGCATGTGGTACAATGATCAAAA |

FIG. 7-122

| 470 | ADXCRAD_BF7268 49_x_at | TLCD2 | Antisense | TLC domain containing 2 [Source: HGNC Symbol; Acc:33522] | 470 | GCCCAGCCTGGATATTTAAATTGTTCTGTGTCTCCTCC TTTTTTCTCTCTGTGATTCTCTTTGTCAGTCCTTGC CTATATTTGCATCTCAGTTGACACCCTGATTCTGACTT GTCCTTATCTTCCTACCAGTCTCTGCCGA |
| 471 | ADXCRPD.13978.C 1_s_at | PEX5 | Sense | peroxisomal biogenesis factor 5 [Source:HGNC Symbol;Acc:9719] | 471 | GTAGGAGTGCTCATGGTTCTGTCATTCTTGGACCTCTCC TGGCTGAGCTCTGATTCCCTGTGAGCACGATGCTGATG CAATAGTCCTGTGTCATCACTGCAGCGGTCCTCAGGAG CTGCCAGGGCCAATTGCTACAGAGAGTGTCTGGGTGTGT GCATAGGAGGAAGGTTTGCTTGTGAAATGAGGCT |
| 472 | ADXCRPIH.928.C1_s_at | SORD | Sense | sorbitol dehydrogenase [Source:HGNC Symbol;Acc:11184] | 472 | ATCTACGCCACTGCTCGTCGGTGGGACCCTCGTGCTGT GGGGCTGGGCTCTGAGATGACCACCGTACCCTACTG CATGCAGCCATCCGGGAGGTGGATATCAAGGGCGTGTT TCGATACTGCAACACGTGGCCAGTGGCGATTTCGATGC TTGCGTCCAAGTCTCTGTGAATGTAAAACCCCTCGTCACC CATAGGTTTCCTCTCGGAGAAAGCTCTGGAGGCCTTTGA AACATTTA |
| 473 | ADXCRPD.1593.C1_s_at | LCP1 | Sense | lymphocyte cytosolic protein 1 (L-plastin) [Source:HGNC Symbol;Acc:6528] | 473 | GAAGTAAGCCTCATCATCAGAGCCTTTCCTCAAAACTGG AGTCCCAAATGTCATCAGGNNNNNNNNNNNCAGCCA CTAAGAACCCCTGCTTTTAACTCTAGAATTTGGGCTT GGACCAGATCTAACATCTTGAATACTCTGCCCTCTAGAG CCTTCAGCGTTAATGGAAGGTT |
| 474 | ADXCRPD.9621.C1_at | C9orf7 | Sense | Calcium channel flower homolog [Source:UniProtKB/Swiss-Prot;Acc:Q9UGQ2] | 474 | TAAAGCGTGGCCGTGGCCTGCCGTGCCTGCCATCT |

FIG.7-123

| | | | | |
|---|---|---|---|---|
| 475 | ADXCRAG_NM_020384_at | CLDN2 | Sense | claudin 2 [Source:HGNC Symbol;Acc:2041] | 475 | AAGTCCTCCTCAGGCTTGGAGAACTTCCTCAGCGTCAC CTCCTTCATTGAGCCTTCTCTGATCACTCCATCCCTC CTACCCCTCCCTCCCCAACCCTCAATGTATAAATTGCT TCTTGATGCTTAGCATTCACAATTTTGATTGATCGTTAT TTGTGTGTGTCCGATCTCACAAGTATATTGTAAAC CCTTCGGTGTGGGTGGGGCCATATCCTAGACCTCTGT ATCCCCAGACTATCTGTAACAGTGCCAGGCACAC |
| 476 | ADXCRAD_BP332315_x_at | SSR3 | Sense | signal sequence receptor, gamma (translocon-associated protein gamma) [Source:HGNC Symbol;Acc:11325] | 476 | TCACTGTAAGGTACAGTTAGGTAACACTTTAGAGGTTT ATTATTTTAAAAACTTTCTTGAACTCCTGGCCAGCAT GGTGAAACCCGTCTCTACTAAAAATACCAAAATTAGCC AGGCGTGATGGTGCGTGGGTGCCTGTGATCTCAGCTACTTGG GAGGCTGAAGCAGGAGAACTGCCTGAACCCAGGAGGC GGAGGTTGCAGTGAGTGAGATCGTGAGATCGTGCTACTACTGCCT GGGTGGGCAAGGGT |
| 477 | ADXCRPD.9270.C1_at | TRIM2 | Sense | tripartite motif-containing 2 [Source:HGNC Symbol;Acc:15974] | 477 | TGCCATTTTCCAAGAATGACGGTGGTGGCTTTTAGTCAG AAAATGGCCTTCTCTGTGCT |
| 478 | ADXCRPDRC.15551.C1_s_at | EPHB4 | Sense | EPH receptor B4 [Source:HGNC Symbol;Acc:3395] | 478 | GGAGAGAAGCAGAATATTCGGACAAACACGGACAGTAT CTCATCGGACATGGTACTAAGGTCTACATCGACCCTT CACTTATGAGACCCTAATGAGGCTGTGAGGAATTTG CAAAAGAGATCGATGTCCTACGTCAAGATTGAAGAG G |

FIG.7-124

| | | | | |
|---|---|---|---|---|
| 479 | ADXCRIH.1483.C1_s_at | AES | Sense | amino-terminal enhancer of split [Source:HGNC Symbol;Acc:307] | 479 | AGCTGCCCCTTTCCCGTCTCCTGGGCACCCGAGTCTCCCCCGACCCCGGGTCCCAGGTATGCTCCCACCTCCACCTGCCCCACTCACCACCTCTGCTAGTTCCAGACACCTCACGCCCACCTGGTCCTCTCCCATCGCCCACAAAGGGGGGGCACGAGGGACGAGCTTAGCTGAGCTGGGAGGAGCAGGGTGAGGGTGGGCGACCCAGGATTCCCCCTCCCCTTCCCAAATAAAGATGAGGGTACT |
| 480 | ADXCRAD_BG179551_x_at | IL17RC | Sense | cysteine-rich with EGF-like domains 1 [Source:HGNC Symbol;Acc:14630] /// interleukin 17 receptor C [Source:HGNC Symbol;Acc:18358] | 480 | AGCGGGAGCAAGTGTCCCGGGCCTTCAGCCAGCCCTGGATAGCTACTTCCATCCCCCGGGGACTCCCGCGCCGGGACGCGGGGTGGGACCAGGTGCGGGACCTGGGGCGGGCGACGGGACTTAAATAAAGGCAGACGCGCTGTTTTCTACCCAAAAA |
| 481 | ADXCRPD.8757.C1_at | FAM83G | Sense | family with sequence similarity 83, member G [Source:HGNC Symbol;Acc:32554] | 481 | AGATGTGCACAAACAGAGCCCCCGCGTACAGGTCCAGCTGCGGAGGAGAGAGCCTTGTGTGGGCTGTATTCCCAGGGCTCCAGCAAGCCACTCCCTGGGTGACCTCCGGCAAGGCCCTCTCTGGGCCTGGCCTCTGTGGATAAGGAGGGGAGACCCCACTGTGGGTTGGGGAAGAACCTGGCCGTGGGGGCCATTGTGAGGTTGGGGAAGAACCTGGCCGTGGAGCTACAAGCTTGTGCGGATGTCAGGGACGTCAGGGGACATTACTGTTGCTAATAAAGTCCAAAGTGGCCAATGCCTT |

FIG.7-125

| | | | | |
|---|---|---|---|---|
| 482 | ADXCRAG_NM_000937_s_at | POLR2A | Sense | polymerase (RNA) II (DNA directed) polypeptide A, 220kDa [Source:HGNC Symbol;Acc:9187] | 482 | CGGTGAACTTCTGGATCCGTTTCTGATGCAGATTCTTG TCTTGTTCTCCACTTGTGCTTGTGTTAGAACTCACTGGCCCA GTGGTGTTCTACCTCCTACCCCACCCACCCCACCCCCTGCCTG TCCCAAATTGAAGATCCTTCCTTGCCTGTGCTTGATG CGGGGCGGGTAAAGGGTATTTTAACTTAGGGTAGTTC CTGCTGTGAGTGGTTACAGCTGATCCTCGGGAAGAACA AAGCTAAAGCTGCCTTT |
| 483 | ADXCRPD.8320.C1_at | GRIN2D | Sense | glutamate receptor, ionotropic, N-methyl D-aspartate 2D [Source:HGNC Symbol;Acc:4588] | 483 | GCGATGAACCCAACCTCCCTGAAGCCAAAACTTCCCAC CCTGCCGCACACTCCGGACCACCCCACTTGCCACCAAG CACATCCTCTCCAAATCCAACCTTATTTGCGACCCTTC AGTGATGACCCAGCAGACCTCCAAAAAGCCTCCTCTGC CCAGATCTCCAGCGGGCTCTGGGGCTGGGTTGCGGAG GGGAGGGTCTGGGAGTCCACACTTCTCCACCAACTTCC CTTCCCACTCTCTTATTCCACATTGCAGTGTTTGGAATA AACC |
| 484 | ADXCRAD_AK021812_s_at | RASA1 | Sense | RAS p21 protein activator (GTPase activating protein) 1 [Source:HGNC Symbol;Acc:9871] | 484 | TGTCCTGGGCACCGTAGCGAGACTCTGCTTTCTACAA |
| 485 | ADXCRAD_AU133980_at | SLC20A2 | Sense | solute carrier family 20 (phosphate transporter), member 2 [Source:HGNC Symbol;Acc:10947] | 485 | GCAGGCAGTAAGAAGCAGGGATTTCTTCAAATGCTAGT AAGCACAAAGAGAGGGAGAAGTTTTTGTAAGTAACGAA CAGGGGCCGGGCATGGTGGCGTGAGAGGCCGAGGT |

FIG. 7-126

| 486 | ADXCRSS.Hs#S3003228_at | C6orf203 | Sense | Uncharacterized protein C6orf203 [Source:UniProtKB/Swiss-Prot;Acc:Q9P0P8] | 486 | GAGCACCAGATCCTATAGAGCCTTTAGACCATCGTAGAGACTTTGCTTTCTCTGAGTGCTTGGTAGGGATTTGAGGAAAGGAGTGACATCGTATGAATGACTTTATTATGTGCCCACGTGGAGGTGTCAAATAGGCAGCTATTGTGTTGCAGGTCCCCAGGTTCATTGATTCACTAAGAGGACTCAAAAGACTCAGCACGTAGTCCTACTCACAGCTGTGATTTATTATCGCACAA |
|---|---|---|---|---|---|---|
| 487 | ADXCRPD.7046.C1_at | MED28 | Sense | mediator complex subunit 28 [Source:HGNC Symbol;Acc:24628] | 487 | CAGATTCTTTTTTATGGTGGCTTGCTTGTTTTAAATTTTTGCATGACTTTTCATCTTTTTATGTGTGTTTCCTGTAGTTTGATCCGAAGGAAAAGAGTATAGTAGCCTGAGAATCAGGAGATGGGAGTTTTAGTCGTAGGCCTTATGATAATTACCCCGCGGTGGTGTGTAGAAAAGTATGTAAATTTGCTCTGTTTTAAGACTTTGAACTACCTCAAGAAGAGG |
| 488 | ADXCRPD.12748.C1_x_at | AC138128.1 (Clone_based_ensembl_gene) | Sense | Novel long non-coding RNA. | 488 | GTGGGAGAAGTTGGCGTCCTAGGCTGGGATTGGTCGGGGGACCTTAAAGAAAAGGCCAGGCTGAGGGTCCTGAGGAGAGAGAGAGGCCACGTGGATGGAGGACTGTCACCCCCTTCTCGGTTCTGTCACCCCCTTGAGTCTAACTCACTGTTGAGGGGAGGAAGAAGAAGGGGGATGGACGGAAGGGAGACCGAGGAGAAAGGCTTTCGGGAGTGGGGACATTATCCACCCAGAGGTGTGCTACCCACAACCACCGCGAGATCCTTAGAGT |
| 489 | ADXCRAG_AB013384_s_at | HIP1R | Sense | huntingtin interacting protein 1 related [Source:HGNC Symbol;Acc:18415] | 489 | CTGTGCTCTGGAAAGGCTACCAAATACTGGCCAAGGTCAGGAGGAGCAAAAATGAGCCAGCCAGCACCAGCGCCTTGGCTTTGTTGTTAGCATTCCTCCTGAAGTGTTCTGTT |

FIG. 7-127

| | | | | |
|---|---|---|---|---|
| 490 | ADXCRAD_BI2234 41_s_at | PRPF8 | Sense | PRP8 pre-mRNA processing factor 8 homolog (S. cerevisiae) [Source:HGNC Symbol;Acc:17340] | 490 | GCTACAGCTGGCGAACCCCAAAGAGTTCTACCACGAGG TGCACAGGCCCTCTCACTTCCTCAACTTTGCTCTCCTGC AGGAGGGGGAGGTTTACTCTGCGGATCGGGAGGACCT GTATGCCTGACCGTTTCCCT |
| 491 | ADXCRPD.6.C2_s_at | OS9 | Sense | osteosarcoma amplified 9, endoplasmic reticulum lectin [Source:HGNC Symbol;Acc:16994] | 491 | GGGAAGCCAAATATAGGCCAAGAGCAGCCTGTGGATGA TGCTGCAGAAGTCCCTCAGAGGGAACCAGAGAAGGA |
| 492 | ADXCRPDRC.3178.C1_s_at | POLR2A | Sense | polymerase (RNA) II (DNA directed) polypeptide A, 220kDa [Source:HGNC Symbol;Acc:9187] | 492 | TACATCCCTTCACCAGGTGGTGCCATGTCTCCCAGCTA CTCGCCAACGTCACCTGCCTACGAGCCCGGCTCTCCTG GGGGCTACACACCCCAGAGTCCCTCTTATTCCCCACT TCACCCTCCTACTCCCTACCTCTCCATCCTATTCTCCA ACCAGTCCCAACTATAGTCCCACATCACCCAGCTATTCG CCAACGTCA |
| 493 | ADXCRAD_BM675 236_at | PLEKHG3 | Sense | pleckstrin homology domain containing, family G (with RhoGef domain) member 3 [Source:HGNC Symbol;Acc:20364] | 493 | GAAGAGGATTCAGGGTCAGCCTAGGGGACCCTGGCTC CCTCCGATAGGCAGGAAGGAGGAGGATGCGGAGGAG AGGCTGAGCCTTCCACGGGCCTCCTGTTAGGGGTGTTG GTGGAGGCCAGGTTGGGAGGAGGAAGCCTAAGGACCCT CCACACCTCCCACAGCACCAGAGTCAGTTGAGGCTGGGA CAAAGGGAAGGAGAGAGGAAGGAGGACCGCCTGAC CTTGCCCAGAAGGAGCTTCCTCTAAACTGC |

FIG.7-128

| | | | | |
|---|---|---|---|---|
| 494 | ADXCRPD.9019.C1_at | BMPR1A | AntiSense | bone morphogenetic protein receptor, type IA [Source:HGNC Symbol;Acc:1076] | 494 | GTAAAGGAGTGGGTGATTTGCAAATAAAGCACATTATACACAA |
| 495 | ADXCRIH.2173.C1_at | IL32 | AntiSense | interleukin 32 [Source:HGNC Symbol;Acc:16830] | 495 | TGCTGCTCCTCATAATAAGCCGCCACTGTCTCCAGGTAGCCCTCTTTGAAGTCGTCCTCCAGCTCTGCCAGGCTCGACATCACCTGTCCACGTCCTGATTCTGCATTTTGCATTTTATCATAAAATCTTTCTATGGCCTGGTGCATTCGGGCCTTCAGCTTCTTCATGTCATCAGAGAGGACCTTCGGAAGCACATGGCGGCCAAAAGTTCAAGGAGCCAAGGCCTGAGATGACCCCAGCTCCAAAGGGA |
| 496 | ADXCRAD_AA527340_at | RP11-357H14.7 (Clone_based_vega_gene) | Sense | Novel processed transcript. | 496 | TCCCCAACAACAACGCTCTGTTCCACCTACGTAGGATCTGTGAAACAGGCTCAGTGCCTTTGAGGGAGGAGGGAACGTTTAGATTGAGACCACCCCACTCCCGGGTGATTAAATAAATATGTCTCTCCCCACCCCACGCAGGATTGGAAAAAGTTAATTGTGGTTTCAGAAAAGTTAACCCCTGCGTTGCTTCGACCCCTTCTCTCCAGGGAAGGGTTGGGTAAATGTCTACGAATCGCCTTGAGAGAGAACTAAAG |
| 497 | ADXCRAD_NM_014985_at | CEP152 | Sense | centrosomal protein 152kDa [Source:HGNC Symbol;Acc:29298] | 497 | TACACAGTTTCCAATTTAAGTAGGCAGACTGAGCATGCCCATCAGTTTCCTATTGCTGCTTCCATCCCTCGAAATGATAGAAAAGATTTTAAACAGCAACAAATAAAGAATGAGAAAAGAAGAAAATTATAAGTGGGTTTTTAAAAAGTTGCAGTGGGCCAGGCATCATGGCTC |

| | | | | |
|---|---|---|---|---|
| 498 | ADXCRP D.10945.C 1_at | AMAC1L1 | Sense | acyl-malonyl condensing enzyme 1-like 1 [Source:HGNC Symbol;Acc:31043] |
| | | | 498 | TGCCCGATCACACAGGAGTATGCCCAAACTCTCTCAGG CCTCTAGCAGCTGACAACCACTGCTTTAAATCCCTATTA CATTTATTATGA |
| 499 | ADXCRA D_BU0730 65_s_at | PNMA2 | Sense | paraneoplastic antigen MA2 [Source:HGNC Symbol;Acc:9159] |
| | | | 499 | CCTGGGGGCAGGACCCCACAGCCAGTGGGCTAAGACCT TTAAAAATTTTTTCTTTAATGTATGGGACTGAAATCAA ACCATGAAAGCCAATTATTGACCTTCCTTCCTTCCTTCC TTCCCTCCTTCCTCCTCTCCTCTCCTCTCCTCCTCTCT CCTCTCCTCCTCCTCTTCCTCCTTCCTCCTTCCTTTTT CTTTTTCTCTTCTCTTATTTCTTGGGTCTCACTCTCAT CACCC |
| 500 | ADXCRA D_BC0332 51_x_at | RHOQ | Sense | ras homolog gene family, member Q [Source:HGNC Symbol;Acc:17736] |
| | | | 500 | TCAAGACGAGCTGGACAACAACAAGACCCCCAATT CTACTAAATTTTTTTTTAATTAGCCAGATGTGGTAATG CATGCCTCTGTAGTCCCAGCTACTCAGGAGGCTGAGGT GGGAGGATCACTTGAGTGCAGGAATTCAAAGCTGCAGT GAGCTATATACAAGGCTTCATTGCACTCCAGCCTAGG CATTAGAGCGAGACCGTGTGTTTATTTAAA |
| 501 | ADXCRIH. 1424.C1_s _at | TAX1BP1 | Sense | Tax1 (human T-cell leukemia virus type I) binding protein 1 [Source:HGNC Symbol;Acc:11575] |
| | | | 501 | TTAAAGGACAAACTCAAGAAGGCACAACATGAAAGAGA ACAACTTGAATGTCAGTTGAAGACAGAGAAGGATGAAAA GGAACTTTATAAGGGTACATTTGAAGAATACAGAAATAG AAAATACCAAGCTTATGTCAGAGGTCCAGACTTTAAAAA ATTTAGATGGGAACAAAGAAAGCGTGATTACTCATTTCA AAAAGAGATTGGCAGGCTGCAGTTATGTTGGCTGAAA GGAAATCTGCAAGACTTTCCTGCTTACAACCTCAAGTAA |

FIG. 7-130

| | | | | |
|---|---|---|---|---|
| 502 | ADXCRPD.11691.C1_s_at | NR6A1 | AntiSense | nuclear receptor subfamily 6, group A, member 1 [Source:HGNC Symbol;Acc:7985] | 502 | CAACATGGACATTTATACTAATAAGGAGGGCAGAGGCGAATATGTGAGAAGGTCCACCACCTCAGAGCTTGAATCAGCTTCACGATGATGGAAAGGTAAGCTTTATCACTGATCTCAACAGCAGACTGGTGGC |
| 503 | ADXCRIH.3022.C1_s_at | XPC | Sense | xeroderma pigmentosum, complementation group C [Source:HGNC Symbol;Acc:12816] | 503 | GAGTCAGGCTTACTAATGCTGCCCTCACTGCCTCTTTGCAGTAGGGGAGAGAGCAGAAGAAGTACAGGTCATCTGCTGGGATCTAGTTTTCCAAGTAACATTTTGTGGTGACAGAAGCCT |
| 504 | ADXCRPDRC.2277.C1_at | PPP3CA | Sense | protein phosphatase 3, catalytic subunit, alpha isozyme [Source:HGNC Symbol;Acc:9314] | 504 | GATCAAATCAAGTCTTGGTTGTGGCTTGCTGAATTAAATATTTATGAGTGGTGCATTTTAAGTATCGTGACCAAGACACCATATTA |
| 505 | ADXCRPD.12620.C1_at | CSNK1A1 | Sense | casein kinase 1, alpha 1 [Source:HGNC Symbol;Acc:2451] | 505 | AATACAGAACTGAGCCTAGGCCAGGAACTGGGATTGGGGTTAGATCTAAGCAAGATCAGCATGTAAGTGATAGTGGAGAAAGTAAATGGAGAGGTGAGGACTCATCCCCTTGGTGGAAATTCGGAATTAATAAAGCAGGAGGAGAGTCAGGATAATGGGCTGTTGAATAAAGAAGTAAGTGACAAGGAAGAGGTAATGTGTATCCAAGAAGTAGGAAAGAAATGAGACTTAAAGCGTAGGGGGTTAGGCTGTGTAAGAGCTCAGTACCCAACAGGTGCTCAGTCAAGTAACTTGAC |

FIG. 7-131

| 506 | ADXCRA G_BC058 002_x_at | MORC3 | Sense | MORC family CW-type zinc finger 3 [Source:HGNC Symbol;Acc:23572] | 506 | TGGGATTGCAGTGCGCCTGCCACCGTGCCCGGCTAACTT TTGTATTTGGTTGAGACAGGGTTTCGCCGTGTTGGCCA GGCTGGTCTAGAACTCCTGACCTCAGGTGATCCACCCG CCTTGGCCTCCCAAAGTGCTGGGATTACAGGCGTGAGC CACCACACCCGGCCAAAAAAATTTTTTTCTATCCC TGCCATTCAGTCTCCATTAGCACTCTATTCTCTCTCATTT ATTCCACCCGTCTT |
|---|---|---|---|---|---|---|
| 507 | ADXCRP D.3154.C1 _s_at | ATP6V0A1 | Sense | ATPase, H+ transporting, lysosomal V0 subunit a1 [Source:HGNC Symbol;Acc:865] | 507 | ACCACCCCTAGCTTTGTGTGTAGTGAGTGATTTTCTGG CTGTCACTCATACTCACTGGGACCAGCCTTGCCCTCT TAGCCTCCATCCATCCAGACAGCCCTTCCCACCTCCTG GTGGTGAGCCAGTCTGCATTCCCACGCCATCCCAAAGC CCTTTCATCTTACCCGTGCATTGTAGATGTGAAGGAGCAC CCATGCCATTCA |
| 508 | ADXCRIH. 2039.C1_s _at | PVR | Sense | poliovirus receptor [Source:HGNC Symbol;Acc:9705] | 508 | AAAAAGGTCTATGATCTTGAGGGCAGACAGCAGAATTC CTCTTATAAAGAAAACTGTTTGGGAAATACGTTGAGGG AGAGAAGACCTTGGGCCAAGATGCTAAATGGGAATGCA AAGCTTGAGCTGCTCTGCAAGAAAAAATAAGCAGGACA GAGGATTTGCTCTGGACAGAGATGGA |
| 509 | ADXCRP D.2058.C2 _s_at | PHLDA1 | Sense | pleckstrin homology-like domain, family A, member 1 [Source:HGNC Symbol;Acc:8933] | 509 | TGGTGAATTTTCTAGGAGGCGATGATGTACTGTAATTGTN NNNNNNNNNNNNNNNNNNNNNNNNNNNNNNNNNNNN NNNNNNNAATGCTTGTTCTAAGACATTTCTGAATGTAGA CCATTTCCAAAAGGAAACTTTATTTCAAAAACCTAAT CCGTAGTAATTCCTAATCTTGGAGAATAAAAAAGGGCGG TGGAGGGGAAAACATTAAGAATTATTCATTATTTCTCG AGTACTTTCAGAAAGTCTGACACTTTCATTGTTGTGCCA GCTGGTTGAAATTAAAACT |

FIG. 7-132

| 510 | ADXCRSS.Hs#S1764949_at | CEACAM5 | AntiSense | carcinoembryonic antigen-related cell adhesion molecule 5 [Source:HGNC Symbol;Acc:1817] | 510 | GATAGTGATGGGTCTTCCCATTGTCCTTAAACCCTGTAC ATATTGTGCAGCCTGGCCTGGGACTGGATGTTTCAGTA GAAATAACACAGGGACACCAGAGGCAAGCCTGGAGG TCAGCTCAGTGCGTTAGGCAGTGGAGGCACAAGGTGGG GCAGTTTTTCCCAGGTGTTTGATGATGACTTGAGC CAGAGACCCTAAAGATAGAGTGGAGTCCAGGAATGA TCTAGAACTTCAGGTGACAGGCAGGAGAGCTGCCCGGATT TAACAGCAGAACCATA |
| 511 | ADXCRIH.50.C1_at | GPRC5A | Sense | G protein-coupled receptor, family C, group 5, member A [Source:HGNC Symbol;Acc:9836] | 511 | CTAACTCTGTCCTGAAGAGTGGGACAAATGCAGCCGGG CGGCAGATCTAGCGGGAGCTCAAAGGGATGTGGGCGA AATCTTGAGTCTTCTGAGAAAACTGTACAAGACACTACG GGAACAGTTTGCCTCTCTCCCAGCCTCAACCACAATTCT TCCATGTCTGGG |
| 512 | ADXCRPD.11875.C1_at | GPRC5A | AntiSense | G protein-coupled receptor, family C, group 5, member A [Source:HGNC Symbol;Acc:9836] | 512 | GATGGACAGGGTTCTGAAAAACTGAAAATGAATTCTAG AAAGCAGCATTTGAGAGGGAAAAGAGAAGTGATCAGCA TTTAGGAATATGAACTGTCTGGAGCTAGAGAAACAGCCT GGGAAAAGAGCAAAGGGCTAGAGCAGGAAAGAGAAAA GAGAATGAGACTAGCGCGGTGGTTTGGATATTATTGTAAC CAAAGTCAAAGGACGGGAGATCTAGAGTCCAGCAACA AGAACTGTCCTCCTATAAAAACCAAATGGACCCCACCCT TCACTTGACGTAGAGGTCCTTTCCT |

FIG. 7-133

| | | | | |
|---|---|---|---|---|
| 513 | ADXCRSS.Hs#S2990374_at | KIAA0319L | Sense | KIAA0319-like [Source:HGNC Symbol;Acc:30071] | 513 | AACATGGTCCTGGAGGTTACAGTGTAGTGAGGGGCAAAGACATGGAGCCAATGGTTGAGCTGAAACCTCATGTGAGGAGTTAACTGGATGGAGAAAGGAGTCAAGAGAGTTCTAGGTAGAGGAGGAGCAGCATGTCAAAGGCACAGTAAAGGGAGGATGAATGGTCCATTTCAGGGATGGAAGAAGGCTGCTAGATTGGAACATAGGGAAGGAGGGAATGTGTGATACAAGCTGGAGCTAGAAAGGTAGGTGGTCAGAACATAG |
| 514 | ADXCRAG_BC001557_s_at | SMC4 | Sense | structural maintenance of chromosomes 4 [Source:HGNC Symbol;Acc:14013] | 514 | GAAAAATTTACACAGCTAGATTTGGAAGATGTTCAAGTTAGAGAAAAGTTAAAACATGCCACGAGTAAAGCCAAAAACTG |
| 515 | ADXCRAD_AW291023_at | PML | AntiSense | promyelocytic leukemia [Source:HGNC Symbol;Acc:9113] | 515 | TTAAAAGGTCCTGCTCTATCGTTCTGTCTGGCTCTGCAAACTGCTGGTATGTAAAAGACCCTCTTTCCAGACAGGCCAGAACTCCCCGAAGGCCGGGCTGGCCTTCTTCTGCCTCTGTCCCAACCTCCCTGACACACCAGAGGGCTCAGTAGAGTTAATAAAACAGGGAACACACCATAATGACTGATTTATAATTTTTATAGCTAAAAACACATCATATAAATTTATTTTTTCCATTAAAGTATTATAACACGATTACAAAAAGCCCTCGTGC |

FIG.7-134

| | | | | |
|---|---|---|---|---|
| 516 | ADXCRP D.13012.C 1_at | TRIO | AntiSense | triple functional domain (PTPRF interacting) [Source:HGNC Symbol;Acc:12303] | 516 | TAGATGCCGTCATCTTCCGTGGTCACGCCCACAATCTT CAGCCGTGGCCTCTCCCAGGTCACTGTAGGAGATGCTGT AGTGACCATCGTTGTTCAAGGTGTTGTTCAGGGCCC TTCCAGGTAATTGAGGCTTTGGGCGGCCACAGACTCG ACATCTAGGAACAACGGTCTCCCCTGTCTCACACGTGA CCTCACTCAATGGAATGACGAATTCTGGGGAACGTCA TAAATGTAGTTGGGATTGAGAAGCTTGTTGCTGAGTCCT TCCCGTGACTTCCGATAA |
| 517 | ADXCRA D_BC0257 70_s_at | RHOJ | Sense | ras homolog gene family, member J [Source:HGNC Symbol;Acc:688] | 517 | CACTATGCAGTTACTGTGACTGTGGGAGGCAAGCAACA CTTGCTCGGACTGTATGACACCGCGGACAGGAGGACT ACAACCAGCTGAGGCCACTCTCCTACCCAACAGACGGAT GTGTTTTTGATCTGCTTCTCTGTCGTAAACCCTG |
| 518 | ADXCRA D_BE1385 16_x_at | ATL2 | AntiSense | atlastin GTPase 2 [Source:HGNC Symbol;Acc:24047] | 518 | GACCAGGAAGTCCTATAAAGAATTATATTCTATAGAATT AAAAATGCAGTTCTGTCAGCCTGACAACAAAGTGAGA CCCCCATAGCTACAAAAAAAAAAAAAGTTTTTTTAAG AGTTGGGCATGGTGGCACACGCCTGTAGTCCTAGCTTC TCGGGAGGCTGAGGTGGGAGGATTGCTTGAGATTGGG AGGTTGAGGCTGCAGTGAGCTGCGTGATCACACCACTGCA CTCCATCCTGGGTAACAGAGTGAGACCACTTAAATTAA |
| 519 | ADXCRA G_AJ3135 24_s_at | MACC1 | Sense | metastasis associated in colon cancer 1 [Source:HGNC Symbol;Acc:30215] | 519 | CAAAGCAACAAATGGAGGCATATGAAATTCCTCATCGAG GAAACACTGGAGATGTTGCTGTTGAGATGATGTGGAAA CCTGCCTATGATTTTCTGTATACCTGGAGTGCTCACTAT GGAAATAACTACAGAGATGTGTTACAAGACCTTCAGTCA GCTTTGGACAGAATGAAAAACCCTGTGACTAAACACTG GAGAGAATTAACTGGAGTTTAATACTAGTAAATTCTTTG GAGGTTTTGAGAGTAACTGCATTCTCCACT |

FIG.7-135

| 520 | ADXCRAD_AL5986 28_at | SCD | Sense | stearoyl-CoA desaturase (delta-9-desaturase) [Source:HGNC Symbol;Acc:10571] | 520 | TGTTAACCCATTCCAGTACAGTATTCTTTAAAATTCAAA AGTATTGAAAGCCAACAACTCTGCCTTTATGATGCTAAG CTGATATTATTTCTTCTTCTTATCCTCTCTCTTCTAGGC CCATTGTCCTCCTTCTTTCACTTTATTGCTATCGCCCTCCTT TCCCTTATTGCCTCCCAGGCAAG |
| 521 | ADXCRIH. 3160.C1_s _at | ATP5G1 | Sense | ATP synthase, H+ transporting, mitochondrial Fo complex, subunit C1 (subunit 9) [Source:HGNC Symbol;Acc:841] | 521 | AGCCACAGTTGGTGTGGCTGGTTCAGGGCTGGCATTG GAACCGTGTTTGGCAGCTTGATCATTGGCTATGCCAGG AACCCGTCTCTCAAGCAGCAGCTCTTCTCCTATGCCATT CTTGGCTTTGCCCCTCTCTGAGGCCATGGGGCTTTCTG TTTGATGGTCGCCTTCCTCATCCTCTCGCCATGTGAGG CTCCATGGGGGGTCACCGGCCGGCCTGTTGCTACTGAAGCT CACACCATTCTTGGTGCTGGGGTGTGTTAAGCTTTACCA TTAAACA |
| 522 | ADXCRSS .Hs#S373 2256_at | DDX17 | AntiSense | DEAD (Asp-Glu-Ala-Asp) box polypeptide 17 [Source:HGNC Symbol;Acc:2740] | 522 | GGCTTAACCAGCTAGACATTCCTCTAAATACATACGTAA CAAAAATTGATGCAGGAGATTTTATTGGGATCACTGGA TACCTACACTCAACAGGCAGAACTTGGCTAATTCCATTT ATACCACTACTGAGACAGTGAAGACAAATTAAGAATCAG AACAGGAAGCACATAGCATAGGGATACCCGTGTCAGCG ACATATTTAATATGCCCCTCAGCTAAGACTCAATACTG AACAGACCAAAAGGCCACCTCAATTGCCGCTCCCGCCA CACTTGCTATTGAAACT |

FIG.7-136

| 523 | ADXCRA D_AI7031 62_at | YLPM1 | AntiSense | YLP motif containing 1 [Source:HGNC Symbol;Acc:17798] | 523 | CCAAGGGCATTGCTAATCTCTGTACTTCAGTAAACACTGA AAAGTCAACGTAACTCTATAGGTCGCATATTCTTGAATG ACAGGGAAAGGCAAACATCTCACAGAGGTGTGATCGA AAGCATTTTACATTAGGTACACAGAAACTTTAAACTCAC ACTATGTAAGCCTCTAATCAGCCTGAGCAAAATCCATTG CCTACACAGTCATTTA |
| 524 | ADXCRA D_CB8529 16_at | IREB2 | Sense | iron-responsive element binding protein 2 [Source:HGNC Symbol;Acc:6115] | 524 | GGTTGAAAGATGAAATGCCTGTATGTGCTCTGAAGAAAT GGTAATTCCAGATTG |
| 525 | ADXCRA D_AI8057 00_at | PTK2 | AntiSense | PTK2 protein tyrosine kinase 2 [Source:HGNC Symbol;Acc:9611] | 525 | TCCACCTGCCGAGAAGCTGAGATTATAGTCACTGTGCC TGGCTGGAATATAGCCTTTCTGACTCCATGTCATTACCCG CACTCTTCGCTCTTCCTGCTGCTGGAATGTATTTCCTGAGCCTGT CTGCCCTAAAAATTCCAATTCTCCTTTAAGCTTTGGCT CAAATGCTATCTATCTATCTGTCTGCCTCCCCCAAGTCCC CTAGTGACACACAGGGTCCTCTTCTGCTCTTCCTTATGT TCTTCTTTGTCAGAGCAACATCACAGCAGTACCCAACA TTTGG |
| 526 | ADXCRA D_AF1724 50_at | N/A | No Genome match | N/A | 526 | GCGGGCGGGGCAGGGCTTGCCTTTCTTAGTCTGATGCCAA G |

FIG.7-137

| | | | | |
|---|---|---|---|---|
| 527 | ADXCRAD_BM711746_s_at | DNAH2 | Sense | dynein, axonemal, heavy chain 2 [Source:HGNC Symbol;Acc:2948] | 527 | GGGCCATGACACCTGATCATTGGATCAAGAGGGCACTGCTCTACTCATGAGCCTGGACAGCTGAGACCTCCTCCTCTTCTCCGCTTGAGAGAGAGGGTCAGGGACTCCAGGAGCTAAGACAGATGTTGCACCTAGGACTGAGGCCGGACCTCACTCAGACTTTGACCTTGGCCGAATTTGTGTGATGTGGCCCTGGAGATACCTAGTTGTGTTAGCCATAAA |
| 528 | ADXCRAD_BE792795_s_at | SCRN2 | Sense | secernin 2 [Source:HGNC Symbol;Acc:30381] | 528 | CAGGAAGGCCTCGAGGCCACACAGGGGCTGCTGGCCGGCGAGTGGGCCCACCCCTCTGGGAGCTGGGCAGCCTCTTCCAGGCCTTCGTGAAGAGGAGAGCCAGGCTTATGCGTAAGCTTCATAGCTTCTGCTGGCCTGGCGGTGGACCCAGGACCCCTGGGGCCTGGGTGCCCTGAGTGGTGGTAAAGTGGAGCAATCCCTTCACGCTCCTCCTTGGCCATGTTCTGAGCGGGCCAGCTTGG |
| 529 | ADXCRPDRC.13647.C1_s_at | CDHR1 | Sense | cadherin-related family member 1 [Source:HGNC Symbol;Acc:14550] | 529 | CTGGTGGACTATTCCATCACCCATGCAGAGCCCGCCAACGTGTTGGACATCAATTCCCACACGGGGGAGATCTGGCTCAAGAATTCCATCCGCTCCCTGATGCCCTGCACAACATCACACCTGGAAGGGACTGCCTATGGTCCCTAGAGGTGCAGGCCAAGGACCGGGGCTCCCACATCACTTCAGCACCACAGCCTTACTCAAGATTGA |

FIG.7-138

| | | | | |
|---|---|---|---|---|
| 530 | ADXCRAG_NM_198389_s_at | PDPN | Sense | 530 | TCGGCCTCAGATTCCATATTTGAACACCAGCTGATTGAGAGAAGGGGAATGAGAAGAGCTGGATGAGTTTAAATAACTCATTGTTCAGATTCCTGAACAGGAGTTGGGATAATGGCCATCTTTTCTTCCTATCCTTTCTTCCCCCCTCACTGTGAAAAATAACAGTCCACCCAAGTCATACACTGGACCCAGTGCCTGCGGGGACAGGACTGTGGGTTTCTTGGTCACACCTGTGTGGTGCTCAATGCAGTGT podoplanin [Source:HGNC Symbol;Acc:29602] |
| 531 | ADXCRSS.Hs#S2733081_at | COMMD10 | AntiSense | 531 | TAGTTTCATTTACTCTTTAGGCAGAAAATAGGTTCAAGGGTCTAGTAAAGGAGGCAAATGGGCAGAAAACAACCTCTTGTTTGCTATCCCACTGCACTTGAAATGGACCTCTATAATTCACTACCATTTATAAGTGTCTCGCATATCAACATCACATTAGGTAATTTACTGCCTCCAATTCCTGGTCCATAATCATCCATCCTGAAAAGTCATATACAATGTTATTGGAACAATCTATTCATATGGTA COMM domain containing 10 [Source:HGNC Symbol;Acc:30201] |
| 532 | ADXCRAG_BC012866_at | TNFRSF10A | Sense | 532 | ATGTATACAAAGTAAATTCTTAGCCAGGTGTAGTGGCTCATGCCTGTAATCCCAGCACTTTGGGAGGCTGAGGCGGGTGGATCACTTGAGGTCAGAAGTTCAAGACCAGCCTGACCAACATCGTGAAATGCCGTCTTTACAAA tumor necrosis factor receptor superfamily, member 10a [Source:HGNC Symbol;Acc:11904] |

FIG.7-139

| | | | | | |
|---|---|---|---|---|---|
| 533 | ADXCRSS.Hs#S3008397_s_at | HELZ | Sense | helicase with zinc finger [Source:HGNC Symbol;Acc:16878] | 533 | AGTGGCTTCCTTGGAGTAGTGGGTGAAAGTCTGCTTAAAAGAGGGCTTAGGAGAGAGAATTGGGGAAGGAATTGAAATACATCAACATAGACAACTCTTGAGGAGTTTTGCCATGAAGAGACACTTTGCATCCAGAGGACACTTTGCATCCAGAGAGTGGCTTCCTTGGAGTAGTGGGTGAAAGTCTGCTTAAAAAGAGGGCTTAGGAGAGAGAATTGGGGAAGGAATTGAATACATCAACATAGACAACTCTTGAGGAGTTTTGCCATGAAG |
| 534 | ADXCRAG_AB080747_s_at | FOXP4 | Sense | forkhead box P4 [Source:HGNC Symbol;Acc:20842] | 534 | GAGCTGGAAAAAAGTCAGACTCTCCACAGACCCCTATGGGGGACCCCCAACTCAAGGCCAAGGACTGGGCGTATCGGATGTCTCATAACACCCCTGGCCTGGCCCCTTTACTGAGAAGACTCCTTGGATATTTCCCAAGAACCCCCACATACACCCCTCACAAGCCACCCCTCCTGAGAGGCAGGGGGCCCTCCGCCCCCTCCCCATGTATTCCCCACCTGTGTTCCGTTTTGACCAGCACAGAAATATT |
| 535 | ADXCRPD.9899.C1_s_at | TAOK2 | Sense | TAO kinase 2 [Source:HGNC Symbol;Acc:16835] | 535 | GGGAGCACACAGTCACCTCTCCACAGCTCCATTATCCAGCGGCTGCCGGGCCTCTGACAACCTATGATGACCCTACCAGCCAGAGATAAC |
| 536 | ADXCRAD_BE386516_s_at | PRKAR2A | Sense | protein kinase, cAMP-dependent, regulatory, type II, alpha [Source:HGNC Symbol;Acc:9391] | 536 | GCTGCCATTGCTGTGGTTATGGGCATTTAGAAAACTTGAAAGTCAGCACTAAAGGATGGGCAGAGGTTCAACCACACCTCCACTTTGCTTCTGAAGGCCATTCATTAGACCACTTGTAAAGATTACTCCAACCCAGTTTTATATCTTTGGTTCAAAACGGCATGTCTCTCCAACAATTTAAGTGCCTGATACAAAGTCCAAAGTATAAACATGCTCCTTTACTCTCTTGCTGCTACTCTTGCTTTTG |

FIG.7-140

| | | | | |
|---|---|---|---|---|
| 537 | ADXCRA G_AB04 5118_at | FRAT2 | Sense | frequently rearranged in advanced T-cell lymphomas 2 [Source:HGNC Symbol;Acc:16048] | 537 | GTAGCTATTGATGTACACTTCGCAACGGAGTGTCTGAA ATTGTGGTGGTCCTGATTTATAGGAT |
| 538 | ADXCRP D.17448. C1_x_at | CAPS | Sense | calcyphosine [Source:HGNC Symbol;Acc:1487] | 538 | CAGAGGTCTTGCAGCCCCTGTGGATGCCCCGCCGA GGTCCCCCGATCCCCGCACCCGGACTGCTGCTCCT GCCCCACCATTGCGGGTCCCCCAGGAAGCCAGGTGA CCCCAGGTGGGAGGCTGTGTGTGAGGCCATCCTGG AAGGAAGTTAGACCTGCCCAGGTGTGGAGCGAGGG GCACAGGGGCATCCTAACCTCAGAAACTGAAATAAAG CCTTTGNNNNNNNNNTCTGTAAAACATCAACCCCAAT CAGAAGATGGCAAATGGGGAATAAAAATAGCAGGTAA CACGTCA |
| 539 | ADXCRA D_CX16 4907_s_ at | RALBP1 | Sense | ralA binding protein 1 [Source:HGNC Symbol;Acc:9841] | 539 | TGACAGCAGCTGATGTTGTTAAACAGTGGAAGGAAAA GAAGAAAAAGAAGAAAAAGCCAATTCAGAGCCAGAGGTG CCTCAGATTGATGTTCCAAATCTCAAACCCATTTTTGG AATTCCTTTGGCTGATGCAGTAGAGAGGACCATGATGT ATGATGGCATTCGGCTGCGCCAGCCGTTTTCCGTGAATG TATAGATT |
| 540 | ADXCRP D.12155. C1_at | AC058791.1 (Clone-based (Vega) | Sense | Novel processed transcript. | 540 | AAAATAGAACATCCTGAGTTACAGAAATTCAGCCCTAG TGTATCCTGGCCTAAAAATACAGAACAATCAAGTTGAG TGGTTGGAAATGAGAGGCTAGGCAGGGTTGGAAACAT GCTAATGTTTACTGAGTGAAATCTTTCCTTCTCAGTAG AGTTGCCCTTGCAGCTGAAA |

FIG.7-141

| | | | | |
|---|---|---|---|---|
| 541 | ADXCRAD_CN479989_at | SLC39A14 | Sense | solute carrier family 39 (zinc transporter), member 14 [Source:HGNC Symbol;Acc:20858] | 541 | TCTCTGGCTGATATGTTCCCTGAGATGAATGAGGTCTGTCAAGA |
| 542 | ADXCRAD_CN298065_x_at | CHP | Sense | Calcium-binding protein p22 (Calcium-binding protein CHP)(Calcineurin homologous protein)(Calcineurin B homolog) [Source:UniProtKB/Swiss-Prot;Acc:Q99653] | 542 | GTTACAGGTGCTACGCATGATGGTCGGAGTAAATATCTCAGATGAGCAGCTGGGCAGCATCGCAGACAGGACCATTCAGGAGGCTGATCAGGATGGGGACAGTGCCATATCTTTCACAGAATTTGTTAAGGTTTTGGAGAAGGTGGATGTAGAACAGAAAATGAGCATCCGATTTCTTCACTAAGGAGACCAAACTGTTCCTTGCGGTCTAGTATTTAAGAACTGGAACTTGAAAGTCCTCCTTCTAC |
| 543 | ADXCRSS.Hs#S1623594_at | TTC39B | AntiSense | tetratricopeptide repeat domain 39B [Source:HGNC Symbol;Acc:23704] | 543 | GAATCCATTATCAATGTTGCTAGTGTAATACACAAGAAAACCCAATGAGAGAAATTCAAATATTAAGAAACAAGCTTTTGTTGATTGAGCTTTAAATGGCCACACACCATTATAATATCTAAGATGCTTGTGCTCCCAATAACCATTTTTGCCTCCAATGAGGATGCAAGTCCTAACTTCTATGCTCCCGAATTTATCATATACTAGCACCTA |

FIG. 7-142

| | | | | |
|---|---|---|---|---|
| 544 | ADXCRAD_D81713_at | LRCH1 | Sense | leucine-rich repeats and calponin homology (CH) domain containing 1 [Source:HGNC Symbol;Acc:20309] | 544 | TAATAAGTGTTAGCATCGTCTGTGTCTTGAAGTATACTTTTGCACTGTAACTTGGGTTACGTTAAAGAGAGCTTAGCACCAAAGGTAGATAAATGAAGAAATGGCATAGGAAAGTGGAGATGATAAAAGTTGATTGTTGAACCAAAAAGGGTTGAAGGGAAGCTTCGACTGAGTATCAGAAATTACTTAAGGCACATAGGACCTGAATCAGGRAACCAGCACTTCTTACAACTGCCAGTTTTA |
| 545 | ADXCRAD_BX101833_s_at | RP11-125K10.4 (Clone_based_vega_gene) /// RCL1 | Sense | Putative processed transcript /// RNA terminal phosphate cyclase-like 1 [Source:HGNC Symbol;Acc:17687] | 545 | TGCAAGGACTCACCTCCTTGAGCCTTGGTTTTGTTGTAGGGATTAAATGAGATAATATGAGTGGCAGCTCTTCATGAGTCCTGCAGTGCTAAGCAAATGTCAGAAATTGGTGTATTAGACTATTTATCTTTGATCTTCTGAATGGATTGCTGTCATGGACACGGACACGGATCTTCATCTGGTTCATTGTATTTATATGTGAGGGATGGATGGC |
| 546 | ADXCRIH.2931.C3_s_at | STAT1 | Sense | signal transducer and activator of transcription 1, 91kDa [Source:HGNC Symbol;Acc:11362] | 546 | GGAGAAGTTAAGCAACATCTAGCAAATGTTATGCATAAAGTCAGTGCCCAACTGTTATAGGTTGTTGGATAAATCAGTGGTTATTTAGGGAACTGCTTGACGTAGGAACGGTAAATTTCTGTGGGAGAATTCTTACATGTTTCTTTGCTTTAAGTGTAACTGGCAGTTTTCCATTGGTTTTACCTGTGAAATAGTTCAAAGCCTAGTTTATATACAATTATATCAGTCCTCTTTCA |

FIG.7-143

| | | | | |
|---|---|---|---|---|
| 547 | ADXCRP D.13803.C 1_at | SLC11A2 | AntiSense | solute carrier family 11 (proton-coupled divalent metal ion transporters), member 2 [Source:HGNC Symbol;Acc:10908] | 547 | GAATTGTCATTCATTAATAACTCTGTGCTATATTACTTGAGGG GCTAAGAAAAATGTATGGTCAGTGAACACAGTAGTGTA CCCTTAAATGCCTTATAAAAGACCATCCATCCAGTCTGC GCTTTTGACTGTGTGCAAGTATCAGTAATAATGCTTTTG GGGGCTCAGATGAACAGGGAACACCAATCAGCCAGGA CTCTGGAAGGAAAGCTCCAAAAATGANGAAGTCCTTTCA ACACCATTTTCCATTACTGTTCTCA |
| 548 | ADXCRP D.9382.C1 _at | SETMAR | Sense | SET domain and mariner transposase fusion gene [Source:HGNC Symbol;Acc:10762] | 548 | TTTGATTAATAAAAATGCGTTGAGCCTAGTTATA |
| 549 | RDCR448 _D01_s_at | FOXO3 | Sense | forkhead box O3 [Source:HGNC Symbol;Acc:3821] | 549 | GTTGCTTCCCCACCCTGAGGAGAGGACACCATGGCTTA CTACTCAGGACAAGTATGCCCCGCTCAGGTGTGATTT CAGGTGGCTTCCAAACTTGTACGCAGTTTAAAGATGGT GGGGACAGACTTTGCCTCTACCTAGTGAACCCCACTTA AAGAATAAGGAGCATTTGAATCTCTTGGAAAAGGCCATG AAG |
| 550 | ADXCRA D_CX7558 99_s_at | GTSE1 | Sense | G-2 and S-phase expressed 1 [Source:HGNC Symbol;Acc:13698] | 550 | TGGGAAATATAGTGAAACTCCTGTCCCTACAAAAATAC AAAAATTAGCCGGGTGTGGTGGTAGTGCATGCCTAGTCC CAGCTACTTGGGAGGCTGAAGTGGGAGGATGGCCTGA GCTCAAGGAGATGCAGGCTGCAGTGGCTGTGATTGTG CCACTGCCACTCCAGCCTGGGCACCAATGTGAGAACCTG TCTTGGAA |

FIG.7-144

| 551 | ADXCRPD.18410.C1_x_at | N/A | No Genome match | N/A | 551 | TTGAAAGACACCAGTGCACACCCAAACTCCTGGCCTTC TGTGGGTTCCCTTTGCTCCAGAACACAGATGTGTCTANN GAAAAACAAACGAAAACGAGCNAAAACNACCAAACCC CAGGGGGGCCGCTCTAAAGAATCCCTGAGGGGCC CAAGCTTACGCGTACCCAGCTTTTCTTGTACAAAGGGG CCCCTAAAGGGAGTCGGAATAAAAACTAAAGGCCT TGGCCCGTCCTTTTACAACGCCCCGGAACTGGGGAAA ACATGCCAACCTTGGGGATCTTTG |
| 552 | ADXCRAG_BC049209_at | C2orf89 | Sense | UPF0632 protein C2orf89 Precursor [Source:UniProtKB/Swiss-Prot;Acc:Q86V40] | 552 | GATGCTCTTCAGTTCAACTATATTCCCTATCTGATAATTC CAGAATCTCTATCATGTCTGAGTCTGATGCTTT CATTGTTTCTTCAGATTGTGATTTTCTTGCCTCCCAGTG TGACTTGTAATTTTAATTGAAAGCTGGATATGATGTATT TGGCAATGGGAAGTGAGGGAAATATGTTTTAGTGTGA GGGTTTATGTGTTAATCTTTCTCAGAGTTGGGCTGTTTAAT GTTTTGCTGTGTGTCTGAATGTTCCTTAAAACT |
| 553 | ADXCRAD_BX38635_s_at | FKBP8 | Sense | FK506 binding protein 8, 38kDa [Source:HGNC Symbol;Acc:3724] | 553 | AAGGATTGGGGTCGTGCAGCCCAGCCAGCAGGAGGG ACTGAGGCCCTCTAGGAGGAAAGCCCAGAGGGGAGGGGG GCCCTCATTCCTTCAGACCCAGTTTTCCCCCACCCT TACCCCGCTGGGCTAGGTCTCCGCCAGGGCTGGCCTC AGTTTCTCCTCCAACAGGCCTGAGTGCCAGCCCCTAC GCCTAGTCCCCGCCTGAGTGCCAGCSCCCCACCCCGC CTGCCGCCCCCGTGTTCAGGTTCCCTCCCGCCACAGTG AAATAA |

FIG. 7-145

| 554 | ADXCR AD_BX4 42668_x _at | PPDPF | Sense | pancreatic progenitor cell differentiation and proliferation factor homolog (zebrafish) [Source:HGNC Symbol;Acc:16142] | 554 | TGCGGAGGGCTAGTCCACCAGAGCBCCTCC CGGCCCCTCTTCCCANTCGGNATCCCTCGCC CCCCTCCCCACCTCCCCACCCCCACCCTGTA AACTAGGCGGCTGCAGCAAGCAGACCTTCGC ATCAACMCMSCASACACCAMAAACCAGTGAG ASCCCCGCTCTCTACCGCCCGGGCCCAGCAC TCGCTAGCTTTCCTGACACCTGGAACTGTGC ACCTGGCACCAAGCGGAAATAAACTCCAAG CAGCCAGTAGCCCGATGGTGTGTGCCTGAC CTGTGTGGCCGGGAGGTTC |
| 555 | ADXCR PD.9655 .C1_at | C17orf63 | Sense | Uncharacterized protein C17orf63 [Source:UniProtKB/ Swiss- Prot;Acc:Q8WU58] | 555 | TTAGGTAGGTAAGGAATGATCACATTGGAGTT TGG |
| 556 | ADXCR AD_AI75 0956_s_ at | COL12A1 | Sense | collagen, type XII, alpha 1 [Source:HGNC Symbol;Acc:2188] | 556 | ACGTGCTTATTAGGAAATGAGTCTGTATGGAA ATCTCACCACAGATAATGGTTAACGAACGG GTCGACATCACAAAGGAGGGTGGAGACTCTT TTTACTAACTTGAATGAGACAAAAGCAGTGGT GTCAGTTTATAATCCTGATGCATTTCAGTAAT AATGTAGAAAAACATTATTTTAAAAAGTTCCA ACACACAGCCATGAGGAGCCTCAGTTTTGAA AGAGGTGCATAATAAAACTACTAACCAGAGGA GTCTATGCCATTTTAAGAA |

FIG.7-146

| 557 | ADXCRA D_CA4403 61_x_at | ROBO1 | Sense | roundabout, axon guidance receptor, homolog 1 (Drosophila) [Source:HGNC Symbol;Acc:10249] | 557 | GCCAGGAGAGTTGGAGCCCACTCTGGGGAAAACATGTTGA GATCTTGCCTCTGCAAAAATAAAGTAAAATAAAATTTAAA AAAAGTAAAAAATAAAATCAGCTACTTTGGAGCATGGTGACATG CACCTGTGGTACCAGCTACTTTGGAGGCTAAGTTGAGA GGCACTGATGGGAGGATCATTTGACGGCCCAGAGGTTG AGGGTCAGTGAGCTGTGTTTGTGTCATTGCACTCCAG CCTGCGTAACAGAGTAAAACCTTCT |
|---|---|---|---|---|---|---|
| 558 | ADXCRA D_BU5851 82_s_at | IGLV2-14 | AntiSense | immunoglobulin lambda variable 2-14 [Source:HGNC Symbol;Acc:5888] | 558 | CTTGGAGCCAGAGAAGCGATTAGAAACCCCTGAGGGCC GATTACTGACATCATAAATCATGAGTTTGGGGGCTTTGC CTGGGTGATGTTGGTACCAGGAGACATAGTTATAACCA CCAACGTCACTGCTGGTTCCAGTGCAGTGCAGGAGATGGTGAT CGACTGTCCAGGAGACCCAGACAGGGAGGCAG |
| 559 | ADXCRA D_AA6825 39_at | AC069513.3 (Clone_based_ vega_gene) | AntiSense | Novel processed transcript. | 559 | GTCTGAATATCTTACTCACAGCTCACCTTTTGGTGCCT TTGATCCGTATTAGAAATTATCCACATCTCTCTCTGGG CAATATTCTACTTTTTATATTGACCCAATTATTTACTGCT TTGGTGTGTCCTTTCTCCTAACACATATGGGTTCACTTT GAAACCCTGAAACCCACATTTACAAAAACATTTCAATAT GAAACATTGTTCCATGACTCATTACTGGAGTACCATCAA CATTTACAT |

FIG.7-147

| 560 | ADXCRP D.8173.C1 _s_at | CD93 | Sense | CD93 molecule [Source:HGNC Symbol;Acc:15855] | 560 | GCAGGTATTTCTACGGGTGTTTGATGTTCCTGAAGTGG AAGCTGTGTTGGCGTGCCACGGTGCCACGGTGGGATTTCGTGA CTCTATAATGATTGTTACTCCCCCTCCCTTTTCAAATTCC AATGTGACCAATTCCGGATCAGGGTGTGAGGAGGCTGG GGCTAAGGGGCTCCCCTGAATATCTTCTCTGCTCACTTC CACCATCTAAGAGGAAAAGGTGAGTTGCTCATGCTGATT AGGATTGAA |
| 561 | ADXCRP D.12400.C 1_at | SSFA2 | Sense | sperm specific antigen 2 [Source:HGNC Symbol;Acc:11319] | 561 | TCCTCTGTCAATGTTCGATTATCTCCAGGAAAAGAGACC AGATGCAGCCCACCTTCCTCACCTATAAGTACACACCT GAAGAGAGCAGGAATTGGAAAAGCGGGTGATGAAC ATGATGGTCAGTCTTTAGTTAAATCGACCATTTTCATCTC TCCATCATCTGTGAAGAAGAAGAAGAAGCCCCCAGAGTG AGGCGCGCGGGTGGAGGAATGCCATCATGGAAGGAC TCCTACCTTGTCACGGCTTGCTCCACCAATGTCTCA GTCTACCTGTTCCCTT |
| 562 | ADXCRP D.1899.C1 _at | RAPH1 | Sense | Ras association (RalGDS/AF-6) and pleckstrin homology domains 1 [Source:HGNC Symbol;Acc:14436] | 562 | GGTAATGAGCTCAATGCCTCCATTTAATCACTTTTATAA GGCTCTCCAATAAGGCTGCTGTGCTGTGCTCCTGCC AGTGTTGGAGTAATAATAACATTTTACTGCACACACCTTA TGGGAAAGTGTTTATACTGAGTGTAGTTTTAGGAGGGGT AAATGAAGATTATTTCCACAACTCTGATGGTATTTACCAAAACAT CACGCCTTTACACAACTCTGATGGTATTTACCAAAACAT GGCATGTCTTTCACGTATATTCCTGAAAACACCAA |

FIG.7-148

| 563 | ADXCRA D_CN341 871_at | IRF6 | Sense | interferon regulatory factor 6 [Source:HGNC Symbol;Acc:6121] | 563 | AGCTTTAAGAGGAAAGAGCTCTATTTTCTTGTTTCTTC TCTGAGCTAGACTGAGCTGGGGATCTAAGATGTACTTCT CTGACTACAAAAGGGACAGTATCATTTAGATTTTTGCA GTTGGAAGAAATGGGTTGTTGAGTGTGTTAAGGCTGGG ATGAAGAAGGGCTGGGCAGTACTCTTCTGGAAAGGCTC ACCTAGCACGAACCTGC |
|---|---|---|---|---|---|---|
| 564 | ADXCRA G_BC021 570_x_at | ZNRF3 | Sense | zinc and ring finger 3 [Source:HGNC Symbol;Acc:18126] | 564 | GGTAATAAAGAGAGCCCTCCTTGTCAACCCAAAATGTGA GCCCCCTGTGGCAAAACCACCCCTACCCCATTAACAA ATCAACAGACAAAATTCTCCGAGTCCTTTGCCTCTTTG ATAACATGTGTTCTGTTTGTAAAGTGTGTGCTTGG GGTTCCGAGGTGTGGGATTGAGTTCTCTGCTTTGTTTTT TTTTAAGATATTGTATGTAAATGTAAAAGTTATTTAAATA TATATTTTAAAGAACCCTAACTGCCAACTTTTGCTGAAAA A |
| 565 | ADXCRP D.4759.C1 _s_at | FOXRED2 | Sense | FAD-dependent oxidoreductase domain containing 2 [Source:HGNC Symbol;Acc:26264] | 565 | GAGTCACCTTTAGTCACCTGGTCCGTAACCATCTTTCCT GTCTAAACTTCTCACCCCACCACTCTGGCTTATACCCCT GCTCTCTTTAAAATAGCCAGTCAGAATTAGCTTAGATTG TGCGGTCCAACCCTAGCCCATAGGGGAACAACACAGCA GTAGGGGGTACCTGCATCAGGGATAAGAACCCATTCCC CTCCCTTGTTCCGGTGTCTCTCGCCATTGCACCATCC ATGAGACGCACTCTTGTATAGAAGTA |

| 566 | ADXCRIH.2824.C1_s_at | TBK1 | Sense | TANK-binding kinase 1 [Source:HGNC Symbol;Acc:11584] | 566 | GGGAACCTCTGAATACCATAGGATTAATATATGAAAAAA TTTCCCTCCCTAAAGTACATCCACGTTATGATTTAGACG GGGATGCTAGCATGGCTAAGGCAATAACAGGGTTGTG TGTTATGCCTGCAGAATTGCCAGTACCTTACTGCTTTAT CAGGAATTAATGCGAAAGGGGATACGATGGCTGATTGA ATTAA |
|---|---|---|---|---|---|---|
| 567 | ADXCRAD_AW449577_s_at | MIR612 | AntiSense | hsa-mir-612 [Source:miRBase;Acc:MI0003625] | 567 | TAAAAGAAACACCTGCGGCGCTCCGCGCCTCCCTCCC TCCCTCCCAGGCTCACCTCCTACCTTCCTTACTTCCCTT GTAAAGGCATAGCCAGGGGACATTGTCCCCAGCTTCA CATCCACATGTCTCCTAGCATGGCACATGCATATCCTGC CCAAGGAGCATGAAGTCAGACCAGCAAACTGAACACGA GGCACAGTCCTGCATGCTCTGGGACCGAGCACTGAG |
| 568 | ADXCRIHRC.2845.C1_s_at | RTEL1 /// TNFRSF6B | Sense | regulator of telomere elongation helicase 1 [Source:HGNC Symbol;Acc:15888] /// tumor necrosis factor receptor superfamily, member 6b, decoy [Source:HGNC Symbol;Acc:11921] | 568 | AGCTGAAGCTGCGTCGGCGGCTCACGAGCTCCTGGG GGCGCAGGACGGGGCGCTGCTGGTGCGGCTGCTGCA GGCGCTGCGCGGTGGCCAGGATGCCCGGGCTGGAGCG GAGCGTCCGTGAGCGCTTCCTCCCTGTGCACTGATCCT GGCCCCCTCTTATTTATTCTACATCCTTGGCACCCCACT TGCACTGAAAGAGAGC |

FIG. 7-150

| | | | | |
|---|---|---|---|---|
| 569 | ADXCRAD_CN341871_x_at | IRF6 | Sense | interferon regulatory factor 6 [Source:HGNC Symbol;Acc:6121] | 569 | AGCTTTAAGAGGAAAGAGCTCTATTTTTCTTGTTTCTTCTCTGAGCTAGACTGAGCTGGGGATCTAAGATGTACTTCTCTGACTACAAAAGGACAGTAGCTATCATTTAGATTTTTGCAGTTGGAAGAAATGGGTTGTTGAGTGTGTTAAGGCTGGGATGAAGAAGGGCTGGGCAGTACTCTTCTGGAAAGGCTCACCTAGCACGAACCTGC |
| 570 | ADXCRIHRC.1844.C1_s_at | NDRG2 | Sense | NDRG family member 2 [Source:HGNC Symbol;Acc:14460] | 570 | GGAATGGGAGTTGGCGGGCAGTGAACGAGTGTGGGGAAGGATTGGTGGTGGGGCAACAGGAAGGGGCCTGGGGCCGTTTGGGTGCCCTAACTTTGGTAGCTCAGTGTGCATTTAGAGTGGGACTGGGAGGGAGGTAAGCTTGGGGTGGGCTGCTTGGGGCTTGGCATAGGGGTGGAAAGGGCTACCCTGGGGCTTTGACCCCCCTGTAGTATGTGTGGAGGGTGCCCTCCCGT |
| 571 | ADXCRAG_BX640630_s_at | SLC30A7 | Sense | solute carrier family 30 (zinc transporter), member 7 [Source:HGNC Symbol;Acc:19306] | 571 | AAACTGCTATTTCTAACTCTTCATGAAAGCATTACCTTTGGAAAGTTAAACTTTTTTTCCTTTCATCACCGTCTTTGAAACAAATTATTTTCCAATTCATAAGAACTTTGGTAAAAAAAAAATAAAAGGAAATTATATGTTTTCTTTGGACATTCATTGGAAGGCTTGTTGAAGACATGATCCCCCAGAAGCCTTAGTGACCCAGATCTCAACCAGAGACTCAAGATAGCCTCAAATACAGTGAAAG |

FIG.7-151

| 572 | ADXCRIH. 2819.C2_x _at | RGPD3 /// RGPD4 /// RGPD5 /// RGPD6 | AntiSense | RANBP2-like and GRIP domain containing 3 [Source:HGNC Symbol;Acc:32416] /// RANBP2-like and GRIP domain containing 4 [Source:HGNC Symbol;Acc:32417] /// RANBP2-like and GRIP domain containing 5 [Source:HGNC Symbol;Acc:32418] /// RANBP2-like and GRIP domain | 572 | AACTGTATTTTAACTTAGCACAATTAACTGCAGCATATTT ACTTCATAGCCCCTTAACATGTCACTTTTACCAACAAAG CTTTTTCCTTCATATTCTAATCACAAAAATTTCTCAACAA TTTATAACAATCTGTAAATCTGACCTTGCAATAAATAGTC ATAAAACGTTATTTTATTACTATTATTATTTTTAGAGACA AGGTCTCCTCGTGCCGAA |
| 573 | ADXCRIH. 3580.C1_a t | RP11-460N11.2 (Clone_based_ vega_gene) | AntiSense | Known pseudogene. | 573 | TCCCACACCAAAATAGATTCCCAAATAGATATTACAAGT AGGAGAATTTTATGACTACTCAGATAAACGACCATTG ATCACTTACAAACATACAAGTCATAAACAATACAGAAATA ATATGTGTATACAAAAACACAGAAATTATTATATGGGAA TAGACATATGACTGATTCATATGTAACTTTGTCTCCACG CTGTCTTAAAGTGTACAGAGTTGAATATTGTCATTCACA ATTGTCACACAAAA |

FIG.7-152

| 574 | ADXCRIH.1401.C1_s_at | KRT18 | Sense | Keratin, type I cytoskeletal 18 (Cytokeratin-18)(CK-18)(Keratin-18)(K18)(Cell proliferation-inducing gene 46 protein) [Source:U+E67niProtK B/Swiss-Prot;Acc:P05783] | 574 | CACCAAAGTTCTGAGGCATTAAGCCAGCAGAA |
|---|---|---|---|---|---|---|
| 575 | ADXCRAD_AA620926_at | RP4-717I23.3 (Clone_based_vega_gene) | AntiSense | Novel processed transcript. | 575 | TAAAACTCTCTGAGACTGTTTTCCCCCCATGTCAAAACACCTATTTTGCATGGCTATATGGAAATTAAATGAAATAGCAAATATGAAAAACTTTTGGCCCAGTGTATAATTCATATCAGGCACTGATCTGTTTCTTTTTGCCCTAACCTACTTTTCCTGCATCATATACCACTACACCTCTTACAAACCTTATTAATAGAGCCACTCTAGACTACTTTATTTCCCCAAGCCATACAATGTACT |
| 576 | ADXCRAG_NM_001909_x_at | CTSD | Sense | cathepsin D [Source:HGNC Symbol;Acc:2529] | 576 | AAAACCCACCTTGTTGGAGCCTGCAGGGTGGTGCTGGGACTGAGCCAGTCCCAGGGGCATGTATTGGCTGGAGGTGGGGTTGGGATTGGGGGCTGGTGCCAGCCTTCCTCTGCAGCTGACCTCTGTTGTCCTCCCCTTGGGCGGCTGAGAGCCCCAGCTGACATGGAAATACAGTTGTTGGCCTCCGGCCT |

FIG.7-153

| 577 | ADXCRA D_AV6969 77_at | LCN12 | Sense | lipocalin 12 [Source:HGNC Symbol;Acc:28733] | 577 | CTAGACCCCACTGTGGTCCCCTTTCTCCCTCCTGCTTCT CACCTGAAGCCACCTGCCCCTCCTTGTGCCCTCCCTT GCTTCCTCCTGGGCTCTGTCCCCTGCTCCCCCTTTGTC CTCCATCCCGACTCCATCTCCCCCACCAGGCTGGTCAC CCCAGGCCAGCGTCTGTTGAAGGATGAAGCAGCTCCTG TCCGGCCCAGCCCTGCCTCACAGCTGTGCGAGCTCTG CCCTTCTCAGCTCTCAAACCTGAATAAATGCACCAGCC CA |
| 578 | ADXCRA G_NM_00 1918_s_at | DBT | Sense | dihydrolipoamide branched chain transacylase E2 [Source:HGNC Symbol;Acc:2698] | 578 | TGGCAGAGCAACACTTCGTCTCAGAAAAAAAAAAA CCAAAAACCAAAAGCCAAGTGTGGTGTGCACCTA TAGTCCCAGCTACTCAGGAAGCTGAGACAAGAGGATCA ATTGAGCCCAGGAGTTCAAAGCTGTAGTGAGCTGTCAT TGTGCCACTATCCTCCAGT |
| 579 | ADXCRP D.8253.C1 _x_at | TEAD3 | AntiSense | TEA domain family member 3 [Source:HGNC Symbol;Acc:11716] | 579 | GGAGCAGTGCCCACCAAGGGTTTGTCAGATTCAAGCCT CAGGCAAGAGAGAAAATCAAAAGCCTTCTGCTACTCTCT CCTCTGGGCCTCTGGTCTGCCCAGAGGCTGGGACTCCT TCCTCTACCTTGCTCTCAATCTGGAGGGTGCTGGGGG TGCCTCCATCTTACTGGGCCCCTGGCTGCCTTGTGGGC TGAGGTGCTAATGGGGTCTAGTAGCCTGCTGTGCTCCCT TCTTCATGCCCAGTCTGAAACAGGTCTGCTCCCCTAACCC AG |
| 580 | ADXCRP D.5008.C1 _s_at | DGAT1 | Sense | diacylglycerol O-acyltransferase homolog 1 (mouse) [Source:HGNC Symbol;Acc:2843] | 580 | CAGGGAGGCCTCTCTGCCCCTATGGGCTCTGTCCTGC ACCCCTCAGGGATGGCGACAGCAGGCCAGACACAGTC TGATGCCAGCTGGGAGTCTTGCTGACCCTGCCCCGGGT CCGAGGGTGTCAATAAAGTGCTGTCCAGTGA |

FIG. 7-154

| 581 | ADXCRP D.13135.C 1_x_at | MLPH | Sense | melanophilin [Source:HGNC Symbol;Acc:29643] | 581 | AGGATCCGAGTGGTAGTGTTTCTGAGAGTCAGGGTCTA GGTGCTGGAGTGCGCACGGAGGCCGATGTAGAGGAGG AGGCCCTGAGGAGGAAGCTGGAGGAGCTGACCAGCAA CGTCAGTGACCAGGAGACCTCGTCCGAGGAGGAGGAG GCCAAGGACGAAAAGGCAGAGCCCAACAGGACAAAT CAGTTGGGCCTCTAGCGT |
|---|---|---|---|---|---|---|
| 582 | ADXCRA D_BM726 905_s_at | FAM118B | Sense | family with sequence similarity 118, member B [Source:HGNC Symbol;Acc:26110] | 582 | AGTAACAATAGCCAGAGGTTGAAGGGCGGGGTAGAAGA GGGGGAATGTTGCAGCGTAATCCTTCATACCACCTGG TTCTTGATATTCTGCGCGCCTGTTCAAGTTCAAGAATAAA AGCGACAGCAGGACCCAAATGCAGCTCCCAACCCACTC CCCAGGCTAGACATGCTTGTGTCCACACAGCACACCAA TGTGATACTTCCAACTGACCGGCT |
| 583 | RDCR301 _B05_at | EME2 | Sense | essential meiotic endonuclease 1 homolog 2 (S. pombe) [Source:HGNC Symbol;Acc:27289] | 583 | ATGCAGTGTGTCTGAGGTCCTGTCACCCCTGAGGCTG TGTGTGTCCTTTGCCAAATTAAAGAGTCTTACTGAATGC GGTGCATCCAGGAGACAG |
| 584 | ADXCRP D.3751.C1 _s_at | YIPF2 | Sense | Yip1 domain family, member 2 [Source:HGNC Symbol;Acc:28476] | 584 | ACTTTTATTTTCTATGCAAAGGTGATTCAGAGAATTTATA TAAAGGCGGGGCGAGGGGCGAGCCGAGCAGGGAGCTTTG GGACAGGGCTGGGGCCCCCATATCCCCCCGGGCCAC CTGCTTTCCCTCCTATGGCTCCCCTGGAACAGGAGGGA GAGCCAAGGGGCGGGCCCCAGCCTGGACAGAGCCCCGC TCCTGCCTGGGTGCACACACGGGCCTGGGCCTGAGCTCCA GCATCTGAGTTTGGGGGTA |

FIG. 7-155

| 585 | ADXCRAD_AA420497_at | BTBD3 | Sense | BTB (POZ) domain containing 3 [Source:HGNC Symbol;Acc:15854] | 585 | TGCACATTGTGACATGTACACTAAAACTTAAAGTATAATAATAATAAAATAAAAAAAAGAAAAGAAACCTAGTGTGTTAAACCTTAAATGCCCTTAGAAATAACCTAGACCAGTGTTTCTTAAACTGTGGTCATGAGATCAGTTGAATGGATTATGACCAACATTGAAA |
|---|---|---|---|---|---|---|
| 586 | ADXCRPDRC.8779.C1_s_at | RBM4B | Sense | RNA binding motif protein 4B [Source:HGNC Symbol;Acc:28842] | 586 | CTTGCTTTCCCTAGGAGTTGAATCCTTCTCCCTGCCTACCTGCAGCATCCTCCTTTCCCTTTAAATGACCATGTAGTGGCAAGCAGCCTTTTACTCTCTTCTGTTAGCTCTGGACTCTTAACACTTAAGTACTCTTCTGAAATTGCTAGGACCATTGGGGNNNNNNNNNNNNNNNNNNNNNATGTCCGACCTGTGATCGTGGGTACAGCATTAGCTGAAATTTACCCTTGT |
| 587 | ADXCRAD_AU147861_at | EGFR | AntiSense | epidermal growth factor receptor (erythroblastic leukemia viral (v-erb-b) oncogene homolog, avian) [Source:HGNC Symbol;Acc:3236] | 587 | AAGGACCCTGAAAAATGACTTCTCATTTCCTGCCTGCAGAAAAGAGAAATATTAGGATAGTGTTGTGTGCAAAAAATGCAAGCTTGCAATGAGAGATGCAGAGTGTGAGGGAGAGAGGCACGAAGGGGTGGAGAAAAAGACAGAGAATTTGAGGTTGACTCACGGCTTTGAAGGAAAACAGGAAGANGAAGAAAGTCTGTCTNCCATGGTCGGCAACCCACACTTTACACATTTT |

FIG. 7-156

| | | | | |
|---|---|---|---|---|
| 588 | RDCR108_G11_at | FAM190A /// SEPP1 /// UBTD1 /// UTY | AntiSense | family with sequence similarity 190, member A [Source:HGNC Symbol;Acc:29349] /// selenoprotein P, plasma, 1 [Source:HGNC Symbol;Acc:10751] /// ubiquitin domain containing 1 [Source:HGNC Symbol;Acc:25683] /// ubiquitously transcribed tetratricopeptide repe | 588 | ATAAGTGTACCAGGACTCTAAAAGAAACTTGTTTGTATA ATGCTATCCAAGGTATGTGACCCATTTTAAGCCTCCGTATCA TGATGTGTGTTATGACCCATTTTAAGCCTCCGTGATCA CAGTTTTTAAAATAAAATTAAGGACTGGTCCTATTTCTAG GTGACACAAGTAAGGTAATAGCTAGAACGGGAAAAAG AGGGGCCCCCAAAATGTAACCTTAAAATTGGTGCTTG TGCCGCTATTGATAGTAAGCAGCATGGAATAGGATGTG GT |
| 589 | ADXCRIH. 1549.C1_a t | ELOVL5 | AntiSense | ELOVL family member 5, elongation of long chain fatty acids (FEN1/Elo2, SUR4/Elo3-like, yeast) [Source:HGNC Symbol;Acc:21308] | 589 | TAACAGTGCATAAATCAATCCAAATTTAGACCCTGGCAA CCAGTTCCCCCATTGCTCATCTACGGGACTCTGTCAACG GTAAATAGGCAATCATCTCTCTTGAAAGTATACATCCT CTCTCGCACTGGTGGAAAGCAAATTGACTTTTTGTTTGC TGTATAAAACCCTTAGCACTTCAA |
| 590 | ADXCRA D_BU5409 35_s_at | FZR1 | Sense | fizzy/cell division cycle 20 related 1 (Drosophila) [Source:HGNC Symbol;Acc:24824] | 590 | GGCAGGAGACCGTGCCACACCAGCTGTCCAGAGTCGGAG GACCCCAGCTCCTCAGCTTGCATGGACTCTGCCTTCCC AGCGCTTGTCCCCGAGGAAAGCGGCTGGGCGGGCGG GGAGCTGGGCCTGAGGGATCCTGGAGTCTCATTAAATG CCTGATTTGTGACCATGTCCACCAGTATCTCGGGGTG |

FIG. 7-157

| | | | | |
|---|---|---|---|---|
| 591 | ADXCRPD.4167.C1_at | POLR2F | AntiSense | polymerase (RNA) II (DNA directed) polypeptide F [Source:HGNC Symbol;Acc:9193] | 591 | TTCGGGCATTCTCCAAGTCATCTCAGCCCTTCATCCTCCTC CACATCATCAAAGTCGTGCGCCATCAAATTGTCCTCGTT GTCTGACATGACACCCTCGCCTCAGCGACCCGCTGC GCCCCGGTCCCGCGCGGAGACCCGCAAACAGCGACAC TACGACTCGGCGGCGGCTCCTAGCTTATCTTGCGCCTCGT GCCGAATTCGCCACCAGGCCTCGCTACAATTACGGAC CGTTATAGTA |
| 592 | ADXCRAD_BX406209_s_at | RABIF | Sense | RAB interacting factor [Source:HGNC Symbol;Acc:9797] | 592 | CAACCTTTTAGCTATGATGACACATAACAAAAGATGTTTA TGTACTAATAGTTGAAATCTGCCTTTTCTCATTCAAGAA GGCATACAAATATCTGAGAGTGACTTTGTTGTATGGCTA CCCTTGTGATCTACAGTAATTTATTCTTT |
| 593 | ADXCRPD.12748.C1_at | AC138128.1 (Clone_based_ensembl_gene) | Sense | Novel long non-coding RNA. | 593 | GTGGGAGAAGTTGGCGTCCTAGGCTGGGATTGGTCG GGGGAGACCCTTAAAGAAAAAGGCCAGGCTGAGGGTCCT GAGGAGAGAGAGAGAGGCCACGTGGATGGAGGACTGT CACCCCCTTCTCGGTTCTCTGTCACCCCTTGAGTCTAACT CACTGTTGAGGGGAGGAGAAGAAGGCTTTCGGGAGTGGACGAAG GGAGACCGAGGAGAAAGGCTTTCGGGAGTGGGGACATTAT CCACCCAGAGGTGTGCTACCCACCACCGCGAGATC CTTAGAGT |
| 594 | ADXCRPD.2825.C4_x_at | SPDYE2 | AntiSense | speedy homolog E2 (Xenopus laevis) [Source:HGNC Symbol;Acc:33841] | 594 | GAACTGATTTCAAGGAATGGGTCCTTCCCTTCAGAGCC ACATGTGTGCGGGACACCCAGACAGAAAACACAAACAC AAAGTCGAGTGGAGGGCATTTGAAGGAGCAGTGAAGC CGAGCCAGGAAATACCAAGATGGCGAGCCAGTGTGCTT GTAGAGATTGTAGAGAGGGTAGAATTGACACTGTGGAC CCTGGCCTCGATAGAGAAGGCATCAGTAAGGAAGTT GTTCA |

FIG.7-158

| 595 | ADXCRPD.2994.C1_s_at | CORO1C | Sense | coronin, actin binding protein, 1C [Source:HGNC Symbol;Acc:2254] | 595 | GAACATTCTGGATAGCAAGCCCACTGCAAACAAGAAGT GCGACCTGATCAGCATCCCAAGAAAACCACAGACACG GCCAGTGTGCAAAATGAAGCCAAGTTGGATGAGATTTA AAAGAGATCAAATCTATAAAAGACACAATCTGCAATCAA GATGAGCCGTATTTCCAAGTTAGAACAAGCAGATGGCA AAGATAGCAGCCTGAAGGTCCCACC |
| 596 | ADXCRAG_BX6473 58_x_at | NPIPL2 | Sense | nuclear pore complex interacting protein-like 2 [Source:HGNC Symbol;Acc:34409] | 596 | TGATAATCTCAAGACTCCTCCCTTAGCTACTCAGGAGGC CGAGGCGGAAAACCACCCAAACCCAAGAGGTGGAGG GTGGATGAGGTGGAACAATCACCGAAACCCAAGAGGC GGAGGGCGGATGAGGTGGAACAATCGCCCAAGCCAA GAGGCAGAGGGAGGCCGAGGCACACAATTACCCAAA CCCAAGAGGCGGAGGTTGAGTAAGCTGAGAACACGCC ATTGCACTCAAGCCTGGGCAATAAGAATAAATCCGTGG GTCGA |
| 597 | ADXCRAD_BX1176 13_at | HIF1A | Sense | hypoxia inducible factor 1, alpha subunit (basic helix-loop-helix transcription factor) [Source:HGNC Symbol;Acc:4910] | 597 | AATTTACCAAGCCACATATTGGAATGGTACCCCAGGC AGAAGGAGTAGAGTAAGCAAGCCAGAAAGGAAATACTA TGGTGCTTTTGAGTAACTGCAGTGTGGCTGAAGAATGT GGAAAATGATGAGGATAAAGAGGTGGACAGGAACTAG GTAAGGGAGGGCCTTCCTTTTAAATAATTAGACCTTGTC CTGTGTACATTTAATGGGATTTTAATCAGGCCATAATGC CAAATTTCTTTACTTCGGAAGGATCTTTATGGTGATGGT TTCAGA |

FIG.7-159

| | | | | |
|---|---|---|---|---|
| 598 | ADXCRAD_CK300213_at | TIMM22 | Sense | translocase of inner mitochondrial membrane 22 homolog (yeast) [Source:HGNC Symbol;Acc:17317] | 598 | ATTTTTCTTGGCCTAGTTGTGTGCCATGGATATTT |
| 599 | ADXCRPD.15724.C1_at | MYO1E | AntiSense | myosin IE [Source:HGNC Symbol;Acc:7599] | 599 | GAGGGATATTATTTCCATAGCCATTACCATGATACATAT GATACTGCCTAGGTAGAGCTGGGACTGTAGGGTGGGG AACCAATGCTGTCCTGCACACTGAAACTATGAATGCCAA GATATCACTGCCAGATCCTTCTGTGGATAGCTGGGGGC AT |
| 600 | ADXCRAD_NM_006932_x_at | RP3-412A9.10 (Clone_based_vega_gene) /// SMTN | Sense | Putative processed transcript /// smoothelin [Source:HGNC Symbol;Acc:11126] | 600 | GAAGCCTGACCCCAAGTGTCTTCACCTATGTGCAGT CGCTCTACAACCACCTGCGACGCCACGAACTGCGCCTG CGGGGCAAGAATGTCTAGCCTGCCGCCGCCGCATGGCC AGCCAGTGGCAAGCTGCGCGTCCGCCCACTCTCCGGGAC CGTCTCCTGCCTGTGCGTCCGCCACCGCTGCCCTGTC TGTTGCGACACCCTCCCCCCACATACACGCAGCGT TTTGATAAATTATTGGT |
| 601 | ADXCRPDRC.13803.C1_s_at | SLC11A2 | Sense | solute carrier family 11 (proton-coupled divalent metal ion transporters), member 2 [Source:HGNC Symbol;Acc:10908] | 601 | GCATTATTACTGATACTTGCACACAGTCAAAAGGCGAGA CTGGATGGATGGTCTTTTATAAGGCATTAAGGGTACAC TACTGTGTTTCACTGACCATACATTTTCTTAGCCCCTCA AGTAATATAGCACAGAGTTATGAATGACAATTCCCCTAA CCATTCCTCTTCATATCTGCCTCTTCCCCTTACCATCGT AATTCTCCAAACTGGTCATAAAGGCACTCTGTG |

FIG. 7-160

| 602 | ADXCRP DRC.8133 .C1_at | SLA | Sense | Src-like-adaptor [Source:HGNC Symbol;Acc:10902] | 602 | CATTAAGTCCTCTGTGTAAGGTGTCAGGCAAGCCNNNNNNN NNNNNNNNNNTGGGTAAGTCCTAACCCCCACAAAGGT GTTCCCAGTGACTACCT |
|---|---|---|---|---|---|---|
| 603 | ADXCRP D.13304.C 1_at | GREM1 | AntiSense | gremlin 1, cysteine knot superfamily, homolog (Xenopus laevis) [Source:HGNC Symbol;Acc:2001] | 603 | TTCGCTGGTTCTGAATGTCATTTTCCTCCTGGTGTGG TTTTACATTTTCAGCTTCTTCCCTTTCTTCTTCTCCCAC CCTCAAAATTCTGCCTTAGCATTGTGTGCTTAATTAAAT CCACTCTGTGCTTTATAGTTGGAGAATGTGGACAATACA AAGATTTGGGGTGGGGTCATACAGTGTATACAAAACAC AGACACTATGTGTTTGGACAAATTCGCCTAGCGTGAGAA TCATCAGTAGTGAGTAAACGTTTGAAATCAGAGCCAA |
| 604 | ADXCRP D.11084.C 1_at | TJP2 | Sense | tight junction protein 2 (zona occludens 2) [Source:HGNC Symbol;Acc:11828] | 604 | TAATTATTGCTGTGTGGATTTCTCTCTAGCATTTTAGCTCAT TCCAGTAAATGATTTTTTCTTTATGAAATAGAACTACCN NNNNNNNNNNNNNNNNGTTCAACAACAACAAACTGA AGGGGGAGAAAAATACACCATTACCACAGCAACAAATT AGTTTATG |
| 605 | ADXCRSS .Hs#S373 9317_at | TEX10 | AntiSense | testis expressed 10 [Source:HGNC Symbol;Acc:25988] | 605 | TTCTCCCAGTACCTCATTTGCACAAGCCTTCCTGCCATT CTTCAAATATGCGAAGCCTGTTCTCACCTCAAAGCCATT GTACTTGCTGTTTCCTATGCCTGAATGTTCTTCCCACAG ATGTTGACAAGACTTGCTCCTTCACTTCAATGACATTCA GATATCTATTCTCAGAGAGCATTTGACAACCTATCTAAA ATAGCTCCCCCTCACTGTTCCTGCCATGCCTGTCTTTATAC CCCATTTTACTTTCATCTTTCTCCTAGTACTGACATTAT |

FIG.7-161

| 606 | ADXCRSS.Hs#S2985244_at | NDUFA13 /// YJEFN3 | AntiSense | NADH dehydrogenase (ubiquinone) 1 alpha subcomplex, 13 [Source:HGNC Symbol;Acc:17194] /// YjeF N-terminal domain containing 3 [Source:HGNC Symbol;Acc:24785] | 606 | AGAACTAGCAAAAGCCAAGGCCCTGGGGCGGGGAGGAGCCTGGTATGTTCAAGGGGCAGAAGGGAGGCTGAAGCAGAGTGATCAAGCGGACAGGCAGGCAGAGCCTCAAATCCCAGACTGAGGAACATGGTGAACGGAGACACTTCGGGGGTCCCACACATAAAGACGGAGACAGAGACTCAGGGCAGGAAAGTCACATGCCCTGGGACACCCAGTAAACAGAGCCAAACTCAAACCTCAGCCTGTCTGCAGCTGACATAGGATGAAGTT |
| 607 | ADXCRPD.13218.C1_s_at | THRA | Sense | thyroid hormone receptor, alpha (erythroblastic leukemia viral (v-erb-a) oncogene homolog, avian) [Source:HGNC Symbol;Acc:11796] | 607 | TAAGTTATTAACTGAGGCTGACCAGAGGGAGGACCCCCCCTTTACCACCCCATGCACTTTGCGAGCTGCCCCTTCTTCCCCACATCAGAGAGAAATGCCCCCACACCAGAGCCCCAAGGGTAGGGCTGCCGATCAGAGCTGTGAGTTAACACAACAGG |
| 608 | ADXCRPD.7267.C1_s_at | MED12 | Sense | mediator complex subunit 12 [Source:HGNC Symbol;Acc:11957] | 608 | AGCACCAGTAGTGGTTGGGCCTCCCCTCAGGCTCCATTTTTAATAAGTTTTTAGTATTTTGTAATGTGAGGCATTGAGCTGTTGGGTTTTGTATATTATTATAGAGACCCCAGAGCTGTTGCACCCAATACACAGAGCTTCTTTGCAA |

FIG.7-162

| 609 | ADXCRAD_BP397177_s_at | KLF6 | Sense | 609 | TACACACATGTGAGTCTGGCTGGGCTGGTATTTTGTTG<br>ATCTTCCTGGAAATGAGCAGTGACTAACGCTCACATAAC<br>TGGTTTTTTTTATCTGGCTGATGAATACATTTACCT<br>AAGAAACTCATTTCGTTTACTTAAGAGGGGAAGTGCAG<br>TTTTCTTTTGGCAGTTCAGAATCCAAGCACTTGATTTGCT<br>GGGTTTGGAAAACTCCTTTTTTGGCCTTCTATGTGCTTA<br>GCCATAACAATTCCAT |
|---|---|---|---|---|---|
| | | | | | Kruppel-like factor 6 [Source:HGNC Symbol;Acc:2235] |
| 610 | ADXCRSS.Hs#S1918301_at | N/A | No Transcript match | 610 | AGAGGGGTCACCATACTTTCTTCAGTTCCATGTTAACT<br>GAACAATCTTTTCTGCTAATCTGAACACCCTGTGCAA<br>TAGAGTCTGACTCCATTTTTGATGTTTGACTGCAGACA<br>TCTTTTCAGCCTACCCTTCCATCCATCTCTCTTCTGTCCAA<br>CACTGGGGCAAGCTGACAAAAATCCTCAGGTGCTCCTC<br>TTCTGTAACCAGCAGTAAGTTCGAATCATACACTGCCAC<br>CCTCACCCCAACCCTGTCCCTTAACCACATTAAAACCCA<br>AAGCCAGTCTCCT |
| | | | | | N/A |
| 611 | ADXCRIHRC.2931.C2_s_at | STAT1 | Sense | 611 | GGGCCTGTTGAAGATGCTTGTATTTACTTTCCCTTGT<br>AAATGCTATTCCCATCCACAGCTGAACTTGTTGAGATCCC<br>CG |
| | | | | | signal transducer and activator of transcription 1, 91kDa [Source:HGNC Symbol;Acc:11362] |

FIG. 7-163

| | | | | |
|---|---|---|---|---|
| 612 | ADXCRSS.Hs#S191 8097_at | ZFAND3 | Sense | 612 | zinc finger, AN1-type domain 3 [Source:HGNC Symbol;Acc:18019] | GAGGAGATAAACTAACAGAGGTCAAGAAGATGAAGAGT TGTTTCAAACATGGTACAGTTGAGATTCCTAGCATTATT CTAGTCAGACGTGTCTGTCAAGTAGGCCATTGGATATC GGGATTGGGATTTGAGGGGAATCCATAGATGGAAATAT AAGTTCAAGAGGCATCAGCATGGATACCCTATTGGATC TGGATGAAATTACCTAAAGGAGAAAATCAGGAGGACG TGATGCTGGGTGATTTTAGAGGAGAAACCATGAAGGATT CCAAGGAGCAGCAGTTGGTCA |
| 613 | ADXCRP DRC.1321 0.C1_s_at | ROD1 | Sense | 613 | ROD1 regulator of differentiation 1 (S. pombe) [Source:HGNC Symbol;Acc:10253] | AAAAATTCATCCCATATCCAGAAAGTACCAGTTATAAAG ATTGCTGACCAAGCAAAGTTTTGCATCAAAGTGTCACCT CATTGCTCTGACCAAAGACTGACTGTTGTGGTTTTAACT |
| 614 | ADXCRP D.5524.C1 _s_at | EML2 | Sense | 614 | echinoderm microtubule associated protein like 2 [Source:HGNC Symbol;Acc:18035] | ACACCAGTGTGCTACAGTGGCGGGTGGTCTGATGCGG CCAGGGAAGAGTCAGTGTGTCAGGCAGGAATTCTATTT TCGGGGAGATGTCTATTGCCGAGTAGAGTAATATATACCC AGAGTATGTCTATAGCAGAGAGGGGTTATGGGGGCGGG AGGGTAGAGACTGACATACAGAGAAGTCTCTATTTATCCGGGT GGGAAGAGGGAGTCACATCGCTTT |

FIG.7-164

| | | | | |
|---|---|---|---|---|
| 615 | ADXCRA D_CA3134 35_s_at | HIST2H2AA4 | AntiSense | histone cluster 2, H2aa4 [Source:HGNC Symbol;Acc:29668] | 615 | CCAGCTGGAGGTGACGAGGGATGATGCGCGTCTTCTTG TTGTCCCGAGCCGCGTTGCCCGCCAGCTCCAGGATCTC GGCGGTCAGATACTCGAGAGACCGCAGCCATGTGACG GGGCGCCGCCCCCACTCGCTCCGCTCCGCTAGTTGCCTT TGCGCAGCAAGCGATGCACTCGCCCTACCGGGAACTG AAGGCCAGCGCGGGACGAGCGCGACTTGGCCTTGGCG CGGGGCCTTGCCTCCTTGCTTGCCACGACCAGACATGAC AGCCGATAGTAGTCACCGAGAG |
| 616 | ADXCRA D_CX8704 01_x_at | BAT1 ///SNORD84 | Sense | small nucleolar RNA, C/D box 84 [Source:HGNC Symbol;Acc:32743] /// HLA-B associated transcript 1 Fragment [Source:UniProtKB/TrE MBL;Acc:B0V2L0] /// small nucleolar RNA, C/D box 84 [Source:HGNC Symbol;Acc:32743] | 616 | GAACTATGATTGCACTACTGTGCTCCAGCTTGGGCAAC AGAGTGAGATCTTGTCTCCAAAAGTCCTTGAAGGATTTT AGGAAGTTGTTAAAGTCTTGAAACGATGTTTGGGGGCA TGTTAGGGTTCTTGAATGTTTAATTCCTCTAATAACTGCT TATTCAAGAGAAGCATTTCTGACTGGGTGCAGGGCA |
| 617 | ADXCRP D.6719.C1 _s_at | FGFBP1 | Sense | fibroblast growth factor binding protein 1 [Source:HGNC Symbol;Acc:19695] | 617 | ATGAACTTTTGTGCTTAGTGAGTGCAACGAAATATTTAA ACAAGTTTTGTATTTTTGCTTTTGTGTTTGGAATTTGC CTTATTTTTCTTGGATGCGATGTTCAGAGGCTGTTTCCT GCAGCATGTATTTCCATGGCCCACACAGCTATGTGTTTG AGCAGCGAAGAGTCTTTGAGCTGAATGAGCCAGAGTGA TAATTTCAGTGCAACGAACTTTCTGCTGAATTAATGGTA |

FIG.7-165

| | | | | |
|---|---|---|---|---|
| 618 | ADXCRAD_AL5471 57_x_at | ANP32A | Sense | acidic (leucine-rich) nuclear phosphoprotein 32 family, member A [Source:HGNC Symbol;Acc:13233] | 618 | GGAGGGATGAAGAGGTTATAACGATGGAGAGGTAGATG ACGAGGAAGATGAAGAGAGCTTGGTGAAGAAGAAGG GGTCAGAAGCGAAAACGAGAACCTGAAGATGAGGGAG AAGATGATGACTAAGTGGATAACCTATTTTGAA |
| 619 | ADXCRAD_AK0219 81_at | AL157877.1 (Clone_based_ensembl_gene) | Sense | Known long non-coding RNA. | 619 | GTGAGCTGTGATGTTGCCGCTACACTCCAGGTGACAGA GCAAGACCCTAAGACCTTATCTCTT |
| 620 | ADXCRIH. 311.C1_s_at | ARHGAP12 | Sense | Rho GTPase activating protein 12 [Source:HGNC Symbol;Acc:16348] | 620 | ATCAACTGAATCCAATATTTCCTGTGGCAAATAACACTTT CCTCATTTCATACCTTTTCTCTCTTCCATGCCAACAT TTCTCCACCCACAACGTACACTTTTATTTCTCCATCAAT ATTTGAAAGCGAGTGATTTGTGACCAGGA |
| 621 | ADXCRAD_BP2098 40_s_at | GOLGA2 | Sense | golgin A2 [Source:HGNC Symbol;Acc:4425] | 621 | CAGGCAACCCCTGCATTCCTTTTTTTACCGGGCTGACGA GAATGATGAGGTGAAGATCACTGTCATCTAAAAGCCGG CTACTGTCAGCAAAGCCTGAAGAAGTGGGGCTGGATAC CCTGCCCCCACCATATCCCTACCATCCCTTCTCAGT |
| 622 | ADXCRPD.15297.C 1_s_at | IGF2R | Sense | insulin-like growth factor 2 receptor [Source:HGNC Symbol;Acc:5467] | 622 | ACAAGCAGACATGCACTCTCTTCTTCCTGGCACACG CCGCTGGCCTGCGAGCAAGCGACGAATGTTCCGTGA GGAATGGAAGCTCTATTGTTGACTTGTCTCCCCTTATTC ATCGCACTGGTGGTTATGAGGCTTATGGTAAGAGTGAG GATGATGCCTCCGATACCAACCCTGATTTCTACATCAAT ATTTGTCAGCAGCCACTAAATCCCATGCACGAGTGCCCTG TCCTGCCGGAGCCGCTGTGTGCAAAGTTC |

FIG.7-166

| 623 | ADXCRP D.16372.C 1_x_at | GLB1 | AntiSense | galactosidase, beta 1 [Source:HGNC Symbol;Acc:4298] | 623 | TCTCCTCCTTCAGTCTTCATCATGTTTTTGTCCCTCAAACA TCAGCCTTACGTCCTCCTCTTTTCTCCCCTCTGCATCCTCTC TCCTTGAGAGACCTCATCCAGCCAGCCCATGTTTTCAACAATC ATCTATACAACAATGATCTTCTACATACATTCCTGGCCC AGATCCCTGCCCTGAATTCCCAGCCTATAGATCCAACAA CCCTCCTCCAATACTGTCTTTCCCAGCCATTCTCCAGGC CTCTGCTATGGTCTGAATGTTTGTGTCCAAAAACATGAT GAAG |
| 624 | ADXCRSS .Hs#S159 1474_at | TMPRSS4 | AntiSense | transmembrane protease, serine 4 [Source:HGNC Symbol;Acc:11878] | 624 | AAGACAGTCCTCAGAAAACCCAAGCTTTCATACAGATGC CAAAAAAGTCCATGGGGTTTAATTCTTTGACCATTTTGA GTGCAGGGACTTATTCATGCTTACATCCTCACAACTCAG CTTGGGGACTGCCTCACACCTGGCAGCTGATCCTTTT GTTTTTAAATGTAAGAAGCCACACAGGACCAGCATTCTTCC GCGGAAAAAGTTAGGACACAGGACCAGCATTCTTCC AGCCACTTGTGTGGATCCCTGATTGAATGTCACCCTTGACT GCCTAACTCATCTCTTTCC |
| 625 | ADXCRP D.8597.C2 _at | FAT1 | AntiSense | FAT tumor suppressor homolog 1 (Drosophila) [Source:HGNC Symbol;Acc:3595] | 625 | CGACTAATCATCTTACGGCAGAGAACAAACACCACCAC CAAGTAAAAATATCCCTGCAACAAACACAACGGATTCCA ATTCCTTCCGGCCAACCCAATGTTCCACGGCGTGGACA CATACTGGTTGGGCGCAGGCATCCTCGCAGTGACGTCC CCTGTACTCGTGGCTGCAGTTGCAGTGATAGGAGCCGT GCGTGTTCTCACAGAGGGCCCCGTGCAGGCAGGGTT TCCAGAGCACTCGTCGTATATCACTCTGACACCTTTCTCC CCTAAAACCCGAATCACACTGACAA |

| | | | | |
|---|---|---|---|---|
| 626 | ADXCRAD_CD721975_s_at | ETNK1 | Sense | ethanolamine kinase 1 [Source:HGNC Symbol;Acc:24649] | 626 | ACTATCCAGGAAAGGAAATTTACAGTATATCTCATTTG GGGTTTGGAAGGATGTGTACAAAATAGTGTAATTGAAAA TTGATAAAAATAAAAATCTTATATACTTATATTGGGTAAA GGAAGATAGGAGAGAAGTGACAGAGCGAGAGAGAGAG AGTGTTTATGTGTGAAGGAAATAAGAAAGCTCAGTCTTA TAAGAAGTCTCAGATAATGTGTAGACTTTACAGAAAAGC AGTTTAAGAATGGTAT |
| 627 | ADXCRAG_XM_374317_s_at | AC011043.1 (Clone_based_ensembl_gene) | Sense | Putative uncharacterized protein DKFZp667B1610 [Source:UniProtKB/TrEMBL;Acc:Q69YS9] | 627 | GTATCCAAGTCCATTGTTACTAGGTTGGAGGCTGGAGA TTCTAAATGGCTTCCAGACCATCTCTCTGATTCTCTTG GGAGATGGGGTCTGAAAGACAATGTCAGTAGTTTTGGG AAATTCTAGAAGTGTGCTTGGAAACGTGGGAAGAGCT CTTGCCTAGTCCTAAATGCTCCATTTGCAGCTCTAGCC AAGTAGATACTTGGTAGGTATAGAGCCGGGTTTGCGTTT ATATTAGCAAAACCTATGTGACGAGTTGAAGA |
| 628 | ADXCRIH.3322.C1_a_t | N/A | No Transcript match | N/A | 628 | TTCTTTATGGTGGGTGGGATGATTATTGTAATCATACTTG GGAACAGAAGTGATGAAAAGGTATGTTACTTGAGATAT GGGAAACGCTATTTCCATGTTAGTTATGGGGTATTCA AGTCTAACTAGTGGAAAGTATGGATACATT |
| 629 | ADXCRAD_BF726849_at | TLCD2 | Antisense | TLC domain containing 2 [Source: HGNC Symbol; Acc:33522] | 629 | TCTGTGATTCTCTTTGTCAGCTCCTTTGCCTATATTTGCA TCTCAGTTGACACCCCTGATTCTGACTTGTCCTTATCTT CCTACCAGTCTCTGCCGA |

FIG. 7-168

| 630 | ADXCRAG_D50419_s_at | ZNF175 | Sense | zinc finger protein 175 [Source:HGNC Symbol;Acc:12964] | 630 | GTTGTATCAACAATGATTAACTCCTTATTATACATACAC ATGAATGTGCATTTTTGGTAAATGCATAAATGAGATTCTA TAATGTTTACTGATCTTTATATTACAGATTTTCTCTTCTTT TAGGATTAGCTCAGCTTGCCCCCCTTTCCATCTCCACC ATCTATAGTGAGCCTCTCCATAATTAGTGCCAACCATTA GTCTCGTTCATATTTTTACACCAGGAGTCAACAAA |
|---|---|---|---|---|---|---|
| 631 | ADXCRAG_BC028135_s_at | P2RY2 | Sense | purinergic receptor P2Y, G-protein coupled, 2 [Source:HGNC Symbol;Acc:8541] | 631 | CCCCAGCCCAAGAGATGAACATCTGGGACTAATATCA TAGACCCATCTGGAGGCTCCCATGGCTAGGAGCCAGT GTGAGGCTGTAACTTATACTAAGGTTGTGTTGCCTGCT |
| 632 | ADXCRPD.3982.C2_at | TNPO3 | Sense | transportin 3 [Source:HGNC Symbol;Acc:17103] | 632 | GAAGACTAAACAGAAACCAGAACTGAAACATTCACCTG GTAGCAAATGACACTTTG |
| 633 | ADXCRSS.Hs#S548 4315_s_at | MEX3A | Sense | mex-3 homolog A (C. elegans) [Source:HGNC Symbol;Acc:33482] | 633 | TTCTCGCCCCACCTAGGGACAGATTCCCCCTGCTCTTT TGTCCTAGAAACCCGCTAGTTTGGGATGGTAGCGTCT GGGGTGGGGAGGGCTTCCCCTTCCCACTCGAGGGTG CGGGTGGGGAAGGGGGTGGGTGGGAGACAGCCCTG GGGCAGGAGGAGGATGGTCTCTCCACTGTAGAAAGTAGAG TAGGATTGTGTCAGACTTAATTTGAGGCATCTAGTGAA GACACGTACAAATCCACCAAGGAA |

FIG.7-169

| 634 | ADXCRPD.13219.C1_at | MUC2 | AntiSense | mucin 2, oligomeric mucus/gel-forming [Source:HGNC Symbol;Acc:7512] | 634 | GCTGGTCATCTCAATGGCAGGTGTAGGGTACTCAGAAGGGTGGGTTGACTCCGTGAGAGGGAAGAGAGGTGGACCGAGAGGTCTGAGGGGTTGAGGACTCAGGCGGAGGATTGGATGTGGTCAACTCAGCAATCGGTGCTGTGCTTGTGTGGGTGGGGGGCCCCGTGCTTCCAGTGGTGGTGGGGTTGGGGTTGGGGTCACCGTAGTGGTGGTCTGATGGGTATCATGGTTGGGGTCTGTGTGCCGGTGGGTGTTGGGGTTGCGGTCACCGATAGTTGTGGTGGTGATGGGTGTCA |
| 635 | ADXCRAD_AU120130_at | ZSWIM6 | Sense | zinc finger, SWIM-type containing 6 [Source:HGNC Symbol;Acc:29316] | 635 | TTTTGAAAAATGTTTACAGCTCCACAAAGATAGACAAATTTCCTTGATGTATGAAAAATGTCAACAAACCAATAAAAAGACTAACAATTCAGTAGAAAATGGACAAAGAACAAATATGGAGATTCATAGAAATGAGAGATAAATGTCATGATGAGAAGGTGAGGTGCTCACTTGATTTATAAGAGAAATGAAAATTAAAAACTACACCAGATGCCATTTTTT |
| 636 | ADXCRPDRC.1976.C2_at | SRSF1 | AntiSense | serine/arginine-rich splicing factor 1 [Source: HGNC Symbol; Acc:10780] | 636 | CGCGGGCGATTCTTGAGGTCGATGTCGCGGGATAGCGCCGTATTTGTAGAACACGTCCTCAATGTCCTTGGTTCGGATGTCTGGAGGTAAGTTACCCACGTAGATGCGGCAATCGTTGTTCCCTGCGGGGCCACGAATCACACCACCTCCCGACATGGCGGGTGACGAAAAGCGCGGACTCGAGAACAGGCCTTCCCACCAAGCCTAGCGCACGGCAGAGCGAGCCGCAGCGGCACCACGTCTCCCGGCGCCCCTCCAAAATGGCGCCTTTTATCAGCTCGG |

FIG.7-170

COLON CANCER GENE EXPRESSION SIGNATURES AND METHODS OF USE

CROSS REFERENCE TO RELATED APPLICATIONS

This application is the U.S. National Stage of International Application No. PCT/US12/22594, filed Jan. 1, 2012, published in English under PCT Article 21(2), which claims the benefit of U.S. Provisional Application No. 61/435,922, filed on Jan. 25, 2011, which is incorporated herein by reference in its entirety.

FIELD OF THE INVENTION

The present disclosure relates to gene expression profiling in colon tissues, such as colon cancer tissues. In particular, the present disclosure concerns sensitive methods to measure mRNA levels in biopsied colon tumor tissues, including archived paraffin-embedded biopsy material. In addition, the disclosure provides sets of expressed transcripts forming gene expression signatures for the prognosis, diagnosis and treatment of colon cancer.

BACKGROUND OF THE INVENTION

Approximately 30% of all colon cancer patients are diagnosed with stage II disease. (Jemal et al., *CA Cancer J. Clin.*, 2004). The 5-year survival for patients with stage II colon cancer treated by surgery is approximately 75-80%, demonstrating that the majority of patients are cured by surgery alone. (Benson, *The Oncologist*, 2006; Nauta et al., *Arch. Surg.*, 1989.) Nevertheless, approximately 20-25% of these patients will develop recurrent disease within their lifetime. (Benson, *The Oncologist*, 2006; Gill et al., *J. Clin. Oncol.*, 2004). In theory, these patients should benefit from adjuvant chemotherapy. However, only around 3-4% of patients have an absolute improvement in survival at 5-years with the use of adjuvant chemotherapy in stage II colon cancer. (Benson, *The Oncologist*, 2006; André et al., *Annals of Surgical Oncology* 2006). As a consequence, the American Society of Clinical Oncology guidelines recommend that these patients should not be routinely treated with adjuvant chemotherapy. (Benson et al., *J. Clin. Oncol.*, 2004). Despite this, it is clear that approximately 20% of stage II colon cancer patients, at higher risk of relapse, may be candidates for adjuvant treatment. (Benson, *The Oncologist*, 2006; Nauta et al., *Arch. Surg.*, 1989; Gill et al., *J. Clin. Oncol.*, 2004; André et al., *Annals of Surgical Oncology* 2006.)

In diseases such as colon cancer, the first treatment is often the most important and offers the greatest chance of success, so there exists a need to use the treatment most effective for a patient's particular stage of colon cancer as the first treatment. This has traditionally been impossible because no method was available for predicting which drug treatment would be the most effective for a particular individual's physiology. Many times patients would needlessly undergo toxic drug therapy. For example, in Stage II tumor node metastasis (TNM) colon cancer, there has been no method of determining which patients will respond to adjuvant chemotherapy after surgery. Only one third of the 20% of stage II patients at risk for relapse after surgery derive any benefit from chemotherapy. This means that prescribing adjuvant chemotherapy exposes some patients to treatment that is unnecessary. Alternatively, a decision to withholding adjuvant chemotherapy at this stage will expose some patients to a higher risk of cancer relapse.

Currently, diagnostic tests used in clinical practice are based on a single analyte test, and therefore do not capture the potential value of knowing relationships between dozens of different markers. Moreover, diagnostic tests are frequently not quantitative, relying on immunohistochemistry. This method often yields different results in different laboratories, in part because the reagents are not standardized, and in part because the interpretations can be subjective and may not be easily quantified. RNA-based tests have not often been used because of the problem of RNA degradation over time and the fact that it is difficult to obtain fresh tissue samples from patients for analysis. Fixed paraffin-embedded tissue is more readily available and methods have been established to detect RNA in fixed tissue. However, these methods typically do not allow for the study of large numbers of genes (DNA or RNA) from small amounts of material. Thus, traditionally fixed tissue has been rarely used other than for immunohistochemical detection of proteins.

Recently, several groups have published studies concerning the classification of various cancer types by microarray gene expression analysis (see, e.g. Golub et al., *Science* 286:531 537 (1999); Bhattacharjae et al., *Proc. Natl. Acad. Sci. USA* 98:13790 13795 (2001); Chen-Hsiang et al., *Bioinformatics* 17 (Suppl. 1):S316 S322 (2001); Ramaswamy et al., *Proc. Natl. Acad. Sci. USA* 98:15149 15154 (2001), Salazar et al., *Journal of Clinical Oncology* 29: 17-24 (2010), O'Conneell et al., *Journal of Clinical Oncology* 28: 3937-3944 (2010) and Kerr et al., *Journal of Clinical Oncology* 27 (suppl) 15s (2009)). However, these studies mostly focus on improving and refining the already established classification of various types of cancer, and generally do not provide new insights into the relationships of the differentially expressed genes, and do not link the findings to treatment strategies in order to improve the clinical outcome of cancer therapy. In addition, cancer treatment and colon cancer clinical trials are still being pursued on the basis of the availability of new active compounds rather than the integrated approach of pharmacogenomics, which utilizes the genetic makeup of the tumor and the genotype of the patient to establish a personalized medication regime.

Although modern molecular biology and biochemistry have revealed more than 100 genes whose activities influence the behavior of tumor cells, state of their differentiation, and their sensitivity or resistance to certain therapeutic drugs, with a few exceptions, the status of these genes has not been exploited for the purpose of routinely making clinical decisions about drug treatments.

SUMMARY OF THE INVENTION

There is a need to identify biomarkers useful for predicting prognosis of patients with colon cancer. The ability to classify patients as high risk (poor prognosis) or low risk (favorable prognosis) would enable selection of appropriate therapies for these patients. For example, high-risk patients are likely to benefit from aggressive therapy, whereas therapy may have no significant advantage for low risk patients. However, in spite of this need, a solution to this problem has not been available.

Therefore, microarray-based prognostic technologies are needed that provide a physician with information on the likelihood of recovery or relapse following administration of a particular treatment regimen, such as resection with or without chemotherapy. Technologies are also needed that can accurately diagnose a colon disease, particularly the diagnosis of a particular stage of colon cancer, or can predict a colon disease patient's response to a particular therapy. Specific knowledge regarding a tumor in a cancer patient would be extremely useful in prolonging remission, increasing the quality of patient life, and reducing healthcare costs. Such technologies may also be used to screen patient candidates for clinical trials for novel therapeutic compounds and methods to facilitate the regulatory approval process.

Disclosed are expression signatures from colon cancer that meet these needs. The disclosed signatures can be used for applications in prognosis of colon cancer, diagnosis of colon cancer and classifying patient groups. In some embodiments, these results permit assessment of genomic evidence of the efficacy of surgery alone, or in combination with adjuvant chemotherapy for treatment of colon cancer. The signatures described herein may be significant in, and capable of, discriminating between two diagnoses or prognostic outcomes. An important aspect of the present disclosure is to use the measured expression of certain genes in colon cancer tissue to match patients to the most appropriate treatment, and to provide prognostic information. Thus, disclosed are methods of using such colon cancer signatures. The disclosed methods include detecting an expression level of at least 2 colon cancer-related nucleic acid molecules listed in Table 6 in a sample comprising nucleic acids obtained from a subject and comparing the expression level of the at least 2 colon cancer-related nucleic acid molecules, or a decision score derived therefrom to a control threshold. Depending of the prediction requested, the control threshold can be indicative of a diagnosis of colon cancer, indicative of known classification of colon cancer, indicative of a known response to treatment, indicative of having a history of long term survival, indicative of a history of recurrence and the like.

In various embodiments, RNA is isolated from a colon tissue sample, and used for preparing a gene expression profile. In certain embodiments involving prognosis of cancer, the sample is a colorectal tumor specimen, such as a colon cancer sample. In certain embodiments, the gene expression profile involves detecting the expression of at least 50 transcripts listed in Table 6, and which may also be listed in Table 1 and/or Table 2. The total number of transcripts detected in the gene expression profile can vary. For example, in some embodiments the total number of transcripts detected in the profile is from about 200 to about 1000, or from about 400 to about 800, or in other embodiments, the number of transcripts is from about 500 to about 700, or from about 550 to about 650. In various embodiments, at least about 50, at least about 100, at least about 200, at least about 300, at least about 400, at least about 500, at least about 600, or all transcripts, listed in Table 6 are detected as part of the total number of transcripts. Where additional transcripts are detected (in addition to those of Table 6), they may be optionally selected from signal or expression level controls, and in some embodiments, are transcripts known to be expressed in colon cancer, such as those determined by Colorectal Cancer DSA™. In certain embodiments, the additional transcripts may also be indicative of colon cancer prognosis.

The patient's expression profile is scored against an expression signature based on expression levels of the transcripts listed in Table 6 in high risk and low risk patient groups, such as patient with a high or low risk of clinical relapse, and the results may be used to determine a course of treatment. For example, a patient determined to be a high risk patient may be treated with adjuvant chemotherapy after surgery. For a patient deemed to be a low risk patient, adjuvant chemotherapy may be withheld after surgery. Accordingly, the invention provides, in certain aspects, a method for preparing a gene expression profile of a colon cancer tumor that is indicative of risk of recurrence.

The disclosure further provides a method for prognosing colon cancer. The method according to this aspect comprises preparing a gene expression profile of a colon cancer specimen (e.g., as described herein). The gene expression profile is then classified or scored against a gene expression signature described herein. In various embodiments, the gene expression signature is based on the expression level of at least 50 transcripts listed in Table 6, and which may also be listed in Table 1 and/or Table 2. In some embodiments, the total number of transcripts on which the signature is based is less than about 800, less than about 700, less than about 600, less than about 500, less than about 400, less than about 300, less than about 200, or less than about 100 transcripts, and which includes transcripts from Table 6. For example, the signature may be based on the expression levels of at least about 400, at least about 500, or at least about 600 transcripts from Table 6. Optionally, the transcripts from Table 6 include the transcripts listed in Table 1.

Also disclosed are methods of preparing a personalized colon cancer genomics profile for a subject. The methods include detecting an expression level of at least 2 colon cancer-related nucleic acid molecules listed in Table 6 in a sample comprising nucleic acids obtained from a subject and creating a report summarizing the data obtained by the gene expression analysis.

In some examples, of the disclosed methods, expression levels are determined from nucleic acids obtained from the subject that comprise RNA and/or cDNA transcribed from RNA extracted from a sample of colorectal tissue obtained from the subject, such as colon cancer sample.

Also disclosed are nucleic acid probes and primers (as well as sets of such probes and primers) for detecting a gene expression signature for colon cancer. In some examples the probes are part of an array for use in the detection of a colon cancer signature.

The foregoing and other features and advantages of the disclosure will become more apparent from the following detailed description of several embodiments, which proceeds with reference to the accompanying figures.

BRIEF DESCRIPTION OF THE DRAWINGS

FIG. 3A provides a graph of the receiver operating characteristic (ROC) curve of the 636 transcript prognostic signature in the training set.

FIG. 3B provides a Kaplan-Meier plot of recurrence from training data from the candidate model.

FIG. 6 is Table 3 as described below.

FIG. 7 is Table 6 as described below.

BRIEF DESCRIPTION OF THE TABLES

Figure 1:
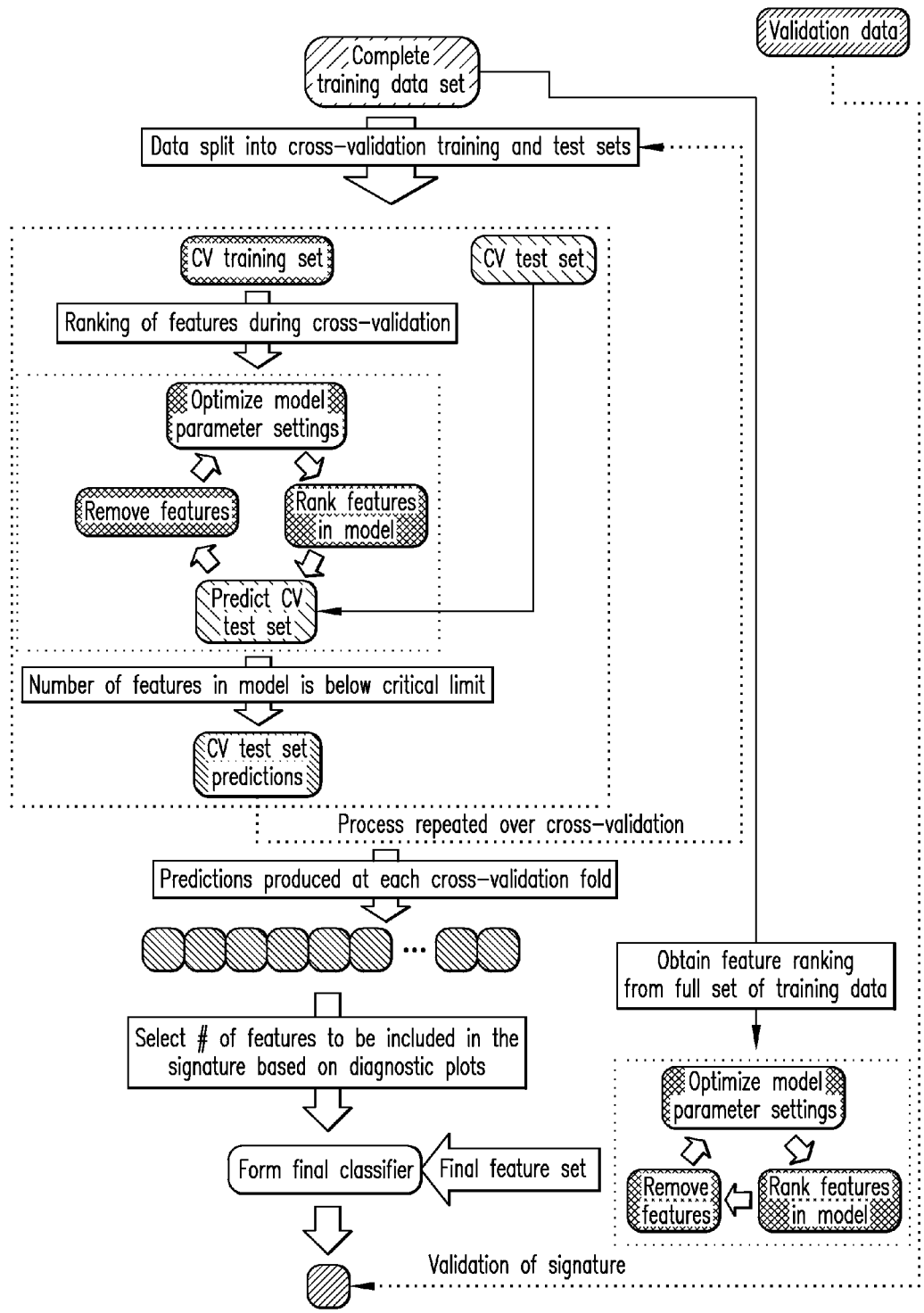
FIG. 1 provides a flow chart showing an exemplary procedure used to derive a colon cancer transcript expression signature.
Figure 2:
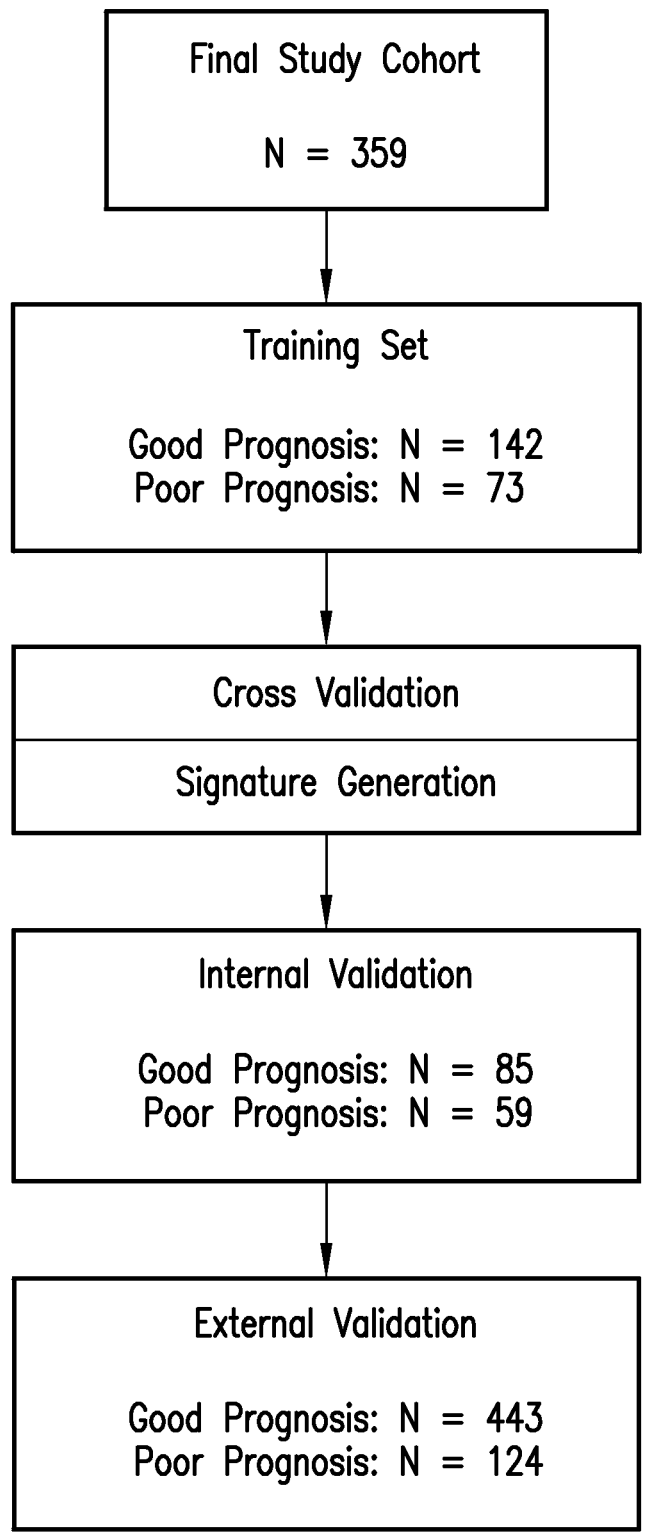
FIG. 2 provides a flow chart showing an exemplary outline of the stage II colon cancer prognostic signature generation and validation, using the Colorectal Cancer DSA™.

Table 1 provides a list of 10 candidate transcripts included in a core colon signature. These transcripts have been identified as having the highest impact on the classification of samples into poor and good prognosis groups Table 2 provides a list 178 unique transcripts included in the colon signature. This table includes the weight rank of the transcript in the 636 transcript signature as well as the orientation of the transcript expressed in colon tissue.

Table 3 provides key patient and tumor characteristics in the study to identify the 636 transcript signature.

Table 4 provides performance metrics for the cross-validated training set and validation set used to identify the transcript signature.

Table 5 provides results of the statistical analysis showing Hazards Ratio for patient age, patient gender, pT-stage, tumor grade, tumor location and mucinous/non-mucinous subtype status.

Table 6 provides a list of the transcripts included in the 636-transcript colon signature.

SEQUENCE LISTING

The nucleic and amino acid sequences listed in the accompanying sequence listing are shown using standard letter abbreviations for nucleotide bases, as defined in 37 C.F.R. § 1.822. Only one strand of each nucleic acid sequence is shown, but the complementary strand is understood as included by any reference to the displayed strand. In the accompanying sequence listing:

SEQ ID NOs: 1-636 are oligonucleotide transcripts from human colon cancer.

The Sequence Listing is submitted as an ASCII text file in the form of the file named ADL-0311_Sequence_Listing.txt, which was created on Jan. 25, 2012, and is 232,154 bytes, which is incorporated by reference herein.

DETAILED DESCRIPTION

I. Summary of Terms

Unless defined otherwise, technical and scientific terms used herein have the same meaning as commonly understood by one of ordinary skill in the art to which this disclosure belongs. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992).

The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

To facilitate review of the various embodiments of this disclosure, the following explanations of terms are provided:

Amplifying a nucleic acid molecule: To increase the number of copies of a nucleic acid molecule, such as a gene or fragment of a gene, for example a transcript shown in Table 6. The resulting products are called amplification products.

An example of in vitro amplification is the polymerase chain reaction (PCR). Other examples of in vitro amplification techniques include quantitative real-time PCR, strand displacement amplification (see U.S. Pat. No. 5,744,311); transcription-free isothermal amplification (see U.S. Pat. No. 6,033,881); repair chain reaction amplification (see International Patent Publication No. WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Array: An arrangement of molecules, such as biological macromolecules (such nucleic acid molecules) or biological samples (such as tissue sections), in addressable locations on or in a substrate. In some examples an array is an array of polynucleotide probes (such as probes that hybridize to the nucleic acids sequences shown in Table 6, or the complement thereof), bound to a solid substrate so as not to be substantially dislodged during a hybridization procedure. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls.

In particular examples, an array includes nucleic acid molecules, such as oligonucleotide sequences. The polynucleotides used on an array may be cDNAs ("cDNA arrays") that are typically about 500 to 5000 bases long, although shorter or longer cDNAs can also be used. Alternatively, the polynucleotides can be oligonucleotides, which are typically about 20 to 80 bases long, although shorter and longer oligonucleotides are also suitable. In one example, the molecule includes oligonucleotides attached to the array via their 5'- or 3'-end.

Within an array, each arrayed sample is addressable, in that its location can be reliably and consistently determined within the at least two dimensions of the array. The number of addressable locations on the array can vary, for example from at least four, to at least 9, at least 10, at least 14, at least 15, at least 20, at least 30, at least 50, at least 75, at least 100, at least 150, at least 200, at least 300, at least 500, least 550, at least 600, at least 800, at least 1000, at least 10,000, or more. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Binding or stable binding: An association between two substances or molecules, such as the association of a nucleic acid to another nucleic acid (such as the binding of a probe to a transcript shown in Table 6 or its complement), or the association of a protein with another protein or nucleic acid molecule. Binding can be detected by any procedure known to one skilled in the art, for example in the case of a nucleic acid, such as by physical or functional properties of the target:oligonucleotide complex.

Physical methods of detecting the binding of complementary strands of nucleic acid molecules, include but are not limited to, such methods as DNase I or chemical footprinting, gel shift and affinity cleavage assays, Northern blotting, dot blotting and light absorption detection procedures. For example, one method involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt. In another example, the method involves detecting a signal, such as a detectable label, present on one or both nucleic acid molecules (or antibody or protein as appropriate).

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

cDNA (complementary DNA): A piece of DNA lacking internal, non-coding segments (introns) and regulatory sequences which determine transcription. cDNA can be synthesized by reverse transcription from messenger RNA (mRNA) extracted from cells and/or tissue samples, such a colon samples, including colon cancer samples.

Clinical outcome: Refers to the health status of a patient following treatment for a disease or disorder, or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Colon cancer: Cancer that forms in the tissues of the colon (the longest part of the large intestine). Most colon cancers are adenocarcinomas (cancers that begin in cells that make line internal organs and have gland-like properties). Cancer progression is characterized by stages, or the extent of cancer in the body. Staging is usually based on the size of the tumor, whether lymph nodes contain cancer, and whether the cancer has spread from the original site to other parts of the body. Stages of colon cancer include stage I, stage II, stage III and stage IV. Unless otherwise specified, the term colon cancer refers to colon cancer at Stage 0, Stage I, Stage II (including Stage IIA or IIB), Stage III (including Stage IIIA, IIIB or IIIC), or Stage IV. In some embodiments herein, the colon cancer is from any stage. In other embodiments, the colon cancer is a stage II colon cancer.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating colon cancer. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., Chemotherapy, Ch. 17 in Abeloff, *Clinical Oncology* 2nd ed., 2000 Churchill Livingstone, Inc; Baltzer and Berkery. (eds): *Oncology Pocket Guide to Chemotherapy*, 2nd ed. St. Louis, Mosby-Year Book, 1995; Fischer Knobf, and Durivage (eds): *The Cancer Chemotherapy Handbook*, 4th ed. St. Louis, Mosby-Year Book, 1993). Chemotherapeutic agents used for treating colon cancer include small molecules such as 5-fluorourcil, leuvocorin, irinotecan, oxaliplatin, and capecitabine, and antibodies such bevacuzimab and cetuximab. Combination chemotherapy is the administration of more than one agent to treat cancer.

Contacting: Placement in direct physical association; includes both in solid and liquid form. Contacting includes contact between one molecule and another molecule, for example; contacting a sample with a nucleic acid probe, such as a probe for any of the sequences shown in Table 6.

Control: A "control" refers to a sample or standard used for comparison with an experimental sample, such as a tumor sample obtained from a patient with colon cancer. In some embodiments, the control is a sample obtained from a healthy patient or a non-cancerous tissue sample obtained from a patient diagnosed with colon cancer, such as a non-cancerous tissue sample from the same organ in which the tumor resides (e.g., non-cancerous colon tissue can serve as a control for a colon cancer). In some embodiments, the control is a historical control or standard value (i.e., a previously tested control sample or group of samples that represent baseline or normal values).

Controls or standards for comparison to a sample, for the determination of differential expression, include samples believed to be normal (in that they are not altered for the desired characteristic, for example a sample from a subject who does not have colon cancer) as well as laboratory values, even though possibly arbitrarily set. Laboratory standards and values may be set based on a known or determined population value and can be supplied in the format of a graph or table that permits comparison of measured, experimentally determined values.

Detecting expression: Determining of a level expression in either a qualitative or quantitative manner can detect nucleic acid. Exemplary methods include microarray analysis, RT-PCR, and Northern blot. In some examples, detecting expression includes detecting the expression of one or more of the transcripts in Table 6.

Differential expression or altered expression: A difference, such as an increase or decrease, in the conversion of the information encoded in a gene (such as any of the genes from Table 1, 2, and/or nucleic acid transcripts in Table 6) into messenger RNA, the conversion of mRNA to a protein, or both. In some examples, the difference is relative to a control or reference value, such as an amount of expression of a nucleic acid transcript in tissue not affected by a disease, such as colon cancer, from the same subject, or an amount expected in a different subject who does not have colon cancer. The difference can also be in a non-cancerous tissue from a subject (that has the cancer in the same organ) as compared to tissue from a different subject not afflicted with colon cancer. Detecting differential expression can include measuring a change in gene or protein expression, such as a change in expression of one or more of the genes listed in Table 1, 2, and/or the expression one or more transcripts shown in Table 6.

Downregulated or decreased: When used in reference to the expression of a nucleic acid molecule, refers to any process that results in a decrease in production of the nucleic acid. A gene product can be RNA (such as mRNA, rRNA, tRNA, and structural RNA) or protein. Therefore, gene downregulation or deactivation includes processes that decrease transcription of a gene or translation of mRNA.

Gene downregulation includes any detectable decrease in the production of a gene product. In certain examples, production of a gene product decreases by at least 1.2 fold, such as at least 2-fold, at least 3-fold or at least 4-fold, as compared to a control (such an amount of gene expression, such as a normalized gene expression in a normal cell). In several examples, a control is a relative amount of gene expression or protein expression in one or more subjects who do not have colon cancer, such as the relative amount of gene expression or protein expression in "cancer-free" subjects who do not have any known cancer.

Exon: In theory, a segment of an interrupted gene that is represented in the messenger RNA product. In theory the term "intron" refers to any segment of DNA that is transcribed but removed from within the transcript by splicing together the exons on either side of it. Operationally, exon sequences occur in the mRNA sequence of a gene as defined by Ref. Seq ID numbers. Operationally, intron sequences are the intervening sequences within the genomic DNA of a gene, bracketed by exon sequences and having GT and AG splice consensus sequences at their 5' and 3' boundaries.

Expression: The process by which the coded information of a gene is converted into an operational, non-operational, or structural part of a cell, such as the synthesis of nucleic acid or a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

The expression of a nucleic acid molecule can be altered, for example relative to expression in a normal (e.g., non-cancerous) sample. An alteration in gene expression, such as differential expression, includes but is not limited to: (1) overexpression; (2) underexpression; or (3) suppression of expression. Alternations in the expression of a nucleic acid molecule can be associated with, and in fact cause, a change in expression of the corresponding protein. "Expression" and/or "relative expression" can be considered the expression value after normalization of a specific transcript with respect to a threshold value, which is defined in the context of the expression of all other transcripts in an expression signature, such as a colon cancer expression signature. The overall expression data for a given sample is normalized using methods known to those skilled in the art in order to correct for differing amounts of starting material, varying efficiencies of the extraction and amplification reactions etc. Using a linear classifier on the normalized data to make a diagnostic or prognostic call (e.g. good or poor prognosis) effectively means to split the data space, i.e. all possible combinations of expression values for all genes in the signature, into two disjoint halves by means of a separating hyperplane. This split is empirically derived on a large set of training examples, for example from patients with good and poor prognosis. Without loss of generality, one can assume a certain fixed set of values for all but one genes, which would automatically define a threshold value for this remaining gene where the decision would change from, for example, good to poor prognosis. Expression values above this dynamic threshold would then either indicate good (for a gene with a negative weight) or poor prognosis (for a gene with a positive weight). The precise value of this threshold depends on the actual measured expression profile of all other genes within the signature, but the general indication of certain genes remains fixed, i.e. high values or "relative over-expression" always contributes to either a poor prognosis decision (genes with a positive weight) or good prognosis decision (genes with a negative weights). Therefore, in the context of the overall gene expression signature relative expression can indicate if either up- or down-regulation of a certain transcript is indicative of good or poor prognosis.

Gene amplification: A process by which multiple copies of a gene or gene fragment are formed in a particular cell or cell line. The duplicated region (a stretch of amplified DNA) is often referred to as an "amplicon." Usually, the amount of the messenger RNA (mRNA) produced, i.e., the level of gene expression, also increases in the proportion of the number of copies made of the particular gene expressed.

Expression profile (or fingerprint or signature): A pattern of gene expression, which is characteristic of, or correlated with, a specific disease stage or a specific prognostic outcome. The gene expression signature may be represented by a set of informative genes, or transcripts thereof, coding or non-coding or both. The expression levels of the transcripts within the signatures can be evaluated to make a prognostic determination with, but not limited to, the methods provided herein. Gene expression levels may be used to distinguish between two clinical conditions or outcomes such as normal and diseased tissue for diagnosis, or responsiveness compared to non-responsiveness for prognostic methods and recurring compared to non-recurring for predictive methods. Differential or altered gene expression can be detected by changes in the detectable amount of gene expression (such as cDNA or mRNA) or by changes in the detectable amount of proteins expressed by those genes. A distinct or identifiable pattern of gene expression, for instance a pattern of high and low expression of a defined set of genes or gene-indicative nucleic acids such as ESTs; in some examples, as few as one or two genes provides a profile, but more genes can be used in a profile, for example at least 2, at least 3, at least 4, at least 5, at least 6, at least 7, at least 9, at least 10 or at least 11 and so on. In some embodiments, the profile comprises at least about 200 genes (or "transcripts") and up to about 1000 transcripts, such as from about 400 transcripts to about 800 transcripts, or about 500 transcripts to about 700 transcripts. The profile comprises transcripts from Table 6 (e.g., at least 100, at least 200, at least 300, at least 400, at least 500, or at least 600 transcripts from Table 6), including in some embodiments the 636 transcripts listed in Table 6. As used herein, the term "gene" refers to an expressed transcript, which may be a characterized gene, or may be an expressed transcript such as an EST. In some embodiments, the detection platform is a microarray, and each probe is considered as determining the expression of a separate "gene" or "transcript."

A gene expression profile (also referred to as a fingerprint or signature) can be linked to a tissue or cell type (such as colon tissue), to a particular stage of normal tissue growth or disease progression (such as colon cancer), or to any other distinct or identifiable condition that influences gene expression in a predictable way. Gene expression profiles can include relative as well as absolute expression levels of specific genes, and can be viewed in the context of a test sample compared to a baseline or control sample profile (such as a sample from a subject who does not have colon cancer). In one example, a gene expression profile in a subject is read on an array (such as a nucleic acid array).

Hybridization: To form base pairs between complementary regions of two strands of DNA, RNA, or between DNA and RNA, thereby forming a duplex molecule, for example a duplex formed between a probe and any of the nucleic acid sequences shown in Table 6 or the complement thereof. Hybridization conditions resulting in particular degrees of stringency will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (detects sequences that share at least 80% identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share at Least 60% Identity)
Hybridization: 6×SSC at RT to 55° C. for 16-20 hours
Wash at least twice: 2×-3×SSC at RT to 55° C. for 20-30 minutes each Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. The term also embraces nucleic acid molecules prepared by recombinant expression in a host cell as well as chemically synthesized nucleic acid molecules. For example, an isolated cell, such as a colon cancer cell, is one that is substantially separated from other types of cells.

Label: An agent capable of detection, for example by ELISA, spectrophotometry, flow cytometry, or microscopy or other visual techniques. For example, a label can be attached to a nucleic acid molecule or protein, thereby permitting detection of the nucleic acid molecule or protein. For example a nucleic acid molecule or an antibody that specifically binds to a target molecule, such as a target nucleic acid molecule. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Long term survival: Disease-free survival for at least 3 years, more preferably for at least 5 years, even more preferably for at least 8 years following surgery or other treatment (e.g., chemotherapy) for colon cancer.

More aggressive: As used herein, a "more aggressive" form of a colon cancer is a colon cancer with a relatively increased risk of metastasis or recurrence (such as following surgical removal of the tumor). A "more aggressive" colon cancer can also refer to a colon cancer that confers an increased likelihood of death, or a decrease in the time until death, upon a subject with the colon cancer. A subject having a "more aggressive" form of a colon cancer is considered high risk (poor prognosis).

Nucleic acid molecules representing genes: Any nucleic acid, for example DNA (intron or exon or both), cDNA, or RNA (such as mRNA), of any length suitable for use as a probe or other indicator molecule, and that is informative about the corresponding gene, such as those listed in Tables 1, or 2, for example the transcripts listed in Table 6.

Oligonucleotide: A relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

Patient: As used herein, the term "patient" includes human and non-human animals. The preferred patient for treatment is a human. "Patient" and "subject" are used interchangeably herein.

Patient response: can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition (i.e. reduction, slowing down or complete stopping) of metastasis; (6) enhancement of anti-tumor immune response, which may, but does not have to, result in the regression or rejection of the tumor; (7) relief, to some extent, of one or more symptoms associated with the tumor; (8) increase in the length of survival following treatment; and/or (9) decreased mortality at a given point of time following treatment.

Polynucleotide: When used in singular or plural, generally refers to any polyribonucleotide or polydeoxribonucleotide, which may be unmodified RNA or DNA or modified RNA or DNA, or even combinations thereof. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. The term "polynucleotide" also includes DNAs and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

Probes and primers: A probe comprises an isolated nucleic acid capable of hybridizing to a target nucleic acid (such one of the nucleic acid sequences shown in Table 6 or the complement thereof). A detectable label or reporter molecule can be attached to a probe. Typical labels include radioactive isotopes, enzyme substrates, co-factors, ligands, chemiluminescent or fluorescent agents, haptens, and enzymes. Methods for preparing and using nucleic acid probes and primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Methods for labeling and guidance in the choice of labels appropriate for various purposes are discussed, for example in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

Probes are generally at least 12 nucleotides in length, such as at least 12, at least 13, at least 14, at least 15, at least 16, at least 17, at least 18, at least 19, least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule, such as a primer of 15-50 nucleotides, 20-50 nucleotides, or 15-30 nucleotides. In some examples, a probe is even longer, such as a cDNA probe, which can be from about 500 to more than 5000 nucleotides in length.

Primers are short nucleic acid molecules, for instance DNA oligonucleotides 10 nucleotides or more in length, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule (such as a nucleic acid sequence shown in Table 6).

The specificity of a primer and/or a probe increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50 or more consecutive nucleotides. In particular examples, a primer is at least 15 nucleotides in length, such as at least 15 contiguous nucleotides complementary to a target nucleic acid molecule. Particular lengths of primers that can be used to practice the methods of the present disclosure include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 15-50 nucleotides, 20-50 nucleotides, or 15-30 nucleotides. One of most important factors considered in PCR primer design include primer length, melting temperature (Tm), and GC content, specificity, complementary primer sequences, and 3'-end sequence. In general, optimal PCR primers are generally 17-30 bases in length, and contain about 20-80%, such as, for example, about 50-60% G+C bases. Tm's between 50° C. and 80° C., e.g. about 50° C. to 70° C. are typically preferred.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction.

Nucleic acid probes and primers can be readily prepared based on the nucleic acid molecules provided herein, for example, by using computer programs intended for that purpose such as Primer (Version 0.5, © 1991, Whitehead Institute for Biomedical Research, Cambridge, Mass.) or PRIMER EXPRESS® Software (Applied Biosystems, AB, Foster City, Calif.).

Further guidelines for PCR primer and probe design may be found in Dieffenbach et al., General Concepts for PCR Primer Design in: PCR Primer, A Laboratory Manual, Cold Spring Harbor Laboratory Press, New York, 1995, pp. 133 155; Innis and Gelfand, Optimization of PCRs in: PCR Protocols, A Guide to Methods and Applications, CRC Press, London, 1994, pp. 5 11; and Plasterer, Primerselect: Primer and probe design. *Methods Mol. Biol.* 70:520 527, 1997.

Prognosis: The likelihood of the clinical outcome for a subject afflicted with a specific disease or disorder. With regard to cancer, the prognosis is a representation of the likelihood (probability) that the subject will survive (such as for one, two, three, four or five years) and/or the likelihood (probability) that the tumor will metastasize. The term "prediction" is used herein to refer to the likelihood that a patient will respond either favorably or unfavorably to a drug or set of drugs, and also the extent of those responses. The predictive methods of the present invention can be used clinically to make treatment decisions by choosing the most appropriate treatment modalities for any particular patient. The predictive methods of the present disclosure are valuable tools in predicting if a patient is likely to respond favorably to a treatment regimen, such as surgical intervention, chemotherapy with a given drug or drug combination, and/or radiation therapy.

Purified: The term "purified" does not require absolute purity; rather, it is intended as a relative term. Thus, for example, a purified oligonucleotide preparation is one in which the oligonucleotide is more pure than in an environment including a complex mixture of oligonucleotides.

Sample: A biological specimen containing genomic DNA, RNA (including mRNA and microRNA), protein, or combinations thereof, obtained from a subject. Examples include, but are not limited to, peripheral blood, urine, saliva, tissue biopsy, aspirate, surgical specimen, and autopsy material, and includes fixed and/or paraffin embedded samples. In one example, a sample includes a biopsy of a colon (such as colon cancer tumor), a sample of noncancerous tissue, or a sample of normal tissue (from a subject not afflicted with a known disease or disorder, such as a cancer-free subject).

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. AppL Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biotechnology (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 60%, 70%, 80%, 90%, 95%, 98%, or 99% sequence identity to a molecule listed in Table 6 determined by this method.

One of skill in the art will appreciate that the particular sequence identity ranges are provided for guidance only; it is possible that strongly significant homologs could be obtained that fall outside the ranges provided.

Splicing or RNA splicing: An RNA processing that removes introns and joins exons to produce mature mRNA with continuous coding sequence that moves into the cytoplasm of a eukaryotic cell.

Transcript or gene product: An RNA molecule that is generated or derived through the process of transcription from its corresponding DNA or a cDNA template. Transcripts include coding and non-coding RNA molecules such as, but not limited to, messenger RNAs (mRNA), alternatively spliced mRNAs, ribosomal RNA (rRNA), transfer RNAs (tRNAs) in addition to a large range of other transcripts, which are not translated into protein such as small nuclear RNAs (snRNAs), antisense molecules such as short interfering RNA (siRNA) and microRNA (miRNA) and other RNA transcripts of unknown function. In some embodiments, a transcript is a nucleic acid sequence shown in Table 6.

Therapeutic: A generic term that includes both diagnosis and treatment.

Treatment: Includes both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. In tumor (e.g. cancer) treatment, a treatment such as surgery, chemotherapy or radiation may directly decrease the pathology of tumor cells, or render the tumor cells more susceptible to further treatment.

Tumor, neoplasia, malignancy or cancer: Neoplastic cell growth and proliferation, whether malignant or benign, and all pre-cancerous and cancerous cells and tissues and the result of abnormal and uncontrolled growth of cells. The terms "cancer" and "cancerous" refer to or describe the physiological condition in mammals that is typically characterized by unregulated cell growth. Neoplasia, malignancy, cancer and tumor are often used interchangeably and refer to abnormal growth of a tissue or cells that results from excessive cell division. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

Tumor-Node-Metastasis (TNM): The TNM classification of malignant tumors is a cancer staging system for describing the extent of cancer in a patient's body. T describes the size of the primary tumor and whether it has invaded nearby tissue; N describes any lymph nodes that are involved; and M describes metastasis. TNM is developed and maintained by the International Union Against Cancer to achieve consensus on one globally recognized standard for classifying the extent of spread of cancer.

Upregulated or activation: When used in reference to the expression of a nucleic acid molecule, refers to any process that results in an increase in production of a gene product. A gene product can be RNA (such as mRNA, rRNA, tRNA, and structural RNA) or protein. Therefore, gene upregulation or activation includes processes that increase transcription of a gene or translation of mRNA, such as an inflammatory gene.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene upregulation can include inhibition of repression as well as stimulation of expression above an existing level. Examples of processes that increase translation include those that increase translational initiation, those that increase translational elongation and those that increase mRNA stability.

Gene upregulation includes any detectable increase in the production of a gene product, such as an inflammatory gene. In certain examples, production of a gene product increases by at least 1.2 fold, such as at least 2-fold, at least 3-fold, at least 4-fold, at least 5-fold, at least 8-fold, at least 10-fold, or at least 15-fold, as compared to a control (such an amount of gene expression and/or normalized gene expression in a normal cell).

Weight: With reference to the gene signatures disclosed herein, refers to the relative importance of an item in a statistical calculation, for example the relative importance of a Transcript in Table 6. The weight of each transcript in a gene expression signature may be determined on a data set of patient samples using analytical methods known in the art. Exemplary procedures are described below.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999; Harlow and Lane, Antibodies: A Laboratory Manual, Cold Spring Harbor Laboratory Press, 1990; Harlow and Lane, Using Antibodies: A Laboratory Manual, Cold Spring Harbor Laboratory Press, 1999 Oligonucleotide Synthesis, (M. J. Gait, ed., 1984); Animal Cell Culture, Freshney, ed., 1987; Methods in Enzymology, Academic Press, Inc.); Handbook of Experimental Immunology, 4.sup.th ed., D. M. Weir & C. C. Blackwell, eds., Blackwell Science Inc., 1987; Gene Transfer Vectors for Mammalian Cells, J. M. Miller & M. P. Calos, eds., 1987); and PCR: The Polymerase Chain Reaction, Mullis et al., eds., 1994. In addition, the materials, methods, and examples are illustrative only and not intended to be limiting.

II. Description of Several Embodiments

A. Colon Cancer Expression Signature and Methods of Use

Disclosed herein are expression signatures from colon cancer. The disclosed signatures can be used for applications in prognosis of colon cancer, diagnosis of colon cancer and classifying patient groups. In some embodiments, a sample obtained from a subject, such as a patient, is processed into a set of polynucleotide binding targets that represent transcripts expressed in the tissue sample. The polynucleotide binding targets are probed with complementary polynucleotide probes representing, or corresponding to the signatures described herein in order to obtain information on expression levels of the transcripts. A decision score is optionally calculated that represents the expression levels of the transcripts in the signature. The decision score is then compared to a control, such as a patient population, and genetically similar samples are correlated with known patient response or clinical outcomes. For example, sensitive methods are also provided to predict patient response to, and prognosis after, treatment for colon cancer, such as surgical resection and/or chemotherapy. Generally, historical patient population data and tissue samples are analyzed to create genetic profiles for patients having a past history of colon cancer. In some embodiments, the genetic profile of a patient sample is converted to a decision score. The clinical outcomes of each patient are correlated to the genetic profile, or decision score derived mathematically from the genetic profile for each patient's individual cancer.

In some embodiments, a mathematical algorithm is generated using the known historical patient data and applied to the predictive methods for new patients with colon cancer. In some embodiment, the algorithm creates a threshold that separates two groups of patients depending on selection criteria, for example patient outcome, response to therapy and recurrence, and the like. In some examples, the mathematical algorithm or threshold is validated using further historical patient population data before being used in the predictive methods described herein. The mathematical algorithm or threshold may then be used as a reference, for example as a control, to compare decision scores derived from genetic profiling of patients desirous of predictive methods of colon cancer. In some embodiments, these results permit assessment of genomic evidence of the efficacy of surgery alone, or in combination with adjuvant chemotherapy for treatment of colon cancer.

The signatures described herein may be significant in, and capable of, discriminating between two diagnoses or prognostic outcomes. An important aspect of the present disclosure is to use the measured expression of certain genes in colon cancer tissue to match patients to the most appropriate treatment, and to provide prognostic information.

In some embodiments, the signatures are developed using a colorectal cancer-focused microarray research tool. In a specific embodiment, this research tool is a colorectal cancer transcriptome-focused research array developed by Almac Diagnostics, Ltd. (Almac Diagnostics, Ltd., N. Ireland) capable of delivering accurate expression data.

The Colorectal Cancer DSA™ research tool contains 61,528 probe sets and encodes 52,306 transcripts confirmed as being expressed in colon cancer and normal tissue. Comparing the Colorectal Cancer DSA™ research tool against the National Center for Biotechnology Information (NCBI) human Reference Sequence (RefSeq) RNA database (available on the world wide web at ncbi.nlm.nih.gov/RefSeq/) using BLAST analysis, 21,968 (42%) transcripts are present and 26,676 (51%) of transcripts are absent from the human RefSeq database. Furthermore 7% of the content represents expressed antisense transcripts to annotated genes. (Johnston et al., *J. Clin. Oncol.* 24: 3519, 2006; Pruitt et al., *Nucleic Acids Research* 33: D501-D504, 2005). In addition, probe-level analysis of the Colorectal Cancer DSA™ compared with leading generic arrays, highlighted that approximately 20,000 (40%) transcripts are not contained on the leading generic microarray platform (Affymetrix) and are unique to the Colorectal Cancer DSA™. Thus, the Colorectal Cancer DSA™ research tool includes transcripts that have not been available in hitherto performed gene expression studies.

In some embodiments, the expression of a transcript in a gene expression signature is considered informative if expression levels are increased or decreased between the conditions of interest. Increases or decreases in gene expression can be assessed by methods known to those skilled in the art that include, but are not limited to, using fold changes, t-tests, F-tests, Wilcoxon rank-sum tests, ANOVA (Cui et al., *Genome Biology* 4:210, 2003)) or dedicated methods for detecting differential expression such as Significance Analysis of Microarrays (Tusher et al., *Proc. Natl. Acad. Sci. USA* 98:5116-21, 2001)) or LIMMA (Smyth, *Stat. Appl. Genet. Mol. Biol.*, 3:Art.3, 2004)).

In some embodiments, the transcripts in the signature are used to form a weighted sum of their signals, where individual weights can be positive or negative. The resulting sum ("decisive function") is compared with a pre-determined reference point. The comparison with the reference point may be used to diagnose, or predict a clinical condition or outcome.

One of ordinary skill in the art will appreciate that the transcripts included in the signature provided in Table 1, 2, and/or 6 will carry unequal weights in a signature for diagnosis or prognosis of colon cancer. Therefore, while as few as 1 sequence may be used to diagnose or predict an outcome, the specificity and sensitivity or diagnosis or prediction accuracy may increase using more sequences. Table 6 ranks the transcripts in order of decreasing weight in the signature, defined as the rank of the average weight in the compound decision score function measured under cross-validation. The weight rank also corresponds to the SEQ ID NO: in the accompanying sequence listing thus the transcript with the greatest weight is SEQ ID NO: 1.

In some embodiments, a signature includes at least 2, such as at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, at least 634, or even all 636 of the transcripts in Table 6 that carry the greatest weight, defined as the rank of the average weight in the compound decision score function measured under cross-validation, and still have prognostic value. In some embodiments, a signature includes the top 10 weighted transcripts, the second top 10 weighted transcripts, the third top 10 weighted transcripts, the fourth top 10 weighted transcripts, the fifth top 10 weighted transcripts, the sixth top 10 weighted transcripts, the seventh top 10 weighted transcripts, the eighth top 10 weighted transcripts, the ninth top 10 weighted transcripts, or the tenth top 10 weighted transcripts listed in Table 6. In yet further embodiments, a signature includes the 636, 634, 620, 610, 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 20, or 10 transcripts having the greatest weight listed in Table 6. In some embodiments, the signature is based on expression levels of from about 200 to about 1000 transcripts, such as from about 400 to about 800 transcripts, such as from about 500 to about 700 transcripts, or in some embodiments, from about 550 to about 650 transcripts, including those from Table 6 (e.g., at least about 50, at least about 100, at least about 200, at least about 300, at least about 400, at least about 500, or at least about 600, or all transcripts from Table 6) as described above.

In one embodiment, a specific signature may be used for the methods disclosed herein that includes transcripts for MUM1 and SIGMAR1. In another embodiment, a signature may be used for the methods disclosed herein that includes transcripts for MUM1, SIGMAR1, ARSD, SULT1C2 and PPFIBP1. In yet another embodiment, a signature may be used for the methods disclosed herein that includes transcripts for ARSD, CXCL9, PCLO, SLC2A3, FCGBP, SLC2A14, SLC2A3, BCL9L and antisense sequences of MUC3A, OLFM4 and RNF39. This signature is represented by Table 1 below.

TABLE 1

10 candidate core transcripts within the 636 transcript signature

| Gene Name | Weight Rank in 636 transcript signature | DAUC (Univariate) | Orientation |
| --- | --- | --- | --- |
| ARSD | 3 | −0.0109 | Sense |
| CXCL9 | 24 | −0.0103 | Sense |
| PCLO | 272 | −0.0095 | Sense |
| SLC2A3 | 23 | −0.0087 | Sense |
| FCGBP | 416 | −0.0062 | Sense |
| SLC2A14 /// SLC2A3 | 55 | −0.0061 | Sense |
| BCL9L | 175 | −0.0059 | Sense |
| MUC3A | 112 | −0.0084 | AntiSense |
| OLFM4 | 61 | −0.0083 | AntiSense |
| RNF39 | 14 | −0.0064 | AntiSense |

In some embodiments, a core set of gene transcripts in colon cancer signature is provided that is identified through a separate study to determine the contribution that each of the 636 probesets makes to the performance of the signature. In this embodiment, ten probesets from the 636 probeset signature were removed and a new signature was created based on 636 probesets, using the training dataset. The new signature was then used to predict the validation dataset (without threshold) and the AUC was measured. The difference in AUC from the 636 probeset signature was recorded. This process was repeated 0.5 million times and the average difference in AUC that occurred for signatures lacking said probeset was recorded. The probesets with the largest negative ΔAUC are recorded in Table 1. In this embodiment, this set of 10 transcripts represents a candidate core set of genes whose absence from the signature significantly impairs the predictive performance of the signature. Thus in certain embodiments, the transcripts representing the genes in Table 1 are included in a colon cancer signature. In Table 1, the DAUC represents the drop in validation AUC if this transcript is omitted from the signature. The orientation describes the orientation of the transcript expressed in colon tissue. Three transcripts in this signature are expressed as antisense transcripts of MUC3A, OLFM4 and RNF39.

In some embodiments, the signature includes a combination of 626-636 transcripts from Table 6, that include ARSD, CXCL9, PCLO, SLC2A3, FCGBP, SLC2A14, SLC2A3, BCL9L, MUC3A, OLFM4 and RNF39. In yet another embodiment, the signature includes transcripts 10-636, 10-50, 50-636, 100-636, listed in Table 6 which includes ARSD, CXCL9, PCLO, SLC2A3, FCGBP, SLC2A14, SLC2A3, BCL9L, MUC3A, OLFM4 and RNF39 where the transcript orientation is noted in Table 6.

Notably, 176 transcripts have been identified as being unrepresented by the leading generic array by probe-level analysis (i.e. they are "unique" to the Colorectal Cancer DSA™ tool described above). This group of 176 transcripts listed in Table 2 are described herein as transcripts that are unique to the colon gene signatures and methods of use herein. Probe-sequence-level homology searches have identified these transcripts as not being contained on the leading generic array (Affymetrix) (i.e. they are "unique" to the Colorectal Cancer DSA™ research tool described above). A number of these transcripts are antisense transcripts not previously reported to be expressed. These 176 transcripts are presented in Table 2 below, where the weight rank corresponds to the numbers shown in Table 6. Thus the sequence of these unique transcripts can be found in Table 6.

TABLE 2

Unique transcripts in 636 transcript signature

| Weight Rank in 636 Transcript Signature | Gene Symbol | Orientation | Gene Description |
|---|---|---|---|
| 424 | AC068491.1 (Clone_based_vega_gene) | Sense | non-protein coding RNA 152 (NCRNA00152), transcript variant 2, non-coding RNA [Source: RefSeq DNA; Acc: NR_024205] |
| 214 | AC004968.2 (Clone_based_ensembl_gene) | Sense | Known long non-coding RNA |
| 50 | AC010522.1 (Clone-based (Ensembl) /// ZNF418 /// ZNF814 | AntiSense | cDNA FLJ52732, moderately similar to Zinc finger protein 418 [Source: UniProtKB/TrEMBL; Acc: B4DR41] /// zinc finger protein 418 [Source: HGNC Symbol; Acc: 20647] /// zinc finger protein 814 [Source: HGNC Symbol; Acc: 33258] |
| 13 | AC018359.1 (Clone_based_vega_gene) /// AC123023.1 (Clone_based_vega_gene) | AntiSense | Novel processed transcript /// Putative processed transcript. |
| 559 | AC069513.3 (Clone_based_vega_gene) | AntiSense | Novel processed transcript. |
| 242 | AC130352.2 (Clone_based_ensembl_gene) | AntiSense | Novel miRNA. |
| 593 | AC138128.1 (Clone_based_ensembl_gene) | Sense | Novel long non-coding RNA. |
| 488 | AC138128.1 (Clone_based_ensembl_gene) | Sense | Novel long non-coding RNA. |
| 177 | ACTN4 | AntiSense | actinin, alpha 4 [Source: HGNC Symbol; Acc: 166] |
| 427 | AL354822.1 (Clone_based_ensembl_gene) /// AC145212.2 (Clone_based_ensembl_gene) | Sense | Putative uncharacterized protein ENSP00000383640 [Source: UniProtKB/TrEMBL; Acc: B 7WNX9] /// Known protein coding. |
| 290 | AL604028.2 (Clone_based_ensembl_gene) | Sense | Known protein coding. |
| 498 | AMAC1L1 | Sense | acyl-malonyl condensing enzyme 1-like 1 [Source: HGNC Symbol; Acc: 31043] |
| 93 | ANGPTL6 | Sense | angiopoietin-like 6 [Source: HGNC Symbol; Acc: 23140] |
| 73 | APBB2 | AntiSense | amyloid beta (A4) precursor protein-binding, family B, member 2 [Source: HGNC Symbol; Acc: 582] |
| 250 | ARHGAP26 | AntiSense | Rho GTPase activating protein 26 [Source: HGNC Symbol; Acc: 17073] |
| 81 | ARHGEF1 | AntiSense | Rho guanine nucleotide exchange factor (GEF) 1 [Source: HGNC Symbol; Acc: 681] |

TABLE 2-continued

Unique transcripts in 636 transcript signature

| Weight Rank in 636 Transcript Signature | Gene Symbol | Orientation | Gene Description |
|---|---|---|---|
| 326 | ARHGEF2 /// RP11-336K24.6 (Clone_based_vega_gene) | Sense | Rho/Rac guanine nucleotide exchange factor (GEF) 2 [Source: HGNC Symbol; Acc: 682] /// Known nncoding transcript with no ORF. |
| 391 | ASPH | AntiSense | aspartate beta-hydroxylase [Source: HGNC Symbol; Acc: 757] |
| 435 | ATP2B4 | Sense | ATPase, Ca++ transporting, plasma membrane 4 [Source: HGNC Symbol; Acc: 817] |
| 108 | AXIN2 | AntiSense | axin 2 [Source: HGNC Symbol; Acc: 904] |
| 217 | BIRC6 | Sense | baculoviral IAP repeat-containing 6 [Source: HGNC Symbol; Acc: 13516] |
| 224 | BLCAP /// RP11-425M5.5 (Clone_based_vega_gene) | AntiSense | bladder cancer associated protein [Source: HGNC Symbol; Acc: 1055] /// Putative processed transcript. |
| 373 | BMPR1A | AntiSense | bone morphogenetic protein receptor, type IA [Source: HGNC Symbol; Acc: 1076] |
| 384 | BMPR1A | AntiSense | bone morphogenetic protein receptor, type IA [Source: HGNC Symbol; Acc: 1076] |
| 552 | C2orf89 | Sense | UPF0632 protein C2orft9 Precursor [Source: UniProtKB/Swiss-Prot; Acc: Q86V40] |
| 486 | C6orf203 | Sense | Uncharacterized protein C6orf203 [Source: UniProtKB/Swiss-Prot; Acc: Q9P0P8] |
| 436 | C8orf38 | Sense | UPF0551 protein C8orf38, mitochondrial Precursor (Putative phytoene synthase) [Source: UniProtKB/Swiss-Prot; Acc: Q330K2] |
| 256 | CAMK1D | Sense | calcium/calmodulin-dependent protein kinase ID [Source: HGNC Symbol; Acc: 19341] |
| 400 | CAPN12 | Sense | calpain 12 [Source: HGNC Symbol; Acc: 13249] |
| 87 | CCND2 | AntiSense | cyclin D2 [Source: HGNC Symbol; Acc: 1583] |
| 82 | CCND2 | AntiSense | cyclin D2 [Source: HGNC Symbol; Acc: 1583] |
| 289 | CD200 | Sense | CD200 molecule [Source: HGNC Symbol; Acc: 7203] |
| 281 | CDC42SE2 | AntiSense | CDC42 small effector 2 [Source: HGNC Symbol; Acc: 18547] |
| 510 | CEACAM5 | AntiSense | carcinoembryonic antigen-related cell adhesion molecule 5 [Source: HGNC Symbol; Acc: 1817] |
| 159 | CHD2 | AntiSense | chromodomain helicase DNA binding protein 2 [Source: HGNC Symbol; Acc: 1917] |
| 309 | CHD2 | Sense | chromodomain helicase DNA binding protein 2 [Source: HGNC Symbol; Acc: 1917] |
| 531 | COMMD10 | AntiSense | COMM domain containing 10 [Source: HGNC Symbol; Acc: 30201] |
| 429 | CPEB2 | Sense | cytoplasmic polyadenylation element binding protein 2 [Source: HGNC Symbol; Acc: 21745] |
| 505 | CSNK1A1 | Sense | casein kinase 1, alpha 1 [Source: HGNC Symbol; Acc: 2451] |
| 466 | CTBP2 | AntiSense | C-terminal binding protein 2 [Source: HGNC Symbol; Acc: 2495] |
| 522 | DDX17 | AntiSense | DEAD (Asp-Glu-Ala-Asp) box polypeptide 17 [Source: HGNC Symbol; Acc: 2740] |
| 63 | DEDD | Sense | death effector domain containing [Source: HGNC Symbol; Acc: 2755] |
| 407 | DHRS11 | AntiSense | dehydrogenase/reductase (SDR family) member 11 [Source: HGNC Symbol; Acc: 28639] |

TABLE 2-continued

Unique transcripts in 636 transcript signature

| Weight Rank in 636 Transcript Signature | Gene Symbol | Orientation | Gene Description |
|---|---|---|---|
| 300 | DLG5 | Sense | discs, large homolog 5 (*Drosophila*) [Source: HGNC Symbol; Acc: 2904] |
| 344 | DSP | AntiSense | desmoplakin [Source: HGNC Symbol; Acc: 3052] |
| 378 | ECE1 | Sense | endothelin converting enzyme 1 [Source: HGNC Symbol; Acc: 3146] |
| 151 | EEF2K | AntiSense | eukaryotic elongation factor-2 kinase [Source: HGNC Symbol; Acc: 24615] |
| 587 | EGFR | AntiSense | epidermal growth factor receptor (erythroblastic leukemia viral (v-erb-b) oncogene homolog, avian) [Source: HGNC Symbol; Acc: 3236] |
| 274 | EPHB4 | AntiSense | EPH receptor B4 [Source: HGNC Symbol; Acc: 3395] |
| 588 | FAM190A /// SEPP1 /// UBTD1 /// UTY | AntiSense | family with sequence similarity 190, member A [Source: HGNC Symbol; Acc: 29349] /// selenoprotein P, plasma, 1 [Source: HGNC Symbol; Acc: 10751] /// ubiquitin domain containing 1 [Source: HGNC Symbol; Acc: 25683] /// ubiquitously transcribed tetratricopeptide repe |
| 192 | FAM60A | AntiSense | family with sequence similarity 60, member A [Source: HGNC Symbol; Acc: 30702] |
| 229 | FANCD2 | Sense | Fanconi anemia, complementation group D2 [Source: HGNC Symbol; Acc: 3585] |
| 625 | FAT1 | AntiSense | FAT tumor suppressor homolog 1 (*Drosophila*) [Source: HGNC Symbol; Acc: 3595] |
| 12 | FNDC3B | Sense | fibronectin type III domain containing 3B [Source: HGNC Symbol; Acc: 24670] |
| 446 | FNDC3B | Sense | fibronectin type III domain containing 3B [Source: HGNC Symbol; Acc: 24670] |
| 183 | GCC2 | Sense | GRIP and coiled-coil domain containing 2 [Source: HGNC Symbol; Acc: 23218] |
| 395 | GFPT1 | AntiSense | glutamine--fructose-6-phosphate transaminase 1 [Source: HGNC Symbol; Acc: 4241] |
| 623 | GLB1 | AntiSense | galactosidase, beta 1 [Source: HGNC Symbol; Acc: 4298] |
| 332 | GMDS | Sense | GDP-mannose 4,6-dehydratase [Source: HGNC Symbol; Acc: 4369] |
| 363 | GNL1 | Sense | guanine nucleotide binding protein-like 1 [Source: HGNC Symbol; Acc: 4413] /// Guanine nucleotide-binding protein-like 1 (GTP-binding protein HSR1) [Source: UniProtKB/Swiss-Prot; Acc: P36915] |
| 512 | GPRC5A | AntiSense | G protein-coupled receptor, family C, group 5, member A [Source: HGNC Symbol; Acc: 9836] |
| 206 | GPT2 | AntiSense | glutamic pyruvate transaminase (alanine aminotransferase) 2 [Source: HGNC SymbokAcc: 18062] |
| 341 | GRB7 | Sense | growth factor receptor-bound protein 7 [Source: HGNC Symbol; Acc: 4567] |
| 62 | GRHL2 | Sense | grainyhead-like 2 (*Drosophila*) [Source: HGNC Symbol; Acc: 2799] |
| 49 | GSTO2 | Sense | glutathione S-transferase omega 2 [Source: HGNC Symbol; Acc: 23064] |
| 56 | GSTO2 | Sense | glutathione S-transferase omega 2 [Source: HGNC Symbol; Acc: 23064] |
| 533 | HELZ | Sense | helicase with zinc finger [Source: HGNC Symbol; Acc: 16878] |
| 412 | HNRNPL | AntiSense | heterogeneous nuclear ribonucleoprotein L [Source: HGNC Symbol; Acc: 5045] |

TABLE 2-continued

Unique transcripts in 636 transcript signature

| Weight Rank in 636 Transcript Signature | Gene Symbol | Orientation | Gene Description |
|---|---|---|---|
| 198 | HSPD1 | Sense | heat shock 60 kDa protein 1 (chaperonin) [Source: HGNC Symbol; Acc: 5261] |
| 114 | IGLL5 | Sense | immunoglobulin lambda-like polypeptide 5 [Source: HGNC Symbol; Acc: 38476] |
| 495 | IL32 | AntiSense | interleukin 32 [Source: HGNC Symbol; Acc: 16830] |
| 394 | INPP4B | Sense | inositol polyphosphate-4-phosphatase, type II, 105 kDa [Source: HGNC Symbol; Acc: 6075] |
| 165 | ITGA6 | AntiSense | integrin, alpha 6 [Source: HGNC Symbol; Acc: 6142] |
| 166 | ITGA6 | AntiSense | integrin, alpha 6 [Source: HGNC Symbol; Acc: 6142] |
| 287 | KANK1 | AntiSense | KN motif and ankyrin repeat domains 1 [Source: HGNC Symbol; Acc: 19309] |
| 226 | KANK1 | AntiSense | KN motif and ankyrin repeat domains 1 [Source: HGNC Symbol; Acc: 19309] |
| 179 | KCNK1 | AntiSense | potassium channel, subfamily K, member 1 [Source: HGNC Symbol; Acc: 6272] |
| 513 | KIAA0319L | Sense | KIAA0319-like [Source: HGNC Symbol; Acc: 30071] |
| 126 | KIF24 | Sense | kinesin family member 24 [Source: HGNC Symbol; Acc: 19916] |
| 278 | KLRAQ1 | AntiSense | KLRAQ motif containing 1 [Source: HGNC Symbol; Acc: 30595] |
| 237 | LRRC37B | AntiSense | leucine rich repeat containing 37B [Source: HGNC Symbol; Acc: 29070] |
| 519 | MACC1 | Sense | metastasis associated in colon cancer 1 [Source: HGNC Symbol; Acc: 30215] |
| 301 | MACF1 | AntiSense | microtubule-actin crosslinking factor 1 [Source: HGNC Symbol; Acc: 13664] |
| 238 | MAVS | AntiSense | mitochondrial antiviral signaling protein [Source: HGNC Symbol; Acc: 29233] |
| 336 | MEF2A | Sense | myocyte enhancer factor 2A [Source: HGNC Symbol; Acc: 6993] |
| 567 | MIR612 | AntiSense | hsa-mir-612 [Source: miRBase; Acc: MI0003625] |
| 431 | MMP1 | AntiSense | matrix metallopeptidase 1 (interstitial collagenase) [Source: HGNC Symbol; Acc: 7155] |
| 397 | MMP25 | Sense | matrix metallopeptidase 25 [Source: HGNC Symbol; Acc: 14246] |
| 72 | MORC3 | Sense | MORC family CW-type zinc finger 3 [Source: HGNC Symbol; Acc: 23572] |
| 506 | MORC3 | Sense | MORC family CW-type zinc finger 3 [Source: HGNC Symbol; Acc: 23572] |
| 634 | MUC2 | AntiSense | mucin 2, oligomeric mucus/gel-forming [Source: HGNC Symbol; Acc: 7512] |
| 110 | MUC6 | Sense | mucin 6, oligomeric mucus/gel-forming [Source: HGNC Symbol; Acc: 7517] |
| 133 | MUC6 | Sense | mucin 6, oligomeric mucus/gel-forming [Source: HGNC Symbol; Acc: 7517] |
| 1 | MUM1 | Sense | melanoma associated antigen (mutated) 1 [Source: HGNC Symbol; Acc: 29641] |
| 385 | MYO10 | Sense | myosin X [Source: HGNC Symbol; Acc: 7593] |
| 599 | MYO1E | AntiSense | myosin IE [Source: HGNC Symbol; Acc: 7599] |
| 448 | N/A | No Transcript match | N/A |
| 57 | N/A | No Transcript match | N/A |
| 628 | N/A | No Transcript match | N/A |
| 370 | N/A | Sense | non-protein coding RNA 152 (NCRNA00152), transcript variant 2, non-coding RNA [Source: RefSeq DNA; Acc: NR_024205] |

TABLE 2-continued

Unique transcripts in 636 transcript signature

| Weight Rank in 636 Transcript Signature | Gene Symbol | Orientation | Gene Description |
|---|---|---|---|
| 6 | N/A | No Transcript match | N/A |
| 66 | N/A | No Genome match | N/A |
| 610 | N/A | No Transcript match | N/A |
| 308 | N/A | No Transcript match | N/A |
| 439 | N/A | No Genome match | N/A |
| 131 | N/A | No Genome match | N/A |
| 359 | NAA50 | AntiSense | N(alpha)-acetyltransferase 50, NatE catalytic subunit [Source: HGNC Symbol; Acc: 29533] |
| 333 | NAA50 | AntiSense | N(alpha)-acetyltransferase 50, NatE catalytic subunit [Source: HGNC Symbol; Acc: 29533] |
| 356 | NBN | AntiSense | nibrin [Source: HGNC Symbol; Acc: 7652] |
| 137 | NCAPD2 | Sense | non-SMC condensin I complex, subunit D2 [Source:HGNC Symbol; Acc:24305] |
| 348 | NCRNA00188 | AntiSense | small nucleolar RNA, C/D box 65 [Source: HGNC Symbol; Acc: 32726] |
| 297 | NCRNA00262 | No Transcript match | non-protein coding RNA 262 [Source: HGNC Symbol; Acc: 26785] |
| 606 | NDUFA13 /// YJEFN3 | AntiSense | NADH dehydrogenase (ubiquinone) 1 alpha subcomplex, 13 [Source: HGNC Symbol; Acc: 17194] /// YjeF N-terminal domain containing 3 [Source: HGNC Symbol; Acc: 24785] |
| 502 | NR6A1 | AntiSense | nuclear receptor subfamily 6, group A, member 1 [Source: HGNC Symbol; Acc: 7985] |
| 420 | NR6A1 | AntiSense | nuclear receptor subfamily 6, group A, member 1 [Source: HGNC Symbol; Acc: 7985] |
| 61 | OLFM4 | AntiSense | olfactomedin 4 [Source: HGNC Symbol; Acc: 17190] |
| 129 | PARP14 | AntiSense | poly (ADP-ribose) polymerase family, member 14 Source: [HGNC Symbol; Acc: 29232] |
| 515 | PML | AntiSense | promyelocytic leukemia [Source: HGNC Symbol; Acc: 9113] |
| 323 | POSTN | AntiSense | periostin, osteoblast specific factor [Source: HGNC Symbol; Acc: 16953] |
| 554 | PPDPF | Sense | pancreatic progenitor cell differentiation and proliferation factor homolog (zebrafish) Source: HGNC Symbol; Acc: 16142] |
| 381 | PPFIBP1 | Sense | PTPRF interacting protein, binding protein 1 (liprin beta 1) [Source: HGNC Symbol; Acc: 9249] |
| 504 | PPP3CA | Sense | protein phosphatase 3, catalytic subunit, alpha isozyme [Source: HGNC Symbol; Acc: 9314] |
| 382 | PRKDC | AntiSense | protein kinase, DNA-activated, catalytic polypeptide [Source: HGNC Symbol; Acc: 9413] |
| 450 | PRPF40A | AntiSense | PRP40 pre-mRNA processing factor 40 homolog A (S. cerevisiae) [Source: HGNC Symbol; Acc: 16463] |
| 525 | PTK2 | AntiSense | PTK2 protein tyrosine kinase 2 [Source: HGNC Symbol; Acc: 9611] |
| 215 | PTP4A1 | AntiSense | protein tyrosine phosphatase type IVA, member 1 [Source: HGNC Symbol; Acc: 9634] |
| 298 | RABGAP1 | AntiSense | RAB GTPase activating protein 1 [Source: HGNC Symbol; Acc: 17155] |
| 194 | RBM47 | Sense | RNA binding motif protein 47 [Source: HGNC Symbol; Acc: 30358] |

TABLE 2-continued

Unique transcripts in 636 transcript signature

| Weight Rank in 636 Transcript Signature | Gene Symbol | Orientation | Gene Description |
|---|---|---|---|
| 461 | RERE | AntiSense | arginine-glutamic acid dipeptide (RE) repeats [Source: HGNC Symbol; Acc: 9965] |
| 355 | RHBDD1 | Sense | rhomboid domain containing 1 [Source: HGNC Symbol; Acc: 23081] |
| 454 | RNF145 | AntiSense | ring finger protein 145 [Source: HGNC Symbol; Acc: 20853] |
| 171 | RNF43 | Sense | ring finger protein 43 [Source: HGNC Symbol; Acc: 18505] |
| 496 | RP11-357H14.7 (Clone_based_vega_gene) | Sense | Novel processed transcript. |
| 573 | RP11-460N11.2 (Clone_based_vega_gene) | AntiSense | Known pseudogene. |
| 172 | RP11-460N11.2 (Clone_based_vega_gene) | AntiSense | Known pseudogene. |
| 155 | RP11-460N11.2 (Clone_based_vega_gene) | AntiSense | Known pseudogene. |
| 247 | RP11-706O15.1 (Clone_based_vega_gene) | AntiSense | HCG1981372, isoform CRA_cNovel protein; [Source: UniProtKB/TrEMBL; Acc: B 1B108] |
| 251 | RP11-761E20.1 (Clone_based_vega_gene) | Sense | Novel processed transcript. |
| 307 | RP11-86H7.1 (Clone_based_vega_gene) | Sense | Novel processed transcript. |
| 575 | RP4-717I23.3 (Clone_based_vega_gene) | Anti Sense | Novel processed transcript. |
| 209 | RUNX1 | AntiSense | runt-related transcription factor 1 [Source: HGNC Symbol; Acc: 10471] |
| 95 | SAMD4B | AntiSense | sterile alpha motif domain containing 4B [Source: HGNC Symbol; Acc: 25492] |
| 17 | SATB2 | AntiSense | SATB homeobox 2 [Source: HGNC Symbol; Acc: 21637] |
| 264 | SH3D19 | AntiSense | SH3 domain containing 19 [Source: HGNC Symbol; Acc: 30418] |
| 235 | SH3GLB1 | AntiSense | SH3-domain GRB2-like endophilin B1 [Source: HGNC Symbol; Acc: 10833] |
| 388 | SIPA1L3 | Sense | signal-induced proliferation-associated 1 like 3 [Source: HGNC Symbol; Acc: 23801] |
| 157 | SLC6A6 | Sense | solute carrier family 6 (neurotransmitter transporter, taurine), member 6 [Source: HGNC Symbol; Acc: 11052] |
| 259 | SLC6A6 | Sense | solute carrier family 6 (neurotransmitter transporter, taurine), member 6 [Source: HGNC Symbol; Acc: 11052] |
| 462 | SMURF2 | Sense | SMAD specific E3 ubiquitin protein ligase 2 [Source: HGNC Symbol; Acc: 16809] |
| 377 | SND1 | Sense | staphylococcal nuclease and tudor domain containing 1 [Source: HGNC Symbol; Acc: 30646] |
| 335 | SNTB2 | AntiSense | syntrophin, beta 2 (dystrophin-associated protein A1, 59 kDa, basic component 2) [Source: HGNC Symbol; Acc: 11169] |
| 329 | SOD2 | AntiSense | superoxide dismutase 2, mitochondrial [Source: HGNC Symbol; Acc: 11180] |
| 263 | SP100 | Sense | SP100 nuclear antigen [Source: HGNC Symbol; Acc: 11206] |
| 243 | SPDYE2 | AntiSense | speedy homolog E2 (*Xenopus laevis*) [Source: HGNC Symbol; Acc: 33841] |
| 594 | SPDYE2 | AntiSense | speedy homolog E2 (*Xenopus laevis*) [Source: HGNC Symbol; Acc: 33841] |
| 636 | SRSF1 | AntiSense | serine/arginine-rich splicing factor 1 [Source: HGNC Symbol; Acc: 10780] |
| 561 | SSFA2 | Sense | sperm specific antigen 2 [Source: HGNC Symbol; Acc: 11319] |
| 369 | TBL1XR1 | AntiSense | transducin (beta)-like 1 X-linked receptor 1 [Source: HGNC Symbol; Acc: 29529] |

TABLE 2-continued

Unique transcripts in 636 transcript signature

| Weight Rank in 636 Transcript Signature | Gene Symbol | Orientation | Gene Description |
|---|---|---|---|
| 605 | TEX10 | AntiSense | testis expressed 10 [Source: HGNC Symbol; Acc: 25988] |
| 453 | TFAM | AntiSense | transcription factor A, mitochondrial [Source: HGNC Symbol; Acc: 11741] |
| 629 | TLCD2 | AntiSense | TLC domain containing 2 [Source: HGNC Symbol; Acc: 33522] |
| 470 | TLCD2 | AntiSense | TLC domain containing 2 [Source: HGNC Symbol; Acc: 33522] |
| 35 | TMEM87A | Sense | transmembrane protein 87A [Source: HGNC Symbol; Acc: 24522] |
| 624 | TMPRSS4 | AntiSense | transmembrane protease, serine 4 [Source: HGNC Symbol; Acc: 11878] |
| 102 | TRIM5 | Sense | tripartite motif-containing 5 [Source: HGNC Symbol; Acc: 16276] |
| 44 | TRPS1 | AntiSense | trichorhinophalangeal syndrome I [Source: HGNC Symbol; Acc: 12340] |
| 221 | TSPAN1 | Sense | tetraspanin 1 [Source: HGNC Symbol; Acc: 20657] |
| 543 | TTC39B | AntiSense | tetratricopeptide repeat domain 39B [Source: HGNC Symbol; Acc: 23704] |
| 342 | U6 (RFAM) | Sense | U6 spliceosomal RNA [Source: RFAM; Acc: RF00026] |
| 288 | WSB1 | AntiSense | WD repeat and SOCS box-containing 1 [Source: HGNC Symbol; Acc: 19221] |
| 523 | YLPM1 | AntiSense | YLP motif containing 1 [Source: HGNC Symbol; Acc: 17798] |
| 386 | YPEL5 | AntiSense | yippee-like 5 (*Drosophila*) [Source: HGNC Symbol; Acc: 18329] |
| 612 | ZFAND3 | Sense | zinc finger, AN1-type domain 3 [Source: HGNC Symbol; Acc: 18019] |
| 76 | ZHX2 | AntiSense | zinc fingers and homeoboxes 2 [Source: HGNC Symbol; Acc: 18513] |
| 161 | ZNF75A | AntiSense | zinc finger protein 75a [Source: HGNC Symbol; Acc: 13146] |
| 409 | ZXDC | AntiSense | ZXD family zinc finger C [Source: HGNC Symbol; Acc: 28160] |

In some embodiments, a signature includes at least 2, such as at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, or even all 176 of the transcripts listed in Table 2, for example those that carry the greatest weight, defined as the rank of the average weight in the compound decision score function measured under cross-validation, and still have prognostic value. In some embodiments, a signature includes the top 10 weighted transcripts, the second top 10 weighted transcripts, the third top 10 weighted transcripts, the fourth top 10 weighted transcripts, the fifth top 10 weighted transcripts, the sixth top 10 weighted transcripts, the seventh top 10 weighted transcripts, the eighth top 10 weighted transcripts, the ninth top 10 weighted transcripts, or the tenth top 10 weighted transcripts listed in Table 2. In yet further embodiments, a signature includes the 176, 160, 150, 140, 130, 120, 110, 100, 90, 80, 70, 60, 50, 40, 30, 20, or transcripts having the greatest weight listed in Table 2.

In some embodiments, the methods described herein include subjecting RNA isolated from a patient to gene expression profiling. Thus, the gene expression profile may be completed for a set of genes that includes at least two of the transcripts listed in Table 6, which in some examples are normalized as described below. In particular embodiments of the methods disclosed herein, the expression level of at least 2, such as at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 474, at least 500, at least 525, at least 550, at least 575, at least 600, at least 634, or even all 636 of the transcripts in Table 6 or their expression products, and/or complement is determined, for example the transcripts in Table 6 that carry the greatest weight, defined as the rank of the average weight in the compound decision score function measured under cross-validation, and still have prognostic value. In some embodiments of this method, the expression level of at least at least 2, such as at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, or even all 176 of the transcripts in Table 2 or their expression products, and/or complement is determined, for example those that carry the greatest weight, defined as the rank of the average weight in the compound decision score function measured under cross-validation, and still have prognostic value. In the methods described herein, the combination of transcripts may be referred to as a signature or expression signature.

The relative expression levels of transcripts in a colon tissue are measured to form a gene expression profile. In one embodiment, the gene expression profile of a set of transcripts from a patient tissue sample is summarized in the form of a compound decision score and compared to a control threshold, such a threshold that is mathematically derived from a training set of patient data. The threshold separates a patient group based on different characteristics such as, but not limited to, good/poor prognosis, responsiveness/non-responsiveness to treatment, cancer detection/diagnosis and cancer classification. The patient training set data is preferably derived from colon tissue samples having been characterized by prognosis, likelihood of recurrence, or long term survival, diagnosis, cancer classification, personalized genomics profile, clinical outcome, treatment response. Expression profiles, and corresponding decision scores from patient samples may be correlated with the characteristics of patient samples in the training set that are on the same side of the mathematically derived decision threshold. In this embodiment, the threshold of the linear classifier compound decision score was optimized to maximize the sum of sensitivity and specificity under cross-validation applied within the training dataset. These methods are also useful for determining prognosis of colon cancer and in a particular embodiment a patient with stage II colon cancer. In some examples, the disclosed methods are predictive of poor clinical outcome, which can be measured, for example, in terms of shortened survival or increased risk of cancer recurrence, e.g. following surgical removal of the cancer, or following surgical removal of the cancer in combination with adjuvant chemotherapy.

Methods are provided for diagnosing colon cancer in a sample obtained from a subject. Such methods include detecting the expression level of at least 2 colon cancer-related nucleic acid molecules listed in Table 6 in a sample comprising nucleic acids obtained from the subject and comparing the expression level of the at least 2 colon cancer-related nucleic acid molecules, or a decision score derived therefrom to a control threshold indicative of a diagnosis of colon cancer, wherein the expression level, or a decision score derived therefrom, on the same side of the threshold indicates a diagnosis of colon cancer. In some examples, a control threshold is a threshold derived from corresponding transcripts from colon cancer-related nucleic acid molecules listed in Table 6 in a known colon cancer sample (or samples.

Methods are provided for classifying a colon cancer sample. Such methods include detecting the expression level of at least 2 colon cancer-related nucleic acid molecules listed in Table 6 in a sample comprising nucleic acids obtained from a subject and comparing the expression level of the at least 2 colon cancer-related nucleic acid molecules, or a decision score derived therefrom, to a control threshold indicative of known classification, wherein the expression level, or a decision score derived therefrom, on the same side of the threshold permits classification of the colon cancer sample. In some examples, a control threshold is a threshold derived from corresponding transcripts from colon cancer-related nucleic acid molecules listed in Table 6 in a colon cancer sample (or samples) of known classification. In some examples, the colon cancer sample is classified as stage I, stage II, stage III and stage IV. In some examples the method further includes choosing a treatment plan that will be effective for the classified colon cancer, for example surgical resection, chemotherapy, radiation or any combination thereof.

Methods are provided for predicting a response to a treatment for colon cancer, such as a subject with stage II colon cancer. Such methods include detecting the expression level of at least 2 colon cancer-related nucleic acid molecules listed in Table 6 in a sample comprising nucleic acids obtained from a subject and comparing the expression level of the at least 2 colon cancer-related nucleic acid molecules, or a decision score derived therefrom, to a control threshold indicative of a known response to treatment, wherein the expression level, or a decision score derived therefrom, on the same side of the threshold indicates a similar response to treatment, thereby predicting response to treatment. In some examples, a control threshold is a threshold derived from corresponding transcripts from colon cancer-related nucleic acid molecules listed in Table 6 in a colon cancer sample (or samples) having a known response to treatment. In some embodiments, the method is a method of predicting response from surgical resection, chemotherapy, radiation or any combination thereof.

Methods are provided for predicting long term survival of a subject with colon cancer, such as a subject diagnosed with stage II colon cancer. These methods include detecting the expression level of at least 2 colon cancer-related nucleic acid molecules listed in Table 6 in a sample comprising nucleic acids obtained from a subject and comparing the expression level of the at least 2 colon cancer-related nucleic acid molecules, or a decision score derived therefrom, to a control threshold indicative of having a history of long term survival, wherein the expression level, or a decision score derived therefrom, on the same side of the threshold indicates long term survival of the subject, thereby predicting long term survival of a subject. In some examples, the control threshold is a threshold derived from corresponding transcripts from colon cancer-related nucleic acid molecules listed in Table 6 in a colon cancer sample (or samples) obtained from a subject (or subjects) having a history of long term survival.

Also provided are methods for predicting of recurrence of colon cancer in a subject, such as subject diagnosed as having stage II colon cancer. These methods include detecting the expression level of at least 2 colon cancer-related nucleic acid molecules listed in Table 6 in a sample comprising nucleic acids obtained from a subject and comparing the expression level of the at least 2 colon cancer-related nucleic acid molecules, or a decision score derived therefrom to a control threshold indicative of a history of recurrence, wherein the expression level, or a decision score derived therefrom, on the same side of the threshold indicates a recurrence in the subject. In some examples, a control threshold is a threshold derived from corresponding transcripts from colon cancer-related nucleic acid molecules listed in Table 6 in a colon cancer sample (or samples) having a history of recurrence.

Methods are provided for preparing a personalized colon cancer genomics profile for a subject. The methods include detecting an expression level of at least 2 colon cancer-related nucleic acid molecules listed in Table 6 in a sample comprising nucleic acids obtained from a subject and creating a report summarizing the data obtained by the gene expression analysis.

In particular embodiments of the methods disclosed herein, the expression levels for at least 2, such as at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 474, at least 500, at least 525, at least 550, at least 575, at least 600, at least 634, or even all 636 of the transcripts in Table 6 or their expression products is determined and compared with a control threshold. In other embodiment of these methods the expression levels for MUM1 and SIGMAR1 or their expression products is determined and compared with a control threshold. In another embodiment, the expression levels for MUM1, SIGMAR1, ARSD, SULT1C2 and PPFIBP1 or their expression products is determined and compared with the control threshold. In additional embodiments, the expression levels for ARSD, CXCL9, PCLO, SLC2A3, FCGBP, SLC2A14, SLC2A3, BCL9L and antisense sequences of MUC3A, OLFM4 and RNF39 or their expression products is determined and compared with a control threshold. In still other embodiments, expression levels for substantially all the transcripts listed in one of Tables 1, 2, and/or 6 are determined in step and compared with a control threshold.

In some embodiments of the disclosed methods, the RNA levels are corrected for (normalize away) both differences in the amount of RNA assayed and variability in the quality of the RNA used. Control transcripts may be included in assays as positive or negative controls and to normalize readings and ensure reliable measurement data, but are preferably omitted for performing the actual prognosis. The exact identity of the former is typically unimportant and a very broad variety of transcripts could be envisaged for all of the purposes disclosed herein. For the normalization controls, a broad variety of transcripts could be envisaged, although they have to fulfill the basic requirements of approximately constant and stable expression between a broad variety of subjects or conditions for the target tissue of interest, in particular between the prognostic groups under consideration. Similarly the RNA degradation controls have to show intensity behavior, suitable for indicating (overly) degraded RNA. This may or may not include RNA controls, which show a stable intensity regardless of the overall RNA degradation of a sample as positive controls. In relation to these controls the intensity pattern for suitable other RNA controls would be analyzed for which an intensity dependency on the RNA degradation stage is observed. This may or may not include specific analyses depending on varying positions of probe sequences with respect to the 3' end of a transcript.

In some embodiments of the disclosed methods, where a microarray is used for quantifying gene expression, one or more of the following controls can be used:

(a) Alignment controls, which are specific transcripts spiked in labeled form, which bind to specific positions on an array and ensure a proper grid alignment in the image processing of a scanned array.

(b) Amplification controls, which are specific unlabeled transcripts, e.g. poly-A control transcripts, spiked in before any amplification is performed, so undergoing the same processing as the sample mRNA to ensure an appropriate performance of the cDNA synthesis and subsequent amplification reactions.

(c) Labeling and hybridization controls, which are specific controls spiked in before the labeling and hybridization to the chip for controlling the efficiency of these two steps separately from the prior amplification reaction.

(d) Background controls, which are probe sequences on the microarray for which no corresponding target sequences should be available in the sample. Thus, in principle no specific target binding should occur. These controls are used to establish background or cross-hybridization intensities. They would potentially be characterized by different GC-contents and a suitable spatial distribution over an entire microarray.

(e) Normalization controls, which are probe sequences detecting specifically chosen target sequences from the sample which are used to correct for varying input mRNA amounts, varying yield of amplification reactions and varying overall sensitivity of the measurement device. They are used to correct the measured intensity values and would thus ensure an increased analytical precision of the overall measurement device including the preparatory laboratory steps.

(f) RNA quality and degradation control, which are probe sequences from various positions with respect to the 3' position of their respective genes designed to indicate the RNA quality and detect RNA degradation. Corresponding probes or probe sets from multiple genes might represent differing RNA degradation behavior from different RNA species.

Whereas controls a)-d) can purely be derived based on sequence considerations and should not be naturally present in the tissue and condition of interest, controls e) and f) can be chosen by suitable analyses of prior patient data. This may or may not be the same training data on which the prognostic gene signature has been derived.

It should be understood that the above controls are only provided as example and that other embodiments of this disclosure could be envisaged (such as qPCR) in which different controls, with similar functionality would be used.

B. Probes, Primers and Arrays

Disclosed are probes and primers specific for the disclosed colon cancer gene signatures. Also disclosed are arrays, which include probes for the disclosed colon cancer signatures. In some embodiments, a probe specific for the disclosed colon cancer gene signature includes a nucleic acid sequence that specifically hybridizes one of SEQ ID NOs: 1-636 or the complement thereof. In some embodiments, a probe set for a disclosed colon cancer signature includes probes that specifically hybridize to at least 2, such as at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 474, at least 500, at least 525, at least 550, at least 575, at least 600, at least 634, or even all 636 of the transcripts in Table 6, that carry the greatest weight, defined as the rank of the average weight in the compound decision score function measured under cross-validation, and still have prognostic value, such as a probe that specifically hybridizes to any one of SEQ ID NOs: 1-636 or the complement thereof. In some embodiments, a probe set for a disclosed colon cancer signature includes probes that specifically hybridize to the top 10 weighted transcripts, the second top 10 weighted transcripts, the third top 10 weighted transcripts, the fourth top 10 weighted transcripts, the fifth top 10 weighted transcripts, the sixth top 10 weighted transcripts, the seventh top 10 weighted transcripts, the eighth top 10 weighted transcripts, the ninth top 10 weighted transcripts, or the tenth top 10 weighted transcripts listed in Table 6. In yet further embodiments, a probe set for a disclosed colon cancer signature includes probes that specifically hybridize to 636, 634, 620, 610, 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 20, or 10 transcripts having the greatest weight listed in Table 6 or the complement thereof. In some embodiments, a probe set for a disclosed cancer signature comprises about 200 to about 1000 probes, such as from about 400 to about 800 probes, such as from about 500 to about 700 probes, such as from about 550 to about 650 probes, where the probes detect transcripts from Table 6. The additional probes may be optionally selected from those that detect transcripts that are expressed in colon cancer, or which function as signal controls or expression level controls. Such optional probes can be selected from those included on the Colorectal Cancer DSA™ tool.

In some embodiments, a probe set for a disclosed colon cancer signature includes probes that specifically hybridize to transcripts for MUM1 and SIGMAR1. In other embodiments, a probe set for a disclosed colon cancer signature includes probes that specifically hybridize to transcripts for MUM1, SIGMAR1, ARSD, SULT1C2 and PPFIBP1. In yet other embodiments, a probe set for a disclosed colon cancer signature includes probes that specifically hybridize to transcripts for ARSD, CXCL9, PCLO, SLC2A3, FCGBP, SLC2A14, SLC2A3, BCL9L and antisense sequences of MUC3A, OLFM4 and RNF39. A set of probes or primers can be prepared that is substantially representative of the gene expression signature. "Substantially representative of the gene expression signature" refers to probe sets that specifically hybridize to at least 50%, 60%, 70%, 80%, 90%, 95%, 99%, or 100% of the coding or non-coding transcripts in the gene expression signature, for example at least 50%, 60%, 70%, 80%, 90%, 95%, 99%, or 100% of the coding or non-coding transcripts in the gene expression signatures shown in Table 1, 2, or 6 or the complement thereof.

It is advantageous to use probes which bind to the 3' regions of transcripts in the gene expression signature, specifically where the patient tissue to be analyzed for gene expression is RNA extracted from paraffin embedded tissue. Typically each probe will be capable of hybridizing to a complementary sequence in the respective transcript, which occurs within 1 kb, or 500 bp, or 300 bp, or 200 bp, or 100 bp of the 3' end of the transcript. In the case of mRNA, the "3' end of the transcript" is defined herein as the polyadenylation site, not including the poly(A) tail.

In one embodiment, a pool of probes making up 30% of the total absolute weight of the signature is used. In alternate embodiments, a pool of probes making up 40%, 60%, 70%, 80%, 90%, 95% or 100% of the total absolute weight of the signature is used in the methods described herein. The basis for inclusion of markers, as well as the clinical significance of mRNA level variations with respect to the reference set, is indicated below. In some embodiments, the disclosed probes are part of an array, for example the probes are bound to a solid substrate. Exemplary nucleic acid array and methods of making such arrays are discussed in Section D below.

In some embodiments, a probe specific for the disclosed colon cancer gene signature is part of a nucleic acid array, such as a microarray. In some examples, such arrays include a nucleic acid sequence that specifically hybridizes one of SEQ ID NOs: 1-636 or the complement thereof. In some embodiments, a nucleic acid array, such as a microarray, includes probes that specifically hybridize to at least 2, such as at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 474, at least 500, at least 525, at least 550, at least 575, at least 600, at least 634, or even all 636 of the transcripts in Table 6. In some embodiments, a nucleic acid array for a disclosed colon cancer signature includes probes that specifically hybridize to the top 10 weighted transcripts, the second top 10 weighted transcripts, the third top 10 weighted transcripts, the fourth top 10 weighted transcripts, the fifth top 10 weighted transcripts, the sixth top 10 weighted transcripts, the seventh top 10 weighted transcripts, the eighth top 10 weighted transcripts, the ninth top 10 weighted transcripts, or the tenth top 10 weighted transcripts listed in Table 6. In yet further embodiments, a nucleic acid array for a disclosed colon cancer signature includes probes that specifically hybridize to 636, 634, 620, 610, 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 20, or 10 transcripts having the greatest weight listed in Table 6 or the complement thereof. In some embodiments, a nucleic acid array for a disclosed colon cancer signature comprises about 200 to about 1000 probes, such as from about 400 to about 800 probes, such as from about 500 to about 700 probes, such as from about 550 to about 650 probes, where the probes detect transcripts from Table 6. The additional probes may be optionally selected from those that detect transcripts that are expressed in colon cancer, or which function as signal controls or expression level controls. Such optional probes can be selected from those included on the Colorectal Cancer DSA™ tool. In some embodiments, a nucleic acid array for a disclosed colon cancer signature comprises more than about 1000 probes.

Also disclosed are primer pairs for the amplification of a gene expression signature for colon cancer nucleic acid. In some examples a primer pair includes a forward primer 15 to 40 nucleotides in length comprising a nucleic acid sequence that specifically hybridizes to any one of the nucleic acid sequences set forth as SEQ ID NOs: 1-636 or its complement and a reverse primer 15 to 40 nucleotides in length comprising a nucleic acid sequence that specifically hybridizes to any one of the nucleic acid sequences set forth as SEQ ID NOs: 1-636 or its complement, wherein the set of primers is capable of directing the amplification of the nucleic acid.

Set of primer pairs for the amplification of a gene expression signature for colon cancer nucleic acids are also disclosed. In some embodiments, a primer set for a disclosed colon cancer signature includes primers that specifically hybridize to and are capable of amplifying at least 2, such as at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 474, at least 500, at least 525, at least 550, at least 575, at least 600, at least 634, or even all 636 of the transcripts in Table 6 that carry the greatest weight, defined as the rank of the average weight in the compound decision score function measured under cross-validation, and still have prognostic value such as primers that specifically hybridize to and are capable of amplifying any one of SEQ ID NOs: 1-636 or the complement thereof. In some embodiments, a primer set for a disclosed colon cancer signature includes primers that specifically hybridize to and are capable of amplifying the top 10 weighted transcripts, the second top 10 weighted transcripts, the third top 10 weighted transcripts, the fourth top 10 weighted transcripts, the fifth top 10 weighted transcripts, the sixth top 10 weighted transcripts, the seventh top 10 weighted transcripts, the eighth top 10 weighted transcripts, the ninth top 10 weighted transcripts, or the tenth top 10 weighted transcripts listed in Table 6. In yet further embodiments, a primer set for a disclosed colon cancer signature includes primers that specifically hybridize to and are capable of amplifying 636, 634, 620, 610, 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 20, or 10 transcripts having the greatest weight listed in Table 6 or the complement thereof.

In some embodiments, a primer set for a disclosed colon cancer signature includes primers that specifically hybridize to and are capable of amplifying transcripts for MUM1 and SIGMAR1. In another embodiment, a primer set for a disclosed colon cancer signature includes primers that specifically hybridize to and are capable of amplifying transcripts for MUM1, SIGMAR1, ARSD, SULT1C2 and PPFIBP1. In yet another embodiment, a probe set for a disclosed colon cancer signature includes probes that specifically hybridize to transcripts for ARSD, CXCL9, PCLO, SLC2A3, FCGBP, SLC2A14, SLC2A3, BCL9L and antisense sequences of MUC3A, OLFM4 and RNF39. A set of probes or primers can be prepared that is substantially representative of the gene expression signature. "Substantially representative of the gene expression signature" refers to probe sets that specifically hybridize to at least 50%, 60%, 70%, 80%, 90%, 95%, 99%, or 100% of the coding or non-coding transcripts in the gene expression signature, for example at least 50%, 60%, 70%, 80%, 90%, 95%, 99%, or 100% of the coding or non-coding transcripts in the gene expression signatures shown in Table 1, 2, or 6 or the complement thereof.

C. Statistical Determination of Colon Cancer Signatures

The disclosed colon cancer signatures can be evaluated by statistical methods. In some embodiments, the gene expression profile of a patient tissue sample is evaluated by a linear classifier. As used herein, a linear classifier refers to a weighted sum of the individual gene intensities into a compound decision score ("decision function"). The decision score is then compared to a pre-defined cut-off threshold, corresponding to a certain set point in terms of sensitivity and specificity, which indicates if a sample, is above the threshold (decision function positive) or below (decision function negative).

Effectively, this means that the data space, i.e. the set of all possible combinations of gene expression values, is split into two mutually exclusive halves corresponding to different clinical classifications or predictions, e.g. one corresponding to good prognosis and the other to poor prognosis. In the context of the overall signature, relative over-expression of a certain gene can either increase the decision score (positive weight) or reduce it (negative weight) and thus contribute to an overall decision of, for example, either poor or good prognosis.

The interpretation of this quantity, i.e. the cut-off threshold for good versus poor prognosis, is derived in the development phase ("training") from a set of patients with known outcome. The corresponding weights and the good/poor prognosis cut-off threshold for the decision score are fixed a priori from training data by methods known to those of ordinary skill in the art. In a preferred embodiment of the present method, Partial Least Squares Discriminant Analysis (PLS-DA) is used for determining the weights. (Ståhle, *J. Chemom.* 1 185-196, 1987; Nguyen and Rocke, *Bioinformatics* 18 39-50, 2002). Other methods for performing the classification, known to those skilled in the art, may also be with the methods described herein when applied to the transcripts of a colon cancer signature.

Different methods can be used to convert quantitative data measured on these genes or their products into a prognosis or other predictive use. These methods include, but not limited to pattern recognition (Duda et al. Pattern Classification, $2^{nd}$ ed., John Wiley, New York 2001), machine learning (Schölkopf et al. Learning with Kernels, MIT Press, Cambridge 2002, Bishop, Neural Networks for Pattern Recognition, Clarendon Press, Oxford 1995), statistics (Hastie et al. The Elements of Statistical Learning, Springer, New York 2001), bioinformatics (Dudoit et al., *J. Am. Statist. Assoc.* 97:77-87, 2002; Tibshirani et al., *Proc. Natl. Acad. Sci. USA* 99:6567-6572, 2002) or chemometrics (Vandeginste, et al., Handbook of Chemometrics and Qualimetrics, Part B, Elsevier, Amsterdam 1998).

In some embodiments, in a training step a set of patient samples for both good and poor prognosis cases are measured and the prediction method is optimised using the inherent information from this training data to optimally predict the training set or a future sample set. In this training step the used method is trained or parameterised to predict from a specific intensity pattern to a specific prognostic call. Suitable transformation or pre-processing steps might be performed with the measured data before it is subjected to the prognostic method or algorithm.

In some embodiments, a weighted sum of the pre-processed intensity values for each transcript is formed and compared with a threshold value optimised on the training set (Duda et al. Pattern Classification, $2^{nd}$ ed., John Wiley, New York 2001). The weights can be derived by a multitude of linear classification methods, including but not limited to Partial Least Squares (PLS, (Nguyen et al., 2002, *Bioinformatics* 18 (2002) 39-50)) or Support Vector Machines (SVM, (Schölkopf et al. Learning with Kernels, MIT Press, Cambridge 2002)).

In some embodiments, the data is transformed non-linearly before applying a weighted sum, for example as described above. This non-linear transformation might include increasing the dimensionality of the data. The non-linear transformation and weighted summation might also be performed implicitly, e.g. through the use of a kernel function. (Schölkopf et al. Learning with Kernels, MIT Press, Cambridge 2002).

In some embodiments, a new data sample is compared with two or more class prototypes, being either real measured training samples or artificially created prototypes. This comparison is performed using suitable similarity measures for example but not limited to Euclidean distance (Duda et al. Pattern Classification, 2$^{nd}$ ed., John Wiley, New York 2001), correlation coefficient (van't Veer, et al., Nature 415:530, 2002) etc. A new sample is then assigned to the prognostic group with the closest prototype or the highest number of prototypes in the vicinity.

In some embodiments, decision trees (Hastie et al. The Elements of Statistical Learning, Springer, New York 2001) or random forests (Breiman, 2001Random Forests, Machine Learning 45:5) are used to make a prognostic call from the measured intensity data for the transcript set or their products.

In some embodiments, neural networks (Bishop, Neural Networks for Pattern Recognition, Clarendon Press, Oxford 1995) are used to make a prognostic call from the measured intensity data for the transcript set or their products.

In some embodiments, discriminant analysis (Duda et al. Pattern Classification, 2$^{nd}$ ed., John Wiley, New York 2001), comprising but not limited to linear, diagonal linear, quadratic and logistic discriminant analysis, is used to make a prognostic call from the measured intensity data for the transcript set or their products.

In some embodiments, Prediction Analysis for Microarrays (PAM, (Tibshirani et al., *Proc. Natl. Acad. Sci. USA* 99:6567-6572, 2002)) is used to make a prognostic call from the measured intensity data for the transcript set or their products.

In some embodiments, Soft Independent Modelling of Class Analogy (SIMCA, (Wold, 1976, *Pattern Recogn.* 8:127-139)) is used to make a prognosis from the measured intensity data for the transcript set or their products.

D. Methods for Detection of mRNA

Gene expression can be evaluated by detecting mRNA encoding the gene of interest. Thus, the disclosed methods can include evaluating mRNA. RNA can be isolated from a sample of a tumor (for example, a colon cancer tumor) from a subject, a sample of adjacent non-tumor tissue from the subject, a sample of tumor-free tissue from a normal (healthy) subject, or combinations thereof, using methods well known to one of ordinary skill in the art, including commercially available kits.

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, *Biotechniques* 6:56-60, 1988, and De Andres et al., *Biotechniques* 18:42-44, 1995. In one example, RNA isolation can be performed using purification kit, buffer set and protease from commercial manufacturers, such as QIAGEN®(Valencia, Calif.), according to the manufacturer's instructions. For example, total RNA from cells in culture (such as those obtained from a subject) can be isolated using QIAGEN® RNeasy® mini-columns. Other commercially available RNA isolation kits include MASTERPURE® Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared from tumor or other biological sample can be isolated, for example, by cesium chloride density gradient centrifugation.

The present signatures and methods described herein accommodate the use of archived paraffin-embedded biopsy material for assay of all markers in the set, and therefore are compatible with the most widely available type of biopsy material. The expression level of transcripts in a colon tissue sample may be determined using RNA obtained from a formalin-fixed, paraffin-embedded tissue sample, fresh frozen tissue or fresh tissue that has been stored in solutions such as RNAlater®. The isolation of RNA can, for example, be carried out following any of the procedures described above or throughout the application, or by any other method known in the art. While all techniques of gene expression profiling, as well as proteomics techniques, are suitable for use in performing the methods described herein, the gene expression levels are often determined by DNA microarray technology.

If the source of the tissue is a formalin-fixed, paraffin embedded tissue sample, the RNA may be fragmented, resulting in loss of information. The signatures provided herein are derived from pools of transcripts sequenced from their 3' end thereby providing an accurate representation of the transcriptome of the tissue. Thus the signatures provided herein are useful for both fresh frozen and fixed paraffin-embedded tissues.

In some embodiments, RNA samples used in the methods described herein may be prepared from a fixed, wax-embedded colon tissue specimen, by using one or more of the following steps, such as all of the following steps:

(a) deparaffinizing using conventional methods and with multiple wash steps in organic solvent;

(b) air drying and treating with protease to break inter- and intracellular bonds, resulting the release of RNA from the tissue;

(c) removing contaminating genomic DNA;

(d) washing in organic solvent; and eluting in a suitable RNase-free elution buffer.

The RNA-extraction methods may also include incubation of the tissue in a highly denaturing lysis buffer, which has the additional function of reversing much of the formalin crosslinking that occurs in tissues preserved this way to improve RNA yield and quality for performance in downstream assays.

Following RNA recovery, the RNA may optionally be further purified resulting in RNA that is substantially free from contaminating DNA or proteins. Further RNA purification may be accomplished by any of the aforementioned techniques for RNA recovery or with the use of commercially available RNA cleanup kits, such as RNeasy® MinElute® Cleanup Kit (QIAGEN®). The tissue specimen may, for example, be obtained from a tumor, and the RNA may be obtained from a microdissected portion of the tissue specimen enriched for tumor cells.

Methods of gene expression profiling include methods based on hybridization analysis of polynucleotides and methods based on sequencing of polynucleotides. In some examples, mRNA expression in a sample is quantified using Northern blotting or in situ hybridization (Parker & Barnes, *Methods in Molecular Biology* 106:247-283, 1999); RNAse protection assays (Hod, *Biotechniques* 13:852-4, 1992); and PCR-based methods, such as reverse transcription polymerase chain reaction (RT-PCR) (Weis et al., *Trends in Genetics* 8:263-4, 1992). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). In one example, RT-PCR can be used to compare mRNA levels in different samples, to characterize patterns of gene expression, to discriminate between closely related mRNAs, and to analyze RNA structure. In specific examples, the disclosed colon cancer signatures are analyzed by nucleic acid microarray techniques, PCR techniques or combinations there of 1. Gene Expression Profiling with Microarray Methods In some embodiments, the expression profile of colon cancer-associated genes and/or transcripts, such as those shown in Table 6, can be measured in either fresh or paraffin-embedded tumor tissue, using microarray technology. In this method, polynucleotide sequences of interest, such as polynucleotide sequences that specifically hybridize to the nucleic acid sequences shown in Table 6 or a complement thereof, are plated, or arrayed, on a microchip substrate. The arrayed sequences are then hybridized with nucleic acids from cells or tissues of interest.

Just as in RT-PCR methods (see below), the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and/or fixed (e.g. formalin-fixed) tissue samples, which are routinely prepared and preserved in everyday clinical practice.

In specific embodiments of the microarray technique, PCR amplified inserts of cDNA clones or oligonucleotides are applied to a substrate in a dense array. Short oligonucleotides may also be synthesized directly on a substrate using, for example, a combination of semiconductor-based photolithography and solid phase chemical synthesis technologies. (Affymetrix, Inc., Santa Clara, Calif.). In one embodiment, at least 10,000 nucleotide sequences are present on the substrate. The microarrayed transcripts, immobilized on the substrate are suitable for hybridization under stringent conditions. Fluorescently labeled nucleotide probes may be generated through incorporation of fluorescent nucleotides by reverse transcription of RNA extracted from tissues of interest. Labeled probes applied to the array hybridize with specificity to each nucleotide on the array. After washing to remove non-specifically bound probes, the array is scanned by confocal laser microscopy or by another detection method, such as a CCD camera. Quantitation of hybridization of each arrayed element allows for assessment of corresponding transcript abundance.

With dual color fluorescence, separately labeled nucleotide probes generated from two sources may be hybridized pairwise to the array. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106 149 (1996)). Microarray analysis can also be performed by commercially available equipment, following manufacturer's protocols, such as by using the Affymetrix GeneChip® technology (Affymetrix, Inc., Santa Clara, Calif.), or Agilent microarray technology (Agilent Technologies, Inc., Santa Clara, Calif.).

The development of microarray methods for large-scale analysis of gene expression makes it possible to search systematically for molecular markers of cancer classification and outcome prediction in a variety of tumor types, such as colon cancer tumors.

In particular embodiments provided herein, arrays can be used to evaluate a colon cancer gene expression profile, for example to prognose or diagnose a patient with colon cancer. When describing an array that consists essentially of probes or primers specific for the genes listed in Table 1, Table 2, and/or the transcripts listed in Table 6, such an array includes probes or primers specific for these colon cancer associated genes, and can further include control probes (for example to confirm the incubation conditions are sufficient). Exemplary control probes include GAPDH, β-actin, and 18S RNA.

i. Array Substrates

The solid support of the array can be formed from inorganic material (such as glass) or an organic polymer. Suitable materials for the solid support include, but are not limited to: polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulformes, hydroxylated biaxially oriented polypropylene, aminated biaxially oriented polypropylene, thiolated biaxially oriented polypropylene, ethyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides are not amenable to non-specific binding, or when non-specific binding occurs, such materials can be readily removed from the surface without removing the oligonucleotides.

In another example, a surface activated organic polymer is used as the solid support surface. One example of a surface activated organic polymer is a polypropylene material aminated via radio frequency plasma discharge. Other reactive groups can also be used, such as carboxylated, hydroxylated, thiolated, or active ester groups.

ii. Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil (0.001 inch) to about 20 mil, although the thickness of the film is not critical and can be varied over a fairly broad range. The array can include biaxially oriented polypropylene (BOPP) films, which in addition to their durability, exhibit low background fluorescence.

The array formats of the present disclosure can be included in a variety of different types of formats. A "format" includes any format to which the solid support can be affixed, such as microtiter plates (e.g., multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217:306-10, 1994. In one example, the oligonucleotides are synthesized onto the support using conventional chemical techniques for preparing oligonucleotides on solid supports (such as PCT applications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels that permit detection of oligonucleotide probe:target sequence hybridization complexes.

2. Gene Expression Profiling with Microarray Methods

One of the most sensitive and most flexible quantitative methods is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of RNA from a target sample such as human tumors or tumor cell lines, and corresponding normal tissues or cell lines, respectively. If the source of RNA is a primary tumor, RNA can be extracted, for example, from frozen or archived paraffin-embedded and/or fixed (e.g. formalin-fixed) tissue samples.

A variation of RT-PCR is real time quantitative RT-PCR, which measures PCR product accumulation through a dual-labeled fluorogenic probe (e.g., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Heid et al., *Genome Research* 6:986-994, 1996). Quantitative PCR is also described in U.S. Pat. No. 5,538,848. Related probes and quantitative amplification procedures are described in U.S. Pat. No. 5,716,784 and U.S. Pat. No. 5,723,591. Instruments for carrying out quantitative PCR in microtiter plates are available from PE Applied Biosystems (Foster City, Calif.).

In other examples, mRNA levels are measured using TaqMan® RT-PCR technology. TaqMan® RT-PCR can be performed using commercially available equipment. The system can include a thermocycler, laser, charge-coupled device (CCD) camera, and computer. In some examples, the system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by an experimental treatment. RNAs commonly used to normalize patterns of gene expression are mRNAs for the housekeeping genes GAPDH, β-actin, and 18S ribosomal RNA.

The steps of a representative protocol for quantitating gene expression using fixed, paraffin-embedded tissues as the RNA source, including mRNA isolation, purification, primer extension and amplification are given in various published journal articles (see Godfrey et al., *J. Mol. Diag.* 2:84 91, 2000; Specht et al., *Am. J. Pathol.* 158:419-29, 2001). Briefly, a representative process starts with cutting about 10 μm thick sections of paraffin-embedded tumor tissue samples. The RNA is then extracted, and protein and DNA are removed. Alternatively, RNA is isolated directly from a tumor sample or other tissue sample. After analysis of the RNA concentration, RNA repair and/or amplification steps can be included, if necessary, and RNA is reverse transcribed using gene specific promoters followed by RT-PCR and/or hybridization to a nucleic acid array.

In alternate embodiments, commonly used methods known in the art for the quantification of mRNA expression in a sample may be used with the colon signatures provided herein. Such methods include, but are not limited to, northern blotting and in situ hybridization (Parker & Barnes, Methods in Molecular Biology 106:247 283 (1999)); RNase protection assays (Hod, Biotechniques 13:852 854 (1992)). Alternatively, antibodies may be employed that can recognize specific duplexes, including DNA duplexes, RNA duplexes, and DNA-RNA hybrid duplexes or DNA-protein duplexes.

Further PCR-based techniques include, for example, differential display (Liang and Pardee, Science 257:967 971 (1992)); amplified fragment length polymorphism (iAFLP) (Kawamoto et al., Genome Res. 12:1305 1312 (1999)); BeadArray™ technology (Illumina, San Diego, Calif.; Oliphant et al., Discovery of Markers for Disease (Supplement to Biotechniques), June 2002; Ferguson et al., Analytical Chemistry 72:5618 (2000)); BeadsArray for Detection of Gene Expression (BADGE), using the commercially available Luminex100 LabMAP system and multiple color-coded microspheres (Luminex Corp., Austin, Tex.) in a rapid assay for gene expression (Yang et al., Genome Res. 11:1888 1898 (2001)); Competitive PCR and MassARRAY (Oeth et al., 2004, SEQUONOME Application Note); and high coverage expression profiling (HiCEP) analysis (Fukumura et al., Nucl. Acids. Res. 31(16) e94 (2003)).

The primers used for the amplification are selected so as to amplify a unique segment of the gene of interest (such as the genes listed in Table 1, Table and Table 6. Primers that can be used to these are commercially available or can be designed and synthesized according to well known methods using the sequences of these genes as available for example in GENBANK®.

An alternative quantitative nucleic acid amplification procedure is described in U.S. Pat. No. 5,219,727. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some examples, gene expression is identified or confirmed using the microarray technique. Thus, the expression profile can be measured in either fresh or paraffin-embedded tumor tissue, using microarray technology. In this method, colon cancer signature nucleic acid sequences of interest (including cDNAs and oligonucleotides) are plated, or arrayed, on a microchip substrate. The arrayed sequences are then hybridized with isolated nucleic acids (such as cDNA or mRNA) from cells or tissues of interest. Just as in the RT-PCR method, the source of mRNA typically is total RNA isolated from human tumors, and optionally from corresponding noncancerous tissue and normal tissues or cell lines.

In a specific embodiment of the microarray technique, PCR amplified inserts of cDNA clones are applied to a substrate in a dense array. In some examples, the array includes probes specific to at least two of the colon cancer signature genes in Tables 1, 2, and 6. The microarrayed nucleic acids are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for colon cancer signature genes in Tables 1, 2, and 6. Microarray analysis can be performed by commercially available equipment, following manufacturer's protocols, such as are supplied with Affymetrix GeneChip® technology (Affymetrix, Santa Clara, Calif.), or Agilent's microarray technology (Agilent Technologies, Santa Clara, Calif.).

3. Additional Methods of Gene Expression Analysis

Serial analysis of gene expression (SAGE) is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., *Science* 270:484-7, 1995; and Velculescu et al., *Cell* 88:243-51, 1997).

In situ hybridization (ISH) is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of cancer survival factor-associated genes.

Sample cells or tissues are treated to increase their permeability to allow a probe, such as a cancer survival factor-associated gene-specific probe, to enter the cells. The probe is added to the treated cells, allowed to hybridize at pertinent temperature, and excess probe is washed away. A complementary probe is labeled so that the probe's location and quantity in the tissue can be determined, for example, using autoradiography, fluorescence microscopy or immunoassay. The sample may be any sample as herein described, such as a non-tumor sample or a breast or lung tumor sample. Since the sequences of the cancer survival factor-associated genes of interest are known, probes can be designed accordingly such that the probes specifically bind the gene of interest.

In situ PCR is the PCR-based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip, which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, $^3$H-CTP or biotin-16-dUTP), which have been incorporated into the PCR products during thermal cycling.

In some embodiments of the detection methods, the expression of one or more "housekeeping" genes or "internal controls" can also be evaluated. These terms include any constitutively or globally expressed gene (or protein, as discussed below) whose presence enables an assessment of cancer survival factor-associated gene (or protein) levels. Such an assessment includes a determination of the overall constitutive level of gene transcription and a control for variations in RNA (or protein) recovery.

The disclosure is further illustrated by the following non-limiting Examples.

EXAMPLES

Example 1

This example describes the generation and validation of an exemplary predictive tool for the categorization of colon cancer samples using the methods and reagents disclosed herein. This example includes materials published by inventors of the subject technology in Kennedy et al, *J. Clin. Oncol.*, 29(35) 4620-4626, 2011, which is specifically incorporated herein by reference in its entirety.

A colorectal cancer transcriptome focused research array was developed (Colorectal Cancer DSA™ (Almac Diagnostics, N. Ireland; which can be found on the world wide web at almac-diagnostics.com)) capable of delivering accurate expression data from FFPE derived RNA (Johnston et al., *J. Clin. Oncol.* 24: 3519, 2006).

The Colorectal Cancer DSA™ research tool contains 61,528 probe sets and encodes 52,306 transcripts confirmed as being expressed in colon cancer and normal tissue. Comparing the Colorectal Cancer DSA™ research tool against the National Center for Biotechnology Information (NCBI) human Reference Sequence (RefSeq) RNA database (which can be found on the world wide web at ncbi.nlm.nih.gov/RefSeq/) using BLAST analysis, 21,968 (42%) transcripts are present and 26,676 (51%) of transcripts are absent from the human RefSeq database. Furthermore 7% of the content represents expressed antisense transcripts to annotated genes. (Johnston et al., *J. Clin. Oncol.* 24: 3519, 2006; Pruitt et al., *Nucleic Acids Research* 33: D501-D504, 2005). In addition, probe-level analysis of the Colorectal Cancer DSA™ compared with leading generic arrays, highlighted that approximately 20,000 (40%) transcripts are not contained on the leading generic microarray platform (Affymetrix) and are unique to the Colorectal Cancer DSA™. Thus, the Colorectal Cancer DSA™ research tool includes transcripts that have not been available in hitherto performed gene expression studies. Finally, because the transcript information used to design the Colorectal Cancer DSA™ was generated in part by a high throughput sequencing approach, it has been possible to generate probes closer to the 3' end of the transcripts than are contained on other generic microarrays. The combination of relevant disease specific content and 3' based probe design has yielded a unique product capable of robust profiling from FFPE derived RNA.

The aim of this study was to assess the use of the Colorectal Cancer DSA™ research array, using FFPE derived tumor material to generate and independently validate a prognostic gene signature capable of accurately classifying stage II colon cancer patients as being at low or high risk of relapse, post surgery. Stage II colon cancer as used in this example is AJCC T3 or T4 node negative (NO) non metastatic (MO) colon cancer.

Methods
Sample Selection.

Samples were collected retrospectively with the following eligibility criteria: stage II colon adenocarcinoma only, with no evidence of residual disease; patient age 45 years or older at time of primary surgery; six or more regional lymph nodes assessed; a minimum of 50% tumor cells present in the tissue section; no family history of colon cancer; no preoperative or postoperative cancer therapy within 1 year of surgery (although therapy given after recurrence was acceptable); and minimum patient follow-up of 5 years for low-risk patients. Low-risk patients were defined as those with no cancer recurrence within 5 years of primary surgery. High-risk patients were defined as those with metastatic cancer recurrence within 5 years of primary surgery. Patients with local disease recurrence were excluded because this recurrence may have been a result of local residual disease after surgery rather than metastatic tumor. Samples were collected from 12 centers. All samples underwent independent histopathologic review by a pathologist. The data set was compared with the Surveillance, Epidemiology, and End Results database to ensure it represented a general population with stage II colon cancer. Key patient and tumor characteristics are given in Table 3 (see FIG. 6).

Gene Expression Profiling from FFPE Tissue.

Total RNA was extracted from FFPE tumor samples using the Roche High Pure RNA Paraffin Kit (Roche, Basel, Switzerland). Amplified cDNA targets were prepared using the Nugen WT-Ovation® FFPE System v2 in combination with the Nugen FL-Ovation® cDNA Biotin Module v2 and were performed in accordance with manufacturer's instructions. Hybridization, washing, staining and scanning of fragmented, labelled cDNA was carried out according to standard Affymetrix protocols. Between 3.0 and 3.5 μg fragmented, labelled cDNA was hybridized to the Colorectal Cancer DSA™ microarray (Almac, Craigavon, United Kingdom) on the Affymetrix 7G scanner (Affymetrix, Santa Clara, Calif.). A sample profile scheduling strategy was used that involved the stratification of samples into batches that were randomized against targeted clinical and sample property factors in addition to operators, reagent, and material lots. Quality control criteria were applied, and biologic and technical factors were balanced between low- and high-risk samples. This is performed in order to minimise systematic bias and diffuse any residual technical bias into technical variation.

Classifier Model Identification.

Model development started with 5,014 probe sets identified as stable and/or having comparable longitudinal stability under FFPE fixation to avoid the issue of differential degradation of probe sets. Signature generation was subsequently performed using the partial least squares classification method with selection of important features based on recursive feature elimination (RFE) during 10 repeats of five-fold cross validation. All aspects of the model development were appropriately nested within the cross validation, including an initial filtering to remove 50% of the probe sets with the lowest variance and intensity, reference-based robust multichip averaging (RefRMA) normalization and summarization, and RFE discarding the least important 10% of probe sets at each iteration. The total number of features to include in the final model was determined by the feature length with the highest average area under the receiver operating characteristics curve (AUC) under cross validation. The threshold for dichotomization of the predictions from each model was selected based on the maximum of the sum of sensitivity and specificity (minimum of the Youden J statistic (Youden, *Cancer* 3:32-35, 1950) from cross-validated training data. In the case of multiple thresholds with largely identical performance, the hazard ratio (HR) from Cox proportional hazards regression was used as a tiebreaker to favor higher HR values.

The precision of the predictions was evaluated by predicting technical replicates of a colorectal cancer cell line (HCT116) embedded in FFPE, which was profiled concurrently with the clinical samples. The repeated technical measurements of this sample were not included in model development but were predicted by all 50 cross-validation training subsets as an independent test set with a view to select models with high repeatability and reproducibility. Additionally, a permutation test was performed where the true class labels were reshuffled randomly 100 times followed by complete model development. This was done to assess what classification performance one can expect by chance from a data set with these characteristics and to reveal any bias in the signature generation procedure.

The independence of the final model in the context of known clinical factors was evaluated using univariate and multivariate Cox proportional hazards regression. The input used was the predicted dichotomized class labels together with tumor stage, patient tumor grade, tumor location, patient age, patient sex, mucinous/nonmucinous subtype, and number of lymph nodes retrieved. Microsatellite instability was not included as a factor because this information was not available for the majority of the samples. Gene Ontology annotation and enrichment of Gene Ontology biologic processes and molecular functions were performed using an internally developed tool based on the genes in the final signature. The hypergeometric distribution with false discovery rate multiple testing correction was used to determine functional classes of genes significantly enriched. The pathway analysis was generated through the use of Ingenuity Pathway Analysis (Ingenuity Systems, Redwood City, Calif.).

Balancing, Randomisation and Quality Control (QC) of Samples.

Target population: The population used to train the assay was matched to reflect the general population properties from the SEER and CRUK databases. The following properties were being considered:

Gender. The gender prevalence amongst in the Stage II population is approximately between 50-60% male (56% in the UK and 57% in the US).

Tumour location (distal/proximal). The prevalence in the Stage II population is approximately 55%-65% proximal and 35%-45% distal.

Patient age. According to NCI's SEER Cancer Statistics Review Colon and Rectum Section, from 2001-2005, 0.1% of patients were diagnosed under age 20; 1.0% between 20 and 34; 3.7% between 35 and 44; 11.6% between 45 and 54; 18.3% between 55 and 64; 25.1% between 65 and 74; 28.2% between 75 and 84 and 12.2% 85+ years of age.

Recurrence-free survival rate. The rate of recurrence-free survival in the Stage II population is reported to be between 13%-22% (Gattaj et al, European Journal of Cancer, 2006) and ~30% from the SEER database.

Pre-balancing: Pre-balancing was performed so that the sample set put forward for hybridization was balanced with respect to selected clinical covariates whilst maintaining the general population statistics presented above. This excludes recurrence-free survival, which was intentionally enriched to increase the power of the biomarker discovery. The training set did not contain any samples with events after 5 years, whereas this was not a constraint in the validation set. The rationale for not using samples that recur after 5 years for signature generation (i.e. in the training set) is to avoid introducing additional heterogeneity in the sample population when performing the biomarker discovery.

The main aim of the balancing procedure was to reduce the association (if any) between the endpoint (high/low risk represented as a binary variable) and any of the factors listed below. Any association between these factors and the high/low risk endpoint would introduce a confounding that could limit the clinical utility of the assay. 603 colorectal samples were subjected to the pre-balancing in order to reduce strong associations between prognosis and any of the following factors: Gender; Tumor location within the bowel; Patient age; Contributing Centre; FFPE block age (date of surgery); Tumor content; and RNA quality.

Continuous parameters were tested using a Kolmogorov-Smirnoff test and categorical parameters were tested using a chi-squared test. A p-value≥0.4 for all parameters was required to achieve balancing. 504 samples remained after balancing (335 low risk and 169 high risk) and were put forward to array profiling.

Randomization of samples during array profiling: Randomization of samples was performed to avoid confounding between known technical and biological factors, primarily the endpoint of interest (prognosis). In this study operator, hybridization-wash-stain (HWS) kit lot, array lot and array batch were considered together with the contributing center and the prognosis. Samples were first randomized into array batches such that each array batch had the same proportion of prognosis and contributing center. Operators were then assigned to each array batch according to availability. Each array batch was then assigned a HWS kit, ensuring that each operator used the same proportion of each kit. Array lots were allocated to each array batch, ensuring that they were evenly distributed amongst the array batches.

Quality control of the training data: QC procedures were applied on the resulting arrays, primarily based on values in the Affymetrix RPT files that contain various quality-related parameters. Limits were calculated based on visual inspection of the distribution for each parameter for all samples: % present calls (≥20% required); Image artefacts were identified to remove arrays with noticeable blotches; Outliers were detected from principal component analysis (PCA) based on the Q residuals and Hotelling's $T^2$.

Assessment of gender genes was used to determine if observed expression levels matched the known gender in clinical information The following Affymetrix quality parameters were also considered during the visual inspection of the distributions; broadly categorised as follows: RNA Quality; Signal Quality & Detection call; Background & Noise; and Background Homogeneity A total of 319 colorectal samples passed the QC procedure. Due to preliminary results suggesting a heterogeneity introduced by the rectal samples, the rectal samples were removed to form a 249 colon-only set, which was put forward for final (post-QC) balancing.

Final post-QC balancing: The 249 colon samples passing QC were balanced using the same principles as the initial pre-balancing, with the addition of criteria for the % present call distribution to be similar in both low risk and high risk groups (this information is only available after hybridisation). A final set of 215 samples remained after QC and balancing.

The final colon set with 215 samples has the following properties compared to the known population distribution: Gender: 53% male (50-60% in population); Tumor location (distal/proximal): 62% proximal (55-65% proximal in population); Patient age: Closely follows the continuous distribution of the population; and Recurrence-free survival rate: 34% poor prognosis (high risk). Intentionally enriched compared to population around 15-20%.

Quality control of the validation set and future sample sets: Using a tailor-made QC procedure on the training set is an important step in order to facilitate the identification of biomarkers from a high-quality data set. However for prediction of future samples, QC has to be applied on a one-sample-at-a-time basis. Also, the QC procedure cannot be too specific to the data set and the system where the data has been generated. For this purpose a separate evaluation was performed using 40 samples replicated across two systems and scanners to identify QC parameters that are stable across systems. The AvgSigA parameter (average signal of the absent probe sets) was determined to be the most stable parameter across the different systems and hence the best candidate for a system-independent QC procedure. For this parameter, higher values imply lower quality and lower values imply higher quality. The AvgSigA values are strongly negatively correlated to the % present call parameter which is a commonly used QC parameter and was the primary QC parameter used on the training set. The lower acceptance value of % present calls from the training set was set to 20%, which corresponds approximately to an upper acceptance value of 43 for the AvgSigA parameter for this data set. To accommodate younger FFPE samples, it was decided not to introduce a lower threshold on the AvgSigA (which will allow inclusion of higher-quality samples). The final inclusion range derived from this study was hence AvgSigA≤43, which was the QC metric applied to the independent validation set and is the QC that will be applied to future samples.

Identifying probe sets that are stable over ffpe block age: It was recognized that mRNA transcripts are likely to degrade at different rates and to different levels in FFPE samples, which could result in a signature generated from old material not performing as expected on fresh FFPE material. Therefore two independent longitudinal studies were performed to identify probe sets that are stable over FFPE block age. In the first study, 9 FFPE blocks were serially sectioned and analyzed by DNA microarray at seven time points in a 16-week timeframe following fixation. These samples were supplemented by a second longitudinal study at three 6 month intervals in a one year timeframe in which 8 FFPE blocks ranging from 6 months to 4 years of age which were serially sectioned and analyzed by DNA microarray resulting in 113 individual samples for analysis. 5014 transcripts were identified that either did not undergo further degradation with time or decayed at an equivalent rate following fixation. This list of probe sets was subsequently used for signature generation. A separate manuscript for presenting the details from this study is in preparation.

Estimating the precision of the classifier during model development: The ability of a classifier to consistently produce the same output from technical replicates is an important aspect of an assay when used in a test setting. For this purpose, a set of 39 reference samples, which are technical replicates of the same colorectal cancer cell line (HCT114), were hybridized together with the clinical samples. During model development, this set was predicted as an external test set during cross-validation in order to estimate the relative variance at each step in the model development process. No information was shared between the training set and the 39 sample reference set during cross-validation. The standard deviation from the predicted signature scores were calculated and visualized as the average with 95% confidence limits. The variability is low for longer signatures, which then gradually increases over the feature selection procedure, which is also reflected in lower accuracy (AUC) for the shorter signatures. At the selected signature length (634 probe sets), the model shows both high precision and accuracy.

Permutation analysis of the classification performance: Permutation analysis was performed to evaluate what classification performance one can expect by chance from a data set with similar properties. This was performed by randomly reshuffling the true class labels (i.e. the true prognosis) and subsequently repeating the entire model development process (with filtering, normalization, feature selection and classification). The signature performance is significantly better than chance at longer signature lengths and specifically at the selected one where the number of probe sets is 634. Additionally, the permutation test reveals any underlying bias in the data set and/or the methodology used to develop the classifier. The median AUC over the random labels is 0.5, denoting chance, which confirms that there is no evident bias in the procedure used.

Results

Development of a Stage II Colon Cancer Prognostic Signature from FFPE Tissues. Disease-free survival at 5 years was used as the primary end point for this study. After balancing for clinical factors and applying quality control criteria to the initial data set, a training set of 215 patients (142 low-risk and 73 high-risk patients) was identified. Fifty percent variance-intensity filtering, RefRMA normalization, RFE feature selection, and partial least squares classification were performed under 10 repeats of five-fold cross validation for estimation of the classification performance. Cross validation indicated a 634-transcript signature to be optimal for prognostic classification. A receiver operating characteristic curve with an AUC of 0.68 (P<0.001) was generated, indicating a significant association between signature score and prognosis (FIG. 3A). The observed AUC was significantly higher than random in the permutation analysis and displayed a low variance in the evaluation of the precision from technical replicates. A threshold of 0.465 for dichotomization of the signature prediction scores was established from the Youden J statistics, yielding an HR of 2.62 (P<0.001; FIG. 3B). Table 4 contains a summary of the classification performance over the signature generation during cross validation.

TABLE 4

Classification Performance of the Training and Independent Validation Sets

| Data Set | AUC | Sensitivity | Specificity | NPV | PPV | HR |
|---|---|---|---|---|---|---|
| Train(95 % CI) | 0.682(0.643-0.720) | 0.478(0.407-0.549) | 0.791(0.737-0.845) | 0.858(0.845-0.872) | 0.365(0.317-0.413) | 2.618(2.041-3.195) |

TABLE 4-continued

Classification Performance of the Training and Independent Validation Sets

| Data Set | AUC | Sensitivity | Specificity | NPV | PPV | HR |
|---|---|---|---|---|---|---|
| Val.(95 % CI) | 0.684(0.594-0.761) | 0.718(0.617-0.811) | 0.559(0.423-0.673) | 0.867(0.828-0.900) | 0.331(0.250-0.434) | 2.526(1.536-4.154) |

The 95% CIs are ±2 standard deviations from cross validation (training set) or bootstrapping with 1,000 repeats (validation set); 80% and 20% priors have been used when calculating the NPVs and PPVs, respectively. The threshold t = 0.465 was used for dichotomization of the signature score. Abbreviations: AUC, area under the receiver operating characteristics curve; HR, hazard ratio; NPV, negative predictive value (negative is low risk); PPV, positive predictive value (positive is high risk)

Figure 4B:
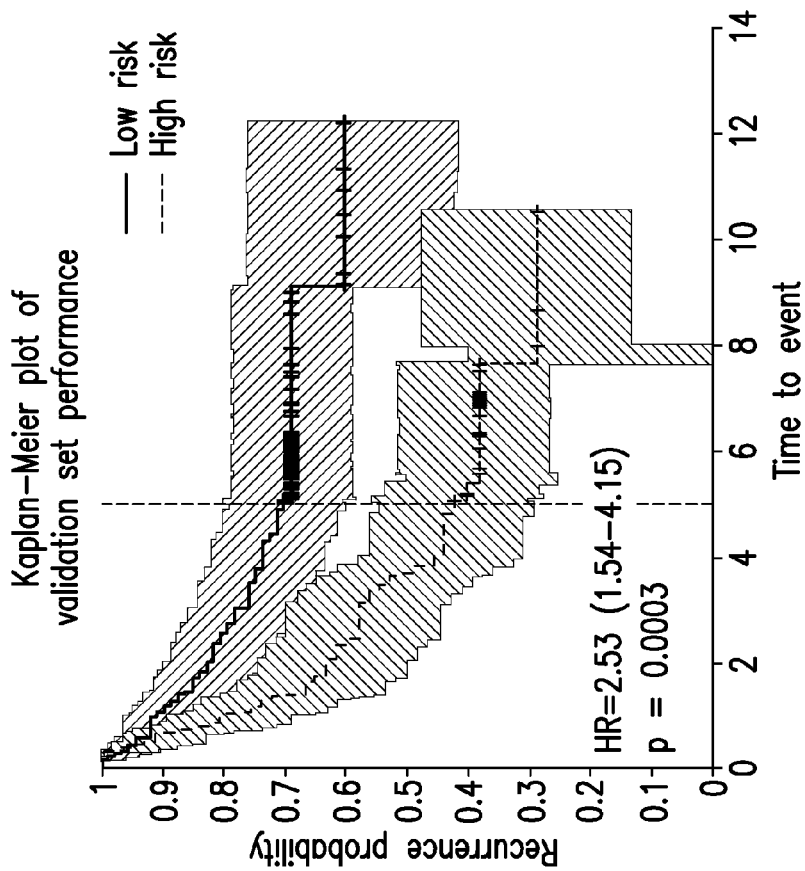
FIG. 4B provides a Kaplan-Meier plot of recurrence from validation data from the candidate model.
Figure 4A:
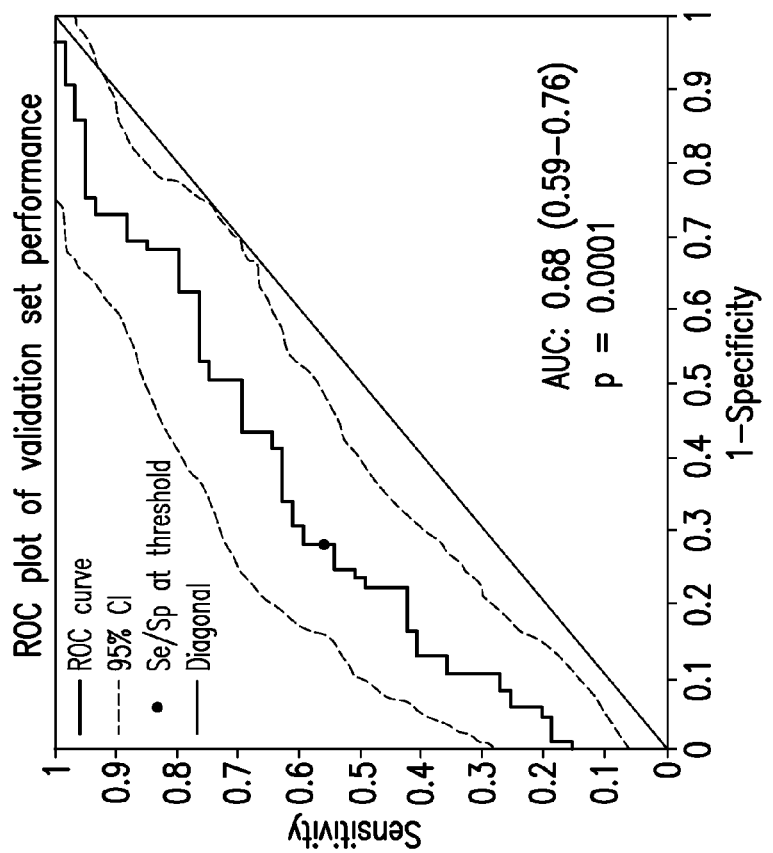
FIG. 4A provides a graph of the receiver operating characteristic (ROC) curve of the 636 transcript prognostic signature in the validation set.
Figure 5:
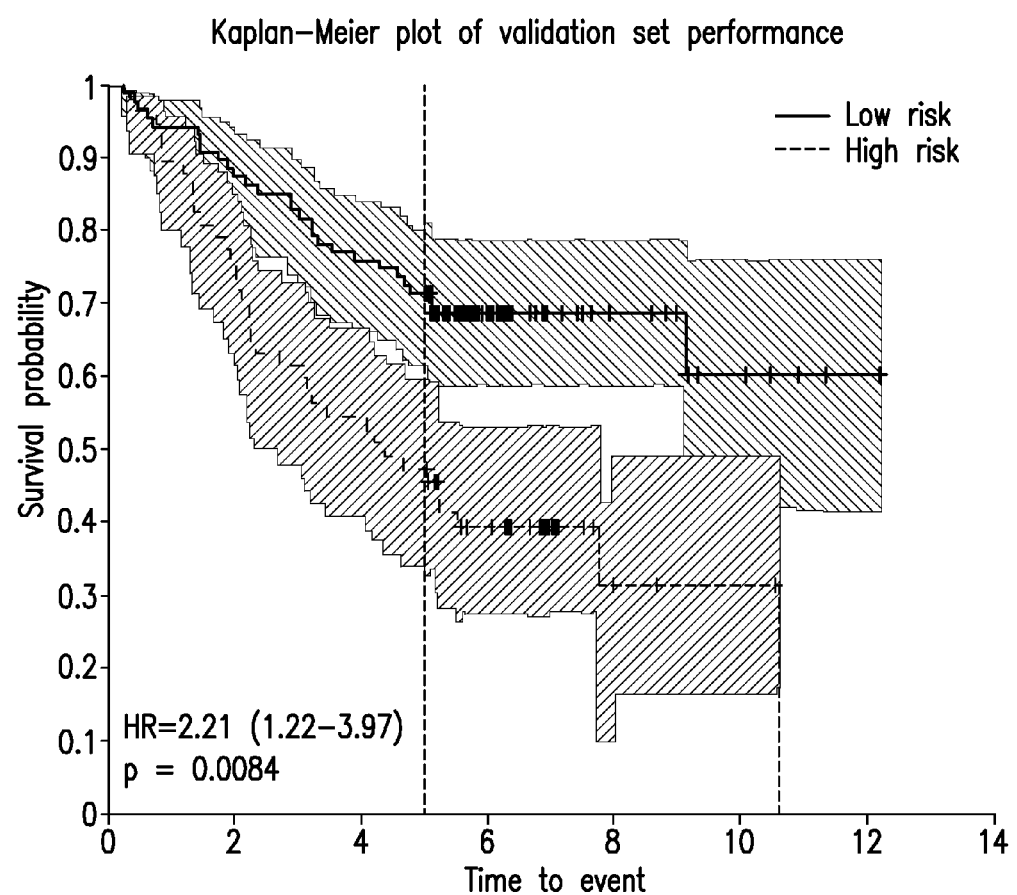
FIG. 5 provides a Kaplan-Meier plot of overall survival from validation data from the candidate model.

Independent Validation of the Stage II Colon Cancer Prognostic Signature: The prognostic signature was applied to an independent validation set of 144 patients enriched for recurrence (85 low-risk and 59 high-risk patients) using the threshold score identified in the training set. The sample analysis was run separately and at a later time to the training set. The signature predicted disease recurrence with an HR of 2.53 (P<0.001) in the high-risk group (FIG. 4 and Table 4). The signature also predicted cancer-related death with an HR of 2.21 (P<0.0084) in the high-risk group (FIG. 5).

The fact that the signature described herein was developed from FFPE derived tumor material facilitates a large scale validation strategy based on retrospective analysis of existing FFPE tumor banks The hazard ratio is an expression of the hazard or chance of events occurring in the stage II colon cancer patients identified by the classifier as high risk as a ratio of the hazard of the events occurring in the patients identified by the classifier as low risk. There was a significantly lower probability of recurrence for the group predicted to have good prognosis compared to those predicted to have poor prognosis, within 5-years post surgery. The negative predictive value is the proportion of patients with negative test results who are correctly diagnosed (predicted negative). In a prognostic setting, the NPV is dependent on the prevalence of disease recurrence. The positive predictive value is the proportion of patients with positive test results who are correctly diagnosed (predictive positive). In a prognostic setting, the PPV is dependent on the prevalence of disease recurrence. Based on a population prevalence of 20% poor prognosis samples, this would imply that patients with a predicted poor prognosis have a 33% probability of recurrence whereas patients with a predicted good prognosis have a 13% probability of recurrence within 5 years.

Assessment of Signature Independence from Known Prognostic Factors: For a prognostic assay to be useful, it must perform independently from known prognostic factors used in the clinic. Therefore the independence of the assay was assessed in both a univariate and multivariate analysis (Table 5).

TABLE 5

Comparison of Transcript Signature to Standard Pathologic Parameters in the Independent Validation Set

| | Univariate | | | Multivariate | | |
|---|---|---|---|---|---|---|
| | HR | CI | p | HR | CI | p |
| Tumor Stage (T4 vs T3) | 1.23 | 0.667-2.269 | 0.5067 | 1.617 | 0.84-3.110 | 0.1501 |
| Patient Age | 1.039 | 1.01-1.069 | 0.0086 | 1.046 | 1.014-1.078 | 0.0041 |
| Tumor Grade II | 0.815 | 0.456-1.456 | 0.4895 | 1.274 | 0.48-3.383 | 0.6265 |
| III | 1.326 | 0.654-2.689 | 0.434 | 2.161 | 0.636-7.339 | 0.2169 |
| Tumor Location (Proximal vs Distal) | 1.766 | 1.075-2.901 | 0.0248 | 2.158 | 1.224-3.804 | 0.0078 |
| Gender | 1.165 | 0.713-1.901 | 0.5426 | 0.971 | 0.549-1.720 | 0.9204 |
| Mucinous subtype | 0.825 | 0.418-1.627 | 0.5787 | 0.896 | 0.433-1.856 | 0.7682 |
| No. of Nodes Retrieved | 1.007 | 0.983-1.032 | 0.5678 | 1.014 | 0.988-1.041 | 0.2824 |
| Prognostic Signature | 2.526 | 1.536-4.154 | <0.001 | 2.551 | 1.471-4.423 | <0.001 |

Both the univariate and multivariate analyses have been performed using Cox proportional hazards regression with P values coming from a log-likelihood test. For tumor grade, grade 1 has been used as the reference point for calculating the HR. Patient age and number of nodes retrieved are analyzed as continuous factors. The interpretation of the HR of patient age is the increased risk for a change in 1 year of age, and correspondingly, the interpretation of the HR of number of nodes retrieved is the increased risk for an increase of one retrieved node. Abbreviation: HR, hazard ratio.

The prediction of prognosis was significant in both the univariate (P<0.001) and multivariate (P<0.001) analysis, demonstrating that the signature provided prognostic information in addition to conventional risk factors. Furthermore, the independence of the signature was assessed with the addition of lymphovascular invasion in the samples where this had been recorded (100 of 144 samples in the validation set). The signature performed independently in the univariate (P<0.001) and multivariate analysis (P<0.001).

Functional Analysis of the Genes in the Prognostic Signature: Next it was asked if the assay detected biologic processes known to be relevant to colon cancer recurrence. The 634 probe sets were analyzed using Ingenuity Pathway Analysis, and a list of statistically significant pathways were identified, the most significant of which was IGF-1 signaling.

Discussion

As disclosed herein a DNA microarray-based assay was developed that identifies patients at higher risk of recurrence after surgery for stage II colon cancer. Specifically, the signature identified a high-risk cohort with an HR of recurrence of 2.53 and an HR of cancer-related death of 2.21 in an independent validation set. Validation of a prognostic assay using a completely separate set is necessary to avoid overestimations of the performance of the signature from the training set. The HR of 2.53 for recurrence compares favorably with histologic factors currently used to make decisions in the clinic, which typically have an HR of approximately 1.5 or less. Moreover, the signature does not require individual interpretation and may offer a more standardized approach than conventional histopathologic factors. Importantly, the assay is performed on FFPE tissue and, therefore, is easily applied in current medical practice.

Although several DNA microarray-based prognostic tests in several cancer types have been published, only one has been introduced into clinical practice, and to date, none is used in colon cancer. This may be a result of two major factors. First, many of the signatures have been developed from fresh or frozen tissue. Second, inappropriate study methodology has resulted in a failure to validate the test in an independent data set.

Regarding the use of frozen tissue samples, although this tissue type provides excellent microarray data, a test generated from this tissue is unlikely to perform adequately in FFPE tissue. This can create difficulty in collecting enough samples to develop and independently validate a prognostic test. In addition, implementation of fresh tissue-based assays requires a change in clinical practice, because samples need to be collected at the time of surgery.

FFPE is the standard for tumor archiving, and numerous tumor banks already exist for assay development. Importantly, no change in sample collection and processing is required for the development and clinical implementation of FFPE-based assays.

The disclosed methods were developed to work with FFPE tissue but using a DNA microarray platform, thereby vastly increasing the number of detectable mRNA transcripts and biologic processes relative to quantitative polymerase chain reaction technology. As a result of using FFPE material with a microarray platform, several methodologic issues needed to be considered. Formalin fixation results in the degradation of mRNA transcripts through the cross linking of RNA to protein. Most of this degradation occurs immediately, but some transcripts continue to degrade with time. The DNA microarray platform used for the study has probe sets designed to the 3' end of mRNA transcripts to enhance the ability to detect degraded transcripts. In addition, a separate set of colon cancer samples was analyzed over time to ensure we did not incorporate probe sets that detected unstable or differentially stable mRNA transcripts as part of the signature.

The predictive value of the signature is above and beyond known prognostic clinical covariates. This performance can largely be attributed to the initial balancing of prognosis against biologic and technical factors that was performed as part of establishing a suitable training set. Biologic factors considered include known prognostic factors such as pT stage and grade, as well as other nonprognostic factors that may have affected gene expression including tumor location, patient age, and sex. Technical factors such as FFPE block age and the contributing center were also balanced between high- and low-risk samples in the training set. In addition, randomization of operators and reagent kits was performed to avoid confounding between technical factors and known clinical factors. This minimized the risk that the assay was dependent on the operator or relied on the use of samples from specific centers or the use of specific batches of reagents. Because the assay was developed to be independent from known prognostic factors, we believe that it may be possible to develop a multiparametric test that incorporates several factors to give an even more accurate prognostic indicator.

Functional analysis of the gene signature revealed that IGF-1 signaling, TGF-β signaling, and HMGB1 signaling were among the most significant pathways identified. All of these have been previously reported to confer a poor prognosis in colon cancer through promoting tumor growth, invasion, and metastasis and preventing apoptosis. In conclusion, disclosed herein is a validated and robust prognostic DNA microarray signature for stage II colon cancer from FFPE stored tumor tissue.

The disclosed signature can help physicians to make more informed clinical decisions regarding the risk of relapse and the potential to benefit from adjuvant chemotherapy. (Andre et al., *Annals of Surgical Oncology* 13:887-898, 2006; Diaz-Rubio et al., *Clin. Transl. Oncol.* 7: 3-11, 2005; Monga et al., *Ann. Surg. Oncol.* 13: 1021-1134, 2006; Sobrero, *Lancet Oncol.* 7: 515-516, 2006). Furthermore, many patients want to know their likelihood of cure and the risks/benefits of treatment. (Gill et al., *J. Clin. Oncol.* 22: 1797-1806, 2004; Kinney et al., *Cancer* 91: 57-65, 2001; Carney et al, *Ann. R. Coll. Surg. Engl.* 88: 447-449, 2006; Salkeld, *Health Expect* 7: 104-1014, 2004). Being able to predict the patient's prognosis provides the physician and the patient with a better assessment of the risks/benefits and the choice of therapy. The ability to offer individualized patient care will hopefully result in improved survival and quality of life for these patients.

In the past, many studies have implicated sample size as the primary reason for lack of convincing statistical evidence and point to larger trials being required to prove the benefit of adjuvant treatment. Using validated prognostic markers, such as the gene signature generated in this study, stage II patients can be stratified into high and low risk sub-populations. This approach may assist in improved clinical trial design by focusing on those patients at high risk of recurrence and therefore more likely to derive a benefit from adjuvant therapy. Thus, the Colorectal Cancer DSA™ may be a useful research tool for stratifying patients for inclusion in clinical trials, for decision-making regarding adjuvant and neo-adjuvant treatment, and for the identification of novel pathways or molecular targets for additional drug development The prognostic signature reported in Table 6 accurately predicted for relapse for stage II colon cancer and is evaluated on an independent FFPE validation set. The overall accuracy for prediction of recurrence was substantial for this heterogeneous disease. Based on a population prevalence of 20% poor prognosis samples, this would imply that patients with a predicted poor prognosis have a 33% probability of recurrence whereas patients with a predicted good prognosis have a 13% probability of recurrence within 5 years. One of the major advantages of the current approach is that it is based on expression profiling from FFPE tissue which is the preferred method of storage for the majority of available tissue banks (Abramovitz *Proteome Sci.* 4:5, 2006). RNA extracted from FFPE tissue samples tends to have a shorter median length due to degradation and formalin-induced modification, which makes it difficult for generic arrays to detect. When defining the colon cancer transcriptome, a 3'-based sequencing approach was employed facilitating design of probesets to the 3' extremity of each transcript. This approach ensures much higher detection rate and is thus optimally designed to detect RNA transcripts from both fresh frozen and FFPE tissue samples. The results from the current study showed that the Almac Diagnostics Colorectal Cancer DSA™ research tool is capable of producing biologically meaningful and reproducible data from FFPE derived tissue.

Example 2

Prognosis of Cancer

This example describes particular methods that can be used to prognose a subject diagnosed with colon cancer.

However, one skilled in the art will appreciate that methods that deviate from these specific methods can also be used to successfully provide the prognosis of a subject with colon cancer.

A tumor sample and adjacent non-tumor sample is obtained from the subject. Approximately 1-100 µg of tissue is obtained for each sample type, for example using a fine needle aspirate. RNA and/or protein is isolated from the tumor and non-tumor tissues using routine methods (for example using a commercial kit).

In one example, the prognosis of a colon cancer tumor is determined by detecting expression levels of 2 or more of the transcript in Tables 1, 2, and/or 6 in a tumor sample obtained from a subject by microarray analysis or real-time quantitative PCR. For example, the disclosed gene signature can be utilized. The relative expression level of in the tumor sample is compared to the control (e.g., RNA isolated from adjacent non-tumor tissue from the subject). In other cases, the control is a reference value, such as the relative amount of such molecules present in non-tumor samples obtained from a group of healthy subjects or cancer subjects.

In view of the many possible embodiments to which the principles of the disclosure may be applied, it should be recognized that the illustrated embodiments.

We claim:

1. A method of treating a stage II adenocarcinoma colon cancer patient comprising:
   (a) detecting an expression level of a colon cancer signature comprising sense sequences of ARSD, CXCL9, PCLO, SLC2A3, FCGBP, SLC2A14///SLC2A3, and BCL9L transcripts and antisense sequences of MUC3A, OLFM4 and RNF39 transcripts in a colon cancer sample from the patient;
   (b) detecting differential expression of the colon cancer signature between the expression of the colon cancer signature in (a) and the expression of the colon cancer signature in colon cancer samples from colon cancer patients known to not be at risk of recurrence of metastatic cancer within 5 years following colon cancer surgical resection;
   wherein the detected differential expression of the colon cancer signature, or a decision score derived therefrom, indicates the stage II adenocarcinoma colon cancer patient is not at risk of recurrence of metastatic cancer within 5 years following colon cancer surgical resection; and
   (c) treating based on the detected differential expression in (b) the patient by surgical resection of the colon cancer.

2. A method of treating a stage II adenocarcinoma colon cancer patient, comprising;
   (a) detecting an expression level of a colon cancer signature comprising sense sequences of ARSD, CXCL9, PCLO, SLC2A3, FCGBP, SLC2A14///SLC2A3, and BCL9L transcripts and antisense sequences of MUC3A, OLFM4 and RNF39 transcripts in a colon cancer sample from the patient;
   (b) detecting differential expression of the colon cancer signature between the expression of the colon cancer signature in (a) and the expression of the colon cancer signature in colon cancer samples from colon cancer patients known to be at risk of recurrence of metastatic cancer within 5 years following colon cancer surgical resection;
   wherein the detected differential expression level, or a decision score derived therefrom, indicates the stage II adenocarcinoma colon cancer patient is at risk of recurrence of metastatic cancer within 5 years following colon cancer surgical resection; and
   (c) treating based on the detected differential expression in (b) the patient by surgical resection of the colon cancer followed by adjuvant therapy comprising chemotherapy, radiation therapy, or a combination thereof.

3. The method of any one of claims 1 or 2, wherein the colon cancer sample obtained from the patient comprises RNA, or comprises cDNA transcribed from RNA extracted from the colon cancer sample obtained from the patient; and
   optionally wherein the colon cancer sample is a biopsy sample;
   optionally wherein the colon cancer sample is a fixed and/or paraffin embedded sample.

4. The method of any one of claims 1 or 2, wherein the expression level of the colon cancer signature is normalized against a control gene or control genes; and/or
   wherein the expression level of the colon cancer signature is determined with PCR and/or microarray-based methods.

5. The method of any one of claims 1 or 2, further comprising detecting the expression levels for:

(a) MUM1 and SIGMAR1 transcripts,
(b) MUM1, SIGMAR1, SULT1C2 and PPFIBP1 transcripts, and/or
(c) the transcripts listed in Table 2.

6. The method of any one of claims 1 or 2, wherein detecting the expression level of the colon cancer signature comprises using a set of nucleic acid probes, wherein each probe comprises a nucleic acid molecule between 20 and 40 nucleotides in length and capable of specifically hybridizing to one of the nucleic acid sequences of SEQ ID NOS: 3, 14, 23, 24, 51, 55, 61, 112, 175 and 272.

7. The method according to claim 6, wherein the nucleic acid probes are labeled, optionally wherein the probe is radiolabeled, fluorescently-labeled, biotin-labeled, enzymatically labeled, or chemically-labeled.

8. The method of claim 6, wherein the set of nucleic acid probes comprises:
(a) at least one probe complementary to each of the transcripts having the nucleic acid sequences of SEQ ID NOS: 1-636, or
(b) at least one probe complementary to each transcript in a subset of the transcripts having the nucleic acid sequences of SEQ ID NOS: 1-636, wherein the subset of the transcripts comprises at least 5%, 10%, 25%, 50%, 75% or 95% of the transcripts having the nucleic acid sequences of SEQ ID NOS: 1-636.

9. The method of claim 6, wherein the set of probes is comprised in a device comprising a nucleic acid array for detecting the expression level of the colon cancer signature.

10. The method of any one of claim 1 or 2, wherein detecting the expression level of the colon cancer signature comprises using a pair of primers for the amplification, comprising:
a forward primer 15 to 40 nucleotides in length comprising a nucleic acid sequence that specifically hybridizes to one of the nucleic acid sequences of SEQ ID NOS: 3, 14, 23, 24, 51, 55, 61, 112, 175 and 272; and
a reverse primer 15 to 40 nucleotides in length comprising a nucleic acid sequence that specifically hybridizes to one of the nucleic acid sequences of SEQ ID NOS: 3, 14, 23, 24, 51, 55, 61, 112, 175 and 272,
wherein the set of primers is capable of directing the amplification of the transcripts of the colon cancer signature.

11. The method of claim 2, wherein the patient is treated with chemotherapy.

12. The method of claim 2, wherein the patient is treated with radiation therapy.

13. The method of claim 2, wherein the patient is treated with a combination of surgical resection, chemotherapy, and radiation therapy.

14. The method of any one of claims 1, 2 and 11-13, wherein detecting an expression level of a colon cancer signature a colon cancer sample from the patient comprises detecting the expression levels of each of the transcripts having the nucleic acid sequences of SEQ ID NOS; 1-634.

* * * * *

SEQUENCE LISTING

```
<160> NUMBER OF SEQ ID NOS: 636

<210> SEQ ID NO 1
<211> LENGTH: 76
<212> TYPE: DNA
<213> ORGANISM: Homo sapiens

<400> SEQUENCE: 1
ctgttttttc ccgtgtagat ttctgatact tcaatcccct actcccccaa aacagttgaa      60
gcccagccca ctctta                                                     76

<210> SEQ ID NO 2
<211> LENGTH: 87
<212> TYPE: DNA
<213> ORGANISM: Homo sapiens

<400> SEQUENCE: 2
ccggtatacc aagggagcca gttgtgttca gacacacaca tcacagcttg actcactaac      60
tgaggccttt ccatagctcc acagctt                                         87

<210> SEQ ID NO 3
<211> LENGTH: 75
<212> TYPE: DNA
<213> ORGANISM: Homo sapiens

<400> SEQUENCE: 3
ttggccagtg tgttttctaa gtcaattcta gtgtgtttca tcctcacctc ttccctctgt      60
ggctttgatg atgga                                                      75

<210> SEQ ID NO 4
<211> LENGTH: 220
<212> TYPE: DNA
<213> ORGANISM: Homo sapiens

<400> SEQUENCE: 4
aggctggtct taactgactg cttttttatta ttaccatgca ctggcaattc caaacaatgt    60
cagtgttaaa atgcttctcc ctgaaaaaga gaaaaaaaaa aggaaaaaaa gaaaagaaaa    120
gtgaaaagaa aaactcttat tggcctaagt tctaaataat agctaggtta ccactgagtt    180
ttaactatat gtatatgagc ttcaaataag cacctttta                          220

<210> SEQ ID NO 5
<211> LENGTH: 138
<212> TYPE: DNA
<213> ORGANISM: Homo sapiens

<400> SEQUENCE: 5
aaatgctgca gcaggtatgt gcagaggcca gaaccaagat gggatttccc tgctgaacta    60
```

```
tgtgagatgc tgcatttcta tgttgtgttt gctctgatgc agcagtaagt ttttttgattc    120 acttagacca gcacatta                                                  138

<210> SEQ ID NO 6
<211> LENGTH: 239
<212> TYPE: DNA
<213> ORGANISM: Homo sapiens

<400> SEQUENCE: 6
gaaggtcagg actttgtgaa catataaaac tgcagatggc tattagatat ccaagtagag    60
atgctgaaga gatgaatgta tatagaagtc tgaatttggg agagagatct ggataggaga   120
tacttacctg gtgttttaaca gcttacagat tgtgtaaagt catgaaacgg ataagaacct  180
taaaagagag aaaagggaat agaggttacc aaatgaattg cagtttccaa attgcagag    239

<210> SEQ ID NO 7
<211> LENGTH: 253
<212> TYPE: DNA
<213> ORGANISM: Homo sapiens

<400> SEQUENCE: 7
ctctgatttg cacacctgaa aatcgcggaa ttgagtttcg atagattgat ttttaaaact    60
tttttggagt aggggtata ggggaatcat ttaatttaaa tcattaagat tcccctgctc    120
aaacccagat tcctgtgtac agatgctatt tagagggaat cagaaaatg ccaagccttt   180 tctcttttgaa tgtgctattt ttataactga acttgtacat atgtataaag agagacacat  240 cttccttta cta                                                      253

<210> SEQ ID NO 8
<211> LENGTH: 42
<212> TYPE: DNA
<213> ORGANISM: Homo sapiens

<400> SEQUENCE: 8
gcttccttgc ctgatgacaa taaagcttgt tgactcagct aa                       42

<210> SEQ ID NO 9
<211> LENGTH: 289
<212> TYPE: DNA
<213> ORGANISM: Homo sapiens
<220> FEATURE:
<221> NAME/KEY: misc_feature
<222> LOCATION: (258)..(258)
<223> OTHER INFORMATION: n is a, c, g, or t

<400> SEQUENCE: 9
gggtcagaaa gatgccttca gttttggtca gtgtctaaaa gttaagtctg tttaggccaa    60
gcatggtggc tcacgcctga atcccagca cttggggagg ccgaggcaag tggatcacaa    120
ggtcaggaga tgagaccatc ttagccaaca tggtgaaacc ccgtctctac taaaatacaa   180
aaaaattagc caggcgtggg ggtgcgtgcc tataatccca gctacttggg aggctgaggc   240
aggggaatcg cttgaacncg ggaggcagag gtcacgccat ggactccag               289

<210> SEQ ID NO 10
<211> LENGTH: 293
<212> TYPE: DNA
<213> ORGANISM: Homo sapiens

<400> SEQUENCE: 10
```

```
ctttctaaaa gttgcatgtt atgtgagtca gcttatagga agtaccaaga acagtcaaac    60
ccatggagac agaaagtaga atagtggttg ccaatgtctc agggaggttg aaataggaga   120
tgaccactaa ttgatagaac gtttcttttgt gtcgtgatga aaactttcta aatttcagta  180
atggtgatgg ttgtaacttt gcgaatatac taaacatcat tgattttaa tcattttaag    240 tgcatgaaat gtatgctttg tacatgacac ttcaataaag ctatccagaa aaa          293
```

<210> SEQ ID NO 11
<211> LENGTH: 64
<212> TYPE: DNA
<213> ORGANISM: Homo sapiens

<400> SEQUENCE: 11

```
agcaagctta ctaaaaactg cacttcacac ttagcttaat gtttgaggga attaacttca    60
taaa                                                                 64
```

<210> SEQ ID NO 12
<211> LENGTH: 113
<212> TYPE: DNA
<213> ORGANISM: Homo sapiens

<400> SEQUENCE: 12

```
accatggcaa cgaggtagtc tgttctattt ttggagtatg aaagtagtgc cttcttaaat    60
ctaataataa atgagagttc cagaaaacca gtgcttcaaa caaatttgat tta          113
```

<210> SEQ ID NO 13
<211> LENGTH: 227
<212> TYPE: DNA
<213> ORGANISM: Homo sapiens

<400> SEQUENCE: 13

```
tgggcttaaa actcagctct gccacttaca ttcctcattt ctttctatcc tgggtctgcc    60
aaaatgtaag aaaagttttc acattttttt accagttttt ctcacccatg accaccctgt   120
ctcaaaatga ttatgcaaca gcccagagtc ccccattcca aaattctttg caaagagcaa   180
gatttccctc gctatttctg aattcatcca cacctctatt tctctct                 227
```

<210> SEQ ID NO 14
<211> LENGTH: 170
<212> TYPE: DNA
<213> ORGANISM: Homo sapiens

<400> SEQUENCE: 14

```
actccccaag ggttctcaat tctcttttcc caggctcgtc catgactgtt tcttgtcctc    60
agagcccttg ccttccttgc tgcctcctca gtcccattct ctgtctcttt cagcggcccc   120
atccttatct accttcccca gtgcatccca gaaaaacatc tgtcccttcc               170
```

<210> SEQ ID NO 15
<211> LENGTH: 78
<212> TYPE: DNA
<213> ORGANISM: Homo sapiens

<400> SEQUENCE: 15

```
cctgagcttg ggtgactcat tgtgtgctaa gaaaaaaaat caaatttcag aacatgcgag    60
acctcgaccc aggtaaat                                                  78
```

<210> SEQ ID NO 16
<211> LENGTH: 211

<212> TYPE: DNA
<213> ORGANISM: Homo sapiens

<400> SEQUENCE: 16

```
gactggagaa agaagaggtg gcataggatt gactaagatg aaggaagggg gccaggcgtg      60
gtggctcacc cctgtaaccc caacactttg ggaggctgag gcgggcagat cacctgaggt     120
caggaattca agaccagcct ggccaacatg gtgaaacccc atctctacta aaagtacaaa     180
aattagccag gcggtagtgg tgtgtgccta t                                    211
```

<210> SEQ ID NO 17
<211> LENGTH: 275
<212> TYPE: DNA
<213> ORGANISM: Homo sapiens

<400> SEQUENCE: 17

```
atcctcaaca gctaatcact ctttaactcc tgaattctgg ctcctgtccc cactacttta      60
atgaaattat actctaaact tcgccagtct tctcccaacc aactgccaaa tctcatgaca     120
tggttttaag cctctctctc ttaacttctc agctttccac aagtagacaa gtcttcttct     180
ggaaactctc cacgcatgtc ctctatactc tcactactgt ctccctcttc ttccttctcc     240
acctgccccc atctcctggc atttctactc tcttt                                275
```

<210> SEQ ID NO 18
<211> LENGTH: 274
<212> TYPE: DNA
<213> ORGANISM: Homo sapiens

<400> SEQUENCE: 18

```
ttctcccagt tcatcctacc tggaatctga cccactaccc acctgcaaca agtcttccag      60
aggcaggaag ataggccctg ccctggcagg atgggttggg gtcacttgac ccctgctccc     120
cctttgaggg gaaaggggtg gaactaagat gggtttataa ctggaacctc caatgaccag     180
atgtatatag agatttacaa agattttat attaatttaa taaaacaaat tcttaaatag     240
aacaaaataa acacctaatg agccacttat atat                                 274
```

<210> SEQ ID NO 19
<211> LENGTH: 83
<212> TYPE: DNA
<213> ORGANISM: Homo sapiens

<400> SEQUENCE: 19

```
atggtggata aatgggactt aggactaaaa ctcatgcctt ggtgtgtttt tgcagtgatg      60
ttttgttctg gggtgcatca caa                                              83
```

<210> SEQ ID NO 20
<211> LENGTH: 95
<212> TYPE: DNA
<213> ORGANISM: Homo sapiens

<400> SEQUENCE: 20

```
gcgtagctaa gtgaaaaggt catagctgag attcctggtt cgggtgttac gcacacgtac      60
ttaaatgaaa gcatgtggca tgttcatcgt ataac                                 95
```

<210> SEQ ID NO 21
<211> LENGTH: 223
<212> TYPE: DNA
<213> ORGANISM: Homo sapiens

<400> SEQUENCE: 21

```
actctcaaga acagtagagg gaaaagaaaa aagaaaaaga acagtggagg ttgtggtaaa    60
ggacatttga gaagagattc atgaaacagg ccaaatggta ggtttgctag ttcgcagggg   120
gagaaccaat gaattaattt agaaagagct tctctgggat tagaatgaaa ataaatcact   180
ggctgggtgc acacctgtaa ttctagctat tcaggcagga gga                    223
```

<210> SEQ ID NO 22
<211> LENGTH: 138
<212> TYPE: DNA
<213> ORGANISM: Homo sapiens

<400> SEQUENCE: 22

```
ttgtctcagc atcagtatat cccatgcaat atttgaggtg tgctcatact aaaattattt    60
gtgtatctga aattcaaatt aaactgggtg tcttttttctt tcatctggc aaccctacta   120
agatcataaa cccttgga                                                138
```

<210> SEQ ID NO 23
<211> LENGTH: 226
<212> TYPE: DNA
<213> ORGANISM: Homo sapiens

<400> SEQUENCE: 23

```
acttgggagg aaatacacag tagttagaaa aagcctccta ggtgattttg atgaatccca    60
gtctcaaatt tcttcatttg gaaatgataa tgtaggccac acgtattact ggagaaaaat   120
gtgctcccga gactttccag agcagcagag ctgggactag gcaggtgagg cagctacgtg   180
caagtgtagc cctgagaatg agcacctctt taaagaatgt accttg                 226
```

<210> SEQ ID NO 24
<211> LENGTH: 66
<212> TYPE: DNA
<213> ORGANISM: Homo sapiens

<400> SEQUENCE: 24

```
gagaggttgt ctgtggccag aatttaaacc tatactcact ttcccaaatt gaatcactgc    60
tcacac                                                              66
```

<210> SEQ ID NO 25
<211> LENGTH: 107
<212> TYPE: DNA
<213> ORGANISM: Homo sapiens

<400> SEQUENCE: 25

```
ttgcattagg tattagtcta gggataaagt atacaggcgg atgtgcgttg gttatataca    60
aatatgtcat tttatgtaag ggacttgagt atacttggat ttttggt                107
```

<210> SEQ ID NO 26
<211> LENGTH: 271
<212> TYPE: DNA
<213> ORGANISM: Homo sapiens

<400> SEQUENCE: 26

```
gaaaaagcgg tacgatgcct tcctgacctc accggcctcc ccaagggtgc cggcactctg    60
ggtggactca cggctgctgg gccccacgtc aaaggtcaag tgagacgtag gtcaagtcct   120
acgtcggggc ccagacatcc tggggtcctg gtctgtcaga caggctgccc tagagcccca   180
cccagtccgg ggggactggg agcagttcca agaccacccc acccctttt gtaaatcttg    240
```
ttcattgtaa atcaaataca gcgtcttttt c                                          271

<210> SEQ ID NO 27
<211> LENGTH: 44
<212> TYPE: DNA
<213> ORGANISM: Homo sapiens

<400> SEQUENCE: 27
tgcctctggt ccttggactc ttgtccatgg ttcctgagct gtgg                             44

<210> SEQ ID NO 28
<211> LENGTH: 244
<212> TYPE: DNA
<213> ORGANISM: Homo sapiens
<220> FEATURE:
<221> NAME/KEY: misc_feature
<222> LOCATION: (200)..(208)
<223> OTHER INFORMATION: n is a, c, g, or t

<400> SEQUENCE: 28
gcccagcctt gaagtcatgt tctaaattgt atttgaattt gtgcctctct gtttttcccc            60
aaaccaaagc cctcaaattg tagtctctgt cggcttctgc agaattctgg aaaatgccag           120
ttttcctccc ccgcccttgt tttccataaa acatatttat atattgtgat gaggagtact           180
ttctgaagag tacttcgtan nnnnnnnnaa ttgccttgtt tgccttcaac ttccttgatt           240
ttca                                                                       244

<210> SEQ ID NO 29
<211> LENGTH: 189
<212> TYPE: DNA
<213> ORGANISM: Homo sapiens

<400> SEQUENCE: 29
aaaagtctag attggtcttg atattgagat aataaaaagt aagtagcatt aagaaaggta            60
acaatcttca ttctacagat gaactcattg aaacaattta ggggaatgag gggcaaaagg           120
ggagaaatac tgctaaagaa catgagcata aaaacgcgtg cgtttcagtg tttaagaagg           180
cttgataaa                                                                  189

<210> SEQ ID NO 30
<211> LENGTH: 241
<212> TYPE: DNA
<213> ORGANISM: Homo sapiens

<400> SEQUENCE: 30
ataattatgg gctcacttcc tactggagat gttgaaagtc taaatcggtt tgaccatttt            60
gattgatggc acaatctggt ttagaaaact ttgtttagat caatgacata accctgctgc           120
ctctgcctgc ccttcccctc ccttctccca tccccttttc cctatctggt gtctgtactt           180
tgatgaaggt gagctataat attggtggtt aatataatcc agaaggctta gttctgtgtg           240
t                                                                          241

<210> SEQ ID NO 31
<211> LENGTH: 286
<212> TYPE: DNA
<213> ORGANISM: Homo sapiens

<400> SEQUENCE: 31
gaggaagggc tgaaatgctt tctattggat actatctggg catattactt cctgtggttc            60

```
actgtctggg tgacaggatt catagaagcc caaactttag caccacgcag catacccttg    120
taacaaagcc gcacacgtac gccctcaagc taaaacaaaa gtggaccggg agccgaggtg    180
ggggatcatg agggtcagga gtttgagacc agcctggcag ataacggtga aaccccgtct    240
ctactaaaat accaaaaaag gttagccgac atggtgcagg tccttt                   286
```

<210> SEQ ID NO 32
<211> LENGTH: 75
<212> TYPE: DNA
<213> ORGANISM: Homo sapiens

<400> SEQUENCE: 32

```
ctttctctct tacctgccta tgcttgaagc ccccgcccct cttcaagttg tcctgccttt    60
caagaccaat gtaca                                                      75
```

<210> SEQ ID NO 33
<211> LENGTH: 278
<212> TYPE: DNA
<213> ORGANISM: Homo sapiens

<400> SEQUENCE: 33

```
gaaaaagtag tccaccacga tccacctttg ctctttgacc tctcaagaga cccttctgag    60
acccacatcc tcacaccagc ctcagagccc gtgttctatc aggtgatgga acgagtccag    120
caggcggtgt gggaacacca gcggacactc agcccagttc ctctgcagct ggacaggctg    180
ggcaatatct ggagaccgtg gctgcagccc tgctgtggcc cgttcccccct gctggtgc     240 cttagggaag atgacccaca ataaatgtct gcagtgaa                            278
```

<210> SEQ ID NO 34
<211> LENGTH: 194
<212> TYPE: DNA
<213> ORGANISM: Homo sapiens

<400> SEQUENCE: 34

```
tcttctgtga agacaggacc tatgcaacgc acagacactt ttggagaccg taaaacaaca    60
gcgccccctc ccttccagtc ctgagccggg aaccatctcc caggaccttg ccctgctcac    120
cctatgtggt cccacctatc ctcctgggcc ttttttcaagt gctttggctg tgactttcat   180
actctgctct tagt                                                       194
```

<210> SEQ ID NO 35
<211> LENGTH: 158
<212> TYPE: DNA
<213> ORGANISM: Homo sapiens

<400> SEQUENCE: 35

```
gtcatgagac gggatttggt caccaaggaa gtgagtatat atagagaaga ggtccaaggg    60 ctgggcccctt gaatatttaa tataatttag aagtctgtaa cgatgaagta gttagcagaa    120
gaaacttgag gagagaccag tgaggtgggt agcaaaac                            158
```

<210> SEQ ID NO 36
<211> LENGTH: 179
<212> TYPE: DNA
<213> ORGANISM: Homo sapiens
<220> FEATURE:
<221> NAME/KEY: misc_feature
<222> LOCATION: (61)..(61)
<223> OTHER INFORMATION: n is a, c, g, or t

<400> SEQUENCE: 36
ccactggaaa ggagtgttgt aagactaggt tttggctaag aacttctcac ctcagcccta      60
nagagggagc ctgtgggttc tcagagagat atcacaattt gagtcccaaa gaagaggcca     120
gatacccacc caccttcccc caaatcttaa gcacctgcgc cagtacagtc aagaagagg     179

<210> SEQ ID NO 37
<211> LENGTH: 222
<212> TYPE: DNA
<213> ORGANISM: Homo sapiens

<400> SEQUENCE: 37
tttgcccttc ctgctaactc tattaccccc acgattcttc accgatgatg accacccaca      60
ctcaacctcc ctctgacctc ataacctaat ggccttggac accagattct tacccattct     120
gtccatgaat catcttcccc acacacaatc attcatatct actcacctaa cagcaacact     180
ggggagagcc tggagcatcc ggacttgccc tatgggagag gg                        222

<210> SEQ ID NO 38
<211> LENGTH: 239
<212> TYPE: DNA
<213> ORGANISM: Homo sapiens

<400> SEQUENCE: 38
ggaagagctc ggtgagcatg atcatggctc aggttctcca tccacatgcc taagacaggg      60
gtgagtgtga agatgggaac tgactcagaa ttaactgtgt gatcatgggc aagttgccaa     120
gttaaccctc atatctaaat tcaggtatcc ttgaacaaac atagacagat actgatgatc     180
cgccatgttt actataacca taaactcttt gtgaattaaa aatggcctct caacctgga     239

<210> SEQ ID NO 39
<211> LENGTH: 35
<212> TYPE: DNA
<213> ORGANISM: Homo sapiens

<400> SEQUENCE: 39
cagggccata cagggtgtgt acatcacaga taggg                                 35

<210> SEQ ID NO 40
<211> LENGTH: 270
<212> TYPE: DNA
<213> ORGANISM: Homo sapiens

<400> SEQUENCE: 40
gtactctcaa gaacagtaga gggaaaagaa aaagaaaaa gaacagtgga ggttgtggta      60
aaggacattt gagaagagat tcatgaaaca ggccaaatgg taggtttgct agttcgcagg     120
gggagaacca atgaattaat ttagaaagag cttctctggg attagaatga aaataaatca     180
ctggctgggt gcacacctgt aattctagct attcaggcag gaggatggct cgagcctagg     240
agttggaggt cagcataggc aacatatggga                                    270

<210> SEQ ID NO 41
<211> LENGTH: 125
<212> TYPE: DNA
<213> ORGANISM: Homo sapiens

<400> SEQUENCE: 41
caagaccggc ccttggctgt tgttacagag atgttgggca gagctatgca ggtgtttcat      60
tgtgaactct agctttgatc atggtaaaaa gttaacccttt tctatttttt aatggatgtt    120
atacc                                                                    125

<210> SEQ ID NO 42
<211> LENGTH: 79
<212> TYPE: DNA
<213> ORGANISM: Homo sapiens

<400> SEQUENCE: 42
gagagacaaa gcaagtggtg atgtcaagga gaagaaaggg aaggggtctc ttggctccca    60
aggggccaag gacgagcca                                                     79

<210> SEQ ID NO 43
<211> LENGTH: 241
<212> TYPE: DNA
<213> ORGANISM: Homo sapiens

<400> SEQUENCE: 43
agcggcggct caaggatcag gaccaggacg aggatgagga ggagaaggag aaacgtggcc    60
gcaggaaggc gagcgagctg cgcatccacg acctggagga cgacctggag atgtcgtccg   120
atgccagtga tgccagtggt gaggaggggg gcagagtctc cgaggccaag aagaacgcgc   180
cgctggctca tggcgggcgg agaaagaaga agaagaaggg ttcagacgac gaggccttcg   240
a                                                                        241

<210> SEQ ID NO 44
<211> LENGTH: 201
<212> TYPE: DNA
<213> ORGANISM: Homo sapiens

<400> SEQUENCE: 44
gggagtccag gattaaggtt ttgcagggtt tggtttctag tgagggcttt cttcctggct    60
tgcagatggc catcttctct ccataggcta acatggcctc tactttgtgt gtgggagagt   120
cagagataga gcaagccctc ttgtgtctct tcatataagc ctactaatcc ccatcagacc   180
aggtccctta tgatctttaaa c                                                 201

<210> SEQ ID NO 45
<211> LENGTH: 126
<212> TYPE: DNA
<213> ORGANISM: Homo sapiens

<400> SEQUENCE: 45
agcaaggtgt ctcagaaccc aattcttacc agtttgttgc aaatcacagg gaacggggggg    60 tctaccattg gctcgagtcc aaccctcct catcacaacg cgccacctgt ctcttcgatg   120
gccggc                                                                   126

<210> SEQ ID NO 46
<211> LENGTH: 95
<212> TYPE: DNA
<213> ORGANISM: Homo sapiens

<400> SEQUENCE: 46
caggtgttgg gacagtccca ccctccctgc tatttatatc cctctgccta tttattgaat    60
cgaacttcgc ctctgtctcc atctgtaaat atgtg                                  95

<210> SEQ ID NO 47
<211> LENGTH: 145
<212> TYPE: DNA
<213> ORGANISM: Homo sapiens

<400> SEQUENCE: 47

```
agagtggcag tttgcatggc gaaccccca cttcctcttt gctgcccctt cactttcttg      60
ctgccccttt cccagtctct cttcacaccc actcctggtc tgtcctgatc ccctcttctg    120
tatcaggttt attggttgta catat                                           145
```

<210> SEQ ID NO 48
<211> LENGTH: 245
<212> TYPE: DNA
<213> ORGANISM: Homo sapiens

<400> SEQUENCE: 48

```
gaatattctg ctggcgaac tcctacacat ccttcaaaac ccacctggta ctgttccagc     60
atcttccctg gatggctgga ggaactccag aaaatatcca tcttcttttt gtggctgcta   120
atggcagaag tgcctgtgct agagttccaa ctgtggatgc atccgtcccg tttgagtcaa   180
agtcttactt ccctgctctc acctactcac agacggggat gctaagccgt gcacctgctg   240
tgggt                                                                245
```

<210> SEQ ID NO 49
<211> LENGTH: 193
<212> TYPE: DNA
<213> ORGANISM: Homo sapiens

<400> SEQUENCE: 49

```
taagacctac tatctgatag ccccacatgg tgactatagt aaataataac ttaattgcac    60
atttaaaaat aacttaaaca gtgtaattgg gttgtttgta attgaaagga taatgcttg    120
ggggagtgga taccccattc tccatgatgt gcttattgca tactgcatgc ctggaccaaa  180
atatgtaccc cat                                                       193
```

<210> SEQ ID NO 50
<211> LENGTH: 36
<212> TYPE: DNA
<213> ORGANISM: Homo sapiens

<400> SEQUENCE: 50

```
atttactacc ttattatgaa gtgtgccctc caaaat                               36
```

<210> SEQ ID NO 51
<211> LENGTH: 43
<212> TYPE: DNA
<213> ORGANISM: Homo sapiens

<400> SEQUENCE: 51

```
cttttctggg tcacagaggc caaatgtgag agcattgaat aaa                       43
```

<210> SEQ ID NO 52
<211> LENGTH: 213
<212> TYPE: DNA
<213> ORGANISM: Homo sapiens

<400> SEQUENCE: 52

```
gacctttttca tcaatagatc gcccttaaag acccattgta aggtcataaa aaacctcggc   60
caactgcaca aagatggtgc ctcactgcaa caagaaacct taaggtgtct taccgacgaa   120
ataaaaaaca taaatgattg ttctccaagg cctgagggca agactcatga tgggcaagtc  180
aaccccaatc tggaacaatg tccctcctct tag                                 213
```

<210> SEQ ID NO 53
<211> LENGTH: 122
<212> TYPE: DNA
<213> ORGANISM: Homo sapiens

<400> SEQUENCE: 53

```
gattatgttt tccatggaag dacaagtctg actgttcata ggctgatttt ctttaagagg      60
attattctgt tttacaattt caattctaga tcacatttta tatatgctgc atgccaaaaa     120
aa                                                                    122
```

<210> SEQ ID NO 54
<211> LENGTH: 96
<212> TYPE: DNA
<213> ORGANISM: Homo sapiens

<400> SEQUENCE: 54

```
acctgtccct gtcctacctt aactgatcaa tcgaccttgt gacagtcttc ttctggacaa      60
tgggtcttat catctcccca ccatgtacct tgtgac                                96
```

<210> SEQ ID NO 55
<211> LENGTH: 203
<212> TYPE: DNA
<213> ORGANISM: Homo sapiens

<400> SEQUENCE: 55

```
tagacagtat gagtcaatgt gcagtgtagc ccacacttga gaggatgaat gtatgtgcac      60
tgtcactttg ctctgggtgg aagtacgtta ttgttgactt attttctctg tgtttgttcc     120
tacagcccct ttttcatatg ttgctcagtc tccctttccc ttcttggtgc ttacacatct     180
cagacccttt agccaaaccc ttg                                             203
```

<210> SEQ ID NO 56
<211> LENGTH: 223
<212> TYPE: DNA
<213> ORGANISM: Homo sapiens

<400> SEQUENCE: 56

```
aagacctact atctgatagc cccacatggt gactatagta aataataact taattgcaca      60
tttaaaaata acttaaacag tgtaattggg ttgtttgtaa ttgaaaggat aaatgcttgg     120
gggagtggat accccattct ccatgatgtg cttattgcat actgcatgcc tggaccaaaa     180
tatgtacccc ataaatatat acacctacta tgtgcccccg aaa                       223
```

<210> SEQ ID NO 57
<211> LENGTH: 240
<212> TYPE: DNA
<213> ORGANISM: Homo sapiens

<400> SEQUENCE: 57

```
gaatttggtt ttgatctccc tattgagaga ctggtgtaca gtatttgtct atccctgcac      60
aaattattaa agcaagtttt gccattctgt tatccttcct catgaatatc ttgattactt     120
ttggccctaa ctcatcaagt tccacagaaa tcccaattgg aatcttagtt aaaattgtgt     180
tgtctatgga ccagttgaag aaaactgaca catttataat actgactctg ttccataaag     240
```

<210> SEQ ID NO 58
<211> LENGTH: 211
<212> TYPE: DNA
<213> ORGANISM: Homo sapiens

```
<220> FEATURE:
<221> NAME/KEY: misc_feature
<222> LOCATION: (123)..(131)
<223> OTHER INFORMATION: n is a, c, g, or t

<400> SEQUENCE: 58
ccagctttaa aggtgagatt gtagagatgc tgtcaaaggg ataaggaaat agcaagattt      60
ttaagtagtg tgtttgtgaa gactgatccc cattttacaa ctgcctgttc tttctccagt    120
ccnnnnnnnn ncagccagct tgactattag aaaagtatga aactggttgg ggtttattta    180
atatttttaa tatattgaga agcatggtct g                                    211

<210> SEQ ID NO 59
<211> LENGTH: 56
<212> TYPE: DNA
<213> ORGANISM: Homo sapiens

<400> SEQUENCE: 59
aaattcaata tggaacttga ggccaaaaaa acagaaggtt actctcaatg ccatcc          56

<210> SEQ ID NO 60
<211> LENGTH: 73
<212> TYPE: DNA
<213> ORGANISM: Homo sapiens

<400> SEQUENCE: 60
tatgtgccaa atctactaga cattggagaa acagtaggaa caacacatgg taccggcaca     60
tggatctttc agg                                                        73

<210> SEQ ID NO 61
<211> LENGTH: 266
<212> TYPE: DNA
<213> ORGANISM: Homo sapiens

<400> SEQUENCE: 61
agtctggttc taatcttctg agctgccttt ggaaggaagt tatgaggtag aagattctac     60
tgacttttag taaggtggac aatgagagaa aagaaaaagc aggtgcctca tctacagatc    120
cttctgggat ttatttgcca tgtacaattt aatgcataaa aaggcctctc tccataaaac    180
tcagcacttt acagatgtag aatatataag catgccaaat ttacttatct gtcacataca    240
aagcatcatt ccaggtgcta gtgagg                                         266

<210> SEQ ID NO 62
<211> LENGTH: 243
<212> TYPE: DNA
<213> ORGANISM: Homo sapiens
<220> FEATURE:
<221> NAME/KEY: misc_feature
<222> LOCATION: (128)..(218)
<223> OTHER INFORMATION: n is a, c, g, or t

<400> SEQUENCE: 62
gtaggacagt aggacagtac acagtagaac agtctaggac agttcagagt acacagtagg     60
acagttcaca gtaagacagt tcacggtacc cagtaggaca gtacacagta gaacagttca    120
cagtgcannn nnnnnnnnn nnnnnnnnnn nnnnnnnnn nnnnnnnnnn nnnnnnnnnn       180
nnnnnnnnnn nnnnnnnnnn nnnnnnnnnn nnnnnnnnat aggacagttc acagtaagac    240
agt                                                                  243

<210> SEQ ID NO 63
```

```
<211> LENGTH: 228
<212> TYPE: DNA
<213> ORGANISM: Homo sapiens

<400> SEQUENCE: 63
gaagctgcca gagggtaatt ggttttccca gaagttctta aatttgggag ctgtcttgcc      60
gcaagccatt gagactggaa attcttggag ttggtattgt ttttgtaaat tgactaatag     120
agagttaggg aagcctggag acttgttggg ggtgagttct ctaaatggtt ttaggcttgt     180
ctgtgtactt ttgcaacgag attgtctaat tctatgggcc tctgaggt                 228

<210> SEQ ID NO 64
<211> LENGTH: 158
<212> TYPE: DNA
<213> ORGANISM: Homo sapiens

<400> SEQUENCE: 64
ttcttgtgca ttattacatt tactcatacc tccaggacaa tgttgaagag aaatgatgta      60
ttagtccatt ttcacactgc tataaagaac tgcctgtatt agcctagcat ggtggcggac     120
acctgtaatc ccagctatgc aagaggctga gacgagaa                            158

<210> SEQ ID NO 65
<211> LENGTH: 183
<212> TYPE: DNA
<213> ORGANISM: Homo sapiens

<400> SEQUENCE: 65
aacccaacct taaagctgaa gacagtcccg gctaaatcct catactgaat tgagaacctg      60
tcttcccatt tggtgtgctt tcctccgatt gatcccaacc cttcacctat tttacgtata     120
cctgcccttt cctaattggt ttttacactg ctgtgcccac cttttgagtg gtgcctttgc     180
ata                                                                  183

<210> SEQ ID NO 66
<211> LENGTH: 37
<212> TYPE: DNA
<213> ORGANISM: Homo sapiens

<400> SEQUENCE: 66
tggtgaaatt ttgtaccccg gatgcagttg gcacttt                              37

<210> SEQ ID NO 67
<211> LENGTH: 138
<212> TYPE: DNA
<213> ORGANISM: Homo sapiens

<400> SEQUENCE: 67
aaaaatgttg gttgggctac acagttaact agtggagctg tgtgggttca gtttaatgat      60
gggtcccagt tggttgtgca ggcaggagtg tcttctatca gttataccte accaaatggt     120 caaacaacta ggtatgga                                                  138

<210> SEQ ID NO 68
<211> LENGTH: 39
<212> TYPE: DNA
<213> ORGANISM: Homo sapiens

<400> SEQUENCE: 68
ttggagataa ggcttttagg aagtcattaa agtgagatg                            39
```

```
<210> SEQ ID NO 69
<211> LENGTH: 177
<212> TYPE: DNA
<213> ORGANISM: Homo sapiens

<400> SEQUENCE: 69
caggttgttt tgttctagtt ctaatttctt aaaaaccact acatggttac aaaattggaa      60
taacatttgg ggacaactgg gttaactaca aagaggagga ttttaagagg agatgtgttg     120
tattgactca ttttgtatta ttttttggctt acagttccca tagctgttag agtctgg       177

<210> SEQ ID NO 70
<211> LENGTH: 284
<212> TYPE: DNA
<213> ORGANISM: Homo sapiens

<400> SEQUENCE: 70
ggccaatgag aacccagcct tcaaataaac aagcttctca ttgttaacac agggttcaaa      60
ggcagggagg ttggaggtgt tttgcagggt atccagaatt ctgatcgctg aatactttag     120
ggcaaagagt aagatttccc acacctcccc ctaaatctta caattccctg atgaggcagg     180
aacatgggaa aaaaaagata caggttaaat tacaaagcag aaaatatgc ccagctagaa      240 gctaaagacc tggtctcaaa acactgaacc gaggagcact gatt                      284

<210> SEQ ID NO 71
<211> LENGTH: 254
<212> TYPE: DNA
<213> ORGANISM: Homo sapiens

<400> SEQUENCE: 71
ccctggcctg agaggttgct tttaagtctt ccaccccttg ttccatctgc ctgccaaccc      60
atcggaaagg aatccacatc atattggaga tgaccccatc aaccccaggg ctccagcact     120
accaagttgg aattccacgc ccgggagtgg ggtagaggaa gacgagacag gacgaggcag     180
aaaagcacat tttaaaaacc agacaagatg gctaggccat caccaaccaa cggacttacc     240
ttacatcttt gtag                                                       254

<210> SEQ ID NO 72
<211> LENGTH: 70
<212> TYPE: DNA
<213> ORGANISM: Homo sapiens

<400> SEQUENCE: 72
ttttttctat ccctgccatt cagtctccat tagcactcta ttctctctca tttattccac      60
cccgtcttcc                                                             70

<210> SEQ ID NO 73
<211> LENGTH: 178
<212> TYPE: DNA
<213> ORGANISM: Homo sapiens

<400> SEQUENCE: 73
gaaacacgtg tattatggga caactgaaa ggtcagcctg aagacttttg ccctgttgct       60
ttctgagagt gctggatatg agtccctgtc tctgaaactt ctaaaaatat gcacccttaa     120
ccagctttcc acggagggat aagcctttgt caatacaaat ggtacagtga gcagcaga      178

<210> SEQ ID NO 74
<211> LENGTH: 176
<212> TYPE: DNA
```

<213> ORGANISM: Homo sapiens

<400> SEQUENCE: 74

```
agtctggccc catagtgact tttgccccat gattctgctt cactgttgga atcctctttg    60
aagttccccc tctctttgct aaagcagtga aggaagagaa cagagacaaa ctctttggac   120
tgtgaaagag aaggtagaga attccaggca acagtctgac caagggtgta aaccag       176
```

<210> SEQ ID NO 75
<211> LENGTH: 274
<212> TYPE: DNA
<213> ORGANISM: Homo sapiens

<400> SEQUENCE: 75

```
gggaggggga gatacacata tataatatta aaaaaatgtc atcttccaca gaaaacactg    60
actctgcctt ccaaaagtca caagtacaga tggagtccaa gttcaggagt ggtgcccaaa   120
cccagatact caaaccaaac tgcagaaaca ttcaggaaaa acaagccaa agccattatt    180
ttagaaacac aacgcaaaac aataagataa aattaagtaa aagggaagta acagatggaa   240
taaaaaccaa gatatcacat tccataaagg gcaa                               274
```

<210> SEQ ID NO 76
<211> LENGTH: 290
<212> TYPE: DNA
<213> ORGANISM: Homo sapiens

<400> SEQUENCE: 76

```
gtggtggtta tcgacaggaa tctgtcagag agcataccca tggagcattt ataattggga    60
gccattccag aattctggtt tgcatacaac tcttaaaaa gccagctacc ctgaaatgta   120
cactatctga gctctgcctt tgcctgtgat gagtgatgtt ggtcctgcct cttagttctg   180
ctctcagtct ccaccatcgg cttctcagat tttccttcca ggaccagcag gcaggtgggt   240
gtggtgactt tgtggcagac actgtggcag attaaaggtg gttgcaaatt               290
```

<210> SEQ ID NO 77
<211> LENGTH: 242
<212> TYPE: DNA
<213> ORGANISM: Homo sapiens

<400> SEQUENCE: 77

```
accacctgaa ggaccaccag aatgggtcca tggctgctgt gaatggacac accaacagct    60
tttcacccct ggaaaacaat gtgaagccaa ggaagctgcg gaaggatgga agtcaaagaa   120
ttgaaaccct ccaaaccacg tcatctgatt gtaagcacaa tatgagttgt gccccaatgc   180
tcgttaacag ctgctgtaac tagtctggcc tacaatagtg tgattcatgt aggacttctt   240
tc                                                                  242
```

<210> SEQ ID NO 78
<211> LENGTH: 89
<212> TYPE: DNA
<213> ORGANISM: Homo sapiens

<400> SEQUENCE: 78

```
cttgtagctg acatttggca aaagcgtcac tgaaaggcaa gctaaatgta gttattttat    60
cctgtggccc tgaagcacaa aataaaaat                                      89
```

<210> SEQ ID NO 79
<211> LENGTH: 284

<212> TYPE: DNA
<213> ORGANISM: Homo sapiens

<400> SEQUENCE: 79

```
gtttaccgaa ggcaccagtt cagccaggag tgaaatccgg agaggagcaa cgccagcctg    60
ggtcacagtc catcaaaccc catgagcccg accactctcg ctcttcctta cattcccacg   120
tcccccttct ctcccaaccc ctcatatcag caagggaaat taattaatga gatttgataa   180
atcagtagat agaatgaggt ccccctttttg aaatatttag cagactggaa ccccccccgca  240
agcctctgta gggggtggat ggagacactt ctaactttaa taaa                    284
```

<210> SEQ ID NO 80
<211> LENGTH: 46
<212> TYPE: DNA
<213> ORGANISM: Homo sapiens

<400> SEQUENCE: 80

```
ctggaggagt gagtccctat gctgaccccca atacttgcag aggtga                  46
```

<210> SEQ ID NO 81
<211> LENGTH: 230
<212> TYPE: DNA
<213> ORGANISM: Homo sapiens

<400> SEQUENCE: 81

```
gcattcacac atgtgcatgc tcacacagag acggttctgg agttgtggag ggaagcctgc    60
cccgccttcc ggccccactc cctgaaccta cagctctctc catggccccc ctcacctgct   120
cgggctgggc cggggcttag ggcgagaggc aggggcaggg actttcaggg atccggcagt   180
ctcagtgatg agagcacacc agctggggag aaaggccaaa tccctgggca                230
```

<210> SEQ ID NO 82
<211> LENGTH: 298
<212> TYPE: DNA
<213> ORGANISM: Homo sapiens

<400> SEQUENCE: 82

```
aggattccctt cttgtgttta agcaggagca ggcagaaaag cctaacaacc cccgtctttc    60
ccatcggcag ccccacgccc atcatcacac aaggccccaa ggatgggaaa gagaaaagct   120
agaaggaccc aggggcctcg ggactacagg aagagtggaa agttacagac tgtaaatgaa   180
gtcgggtagg cttgtgccct tccttatttg tccggttctt tcatttgctg cttctgttta   240
agctcaaggg tcagtcacca tgaaatgaat ttgcacctcg gtttctcttt aggctcca     298
```

<210> SEQ ID NO 83
<211> LENGTH: 278
<212> TYPE: DNA
<213> ORGANISM: Homo sapiens

<400> SEQUENCE: 83

```
ctcagagaag gaaaggttgg ccaaagacac atccaggagg ggaacagaag gaggggacag    60
aagcaagtct gcagatcaga ggaaagaaga aagagcagag gagggagatt ggaagtagaa   120
atgctgaatg cagaggcaaa aaaggaaaat gaaggacagg aggattaaac agacagaggc   180
aaggatgatg agagaggagc agacagcaag aatgaaaagc agaaaataca atagaggaaa   240
tgaagaaaag taggcctgct ggagctagat gatgatgt                           278
```

<210> SEQ ID NO 84

<211> LENGTH: 218
<212> TYPE: DNA
<213> ORGANISM: Homo sapiens

<400> SEQUENCE: 84
gggcccatgg attaacgccc tcatcccaag gtccgtccca tgacataaca ctccacaccc    60
gccccagcca acttcatggg tcactttttc tggaaaataa tgatctgtac agacaggaca   120
gaatgaaact cctgcggctc tttggcctga aagttgggaa tggttgggga gagaaggcag   180
cagcttattg gtggtctttt caccattggc agaaacag                            218

<210> SEQ ID NO 85
<211> LENGTH: 179
<212> TYPE: DNA
<213> ORGANISM: Homo sapiens

<400> SEQUENCE: 85
gggaaactct gtcactactg aaaatacaaa agtacaaaaa aaaaaaaaaa attagctggg    60
catggtggtg caagcctata ctcccagcta ctcaggaggc tgaatttgga ggatcccttg   120
agcccagggg ggttgaggct gcattgaggt ataattttgc cactgtattt cagcctggg    179

<210> SEQ ID NO 86
<211> LENGTH: 146
<212> TYPE: DNA
<213> ORGANISM: Homo sapiens

<400> SEQUENCE: 86
ggctctgcca ccctacctgt tcagtgtccc gggcccgttg aggatgaggc cgctagaggc    60
ctgaggatga gctggaagga gtgagagggg acaaaaccca ccttgttgga gcctgcaggg   120
tggtgctggg actgagccag tcccag                                        146

<210> SEQ ID NO 87
<211> LENGTH: 166
<212> TYPE: DNA
<213> ORGANISM: Homo sapiens

<400> SEQUENCE: 87
gggcctcggg actacaggaa gagtggaaag ttacagactg taaatagagt cgggtaggct    60
tgtgcccttc cttatttgtc cggttctttc atttgctgct tctgtttaag ctcaagggtc   120
agtcaccatg aaatgaattt gcacctcggt ttctctttag gctcca                  166

<210> SEQ ID NO 88
<211> LENGTH: 217
<212> TYPE: DNA
<213> ORGANISM: Homo sapiens

<400> SEQUENCE: 88
gagagctctg cctagtctgg tttggcgagg gcccttgatc accttgcccc tcctccctgt    60
cttctctgat tcttttccct caaaatagtc ctgagaacta attgtcacag acattggaat   120
atttgtactg ctctcgtgcc atttgagagg ctgctgcccc aggcaggcca gccctactc   180 ctcttggcta cactcatgtt gctcagacta tatttca                            217

<210> SEQ ID NO 89
<211> LENGTH: 211
<212> TYPE: DNA
<213> ORGANISM: Homo sapiens

<400> SEQUENCE: 89

```
ctgggaactg gcactgggtc gcttttggga ttacctgcgc tgggtgcaga cactgtctga      60
gcaggtgcag gaggagctgc tcagctccca ggtcacccag gaactgaggg cgctgatgga     120
cgagaccatg aaggagttga aggcctacaa atcggaactg gaggaacaac tgaccccggt     180
ggcggaggag acgcgggcac ggctgtccaa g                                    211
```

<210> SEQ ID NO 90
<211> LENGTH: 94
<212> TYPE: DNA
<213> ORGANISM: Homo sapiens

<400> SEQUENCE: 90

```
gatgaagagg gctgattgta tctaacttag ggtcttgcat gcagctggca cttaatgcat      60
tttattgact gttttagcta acattcaatg gaca                                  94
```

<210> SEQ ID NO 91
<211> LENGTH: 197
<212> TYPE: DNA
<213> ORGANISM: Homo sapiens

<400> SEQUENCE: 91

```
gccagactgg gctgtagtta gcttttcatc cctaaagaag gctttcccta aggaaccata      60
gaagagagga agaaaacaaa gggcatgtgt gagggaagct gcttgggtgg gtgttagggc     120
tatgaaatct tggatttggg gctgaggggt gggagggagg gcagagctct gcacactcaa     180
aggctaaact ggtgtca                                                    197
```

<210> SEQ ID NO 92
<211> LENGTH: 39
<212> TYPE: DNA
<213> ORGANISM: Homo sapiens

<400> SEQUENCE: 92

```
aagctgagaa actacctgag gtgtctaaag aaatgtatt                             39
```

<210> SEQ ID NO 93
<211> LENGTH: 212
<212> TYPE: DNA
<213> ORGANISM: Homo sapiens

<400> SEQUENCE: 93

```
ggaattaagg ctattactct gaagaaagtt gggggggccag ggctcctatt tttttgctga     60
ggagatggaa gatcagggct tgtattcaat aagaatggga ggggcaggg gatgcctggc     120 aaaagccttg cactgtgagg tgcaggtaga ggcttttatt ctggtgagag gacatggact     180
ctctctctcc cctcaggtaa ctgtgccctg ta                                   212
```

<210> SEQ ID NO 94
<211> LENGTH: 104
<212> TYPE: DNA
<213> ORGANISM: Homo sapiens

<400> SEQUENCE: 94

```
actccgcagg ggctgtgaat cccactggga gggcggcggg cctgcagccc gaggaaggct      60
tgtgtgtcct cagttaaaac tgtgcatatc gaaatatatt ttgt                      104
```

<210> SEQ ID NO 95
<211> LENGTH: 251
<212> TYPE: DNA

<213> ORGANISM: Homo sapiens

<400> SEQUENCE: 95

| | | | | | |
|---|---|---|---|---|---|
| ggagttctac | gggatctgag | agaaaaacca | tgaggaaagt | tttcaggatc | cttaaacaat | 60 |
| ttttggagcg | tgtgatgtgg | gggactggaa | aagatgtgga | gtatgtaaaa | gggattttgg | 120 |
| aagaagcttt | tggaatatga | tgctgagagt | cctctggaga | tttcaggcaa | ttgctggaga | 180 |
| tttttagaat | gagtgggggt | ggggaagggg | atcccggtga | agatcactgg | gctacatgag | 240 |
| ggtgatctct | a | | | | | 251 |

<210> SEQ ID NO 96
<211> LENGTH: 155
<212> TYPE: DNA
<213> ORGANISM: Homo sapiens

<400> SEQUENCE: 96

| | | | | | |
|---|---|---|---|---|---|
| ggagcggcgc | aaggagagac | aggaagccct | ggaggctaaa | cttgaggaaa | aaggaaaaa | 60 |
| ggaagaagag | aaacggttaa | gagaagaaga | gaagcgcatt | aaagcagaga | aggccgaaat | 120 |
| cacgaggttc | ttccagaaac | caaagactcc | acagg | | | 155 |

<210> SEQ ID NO 97
<211> LENGTH: 220
<212> TYPE: DNA
<213> ORGANISM: Homo sapiens

<400> SEQUENCE: 97

| | | | | | |
|---|---|---|---|---|---|
| ttaattttca | tgttgcggag | ccctactac | aagtatgaag | agaaagaaa | aaaaaatga | 60 |
| aggaaacaac | cactggccca | gggtagagat | gcctacaggg | tggttgcttg | ttggatacaa | 120 |
| tacaaggaac | actgctcaga | acccacgtct | tcagcagcat | ttgaaacact | ggcagcaatg | 180 |
| cacaagagca | agatggtgtc | aggaaccatg | tcaaaccctc | | | 220 |

<210> SEQ ID NO 98
<211> LENGTH: 119
<212> TYPE: DNA
<213> ORGANISM: Homo sapiens

<400> SEQUENCE: 98

| | | | | | |
|---|---|---|---|---|---|
| taagctttta | agcatcatga | agaacaattt | atgttcacat | taagatacgt | tctaaagggg | 60 |
| gatggccaag | gggtgacatc | ttaattccta | aactaccttag | gctgcatagt | ggaagagga | 119 |

<210> SEQ ID NO 99
<211> LENGTH: 103
<212> TYPE: DNA
<213> ORGANISM: Homo sapiens

<400> SEQUENCE: 99

| | | | | | |
|---|---|---|---|---|---|
| gcctggagcg | tgagcccaga | cccaactcca | gccccagccc | cagccccggc | caggcctctg | 60 |
| agaccccgca | cccacgaccc | tcataataaa | cacgtcgatt | ctg | | 103 |

<210> SEQ ID NO 100
<211> LENGTH: 122
<212> TYPE: DNA
<213> ORGANISM: Homo sapiens

<400> SEQUENCE: 100

| | | | | | |
|---|---|---|---|---|---|
| tatgtgccaa | atctactaga | cattggagaa | acagtaggaa | caacacatgg | taccggcaca | 60 |
| tggatctttc | aggaaaacga | agtaggtaat | aaacaggaaa | aagcccgagt | ctgatgctaa | 120 |

```
ga                                                                       122

<210> SEQ ID NO 101
<211> LENGTH: 93
<212> TYPE: DNA
<213> ORGANISM: Homo sapiens

<400> SEQUENCE: 101
ctgcctgtat cctcattggt gggagcccag ccatggccct aattgtgcct gagcttgact        60
ttcagtcagg gccacagtga gcattaaatt att                                     93

<210> SEQ ID NO 102
<211> LENGTH: 70
<212> TYPE: DNA
<213> ORGANISM: Homo sapiens

<400> SEQUENCE: 102
ggagttaaat gtagtgcttt ccaggatagt tccttccata ctccttctgt tcctttcatt        60
gtgcccctct                                                               70

<210> SEQ ID NO 103
<211> LENGTH: 238
<212> TYPE: DNA
<213> ORGANISM: Homo sapiens

<400> SEQUENCE: 103
cagccgtttc cctgcagaat cagctctgtc tcatgtggaa gtggagaatc agccttgcct        60
ggcctttagg aacttttgtg gggaagagag ctttgaagag aggaggggga ctttagagag       120
ggatgaaaat gagccctggg agggaggaag ggacgaggag gggtggctgc atgttaccgt       180
cccctacctc tccccacgtg gagggtggag cagttatgag ggaggaagtc aactgctg         238

<210> SEQ ID NO 104
<211> LENGTH: 269
<212> TYPE: DNA
<213> ORGANISM: Homo sapiens

<400> SEQUENCE: 104
caggcattcc tttctatcga taattactct ttcaaccaat tgccaatcag aaaattgtta        60
tatctaccta taatctagaa gcccccacat caagttgttt tgccttttctg gacaggacca     120 atgtatatct taaatgtatt tgattgatct ctcatgtctc cctaaaatgt ataaaaccac       180
gctgttcccc gaccacctgg agcacatgtt ctcagggtct cctgagggct gtgtcacagg       240
ccatgttcac ttacatttgg ctcagaata                                         269

<210> SEQ ID NO 105
<211> LENGTH: 291
<212> TYPE: DNA
<213> ORGANISM: Homo sapiens
<220> FEATURE:
<221> NAME/KEY: misc_feature
<222> LOCATION: (258)..(258)
<223> OTHER INFORMATION: n is a, c, g, or t

<400> SEQUENCE: 105
gggtcagaaa gatgccttca gttttggtca gtgtctaaaa gttaagtctg tttaggccaa        60
gcatggtggc tcacgcctga aatcccagca cttggggagg ccgaggcaag tgatcacaa       120 ggtcaggaga tgagaccatc ttagccaaca tggtgaaacc ccgtctctac taaaatacaa       180
```

```
aaaaattagc caggcgtggg ggtgcgtgcc tataatccca gctacttggg aggctgaggc    240
aggggaatcg cttgaacncg ggaggcagag gtcacgccat ggactccagc c              291
```

<210> SEQ ID NO 106
<211> LENGTH: 36
<212> TYPE: DNA
<213> ORGANISM: Homo sapiens

<400> SEQUENCE: 106

```
cgcaccattg cactagtgat aagatcgaaa ctccat                               36
```

<210> SEQ ID NO 107
<211> LENGTH: 243
<212> TYPE: DNA
<213> ORGANISM: Homo sapiens

<400> SEQUENCE: 107

```
tttgaaatca ccatgtctga taaaaacatg caattgcttt ggtgaatttg tttgtttat     60 tgttgttgct ttgagtgaat gcttcagttt gctctagatt ttactttgtt tgttaaaaat   120
taccatgttt taaccccga aaacatttaa tgtttttgaa atgattttt cataacaatc     180 ttatgagtct attatataat aggaagtatt ttggaaattt aatggtgata tttctttgga   240
aaa                                                                 243
```

<210> SEQ ID NO 108
<211> LENGTH: 220
<212> TYPE: DNA
<213> ORGANISM: Homo sapiens

<400> SEQUENCE: 108

```
tgtgcacagg agactcagga cagtgggggg aaaagtcact tctccacata agaggctcaa   60
atcccaacgc caccctccgt cagacccctt tggccccagc tccgacccct ccagggttta   120
ccaagttggg ctttcacagc atgtctgagc aaacacgcag cgaccttta cataattgca    180 acctcctcca gagaggagag aggccacatt ctctcggccc                          220
```

<210> SEQ ID NO 109
<211> LENGTH: 263
<212> TYPE: DNA
<213> ORGANISM: Homo sapiens
<220> FEATURE:
<221> NAME/KEY: misc_feature
<222> LOCATION: (116)..(116)
<223> OTHER INFORMATION: n is a, c, g, or t

<400> SEQUENCE: 109

```
taacggagtg tcactttcaa ccggcctccc ctacccctgc tggccgggga tggagacatg   60
tcatttgtaa aagcagaaaa aggttgcatt tgttcacttt tgtaatattg tcctgngcct   120 gtgttgggt gttgggggaa gctgggcatc agtggccaca tgggcatcag gggctggccc    180
cacagagacc ccacagggca gtgagctctg tcttcccca cctgcctagc ccatcatcta    240
tctaaccggt ccttgattta ata                                           263
```

<210> SEQ ID NO 110
<211> LENGTH: 278
<212> TYPE: DNA
<213> ORGANISM: Homo sapiens

<400> SEQUENCE: 110

```
catgcacaga tggccacatt ctgcctccat ccactcaatg ccaacaggca cgattcctcc   60
```
accgacaacg ctcaaggcca cagggtccac ccacacagcg ccaacaatga cgctgaccac    120
cagcgggacc agccaagccc tgagctcatt aaacacagcc aaaacctcta catccctaca    180
ttcacacact tcctccacac accatgctga agccacctca acttctacca ccaacatcac    240
ccccaaaccc accagtacag gaaccccacc aatgacag                            278

<210> SEQ ID NO 111
<211> LENGTH: 107
<212> TYPE: DNA
<213> ORGANISM: Homo sapiens

<400> SEQUENCE: 111
ccccattatg tcatgacctc acttaagtgg aacactatat cataacccag agattcgtcc    60
cagccccaga gtccgacaga ctgtctggtc cctattccta atgaggg                  107

<210> SEQ ID NO 112
<211> LENGTH: 292
<212> TYPE: DNA
<213> ORGANISM: Homo sapiens
<220> FEATURE:
<221> NAME/KEY: misc_feature
<222> LOCATION: (65)..(99)
<223> OTHER INFORMATION: n is a, c, g, or t

<400> SEQUENCE: 112
cacatctggc ctgacgttct cgttgcatca agccatcatc caccgggcgc ccctggacgc    60
gcgtnnnnnn nnnnnnnnnn nnnnnnnnnn nnnnnnnnna atgctgaccc actcagtaga    120
gcaggggcca gccagagggg gacgaagtca ccaatccagg caccaccttc ccacatgtcc    180
ctgcaacttc tctctttcca gtgtgctgaa gaagggaggt gccacccctc ctccagataa    240 atggcccag aaaacgatcc aaaaaaatac ccagggagcg attccttatg ta             292

<210> SEQ ID NO 113
<211> LENGTH: 157
<212> TYPE: DNA
<213> ORGANISM: Homo sapiens
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t

<400> SEQUENCE: 113
gatgatcaac tctgctagga agcggggtgg gaagaaggga ggggatgggg ttgggagagg    60
tganggcang attaagatcc ccactgtcaa tgggggattg tctcagcccc tcttcccttc    120
ccctcacctg gaagcttctt caaccaatcc cttcaca                             157

<210> SEQ ID NO 114
<211> LENGTH: 236
<212> TYPE: DNA
<213> ORGANISM: Homo sapiens

<400> SEQUENCE: 114
gcagtctcag acaccaagga ggggagagtg actagaaaga aaaccttctt gcagagacat    60
aggggatggg gaagaactgc agactgaact ggggcaaagg actgtaggac ttaaccagag    120
agatttgagg gagagatgag gctgagagcc aggggatcct gccatgtccc agcataaaaa    180
cagtacctga cacagatagg tgcttgggaa gctgttgtcg gatgaatgag tggaca        236

<210> SEQ ID NO 115
<211> LENGTH: 137
<212> TYPE: DNA
<213> ORGANISM: Homo sapiens

<400> SEQUENCE: 115
aagctggcaa ctggtgagag tatagcagtc aaaaaaagaa aatgctcact cttagatacc   60
taagaattca aagcgtttca acctagagca accactaaaa aacctgcaca gagatgacag  120
tcaatattac aatagag                                                 137

<210> SEQ ID NO 116
<211> LENGTH: 65
<212> TYPE: DNA
<213> ORGANISM: Homo sapiens

<400> SEQUENCE: 116
agcccagcag atcctacaca cattttcaca aactaacccc agaacaggct gcaaacctat   60
accaa                                                               65

<210> SEQ ID NO 117
<211> LENGTH: 269
<212> TYPE: DNA
<213> ORGANISM: Homo sapiens

<400> SEQUENCE: 117
tcactttcct ggattgtcac tgtgagtgta attccggttg gctggaaccg cttttggaaa   60
ggattgggag agatgaaaca gcagttgtgt gtcctgttat agacacaatt gattggaata  120
cttttgaatt ctatatgcag ataggggagc ccatgattgg tgggtttgac tggcgtttag  180
catttcagtg gcattctgtc cccaaacagg aaagggacag gcggatatca agaattgacc  240
ccatcagatc acctaccatg gctggagga                                    269

<210> SEQ ID NO 118
<211> LENGTH: 225
<212> TYPE: DNA
<213> ORGANISM: Homo sapiens

<400> SEQUENCE: 118
tagtgttttg ccctaaatct aaggatggtg cctagtggtg gccctgtgtt ctgaggacag   60
agagagctgg agggtggag gggaatgcat cggcactcat ttggtgtaac caagaagagg  120
gggaaagatg tcttgataga atcaaagttg ccaaaaacaa agaagagtct atcaagcaga  180
tttctaacat ttagctagaa actacttcat agctctcatt tttag                  225

<210> SEQ ID NO 119
<211> LENGTH: 61
<212> TYPE: DNA
<213> ORGANISM: Homo sapiens

<400> SEQUENCE: 119
cactaccgcc ccgcgctggc ttgccctcct gttctccaga gcaataaagt tggacgagac   60
t                                                                   61

<210> SEQ ID NO 120
<211> LENGTH: 36
<212> TYPE: DNA
<213> ORGANISM: Homo sapiens

```
<400> SEQUENCE: 120
gagagccacc acaagactaa gtaaagaccg agttga                                36

<210> SEQ ID NO 121
<211> LENGTH: 35
<212> TYPE: DNA
<213> ORGANISM: Homo sapiens

<400> SEQUENCE: 121
gaataaatgg ggttgggcat atcaaactaa agatg                                 35

<210> SEQ ID NO 122
<211> LENGTH: 260
<212> TYPE: DNA
<213> ORGANISM: Homo sapiens

<400> SEQUENCE: 122
ttctctgcat cggtcaggtt agtgatatta acagcgaaaa gagattttg tttaggggaa       60 agtaattaag ttaacactgt ggatcaccct cggccaaggg acacgactgg agattaaacg     120
taagtaattt tcactattg tcttctgaaa tttgggtctg atggccagta ttgactttta      180
gaggcttaaa taggagtttg gtaaagattg gtaaatgagg gcatttaaga tttgccatgg    240
gttgcaaaag ttaaactcag                                                260

<210> SEQ ID NO 123
<211> LENGTH: 285
<212> TYPE: DNA
<213> ORGANISM: Homo sapiens

<400> SEQUENCE: 123
caaatataca aaatgcctcc aagctcaaat agctataact gtaccaaaga catggaagaa      60
accaaaagat cggaccccgaa ccactgaaga gatgttagag gcagaattgg agcttaaagc   120
tgaagaggag cttccattg acaaagtact tgaatctgaa caagataaaa tgagccaggg     180
gtttcatcct gaaagagacc cctctgacct aaaaaaagtg aaagctgtgg aagaaaatgg    240
agaagaagct gagccagtac gtaatggtgc tgagagtgtt tctga                    285

<210> SEQ ID NO 124
<211> LENGTH: 39
<212> TYPE: DNA
<213> ORGANISM: Homo sapiens

<400> SEQUENCE: 124
ccgcaggcag gtgtcaggac cggcctaata aacatgtgt                             39

<210> SEQ ID NO 125
<211> LENGTH: 266
<212> TYPE: DNA
<213> ORGANISM: Homo sapiens

<400> SEQUENCE: 125
aaatgtgact gctttgtaaa actccagagt caaggactca taggcaggag gatgtcataa      60
attaacagga aaggatgaga atctccact ccactccctc ctccctccct tgatcactca     120
ttccctctct tccattcatt aaccacccac tacatgccat gccctaagga agcagctatc    180
taagaagtcc ctgcctgcag gggctttaca gaccaggagg aaggcaaccc atagagccag    240
gatcctgata accactgctg actgcc                                          266
```

<210> SEQ ID NO 126
<211> LENGTH: 159
<212> TYPE: DNA
<213> ORGANISM: Homo sapiens
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t

<400> SEQUENCE: 126
aaaccctgga agaatctttc acttgaactc aacttgactg gngttcagtc aaccantctc    60
aggggaaggg gggaagcact atctccacan cancactnan tctgggcctc ccgccccatc   120
tcccccagcc cctctcagca actaggccag gcttcagct                          159

<210> SEQ ID NO 127
<211> LENGTH: 262
<212> TYPE: DNA
<213> ORGANISM: Homo sapiens

<400> SEQUENCE: 127
gcagggctgc cggagcgtcg aggagttcca gtgcctgaac aggatcgagg agggcaccta    60
tggagtggtc tacagagcaa aagacaagaa aacagatgaa attgtggctc taaagcggct   120
gaagatggag aaggagaagg agggcttccc gatcacgtcg ctgagggaga tcaacaccat   180
cctcaaggcc cagcatccca acatcgtcac cgttagagag attgtggtgg gcacacatta   240
tggaggcgca gtcgcctacg ca                                           262

<210> SEQ ID NO 128
<211> LENGTH: 59
<212> TYPE: DNA
<213> ORGANISM: Homo sapiens

<400> SEQUENCE: 128
aggagtcagg agaacaagtc agggattagg agacagcggt ttggtttatt gttatccag     59

<210> SEQ ID NO 129
<211> LENGTH: 267
<212> TYPE: DNA
<213> ORGANISM: Homo sapiens

<400> SEQUENCE: 129
aataattctc aatttcttag tctcttaatt cttaaattta aaaggttgt ttcttaccttt    60 ttaaaatttt taaaaataat tatgtcaagt aattttgaa tatagtaacc tgattctaca   120
tttctcatgg gataaattct aaggtaaaaa aaattgcaaa taaatcttaa actttattta   180

```
gtaggtttat tattagcagc agatgtctag ccagggtaga ttactttat cagaccaacc      240 tctcaccaac aactactaga agagcta                                         267

<210> SEQ ID NO 130
<211> LENGTH: 129
<212> TYPE: DNA
<213> ORGANISM: Homo sapiens

<400> SEQUENCE: 130
ctgggaaatc cagtgtttgt atgtaaaaat aaaaggtaag ttaattctag attgaggggc      60
agaggctatt tcttaatctc caatctcctt gggaagggaa agtattagga ggcagtaatg     120
gagtagaaa                                                            129

<210> SEQ ID NO 131
<211> LENGTH: 276
<212> TYPE: DNA
<213> ORGANISM: Homo sapiens

<400> SEQUENCE: 131
ggtacactgg gcacgcaatg cgcgtgttag tagccaaata gtaaaagggc cgtatttcaa      60
cagcgactcc aagacaactg gcgttgccca ttctcagtct ccggcctatc ctacacatct     120
aatacccggc tacaatataa agctatagta aaggttcacg gggtcttttc gtcccgttgc     180
gggtaatcgg catcttcacc gatactacaa tttcaccgag ctcgcggttg agacagtgcc     240
cagatcgtta caccattcgt gtatggacgg gctctg                              276

<210> SEQ ID NO 132
<211> LENGTH: 71
<212> TYPE: DNA
<213> ORGANISM: Homo sapiens

<400> SEQUENCE: 132
ggacagcagc cactcagttc ttcctccacc tccacccagt gatcccaata aacgaattct      60
gtctccccgt g                                                          71

<210> SEQ ID NO 133
<211> LENGTH: 279
<212> TYPE: DNA
<213> ORGANISM: Homo sapiens

<400> SEQUENCE: 133
acagatggcc acattctgcc tccatccact caatgccaac aggcacgatt cctccaccga      60
caacgctcaa ggccacaggg tccacccaca cagcgccaac aatgacgctg accaccagcg     120
ggaccagcca agccctgagc tcattaaaca cagccaaaac ctctacatcc ctacattcac     180
acacttcctc cacacaccat gctgaagcca cctcaacttc taccaccaac atcaccccca     240
aacccaccag tacaggaacc ccaccaatga cagtgacca                           279

<210> SEQ ID NO 134
<211> LENGTH: 237
<212> TYPE: DNA
<213> ORGANISM: Homo sapiens

<400> SEQUENCE: 134
tagtacctgc ctcattcagc taacgtgagg atctagagca gcatttgcat aaatgacgcg      60
tggggcacag agcagactca acacagagca gcttacgtta tgaggcttgg caggctggga     120
```

```
gctcctgtcg gcctctctcc tcagctctgt gcccactgag ctcggcacaa gggttggccc      180
atgacaggtg tttattatgt ggaaataaat gagagggaca agacatttgc tgatttc         237

<210> SEQ ID NO 135
<211> LENGTH: 170
<212> TYPE: DNA
<213> ORGANISM: Homo sapiens

<400> SEQUENCE: 135
gcctcatcag ggaattgtaa gatttagggg gaggtgtggg aaatcttact ctttgcccta      60
aagtattcag cgatcagaat tctggatacc ctgcaaaaca cctccaacct ccctgccttt     120
gaaccctgtg ttaacaatga aagcttgtt  tatttgaagg ctgggttctc                170

<210> SEQ ID NO 136
<211> LENGTH: 292
<212> TYPE: DNA
<213> ORGANISM: Homo sapiens

<400> SEQUENCE: 136
ggacagatga agactcttaa gatgacagaa ggtgattttt ctggtgatcg aggacttccg      60
gggtaatgac agtgatgaaa tgcaggggac ctggttgccc ccaagtttcc tggcagtgtg    120
tgatactgag gaggtgagct tgtttctgga gctgtgcttt aagattcatg ttacatgtaa    180
agctgtcctc atttgtgact atggacctat ggagttggga caatctctat gggaagcaga    240
aggcaaggac cccggtcatt ttaggtagaa acaacagcat gctaatgcaa aa             292

<210> SEQ ID NO 137
<211> LENGTH: 194
<212> TYPE: DNA
<213> ORGANISM: Homo sapiens

<400> SEQUENCE: 137
aagagagaag cttctgcacg ccagaggcac ccagtcccac aggcgcctac ctgccccgga      60
taagaggttc cctgccattt ctctagtctc ccccttcaa  cagcacacca aataagccca    120
agaagatgac aggaaccgtc cccgccaact tcacacgagt gctaaggcga agacagccat    180
cttgggcctt cgga                                                      194

<210> SEQ ID NO 138
<211> LENGTH: 202
<212> TYPE: DNA
<213> ORGANISM: Homo sapiens

<400> SEQUENCE: 138
tgcctgatgc ctcaggtgac agaaggcagg acgttccatg ccgaggctgc cccctcaccc     60
agaagtctga gcccagcctc aggaggggcc aagaaccagg gggccatcaa aagcatcggg   120
atttggcatt ggttccagat gagcttttaa agcaaacata gcagttgttt gccatttctt   180
gcactcagac ctgtgtaata ta                                             202

<210> SEQ ID NO 139
<211> LENGTH: 86
<212> TYPE: DNA
<213> ORGANISM: Homo sapiens

<400> SEQUENCE: 139
gccccaacct gggattgctg agcagggaag ctttgcatgt tgctctaagg tacatttta      60 aagagttgtt ttttggccgg gcgcag                                         86
```

<210> SEQ ID NO 140
<211> LENGTH: 199
<212> TYPE: DNA
<213> ORGANISM: Homo sapiens

<400> SEQUENCE: 140
accaaagttt gcagcctata cctcaataaa acagggatat tttaaatcac atacctgcag    60
acaaactgga gcaatgttat ttttaaaggg ttttttttcac ctccttattc ttagattatt   120
aatgtattag ggaagaatga gacaattttg tgtaggcttt ttctaaagtc cagtactttg   180
tccagatttt agattctca                                                199

<210> SEQ ID NO 141
<211> LENGTH: 297
<212> TYPE: DNA
<213> ORGANISM: Homo sapiens

<400> SEQUENCE: 141
attgattcct gaccatagca gtgagaggcc attttttgtg caggaaatgt gcttaggact    60
cagtcttgtt ttcgattatc caccacagaa accctgagac acagagcagc ttagaagtct   120
ctacccaggc gtaaatagag ctccctactc cagaccacct gccacccacc tcccaagttg   180
agaacacaag ctccagctgg gctggagagt caggcttggt gcaggtgac tttggcgaag    240 ttttgtcaga tccataaagc aaactggaat ttgagctttc acttaccta gtatacg       297

<210> SEQ ID NO 142
<211> LENGTH: 110
<212> TYPE: DNA
<213> ORGANISM: Homo sapiens

<400> SEQUENCE: 142
ttctttccac agaagctcca ggtagagggt gtgtaagtag ataggccatg ggcactgtgg    60
gtagacacac atgaagtcca agcatttaga tgtataggtt gatggtggta               110

<210> SEQ ID NO 143
<211> LENGTH: 269
<212> TYPE: DNA
<213> ORGANISM: Homo sapiens
<220> FEATURE:
<221> NAME/KEY: misc_feature
<222> LOCATION: (92)..(115)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t

<400> SEQUENCE: 143
tgagttgttt gttcaccagt gatgctatgt tatgcatttg tttacatctc ataacatgtg    60
gtaaatattt atgcaagatg gctagccaga cnnnnnnnnn nnnnnnnnnn nnnncancc    120 gtgaaataga gaatgcaggg tgacccatgt aaacaggcta gagatacatt tgaaaaagat   180
gagggttaaa gagtgtgtac atgttggcag gtaaagagat agcatcctct agggaggata   240
ttatcaggag tcagagtaat cttggtaaa                                     269

<210> SEQ ID NO 144
<211> LENGTH: 106
<212> TYPE: DNA
<213> ORGANISM: Homo sapiens

<400> SEQUENCE: 144
aatcattgat tgacttgtct gtgaacttgc aggaactgtt tcatagtttc attacacaga      60
gtaaactgtt tgccatgcaa ggttattttg catctgcatt taagtg                   106

<210> SEQ ID NO 145
<211> LENGTH: 184
<212> TYPE: DNA
<213> ORGANISM: Homo sapiens

<400> SEQUENCE: 145
gacattaact cattagactg gaacttgaac tgattcacat ctcattttc cgtaaaaatg      60 atttcagtag cacaagttat ttaaatctgt ttttctaact gggggaaaag attcccaccc   120
aattcaaaac attgtgccat gtcaaacaaa tagtctatca accccagaca ctggtttgaa   180
gaat                                                                 184

<210> SEQ ID NO 146
<211> LENGTH: 247
<212> TYPE: DNA
<213> ORGANISM: Homo sapiens

<400> SEQUENCE: 146
gtatgtgaaa gtctctattt gtgtatttct ctcctaaagt tgtgtctctt tgggaattgg      60
atttgatttt tattatttaa tacctcactt tggcccgtcc cccctcccaa cacttctgta   120
tcctcgccct gccgccccag cctggacgct ctgcgtggaa gtgcgtgttt gtagcagctc   180
gggcctcatc tcagcgctcg gatccctcct gctgccagaa tccactggcc tctgtctcat   240
tcttggg                                                              247

<210> SEQ ID NO 147
<211> LENGTH: 277
<212> TYPE: DNA
<213> ORGANISM: Homo sapiens

<400> SEQUENCE: 147
tccctcagga agcagtcccc tcgtctccct ttctgggcag cttccttgag gacagaaact      60
tgaaaacaaa cacaaaccaa agtttctggc catctgtggc tggagggttc tgaatgtcct   120
ctctccatgt caggcagagg gtcagccccc atgcttctgc ctcaggcccc accccacccc   180
accccaggcc tgcccctcac ctcagggcca tacccacagc gccctgatgg aggaaccaga   240
ccgcaggctg tgccaccatt aaacaagagc ggctgtg                             277

<210> SEQ ID NO 148
<211> LENGTH: 32
<212> TYPE: DNA
<213> ORGANISM: Homo sapiens

<400> SEQUENCE: 148
aaggaggcag atgagatttc atatcaaaaa ga                                   32

<210> SEQ ID NO 149
<211> LENGTH: 174
<212> TYPE: DNA
<213> ORGANISM: Homo sapiens

<400> SEQUENCE: 149
tgacttctac ctcccatgtt tgctctccca actcattagc tcctgggcag catcctcctg      60
agccacatgt gcaggtactg gaaaacctcc atcttggctc ccagagctct aggaactctt   120
catcacaact agatttgcct cttctaagtg tctatgagct tgcaccatat ttaa        174

<210> SEQ ID NO 150
<211> LENGTH: 37
<212> TYPE: DNA
<213> ORGANISM: Homo sapiens

<400> SEQUENCE: 150
ccaccgtaaa gtactgcgcg acaatatcca gggcatc        37

<210> SEQ ID NO 151
<211> LENGTH: 248
<212> TYPE: DNA
<213> ORGANISM: Homo sapiens
<220> FEATURE:
<221> NAME/KEY: misc_feature
<222> LOCATION: (223)..(223)
<223> OTHER INFORMATION: n is a, c, g, or t

<400> SEQUENCE: 151
gtggaataag ttctcctagc tcagaaggat ctcaacctct tgcaagttac ttttcacttt        60
taagggccct taaagaagca tttgcttagc tctgtatcca ggccatctct ccctccccga       120
agagcaacag accagcaact gacattaagg tcacatgggt gggtggggag tagaattgcg       180
ggggtgacag ttccagccaa tccagacacg aatcatgttt ganggacccg agcctcaagg       240
gtgattcc        248

<210> SEQ ID NO 152
<211> LENGTH: 39
<212> TYPE: DNA
<213> ORGANISM: Homo sapiens

<400> SEQUENCE: 152
agacatatga caatgttcag caggtcatct ttaatgcag        39

<210> SEQ ID NO 153
<211> LENGTH: 53
<212> TYPE: DNA
<213> ORGANISM: Homo sapiens

<400> SEQUENCE: 153
acgaaagcgc aagaaatccc ggtataagtc ctggagcgtt ccctgtgggc ctt        53

<210> SEQ ID NO 154
<211> LENGTH: 215
<212> TYPE: DNA
<213> ORGANISM: Homo sapiens

<400> SEQUENCE: 154
cctcgtggat catcaaggac gacgcggagg tggagcggct gacctgtgag gaggaggagg        60
agaagatgtt cggccgtggc tcccgccacc gcaaggaggt ggactacagc gactcactga       120
cggagaagca gtggctcaag gccatcgagg agggcacgct ggaggagatc gaagaggagg       180
tccggcagaa gaaatcatca cggaagcgca agcga        215

<210> SEQ ID NO 155
<211> LENGTH: 277
<212> TYPE: DNA
<213> ORGANISM: Homo sapiens

<400> SEQUENCE: 155

```
tagggtttct ctccactatg aatgatctga tgtatagtaa ggttcgaaga ccacttaaaa      60
attttgccac aatctttgca tttgtagggt tgtctccag tatgaactat gttatgttga      120
gtaaggcctg aggaatagta aaaagctttg ccacattctt cacatttata gggtttctct    180
caagtatgaa ttcttttatg ttctttcagt tttgaggatt ttctaaaggc tttgccacat    240
tcatcacatt tgtagggttt ctctcccata tgaataa                              277

<210> SEQ ID NO 156
<211> LENGTH: 125
<212> TYPE: DNA
<213> ORGANISM: Homo sapiens

<400> SEQUENCE: 156
actggagggt ctccgggcac actctggccc ttcccagaaa gggggtcgtt tttctcgaat      60
cttcaaccag ttgtgtattg gaaactaggg cgcattttac tattgatcac agtcattata    120
ttgtt                                                                  125

<210> SEQ ID NO 157
<211> LENGTH: 151
<212> TYPE: DNA
<213> ORGANISM: Homo sapiens

<400> SEQUENCE: 157
ttcggaaata gggaagactg tctctgaaga aggaggaagt gtagcttatg ggaggctgag      60
gagtttggag tttctccttg tgggaaggtg ggagccatgg aggctgaaga cagttgtcca    120
actcagggca tacaaattga tgaggaactc a                                     151

<210> SEQ ID NO 158
<211> LENGTH: 233
<212> TYPE: DNA
<213> ORGANISM: Homo sapiens

<400> SEQUENCE: 158
aggacctcag agatgtaagc attttagcag ccacacaaaa tctctggcta tgaaagggac      60
ttcatgacca tccagtccaa tataacactt gcagacagag aaactgaggt cttccatgac    120
ttgcctagtc tcccagctag tttgaggcaa aactggattc ccactctggt attctttctt    180
ccttttacat cattttccct cctttaaaat gtcctgagag accagaactc aca              233

<210> SEQ ID NO 159
<211> LENGTH: 169
<212> TYPE: DNA
<213> ORGANISM: Homo sapiens

<400> SEQUENCE: 159
actaaagaca ttaagcattt gcacttaatt gggtacttcg ggaagaagt gtgtaggttg       60 gcattaaagg tacttcttac actgcatgtt ctgtaaggac agcaaaatac atctatatag    120
gttcactgtt aaattctcga ggactaatgg atccgcatgt gaaaagtaa                 169

<210> SEQ ID NO 160
<211> LENGTH: 123
<212> TYPE: DNA
<213> ORGANISM: Homo sapiens

<400> SEQUENCE: 160
tgagccccgt gcctggcctg gtcatttctc ttgctgtgcc caacctgcca ttaatcccat      60
ccatcctgag cccgacgtgg tcatttctct caccacccag cataccgccc aacgtggtcc    120
``` ttt 123

<210> SEQ ID NO 161
<211> LENGTH: 274
<212> TYPE: DNA
<213> ORGANISM: Homo sapiens

<400> SEQUENCE: 161
taagtactta agtcctgtct ccttggccaa gccagactag gcccaacacc ctcaattcac    60
cctggctcca aagagggcaa aagcaactct ctttctctaa ggccagggaa gtatctacca   120
caatctctga aacctgtgaa cttttctgtg ggcctgtagt ttcaagtccc accttaactg   180
tccttaaaaa aaaaaccaaa caatgaccta cctaatccat ctaatttctc aactaactgc   240
caccatctct actatatcca cctgcatcct attt                               274

<210> SEQ ID NO 162
<211> LENGTH: 53
<212> TYPE: DNA
<213> ORGANISM: Homo sapiens

<400> SEQUENCE: 162
taggcttagc ttgatttctg ggcccactgt ctgtgttctt aagatgccaa cct           53

<210> SEQ ID NO 163
<211> LENGTH: 169
<212> TYPE: DNA
<213> ORGANISM: Homo sapiens

<400> SEQUENCE: 163
tatgatgcac agttcgtgtc aacaggaaat gatggatgtc aagcaattca ttggtaaact    60
cctacctcca attgattgac gtcactaaga ggccttgtgt agaagtacac cagcatcatt   120
gtagtagagt gtaaaccttt tcccatgccc agtcttcaaa tttctaatg              169

<210> SEQ ID NO 164
<211> LENGTH: 260
<212> TYPE: DNA
<213> ORGANISM: Homo sapiens

<400> SEQUENCE: 164
cagctgggcc ctggctgatg tcatgagcca actcaagaag aagagggcag ccactacatt    60
agatgagaag attgagaaag ttcgaaagaa aaggaaaaca gaggataaag aagccaagtc   120
tgggaagttg gaaaaggtag aaagaagcaa aggaaggctc tgaaccaaag gagcaggaag   180
accttcaaga gaatgatgag gaaggctcag aagatgaagc ctcggagact gactactcat   240
cagctgatga gaacatcctc                                              260

<210> SEQ ID NO 165
<211> LENGTH: 239
<212> TYPE: DNA
<213> ORGANISM: Homo sapiens

<400> SEQUENCE: 165
aacccactcc aattaggcat tgctcccact cctccccatc agtgctctca caaggtcacc    60
agtggcttct acattgccaa tctagcgatc aaatctcagt aagtgtcatt tgatataact   120
gatctttcac ttcctctttg aaaccccatc atgtggtttc caggaccaca cactccctcc   180
ctctcctcct gccatgggtg tcagtctcca gggctctccc taacctccat gtgtaagaa   239

<210> SEQ ID NO 166
<211> LENGTH: 278
<212> TYPE: DNA
<213> ORGANISM: Homo sapiens

<400> SEQUENCE: 166

```
tgcccattct ccaaaaagca cgtgcccagc ccccaatccc ctctatatct cagctgaagc    60
atcacctcca ttaatgaagc ctagtccttt cctgcctcgt gtgttgcttt gttgctgctc   120
acacctttag acaagacttg ctgccactga ctcccaccag tccctgttcc ctggaagaaa   180
tcaaggaagc ccaccttgat ctcatttgag ctcctaattt tacagaaata gggacaaagg   240
ttcaaaggga gcctcacagg tcgcatggtg aaccaagc                           278
```

<210> SEQ ID NO 167
<211> LENGTH: 214
<212> TYPE: DNA
<213> ORGANISM: Homo sapiens

<400> SEQUENCE: 167

```
agcatctgaa actatatcca gaatgacact ggattttcat aaaagtgttg atcctcacac    60
ctctttatag tcttgcacct agcacagtgg agtgaaaaca tttaaatagc acttgttcct   120
tgagtatata tggaaaaaag tgaagtattg ataagtgctc agctaatatg agcagcatct   180
caggagtctc caattcttga attaccaggg agta                               214
```

<210> SEQ ID NO 168
<211> LENGTH: 193
<212> TYPE: DNA
<213> ORGANISM: Homo sapiens

<400> SEQUENCE: 168

```
ggagttggag cccactctgg ggaaaacatg ttgagatctt gcctctgcaa aaataaagta    60
aaataaaatt taaaaaaagt aaaaaaataa aatcagctga gcatggtgac atgcacctgt   120
ggtaccagct actttggagg ctaagttgag aggcactgat gggaggatca tttgacggcc   180
cagaggttga ggc                                                      193
```

<210> SEQ ID NO 169
<211> LENGTH: 240
<212> TYPE: DNA
<213> ORGANISM: Homo sapiens

<400> SEQUENCE: 169

```
ggcagctggc ggtcatttac atcccccgc tgcagagggt cttccagacg gagaacctgg     60
gagcgcttga tttgctgttt ttaactggat tggcctcatc cgtcttcatt ttgtcagagc   120
tcctcaaact atgtgaaaaa tactgttgca gcccaagag agtccagatg caccctgaag   180
atgtgtagtg daccgcactc cgcggcacct tccctaatca tctcgatctg gttgtgactg   240
```

<210> SEQ ID NO 170
<211> LENGTH: 284
<212> TYPE: DNA
<213> ORGANISM: Homo sapiens
<220> FEATURE:
<221> NAME/KEY: misc_feature
<222> LOCATION: (213)..(213)
<223> OTHER INFORMATION: n is a, c, g, or t

<400> SEQUENCE: 170

```
atagtgttgg gcactgtctg accatgttgc atttggaagg ctaaatgggg ccatgaagaa    60
```

```
ggctggaagg dacaggtggt gatggcagcc tacctggtgt cccctacccc acctgttctc        120
ggagaaccaa gttgctacac aggaagttct ccaaggtcca gtttcctttc tcccaccagt        180
tggtggaggc ttcagggaag accagagtcc tgnacagaga gggtaacagg aggagtcggg        240
gataaacatc aaacatcaat cgtgtgtcct gatttgggag tgat                        284

<210> SEQ ID NO 171
<211> LENGTH: 245
<212> TYPE: DNA
<213> ORGANISM: Homo sapiens

<400> SEQUENCE: 171
gggccttccg tgctggcaga acaaagaaat gaatggatgc atggacagat agagagacta        60
atgcagcttg ttgagacagg ggctacagct tcactgatga agaacaact ccaccctcat         120 gccccagcct ttttcttggg gcaggggcac atgataacct ttctcccaca ctaaaccttg        180
ctcactacca gactagtagg ccttaaactc tgggagcaag aatggaactc cttcctatct        240
caaca                                                                   245

<210> SEQ ID NO 172
<211> LENGTH: 142
<212> TYPE: DNA
<213> ORGANISM: Homo sapiens

<400> SEQUENCE: 172
ctccactatg aatgatctga tgtatagtaa ggttcgaaga ccacttaaaa attttgccac        60
aatctttgca tttgtagggt ttgtctccag tatgaactat gttatgttga gtaaggcctg        120
aggaatagta aaaagctttg cc                                                142

<210> SEQ ID NO 173
<211> LENGTH: 256
<212> TYPE: DNA
<213> ORGANISM: Homo sapiens

<400> SEQUENCE: 173
aactagtggc tagcatcggc ttgacctgcc tcattcccct cgaataactg aagatcctgt        60
acaacaatgg agactctcgg aacatttatc cacagtgcaa ttacagaaag cagttcgtga        120
tttctctaga aataataaat atggctcact ggtgaccatt cccctcacgt gtcctctgtg        180
gtgcccacac gtgcgccggg atgtgcaggc gtggacgcag agacgcccct gtggaaagca        240
cacatgcggt gcacac                                                       256

<210> SEQ ID NO 174
<211> LENGTH: 99
<212> TYPE: DNA
<213> ORGANISM: Homo sapiens

<400> SEQUENCE: 174
tggaggtgcc acaaaaatca tctggtaaat tgtttaaagt aatcccaaat gcaactcaaa        60
tctacagaat cccaggtgaa gctcagtaat ctgtattttt                             99

<210> SEQ ID NO 175
<211> LENGTH: 227
<212> TYPE: DNA
<213> ORGANISM: Homo sapiens

<400> SEQUENCE: 175
```

```
tgtctcctcg tgtccgcatt gctggagctc cacctccctc ttggtttctc cgcacccgcc    60
cattttcctt ctgtctttac ctgcttcgta tcctttccct gctgatgtgg ctgacccctc   120
tcccacccct ccctgcaggc ggctggccag gtgggcaggt gccagccgga gctgtaaata   180
gagcgctgcg cttttgtgct ggtttgtgcg tgtgctgtat ttctgtg                  227
```

<210> SEQ ID NO 176
<211> LENGTH: 41
<212> TYPE: DNA
<213> ORGANISM: Homo sapiens

<400> SEQUENCE: 176

```
ccatgggcca caaatctcta caagtgcctg ctatccctct c                         41
```

<210> SEQ ID NO 177
<211> LENGTH: 270
<212> TYPE: DNA
<213> ORGANISM: Homo sapiens

<400> SEQUENCE: 177

```
gtatctgctc aagtagaagc ttccgtctct cttgtaacag gtcagtgctt cagttaccac    60
tgccattgaa ttacccactc gctatcactt gcctcttatt tccataaaaa aagaaacgga   120
ggaaaaaact gtttaagttt taccttgttt aaaagtaaca cgagtgcttt tgttattctg   180
taaactaaat acataaatga aggcaaagga aggaaactga gggaagggaa caaaatgtga   240
gtgatgaaaa cacggagttc attaaatgaa                                     270
```

<210> SEQ ID NO 178
<211> LENGTH: 191
<212> TYPE: DNA
<213> ORGANISM: Homo sapiens
<220> FEATURE:
<221> NAME/KEY: misc_feature
<222> LOCATION: (109)..(126)
<223> OTHER INFORMATION: n is a, c, g, or t

<400> SEQUENCE: 178

```
gcaggtcaaa aacctgccct cctgtgactt attccctgag acttttcagg agagccagcc    60
cacagatgat gaagaaatga tggaagttca tttggagagt caaatgggnn nnnnnnnnn   120 nnnnnnctgc ctttgataca ggcaattcag tggactataa aatagtggga gggttgagat   180
gtagagtttt t                                                         191
```

<210> SEQ ID NO 179
<211> LENGTH: 211
<212> TYPE: DNA
<213> ORGANISM: Homo sapiens

<400> SEQUENCE: 179

```
gtgctatggg aaccaggtgc caggtgaggc caggtgaaga caggtgaggc caggtgaaga    60
taggtgaggc caggtgaaga cagatgttac gggaaccagc aggtagaaag ctaagtgctg   120
tggagaaaga gcgggaagaa atggaggagg tgtctgggac aacagaactt gaaaagaacc   180
tgcttctcag tagccccaag tcctgtgtgt g                                   211
```

<210> SEQ ID NO 180
<211> LENGTH: 205
<212> TYPE: DNA
<213> ORGANISM: Homo sapiens

<400> SEQUENCE: 180

```
tgaagagcct tctgggtacc tagaggtgct gggaaggagt ttggatttaa tcttggctgt      60
cctgtgacag ggattcggag gccatgggg agggttgagc agggagacag gagacaggca      120
agaggcgctg tgagaagcgt gggctgagtg acctgctcct tggtgagtga aagtcctag      180 aactgagcac catggcatgc acctg                                            205

<210> SEQ ID NO 181
<211> LENGTH: 287
<212> TYPE: DNA
<213> ORGANISM: Homo sapiens
<220> FEATURE:
<221> NAME/KEY: misc_feature
<222> LOCATION: (235)..(248)
<223> OTHER INFORMATION: n is a, c, g, or t

<400> SEQUENCE: 181
atccttccac agtctgcaaa ccagttcctt ctgcagtgtt ttcctctggg agtgtcttgg     60
gctaagccac agcggtgtca ccccaccaca cacactgccc tgcaaaagga ctgccaatac   120
ccccagccca ttccccagcc tcacatataa ataaggactt gcgacccaga atcacatcca   180
gaagggaagt ttcacatggc ttggaatcct ttaaaaaagg acagcaaacc aaatnnnnnn   240
nnnnnnnncc ctccctaccc acaacatcca gcctgatccc gggaatt                  287

<210> SEQ ID NO 182
<211> LENGTH: 294
<212> TYPE: DNA
<213> ORGANISM: Homo sapiens

<400> SEQUENCE: 182
cgacagccct gtttcggtca ccagactctg aacatgctac atcctgccca agactgcacc     60
tctggaggtg cagggcaccc ttgagaagcc cctcacccct aggccgcctc caggtgctac   120
ccaggagtcc cctccatgta cacacacaca actcagggaa ggaggtcctg ggactccaag   180
ttcagcgctc caggtctggg acagggcctg catgcagtca ggctggcagt ggcgcggtac   240
agggagggaa ctggtgcata ttttagcctc aggaataaag atttgtctgc tcaa          294

<210> SEQ ID NO 183
<211> LENGTH: 193
<212> TYPE: DNA
<213> ORGANISM: Homo sapiens

<400> SEQUENCE: 183
atgagtactg agacctgacc actgcgttaa gcaacataga ggtcagtgtc catgacatgc     60
tggaaccaga gcttgattgc agttggttct agaaaaaaat ggggaggca atgtttgaga   120 gcatatatag acaactcttt tcaagggatt tgctataggg agaaaaaaag cgatgggaca   180
aaactagagg gac                                                        193

<210> SEQ ID NO 184
<211> LENGTH: 168
<212> TYPE: DNA
<213> ORGANISM: Homo sapiens

<400> SEQUENCE: 184
gaccagttta ggcaacatag tggaaccctg tgtctacaaa aaataaaaaa atttagctgg     60
gcattttggc atatgcctat agtcccagct acttgggagg ctgaggaggg aggatcactt   120
gagcccagga ggtcaagttt gcagtgaact acgattgcac cattgcat                 168
```

<210> SEQ ID NO 185
<211> LENGTH: 156
<212> TYPE: DNA
<213> ORGANISM: Homo sapiens
<220> FEATURE:
<221> NAME/KEY: misc_feature
<222> LOCATION: (131)..(131)
<223> OTHER INFORMATION: n is a, c, g, or t

<400> SEQUENCE: 185
gggcactcgc atttggtcat tctcttgaga gctaggaggg gtcagcctga ggccggagag    60
gaagggcttt tgcctggggt gagagggtga gagacttgac ctgaaagcag ctcctgcccc   120
tgaggtgcaa nccagagtcc tgtgtgcgga cagaga                             156

<210> SEQ ID NO 186
<211> LENGTH: 109
<212> TYPE: DNA
<213> ORGANISM: Homo sapiens

<400> SEQUENCE: 186
aatttttact attggtcatt tgcagaacag taaattctgt gtgttggtac agagtgctct    60
gtaccagtgc tcatcatccc ttcttcatac caacggtccc tagttatag               109

<210> SEQ ID NO 187
<211> LENGTH: 106
<212> TYPE: DNA
<213> ORGANISM: Homo sapiens

<400> SEQUENCE: 187
tagagatggg ttcttctggt tgatacagac tatgcattgc gtctagcaga tggggtaaac    60
tggcctaaaa caagtctttg cagaatacat gccaatttcc aaaaaa                  106

<210> SEQ ID NO 188
<211> LENGTH: 188
<212> TYPE: DNA
<213> ORGANISM: Homo sapiens

<400> SEQUENCE: 188
tctccctgcc tcacaggatt gtgactcccc agccctgcc ctcaaagctt cagacccctc    60
aggtagcagc aggaccttgt gatcttggcc ccttggatct gagatggttt tgcatctttc   120
caggagagcc tcacattctt cttccaggtt gtatcacccc cgagttagca tatcccaggc   180
tcgcagac                                                             188

<210> SEQ ID NO 189
<211> LENGTH: 148
<212> TYPE: DNA
<213> ORGANISM: Homo sapiens

<400> SEQUENCE: 189
ggtagccatt ggttcttgga tctgtgttag aatgagtgct ttcccttcct actgatgtga    60
ttgtggatta ggaattcgtg accgagtgat ttttggccag tggttgggtt taaaattcta   120
ttaaaatttg tagtttgggc tgggtgct                                      148

<210> SEQ ID NO 190
<211> LENGTH: 184
<212> TYPE: DNA
<213> ORGANISM: Homo sapiens

<400> SEQUENCE: 190

```
gaaggtttgg acgattattt gactcgcctg atagaagaaa gggatacttt gatgagaacg    60
ggtgtgtata atcacgagga tcgaataata agtgaactcg accgacagat cagagagatt   120
ttggcaaaaa gcaatgccag taattaataa catttggaaa agctttatag agactctaag   180
tcta                                                                184

<210> SEQ ID NO 191
<211> LENGTH: 123
<212> TYPE: DNA
<213> ORGANISM: Homo sapiens

<400> SEQUENCE: 191
ttgccaggca cggcggctca tgcctgtagt cgcaacactt tgggagacca aggcaggagg    60
atcacttgag tccaggagtt tgagaccagc ctgggcaaca tacagatgtc tacaaaaata   120
aaa                                                                 123

<210> SEQ ID NO 192
<211> LENGTH: 263
<212> TYPE: DNA
<213> ORGANISM: Homo sapiens
<220> FEATURE:
<221> NAME/KEY: misc_feature
<222> LOCATION: (65)..(76)
<223> OTHER INFORMATION: n is a, c, g, or t

<400> SEQUENCE: 192
tcatacaaca aatcccatct ctgtcccctg aaattcccct agtttcattc attagaaggg    60
gattnnnnnn nnnnnngact taaagagcac tttacagcag cattcagctt tcctatgaaa   120
tactcagcat cttaaatatt atatacaact ctttttttag taagctagac actggcttca   180
gagttcgtgg gagtggggga aatcaaccca ttcaaaacta ctctagaaat tgtcttttgg   240
cagaatagca ggtatccaag tta                                           263

<210> SEQ ID NO 193
<211> LENGTH: 45
<212> TYPE: DNA
<213> ORGANISM: Homo sapiens

<400> SEQUENCE: 193
agttctaggg gatatttgtg caataaatac acatgtcaac ttgaa                    45

<210> SEQ ID NO 194
<211> LENGTH: 125
<212> TYPE: DNA
<213> ORGANISM: Homo sapiens

<400> SEQUENCE: 194
aaagcaggta gttagttacc atttggagag ggattccgga acctagagag agatgaggct    60
gaagaggcgg gaagaaacca gatggcaagg actttgtctc atgcgcaaag catataattt   120
ataga                                                               125

<210> SEQ ID NO 195
<211> LENGTH: 233
<212> TYPE: DNA
<213> ORGANISM: Homo sapiens

<400> SEQUENCE: 195
agaggtaata tccttcctat tcttccttca cttctgcccc tcctcccacc tcttcccagc    60
```

```
ctccctcacc tgacctattt aggggtgat gggatgaaaa gaagagagtg aaggatatgt    120
aatcaagtgc aaaatactgt ggtaagtaca gagaatgaat aaggtggaaa ggaaagtgaa    180
aagtgtggga tggttagggg ctttaaggac ttcccaggaa aataggattc tgg           233
```

<210> SEQ ID NO 196
<211> LENGTH: 197
<212> TYPE: DNA
<213> ORGANISM: Homo sapiens
<220> FEATURE:
<221> NAME/KEY: misc_feature
<222> LOCATION: (142)..(142)
<223> OTHER INFORMATION: n is a, c, g, or t

<400> SEQUENCE: 196

```
gaccagggcc tctcctgtgg gatctttgtt ttgtgtttaa ccataatggt tgtgtactga    60
accacttcat atttgttata tataatatat atatatataa tctccttaag actcagcctc   120
ctggtttacc ccccggcct gngcatctga cctcccccac cccagtgtga tttaacatcc    180
aggaactgag gcctgaa                                                  197
```

<210> SEQ ID NO 197
<211> LENGTH: 289
<212> TYPE: DNA
<213> ORGANISM: Homo sapiens

<400> SEQUENCE: 197

```
taagagctgt ggaggactga aaactggata aaaggggggt ccttttcctt gccctgtct    60 ctcactcaga tgcgcttctt tttcgccact gtttggcaaa gttttctgtt aagcccccct   120 cccctgccc cagttctcca ggtgcgttac tatttctggg atcatggggt cagttttagg    180
acacttgaac acttcttttc cccccttccc ttcacagtaa ctggggcagg ggcctacggg   240
gaggggcttg tactgaacta tctagtgatc acgttaacac ctaactctc                289
```

<210> SEQ ID NO 198
<211> LENGTH: 195
<212> TYPE: DNA
<213> ORGANISM: Homo sapiens

<400> SEQUENCE: 198

```
ggactgcagc taagtgtcca ctccccaaag tcttcctatt cctaactcca tgacagctcc    60
tcagtagagc tttcctcctc agaagcaact agaacaatgc agttaacatt atttggcccc   120
aacggcgttt actgtgtatt ttggctgaga tctttagaag cccgaggcct aaacaattaa   180
ctgaggaaca tctaa                                                   195
```

<210> SEQ ID NO 199
<211> LENGTH: 213
<212> TYPE: DNA
<213> ORGANISM: Homo sapiens

<400> SEQUENCE: 199

```
ttactgaact acagcctggt ttgtagactt cctgtttcta cactgctgct cttccaccatt    60 ggaattcact gtggtattta tattactggc ttcagtccga gccacaggta ataaaaggat   120
atcatctgta tttctcaacc atatcatggt gtatagatgc tgttattcag gcgaacttgc   180
tcatgggtgg actaacacct ggtttggtac aga                                213
```

<210> SEQ ID NO 200
<211> LENGTH: 221

<212> TYPE: DNA
<213> ORGANISM: Homo sapiens

<400> SEQUENCE: 200

```
gagccatgat tgtgttactg ccttccagcc tgggcaacag agtgagactc catctcaaaa      60
aaaaaaaaaa gaaagaaaga aaatcagact ctgaggctgc aggcggtggc tcactcttgt     120
aatcccagca ctttgagagg ctgaggcagg aagattgctt gagcccagga gtttgagacc     180
aacttgagca acacagtggc accctatctc tacctaaaaa a                         221
```

<210> SEQ ID NO 201
<211> LENGTH: 278
<212> TYPE: DNA
<213> ORGANISM: Homo sapiens

<400> SEQUENCE: 201

```
ggagccgcca cggaattgcg aaagcccagc tacgcagaga tttgtcagag aacgagtaaa      60
gagcctcctt cttccccatt gcaaccccaa aaagaacaaa agccaaacac tgttggttgt     120
gggaaggagg aaaagaagct ggcagagccc gcagagagat accgggagcc cccagccctc     180
aagtccacac ctggagcccc cagagaccag aggcggccgg cggggggccg gccctcgccc     240
tcggccatgg ggaagcgtct cagccgagag cagagcac                             278
```

<210> SEQ ID NO 202
<211> LENGTH: 198
<212> TYPE: DNA
<213> ORGANISM: Homo sapiens

<400> SEQUENCE: 202

```
cgtgctacca tcacagctga atgcaatgaa aggcggtcct ctgagaggag cagggtggag      60
atgctaaagt ggaggccccg tcccattgct gatagatcct catctggcat gcgctccacc     120
ctccccattc tctgctccca cgtatcgtag ccccatcaca gaagatgcga catggaaaaa     180
cgcactgtgt ccacccta                                                   198
```

<210> SEQ ID NO 203
<211> LENGTH: 50
<212> TYPE: DNA
<213> ORGANISM: Homo sapiens

<400> SEQUENCE: 203

```
gctgtgccca acctgccatt aatcccatcc atcctgagcc cgacgtggtc                 50
```

<210> SEQ ID NO 204
<211> LENGTH: 217
<212> TYPE: DNA
<213> ORGANISM: Homo sapiens

<400> SEQUENCE: 204

```
ttttagcaac cagccagaga gggcgtgggt tcatgaaaaa cgggtacgag agtataaagg      60
tcataaacag tatgaagaat tactggctga ggcaaccaaa caagccagca atcactctga     120
gaaacaaaag attcggaaac cccgacctca gagagaacgt gctcagtggg atattggcat     180
tgcccatgca gagaaagcat tgaaaatgac tcgagaa                              217
```

<210> SEQ ID NO 205
<211> LENGTH: 175
<212> TYPE: DNA
<213> ORGANISM: Homo sapiens

<400> SEQUENCE: 205

```
cctcgtgggc acgtggagaa gggcccacgt gtctccacac gccagccaca ggggagccct      60
ggccaggcgc ccagccaggg gagcgtgtgc ctgggatggg tcacagaacc agcgggcacc     120
tgtgaggctg ccagcaccg tggggctgtg ggaatcgctc ttatttatat ttaaa           175
```

<210> SEQ ID NO 206
<211> LENGTH: 265
<212> TYPE: DNA
<213> ORGANISM: Homo sapiens

<400> SEQUENCE: 206

```
ttccaagtgc gacctcaaat gacaactttc tcaggtggtg cctggatagg aaaggcaccg      60
gaacagaatc tgtagaaaac caaacctatc atgatcagca ttcctacccg acgttaacct    120
cctagactag ctgaccttat ttattttgaa agcaaatcaa gtgtatacag tctcttttta    180
aaaaactgtg taaacgttgt aaagttttta ggggctgttt ataatctgaa gatttataaa    240
aaattactgg acttgttagg actat                                           265
```

<210> SEQ ID NO 207
<211> LENGTH: 223
<212> TYPE: DNA
<213> ORGANISM: Homo sapiens
<220> FEATURE:
<221> NAME/KEY: misc_feature
<222> LOCATION: (115)..(132)
<223> OTHER INFORMATION: n is a, c, g, or t

<400> SEQUENCE: 207

```
tgagatgatc agacaccgga gttcaacgtc ccagcagtct tggtaaaagg agggagccta      60
ctgagccagg agggagaaaa gaagattgac cagcttgcta gaaaaatact tagcnnnnnn    120
nnnnnnnnnn nngtggaggg gggacggaga ggaacaagga tggggaggta ggaatgaggt    180
atagaaaaga gatagcatct tctttggcac aagactagtg gct                       223
```

<210> SEQ ID NO 208
<211> LENGTH: 188
<212> TYPE: DNA
<213> ORGANISM: Homo sapiens

<400> SEQUENCE: 208

```
cccaggatgc gtcagtctgt tcagtggtca gcaggccccc cacccccgc cgactgccct       60
cgccatcgtg gtcagacccc cctcccaaca caacacgctg ctggtctgtg tcagcctttg    120
taacgtggga ggctctgccg tgtcttccgg gtgaactgta tttggattgc gcgcattgtc    180
acggtccg                                                             188
```

<210> SEQ ID NO 209
<211> LENGTH: 254
<212> TYPE: DNA
<213> ORGANISM: Homo sapiens

<400> SEQUENCE: 209

```
ataggtagca aagctaaggc ccagaaaggt taagtaattt tcccaaagtc acacagcttt      60
gatatacagc aaaactcata tccctgagct ttctactcac tgttcttccg gttattatcc    120
ctgaggtcat aaatctccac ccgcaaaccc aatagcacca gtacaagaaa tctggactgg    180
agatacttta tccacaccta ccactgcccc aaaaagtaaa atctgactct gtgattctaa    240
tgtaccaatg gtac                                                      254
```

<210> SEQ ID NO 210
<211> LENGTH: 158
<212> TYPE: DNA
<213> ORGANISM: Homo sapiens

<400> SEQUENCE: 210

```
atttttattg cagtaggagg aaatatattt aaaatatttg tagatttata gcaaatagag      60
actcgttatt taaaggttaa ataacaattt gttcttttgt tgttttttgcc agtttagggc    120 agtagctgct tttgtcataa atatcttcct accacatc                            158
```

<210> SEQ ID NO 211
<211> LENGTH: 135
<212> TYPE: DNA
<213> ORGANISM: Homo sapiens
<220> FEATURE:
<221> NAME/KEY: misc_feature
<222> LOCATION: (94)..(94)
<223> OTHER INFORMATION: n is a, c, g, or t

<400> SEQUENCE: 211

```
cttgagtaaa gacattttgc ttaatttctt ttttcttatt ccccacttgt atatcccta       60 ccagtaccgg gatctgcaca catctttttg cagntacctc ttcatagcca tgaaccaaaa    120
cgttctatga ggagc                                                     135
```

<210> SEQ ID NO 212
<211> LENGTH: 248
<212> TYPE: DNA
<213> ORGANISM: Homo sapiens

<400> SEQUENCE: 212

```
ccttcctgat tgtttacagt cattggaata aggcatggct cagatcggcc acagggcggt      60
accttgtgcc cagggttttg ccccaagtcc tcatttaaaa gcataaggcc ggacgcatct    120
caaaacagag ggctgcattc gaagaaaccc ttgctgcttt agtcccgata gggtatttga    180
ccccgatata ttttagcatt ttaattctct cccccctattt attgactttg acaattactc    240
aggtttga                                                             248
```

<210> SEQ ID NO 213
<211> LENGTH: 259
<212> TYPE: DNA
<213> ORGANISM: Homo sapiens

<400> SEQUENCE: 213

```
tcctgtcctt gcaggtaaga cctgctccgg ggtccccgcc ccgccgccgc acactcccgc      60
ggtcgtctgg gctgtcacta ggagatccgt agcccagacg gtgactttcg tatgagctat    120
ttaactttat tttcttcaga atctgctgta gattgagctg tgcgtgaaat tgctagtaag    180
ttctgacatg ttaatgcgtc tgtctttaaa tctgaattgt taccataaac gtgtttaatg    240
gaacttgctg gtctgtgga                                                 259
```

<210> SEQ ID NO 214
<211> LENGTH: 262
<212> TYPE: DNA
<213> ORGANISM: Homo sapiens

<400> SEQUENCE: 214

```
acctcatccc cgaataataa ctaagcacta gagtgatgct ggggatgctg gggcttggtt      60
```

```
taggtggctg gggaagttat cttggaggtg agactccagt ggactctgcg gatgggtaag      120
gtctcagaga ggttggggaa gttatcttgg aggtgagact ccagtggact ctgcggattg      180
gtaaggtctc agagaggttg aggttaagaa gagagcattc agaccattc caaaatcagc      240 acataacaca catggcttga aa                                               262

<210> SEQ ID NO 215
<211> LENGTH: 161
<212> TYPE: DNA
<213> ORGANISM: Homo sapiens

<400> SEQUENCE: 215
gtttctacag ttcacttgtc tgcatagagg tcgtgctgtg cctggcagta atctccactg       60
cccttcagaa actccataaa tgtgtgacca agaacaccac agaattgagg aatatgttta      120
ctcattgaag attgtggcct aatcatacag ccggtcccga g                          161

<210> SEQ ID NO 216
<211> LENGTH: 135
<212> TYPE: DNA
<213> ORGANISM: Homo sapiens

<400> SEQUENCE: 216
atgcaagtag gcagccagcc cgtctgttcc ctctccgccc cgccccgccc cgccccgtc        60 actgcgcttc tgttatacca tctttgcctg actctctacg gcttctccat tgaatggcta     120
atgtgtatgt gaaat                                                      135

<210> SEQ ID NO 217
<211> LENGTH: 278
<212> TYPE: DNA
<213> ORGANISM: Homo sapiens
<220> FEATURE:
<221> NAME/KEY: misc_feature
<222> LOCATION: (177)..(247)
<223> OTHER INFORMATION: n is a, c, g, or t

<400> SEQUENCE: 217
tacacaaact ttattacagg cacaaaatta tcaaaaatac ggtataaaat taccttaagg       60
ctatgtatat aagggatgtg tgtatgtgtg tatacacaca aaaataaatt ttgtgtttcc      120
acttggatcc cctccctaag ataactcatt gtgtacatgc aaatattaga aaatgcnnnn      180
nnnnnnnnnn nnnnnnnnnn nnnnnnnnnn nnnnnnnnnn nnnnnnnnnn nnnnnnnnnn      240
nnnnnnncta ttttatcacc attttcatgc tgtattaa                              278

<210> SEQ ID NO 218
<211> LENGTH: 242
<212> TYPE: DNA
<213> ORGANISM: Homo sapiens

<400> SEQUENCE: 218
aactgcatga tgcacctgct ccgctccctg cccgacccca acctcatcac cttcctcttc       60
ctgctggaac acttgaaaag ggttgccgag aaggagccca tcaacaaaat gtcacttcac      120
aacctggcta ccgtgtttgg acccacgtaa ctgagaccct cagaagtgga gagcaaagca      180
caactcacct cggctgcgga catctggccc catgacgtca tggcgcaggt ccaggtcctc      240
ct                                                                     242

<210> SEQ ID NO 219
<211> LENGTH: 205
```

```
<212> TYPE: DNA
<213> ORGANISM: Homo sapiens

<400> SEQUENCE: 219
gctcataaca aatataccag cattcatgat agcatttcag cattttccaa ggtaccaagt    60
gtacttattt tgttgttgtt gttgttgttg tattttagaa ggaattcagc tctgatgttt   120
ttaaagaaaa ccagcatctc tgatgttgca acatacgtgt aaaatgggtg ttacatctat   180
cctgccattt aaccccacag ttaat                                         205

<210> SEQ ID NO 220
<211> LENGTH: 94
<212> TYPE: DNA
<213> ORGANISM: Homo sapiens

<400> SEQUENCE: 220
tatccaacgg tatagatcac aagggggga tgttaaatgt taatctaaaa tatagctaaa    60
aaaagatttt gacataaaag agccttgatt ttaa                                94

<210> SEQ ID NO 221
<211> LENGTH: 273
<212> TYPE: DNA
<213> ORGANISM: Homo sapiens

<400> SEQUENCE: 221
gacaaagctc taggatgatg gctgaggggt agaagaaggg gcaagggaga cagaggtctt    60
ggagatgacg cccatatctc tggcatgagc aacccagatg gcaggggtg gggcctggtt   120 tgtgggaagg ggtgtcccac tagcagatgt gtacccagtg gaggtgcagc tcagattgga   180
gctggccatg ggtatttgaa aatcatgtgc gcacaggtag ccactgaagc catgggagtg   240
aaagagaaca cttggaaagt gaactctggg aaa                                273

<210> SEQ ID NO 222
<211> LENGTH: 168
<212> TYPE: DNA
<213> ORGANISM: Homo sapiens

<400> SEQUENCE: 222
tggaccgtcc aagaaggagc tacatcagag gttttggtag atgctgctgt agacctcata    60
tccgatgaat gggaagctgc taatgccata cccagcagag agaaggaagc aggatgcagc   120
cccgcttgag gccgccagcg tgccttctgc agactgtgag cagagcaa                168

<210> SEQ ID NO 223
<211> LENGTH: 277
<212> TYPE: DNA
<213> ORGANISM: Homo sapiens

<400> SEQUENCE: 223
agctttgcag ttataggctc taacctggac atgtcagaag ccaactacaa actgatggaa    60
cttaatctgg aaataagaga gtctctacgc atggtgcaat cataccaact tctagcacag   120
gccaaaccaa tgggaaatat ggtgagcact ggattctgag acacttcagg cctttagga   180 aagaaactaa actgaagatg atgaagaata ttaaccaagc accttttaat ggacccttgc   240
ttcactgata actttctggc agcatctact ttttagt                            277

<210> SEQ ID NO 224
<211> LENGTH: 290
<212> TYPE: DNA
```

<213> ORGANISM: Homo sapiens

<400> SEQUENCE: 224

| aggtctagga gatgcctgag cctccactga cctctgtgca tgtggcccac cagtggccac | 60 |
| tctgtccttt tggaaactgt cctctggctt tctaggaacc ccatgttttt ggtcttctcc | 120 |
| tctgcccct ccttctcagt ctcctcagca ggactctatt cctgtaccca ttcctaaaat | 180 |
| gtcacgaact cgtttctggc cttgtccttc tttgagtgca tctctggttc ttcatctatc | 240 |
| cctgttgaga tgctcaccct tctttggtga gctcccaacc ggtacaggta | 290 |

<210> SEQ ID NO 225
<211> LENGTH: 68
<212> TYPE: DNA
<213> ORGANISM: Homo sapiens

<400> SEQUENCE: 225

| aattgtgcct acctcagata gacagtgcca gaattaagtg agtcaagcca agtaaagccc | 60 |
| agagaaga | 68 |

<210> SEQ ID NO 226
<211> LENGTH: 105
<212> TYPE: DNA
<213> ORGANISM: Homo sapiens

<400> SEQUENCE: 226

| tcttcacaca gacaattcga tcagtccttc aggtcttaag tcacttctca agaatgccgt | 60 |
| acttgcctag gctagattag atcctactgt tacatgctcc cttta | 105 |

<210> SEQ ID NO 227
<211> LENGTH: 98
<212> TYPE: DNA
<213> ORGANISM: Homo sapiens

<400> SEQUENCE: 227

| tttagtaggt acgtcatgac aactaccatt tttttaagat gttgagaatg ggaacagttt | 60 |
| ttttagggtt tattcttgac cacagatctt aagaaaat | 98 |

<210> SEQ ID NO 228
<211> LENGTH: 206
<212> TYPE: DNA
<213> ORGANISM: Homo sapiens

<400> SEQUENCE: 228

| ggcggcgtcc ccagctggtt cgggctgtga cggggtggcc agcagggacg cgccccaggt | 60 |
| gggcagctgt ggcagagcag cgacccgcgg cggggcggca tccccagctg gttcgggccg | 120 |
| tgacggggcg gccagcaggg acgcgcccca ggtgggcagc tgtggcagag cagtcccgac | 180 |
| acctaaataa aagtcttgct gcagga | 206 |

<210> SEQ ID NO 229
<211> LENGTH: 99
<212> TYPE: DNA
<213> ORGANISM: Homo sapiens

<400> SEQUENCE: 229

| agataaattg ttgcctgctt ctgtgtctct gccagcctgt gatcatattg ggttagagtt | 60 |
| agaaatccgc tgtttgcctt tcttactggt aggatccctt | 99 |

```
<210> SEQ ID NO 230
<211> LENGTH: 147
<212> TYPE: DNA
<213> ORGANISM: Homo sapiens

<400> SEQUENCE: 230
atcctcgcca ttcgaatttc agttctgtac atctgcctat attccttgtg atagtgcttt    60 gcttttcat agataagctt cctccttgcc tttcgaagca tcttttgggc aaacttcttt    120
ctcaggcgct tgatcttcag ctctgcg                                       147

<210> SEQ ID NO 231
<211> LENGTH: 57
<212> TYPE: DNA
<213> ORGANISM: Homo sapiens

<400> SEQUENCE: 231
aaacgaactg taaaagacca tgcaagaggc aaaataaaac ttgaagtgaa tgcttaa      57

<210> SEQ ID NO 232
<211> LENGTH: 269
<212> TYPE: DNA
<213> ORGANISM: Homo sapiens

<400> SEQUENCE: 232
agcacgctac caaatctcaa aatatcctaa gactaacaca aggcagctgt gtctgagccc    60
aacccttcta acggtgacc tttagtgcca acttcccctc taactggaca gcctcttctg    120
tcccacagtc tccacgagag aaatcaggcc tgatgagggg gaattcctgg aacctggacc    180
ccagccttgg tgggggagcc ctctggaatg catgggcgg gtcctagctg ttagggacat    240
ttccaagctg ttagttgctg tttaaaata                                     269

<210> SEQ ID NO 233
<211> LENGTH: 204
<212> TYPE: DNA
<213> ORGANISM: Homo sapiens

<400> SEQUENCE: 233
catcatgttt ttgtgggcaa atacaagttg ttataattaa aaccctaat ttgaatattt    60 ttgttaccaa gaaccaaggc aaatgtttaa tttgttataa aacctgtttg tgaagtgctg    120
tgttaaattg tgctgctggc taataggcct catttcaatt taataaatat ttattgagga    180
ctggctttat gtctggccct gtgc                                          204

<210> SEQ ID NO 234
<211> LENGTH: 155
<212> TYPE: DNA
<213> ORGANISM: Homo sapiens

<400> SEQUENCE: 234
agtatctgat atgtgtgtgg aggcagccat cttttcctga aagtccttttt aggaatcatt   60 atttctggtc ctctgaagtt tgccgctacc actcataaat atctatccac accccttaca   120
agaagaataa ggaagatctt aagacctaga aggaa                              155

<210> SEQ ID NO 235
<211> LENGTH: 272
<212> TYPE: DNA
<213> ORGANISM: Homo sapiens

<400> SEQUENCE: 235
```

```
acttgaccta ggcagtgacc attctctccc actttcacac atgttcactt gacttccagg      60
ccatactctt agtttccatt ttacctcact gcctcactcg ttatcatctt ccttgcctcg     120
ttcctcaact ctctatgcta gagtacttca gggatcagtc cttgatcctc tccttttctc    180
tatacttact cctttgaggg tttatctagt ctcacagatt taaatatctt tgatatgctg    240
acaactctct aattatctaa ttcaccctgc cc                                  272
```

```
<210> SEQ ID NO 236
<211> LENGTH: 277
<212> TYPE: DNA
<213> ORGANISM: Homo sapiens

<400> SEQUENCE: 236
aaaatttctc tttgctcttt cgtagaaata aaacttaaca gttggatagg ccctgatccc      60
agctttctgg catgtctgag cataagcctg acagtctact tttccagctt tcactttttcc   120 tttaatcatc ctagccaaga gctcaaattc tggagcaaaa ttctggcaag gtccacacca    180
aggagcatag aaatcaatca cccaatgatt tttcccttgt agaactttt cactgaaagt     240 ctgaggtgtt agatctgtgg atacttgatc ccgggaa                             277
```

```
<210> SEQ ID NO 237
<211> LENGTH: 272
<212> TYPE: DNA
<213> ORGANISM: Homo sapiens
<220> FEATURE:
<221> NAME/KEY: misc_feature
<222> LOCATION: (106)..(189)
<223> OTHER INFORMATION: n is a, c, g, or t

<400> SEQUENCE: 237
ggcacaacat ttttgaggac aattaaaatt ttatatctac atagtcttca ccccaactct      60
tccatttcta gatatctatg ctacaggaat acttgcccac taagcnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnt ggggtgaccc tctaagtcct aggaaggaaa gaaattatga agtgaaagaa    240
tatcatataa gtgataccat gaagtgaaag aa                                  272
```

```
<210> SEQ ID NO 238
<211> LENGTH: 300
<212> TYPE: DNA
<213> ORGANISM: Homo sapiens
<220> FEATURE:
<221> NAME/KEY: misc_feature
<222> LOCATION: (36)..(213)
<223> OTHER INFORMATION: n is a, c, g, or t

<400> SEQUENCE: 238
ggagtagcca agactcctgt ttctctgcat ttttcnnnnn nnnnnnnnnn nnnnnnnnnn      60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnntgggggtc cctgttgccc agcatgcctg    240
gaccctcaac acttaatagt gataataaca tatatccaac ccttggtaaa tgccaggact    300
```

```
<210> SEQ ID NO 239
<211> LENGTH: 229
<212> TYPE: DNA
<213> ORGANISM: Homo sapiens

<400> SEQUENCE: 239
```

```
ggcctttagt taacatccga gtgacgaagc cgggttcccc agtacagctg tcttttgggt      60
gcggtcattg tgaggaaggg gatgagtgag tgtgggtgtg gctggaggag gagctagatg     120
ccggtggaca gtgggcaggt ggatttgggg aggagaggat cagcagcagc agaagtactc     180
agtgataggg ggctggctgg gtcaggaatg gtgagatgaa catgcaagt                229
```

<210> SEQ ID NO 240
<211> LENGTH: 51
<212> TYPE: DNA
<213> ORGANISM: Homo sapiens

<400> SEQUENCE: 240

```
acttgaaccc cgaaggcagt gtttgtggtg agcagaaatt gcttcattgc a             51
```

<210> SEQ ID NO 241
<211> LENGTH: 300
<212> TYPE: DNA
<213> ORGANISM: Homo sapiens
<220> FEATURE:
<221> NAME/KEY: misc_feature
<222> LOCATION: (203)..(203)
<223> OTHER INFORMATION: n is a, c, g, or t

<400> SEQUENCE: 241

```
gggccatggc actgctgttc agctcaggca caggggcaca gcagaggttt gggaagcggt      60
ctccccaccg gcactgggat tggcgggtcc aagcccagca accggcttcg ctccacaaca     120
cacaccacac ctgggactgt ttttaataca tagcaacaga ctgggttatt tatttaagat     180
gtgtattgtg tcatatgaag ttnaagagac ataaatggca ttttgttatt tattaagaca     240
aactccaatt gttctctggc tgttttttttc agttgtgtct agcaaatact tatctgccct     300
```

<210> SEQ ID NO 242
<211> LENGTH: 286
<212> TYPE: DNA
<213> ORGANISM: Homo sapiens

<400> SEQUENCE: 242

```
agactgactg ctaaactgta tgaatgatga ggggatttgc acgtataatc ttaactgtac      60
atcaaatgtt aatttttat tttatccact gtctttgaaa acctaactct tgactaagaa     120
ctgactttcc tgtacttgtt gttgactcta agtaaacttc caattccaca tagtccaaag     180
atgatgtgct gagaaatctc tcaaaggaaa aatgctaaga atacaggcag agttatgcgg     240
caaattttgc agaattaaca caattgcact tgtgagtatg aagcac                   286
```

<210> SEQ ID NO 243
<211> LENGTH: 109
<212> TYPE: DNA
<213> ORGANISM: Homo sapiens

<400> SEQUENCE: 243

```
atggacagaa cggagactag gttccgtaag aggggacaga ttacgggaaa gatcacgacc      60
agccgtcaac cccacccca gaatgagcag agtccccagc ggagcacct                 109
```

<210> SEQ ID NO 244
<211> LENGTH: 37
<212> TYPE: DNA
<213> ORGANISM: Homo sapiens

<400> SEQUENCE: 244
tttgttacat atgcaataaa ctcacgactt tacattt                                    37

<210> SEQ ID NO 245
<211> LENGTH: 34
<212> TYPE: DNA
<213> ORGANISM: Homo sapiens

<400> SEQUENCE: 245
ggaagtggac gcaaagtgga tgcggcagca gaaa                                       34

<210> SEQ ID NO 246
<211> LENGTH: 287
<212> TYPE: DNA
<213> ORGANISM: Homo sapiens

<400> SEQUENCE: 246
tggccatgca tgatggctta cacctgtaat tccaacactt tgggagtctg aggtgggagg           60
attgcttggg tccaggagtt taagaccagc ctggccaaca tggtgaaacc ctgcctctac          120
aaaaaataca aaaattaggc aggcatgatg gtgtgcacct gtggtcccag ctactcagga          180
tgctgaggtg ggaggatcac ttgagcctgg gagatggagg ttgcagtgag ccgtgatcat          240
gccattgcac tccagcctgg gtgacagggt aagaaactgt ctcaaaa                        287

<210> SEQ ID NO 247
<211> LENGTH: 196
<212> TYPE: DNA
<213> ORGANISM: Homo sapiens

<400> SEQUENCE: 247
tggagtgcat aggtagcagt gcttctcccc caaggctggg gcgatggaat cagttagact           60
attgagggca tctggaaggg catctgtgtc agggttagtc ctcagggtat ggtggccaat          120
gggtttcttt tggttgactg ttgacaatgc gtttgttgaa tggcagcctg cactaggtga          180
cgctgaagcc acagaa                                                          196

<210> SEQ ID NO 248
<211> LENGTH: 189
<212> TYPE: DNA
<213> ORGANISM: Homo sapiens

<400> SEQUENCE: 248
ttcattccca caaaaacctg aggcagctct tttgcccaga gcgttccctg tagccacccc           60
caccccactt gcccttggtt ctttagaagg agcacacaca tcccttgatt cctccctgat          120
gtggtaaact ggcacactcc aggggtctaa aacataaaac agttgtgttt agggaacctt          180
aagtcatgc                                                                  189

<210> SEQ ID NO 249
<211> LENGTH: 35
<212> TYPE: DNA
<213> ORGANISM: Homo sapiens

<400> SEQUENCE: 249
acagaggctt cttcagatca gtgcttgagt ttggg                                      35

<210> SEQ ID NO 250
<211> LENGTH: 247
<212> TYPE: DNA
<213> ORGANISM: Homo sapiens

<400> SEQUENCE: 250

```
attctgcatg attcacggac taggagtccc tggtcaaaaa cttcaaaaac taagtgatgg    60
gtcccaagtt actcagtggc agaaacttga ttcagtaaca tgtcagcttg tgggcttgaa   120
aagtcttaag tgtctctact tcttctatcc ttgtgctttc ccgggacttt acacaatccc   180
acctcccact ggacaattgt caaatcccag agagtatggg aagtctgttc atctctgatc   240
accataa                                                              247

<210> SEQ ID NO 251
<211> LENGTH: 282
<212> TYPE: DNA
<213> ORGANISM: Homo sapiens

<400> SEQUENCE: 251
gacggtccgc cgtgcccaag aggaacggga tgacattcaa ctgggacttg cctcaccttg    60
gcttggggga cctcgagagc ggtcccgtgg gggcagtgtt actcgtggtg gtagaagtgg   120
agggcgtgtc cgggtacttg agttcatggg catctctccc gccgcctctc agcctatctg   180
caccatgtct cacacgttca gttgcagctc ttaccgtttt gaaggcgcac gtgggcaaga   240
agtcctgggc agcacaagaa agtcaatcac gttgagacag ag                      282

<210> SEQ ID NO 252
<211> LENGTH: 226
<212> TYPE: DNA
<213> ORGANISM: Homo sapiens

<400> SEQUENCE: 252
gactctagcc acagcctaac caaggattat caaaggaggt ggacactcaa ggaagggcca    60
cgccaggctg cgtttcctgc aaggactcag atgttcagta ccttatgata cagggaagat   120
agttttctta caagtagttt ggtaatattt ttttcttaa gttgtacatt tgactcagct   180
gtcaaatttc tcacacttgt atatatctac acacaactaa gttaaa                  226

<210> SEQ ID NO 253
<211> LENGTH: 188
<212> TYPE: DNA
<213> ORGANISM: Homo sapiens
<220> FEATURE:
<221> NAME/KEY: misc_feature
<222> LOCATION: (135)..(144)
<223> OTHER INFORMATION: n is a, c, g, or t

<400> SEQUENCE: 253
gggaacaggg aatgccgatt ttatatacat ggtacacaga gagggtgtc acttcacaaa     60 atcttccagc atgttcttca gaatattaat ttatatgcga ggtgaggttg ggaatgaaaa   120
gaacaggtca gcacnnnnnn nnnncctata acatacaaaa gaacatggtg gactttcagg   180
gagtgcaa                                                             188

<210> SEQ ID NO 254
<211> LENGTH: 269
<212> TYPE: DNA
<213> ORGANISM: Homo sapiens

<400> SEQUENCE: 254 gagattttg tggtcggtgt attcgagaat tccttaaatg gtccattaag caaataacac     60
cacagcagca ggagaagagt ccagtaaaca ccaaatcgct tttcaagcga ctttatagcc   120
ttgcgcttca ccccaatgct ttcaagaggc tgggagcatc acttgccttt aataatatct   180
```

```
acagggaatt cagggaagaa gagtctctgg tggaacagtt tgtgtttgaa gccttggtga    240
tatacatgga gagtctggcc ttagcacat                                      269

<210> SEQ ID NO 255
<211> LENGTH: 273
<212> TYPE: DNA
<213> ORGANISM: Homo sapiens

<400> SEQUENCE: 255
ttccttctga gtttgctgtt ggtgcaggaa taagggaaag gcccaaggta tccaagcctg     60
gggaagggca ggccagccag cacctctgcc ttctcaggga caagagtagt cctttaccac   120
cctcactctg cctgtcccct ctcctactct acagcattaa agactgtggg accaggaccc   180
taagtctcct ttccttctgg gtggggagtt ctggggttct tggtgtgtgg gagaagtttt   240
ataattgctt ccaaacagct gggtttaaat ata                                273

<210> SEQ ID NO 256
<211> LENGTH: 279
<212> TYPE: DNA
<213> ORGANISM: Homo sapiens

<400> SEQUENCE: 256
ttctggatgt atcttcagga gcattagcat tccctggtag gttgaagatg ggccagtaag     60
ggaaacagaa gggtcaaagg tgatgccaag attttttgccc aaagcacctg aaagatggag  120
ttgcccatga ctaagatggg gaagcacggg gtcagcaccg atttgggggg aagatcagga   180
tttcattctt ggatgtgctg agtttgaaac atctgagtca tatccaagtg aagagtttga   240
ataggccgtt ggatatattt aggataaaag cctgggcta                          279

<210> SEQ ID NO 257
<211> LENGTH: 174
<212> TYPE: DNA
<213> ORGANISM: Homo sapiens

<400> SEQUENCE: 257
accagcgcat cctcgagttc tttggcctga agaaggaaga gtgcccggcc gtgcgcctca     60
tcaccctgga ggaggagatg accaagtaca agcccgaatc ggaggagctg acggcagaga   120
ggatcacaga gttctgccac cgcttcctgg agggcaaaat caagccccac ctga          174

<210> SEQ ID NO 258
<211> LENGTH: 109
<212> TYPE: DNA
<213> ORGANISM: Homo sapiens

<400> SEQUENCE: 258
cgtgctacca tcacagctga atgcaatgaa aggcggtcct ctgagaggag cagggtggag     60
atgctaaagt ggaggccccg tcccattgct gatagatcct catctggca               109

<210> SEQ ID NO 259
<211> LENGTH: 167
<212> TYPE: DNA
<213> ORGANISM: Homo sapiens

<400> SEQUENCE: 259
tgatctagag gtccccttc ggaaataggg aagactgtct ctgaagaagg aggaagtgta      60
gcttatggga ggctgaggag tttgagtttt tccttgtgg gaaggtggga gccatggagg    120
ctgaagacag ttgtccaact cagggcatac aaattgatga ggaactc                 167
```

<210> SEQ ID NO 260
<211> LENGTH: 155
<212> TYPE: DNA
<213> ORGANISM: Homo sapiens

<400> SEQUENCE: 260
ctgcccctcg agtgagactg ggacaagatg ctctgctgga cttgagctttt gcctacatgc      60 ccccacctc cgaggccgcc tcatctctgg ctccgggtcc ccctcccttt gggctagagt      120
ggcgacgcca gcacctgggt aagggacatc tgctc      155

<210> SEQ ID NO 261
<211> LENGTH: 37
<212> TYPE: DNA
<213> ORGANISM: Homo sapiens

<400> SEQUENCE: 261
gtgagccaag ttcgaactcc tgcattccaa ccagcct      37

<210> SEQ ID NO 262
<211> LENGTH: 110
<212> TYPE: DNA
<213> ORGANISM: Homo sapiens

<400> SEQUENCE: 262
gatgggataa tttgggaggc ttctcattct ggcttctatt tctatgtgag taccagcata      60
tagagtgttt taaaaacaga tacatgtcat ataatttatc tgcacagact      110

<210> SEQ ID NO 263
<211> LENGTH: 190
<212> TYPE: DNA
<213> ORGANISM: Homo sapiens

<400> SEQUENCE: 263
accaaatacc acaggttctc agttgtgagt gggagctaaa tgatgagaac tcatgaacac      60
aatgaaggga acagacacta gggtctactt gagggtggaa gatggaagaa gggagaggag      120
cagaaaaagt acctattggt gatgaagtac tctgtacaac aaacccgtga caagagtttc      180
cctatataac      190

<210> SEQ ID NO 264
<211> LENGTH: 291
<212> TYPE: DNA
<213> ORGANISM: Homo sapiens

<400> SEQUENCE: 264
aacagctgct tttggtatca ataccctgtt ggttattagt ttaaaatttt agtcaatgat      60 gcttttggg tgggtgtgaa gggggaagaa aatcttgagc atgtaatgac ttaaattgtt      120
tcccaaatca aattaaattc tgggccagta taagacctac acactcacat ttcacaagtg      180
agggcatgga tgggggtagg ggcaggcagg gaaaggagaa aagaggacaa tcagcacccc      240 tgagggctg aacataggg gcatccaaaa cgtgcttgct gtgggaagaa t      291

<210> SEQ ID NO 265
<211> LENGTH: 263
<212> TYPE: DNA
<213> ORGANISM: Homo sapiens

<400> SEQUENCE: 265

```
cattttggat gacgacacga tcataaccac tctggagaac ctgaagagag aggctgcaga    60
ggtcaccagg aaagttgagg agacggacat tgtcatgcag gaggtggaga ccgtgtccca   120
gcagtacctc ccgctctcca ccgcctgcag cagcatctac ttcaccatgg agtccctcaa   180
gcagatacac ttcttgtacc agtactccct ccagttttc ctggacattt atcacaacgt   240
cctatacgag aacccgaacc tga                                          263

<210> SEQ ID NO 266
<211> LENGTH: 144
<212> TYPE: DNA
<213> ORGANISM: Homo sapiens

<400> SEQUENCE: 266
atgacataca gtgcatggct cacaatccca ggagatgagg gcagcacagc tgcagagcaa    60
cacagagtgg ggagaacatc caggatgcac attcaaccag caggtgggga gcaagacaga   120
cagggacctg tgggccaaag cgtt                                         144

<210> SEQ ID NO 267
<211> LENGTH: 248
<212> TYPE: DNA
<213> ORGANISM: Homo sapiens

<400> SEQUENCE: 267
taggcttagc ttgatttctg ggcccactgt ctgtgttctt aagatgccaa cctgttgctt    60 ttttttttt ttttcccca tttaaaagga tagtacctac tccctctaac cacctcaccc    120
cattcttgaa tgcattttta tccttcggaa agaacaaggc tgtgatgtag tgactattgt   180
ctgtgtctcc tgtgtgtgtc tgttcttgtc acaaatgtat ttggggacgt tggatgcatt   240
cattttct                                                           248

<210> SEQ ID NO 268
<211> LENGTH: 45
<212> TYPE: DNA
<213> ORGANISM: Homo sapiens

<400> SEQUENCE: 268
gccccactgt cactaactgt aaactcaggc tcaggcttca actgc                   45

<210> SEQ ID NO 269
<211> LENGTH: 265
<212> TYPE: DNA
<213> ORGANISM: Homo sapiens

<400> SEQUENCE: 269
aagattcttc tttgtatatg aggatggtca ggtgggcgat gccaacatta atactcagga    60
ccccaagata cagaaggaaa tcatgcgtgt gatcggaact caggtttaca caaactgagg   120 gggcccagc cctcgtacca cccctgttac cccaggatcc atctgccctc ataaagtgt    180 tcaggtacag cagctgaggc tgccctgagg aatcaagggg ccattaccaa ggggcaggaa   240
aaggatatgt aagaggtggc cttca                                        265

<210> SEQ ID NO 270
<211> LENGTH: 33
<212> TYPE: DNA
<213> ORGANISM: Homo sapiens

<400> SEQUENCE: 270
ttgcagcgag tcaggatcgc agcactacac tcc                                33
```

<210> SEQ ID NO 271
<211> LENGTH: 234
<212> TYPE: DNA
<213> ORGANISM: Homo sapiens

<400> SEQUENCE: 271
ttcacaggaa gtaggtaaac accgaaattt agtcagtgtc attattagag ttgtgctttc    60
ataaaaagaa tctctcaagt gtgacaaggc taaattagaa agaagagact ggaggtagag   120
gccagttagg agatccttgt aataatccac agttgatgga atgaggatct atagtagcca   180
ggctggaggt aacaaagagg gacaggaggg caggagtact ctactttaaa gtag          234

<210> SEQ ID NO 272
<211> LENGTH: 61
<212> TYPE: DNA
<213> ORGANISM: Homo sapiens

<400> SEQUENCE: 272
agttgttaag tgtatcagat gtgttgggca tgtgaatctc caagtgcctg tgtaataaat    60
a                                                                    61

<210> SEQ ID NO 273
<211> LENGTH: 157
<212> TYPE: DNA
<213> ORGANISM: Homo sapiens

<400> SEQUENCE: 273
gtggttgtca tgtgatgggt cccctccagg ttactaaagg gtgcatgtcc cctgcttgaa    60
cactgaaggg caggtggtgg gccatggcca tggtccccag ctgaggagca ggtgtccctg   120
agaacccaaa cttcccagag agtatgtgag aaccaac                            157

<210> SEQ ID NO 274
<211> LENGTH: 293
<212> TYPE: DNA
<213> ORGANISM: Homo sapiens

<400> SEQUENCE: 274
ggagacatcg atctcttttg caaattccct cacagcctca ttagggtctt cataagtgaa    60
ggggtcgatg tagaccttag taccatgtcc gatgagatac tgtccgtgtt tgtccgaata   120
ttctgcttct ctcccattgc tctgcttcct gaggcagaga actgcgacca caatgaccac   180
caggaccagg accacaccca cgactgccgt gcccgcaatc agggccagct gctcccgcca   240
gccctcgctc tcatccagtt gggtccggct gtgatgttcc tggccgaagg gcc          293

<210> SEQ ID NO 275
<211> LENGTH: 253
<212> TYPE: DNA
<213> ORGANISM: Homo sapiens

<400> SEQUENCE: 275
ggagtttgtg actagatggg caatatagta agatgtcatc ttttaaaaat gaaaaaatta    60
gctggccact gtggcacacg cctgtagtcc cagctacttg ggaagctgag gtaggaggat   120
tgcttgagcc caggagttca aggctgcagt gagctatgat tgtgcttatg aatagccact   180
gcactccagt ctgggcaata gtgagtcggt caaattccat ttccccctcc gccccatacc   240
tcttcaaatg ttt                                                      253

<210> SEQ ID NO 276
<211> LENGTH: 195
<212> TYPE: DNA
<213> ORGANISM: Homo sapiens

<400> SEQUENCE: 276
actgcatcag gtctcagtgt ccctatctgt aagatcaaca agaaacacgg ttaagggagg    60
tcgtcactgg ggtgggagaa gaggggctgg tagaccgaag ccttgtgcat aaggattttt   120
tcccaggaaa agatagactt tataaacagt gggagcccat gaacaaacat ataaaagtag   180
caacagataa tgacc                                                     195

<210> SEQ ID NO 277
<211> LENGTH: 195
<212> TYPE: DNA
<213> ORGANISM: Homo sapiens

<400> SEQUENCE: 277
tattgtaact cttccgccct tttcaggcgc agacaacaga acaaagtata gaggaacaac    60
aaaatatata attagccctc cctcccccc ataaagcaat tcacggatac agaatacatt    120
ctcttcacag taaacctaag aacacttgta acaattgccc cagcgcgca tgctaactaa    180 agtaacctct tttga                                                     195

<210> SEQ ID NO 278
<211> LENGTH: 297
<212> TYPE: DNA
<213> ORGANISM: Homo sapiens

<400> SEQUENCE: 278
tactgcttgc atatcctttc ctcagctaac cgtcctcctg ggcccttctg cttctgaccc    60
cctcaggacc ttaggacata atcactccct gcttctatct tcagtatctc ctcattacaa   120
ataaagcatt tgctgcagct catttaactc ttgtgtccac agtgagtctc ttccattact   180
taatcacact taattctctg tcctgactcc tgtccccagc cttttctttc actttgcccg   240
tctgtcaggc tctcatgctt ctccatttgg caacttcagg aaggtacgcg agctccc      297

<210> SEQ ID NO 279
<211> LENGTH: 256
<212> TYPE: DNA
<213> ORGANISM: Homo sapiens

<400> SEQUENCE: 279
gccagtcacc ctgcggatcg agagagggg tagagtcttc ttcaaatggc agttttactt    60
caaatggcag atttcacaag agttggttat ttttttacaat ggtttaggtt gttaagtctc   120
ctttgtatgt aaggtagttt tttcaacatc taaaattttt gttttagcct tcaaaaccaa   180
cttaccaacc tcagtccagc tgggaaggca gcgttgatta tggtagtttg tcaagaatat   240
atggacctgg aaacac                                                    256

<210> SEQ ID NO 280
<211> LENGTH: 223
<212> TYPE: DNA
<213> ORGANISM: Homo sapiens

<400> SEQUENCE: 280
cactgctcag ggttggaggc tcagtcccct tgccctgtct gttccagctc tggagctaac    60
tcagggatcc ctgatcaggg ttacataggt ttggtaaaat gagtgctgga aattaacttt   120

```
ctcccagtag tcttaggtca tgctcagtga acttaaactt tatccagata tggttttcct      180
tcagcctttc tattcccttt ctagccagtg aaagacccgc tgc                        223

<210> SEQ ID NO 281
<211> LENGTH: 140
<212> TYPE: DNA
<213> ORGANISM: Homo sapiens

<400> SEQUENCE: 281
cgagagtata tcagttaaag ggtaagaaat gtagacccca tattttaatt cagtagcacc       60
agttcaaatc cagttattca gaattaacaa agcaactgtt gctcaaaaaa atgccaataa      120
actcccgagc caactgagat                                                  140

<210> SEQ ID NO 282
<211> LENGTH: 112
<212> TYPE: DNA
<213> ORGANISM: Homo sapiens

<400> SEQUENCE: 282
accaaggagc tggtcagacg gccctttcta atcctacatg ttgagcttat gtaaaaaatg       60
ttgtttcctc ctgttttttgg ttcctttctt acccacaaac cattactact tg             112

<210> SEQ ID NO 283
<211> LENGTH: 34
<212> TYPE: DNA
<213> ORGANISM: Homo sapiens

<400> SEQUENCE: 283
caacagagtg agacttaatc ttgaaaaata aata                                   34

<210> SEQ ID NO 284
<211> LENGTH: 166
<212> TYPE: DNA
<213> ORGANISM: Homo sapiens

<400> SEQUENCE: 284
agtagagggc cctcaaccca cacactggct gaaactgcca ccaactgcca cgatgaaccc       60
aactgctgtt tatgccccca ttttcctttt tttgtatcta cacccacacg attcccaatg      120
ttggatattt ctacatgaat aaagcaagga tcagtgcctc ttatgt                     166

<210> SEQ ID NO 285
<211> LENGTH: 288
<212> TYPE: DNA
<213> ORGANISM: Homo sapiens
<220> FEATURE:
<221> NAME/KEY: misc_feature
<222> LOCATION: (78)..(157)
<223> OTHER INFORMATION: n is a, c, g, or t

<400> SEQUENCE: 285
agggcaaaac aggagatgag gaaatgttaa aggataaagg aaagccagag agtgagggag       60
aggcaaaaga aggaaagnnn nnnnnnnnn nnnnnnnnn nnnnnnnnn nnnnnnnnn          120 nnnnnnnnnn nnnnnnnnnn nnnnnnnnnn nnnnnntga aggagagcca gggagtgaaa      180
caagggctgc aggaaagcgc ccagctgagg atgatgtacc caggaaagcc aaaagaaaaa      240
ctaataaggg gctggctcat tacctcaagg agtataaaga ggccatac                   288

<210> SEQ ID NO 286
```

<211> LENGTH: 276
<212> TYPE: DNA
<213> ORGANISM: Homo sapiens

<400> SEQUENCE: 286

```
tgtggggtga cagttttaca tttacttttt cttcttaatg cagctggatc taagtaaaat    60
gttttgaagt ttatcagaaa ctaaatgtac ttttaaaacg tatagggtca gggttggggg   120
aaaaatacag gtatagtaag taagaaaagt gacccatgaa gaaagcatcg tgaggttgta   180
tgttggttga ctgtgattaa aatgcggggc tggtgtaagt tgtaagtggt ggctgattgc   240
cgtgtactat gtacatgatt gttgggatgg ctgtcc                             276
```

<210> SEQ ID NO 287
<211> LENGTH: 183
<212> TYPE: DNA
<213> ORGANISM: Homo sapiens

<400> SEQUENCE: 287

```
gaaaacctat aacatgatga gtaagagttc tatggtagag aggtaggaga ggaaaggtga    60
aaactgccac aagccaaatg agactgcagc aaagtatgta aggagcctgt tctcaggtcc   120
acccacatcc agctatcacc ctctctgacc gccttttccc atgagcctga aagggtcaca   180
gac                                                                 183
```

<210> SEQ ID NO 288
<211> LENGTH: 295
<212> TYPE: DNA
<213> ORGANISM: Homo sapiens

<400> SEQUENCE: 288

```
gacgcacaac cttcaacact aattgccctt tactaagccg accagggcta gacactaagc    60
cagaaaagcc ttttccagag tttcctcttc cgcacaaaag ctttccttct gtcactccac   120
ccaaccaccc agctcctccc ttaagtgttt gaaagatat tctaaaagtc tcctccccg    180
aaccgctgcg tttcttaagg ccacaccatt ttaaaaatac tgtattgctt ttgccaggct   240
gttgggacct cttccatctc atttctatct aagagtggtt ggtacacacg aggac        295
```

<210> SEQ ID NO 289
<211> LENGTH: 285
<212> TYPE: DNA
<213> ORGANISM: Homo sapiens

<400> SEQUENCE: 289

```
aaagcagatg ggtgtgttca gacaagatct ggaagctgtg gcatggcaga caaagggaga    60
tgggaccccct ttggcactgg aggaagaggc ttgaatcttc ttggagcact aaaagttcca  120
aaagacctaa gcagaaaatg cttccgaaga ggaggatctg tatggcaaga tgactgtaat   180
caggctcata aaagtaagac cttacataaa tacaagtgag ggggaagaca tttcatgtag   240
gaggaatggc tcaagcaaaa ataccaaggc gggaaattgc gtggt                   285
```

<210> SEQ ID NO 290
<211> LENGTH: 129
<212> TYPE: DNA
<213> ORGANISM: Homo sapiens

<400> SEQUENCE: 290

```
agaagttttg agaagcagtt ttgtttgggt caaggggtac tttcaaatta cacttatgag    60
tcagtatcta taaaaagttt cagaagtacc tacaatttag ccctctacat ccaagcagta   120
```

```
gctttgcag                                                                    129
```

<210> SEQ ID NO 291
<211> LENGTH: 70
<212> TYPE: DNA
<213> ORGANISM: Homo sapiens

<400> SEQUENCE: 291

```
cagtgagcta taatacaagg cttcattgca ctccagccta ggcattagag cgagaccgtg    60
tttatttaaa                                                           70
```

<210> SEQ ID NO 292
<211> LENGTH: 135
<212> TYPE: DNA
<213> ORGANISM: Homo sapiens

<400> SEQUENCE: 292

```
gcagatgcag gaaacaccta gagcagcccc agagtcacgg ggctgagggg gcgggagctg    60
cccctgtcat agggaggggg attcccagcg tctgtagtgc ttcctgtttg ctgaataaag   120
gtctctttct cacac                                                    135
```

<210> SEQ ID NO 293
<211> LENGTH: 156
<212> TYPE: DNA
<213> ORGANISM: Homo sapiens

<400> SEQUENCE: 293

```
cagaaatgtt agtgccgtgc tctaaccaag taagcttagt gttccccaca gtgatctgta    60
tctggcctga gtctcctcaa gcagcaaccc ccactgtcca gcatgtggaa ggtagatcct   120
tatgacaaca ccagacccat agttaccagg aaagaa                             156
```

<210> SEQ ID NO 294
<211> LENGTH: 175
<212> TYPE: DNA
<213> ORGANISM: Homo sapiens

<400> SEQUENCE: 294

```
gtgtttaagg gcatttcaca gatgggaaat aaggtgcaga gggctagaga gatgggctca    60
aggctgtggt gccagtgaca ctggcttccc ctgtgttgtc ctttgctctt gaacatcacg   120
ccacgcagca gcagaacaaa gataaagaac caattccaaa accaggcgtg gtggc        175
```

<210> SEQ ID NO 295
<211> LENGTH: 112
<212> TYPE: DNA
<213> ORGANISM: Homo sapiens

<400> SEQUENCE: 295

```
ggccgagaag atgctgggca cccacccagc accccatct accaacacca gcggctgggg     60 gcggggcgg accttgtgag gctcagttga cccgttactt gcaacctgaa aa            112
```

<210> SEQ ID NO 296
<211> LENGTH: 149
<212> TYPE: DNA
<213> ORGANISM: Homo sapiens
<220> FEATURE:
<221> NAME/KEY: misc_feature
<222> LOCATION: (46)..(86)
<223> OTHER INFORMATION: n is a, c, g, or t

```
<400> SEQUENCE: 296
caagaatctg gcatttctct tcagttatct tatatgtaca tataannnnn nnnnnnnnnn      60
nnnnnnnnnn nnnnnnnnnn nnnnnnggag atgaaggtct cagtctctta cccactgcac     120
tctagcccag gcggtaagag agactccat                                       149

<210> SEQ ID NO 297
<211> LENGTH: 239
<212> TYPE: DNA
<213> ORGANISM: Homo sapiens

<400> SEQUENCE: 297
cctctacgcc agagaaggga atggagaggt caggctggct agagagtggg gttgagtcgt      60
ccatgccctt gaatgccagg atgagggcta aagagtcaaa tggaatgggt gacttcatat     120
gcagaagttt ttacaagaga agagaactca gttgggccaa gagaagtggg gtcgtcatgt     180
gggtaatcac gtaacagtga tcgttcagtc atgcggaatg ctttcaaggt gttggacac     239

<210> SEQ ID NO 298
<211> LENGTH: 278
<212> TYPE: DNA
<213> ORGANISM: Homo sapiens

<400> SEQUENCE: 298
cctctacgag gtgtgctatt ctcatcctca tcttataggc aagttaactg aggtataagg      60
aggttggtta tgtaacttga ccaaagtcac acaataaggg actgggagat ctgggatttg     120
agccctggca gatggactcc atccaaagtc ctcactatcc tagcacctct ctatcccctc     180
cctttcctct ctcctacctt cttctgtgct gctttcaaac agacagttat ctctaccctt     240
aaaaacacag ctgtgctgac tactctgctt agatgccc                             278

<210> SEQ ID NO 299
<211> LENGTH: 145
<212> TYPE: DNA
<213> ORGANISM: Homo sapiens
<220> FEATURE:
<221> NAME/KEY: misc_feature
<222> LOCATION: (79)..(112)
<223> OTHER INFORMATION: n is a, c, g, or t

<400> SEQUENCE: 299
cctctgggac aagtaagtca atgtgggcag ttcagtcgtc tgggtttttt cccctttttct     60 gttcatttca tctggctcnn nnnnnnnnnn nnnnnnnnnn nnnnnnnnnn nntgcttccc     120
ctcactgccc aggtcgatca agtgg                                           145

<210> SEQ ID NO 300
<211> LENGTH: 42
<212> TYPE: DNA
<213> ORGANISM: Homo sapiens

<400> SEQUENCE: 300
tggtcaagaa ggactatgac gcccttcgga agaggtacag tg                        42

<210> SEQ ID NO 301
<211> LENGTH: 256
<212> TYPE: DNA
<213> ORGANISM: Homo sapiens

<400> SEQUENCE: 301
agaatagcaa ctggctcagt cctttaggtg tctacactaa tatcaaagga acaggccagg     60
```

```
cccaaggaga gagagggaat atgtttctgt gcctgatcct ttctctagat tttatctcag    120
ttgtatgaca ttgaagcacc tgactgagca attgagcatg atgtgttctc ctgaccatcc    180
ttctaaaacc attttccacc agttctacc ttctgatggc gctttagtca cctgcactta     240
caaacaggtg cccaaa                                                    256

<210> SEQ ID NO 302
<211> LENGTH: 274
<212> TYPE: DNA
<213> ORGANISM: Homo sapiens

<400> SEQUENCE: 302
ggctctgatg atggaccctc agtgatggat gaaacaagca atgatgcctt tgattcttta    60
gaaaggaagt gtatggaaaa agaaaaatgt aaaaaaccct ctagtttaaa acctgaaaag    120
attccttcca agagcctaaa gtcagcccgt cccattgccc ctgccatccc cccacagcaa    180
atctacacct tccagacagc caccttcaca gcagcgagcc caggctcttc ctcaggcttg    240
accgccacag tggcacaagc catgcccaac agtc                                274

<210> SEQ ID NO 303
<211> LENGTH: 78
<212> TYPE: DNA
<213> ORGANISM: Homo sapiens

<400> SEQUENCE: 303
ttttcatgca gattagttag aattcactgc caggtttctt ctgcccacca aaatgatcca    60
gtctggaata acattttg                                                  78

<210> SEQ ID NO 304
<211> LENGTH: 137
<212> TYPE: DNA
<213> ORGANISM: Homo sapiens

<400> SEQUENCE: 304
gtaggctagg gatcatgggg gaatagttag taatgacagg gatagttgaa cttaaaaaaa    60
aagtttgtga ggctgacaaa gatgaaacgg acacatttcc tgatcttgga gggttcatag    120
ggtagaagat ggtagat                                                   137

<210> SEQ ID NO 305
<211> LENGTH: 161
<212> TYPE: DNA
<213> ORGANISM: Homo sapiens

<400> SEQUENCE: 305
gatggtggga tatttgtgtc tgtgttctta taatatatta ttattcttcc ttggttctag    60
aaaaatagat aaatatattt ttttcaggaa atagtgtggt gtttccagtt tgatgttgct    120
gggtggttga gtgagtgaat tttcatgtgg ctgggtgggt t                        161

<210> SEQ ID NO 306
<211> LENGTH: 255
<212> TYPE: DNA
<213> ORGANISM: Homo sapiens

<400> SEQUENCE: 306
gaaacagcat gggaccgtgt gattgggtcc aggctgggct gtcagggaag cgccctggtg    60
tctccgactc atcaattctc gggtcttttt ttaaaagcca ggctccccaa agcactcttt    120
```

```
gtctcgcaat tttgaggagg ttgttccgac ctggaagcgt taaactgctg catgtcatct    180
ggcgtcagct gtgaggctgc gctctgcgtg ttgtgcgttt gcaaaatgta ttggcgtgac    240
tgtaaacaca tcgtt                                                     255

<210> SEQ ID NO 307
<211> LENGTH: 289
<212> TYPE: DNA
<213> ORGANISM: Homo sapiens

<400> SEQUENCE: 307
gtcaagctca gttgagggtt aatgatgagg caggctgatg cgggttcttt gcccagtccc     60
agggttccaa gaagccttcc tgggagaggg ggcctgagtt gaatggtgca agatgaacaa    120
gaaatggcaa gatagagaaa ggtgggagg gcttcccagg cagaagagag agcatggcta    180
aagggctagg ggcatgaagc agcaggggac ccccagccat gtagtatcac tggaggatga    240
gaataagggg gagaaggagg gagggagaga aggtatactt ctgagggca                289

<210> SEQ ID NO 308
<211> LENGTH: 181
<212> TYPE: DNA
<213> ORGANISM: Homo sapiens

<400> SEQUENCE: 308
agttcagggc tatagtgcgc tatgttgatc tggtgttcat gctaagttcc gcatcaatat     60
ggtgacttct agggagtggg ggaccaccag gttgcctaag gaggggtgaa cctgcctacg    120
ttggaaatag agctggtcaa aactcctgtg ctcatcagta gtagaatagc acctgtgaat    180
a                                                                    181

<210> SEQ ID NO 309
<211> LENGTH: 253
<212> TYPE: DNA
<213> ORGANISM: Homo sapiens

<400> SEQUENCE: 309
gacagcttgg aaggaaggat tgaccatggg ttgattccat ggaggtagag aagcaagaga     60
gacctgatga ttacaatgat ggctaagtgt agtatgccca ttaggattga attgaattag    120
gggaaattgt gtgaagtgtt tggaaggaag caatattgtg tgattagctc caaagctggc    180
cactggtaga agttgtttca atggaagaac aaggatggaa ttgagtgggc cagagagccc    240
tagattaatg ggt                                                       253

<210> SEQ ID NO 310
<211> LENGTH: 159
<212> TYPE: DNA
<213> ORGANISM: Homo sapiens

<400> SEQUENCE: 310
tattcagcga aacttacctg aaggggttgc catggaagta acaaagacac aattagaaca     60
gttaccagaa cacatcaagg agccaatctg ggaaaacact atcagaagaa aagaagaaa    120 gctagtcata aagcctcagg gaggccattt ttgcctaaa                           159

<210> SEQ ID NO 311
<211> LENGTH: 269
<212> TYPE: DNA
<213> ORGANISM: Homo sapiens

<400> SEQUENCE: 311
```

```
caaatgcgag atcttcagtt gcagtgtgaa gccaatgtcc gcgaactgca tcagctgcag    60
aatgaaaaat gccacttgtt ggttgagcat gagactcaga aactgaagga gttagatgag   120
gaacatagcc aagaattaaa ggagtggaga gagaaattga gacctaggag aaaggcactg   180
gaagaagagt ttgccaggaa actacaggaa caggaagtat tatataaaat gactggggag   240
tctgaatgcc ttaacacatc aaccccgga                                     269
```

<210> SEQ ID NO 312
<211> LENGTH: 234
<212> TYPE: DNA
<213> ORGANISM: Homo sapiens

<400> SEQUENCE: 312

```
tttcagaaac tgtcaaatgt accatatttg tattaagagt tgttgggaat ttttgtacaa    60
tgaatttaca tttatttatg gtgacatatt tacgcttgtg atcaaataat gatgttaaat   120
tcttaaatca tatttgctat gcagctgaag atgatatttt gatttgtatt ttgggggtac   180
ctgtgttgag ttgataaaca tttccatctt cattaaaact gcttccaaac taaa         234
```

<210> SEQ ID NO 313
<211> LENGTH: 32
<212> TYPE: DNA
<213> ORGANISM: Homo sapiens

<400> SEQUENCE: 313

```
taaagcatgg atctcgcttt ggttgtaaaa aa                                  32
```

<210> SEQ ID NO 314
<211> LENGTH: 221
<212> TYPE: DNA
<213> ORGANISM: Homo sapiens

<400> SEQUENCE: 314

```
atggtggggg tctctcacct tcttgaccct ctctccatca ttcagctgcc agcccaggct    60
tcacacccaa gctggctcag cagccgagcc tggcaccgag ggtccctgca ggctccctgg   120
gcagggagag ggccaaggac aattgggagg gcagcaggca gcccgcagat ggtggccatg   180
tggcacgctg ctgagacgac actaccaata aaccaaactg c                       221
```

<210> SEQ ID NO 315
<211> LENGTH: 238
<212> TYPE: DNA
<213> ORGANISM: Homo sapiens

<400> SEQUENCE: 315

```
ctgcccgtct gtaagttcca ggtggtgatt ccgaaatcct aagcctgcct cgcacctgct    60
gagccgcact gctgcccctg gcctcaccgg cctcaggaga cggtggggcc gctgcatttc   120
ggggtggtct tgggaatccc aggccctagg ggtcacattt gctcaggaag tgggtatcaa   180
attgaggtgg gggtgtcaga ggaggcaaag gggtcccagc tgcggtcagg actgtggt    238
```

<210> SEQ ID NO 316
<211> LENGTH: 36
<212> TYPE: DNA
<213> ORGANISM: Homo sapiens

<400> SEQUENCE: 316

```
cctgggtgac ggaataagac tcggtctcca aaagaa                              36
```

<210> SEQ ID NO 317
<211> LENGTH: 87
<212> TYPE: DNA
<213> ORGANISM: Homo sapiens

<400> SEQUENCE: 317
aaggctgcta gggatgttag acctcggcca ggacccacca cattgcttcc taatacccac    60
ccttcctcac gacctcattt ctgggca                                        87

<210> SEQ ID NO 318
<211> LENGTH: 59
<212> TYPE: DNA
<213> ORGANISM: Homo sapiens

<400> SEQUENCE: 318
tacctgttta tctgtaactg ttatccaaac aaattaaata ctgtggatgc ctttaaaaa     59

<210> SEQ ID NO 319
<211> LENGTH: 299
<212> TYPE: DNA
<213> ORGANISM: Homo sapiens

<400> SEQUENCE: 319
gacagtggat aactttcaaa gaggcatctt tgtgtggccc atgaactttg gttggagaac    60
aattcctcca gatgtcactg caaaaaaaca gaattaaaga aactgataca ataaggtgcc   120
ctgtcatggc tggtggattg tttttctactg acaaaagtta cttttttgaa cttggaacat   180
acgaccctgg ccttgatgtt tggggtgggg aaaatatgga gctctcattc aaggtgtgga   240
tgtgtggtgg tgaaattgag atcattccct gctcccgagt gggccatata ttcagaaat    299

<210> SEQ ID NO 320
<211> LENGTH: 260
<212> TYPE: DNA
<213> ORGANISM: Homo sapiens

<400> SEQUENCE: 320
atgagtatct cagctccttc aaggtggcac agtacgtcgt gcgggaagaa gacaagattg    60
aggaaattga gcgagagatc atcaagcagg aggagaatgt ggaccctgac tactgggaga   120
agctgctgag gcatcactat gagcaacagc aggaagacct agcccggaat ctaggcaagg   180
gcaagcgggt tcgcaagcaa gttaactaca atgatgctgc tcaggaagac caagacaacc   240
agtcagagta ctcggtgggt                                               260

<210> SEQ ID NO 321
<211> LENGTH: 131
<212> TYPE: DNA
<213> ORGANISM: Homo sapiens

<400> SEQUENCE: 321
ctatggccgg ataactaagg atgtggtgct ccaatgggga gaaatgccca cgtctgtggc    60
ctacattcat tccaatcaga taatgggctg ggcgagaaa gctattgaga tccggtcagt    120
ggaaacagga c                                                        131

<210> SEQ ID NO 322
<211> LENGTH: 137
<212> TYPE: DNA
<213> ORGANISM: Homo sapiens

<400> SEQUENCE: 322

```
ccaccattgc gggtccccca ggaagccagg tgaccccagg tgggaggctg tgtgtggagg      60
ccatcctgga aggaagttta gacctgccca ggtgtggagc gaggggcaca ggggcatcct     120
aacctcagaa actgaaa                                                    137
```

<210> SEQ ID NO 323
<211> LENGTH: 277
<212> TYPE: DNA
<213> ORGANISM: Homo sapiens

<400> SEQUENCE: 323

```
agcaaagtgt attctccatc tggcctcaga gcagatgcca agcctaattg ggccaccaga      60
tccgtgaagg tggtttgctg ttttccagcc agctcaataa cttgtttggc agaatcagga    120
attaggacct gatcaatcaa atggatcaca ccattagttg gtcacaatat cctttgttgt    180
tcaccatttt gattccattt actgttatac tgtcaccgtc acatcctatc tcaattgtat    240
ttccttccag cgtctcaaga ctgctactcc cataata                             277
```

<210> SEQ ID NO 324
<211> LENGTH: 271
<212> TYPE: DNA
<213> ORGANISM: Homo sapiens

<400> SEQUENCE: 324

```
gcttgcccca gaacttagtc tctttgccca gcctcacccc tcctggtgct catcagactc      60
ttgccacccc tggctcccac tccctgcttg cctctggtgg agctgcacag agctctggga    120
agaggccctc ttcctccccg cactggggcg atgggcgcac ctcagactta cccactgctg    180
ctgccaccac caacccttg atccctcagt cctcccacac agcttctgtc caccccaggt    240
ttccctcacc ccacctttgc taagtcttcc t                                    271
```

<210> SEQ ID NO 325
<211> LENGTH: 225
<212> TYPE: DNA
<213> ORGANISM: Homo sapiens

<400> SEQUENCE: 325

```
gccctgctgc gaagtggagt ccgaggtcat gatgagtgac tatgagagcg gggacgacgg      60
tcacttcgaa gaggtgacga tcccgccccct ggattcccag cagcacacgg aagtctgact    120
ctcaactccc cccaaagtgc ctgactttag tgaacctaga ggtgatgtgc gtcatccgcg    180
ctgttctttg cagcagtgct tccaagcttt tttgggtgag ccgaa                    225
```

<210> SEQ ID NO 326
<211> LENGTH: 68
<212> TYPE: DNA
<213> ORGANISM: Homo sapiens

<400> SEQUENCE: 326

```
agaagcaaca cgatgatggg ccccccagtt tgaatttcag acagtggagg agggaatatt      60
gctaggag                                                              68
```

<210> SEQ ID NO 327
<211> LENGTH: 272
<212> TYPE: DNA
<213> ORGANISM: Homo sapiens

<400> SEQUENCE: 327

```
tactctcagc agtcagaggc ttgcttgctc tgtgcagatt tttaattttc ttttttggcc    60
ctaggctggt tgggacctct acagcttcat tctttcacca ttaaatagtg gcctttttca   120
gtattttccc tcttcccctt tataaattat gctaaagcca caaagcacat ttttggggat   180
catagaaggt tggggttcca gaaaggcatc tgtgtgatgg ttccattgat gtgggatttc   240
cctacttgct gtattctcag tttctaataa aa                                 272

<210> SEQ ID NO 328
<211> LENGTH: 285
<212> TYPE: DNA
<213> ORGANISM: Homo sapiens

<400> SEQUENCE: 328
aaggactgtc caagagccag ccagttcagg gctcaggcct cacccattgc ccactcctgg    60
ggagaccatc acctggctca tcgtttccac caagagtgcc ccacaggagt gccccacaga   120
cccgctggac cagcctgctg cgggtcctgg ccaggggtct ggctaacggt gagggctgac   180
tctgaactgt ctctcagtct ccagaaagtg ttcaagcctg ttgtgttccc aaatctgatt   240
cctcctattg tcttgtaaat caaactctaa gtgaaaactt cccat                   285

<210> SEQ ID NO 329
<211> LENGTH: 231
<212> TYPE: DNA
<213> ORGANISM: Homo sapiens

<400> SEQUENCE: 329
gaaggtcata acagtttcaa acaatagcca gggaagttag agtcacctag agacatcctt    60
aacacgtgcc cctgagctac ttttcagaaa cccagacccc caccaaatgg attcacacag   120
acgtcagata agggggaaca ccagggacta aactctgacc tccattcttt gctctcagtt   180
tcttcctgag gggcctggcc agaccttaat gttcctttct gcggaccccc a            231

<210> SEQ ID NO 330
<211> LENGTH: 273
<212> TYPE: DNA
<213> ORGANISM: Homo sapiens

<400> SEQUENCE: 330
cacctgcact ctagtgaccc tgggtgccgc cagacccttc tcttctacaa agacccagc     60 aggagtggga gggtctgcaa tggcatcgcc ctgtcctgcc ttggccagaa gcctggagct   120
ttggtttgag gaggtagaga tatgtgtatc cataggaaga gatctgtcag aacaggcagc   180
tgttgagctc ggggtgtctt cctcaaggca tgtggctcag cagcaagaaa ggcaagttgc   240
tcctgctggg gccctggact ctgccttagc tcc                                273

<210> SEQ ID NO 331
<211> LENGTH: 133
<212> TYPE: DNA
<213> ORGANISM: Homo sapiens

<400> SEQUENCE: 331
tctctccagc ctctcttagg aggggtaatg gtggagttgg catcttgtaa ctctcctttc    60
tcctttcttc cccttttctct gcccgccttt cccatcctgc tgtagacttc ttgattgtca   120
gtctgtgtca cat                                                     133

<210> SEQ ID NO 332
<211> LENGTH: 292
```

<212> TYPE: DNA
<213> ORGANISM: Homo sapiens

<400> SEQUENCE: 332

```
atccacggcc gcgttagaaa gagggtcgca cgctgccgcc gaggtagagg ggtccccgag    60
tcctggggcc tcgcacccca cagcccgagt cccttcccg cggaagggac tcgtggctgt   120
gggtagagac gcgcgcttgg cgcggccagc cctgcaggca ggagctgagc ggcgcaggga   180
cacgggcagc tgggaggggc gcctggtgat ttactcactt ccctcctagc cagagaagtg   240
cagcaattcc aaacagttct cataggagcg tccctgacaa cttcatgtta ta           292
```

<210> SEQ ID NO 333
<211> LENGTH: 211
<212> TYPE: DNA
<213> ORGANISM: Homo sapiens

<400> SEQUENCE: 333

```
gtaccacaaa cacactcaac ttgtctatga attagagaac aagatactgc tgctgcttct    60
ttttgacttt tgaaatatac aatgttttgt aggctctgcc cttcaatgtg aaagcaggac   120
attaaatttg aaattatttg acaattaaat gtttaggacc atctaacttc aactgcaaaa   180
ctaaacagat ctaccttgtc cttccttcaa a                                  211
```

<210> SEQ ID NO 334
<211> LENGTH: 142
<212> TYPE: DNA
<213> ORGANISM: Homo sapiens

<400> SEQUENCE: 334

```
ggttcatttt agtttcagat agatggcttc accaaagaac tcttgaaaga atactgatta    60
gggaggggca gggaagtagg agcttatggt atattataag gctgggaaaa atctatgatg   120
caaacccttt ccacatagta ct                                            142
```

<210> SEQ ID NO 335
<211> LENGTH: 208
<212> TYPE: DNA
<213> ORGANISM: Homo sapiens
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t

<400> SEQUENCE: 335

```
actcattctt aacctaatca cctaaaataa ttcttatcat ctattcttct tcaggnaaaa    60
atggngccct gggtgttatt ttaacgactt gccatccttc tgttttgag agtntctttg   120
ttaactgggg gcataccttc gngacccggt cctaccttcc tcattcagac ctgtgctgtt   180
cattgctgta ttcccagtcc cttaaaaa                                      208
```

<210> SEQ ID NO 336

```
<211> LENGTH: 227
<212> TYPE: DNA
<213> ORGANISM: Homo sapiens

<400> SEQUENCE: 336
atatctgaca gatgtgtaaa ccaagttacc agcatggtgt ggaatcgtag ttccaagtca    60
tataatacca gacattcaag aaaactagtg ccctgttaac tgggggaagc aaatttatat   120
ccttttggaa gaaagtcacc ttattctgtg tatcagaaat ctctttcaaa taaccttttca  180
gaactataga gcatcataca aagatgacca agcatacaag aaaacaa                227

<210> SEQ ID NO 337
<211> LENGTH: 101
<212> TYPE: DNA
<213> ORGANISM: Homo sapiens

<400> SEQUENCE: 337
aacatcaaag ctggattaga acatctgcca ccagctgaac aggccaaagg cagactacag    60
ctggttcttg aagctgctgc aaaagctgat gaagcattga a                       101

<210> SEQ ID NO 338
<211> LENGTH: 212
<212> TYPE: DNA
<213> ORGANISM: Homo sapiens

<400> SEQUENCE: 338
agccttagca aaaatgcctc ctcaccactc cccaggagaa tttttataaa aagcataatc    60
actgattcct tcactgacat aatgtaggaa gcctctgagg agaaaaacaa agggagaaac   120
atagagaacg gttgctactg gcagaagcat aagatctttg tacaatattg ctggccctgg   180
ttcacctgtt tactgttatc acaataatgc ta                                 212

<210> SEQ ID NO 339
<211> LENGTH: 235
<212> TYPE: DNA
<213> ORGANISM: Homo sapiens

<400> SEQUENCE: 339
acagagtcat ttgagctttc tccctcccg ctagtatctt tacaggagca gggaagagca     60
gtagaggatg tataattttg ggcgaagtta aattacaatt tatttgaggt tattcctaaa   120
cctatttatt tggtgttttg gaggagatca cacactaaga gaacgttgat tgcctcggct   180
attgtgctgg ctggacactt tggtcacttt tgaagcatgt taataaatgt cactg        235

<210> SEQ ID NO 340
<211> LENGTH: 271
<212> TYPE: DNA
<213> ORGANISM: Homo sapiens

<400> SEQUENCE: 340
tccaaacacc ggcagaaaac ggagagtgct tgggtggtgg gtgctggagg attttccagt    60
tctgacacac gtatttatat ttggaaagag accagcaccg agctcggcac ctccccggcc   120
tctctcttcc cagctgcaga tgccacacct gctccttctt gctttccccg ggggaggaag   180
ggggttgtgg tcggggagct ggggtacagg tttggggagg gggaagagaa attttttattt  240
ttgaacccct gtgtccctttt tgcataagat t                                 271

<210> SEQ ID NO 341
<211> LENGTH: 270
```

```
<212> TYPE: DNA
<213> ORGANISM: Homo sapiens

<400> SEQUENCE: 341
tgaggagcgg gagggttccg ccactccagt tttctcctct gcttctttgc ctccctcaga    60
tagaaaacag cccccactcc agtccactcc tgacccctct cctcagggaa aggccttggg   120
tggccccctc tccttctcct agctctggag gtgctgctct agggcaggga attatgggag   180
aagtgggggc agcccaggcg gtttcacgcc ccacactttg tacagaccga gaggccagtt   240
gatctgctct gttttatact agtgacaata                                    270

<210> SEQ ID NO 342
<211> LENGTH: 207
<212> TYPE: DNA
<213> ORGANISM: Homo sapiens

<400> SEQUENCE: 342
aaagactcat cataagggtc cttcctcttt tctatcctcc ctccatattc agttgctaag    60
tctcaactac tttgctccca tcaagattct ctttactatt tcttctatcc agaccttcct   120
ctttattcct attgtcattg tcttattttta ggttctcatc atctttcact aagataacta   180
caacagcttc gtgaccagcg taggcaa                                       207

<210> SEQ ID NO 343
<211> LENGTH: 189
<212> TYPE: DNA
<213> ORGANISM: Homo sapiens

<400> SEQUENCE: 343
gctcaaatag ctataactgt accaaagaca tggaagaaac caaaagatcg gacccgaacc    60
actgaagaga tgttagaggc agaattggag cttaaagctg aagaggagct ttccattgac   120
aaagtacttg aatctgaaca agataaaatg agccaggggt ttcatcctga aagagacccc   180
tctgaccta                                                           189

<210> SEQ ID NO 344
<211> LENGTH: 292
<212> TYPE: DNA
<213> ORGANISM: Homo sapiens

<400> SEQUENCE: 344
tgcgaatctt ctgcagctcc atcagcatcc atgtatcttg cttgtcattt tctctgttgg    60
ttacaattac tttattatgg ttgacatctt ggcaggttcc atgatgagtg atttcagtag   120
tggtcactgt ctggtgctgg ggatagccag ggagctgaat gaccagggtc tggtaatgct   180
tctgggcatc ggtgaactga gactgtattt tccgcttgtc atcatctcca aacatctcta   240
agccttggct atttctgatg aactcttggc actgtaactc aaggtcggat at           292

<210> SEQ ID NO 345
<211> LENGTH: 286
<212> TYPE: DNA
<213> ORGANISM: Homo sapiens

<400> SEQUENCE: 345
caactatgcg gagcgggtcg gtgctggagc gccggtgtac ctggcggcgg tgctggagta    60
cctgaccgcc gagatcctgg agctggctgg caacgcggcc cgcgacaaca agaagactcg   120
catcatcccg cgtcacctcc agctggccat ccgcaacgat gaggagctca acaagcttct   180
```

```
gggcaaagtc accatcgcac agggtggcgt cctgcccaac atccaggccg tgctgctgcc    240
aaagaaaact gagagccacc acaagactaa gtaaagaccg agttga                   286
```

<210> SEQ ID NO 346
<211> LENGTH: 247
<212> TYPE: DNA
<213> ORGANISM: Homo sapiens
<220> FEATURE:
<221> NAME/KEY: misc_feature
<222> LOCATION: (80)..(131)
<223> OTHER INFORMATION: n is a, c, g, or t

<400> SEQUENCE: 346

```
catatttcag cggatcatca acttttcctc ctaccatact atcctcagac aaagaaacca    60
ttgaaattat agacctagcn nnnnnnnnn nnnnnnnnnn nnnnnnnnnn nnnnnnnnnn     120
nnnnnnnnnn ngtggctggt aaagaggata atacagacac tgaccaagag aagaaagaag   180
aaaagggtgt ttcggaaaga gaaaacaatg aattagaagt ggaagaaagt caagaagtga    240
gtgatca                                                              247
```

<210> SEQ ID NO 347
<211> LENGTH: 55
<212> TYPE: DNA
<213> ORGANISM: Homo sapiens

<400> SEQUENCE: 347

```
tgctcttaaa cccaaagggg cttcactgaa gagcccactt ccaagtcaat aaaaa          55
```

<210> SEQ ID NO 348
<211> LENGTH: 291
<212> TYPE: DNA
<213> ORGANISM: Homo sapiens

<400> SEQUENCE: 348

```
cttctcttgg gctgagatgc tgctgccagc tctaaaacag cactctgttc tcaaaacctc    60
atggcaggct cctggctcca atactcagct gccaaacatg atgctgattc ttcacgaatt   120
tgcaacccag ttctctcggg tttgcacacc cccactgtgg gccggggaac cgggtcccgg    180
ccttcgcaga ctccaggctc tggcagatgt ggccctccat aacaacggga atgaaaggt    240 cacaccttat gtgcgccagg cccttaagga gtcggaatat cccaatcctc c             291
```

<210> SEQ ID NO 349
<211> LENGTH: 47
<212> TYPE: DNA
<213> ORGANISM: Homo sapiens

<400> SEQUENCE: 349

```
tgctgtggta ctttgctgtg tactccgtgg catcatgtta ctgtgta                  47
```

<210> SEQ ID NO 350
<211> LENGTH: 255
<212> TYPE: DNA
<213> ORGANISM: Homo sapiens

<400> SEQUENCE: 350

```
ggagtttgtg actagatggg caatatagta agatgtcatc tttaaaaat gaaaaaatta     60 gctggccact gtggcacacg cctgtagtcc cagctacttg ggaagctgag gtaggaggat   120
tgcttgagcc caggagttca aggctgcagt gagctatgat tgtgcttatg aatagccact    180
gcactccagt ctgggcaata gtgagtcggt caaattccat ttccccctcc gccccatacc   240
```

```
tcttcaaatg tttaa                                                    255

<210> SEQ ID NO 351
<211> LENGTH: 145
<212> TYPE: DNA
<213> ORGANISM: Homo sapiens

<400> SEQUENCE: 351
cacttcctga cggatgccag cttgggcact gctgtctact gaccccaacc cttgatgata   60
tgtatttatt catttgttat tttaccagct atttattgag tgtcttttat gtaggctaaa  120
tgaacatagg tctctggcct cacgg                                        145

<210> SEQ ID NO 352
<211> LENGTH: 150
<212> TYPE: DNA
<213> ORGANISM: Homo sapiens

<400> SEQUENCE: 352
agcctaggca atgcagcgag gccttgtcta gaaaatttaa aaaaaaaaaa aaaattagc   60 tgggcgtggt ggcacgtacc tgtagttcca gctactcggg aggctgaggc ggcaggatct  120
cttgagctaa gtagttcgag gctgaagtga                                   150

<210> SEQ ID NO 353
<211> LENGTH: 173
<212> TYPE: DNA
<213> ORGANISM: Homo sapiens

<400> SEQUENCE: 353
ttagccaagt atggtggcac gcgcctgtaa tcccagcaac ttggaaggct gaggcaggag   60
aatcgcttga acctgggagg cagaggttgc agtgagccaa gatcagacca ctaccgcccc  120
gcgctggctt gccctcctgt tctccagagc aataaagttg gacgagacta ccc         173

<210> SEQ ID NO 354
<211> LENGTH: 178
<212> TYPE: DNA
<213> ORGANISM: Homo sapiens

<400> SEQUENCE: 354
cacagctctt cttggcgtat ttatactcac tgagtcttaa cttttcacca ggggtgctca   60
cctctgcccc tattgggaga ggtcataaaa tgtctcgagt cctaaggcct taggggtcat  120
gtatgatgag catacacaca ggtaattata aacccacatt cttaccattt cacacata    178

<210> SEQ ID NO 355
<211> LENGTH: 295
<212> TYPE: DNA
<213> ORGANISM: Homo sapiens

<400> SEQUENCE: 355
ggatggcacc atgtttgaga ggctacagag gagacccaga gccagtaagc aagacataga   60
gtttatagag aggacttaca gcatagtcca gtggcagcgg gctagacagg agaaccgcaa  120
tggcttgaaa aagcacgaag tataaagcgt tgagctcaac ggtttatact tcagagaaac  180
tcaacaatca actgaaggca ctaactgaga aaaacaaaga acttgaaatg gctcaggatc  240
gcaatatggc cattcagagc caatttacaa gaccaaagga agcatcagaa gctga        295

<210> SEQ ID NO 356
```

```
<211> LENGTH: 255
<212> TYPE: DNA
<213> ORGANISM: Homo sapiens

<400> SEQUENCE: 356
atttctttag ctgaccatag tgagtcttcc ttgagttcac gtttcttccc aatttcattt     60
tcttgagata ttttgctact ttctggtact gcttcatcac tgaaagtgtc atttgtttct    120
atatccatcc ttggcctttt tctaacattg acatcttcct cctgttttg aactttcaca     180 tcaatttcta actctggttt tgtgtccttg aataactgtt ccaatacttc atcttctatg    240
gccacatcat ccatt                                                     255

<210> SEQ ID NO 357
<211> LENGTH: 266
<212> TYPE: DNA
<213> ORGANISM: Homo sapiens

<400> SEQUENCE: 357
gtatcaaatt cacgccatgc aaaaagatta taaatgtaat aagcatgtat gtgtgtgagg     60
agattcagtc ataacccaac gctcattcaa catcaaagaa tttataccta agagaactta    120
tttgggtgta gtaaatggca gatctttcaa taggagttta actagtcttt gtcatatcag    180
aatatccata gtagacaaga atttgatgta acgcaaatgg aaaaactcga caccacattt    240
caggctttac ccaacatcga ataat                                          266

<210> SEQ ID NO 358
<211> LENGTH: 271
<212> TYPE: DNA
<213> ORGANISM: Homo sapiens
<220> FEATURE:
<221> NAME/KEY: misc_feature
<222> LOCATION: (136)..(136)
<223> OTHER INFORMATION: n is a, c, g, or t

<400> SEQUENCE: 358
cgttcagtac aaacattat gcggtaggct cagatgttgt aatttgcact taggtaccag      60
gtgtcaggaa acagactaaa aagaattcca ccaggctgtt tggagatcct catcttggag    120 cttttttcaaa agcggngctt catctgcaaa gggccctttc atcttgaagt ttttcccctc   180
cgtctttccc ctcccctggc atggacacct tgtgttaggg atcatctctg caagtttcct   240
aggtctgaat ctgcgagtag atgaacctgc a                                   271

<210> SEQ ID NO 359
<211> LENGTH: 204
<212> TYPE: DNA
<213> ORGANISM: Homo sapiens

<400> SEQUENCE: 359
gtaccacaaa cacactcaac ttgtctatga attagagaac aagatactgc tgctgcttct     60
ttttgacttt tgaaatatac aatgttttgt aggctctgcc cttcaatgtg aaagcaggac    120
attaaatttg aaattatttg acaattaaat gtttaggacc atctaacttc aactgcaaaa    180
ctaaacagat ctaccttgtc cttc                                           204

<210> SEQ ID NO 360
<211> LENGTH: 185
<212> TYPE: DNA
<213> ORGANISM: Homo sapiens

<400> SEQUENCE: 360
```

```
attacagtta tagctctctc aagcaaaaaa acagcagaga aaaacttagt ttaccttagg      60
ggctatttat ttacttaggg atttgttaaa aggtcgaatg gggtcacaca gaatactaag     120
aagagctgtt cacccaggcc tcactaagaa ctcttcttca ttcagtagct gtatagtaac    180
atgac                                                                 185

<210> SEQ ID NO 361
<211> LENGTH: 54
<212> TYPE: DNA
<213> ORGANISM: Homo sapiens

<400> SEQUENCE: 361
ctttagtagt ttctcgtcag tcccgcagcc accgcagccg ggtcccccct cgtg           54

<210> SEQ ID NO 362
<211> LENGTH: 261
<212> TYPE: DNA
<213> ORGANISM: Homo sapiens

<400> SEQUENCE: 362 agagagggg ctcacctctt atcctcggcg acccactgca caagcaggcc gctctcccag      60
acttaaaatg tatcaccact aacctgtgag ggggacccaa tctggactcc ttccccgcct    120
tgggacatcg caggccggga agcagtgccc gccaggcctg gccaggaga gctccaggaa     180 gggcactgag cgctgctggc gcgaggcctc ggacatccgc aggcaccagg gaaagtctcc    240
tggggcgatc tgtaaataaa c                                               261

<210> SEQ ID NO 363
<211> LENGTH: 236
<212> TYPE: DNA
<213> ORGANISM: Homo sapiens

<400> SEQUENCE: 363
ctgaatgggc agagctggat tttacagggt tgggattttg ccaggtgagt aagatagagg     60
ggagaagtgg gaccaggaag ttccaggtct gtgaacgggc ctggctgagg agctggatca    120
tgaaatctcg agtcaagtaa aaggaaatt gaggacacga gttgggtatt gcatagtgtt    180
actgtgttaa ggtcaggggt caaagactta ctggcatgga gtaaccagag taagtg        236

<210> SEQ ID NO 364
<211> LENGTH: 179
<212> TYPE: DNA
<213> ORGANISM: Homo sapiens

<400> SEQUENCE: 364
caggcaaaaa cgtccccgaa gccagcagtt gtagagactg ttacaacagc caagccacag     60
cagatacaag cgctgatgga tgaagtgaca aaacaaggaa acattgtccg aaaactgaaa    120
gcacaaaagg cagacaagaa cgaggttgct gcggaggtgg cgaaactctt ggatctaaa     179

<210> SEQ ID NO 365
<211> LENGTH: 167
<212> TYPE: DNA
<213> ORGANISM: Homo sapiens

<400> SEQUENCE: 365
cagagtcccg tgtgtcctaa aaatctccta aaaccagtct atgaactcag ggctttaaaa     60 cattttaat ttatttggtc attcaattta cttgttttta atacatgatt ctctatgaaa     120
```
ttgatgggct caaactagct gtgaatcttc tgagagtgaa agcaaca    167

<210> SEQ ID NO 366
<211> LENGTH: 280
<212> TYPE: DNA
<213> ORGANISM: Homo sapiens

<400> SEQUENCE: 366
tataaagtaa ccctatgatg ctccccttac gagaaaacaa aactgtacac atttataaac    60
aaacagtctc tcccatcagt taacacacag agccttctct acaccaaagt ctctttccgt    120
ttgccaccag aaagggcttt gtccctcgct cttcggatgc cgggctgtgt ctggtgtgtc    180
tttaagctct tgctgtcctc tgccatctgc atgccagagc cacatctgta agcgttttca    240
tcaacttcta cctgagtaac actggaaact gtcctcgtgc    280

<210> SEQ ID NO 367
<211> LENGTH: 176
<212> TYPE: DNA
<213> ORGANISM: Homo sapiens

<400> SEQUENCE: 367
acagctcctt tgacctcagt gacaggcact cacctacctg accccaaac tgaagcctca    60 cttttcccag ccgtgtccac accctctggg ctaccccatt accatgacaa gtattccctc    120
tgctccagga gaaaagccag gtcccagacc tgacccatta aacccaatc attcca    176

<210> SEQ ID NO 368
<211> LENGTH: 69
<212> TYPE: DNA
<213> ORGANISM: Homo sapiens

<400> SEQUENCE: 368
gaccaggaag tcctataaag aattatattt ctatagaatt aaaaatgcag ttctgtcagc    60
ctggacaac    69

<210> SEQ ID NO 369
<211> LENGTH: 200
<212> TYPE: DNA
<213> ORGANISM: Homo sapiens
<220> FEATURE:
<221> NAME/KEY: misc_feature
<222> LOCATION: (55)..(55)
<223> OTHER INFORMATION: n is a, c, g, or t

<400> SEQUENCE: 369
ataagaactt atgggatttc ctacacggag acaaaaaaag atattccttt atgtngttta    60
aaagtggcag ctgctctttc tttattccat tttaatcaat gagtattgat tcaagttttc    120
ctttctattt ttccttatga taagtttctt acagtagctt atacaacaac aaatagcata    180
gaaaaactac tggattcaat    200

<210> SEQ ID NO 370
<211> LENGTH: 110
<212> TYPE: DNA
<213> ORGANISM: Homo sapiens

<400> SEQUENCE: 370
acaggtaacc ttctcactaa gtgggggtgt ctgaggccag ggagagctct actcattccc    60
ctgtgtgatc ccagcagtga gcatagagca ggtgccctgc aatgttaagc    110

<210> SEQ ID NO 371
<211> LENGTH: 156
<212> TYPE: DNA
<213> ORGANISM: Homo sapiens

<400> SEQUENCE: 371

```
agaaagaata aagcaggatc catagaaata attaggaaaa cgatgaacct gcaggaaagt      60
gaatgatggt tgttgttct tctttcctaa attagtgatc ccttcaaagg ggctgatctg      120
gccaaagtat tcaataaaac gtaagatttc ttcatt                               156
```

<210> SEQ ID NO 372
<211> LENGTH: 50
<212> TYPE: DNA
<213> ORGANISM: Homo sapiens

<400> SEQUENCE: 372

```
gattgctgag cagggaagct tgcatgttg ctctaaggta cattttaaa                  50
```

<210> SEQ ID NO 373
<211> LENGTH: 64
<212> TYPE: DNA
<213> ORGANISM: Homo sapiens

<400> SEQUENCE: 373

```
caccccatgc actgtacaaa tactgcaaac actatagttg cattcatagg accattaaaa     60
aaaa                                                                    64
```

<210> SEQ ID NO 374
<211> LENGTH: 95
<212> TYPE: DNA
<213> ORGANISM: Homo sapiens

<400> SEQUENCE: 374

```
ttctgaggga ctgcttctgg agccggccct cttgtgtgat tgaattagtc agtgatggtt     60
ctcaggacta gattagattg ttactcttaa aataa                                 95
```

<210> SEQ ID NO 375
<211> LENGTH: 291
<212> TYPE: DNA
<213> ORGANISM: Homo sapiens

<400> SEQUENCE: 375

```
ggccgcttca gacaaccacc tgaaaaagcc aaagcacaga gacccagaga aagccaaatt     60
ggacaaaagc aagcaaggtc tggacagctt tgacacagga aaaggagcag gagacctgtt     120
gcccaaggta aagagaagg gttctaacaa cctaaagact ccagaaggga aagtcaaaac      180
taatttggat agaaagtcac tgggctccct ccctaaagtt gaggagacag atatggagga     240
tgaattcgag cagccaacca tgtcttttga atcctacctc agctatgacc a              291
```

<210> SEQ ID NO 376
<211> LENGTH: 269
<212> TYPE: DNA
<213> ORGANISM: Homo sapiens

<400> SEQUENCE: 376

```
acaactggaa ttaggatttt ctcctgatga aggaaaaaaa gacattaagt ctgcattata     60
tttttaaacc catgaaaaga ctgaaaccaa ccaaacaaaa gaaaaacttg acttgttatt     120
agaacagtca ttattatttt ttttcttctt caaaactgtt attttaccat gttgtatctt     180
```

```
cttcccaaag taatatgcag atgaagcaaa ataactcagc aaagtgtcat ggaccaagcc    240
ctttccatca tttctagcat taaagtgaa                                     269
```

<210> SEQ ID NO 377
<211> LENGTH: 291
<212> TYPE: DNA
<213> ORGANISM: Homo sapiens

<400> SEQUENCE: 377

```
tggatgtgtt gctgttggcc aagaagaatg agaaggagcg aatttgggca gtgggacctc    60
caggcagcct tacagttttc agttggggag tgagatgaga cctggaattt aggggtctgt   120
gtagttaaaa ccatgcggtg tacaagattg cccagattga gtatgtggaa ggtgtgatgg   180
ggaggagaga gagtgttagg aagtgctggg gtcctgccat ctgagaacag gagcccagag   240
gcagcatatg cagcccgaaa ggagagaatc catgctgagg gtcgtgaata c            291
```

<210> SEQ ID NO 378
<211> LENGTH: 43
<212> TYPE: DNA
<213> ORGANISM: Homo sapiens

<400> SEQUENCE: 378

```
gagaaacagc tgtcacctcc cgcagaccct aatcctctct cgc                      43
```

<210> SEQ ID NO 379
<211> LENGTH: 44
<212> TYPE: DNA
<213> ORGANISM: Homo sapiens

<400> SEQUENCE: 379

```
aatattgttg ctgatttcag agggatattc actaataaat gtat                     44
```

<210> SEQ ID NO 380
<211> LENGTH: 187
<212> TYPE: DNA
<213> ORGANISM: Homo sapiens

<400> SEQUENCE: 380

```
attctgaatc atcactggga gcaaaacaca gactcacaag aggaagggca agagaagggt    60
aaagaacaag agagaccacc tgaggcagtg agcaagtttg caaagcggaa caatgaagaa   120
actgtaatgt cagctagaga caggtacttg gccaggcaga tggcgcgggt taatgcaaag   180
acctata                                                             187
```

<210> SEQ ID NO 381
<211> LENGTH: 152
<212> TYPE: DNA
<213> ORGANISM: Homo sapiens

<400> SEQUENCE: 381

```
attgcttgaa ctgggtaact gatttgatgt aaatgccaaa ggagaaggag taaaaggaaa    60
atgacataga gtctgagcta gagtaacagg gacagtatta attaatatta accaaatatc   120
aaataagaac atttaagaga cgagccacca tg                                 152
```

<210> SEQ ID NO 382
<211> LENGTH: 272
<212> TYPE: DNA
<213> ORGANISM: Homo sapiens

<400> SEQUENCE: 382

```
ctgctgtggt gttatttgct taatggacca tttaaggaat tctcgaatac accgaccaca    60
aaaatctctt aaagtactgt caacagggtc cacaattcca tccaatatag cttctagtaa   120
ggcaacagta tcctgacttt caaatttctt gttgttagtg aaccagtgaa tcagctgcat   180
aactagtggc tcatacagtt gccttgtcac ctgatcaaca tcacacgcaa gtcgaagcag   240
cacaggaaac gtccgcttat agagctggta ca                                 272
```

<210> SEQ ID NO 383
<211> LENGTH: 184
<212> TYPE: DNA
<213> ORGANISM: Homo sapiens

<400> SEQUENCE: 383

```
ctgaatttgc ccatccacct gggtcacttt gagagttgtg cagggggget gggagcactg    60 gtgttcacgt gggaccacag gctgcaccat aagcccact cacaataaaa aaataaaagg    120
ccgagccggg catggttgct cactcccgta ataaaaaaat aaaagaacag gctgagccgg   180
gaaa                                                                184
```

<210> SEQ ID NO 384
<211> LENGTH: 191
<212> TYPE: DNA
<213> ORGANISM: Homo sapiens

<400> SEQUENCE: 384

```
ccagaaaaag cacccatgc actgtacaaa tactgcaaac actatagttg cattcatagg     60
accattaaaa aaaagagcc aaattacaaa acaatctata ttttacaaac atttcagttg    120
ggttcttaag ctaaagatat tactgtttac tttggtacga taactagaaa acacaaacat   180
tatgctccag a                                                        191
```

<210> SEQ ID NO 385
<211> LENGTH: 278
<212> TYPE: DNA
<213> ORGANISM: Homo sapiens

<400> SEQUENCE: 385

```
tctttgtcct ggtcgtcttg gtaaatgtgt agtcgcgtat ctgagacata gattgtgctt    60
tattcggtgc tgtggagagt agaaactagc agcagtacct ggaaaggggc cctgatctgc   120
gggtgtggat gagtagagac tcttcagttg agatttagct ctagtgaggg ttgggtgcaa   180
caaatgtagg aaagagtgaa gagatgagca gctcatgtct gagtttattc tgtttctgtt   240
actgtgtcac agaccagcct cagatcatag ttcatgat                           278
```

<210> SEQ ID NO 386
<211> LENGTH: 281
<212> TYPE: DNA
<213> ORGANISM: Homo sapiens

<400> SEQUENCE: 386

```
gctcattgct gactgttttc cttaaaagct gggaaggctg tgggtcaatt cagctcgcca    60
cctgtttctg tactgcccac aagctgagaa tgaattttgt actttaaat ggttgggggg    120 aggggagaat attttctgac acaagatata tgacattcac acttgagtgt caaagttttt   180
aggaacacag ccacgcccat tgtttacac tttactcctt ccactttaca atgaagaggt    240
atgaggagct gctacagaaa ccttctggct tgcaaagttt a                       281
```

<210> SEQ ID NO 387
<211> LENGTH: 94
<212> TYPE: DNA
<213> ORGANISM: Homo sapiens

<400> SEQUENCE: 387
attttggaga aaatacgct agattttaaa tgttagagct gttcccggag acttattgca    60
gaaatagatg agaagcaaat caagactact attc    94

<210> SEQ ID NO 388
<211> LENGTH: 265
<212> TYPE: DNA
<213> ORGANISM: Homo sapiens

<400> SEQUENCE: 388
gctgacagtg agtactgatg gcctggatgt aggggtgaga gaaagagagg gggctaggat    60
gaccctgagg tttgggcctg acaccagct gaggggtgaa gatactgcat tgagggaccc   120
cagggtcggg gtttgcaggg agtggccaga aggccttgtg aagaatcaga gacgtggctg   180
agtctgttcg gtgctgggtg cccgtcagac agctgcgtga gatggcaagg agacagttgg   240
atacgcatac ctgaagttga gagag                                         265

<210> SEQ ID NO 389
<211> LENGTH: 261
<212> TYPE: DNA
<213> ORGANISM: Homo sapiens

<400> SEQUENCE: 389
actgcctggc agaacatacc actgaactag tatgtgctag aggagggcac aaacatccgc    60
tccttcccta ggcctgctgg ctctggtttt ctatgcagat gattcattgg attggggtg   120 agtgttttgt ttttctgggg gcagtgtgag ctttgagggt tggaatattg ggaggcattc   180
cttagtttcc tcaactagcc tggaaagtta ggagtctagg gtaattaccc cccaatgagt   240
ctagcctact attcactgct t                                             261

<210> SEQ ID NO 390
<211> LENGTH: 194
<212> TYPE: DNA
<213> ORGANISM: Homo sapiens

<400> SEQUENCE: 390
aaagctgtgt ttatatggaa gaaagtaagg tgcttggagt ttacctggct tatttaatat    60
gcttataacc tagttaaaga aggaaaaga aaacaaaaaa cgaatgaaaa taactgaatt   120
tggaggctgg agtaatcaga ttactgcttt aatcagaaac cctcattgtg tttctaccgg   180
agagagaatg tatt                                                     194

<210> SEQ ID NO 391
<211> LENGTH: 268
<212> TYPE: DNA
<213> ORGANISM: Homo sapiens

<400> SEQUENCE: 391
aaagaacttc tatccagaat gcataaagaa ttaccgctca gcaacaaaaa acaataaaat    60
tagaaatggg caaaaagaa acttcactaa agataatggg tgtagccaat aagcacaaga   120 aaagtgctt gacatcatta ttcatcaggg aattgcaaat gtaaactaca gtaagaagcc   180
acggcatacc caccagaatg gctaaaatta aaaagactga caccaccaaa tgttggtaca   240

```
tatgtagaac aaccaattcc acacatag                                        268
```

<210> SEQ ID NO 392
<211> LENGTH: 262
<212> TYPE: DNA
<213> ORGANISM: Homo sapiens

<400> SEQUENCE: 392

```
ttttatagcg tgtagttgac ccttgaacaa tttgagtgcc aacctcctgt gcagctgaaa    60
ttcatgtata acttttgact ccccaaaaat ttaactacta atagcctatt gttgaccaga   120
agccttacct ataatataaa cagttgattc acacatattt tgcatgttat atatatatta   180
tatacagtat tctttttttct ttgcacatta aaaaaagaca tttattctgc atcatgatca   240
gacttacatt tagcaatcaa ca                                            262
```

<210> SEQ ID NO 393
<211> LENGTH: 203
<212> TYPE: DNA
<213> ORGANISM: Homo sapiens

<400> SEQUENCE: 393

```
gaggtgcatg atattgttag ccaaaaggga gaagacatac agacggttaa tatcgatgcc    60
agaaaagaga tgaccccccg acaagaaggg actgacaatg aggatccagt cgtgtgcctg   120
gacaagaaac cagtgatcat cattttcgat gagcccatgg acatccggtc tgcctataag   180
agactttcaa ctatctttga gga                                           203
```

<210> SEQ ID NO 394
<211> LENGTH: 230
<212> TYPE: DNA
<213> ORGANISM: Homo sapiens

<400> SEQUENCE: 394

```
gaggagtcga acatgatctt gaggactcta ctcttggagg cttaaaggaa tgtgttgtct    60
gtaattgtca cagggaatca ggaaggaaga gccagttagg gtcaagcgtt agaatatgtt   120
aagcttaata ggctttgaca ctcagatgtg cccatcaagc agttaggaat tggattattt   180
tgtttggaag aggtcagaac tagtcaagag atttcatagt ccttggtaaa               230
```

<210> SEQ ID NO 395
<211> LENGTH: 235
<212> TYPE: DNA
<213> ORGANISM: Homo sapiens
<220> FEATURE:
<221> NAME/KEY: misc_feature
<222> LOCATION: (66)..(98)
<223> OTHER INFORMATION: n is a, c, g, or t

<400> SEQUENCE: 395

```
cagaattcta tgcttctctg gcaacaacaa taactattag aaaatcttaa cctcacccag    60
aagttnnnnn nnnnnnnnnn nnnnnnnnnn nnnnnnnnca gcttacttaa ataattgtgc   120
taaatagctt atcttcacaa tttaaaagta aaaacctttg aaaagaagg acttcaccaa    180 aaacaaacac actctcccta tagccctgaa gatctggcca gaaaagctcc attaa         235
```

<210> SEQ ID NO 396
<211> LENGTH: 283
<212> TYPE: DNA
<213> ORGANISM: Homo sapiens
<220> FEATURE:

<221> NAME/KEY: misc_feature
<222> LOCATION: (124)..(124)
<223> OTHER INFORMATION: n is a, c, g, or t

<400> SEQUENCE: 396
gataataacc tttaatgaac tcaatactcg ggaaaggctt cacatttctg ggactcagca    60
ttatccaaaa tatctattaa gagccataca ccattctagc tgcaattgat tatacaaaaa   120
aaangaccaa agtggttaca ataataaaat agaacacaga gaaagaagaa aactacatgt   180
gttacaattt ggtaagataa acaaacaaac aacaaaaatt aatcactttt tttggtcctg   240
tgacacacat gataattttt gtcttaattc tcctaacaaa tga                     283

<210> SEQ ID NO 397
<211> LENGTH: 259
<212> TYPE: DNA
<213> ORGANISM: Homo sapiens

<400> SEQUENCE: 397
cggcagggtc ctggatcacc aaggaccttg aaagcatgtg gaagactttg atcaatgggg    60
gaatcattaa ggggttttgc attccggaac tatcatcagc ttcagcgggg gcagggggt   120 aggatagagg cagggaggca ggaagttctc gcagggtcca ggcaagagat ggtggagtgt   180
ggtcctgggg aaggggcag tggacggatc tgagggaggt tcagttagga tgggcaagga   240
ttgagatctg gctggatcc                                                259

<210> SEQ ID NO 398
<211> LENGTH: 202
<212> TYPE: DNA
<213> ORGANISM: Homo sapiens

<400> SEQUENCE: 398
gggacatccg aaagctacac cacagatgcc agtggttcat gccttcttcc cgcaacttta    60
ggaaaattta tttatttatt gtttattagt tatgggggga gagggagat ttaaaggacc   120 agggacatgg gaaccaagcc atagggatca gagggccttg tccttgaaca ctactggggt   180
atattcaggc tcatccacgc ag                                            202

<210> SEQ ID NO 399
<211> LENGTH: 257
<212> TYPE: DNA
<213> ORGANISM: Homo sapiens
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t

<400> SEQUENCE: 399
caggcaagaa aagcgcagag aaatcggtgt ctgacgattt tggaaatgag aacaatctca    60
aaaaaaaaaa aaaaaaaaaa aaaaaaaaan gaaagagaa aaaaaagact agccagccag   120
gaagatgaat cctagcttct tccattggaa aatttaagac aagntcaaca acaaaacatt   180
tgctctgggg ggcagggaaa acacagatgt gttgcaaagg taggttgaag ggacctctct   240
cttaccagta ccagaaa                                                  257

<210> SEQ ID NO 400
<211> LENGTH: 91

```
<212> TYPE: DNA
<213> ORGANISM: Homo sapiens

<400> SEQUENCE: 400
agagcaggag agacggcaga gatatgttgc taggtgaata tatatttata taataaatcc      60
gtaagttaat aaagtaaata gtaattctct g                                     91

<210> SEQ ID NO 401
<211> LENGTH: 132
<212> TYPE: DNA
<213> ORGANISM: Homo sapiens

<400> SEQUENCE: 401
gtatggactg agaggcattt aaattctggc aagggaggtg gaaatgctga caatgaggag      60
gaagcttata gtgggtcaaa caaggaggtg tctagtgtgt tgtttaaaaa gaaggcttac     120
aattagccag gc                                                        132

<210> SEQ ID NO 402
<211> LENGTH: 158
<212> TYPE: DNA
<213> ORGANISM: Homo sapiens

<400> SEQUENCE: 402
tcccaagggt cgctagaaac tcgtcttcgc gttgccccct ttctggctct cagcgccgtc      60
gccactcggg agaggctggg tgaggcccgt gtgaggactg accctggatt cctcgaaact     120
gccattgtga tcattactct gctctttgga aatggctg                            158

<210> SEQ ID NO 403
<211> LENGTH: 271
<212> TYPE: DNA
<213> ORGANISM: Homo sapiens

<400> SEQUENCE: 403
gttacatgaa atagtgccag ctggaggttc tttgccagca ccatgccaag tgaaataata      60
tatttactct ctctattata caccagtgtg tgcctgcagc agcctccaca gccacgatgg     120 gtttgttttct gttttcttgg gtggggagca gggacgggcg gagggaggag agcaggtttc    180
agatccttac ttgccgagcc gtttgtttag gtagagaaga caagtccaaa gagtgtgtgg     240
gctttcctgt ttctaaactt tcgctactat a                                   271

<210> SEQ ID NO 404
<211> LENGTH: 77
<212> TYPE: DNA
<213> ORGANISM: Homo sapiens

<400> SEQUENCE: 404
tgtctgtgcc tcatggaatt gccaatgaag atattgtctc tcaaaacccc ggagaactct      60
cttgtaagcg tgggat                                                     77

<210> SEQ ID NO 405
<211> LENGTH: 131
<212> TYPE: DNA
<213> ORGANISM: Homo sapiens

<400> SEQUENCE: 405
ccctgtgctt tttgccgtcg ggcctctgca cctgggtcca tggggtctgc ggggtctgcg      60
gggtctgcct ggcctgtggg ttctgccggt ggggcttcag gagtaataaa gtgtcaccct     120
```

```
atccttgtaa a                                                           131

<210> SEQ ID NO 406
<211> LENGTH: 226
<212> TYPE: DNA
<213> ORGANISM: Homo sapiens

<400> SEQUENCE: 406
ggccatccga aaatagcaac aacccagact ggctcctcac tcccttttcc atcactaaaa      60
atcacagagc agtcagaggg acccagtaag accaaaggag gggaggacag agcatgaaaa     120
ccaaaatcca tgcaaatgaa atgtaattgg cacgaccctc accccaaat cttacatctc      180 aattcccatc ctaaaaagca ctcatacttt atgcatcccc gcagct                    226

<210> SEQ ID NO 407
<211> LENGTH: 171
<212> TYPE: DNA
<213> ORGANISM: Homo sapiens

<400> SEQUENCE: 407
gatatttgtc tatgaacagt agcacagacc ctctaattcc atagggaatc atttccatga      60
cttcccccaa atacccact cttctctatc tctgtgacag tctctggccc tgctccctcc      120
taaactgctc aaaatcctta ccaaaatggc ttacaaatct ctctcctccg g              171

<210> SEQ ID NO 408
<211> LENGTH: 266
<212> TYPE: DNA
<213> ORGANISM: Homo sapiens

<400> SEQUENCE: 408
ccctgtggat cccaaccagg aagttcctcc tgggccacct cggttccagc aagttcctac      60
ggatgccctg ccaacaagt tgtttggtgc tcctgagccc tccaccatcg cccgctctct      120
accaaccact gtcccagagt caccaaaacta ccgcaacacc aggacccctc gcactccccg    180
gacaccacag ctcaaagact caagccagac atcacggttt tacccagtgg tgaaagaagg    240
acggacactg gatgccaaga tgcctc                                          266

<210> SEQ ID NO 409
<211> LENGTH: 300
<212> TYPE: DNA
<213> ORGANISM: Homo sapiens

<400> SEQUENCE: 409
tatagttctg ttgtaggcta cacatgaaca gcaaccaaaa agaggaaaaa tcttctttgt      60
ccccatgctt tttccttgaa ttctgcactt tcatattaa cattagccct tgctttgtga      120
tttgcctttg ctttatttta ccctgtctta atcttaacct tcccaaatat ttccatacag     180
ggtgcacctc tcctagacaa cacacagcgg agagtgtgct tcccatgtat tcaatcttcg     240
tctcttgaaa ggagaggtgc cctcattaca cttcactgtg acacaggata cccttggttt     300

<210> SEQ ID NO 410
<211> LENGTH: 67
<212> TYPE: DNA
<213> ORGANISM: Homo sapiens

<400> SEQUENCE: 410
atggaaaaga acacgatgag aattagacac tggaaaatat gtatgtgtgg ttaataaagt      60
gctttaa                                                               67
```

<210> SEQ ID NO 411
<211> LENGTH: 274
<212> TYPE: DNA
<213> ORGANISM: Homo sapiens

<400> SEQUENCE: 411
tcaggttgtg aggtttatta gtccccaagg caaacacaaa tattagatta ataatccaac    60
tttaatagta tacatttaaa agaaaaaaaa caaaagccct ggaagttgag gccaagcctg   120
ctgagtattg cagctgcatt tgcccaaagg gaatccagaa caagtccctc cctgtatttt   180
gttcttgaga ggggtcagtc tagaagctag atcctatcag gatgaggagc agcagcccag   240
ggcttgtctg gatcagcacc aacgatttta aaga                               274

<210> SEQ ID NO 412
<211> LENGTH: 265
<212> TYPE: DNA
<213> ORGANISM: Homo sapiens

<400> SEQUENCE: 412
gtggtgttct tgatgtagtg agctcaagtc tgcggctgtt tctggggacg tggtggaggc    60
tgcatgttct gttctctcca ggaagagcta gtggttttct accctgtgtg ttggtgagca   120
atgtgcagag gcagagccgc tgaagtatgg ttcctgaggg gtggcgaagc accgccctca   180
ctccaggtca cctcatcagc cctcgttttt ttttgggccc caccttgggg cttgccaaac   240
tgagaggcat tcaaaaccat ggcac                                         265

<210> SEQ ID NO 413
<211> LENGTH: 120
<212> TYPE: DNA
<213> ORGANISM: Homo sapiens

<400> SEQUENCE: 413
aggacgcggg ctctcgctgg cccgagctct acctctactc gagggctgac gaagtagtcc    60
tggccagaga catagaacgc atggtggagg cacgcctggc acgccgggtc ctggcgcgtt   120

<210> SEQ ID NO 414
<211> LENGTH: 102
<212> TYPE: DNA
<213> ORGANISM: Homo sapiens

<400> SEQUENCE: 414
gaagcatttg gaggaattcc tagacattgc gtttctgtg ttgccaaaat cccttccgac    60
atttctcaga catctcccaa gttcccatca cgtcagattt gg                      102

<210> SEQ ID NO 415
<211> LENGTH: 281
<212> TYPE: DNA
<213> ORGANISM: Homo sapiens

<400> SEQUENCE: 415
atgtctccag attccaggtg caggttctta gcacctccgc agccgctctc tcttgagtcc    60
atcctcagtc tctcctaccc cttgaagtag ggggaccctg aatttgccca tccacctggg   120
tcactttgag agttgtgcag gggggctggg agcactggtg ttcacgtggg accacaggct   180
gcaccataag acccactcac aataaaaaaa taaaggccg agccgggcat ggttgctcac   240
tcccgtaata aaaaaataaa agaacaggct gagccgggaa a                       281

<210> SEQ ID NO 416
<211> LENGTH: 265
<212> TYPE: DNA
<213> ORGANISM: Homo sapiens

<400> SEQUENCE: 416
tgtgattgtc agcaatgacc atgctgggaa actgtgtggg gcctgtggaa actttgacgg    60
ggaccagacc aatgattggc atgactccca ggagaagcca gcgatggaga atggagagc   120 gcaggacttc tccccatgtt atggctgatc agtcatccac caggaacgaa gatttcctga   180
agaagacctg gtccctctgg aggttgcggt ggctgaagga tgcatcatgt gctcctaccc   240
tgctctaccg cttttctggg tcaca                                        265

<210> SEQ ID NO 417
<211> LENGTH: 203
<212> TYPE: DNA
<213> ORGANISM: Homo sapiens

<400> SEQUENCE: 417
acattggaaa gttaagagag ttcgagggaa gaattataaa gactaggagt cctagaaaga    60
gaaaatttag agaataaaag gagaggcagt acttgaaaga taacacaatt tttacaaatt   120
tgttggaaaa acatgaattc ataaattcag gaagcacaat atatacccaa catatattta   180
aataaaatcc aggcctagac tca                                          203

<210> SEQ ID NO 418
<211> LENGTH: 274
<212> TYPE: DNA
<213> ORGANISM: Homo sapiens
<220> FEATURE:
<221> NAME/KEY: misc_feature
<222> LOCATION: (108)..(118)
<223> OTHER INFORMATION: n is a, c, g, or t

<400> SEQUENCE: 418
ttcccccttt gaatgaggtc ttccatgttt gagggaaagt cttgcactat tgcatatatt    60
ttggggacac agattttcat agtttccatt tttgggggc ttaaggannn nnnnnnnnct   120
gtttgaaaca gttttatact ttctgatata gtacttgaaa ttcttaccag aaaattactt   180
tggagttttg aagcctttat taatactact tttaaagaag cagttgtttt attgtcaatg   240
ttttttttcc cccacgcata ttttcttgta tttc                              274

<210> SEQ ID NO 419
<211> LENGTH: 71
<212> TYPE: DNA
<213> ORGANISM: Homo sapiens

<400> SEQUENCE: 419
tgagatggtt tgatggtttg ctgcattaaa ggtatttggg caaacaaaat tggagggcaa    60
gtgactgcag t                                                        71

<210> SEQ ID NO 420
<211> LENGTH: 269
<212> TYPE: DNA
<213> ORGANISM: Homo sapiens

<400> SEQUENCE: 420
tactaacttt cctgcactaa accaccaagt ctgtctcctc tgcaatgtgt agttcctgat    60
ggctccggtt tttccccccca ccttttttatt ttgaagcctg acttgcagga gatacccctc   120

```
taactgtata gcttcctact ccattaaaga ttagtcagag atggtaatca acccacctga    180
gctctttcac tacctgctgc tgcaactatg gtcaggataa ggggagcaca ctcacacttc    240
aggccttcac gtctgttcca gttactttt                                      269
```

<210> SEQ ID NO 421
<211> LENGTH: 47
<212> TYPE: DNA
<213> ORGANISM: Homo sapiens

<400> SEQUENCE: 421

```
ctttgaacca ctttgcaatt gtagattccc aacaataaaa ttgaaga                   47
```

<210> SEQ ID NO 422
<211> LENGTH: 149
<212> TYPE: DNA
<213> ORGANISM: Homo sapiens

<400> SEQUENCE: 422

```
ggactaggaa gggctattcc aggctcagcc ctgctcctgc agctttgccg ctgagtgtag     60
gaaaaacagg catgacagac cagggtgagg gttgtgccca gctgggccac ggccatgcgt    120
ggggtggccc aataaacacc gtggactcc                                      149
```

<210> SEQ ID NO 423
<211> LENGTH: 185
<212> TYPE: DNA
<213> ORGANISM: Homo sapiens

<400> SEQUENCE: 423

```
tttctctttc tgtccggtgt ccggactttc ctaattggag tttgaggccc ctaagctggc     60
atcaacccca ggccacgctc gctctttcct tccctcccct cccctctgc cttttgtacg    120 ccagttctca gaaataaaga tcttttgtcc gttttttttaa cctcggattc tgtaattggt    180
tctta                                                                185
```

<210> SEQ ID NO 424
<211> LENGTH: 105
<212> TYPE: DNA
<213> ORGANISM: Homo sapiens

<400> SEQUENCE: 424

```
ccacaggtaa ccttctcact aagtgggggt gtctgaggcc agggagagct ctactcattc     60
ccctgtgtga tcccagcagt gagcatagag caggtgccct gcaat                    105
```

<210> SEQ ID NO 425
<211> LENGTH: 122
<212> TYPE: DNA
<213> ORGANISM: Homo sapiens

<400> SEQUENCE: 425

```
cccccatgcc ctgtggagat ggaggtgtgt gctgatccct cgtgcccctg tggagataga     60
ggtgtgtact gatccctgt tcccctatct agatgaaggt gtgtactgct gatccccgt     120 cc                                                                   122
```

<210> SEQ ID NO 426
<211> LENGTH: 255
<212> TYPE: DNA
<213> ORGANISM: Homo sapiens

<400> SEQUENCE: 426

```
tttttgacag tgttgaaaat gttcagaagg ttgctctaga ttgagagaag agacaaacac    60
ctcccaggag acagttcaag aaagcttcaa actgcatgat tcatgccaat tagcaattga   120
ctgtcactgt tccttgtcac tggtagacca aaataaaacc agctactg gtcttgtgga     180
attgggagct tgggaatgga tcctggagga tgcccaatta gggcctagcc ttaatcagtc   240
ctcagagatt tcttc                                                    255
```

<210> SEQ ID NO 427
<211> LENGTH: 236
<212> TYPE: DNA
<213> ORGANISM: Homo sapiens

<400> SEQUENCE: 427

```
cccactctgt gtagtcttaa cttatttctt ctaaactcac cattaaccta aataatagtc    60
aaatttaggg gggctgtatt tgtcttactc gagtcttcta ccatagttga aactgtcgta   120
cccaaacgag ttacagagaa atgccacact ttgagacgaa ttcaggagtc ctttattagc   180
tggtgactga gagacggcta acacaggaaa tactctcggc cctaaagaat gggcta        236
```

<210> SEQ ID NO 428
<211> LENGTH: 275
<212> TYPE: DNA
<213> ORGANISM: Homo sapiens

<400> SEQUENCE: 428

```
gaagacgcca atgatggctg aagagttttt cccagattta caagccactg gagacccctt    60
ttttctgata caatgcacga ttctctgcgc gcaaggaccc tcgactcacc cccatgtttc   120
agtgtcacag agacattctt tgataaggaa atggcacaaa cataagggga aaggctgcta   180
atttttcttg gcagattgta ttggccagca ggaaagcaag ctctccagag aatgccccca   240
gttaaatacc tcctctacct ttacctaagt tgctc                              275
```

<210> SEQ ID NO 429
<211> LENGTH: 223
<212> TYPE: DNA
<213> ORGANISM: Homo sapiens

<400> SEQUENCE: 429

```
tgatctggtc agtagtggaa ttcgatttta tgcagactgg atgtaatatt tgtaatccct    60
gtgcaatttt gtgacgtgcg gttctaattc atgtgcagtg atatagtata gataaaagaa   120
tgagtaaaag aaaatacaag aattctaaag aaagttggtt ttagcccctt tgatagtcca   180
tggttaagac atcctttata aaccaaagat ggccagcaca ctg                     223
```

<210> SEQ ID NO 430
<211> LENGTH: 273
<212> TYPE: DNA
<213> ORGANISM: Homo sapiens

<400> SEQUENCE: 430

```
cagaagaggg ctcaacttag ccaatatttt gatgctgtca agaatgctca gcatgtggaa    60
gtggagagta ttcctttgcc agatatgcca catgctcctt ccaacatttt gatccaggac   120
attccacttc ctgggtgccc agccaccctc tatcctaaag aaaacctcag cctatggacc   180
tcccaactcg ggccagtttc tatccttccc tccttccttg dacatggggg tttccaccgt   240
ttgcccccct ggcagaaaaa cctccctggg cct                                273
```

<210> SEQ ID NO 431
<211> LENGTH: 112
<212> TYPE: DNA
<213> ORGANISM: Homo sapiens

<400> SEQUENCE: 431
gagtccaaga gaatggccga gttcatgagc tgcacacgat gtaagttgta ctctctgaaa      60
ttgttggtcc acctttcatc ttcatcaaat gagcatcccc tccaataccct gg            112

<210> SEQ ID NO 432
<211> LENGTH: 262
<212> TYPE: DNA
<213> ORGANISM: Homo sapiens

<400> SEQUENCE: 432
gagtcacgaa ccttattctc caaaacaaaa gcaacaagga ctttgacttc tcagcagcac      60
tcagctctgg ttcttgaaac accccgtta cttgctattc ctcctacctc ataacaatct      120
ccttcccagc tctactgct gccttctctg agttcttccc agggtcctag gctcagatgt      180
agtgtagctc aaccctgcta cacaaagaat cttctgaaag cctgtaaaaa tgtccatgca     240
tgttctgtga gtgatctacc aa                                             262

<210> SEQ ID NO 433
<211> LENGTH: 152
<212> TYPE: DNA
<213> ORGANISM: Homo sapiens

<400> SEQUENCE: 433
ccggggtagc cattggttct tggatctgtg ttagaatgag tgctttccct tcctactgat      60
gtgattgtgg attaggaatt cgtgaccgag tgattttttgg ccagtggttg ggtttaaaat    120
tctattaaaa tttgtagttt gggctgggtg ct                                   152

<210> SEQ ID NO 434
<211> LENGTH: 99
<212> TYPE: DNA
<213> ORGANISM: Homo sapiens

<400> SEQUENCE: 434
gtggaggccc attaccgggc ctgcttgtat gctggagtca agattgcggg gactaatgcc      60
gaggtcatgc ctgcccagtg ggaatttcag attggacct                            99

<210> SEQ ID NO 435
<211> LENGTH: 207
<212> TYPE: DNA
<213> ORGANISM: Homo sapiens
<220> FEATURE:
<221> NAME/KEY: misc_feature
<222> LOCATION: (115)..(115)
<223> OTHER INFORMATION: n is a, c, g, or t

<400> SEQUENCE: 435
ttcatttttc ttcccctctg ctagtttgga agttatatta taccaagttt tttagtatta      60
gcctagaaat cttaacataa agacttctaa taagcaatat ctttaatttt ttttnectac     120 ccaatactag atcatgagca ttttcccaca tcataaagaa ttggtcacaa gtcagcccca     180
aacatagtcc agtggaatcc aatgata                                         207

<210> SEQ ID NO 436

```
<211> LENGTH: 231
<212> TYPE: DNA
<213> ORGANISM: Homo sapiens

<400> SEQUENCE: 436
aaggcaacac ttctgtcagt agaattgctt tggattgtaa atatgtttac ttcagaggaa      60
atcagtcaga gtggatggct cagcaaaacc catcacaact gcggaaaaag gaagtgactg     120
gctagaggta aggaaataga ttttctctaa gttaactggc ctacgtgtga atcgaaccct     180
gcaccctggc ctcattagca ccaacactgt gaagaacagc tgtggcagag a              231

<210> SEQ ID NO 437
<211> LENGTH: 133
<212> TYPE: DNA
<213> ORGANISM: Homo sapiens

<400> SEQUENCE: 437
ttcacccctc tacttacata ttgtaaagtt gtataaatct atcattgaaa ggtcccctct      60
gccagcagtg gtgccaccct ttggtttgct gtggtacttt gctgtgtact ccgtggcatc     120
atgttactgt gta                                                        133

<210> SEQ ID NO 438
<211> LENGTH: 66
<212> TYPE: DNA
<213> ORGANISM: Homo sapiens

<400> SEQUENCE: 438
tttctctttc tgtccggtgt ccggactttc ctaattggag tttgaggccc ctaagctggc      60
atcaac                                                                 66

<210> SEQ ID NO 439
<211> LENGTH: 233
<212> TYPE: DNA
<213> ORGANISM: Homo sapiens

<400> SEQUENCE: 439
tacaaagagt accacgagac acgagaaacc ttgtgggaac acaggggac caccccctaa       60 ggctaaatac tacttggtga ccgatagcga acaagtaccg tgagggaaag gtgaaaagaa     120
ccccgagagg ggagtgaaaa agaatctgaa acctagtgtt tacaagcagc gaaaatggca     180
caagccatga atcgtgtact ttttgtagaa cgggccagcg agttatgaca aaa            233

<210> SEQ ID NO 440
<211> LENGTH: 260
<212> TYPE: DNA
<213> ORGANISM: Homo sapiens

<400> SEQUENCE: 440
tctcttccga ggtcgaggcc ctgaggcggc agttactcca ggaacaggaa agtgtcaaac      60
aagctcactt gaggaatgag catttccaga aggcgataga agataaaagc agaagcttaa     120
gtgaaagcaa aatacgaaat tgagaggctg cagtctctca cagagaacct gaccaaggag     180
cacttgatgt tagaagaaga actgcggaac ctgaggctgg agtacgatga cctgaggaga     240
gacgaaacga gccccacagc                                                 260

<210> SEQ ID NO 441
<211> LENGTH: 270
<212> TYPE: DNA
<213> ORGANISM: Homo sapiens
```

<400> SEQUENCE: 441

```
catagccaag gcttcaagct ctcaggactt ggctatggag gaggacgaag aaggcaggag      60
ctcatccagt ccagccttac ctacagcagg aaactgcacc agctagactc cattctggga     120
ccatctccag gagtccatga gaggctttct tctcctatgt cccaattctc agaactcaga     180
tgtggctaga ccaacccctg ggaaactgcc ccagcttctc ccaccatagg ggccggaccc     240
ccatcaccag cctagatcca gggctgcctc                                      270
```

<210> SEQ ID NO 442
<211> LENGTH: 156
<212> TYPE: DNA
<213> ORGANISM: Homo sapiens

<400> SEQUENCE: 442

```
aacttgtgcg cgcagcccaa actaacctca cgtgaagtga cggactgttc tatgactgca      60
aagatggaaa cgaccttcta tgacgatgcc ctcaacgcct cgttcctccc gtccgagagc     120
ggaccttatg gctacagtaa ccccaagatc ctgaaa                               156
```

<210> SEQ ID NO 443
<211> LENGTH: 103
<212> TYPE: DNA
<213> ORGANISM: Homo sapiens
<220> FEATURE:
<221> NAME/KEY: misc_feature
<222> LOCATION: (48)..(48)
<223> OTHER INFORMATION: n is a, c, g, or t

<400> SEQUENCE: 443

```
gttttgagat catacactgt tacagagaaa gagaggaggc atattatnaa cgtgtggact      60
tcagtgttat tccttctctt caaaatgatg ttccaggtgt cta                      103
```

<210> SEQ ID NO 444
<211> LENGTH: 101
<212> TYPE: DNA
<213> ORGANISM: Homo sapiens

<400> SEQUENCE: 444

```
ctcggcggcc tttatttatt ctgttccccc agctcggcca cttctctgaa ggagggctgg      60
gttctgggcc tgtatcgaat aaacacaaac ctggatggcg c                         101
```

<210> SEQ ID NO 445
<211> LENGTH: 144
<212> TYPE: DNA
<213> ORGANISM: Homo sapiens

<400> SEQUENCE: 445

```
ggaggatggt caggcgtcac caacaacccc atcacccagt aacaagaacc ttgactctcg      60
tcagtccctc tgcatcaaga cacttaccca tttcccacct catgcctgct aacttgaatg     120
aaacaatcgc tgggaaagca ttaa                                            144
```

<210> SEQ ID NO 446
<211> LENGTH: 276
<212> TYPE: DNA
<213> ORGANISM: Homo sapiens

<400> SEQUENCE: 446

```
atgtgagagt gctttgcagt tggaaagtgc tgtaggaacc ctgaattcat ctgaaactgt      60
```

| | |
|---|---|
| agcttagtgt ttaaatgatg tctgttatta ctttttttgaa tagtctggag tgcttgttaa | 120 |
| agaaaaaatt attctgtgat atttgttgaa tgaagcacag tgaggaagac tttactcagg | 180 |
| gcccttgtaa tagctatagg gaccactgca atagggtctt gcagtggggg agagagaata | 240 |
| ggctcaattc tgaatacatc atcatgggca agtggg | 276 |

<210> SEQ ID NO 447
<211> LENGTH: 48
<212> TYPE: DNA
<213> ORGANISM: Homo sapiens

<400> SEQUENCE: 447

| | |
|---|---|
| tctaaagctg ttttttaactc cgagattaca acttagagga accaagga | 48 |

<210> SEQ ID NO 448
<211> LENGTH: 168
<212> TYPE: DNA
<213> ORGANISM: Homo sapiens

<400> SEQUENCE: 448

| | |
|---|---|
| aaattgaagg atttgctgtt attcctacct gcattggact tgacctgggt gttgggtgag | 60 |
| tagcaatctg ttactgtttc tctatgtgga cgatgaggaa agggttgaga aatccagcga | 120 |
| aaggacactt ctgttaatag ctcaatctgc tgcccatggt tgggaaaa | 168 |

<210> SEQ ID NO 449
<211> LENGTH: 147
<212> TYPE: DNA
<213> ORGANISM: Homo sapiens

<400> SEQUENCE: 449

| | |
|---|---|
| tttttctgta tgaaacccag atgtcaccaa atggacatta atagttgcat taaggatcag | 60 |
| tagcattaac aaaagttgct ttaaaagcca ttatgtaaat caagacttga aaatgagtga | 120 |
| gggaatttta gcgacactgt ctgagca | 147 |

<210> SEQ ID NO 450
<211> LENGTH: 272
<212> TYPE: DNA
<213> ORGANISM: Homo sapiens

<400> SEQUENCE: 450

| | |
|---|---|
| tgaattccca actttccgag atgttgttta atgagactca cccttatttt tcaattcttc | 60 |
| cttcattctc tccctcttaa ctggtttcct cttacccaag aaaagccttt ctcttaactg | 120 |
| caagcttatt tgaattttac cttattgaat atctttcaac tatttggcag accttttaact | 180 |
| ttccctacca tgccaatggt cactaaacac cttaaatgcc actcttaaca ccttaaatgc | 240 |
| cacccttaac agtattcttt cagtcctcat tc | 272 |

<210> SEQ ID NO 451
<211> LENGTH: 267
<212> TYPE: DNA
<213> ORGANISM: Homo sapiens

<400> SEQUENCE: 451

| | |
|---|---|
| tgtccagcaa gtgcagggtg cctgcacttc accctgtgca gagaggtggg atggggccgt | 60 |
| gcacacaggg atgcccgctc cacatcctgc ctgcccctca gccctggccc aggcccttt | 120 |
| tggaggcagc tgaggaagga tgctgggaa agccctcttc tgcagctttg tggaaggctg | 180 |
| atcagtggct gctgggtggc gggtacccctt gctcagatgc ctggcagggc tgggtggcga | 240 | ttcataaaga cctcgtgttg attcccc                                              267

<210> SEQ ID NO 452
<211> LENGTH: 138
<212> TYPE: DNA
<213> ORGANISM: Homo sapiens

<400> SEQUENCE: 452
caggagagaa gaggccccgg catggggatc tgggttctag agggcatgtg atgactgtaa           60
atgttcactg ggtgggtagg gagtggtatc cagtgttcaa gtgcagaaat ctttggcttt          120
gctaccagtt ccatatga                                                        138

<210> SEQ ID NO 453
<211> LENGTH: 176
<212> TYPE: DNA
<213> ORGANISM: Homo sapiens

<400> SEQUENCE: 453
ggttaatctt tgttactagc cctcactact cagaattggt gagacctctc catttctgct           60
tcactcagct tacgtggttt gctcacactg acaccaacaa acacctgtca atccctatgt          120
ccctcctgtc ttccaaaaat acctagaaat tgctgctcta ttgacggtag tatttc              176

<210> SEQ ID NO 454
<211> LENGTH: 256
<212> TYPE: DNA
<213> ORGANISM: Homo sapiens

<400> SEQUENCE: 454
gctctaaaag ttatgaacct gacattcttg gtcttacaca atctggaccc agtctactct           60
tctataacca tcttccactt aatttacaaa tctttattaa ggcacaggta ctcctactta          120 tccctattg cctctctcat gctgaatcaa tcatgccaaa agctaagaaa acatgagcat           180
gcttgggact aaagaaacag aactgaggat ttcctacaca tcctaactgc aaggacagtc          240
catcaaaagc cagaga                                                          256

<210> SEQ ID NO 455
<211> LENGTH: 101
<212> TYPE: DNA
<213> ORGANISM: Homo sapiens

<400> SEQUENCE: 455
ggaagcttta gctaccaatc cagtaccctc ctaactagaa tgtatacaca tcagccagga           60
ctgactgact acttcattag agatatactg tactcattgg g                              101

<210> SEQ ID NO 456
<211> LENGTH: 230
<212> TYPE: DNA
<213> ORGANISM: Homo sapiens
<220> FEATURE:
<221> NAME/KEY: misc_feature
<222> LOCATION: (131)..(131)
<223> OTHER INFORMATION: n is a, c, g, or t

<400> SEQUENCE: 456
tacctgtggt tccaggtacc tggagggctg acgtaggagg attgcctgag cccagcaggc           60
caaagctaca gtgagctgtg attgtgccac tgcactccag cctgggcgag gagagcaaga          120
ctctgtctca naaataaata cataaaatac agcgtccaaa agtgtgtcat cttctttctc          180 ttcacaatttt tataataagg gggtaaaatg cctgtgagtc tattcattat          230

<210> SEQ ID NO 457
<211> LENGTH: 38
<212> TYPE: DNA
<213> ORGANISM: Homo sapiens

<400> SEQUENCE: 457
ctttggacta aagaatatat tgggcgaaga atagaggg                         38

<210> SEQ ID NO 458
<211> LENGTH: 154
<212> TYPE: DNA
<213> ORGANISM: Homo sapiens

<400> SEQUENCE: 458
ttctgctttt cctgttccct atccttacgc aggattgttt tactgttagc caggttaagt  60
ttaagcttct tgaggacttt agtactgaaa gacaatggct cacttgtaag acctagttga  120
agagtacaga tttagatttg ttcagtgtgc tgtg                              154

<210> SEQ ID NO 459
<211> LENGTH: 156
<212> TYPE: DNA
<213> ORGANISM: Homo sapiens

<400> SEQUENCE: 459
aacatatgtg tagtgtgctg cagcataaga tggaagaact taaagaaggc ctgcggcaaa  60
gagatgagct tattgagaaa catggcttag ttataatccc cgatggcact cccaatggtg  120
atgtcagtca tgaaccagtg gctggagcca tcactg                            156

<210> SEQ ID NO 460
<211> LENGTH: 267
<212> TYPE: DNA
<213> ORGANISM: Homo sapiens

<400> SEQUENCE: 460
aagcttttag agaatacact acaccaggga gtatgactac tagtatgact attaggaggg  60
taataccaag agttggacta cgcaccttag gcaagataca aaccaactaa aatagaataa  120
agaatgagtc agatgagtgt agccatttta accaagcagc acatttgtta atttctacaa  180
cttagtctca gcgatacccca ttgtatttag ccatgttcaa caacaagtgt cagaaactgc  240
acagactcct ccctgttcag ctggtag                                      267

<210> SEQ ID NO 461
<211> LENGTH: 143
<212> TYPE: DNA
<213> ORGANISM: Homo sapiens

<400> SEQUENCE: 461
ctttgtccgc tgtcatgatt cgccacgtgc cttcttctgt cctctcacgg ctaggcctcc  60
agtgaaaggt agacagtaag cctgggcatt cagtcttctg aatttctcac atcaattcca  120
gggaaaatcc aaccactcca aca                                          143

<210> SEQ ID NO 462
<211> LENGTH: 270
<212> TYPE: DNA
<213> ORGANISM: Homo sapiens

<400> SEQUENCE: 462

```
atccagcaag gaatagtgca gcacctaggg actagcaatg ataggaagtt gcaccatatt      60
tggcccagca agggcaaagg gagagagtag ttgtgggagt ccagagagac cctggttgtt     120
gcttctcatt tattgaaccc gatttaaagc cagagaacaa agagcccagt ttatgtagta     180
catgacgcag cctcctaggc acagggtaaa ggatggagaa tagatctgga ggattaaata     240
gtaacaacaa cgcgcgagat cctctaagtc                                      270
```

<210> SEQ ID NO 463
<211> LENGTH: 88
<212> TYPE: DNA
<213> ORGANISM: Homo sapiens

<400> SEQUENCE: 463

```
ttgagaacag aaatagtggc attgcatgcc cagcaagatc gggcccttac ccagacagac      60
aggaagatcg aaactgaggt tgctggcc                                         88
```

<210> SEQ ID NO 464
<211> LENGTH: 102
<212> TYPE: DNA
<213> ORGANISM: Homo sapiens

<400> SEQUENCE: 464

```
tatttcttat gctgtcagat tacattttc ctttgagtgc tttgggtgca gccgtggaat       60
cctgatgtaa aagcataggt tcttgcatta ctgagtaaac at                        102
```

<210> SEQ ID NO 465
<211> LENGTH: 221
<212> TYPE: DNA
<213> ORGANISM: Homo sapiens

<400> SEQUENCE: 465

```
gcagatggca agtgcaccaa ggagaaggca ggaacactgg agcctgcaat aagggaggag      60
aggggactgg agagtgtggg gaatgggaag aagtagttta ctttggacta aagaatatat    120
tgggcgaaga atagaggggg agcttgcagg aaccagcaat gagaaggcca ggaaaagaaa    180
gagctgaaaa tggagaaaac cagagttaga actgttggat a                        221
```

<210> SEQ ID NO 466
<211> LENGTH: 281
<212> TYPE: DNA
<213> ORGANISM: Homo sapiens

<400> SEQUENCE: 466

```
caccettctt gaccacaaaa aggtggccat cctgactggt ctctaccttc aggaaaacaa      60
atggggacct gagggcgctc aaccacccca gaccacccag aagtcacagg agcacggaac    120
aggaagcagg gagacagcac acagtaagca catggcaagc acacagtaaa cacacggcaa    180
gtacatggca aatacacagc aggtacacag cgagcacaca gtaagcacac ggtaaacact    240
cagcaagtac atggcaaatg cacagcaggt acacagcgag c                        281
```

<210> SEQ ID NO 467
<211> LENGTH: 133
<212> TYPE: DNA
<213> ORGANISM: Homo sapiens

<400> SEQUENCE: 467

```
cccgggccag gcaaggtggg tcacacctgt aatcccagca ctttggggaa caaggtggga      60
```

```
gaatcacttg agtccggcag tttgagacca gcctggccaa cataatgaga ccgcatcttc    120
acaaaaaata tgt                                                      133

<210> SEQ ID NO 468
<211> LENGTH: 62
<212> TYPE: DNA
<213> ORGANISM: Homo sapiens

<400> SEQUENCE: 468
agctcggcca cttctctgaa ggagggctgg gttctgggcc tgtatcgaat aaacacaaac     60
ct                                                                   62

<210> SEQ ID NO 469
<211> LENGTH: 266
<212> TYPE: DNA
<213> ORGANISM: Homo sapiens

<400> SEQUENCE: 469
acttcaggaa caggagcaac tactaaaaga gggatttcaa aaagaaagca gaataatgaa     60
aaatgagata caggatctcc agacgaaaat gagacgacga aaggcatgta ccataagcta    120
aagaccagag ccttcctgtc acccctaacc aaggcataat tgaaacaatt ttagaatttg    180
gaacaagcgt cactacattt gataataatt agatcttgca tcataacacc aaaagtttat    240
aaaggcatgt ggtacaatga tcaaaa                                        266

<210> SEQ ID NO 470
<211> LENGTH: 147
<212> TYPE: DNA
<213> ORGANISM: Homo sapiens

<400> SEQUENCE: 470
gcccagcctg gatatttaaa ttgttctgtg ctctcctcct ttttttttctc tctgtgattc    60 tctttgtcag ctcctttgcc tatatttgca tctcagttga caccctgat tctgacttgt    120 ccttatcttc ctaccagtct ctgccga                                       147

<210> SEQ ID NO 471
<211> LENGTH: 187
<212> TYPE: DNA
<213> ORGANISM: Homo sapiens

<400> SEQUENCE: 471
gtaggagtgc tcatggttct gtcattcttg gacctctcct ggctgagctc tgattccctg     60
tgagcacgat gctgatgcaa tagtcctgtg tcatcactgc agcggtcctc aggagctgcc    120
agggccaatt gctacagagt gtctgggtgt gtggcatagg aggaaggttt gcttgtgaaa    180
tgaggct                                                             187

<210> SEQ ID NO 472
<211> LENGTH: 235
<212> TYPE: DNA
<213> ORGANISM: Homo sapiens

<400> SEQUENCE: 472
atctacgcca ctcgctctgg tgggaccctc gtgcttgtgg ggctgggctc tgagatgacc     60
accgtacccc tactgcatgc agccatccgg gaggtggata tcaagggcgt gtttcgatac    120
tgcaacacgt ggccagtggc gatttcgatg cttgcgtcca gtctgtgaa tgtaaaaccc    180 ctcgtcaccc ataggtttcc tctggagaaa gctctggagg cctttgaaac attta        235
```

<210> SEQ ID NO 473
<211> LENGTH: 177
<212> TYPE: DNA
<213> ORGANISM: Homo sapiens
<220> FEATURE:
<221> NAME/KEY: misc_feature
<222> LOCATION: (59)..(71)
<223> OTHER INFORMATION: n is a, c, g, or t

<400> SEQUENCE: 473
gaagtaagcc tcatcatcag agcctttcct caaaactgga gtcccaaatg tcatcaggnn    60
nnnnnnnnnn ncagccacta agaaccctc tgcttttaac tctagaattt gggcttggac   120
cagatctaac atcttgaata ctctgccctc tagagccttc agccttaatg gaaggtt     177

<210> SEQ ID NO 474
<211> LENGTH: 34
<212> TYPE: DNA
<213> ORGANISM: Homo sapiens

<400> SEQUENCE: 474
taaagcgtgg ccgtggctcg cgtgcctgcc atct                               34

<210> SEQ ID NO 475
<211> LENGTH: 268
<212> TYPE: DNA
<213> ORGANISM: Homo sapiens

<400> SEQUENCE: 475
aagtcctcct caggcttgga gaacttcctc agcgtcacct ccttcattga gccttctctg    60
atcactccat ccctctccta cccctccctc ccccaaccct caatgtataa attgcttctt   120
gatgcttagc attcacaatt tttgattgat cgttatttgt gtgtgtgtgt ccgatctcac   180
aagtatattg taaacccttc ggtgggtggg ggccatatcc tagacctctc tgtatccccc   240
agactatctg taacagtgcc aggcacac                                     268

<210> SEQ ID NO 476
<211> LENGTH: 244
<212> TYPE: DNA
<213> ORGANISM: Homo sapiens

<400> SEQUENCE: 476
tcactgtaag gtacagttag ggtaacactt tagaggttta ttatttttaa aaaactttc    60
ttgaactcct ggccagcatg gtgaaacccc gtctctacta aaataccaa aattagccag   120
gcgtgatggt gggtgcctgt gatctcagct acttgggagg ctgaagcagg agaactgcct   180
gaacccagga ggcggaggtt gcagtgagtc gagatcgtgc tactactgcc tgggtggcaa   240
gggt                                                               244

<210> SEQ ID NO 477
<211> LENGTH: 57
<212> TYPE: DNA
<213> ORGANISM: Homo sapiens

<400> SEQUENCE: 477
tgccattttc caagaatgac ggtggtggct tttagtcaga aaatggcctt ctgtgct       57

<210> SEQ ID NO 478
<211> LENGTH: 153
<212> TYPE: DNA

<213> ORGANISM: Homo sapiens

<400> SEQUENCE: 478

| ggagagaagc agaatattcg acaaacacg gacagtatct catcggacat ggtactaagg | 60 |
| tctacatcga ccccttcact tatgaagacc ctaatgaggc tgtgagggaa tttgcaaaag | 120 |
| agatcgatgt ctcctacgtc aagattgaag agg | 153 |

<210> SEQ ID NO 479
<211> LENGTH: 247
<212> TYPE: DNA
<213> ORGANISM: Homo sapiens

<400> SEQUENCE: 479

| agctgcccct ttcccgtcct gggcaccccg agtctccccc gaccccgggt cccaggtatg | 60 |
| ctcccacctc cacctgcccc actcaccacc tctgctagtt ccagacacct ccacgcccac | 120 |
| ctggtcctct cccatcgccc acaaaggggg gggcacgagg gacgagctta gctgagctgg | 180 |
| gaggagcagg gtgagggtgg gcgacccagg attccccctc cccttcccaa ataaagatga | 240 |
| gggtact | 247 |

<210> SEQ ID NO 480
<211> LENGTH: 154
<212> TYPE: DNA
<213> ORGANISM: Homo sapiens

<400> SEQUENCE: 480

| agcggagcaa gtgtcccggg ccttcagcca gccctggata gctacttcca tcccccgggg | 60 |
| actcccgcgc cgggacgcgg ggtgggacca ggtgcgggac ctggggcggg cgacgggact | 120 |
| taaataaagg cagacgctgt tttctaccca aaaa | 154 |

<210> SEQ ID NO 481
<211> LENGTH: 292
<212> TYPE: DNA
<213> ORGANISM: Homo sapiens

<400> SEQUENCE: 481

| agatgtgcac aaacagagcc cccgcgtaca ggtccagctg cggagggaga gagccttgtg | 60 |
| tggggctgtt attcccaggg ctccagcaag ccactccctg ggtgacctcc ggcaaggccc | 120 |
| tctctgggcc tcggtggcct gtggataagg aggggagacc cccactcgcc tgcctgcctg | 180 |
| catcacgggg ccattgtgag gttgggggaa gacctggccg tggagctaca agcttgtgcg | 240 |
| gatgtcaggg gacattactg ttgctaataa agtccaaagt ggccaatgcc tt | 292 |

<210> SEQ ID NO 482
<211> LENGTH: 248
<212> TYPE: DNA
<213> ORGANISM: Homo sapiens

<400> SEQUENCE: 482

| cggtgaactt ctggatcccg tttctgatgc agattcttgt cttgttctcc acttgtgctg | 60 |
| ttagaactca ctggcccagt ggtgttctac ctcctacccc acccacccccc tgcctgtccc | 120 |
| caaattgaag atccttcctt gcctgtggct tgatgcgggg cgggtaaagg gtattttaac | 180 |
| ttaggggtag ttcctgctgt gagtggttac agctgatcct cgggaagaac aaagctaaag | 240 |
| ctgcctttt | 248 |

```
<210> SEQ ID NO 483
<211> LENGTH: 271
<212> TYPE: DNA
<213> ORGANISM: Homo sapiens

<400> SEQUENCE: 483
gcgatgaacc caacctccct gaagccaaaa cttcccaccc tgccgcacac tccggaccac      60
cccacttgcc accaagcaca tcctctccaa atccaaccct tatttgcgac ccttcagtga     120
tgacccagca gacctccaaa aagcctcctc tgcccagatc tccagccggg tctggggctg     180
ggttgcggag gggagggtct gggagtccac acttctccac caacttccct tcccactctc     240
ttattccaca ttgcagtgtt tggaataaac c                                     271

<210> SEQ ID NO 484
<211> LENGTH: 37
<212> TYPE: DNA
<213> ORGANISM: Homo sapiens

<400> SEQUENCE: 484
tgtcctgggc accgtagcga gactctgctt tctacaa                               37

<210> SEQ ID NO 485
<211> LENGTH: 110
<212> TYPE: DNA
<213> ORGANISM: Homo sapiens

<400> SEQUENCE: 485
gcaggcagta agaagcaggg atttcttcaa atgctagtaa gcacaaagag agggagaagt      60
ttttgtaagt aacgaacagg gccgggcatg gtggcgtgag aggccgaggt                 110

<210> SEQ ID NO 486
<211> LENGTH: 238
<212> TYPE: DNA
<213> ORGANISM: Homo sapiens

<400> SEQUENCE: 486
gagcaccaga tcctatagag cctttagacc atcgtagaga ctttgctttt ctctgagtgc      60
tttggtaggg atttgaggaa aggagtgaca tcgtatgaat gacttttatta tgtgcccacg     120 tggaggtgtc aaataggcag ctattgtgtt gcaggtcccc aggttcattg attcactaag     180
aggactcaaa agactcagca cgtagtccta ctcacagctg tgatttatta tcgcacaa      238

<210> SEQ ID NO 487
<211> LENGTH: 226
<212> TYPE: DNA
<213> ORGANISM: Homo sapiens

<400> SEQUENCE: 487
cagattcttt ttatggtgg ctttgcttgt tttaaatttt tgcatgactt ttcatcttttt      60 tatgtgtgtt tcctgtagtt tgatccgaag gaaaagagta tagtagcctg agaatcagga     120
gatgggagtt ttagtcgtag gccttatgat aattaccccg cggtggtgtg tagaaaagta     180
tgtaaatttg ctctgttttta agactttgaa ctacctcaag aagagg                    226

<210> SEQ ID NO 488
<211> LENGTH: 271
<212> TYPE: DNA
<213> ORGANISM: Homo sapiens

<400> SEQUENCE: 488
```

```
gtgggagaag ttggcgtcct aggctgggga ttggtcgggg gaccttaaag aaaaaggcca      60
gggctgaggg tcctgaggag agagagagag gccacgtgga tggaggactg tcacccctt      120 ctcggttctg tcaccccctt gagtctaact cactgttgag gggaggaaga aggggatgg      180 acggaaggga gaccgaggaa aggctttcgg gagtggggac attatccacc cagaggtgtg     240
ctacccacaa ccaccgcgag atccttagag t                                    271

<210> SEQ ID NO 489
<211> LENGTH: 109
<212> TYPE: DNA
<213> ORGANISM: Homo sapiens

<400> SEQUENCE: 489
ctgtgctctg gaaaggctac caaatactgg ccaaggtcag gaggagcaaa aatgagccag      60
caccagcgcc ttggctttgt gttagcattt cctcctgaag tgttctgtt                109

<210> SEQ ID NO 490
<211> LENGTH: 134
<212> TYPE: DNA
<213> ORGANISM: Homo sapiens

<400> SEQUENCE: 490
gctacagctg gcgaacccca aagagttcta ccacgaggtg cacaggccct ctcacttcct      60
caactttgct ctcctgcagg aggggaggt ttactctgcg gatcgggagg acctgtatgc     120
ctgaccgttt ccct                                                       134

<210> SEQ ID NO 491
<211> LENGTH: 74
<212> TYPE: DNA
<213> ORGANISM: Homo sapiens

<400> SEQUENCE: 491
gggaagccaa atataggcca agagcagcct gtggatgatg ctgcagaagt ccctcagagg      60
gaaccagaga agga                                                        74

<210> SEQ ID NO 492
<211> LENGTH: 201
<212> TYPE: DNA
<213> ORGANISM: Homo sapiens

<400> SEQUENCE: 492
tacatccctt caccaggtgg tgccatgtct cccagctact cgccaacgtc acctgcctac      60
gagccccgct ctcctggggg ctacacaccc cagagtccct cttattcccc cacttcaccc     120
tcctactccc ctacctctcc atcctattct ccaaccagtc ccaactatag tcccacatca     180
cccagctatt cgccaacgtc a                                               201

<210> SEQ ID NO 493
<211> LENGTH: 253
<212> TYPE: DNA
<213> ORGANISM: Homo sapiens

<400> SEQUENCE: 493
gaagaggatt cagggtcagc ctaggggacc ctggctccct ccgataggca ggaaggagga      60
gggatgcgga ggagaggctg agccttccac gggcctcctg ttaggggtgt tggtggaggc     120
caggttgggg agggaagcct aaggaccctc cacacctccc acagccagag tcagttgagg     180
ctgggacaaa ggggaaggag agagggaagg aggaccgcct gaccttgccc agaaggagct     240
```

```
tcctctaaac tgc                                                      253

<210> SEQ ID NO 494
<211> LENGTH: 43
<212> TYPE: DNA
<213> ORGANISM: Homo sapiens

<400> SEQUENCE: 494
gtaaaggagt gggtgatttg caaataaagc acattataca caa                     43

<210> SEQ ID NO 495
<211> LENGTH: 250
<212> TYPE: DNA
<213> ORGANISM: Homo sapiens

<400> SEQUENCE: 495
tgctgctcct cataataagc cgccactgtc tccaggtagc cctctttgaa gtcgtcctcc   60
agctctgcca ggctcgacat cacctgtcca cgtcctgatt ctgcattttg cattttatca  120
taaaatcttt ctatggcctg gtgcattcgg gccttcagct tcttcatgtc atcagagagg  180
accttcggga agcacatggc ggccaaaagt tcaaggagcc aaggcctgag atgacccagc  240
tccaaaggga                                                         250

<210> SEQ ID NO 496
<211> LENGTH: 262
<212> TYPE: DNA
<213> ORGANISM: Homo sapiens

<400> SEQUENCE: 496
tccccaacaa cacaacgcgt cctgttccac ctacgtagga tctgtgaaac aggctcagtg   60
cctttgaggg aggagggaac gtttagattg agaccacccc actcccgggt gattaaataa  120
atatgtctct cccccacccc acgcaggatt ggaaaaagtt aattgtggtt tcagaaaagt  180
taacccctgc gttgcttcga ccccttctct ccagggaagg gttgggtaaa tgtctacgaa  240
tcgccttgag agagaactaa ag                                           262

<210> SEQ ID NO 497
<211> LENGTH: 170
<212> TYPE: DNA
<213> ORGANISM: Homo sapiens

<400> SEQUENCE: 497
tacacagttt ccaatttaag taggcagact gagcatgccc atcagtttcc tattgctgct   60
tccatccctc gaaatgatag aaaagatttt aaacagcaaa taagaatga gaaaagaag   120 aaattataag tgggttttaa aaagttgcag tgggccaggc atcatggctc              170

<210> SEQ ID NO 498
<211> LENGTH: 89
<212> TYPE: DNA
<213> ORGANISM: Homo sapiens

<400> SEQUENCE: 498
tgcccgatca cacaggagta tgcccaaact ctctcaggcc tctagcagct gacaaccact   60
gctttaaatc cctattacat ttattatga                                    89

<210> SEQ ID NO 499
<211> LENGTH: 242
<212> TYPE: DNA
```

<213> ORGANISM: Homo sapiens

<400> SEQUENCE: 499

```
cctgggggca ggacccacag ccagtgggct aagacccttta aaaatttttt ttctttaatg      60
tatgggactg aaatcaaacc atgaaagcca attattgacc ttccttcctt ccttccttcc     120
ctcccttcct ccttctctcc ttctctcctc ctctctcctc tcctctcctc tctttccttc     180
cttccttcct ttttttcttt ttctctttct tctttatttc ttgggtctca ctctcatcac     240
cc                                                                    242
```

<210> SEQ ID NO 500
<211> LENGTH: 220
<212> TYPE: DNA
<213> ORGANISM: Homo sapiens

<400> SEQUENCE: 500

```
tcaagacgag cctggacaac acaacaagac ccccaattct actaaatttt ttttttttaat     60
tagccagatg tggtaatgca tgcctctgta gtcccagcta ctcaggaggc tgaggtggga    120
ggatcacttg agtgcaggaa ttcaaagctg cagtgagcta taatacaagg cttcattgca    180
ctccagccta ggcattagag cgagaccgtg tttatttaaa                          220
```

<210> SEQ ID NO 501
<211> LENGTH: 271
<212> TYPE: DNA
<213> ORGANISM: Homo sapiens

<400> SEQUENCE: 501

```
ttaaaggaca aactcaagaa ggcacaacat gaaagagaac aacttgaatg tcagttgaag      60
acagagaagg atgaaaagga actttataag ggtacatttg aagaatacag aaatagaaaa    120
taccaagctt atgtcagagg tccagacttt aaaaaattta gatgggaaca agaaagcgt     180
gattactcat ttcaaaaaga gattggcagg ctgcagttat gtttggctga aaggaaatct    240
gcaagacttt cctgcttaca acctcaagta a                                    271
```

<210> SEQ ID NO 502
<211> LENGTH: 133
<212> TYPE: DNA
<213> ORGANISM: Homo sapiens

<400> SEQUENCE: 502

```
caacatggac attttatacta ataaggaggg cagaggcgaa tatgtgagaa ggtccaccac     60
ctcagagctt gaatcagctt cacgatgatg gaaaggtaag ctttatcact gatctcaaca   120
gcagactggt ggc                                                        133
```

<210> SEQ ID NO 503
<211> LENGTH: 119
<212> TYPE: DNA
<213> ORGANISM: Homo sapiens

<400> SEQUENCE: 503

```
gagtcaggct tactaatgct gccctcactg cctctttgca gtaggggaga gagcagagaa     60
gtacaggtca tctgctggga tctagttttc caagtaacat tttgtggtga cagaagcct    119
```

<210> SEQ ID NO 504
<211> LENGTH: 87
<212> TYPE: DNA
<213> ORGANISM: Homo sapiens

<400> SEQUENCE: 504
gatcaaatca agtcttggtt gtggcttgct gaattaaata tttatgagtg gtgcattttt      60
aagtatcgtg accaagacac catatta                                          87

<210> SEQ ID NO 505
<211> LENGTH: 298
<212> TYPE: DNA
<213> ORGANISM: Homo sapiens

<400> SEQUENCE: 505
aatacagaac tgagcctagg ccagggaact gggattgggg ttagatctaa gcaagatcag      60
catgtaagtg atagtggaga aagtaaatgg agaggtgagg actcatcccc ttggtggaaa     120
ttcggaatta ataaagcagg aggagagtca ggataatggg ctgttgaata agaaagtaa      180 gtgacaagga agaggtaatg tgtatccaag aagtaggaaa gaaatgagac ttaaagcgta     240
gggggttagg ctgtgtaaga gctcagtacc caacaggtgc tcagtcaagt aacttgac      298

<210> SEQ ID NO 506
<211> LENGTH: 247
<212> TYPE: DNA
<213> ORGANISM: Homo sapiens

<400> SEQUENCE: 506
tgggattgca gtcgcctgcc accgtgcccg gctaactttt gtattttggt tgagacaggg      60
tttcgccgtg ttggccaggc tggtctagaa ctcctgacct caggtgatcc acccgccttg     120
gcctcccaaa gtgctgggat tacaggcgtg agccaccaca cccggccaaa aaaaaatttt     180
tttttctatc cctgccattc agtctccatt agcactctat tctctctcat ttattccacc     240
ccgtctt                                                               247

<210> SEQ ID NO 507
<211> LENGTH: 204
<212> TYPE: DNA
<213> ORGANISM: Homo sapiens

<400> SEQUENCE: 507
accaccccta gctttgtgtg tagtgtagtg attttctggc tgtcactcat actcactggg      60
caccagcctt gccctcttag cctccatcca tccagacagc ccttcccacc tcctggtggt     120
gagccagtct gcattcccac gccatcccaa agccctttca tcttacccgt gcattgtaga     180
tggaaggagc acccatgcca ttca                                            204

<210> SEQ ID NO 508
<211> LENGTH: 179
<212> TYPE: DNA
<213> ORGANISM: Homo sapiens

<400> SEQUENCE: 508
aaaaaggtct atgatcttga gggcagacag cagaattcct cttataaaga aaactgtttg      60
ggaaaatacg ttagggagaa gaagaccttg ggccaagatg ctaaatggga atgcaaagct     120
tgagctgctc tgcaagaaaa aataagcagg acagaggatt tgctctggac agagatgga     179

<210> SEQ ID NO 509
<211> LENGTH: 291
<212> TYPE: DNA
<213> ORGANISM: Homo sapiens
<220> FEATURE:

```
<221> NAME/KEY: misc_feature
<222> LOCATION: (39)..(83)
<223> OTHER INFORMATION: n is a, c, g, or t

<400> SEQUENCE: 509
tggtgaattt tctaggagcg atgatgtact gtaattgtnn nnnnnnnnnn nnnnnnnnnn    60
nnnnnnnnnn nnnnnnnnnn nnnaatgctt gttctaagac atttctgaat gtagaccatt   120
ttccaaaaag gaaactttat tttcaaaaac ctaatccgta gtaattccta atcttggaga   180
ataaaaaagg gcggtggagg ggaaaacatt aagaatttat tcattatttc tcgagtactt   240
tcagaaagtc tgacactttc attgttgtgc cagctggttg aaattaaaac t            291

<210> SEQ ID NO 510
<211> LENGTH: 282
<212> TYPE: DNA
<213> ORGANISM: Homo sapiens

<400> SEQUENCE: 510
gatagtgatg ggtcttccca ttgtccttaa accctgtaca tattgtgcag cctggcctgg    60
gactggatgt ttcagtagaa ataacacagg ggacaccaga ggcaagcctg gaggtcagct   120
cagtcgttag gcagtggagg cacaaggtgg ggcagttttt cccaggtgtt tgatgatgac   180
tgacttgagc cagagacccc taaagataga gtggagtcca gggaatgatc tagaacttca   240
ggtgacaggc aggagctgcc cggatttaac agcagaacca ta                      282

<210> SEQ ID NO 511
<211> LENGTH: 164
<212> TYPE: DNA
<213> ORGANISM: Homo sapiens

<400> SEQUENCE: 511
ctaactctgt cctgaagagt gggacaaatg cagccgggcg gcagatctag cgggagctca    60
aagggatgtg ggcgaaatct tgagtcttct gagaaaactg tacaagacac tacgggaaca   120
gtttgcctct ctcccagcct caaccacaat tcttccatgc tggg                    164

<210> SEQ ID NO 512
<211> LENGTH: 294
<212> TYPE: DNA
<213> ORGANISM: Homo sapiens

<400> SEQUENCE: 512
gatggacagg gttctgaaaa aactgaaaat gaattctaga aagcagcatt tgagagggaa    60
aagagaagtg atcagcattt aggaatatga actgtctgga gctagagaaa cagcctggga   120
aaagagcaaa gggctagagc aggaaagaga aaagagaatg agactagcgg tggtttggat   180
attatttgta accaaagtca aaggacggga gatctagagt ccagccaaca aagaacttgc   240
tcctataaaa accaaatgga ccccacccct cacttgacgt agaggtcctt tcct          294

<210> SEQ ID NO 513
<211> LENGTH: 262
<212> TYPE: DNA
<213> ORGANISM: Homo sapiens

<400> SEQUENCE: 513
aacatggtcc tggaggttac agtgtagtga ggggcaaaga catggagcca atggttgagc    60
tgaaacctca tgtgaggagt taactggatg gagaaaggag tcaagagagt tctaggtaga   120
ggaggcagca tgtcaaaggc acagtaaagg gaggatgaat ggtccatttc agggatggaa   180
```
gaaggctgct agattggaac atagggaagg agggaatgtg tgatacaagc tggagctaga    240
aaggtaggtg gtcagaacat ag    262

<210> SEQ ID NO 514
<211> LENGTH: 81
<212> TYPE: DNA
<213> ORGANISM: Homo sapiens

<400> SEQUENCE: 514
gaaaaattta cacagctaga tttggaagat gttcaagtta gagaaaagtt aaaacatgcc    60
acgagtaaag ccaaaaaact g    81

<210> SEQ ID NO 515
<211> LENGTH: 296
<212> TYPE: DNA
<213> ORGANISM: Homo sapiens

<400> SEQUENCE: 515
ttaaaaggtc ctgctctatc gttctgtgtc tggctctgca aactgctggt atgtaaaaga    60
ccctctttcc agacaggcca cgaactcccc gaaggccggg ctggcctctt ctctgcctct    120
gtcccaacct ccctgacaca ccctccatcc acgttaataa aacagggaac acaccagagg    180
gctcagtaga gaaaaacaca tcataatgac tgatttataa ttttttatagc tttaaaataa    240 taaatttatt ttttccatt aaagtattat aacacgatta caaaaagccc tcgtgc    296

<210> SEQ ID NO 516
<211> LENGTH: 285
<212> TYPE: DNA
<213> ORGANISM: Homo sapiens

<400> SEQUENCE: 516
tagatgccgt catcttccgt ggtcacgccc acaatcttca gcgtggcctc tcccaggtca    60
ctgtaggaga tgctgtagtg accatcgttg ttcaaggtgt tgtgttcagg gcccttccag    120
gtaattgagg ctttggggcg gccacagact cgacatctag gaacaacggt ctcccctgtc    180
tcacacgtga cctcactcaa tggaatgacg aattctgggg gaacgtcata aatgtagttg    240
ggattgagaa gcttgttgct gagtccttcc cgtgacttcc gataa    285

<210> SEQ ID NO 517
<211> LENGTH: 148
<212> TYPE: DNA
<213> ORGANISM: Homo sapiens

<400> SEQUENCE: 517
cactatgcag ttactgtgac tgtgggaggc aagcaacact tgctcggact gtatgacacc    60
gcgggacagg aggactacaa ccagctgagg ccactctcct accccaacac ggatgtgttt    120
ttgatctgct tctctgtcgt aaaccctg    148

<210> SEQ ID NO 518
<211> LENGTH: 269
<212> TYPE: DNA
<213> ORGANISM: Homo sapiens

<400> SEQUENCE: 518
gaccaggaag tcctataaag aattatattt ctatagaatt aaaaatgcag ttctgtcagc    60
ctggacaaca aagtgagacc cccatagcta caaaaaaaaa aaaaaaagtt tttttaagag    120

```
ttgggcatgg tggcacacgc ctgtagtcct agcttctcgg gaggctgagg tgggaggatt    180
gcttgagatt gggaggttga ggctgcagtg agccgtgatc acaccactgc actccatcct    240
gggtaacaga gtgagaccac ttaaattaa                                       269
```

<210> SEQ ID NO 519
<211> LENGTH: 263
<212> TYPE: DNA
<213> ORGANISM: Homo sapiens

<400> SEQUENCE: 519

```
caaagcaaca aatggaggca tatgaaattc ctcatcgagg aaacactgga gatgttgctg     60
ttgagatgat gtggaaacct gcctatgatt ttctgtatac ctggagtgct cactatggaa    120
ataactacag agatgtgtta caagaccttc agtcagcttt ggacagaatg aaaaaccctg    180
tgactaaaca ctggagagaa ttaactggag ttttaatact agtaaattct ttggaggttt    240
tgagagtaac tgcattctcc act                                             263
```

<210> SEQ ID NO 520
<211> LENGTH: 182
<212> TYPE: DNA
<213> ORGANISM: Homo sapiens

<400> SEQUENCE: 520

```
tgttaaccca ttccagtaca gtattctttt aaaattcaaa agtattgaaa gccaacaact     60
ctgcctttat gatgctaagc tgatattatt tcttctctta tcctctctct cttctaggcc    120
cattgtcctc cttttcactt tattgctatc gccctccttt cccttattgc ctcccaggca    180
ag                                                                    182
```

<210> SEQ ID NO 521
<211> LENGTH: 276
<212> TYPE: DNA
<213> ORGANISM: Homo sapiens

<400> SEQUENCE: 521

```
agccacagtt ggtgtggctg gttcaggggc tggcattgga accgtgtttg gcagcttgat     60
cattggctat gccaggaacc cgtctctcaa gcagcagctc ttctcctatg ccattcttgg    120 cttttgccctc tctgaggcca tggggctttt ctgtttgatg gtcgccttcc tcatcctctt    180
cgccatgtga ggctccatgg ggggtcaccg gcctgttgct actgcaactc cacaccattc    240
ttggtgctgg ggtgtgttaa gctttaccat taaaca                               276
```

<210> SEQ ID NO 522
<211> LENGTH: 288
<212> TYPE: DNA
<213> ORGANISM: Homo sapiens

<400> SEQUENCE: 522

```
ggcttaacca gctagacatt cctctaaata catacgtaac aaaaattgat ggcaggagat     60
tttattggga tcactggata cctacactca acaggcagaa cttggctaat tccatttata    120
ccactactga gacagtgaag acaaattaag aatcagaaca ggaagcacat agcataggga    180
tacccgtgtc agcgacatat ttaatatgcc cctcagctta agactcaata ctgaacagac    240
caaaaggcca cctcaattgc cgctcccgcc acacttgcta ttgaaact                 288
```

<210> SEQ ID NO 523
<211> LENGTH: 210

<212> TYPE: DNA
<213> ORGANISM: Homo sapiens

<400> SEQUENCE: 523

```
ccaaggcatt gctaatctct gtacttcagt aaacactgaa aagtcaacgt aactctatag      60
gtcgcatatt cttgaatgac agggaaaggc aaacatctct acagaggtgt gatcgaaagc     120
attttacatt aggtacacag aaactttaaa ctcacactat gtaagcctct aatcagcctg     180
agcaaaatcc attgcctaca cagtcattta                                      210
```

<210> SEQ ID NO 524
<211> LENGTH: 54
<212> TYPE: DNA
<213> ORGANISM: Homo sapiens

<400> SEQUENCE: 524

```
ggttgaaaga tgaaatgcct gtatgtgctc tgaagaaatg gtaattccag attg            54
```

<210> SEQ ID NO 525
<211> LENGTH: 277
<212> TYPE: DNA
<213> ORGANISM: Homo sapiens

<400> SEQUENCE: 525

```
tccacctgcc gagaagctga gattatagtc actgtgcctg ctggaatat agccttttga      60
ctccatgtca ttacccgcac tcttcgctct tcctggaatg tatttcctga gcctgtctgc    120
cctaaaaatt ccaatttctc ctttaagctt tggctcaaat gctatctata ctctgctgcc    180
tcccccaagt cccctagtg acacacaggg tcctcttctg ctcttcctta tgttcttctt     240
tgtcagagca acatcacagc agtaccccaa catttgg                              277
```

<210> SEQ ID NO 526
<211> LENGTH: 39
<212> TYPE: DNA
<213> ORGANISM: Homo sapiens

<400> SEQUENCE: 526

```
gcggcgggca gggcttgcct ttcttagtct gatgccaag                             39
```

<210> SEQ ID NO 527
<211> LENGTH: 223
<212> TYPE: DNA
<213> ORGANISM: Homo sapiens

<400> SEQUENCE: 527

```
gggccatgac acctgatcat tggatcaaga ggggcactgc tctactcatg agcctggaca     60
gctgagacct cctcctcttc tccgcttgag agagagggtc agggactcca ggagctaaga   120
cagatgttgc acctaggact gaggccggac ctcactcaga ctttgacctt ggccgaattt   180
gtgtgatgtg gccctggaga tacctagttg tgttagccat aaa                       223
```

<210> SEQ ID NO 528
<211> LENGTH: 239
<212> TYPE: DNA
<213> ORGANISM: Homo sapiens

<400> SEQUENCE: 528

```
caggaaggcc tcgaggccac acaggggctg ctggccggcg agtgggcccc acccctctgg     60
gagctgggca gcctcttcca ggccttcgtg aagagggaga gccaggctta tgcgtaagct   120
```

```
tcatagcttc tgctggcctg gggtggaccc aggacccctg gggcctgggt gccctgagtg    180
gtggtaaagt ggagcaatcc cttcacgctc cttggccatg ttctgagcgg ccagcttgg    239
```

<210> SEQ ID NO 529
<211> LENGTH: 211
<212> TYPE: DNA
<213> ORGANISM: Homo sapiens

<400> SEQUENCE: 529

```
ctggtggact attccatcac ccatgcagag cccgccaacg tgttcgacat caattcccac     60 acggggggaga tctggctcaa gaattccatc cgctccctgg atgccctgca caacatcaca    120
cctggaaggg actgcctatg gtccctagag gtgcaggcca aggaccgggg ctcccacatc    180
acttcagcac cacagcctta ctcaagattg a                                   211
```

<210> SEQ ID NO 530
<211> LENGTH: 256
<212> TYPE: DNA
<213> ORGANISM: Homo sapiens

<400> SEQUENCE: 530

```
tcggcctcag attccatatt tgaacaccag ctgattgaga aaggggaat gagaagagct      60 ggatgagttt aaataactca ttgttcagat tcctgaacag gagttgggat aatggccatc    120
ttttctttcc tatcctttct tccccctca ctgtgaaaaa taacagtcca ccccaagtca    180
tacactggac ccagtgcctg cggggacagg actgtgggtt tcttggtcac acctgtgttg    240
gtgctcaatg cagtgt                                                    256
```

<210> SEQ ID NO 531
<211> LENGTH: 250
<212> TYPE: DNA
<213> ORGANISM: Homo sapiens

<400> SEQUENCE: 531

```
tagtttcatt tactctttag gcagaaaata ggttcaaggg tctagtaaag gaggcaaatg     60
ggcagaaaac aacctcttgt ttgctatccc actgcacttg aaatggacct ctataattca    120 ctaccatttta taagtgtctc gcatatcaac atcacattag gtaatttact gcctccaatt   180
cctggtccat aactattcca tcctgaaaag tcataataca atgttattgg aacaatctat   240
tcatatggta                                                           250
```

<210> SEQ ID NO 532
<211> LENGTH: 143
<212> TYPE: DNA
<213> ORGANISM: Homo sapiens

<400> SEQUENCE: 532

```
atgtatacaa agtaaattct tagccaggtg tagtggctca tgcctgtaat cccagcactt     60
tgggaggctg aggcgggtgg atcacttgag gtcagaagtt caagaccagc ctgaccaaca    120
tcgtgaaatg ccgtctttac aaa                                            143
```

<210> SEQ ID NO 533
<211> LENGTH: 273
<212> TYPE: DNA
<213> ORGANISM: Homo sapiens

<400> SEQUENCE: 533

```
agtggcttcc ttggagtagt gggtgaaagt ctgcttaaaa agagggctta ggagagaatt     60
```

```
gggggaagga attgaaatac atcaacatag acaactcttg aggagttttg ccatgaagag    120
acactttgca tccagaggac actttgcatc cagagagtgg cttccttgga gtagtgggtg    180
aaagtctgct taaaaagagg gcttaggaga gaattggggg aaggaattga aatacatcaa    240
catagacaac tcttgaggag ttttgccatg aag                                 273

<210> SEQ ID NO 534
<211> LENGTH: 250
<212> TYPE: DNA
<213> ORGANISM: Homo sapiens

<400> SEQUENCE: 534
gagctggaaa aaagtcagac tctccacaga cccctatgg gggacccca actcaaggcc      60 aaggactggg cgtatcggat gctcataaca cccctggcct ggccccttta ctgagaagac   120
tccttggata tttcccaaga acccccaca tacacccctc acaagccacc cctcctgaga    180 ggcaggggc cctccgcccc ctccccatgt attccccacc tgtgttccgt ttgaccagca    240
cagaaatatt                                                          250

<210> SEQ ID NO 535
<211> LENGTH: 91
<212> TYPE: DNA
<213> ORGANISM: Homo sapiens

<400> SEQUENCE: 535
gggagcacac agtcacctct cacagctcca ttatccagcg gctgccgggc tctgacaacc     60
tatatgatga cccctaccag ccagagataa c                                   91

<210> SEQ ID NO 536
<211> LENGTH: 250
<212> TYPE: DNA
<213> ORGANISM: Homo sapiens

<400> SEQUENCE: 536
gctgccattg ctgtggttat gggcatttag aaaacttgaa agtcagcact aaaggatggg     60
cagaggttca acccacacct ccactttgct tctgaaggcc cattcattag accacttgta   120
aagattactc caacccagtt tttatatctt tggttcaaaa cggcatgtct ctccaacaat   180
ttaagtgcct gatacaaagt ccaaagtata aacatgctcc tttactctct tgctgctact   240
cttgcttttg                                                          250

<210> SEQ ID NO 537
<211> LENGTH: 64
<212> TYPE: DNA
<213> ORGANISM: Homo sapiens

<400> SEQUENCE: 537
gtagctattg atgtacactt cgcaacggag tgtctgaaat tgtggtggtc ctgatttata     60
ggat                                                                 64

<210> SEQ ID NO 538
<211> LENGTH: 299
<212> TYPE: DNA
<213> ORGANISM: Homo sapiens
<220> FEATURE:
<221> NAME/KEY: misc_feature
<222> LOCATION: (224)..(232)
<223> OTHER INFORMATION: n is a, c, g, or t
```

<400> SEQUENCE: 538

```
cagaggtctt gcagccctg tggatgcccc cgccgaggtc ccccgatccc cgcacccgga      60
ctgctgctcc ctgccccacc attgcgggtc ccccaggaag ccaggtgacc ccaggtggga     120
ggctgtgtgt ggaggccatc ctggaaggaa gtttagacct gcccaggtgt ggagcgaggg    180
gcacagggc atcctaacct cagaaactga aataaagcct ttgnnnnnnn nntctgtaaa     240
acatcaaccc ccaatcagaa gatggcaaat ggggaataaa aatagcaggt aacacgtca    299
```

<210> SEQ ID NO 539
<211> LENGTH: 195
<212> TYPE: DNA
<213> ORGANISM: Homo sapiens

<400> SEQUENCE: 539

```
tgacagcagc tgatgttgtt aaacagtgga aggaaaagaa gaaaagaaa aagccaattc      60
aggagccaga ggtgcctcag attgatgttc caaatctcaa acccatttt ggaattcctt    120
tggctgatgc agtagagagg accatgatgt atgatggcat tcggctgcca gccgttttcc   180
gtgaatgtat agatt                                                    195
```

<210> SEQ ID NO 540
<211> LENGTH: 171
<212> TYPE: DNA
<213> ORGANISM: Homo sapiens

<400> SEQUENCE: 540

```
aaaatagaac atcctgagtt acagaaattc agccctagtg tatcctggcc taaaaataca     60
gaacaatcaa gttgagtggt tggaaatgag aggctaggca gggttggaaa catgctaatg   120
tttactgagt gaaatctttc cttctcagta gagttgccct tgcagctgaa a             171
```

<210> SEQ ID NO 541
<211> LENGTH: 44
<212> TYPE: DNA
<213> ORGANISM: Homo sapiens

<400> SEQUENCE: 541

```
tctctggctg atatgttccc tgagatgaat gaggtctgtc aaga                      44
```

<210> SEQ ID NO 542
<211> LENGTH: 249
<212> TYPE: DNA
<213> ORGANISM: Homo sapiens

<400> SEQUENCE: 542

```
gttacaggtg ctacgcatga tggtcggagt aaatatctca gatgagcagc tgggcagcat     60
cgcagacagg accattcagg aggctgatca ggatggggac agtgccatat ctttcacaga   120
atttgttaag gttttggaga aggtggatgt agaacagaaa atgagcatcc gatttcttca   180
ctaaaggaga ccaaactgtt ccttgcggtc tagtatttaa gaactggaac ttgaaagtcc   240
tccttctac                                                           249
```

<210> SEQ ID NO 543
<211> LENGTH: 213
<212> TYPE: DNA
<213> ORGANISM: Homo sapiens

<400> SEQUENCE: 543

```
gaatccatta tcaatgttgc tagtgtaata cacaagaaaa cccaatgaga gaaattcaaa     60
```

| | | |
|---|---|---|
| tattaagaaa caagcttttg ttgattgagc tttaaatggc cacacaccat tataatatct | | 120 |
| aagatgcttg tgctccccaa taaccaattt ttgcctccaa tgaggatgca agtcctaact | | 180 |
| tctatgctcc cgaatttatc atactagcac cta | | 213 |

<210> SEQ ID NO 544
<211> LENGTH: 242
<212> TYPE: DNA
<213> ORGANISM: Homo sapiens

<400> SEQUENCE: 544

| | | |
|---|---|---|
| taataagtgt tagcatcgtg tgtcttgaag tatacttttg cactgtaact tgggttacgt | | 60 |
| taaagagagc ttagcaccaa aggtagataa tgaagaaatg gcataggaaa gtggagatga | | 120 |
| taaaaagttg attgttgaac caaaaagggt ttgaagggaa gcttcgactg agtatcagaa | | 180 |
| attacttaag gcacatagga cctgaatcag graaccagca cttcttacaa ctgccagttt | | 240 |
| ta | | 242 |

<210> SEQ ID NO 545
<211> LENGTH: 215
<212> TYPE: DNA
<213> ORGANISM: Homo sapiens

<400> SEQUENCE: 545

| | | |
|---|---|---|
| tgcaaggact cacctccttg agccttggtt tttgttgtag ggattaaatg agataatatg | | 60 |
| agtggcagct cttcatgagt cctgcagtgc taagcaaatg tcagaaattg gtgtattaga | | 120 |
| ctatttatct ttgatcttct gaatggattg ctgtcatgga cacggacacg gatcttcatc | | 180 |
| tggttcattg tatttatatg tgagggatgg atggc | | 215 |

<210> SEQ ID NO 546
<211> LENGTH: 237
<212> TYPE: DNA
<213> ORGANISM: Homo sapiens

<400> SEQUENCE: 546

| | | |
|---|---|---|
| ggagaagtta agcaacatct agcaaatgtt atgcataaag tcagtgccca actgttatag | | 60 |
| gttgttggat aaatcagtgg ttatttaggg aactgcttga cgtaggaacg gtaaatttct | | 120 |
| gtgggagaat tcttacatgt tttctttgct ttaagtgtaa ctggcagttt tccattggtt | | 180 |
| tacctgtgaa atagttcaaa gcctagtttta atacaatta tatcagtcct ctttcaa | | 237 |

<210> SEQ ID NO 547
<211> LENGTH: 257
<212> TYPE: DNA
<213> ORGANISM: Homo sapiens
<220> FEATURE:
<221> NAME/KEY: misc_feature
<222> LOCATION: (220)..(220)
<223> OTHER INFORMATION: n is a, c, g, or t

<400> SEQUENCE: 547

| | | |
|---|---|---|
| gaattgtcat tcataactct gtgctatatt acttgagggg ctaagaaaaa tgtatggtca | | 60 |
| gtgaaacaca gtagtgtacc cttaaatgcc ttataaaaga ccatccatcc agtctgcgct | | 120 |
| tttgactgtg tgcaagtatc agtaataatg cttttggggg ctcagatgaa cagcgaacac | | 180 |
| caatcagcca ggactctgga aggaaagctc caaaaatgan gaagtccttt caacaccatt | | 240 |
| ttccattact gttctca | | 257 |

```
<210> SEQ ID NO 548
<211> LENGTH: 34
<212> TYPE: DNA
<213> ORGANISM: Homo sapiens

<400> SEQUENCE: 548
tttgattaat aaaaatgcgt tgagcctagt tata                                34

<210> SEQ ID NO 549
<211> LENGTH: 194
<212> TYPE: DNA
<213> ORGANISM: Homo sapiens

<400> SEQUENCE: 549
gttgcttccc caccctgagg agaggacacc atggcttact actcaggaca agtatgcccc    60
gctcagggtg tgatttcagg tggcttccaa acttgtacgc agtttaaaga tggtggggac   120
agactttgcc tctacctagt gaaccccact taaagaataa ggagcatttg aatctcttgg   180
aaaaggccat gaag                                                    194

<210> SEQ ID NO 550
<211> LENGTH: 198
<212> TYPE: DNA
<213> ORGANISM: Homo sapiens

<400> SEQUENCE: 550
tgggaaatat agtgaaactc ctgtccctac aaaaaataca aaaattagcc gggtgtggta    60
gtgcatgcct gtagtcccag ctacttggga ggctgaagtg gaggatggc ctgagctcaa   120 ggagatgcag gctgcagtgg gctgtgattg tgccactgca ctccagcctg gcaccaatg   180 tgagaacctg tcttggaa                                                198

<210> SEQ ID NO 551
<211> LENGTH: 292
<212> TYPE: DNA
<213> ORGANISM: Homo sapiens
<220> FEATURE:
<221> NAME/KEY: misc_feature
<222> LOCATION: (76)..(77)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t

<400> SEQUENCE: 551
ttgaaagaca ccagtgcaca cccaaactcc tggccttctg tgggttccct ttgctccaga    60
acacagatgt gtctanngaa aaacaaacga aaaccgagcc naaacnacca aaccccaggg   120
gggggccgct ctaaagaatc cctcgagggg cccaagctta cgcgtaccca gcttttcttg   180
tacaaagggg cccctaaagg ggagtcggaa taaaaaacta aaggcccttg gcccgtcctt   240
tttacaacgc cccggaactg gggaaaacat gccaaccttg ggggatcttt tg           292

<210> SEQ ID NO 552
<211> LENGTH: 268
<212> TYPE: DNA
<213> ORGANISM: Homo sapiens

<400> SEQUENCE: 552
```

```
gatgctcttc agttcaacta tattccctat ctgataattc cagaatctct atcatgtctg    60
agtctgggtc tgatgctttc attgtttctt cagattgtga ttttcttgc ctcccagtgt   120 gacttgtaat ttttaattga aagctggata tgatgtattt ggcaatggga agtgagggaa   180
atatgttttt agtgtgaggg tttatgttaa tctttctcag agttgggctg tttaatgttt   240
tgctgtggtc tgaatgttcc ttaaaact                                      268
```

<210> SEQ ID NO 553
<211> LENGTH: 269
<212> TYPE: DNA
<213> ORGANISM: Homo sapiens

<400> SEQUENCE: 553

```
aaggattggg ggtcgtgcag cccagccagc aggagggact gaggccctct aggaggaaag    60
cccagaggga gggggccctc attccttcag acccagtttt cccccaccct ccttaccccg   120
ctgggctagg tctccgccag ggctggcctc agtttctcct caacaggcct gggggcagcc   180
cttcccctgc ctagtccccg cctgagtgcc agcscccac cccgcctgcc gccccctgtt   240
caggttccct ccccgccaca gtgaaataa                                     269
```

<210> SEQ ID NO 554
<211> LENGTH: 297
<212> TYPE: DNA
<213> ORGANISM: Homo sapiens
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 554

```
tgcggaggcg ctagtccacc agagcbcctc cccgcccctc ttcccantcc gnatccctcg    60 ccccctccc cacctcccac ccccacccct gtaaactagg cggctgcagc aagcagacct   120
tcgcatcaac mcmscasaca ccamaaacca gtgagasccc cgctctctac cgcccgggcc   180
cagcactcgc tagcttttcct gacacctgga actgtgcacc tggcaccaag cggaaaataa   240
actccaagca gccagtagcc ccgatggtgt gtgcctgacc tgtgtggccg gaggttc      297
```

<210> SEQ ID NO 555
<211> LENGTH: 35
<212> TYPE: DNA
<213> ORGANISM: Homo sapiens

<400> SEQUENCE: 555

```
ttaggtaggt aaggaatgat cacattggag tttgg                               35
```

<210> SEQ ID NO 556
<211> LENGTH: 273
<212> TYPE: DNA
<213> ORGANISM: Homo sapiens

<400> SEQUENCE: 556

```
acgtgcttat taggaaatga gtctgtatgg aaatctcacc acagataatg gttaacgaac    60
cgggtcgaca tcacaaagga gggtggagac tctttttact aacttgaatg agacaaaagc   120
agtggtgtca gtttataatc ctgatgcatt tcagtaataa tgtagaaaaa cattatttta   180
```

```
aaaaagttcc aacacacagc catgaggagc ctcagttttg aaagaggtgc ataataaaac    240
tactaaccag aggagtctat gccattttaa gaa                                 273

<210> SEQ ID NO 557
<211> LENGTH: 256
<212> TYPE: DNA
<213> ORGANISM: Homo sapiens

<400> SEQUENCE: 557
gccaggagtt ggagcccact ctggggaaaa catgttgaga tcttgcctct gcaaaaataa    60
agtaaaataa aatttaaaaa aagtaaaaaa ataaaatcag ctgagcatgg tgacatgcac    120
ctgtggtacc agctactttg gaggctaagt tgagaggcac tgatgggagg atcatttgac    180
ggcccagagg ttgaggctgc agtgagctgt gtttgtgtca ttgcactcca gcctgcgtaa    240
cagagtaaaa ccttct                                                    256

<210> SEQ ID NO 558
<211> LENGTH: 185
<212> TYPE: DNA
<213> ORGANISM: Homo sapiens

<400> SEQUENCE: 558
cttggagcca gagaagcgat tagaaacccc tgagggccga ttactgacat cataaatcat    60
gagtttgggg gctttgcctg ggtgatgttg gtaccaggag acatagttat aaccaccaac    120
gtcactgctg gttccagtgc aggagatggt gatcgactgt ccaggagacc cagacacgga    180
ggcag                                                                185

<210> SEQ ID NO 559
<211> LENGTH: 246
<212> TYPE: DNA
<213> ORGANISM: Homo sapiens

<400> SEQUENCE: 559
gtctgaatat cttactcaca gctcaccttt ttggtgcctt tgatccgtat tagaaattat    60
ccacatcttc tctctgggca atattctact ttttatattg acccaattat tttactgctt    120
tggtgtgtcc tttctcctaa cacatatggg ttcactttga aaccctgaaa cccacattta    180
caaaaacatt ttcaatatga acattgttc catgactcat tactggagta ccatcaacat    240
ttacat                                                               246

<210> SEQ ID NO 560
<211> LENGTH: 242
<212> TYPE: DNA
<213> ORGANISM: Homo sapiens

<400> SEQUENCE: 560
gcaggtattt tctacgggtg tttgatgttc ctgaagtgga agctgtgtgt tggcgtgcca    60
cggtggggat ttcgtgactc tataatgatt gttactcccc ctccctttc aaattccaat    120 gtgaccaatt ccggatcagg gtgtgaggag ctggggcta aggggctccc ctgaatatct    180
tctctgctca cttccaccat ctaagaggaa aaggtgagtt gctcatgctg attaggattg    240
aa                                                                   242

<210> SEQ ID NO 561
<211> LENGTH: 285
<212> TYPE: DNA
<213> ORGANISM: Homo sapiens
```

<400> SEQUENCE: 561

```
tcctctgtca atgttcgatt atctccagga aaagagacca gatgcagccc accttccttc    60
acctataagt acacacctga agaggagcag gaattggaaa agcgggtgat ggaacatgat   120
ggtcagtctt tagttaaatc gaccattttc atctctccat catctgtgaa gaagaagaa    180
gccccccaga gtgaggcgcc gcgggtggag gaatgccatc atggaaggac tcctacctgt   240
tcacggcttg ctccaccacc aatgtctcag tctacctgtt cccctt                  285
```

<210> SEQ ID NO 562
<211> LENGTH: 271
<212> TYPE: DNA
<213> ORGANISM: Homo sapiens

<400> SEQUENCE: 562

```
ggtaatgagc tcaatgcctc catttaatca cttttataag gctctctcca ataaggctgc    60
tgtgctgtgc tcctgccagt gttggagtaa tataacattt ttactgcaca caccttatgg   120
gaaagtgttt atactgagtg tagttttagg aggggtaaat gaagattatt ccacaaatt    180
aagattgcac ttagtacacg cctttacaca actctgatgg tatttaccaa aacatggcat   240
gtcttttcac gtatattcct gaaaacacca a                                  271
```

<210> SEQ ID NO 563
<211> LENGTH: 211
<212> TYPE: DNA
<213> ORGANISM: Homo sapiens

<400> SEQUENCE: 563

```
agctttaaga ggaaagagct ctattttct tgttttcttc tctgagctag actgagctgg    60
ggatctaaga tgtacttctc tgactacaaa agggacagta tcatttagat tttttgcagt   120
tggaagaaat gggttgttga gtgtgttaag gctgggatga agaagggctg ggcagtactc   180
ttctggaaag gctcacctag cacgaacctg c                                  211
```

<210> SEQ ID NO 564
<211> LENGTH: 276
<212> TYPE: DNA
<213> ORGANISM: Homo sapiens

<400> SEQUENCE: 564

```
ggtaataaag agagccctcc ttgtcaaccc aaaatgtgag cccctgtgg caaaaccacc     60
ccctacccca ttaacaaatc aacagacaaa attctccgag tcctttgcct cttttgataa   120
catgttgttc tgttttgtaa agtgtgtgtg cttggggttc cgaggtgtgg gattgagttc   180
tctgctttgt tttttttaa gatattgtat gtaaatgtaa aaagttattt aaatatatat   240
tttaaagaac cctaactgcc aacttttgct gaaaaa                             276
```

<210> SEQ ID NO 565
<211> LENGTH: 257
<212> TYPE: DNA
<213> ORGANISM: Homo sapiens

<400> SEQUENCE: 565

```
gagtcacctt tagtcacctg gtccgtaacc atctttcctg tctaaacttc tcaccccacc    60
actctggctt ataccctgc tctctttaaa atagccagtc agaattagct tagattgtgc   120
ggtccaaccc tagcccatag gggaacaaca cagcagtagg gggtacctgc atcagggata   180
```

```
agaacccatt cccctccctt gttccggtgt gctctcgcca ttgcaccatc catgagacgc    240
actcttgtat agaagta                                                   257

<210> SEQ ID NO 566
<211> LENGTH: 198
<212> TYPE: DNA
<213> ORGANISM: Homo sapiens

<400> SEQUENCE: 566
gggaacctct gaataccata ggattaatat atgaaaaaat ttccctccct aaagtacatc    60
cacgttatga tttagacggg gatgctagca tggctaaggc aataacaggg gttgtgtgtt   120
atgcctgcag aattgccagt accttactgc tttatcagga attaatgcga aagggatac    180 gatggctgat tgaattaa                                                 198

<210> SEQ ID NO 567
<211> LENGTH: 228
<212> TYPE: DNA
<213> ORGANISM: Homo sapiens

<400> SEQUENCE: 567
taaaagaaac acctgcggcg gctccgcgcc tccctccctc cctcccaggc tcacctccta    60
ccttccttac ttcccttgta aaggcatagc caggggacat tgtccccag cttcacatcc    120 acatgtctcc tagcatggca catgcatatc ctgcccaagg agcatgaagt cagaccagca   180
aactgaacac gaggcacagt cctgcatgct ctgggaccga gcactgag                228

<210> SEQ ID NO 568
<211> LENGTH: 201
<212> TYPE: DNA
<213> ORGANISM: Homo sapiens

<400> SEQUENCE: 568
agctgaagct gcgtcggcgg ctcacggagc tcctgggggc gcaggacggg gcgctgctgg    60
tgcggctgct gcaggcgctg cgcgtggcca ggatgcccgg gctggagcgg agcgtccgtg   120
agcgcttcct ccctgtgcac tgatcctggc ccctcttat ttattctaca tccttggcac    180
cccacttgca ctgaaagagg c                                             201

<210> SEQ ID NO 569
<211> LENGTH: 211
<212> TYPE: DNA
<213> ORGANISM: Homo sapiens

<400> SEQUENCE: 569
agctttaaga ggaaagagct ctatttttct tgttttcttc tctgagctag actgagctgg    60
ggatctaaga tgtacttctc tgactacaaa agggacagta tcatttagat tttttgcagt   120
tggaagaaat gggttgttga gtgtgttaag gctgggatga agaagggctg ggcagtactc   180
ttctggaaag gctcacctag cacgaacctg c                                  211

<210> SEQ ID NO 570
<211> LENGTH: 233
<212> TYPE: DNA
<213> ORGANISM: Homo sapiens

<400> SEQUENCE: 570
ggaatgggag ttggcgggca gtgaacgagt gtggggaagg attggtggtg gggcaacagg    60
aaggggcctg gggccgtttg ggtgccctaa ctttggtagc tcagtgtgca tttagagtgg   120
```

```
gactggggag ggaggtaagc ttggggtggg ctgcttgggg cttggcatag ggtggaaagg    180
gctaccctgg ggctttgacc ccctgtagt atgtgtggag ggtgccctcc cgt             233
```

<210> SEQ ID NO 571
<211> LENGTH: 251
<212> TYPE: DNA
<213> ORGANISM: Homo sapiens

<400> SEQUENCE: 571

```
aaactgctat ttctaactct tcatgaaagc attacctttg gaaagttaaa cttttttttt    60
cctttcatca ccgtctttga acaaattat tttccaattc ataagaactt tggtaaaaaa    120
aaaaataaaa ggaaattata tgttttctt tggacattca ttggaaggct tgttgaagac    180
atgatccccc agaagcctta gtgacccaga tctcaaccag agactcaaga tagcctcaaa   240
tacagtgaaa g                                                         251
```

<210> SEQ ID NO 572
<211> LENGTH: 218
<212> TYPE: DNA
<213> ORGANISM: Homo sapiens

<400> SEQUENCE: 572

```
aactgtattt taacttagca caattaactg cagcatattt acttcatagc cccttaacat    60 gtcacttta ccaacaaagc ttttccttc atattctaat cacaaaaatt tctcaacaat     120
ttataacaat ctgtaaatct gaccttgcaa taaatagtca taaaacgtta tttttattac   180
tattattatt tttagagaca aggtctcctc gtgccgaa                            218
```

<210> SEQ ID NO 573
<211> LENGTH: 250
<212> TYPE: DNA
<213> ORGANISM: Homo sapiens

<400> SEQUENCE: 573

```
tcccacacca aaatagattc ccaaatagat attacaagta ggagaatttt tatgactact    60
cagataaaac gaccattgat cacttacaaa catacaagtc ataaacaata cagaaataat   120
atgtgtatac aaaacacag aaattattat attgggaata gacatatgac tgattcatat    180
gtaactttgt ctccacgctg tcttaaagtg tacagagttg aatattgtca ttcacaattg   240
tcacacaaaa                                                           250
```

<210> SEQ ID NO 574
<211> LENGTH: 32
<212> TYPE: DNA
<213> ORGANISM: Homo sapiens

<400> SEQUENCE: 574

```
caccaaagtt ctgaggcatt aagccagcag aa                                  32
```

<210> SEQ ID NO 575
<211> LENGTH: 245
<212> TYPE: DNA
<213> ORGANISM: Homo sapiens

<400> SEQUENCE: 575

```
taaaactctc tgagactgtt ttcccccat gtcaaaacac ctattttgca tggctatatg     60
gaaattaaat gaaatagcaa atatgaaaaa cttttggccc agtgtataat tcatatcagg   120
```

```
cactgatctg ttttcttttt gccctaacct acttttcctg catcatatac cactacacct    180
ctttacaaac cttattaata gagccactct agactacttt atttccccaa gccatacaat    240
gtact                                                                 245

<210> SEQ ID NO 576
<211> LENGTH: 192
<212> TYPE: DNA
<213> ORGANISM: Homo sapiens

<400> SEQUENCE: 576
aaaacccacc ttgttggagc ctgcagggtg gtgctgggac tgagccagtc ccaggggcat     60
gtattggcct ggaggtgggg ttgggattgg gggctggtgc cagccttcct ctgcagctga   120
cctctgttgt cctcccttg gcggctgag agccccagct gacatggaaa tacagttgtt    180
ggcctccggc ct                                                        192

<210> SEQ ID NO 577
<211> LENGTH: 269
<212> TYPE: DNA
<213> ORGANISM: Homo sapiens

<400> SEQUENCE: 577
ctagacccac tgctggtccc ctttctccct cctgcttctc acctgaagcc acctgccct     60 cctttgtgcc ctcccttgct tcctcctggg ctctgtcccc tgctccccct ttgtcctcca   120
tcccgactcc atctccccca ccaggctggt caccccaggc cagcgtctgt tgaaggatga   180
agcagctcct gtccggccca gccctgcctc acagctgtgc gagctctgcc cttctcagct   240
ctcaaacctg aataaatgca ccaagccca                                      269

<210> SEQ ID NO 578
<211> LENGTH: 172
<212> TYPE: DNA
<213> ORGANISM: Homo sapiens

<400> SEQUENCE: 578
tggcagagca acacttcgtc tcagaaaaaa aaaaaaaaac caaaaaccaa aaagccaagt     60
gtggtggtgt gcacctatag tcccagctac tcaggaagct gagacaagag gatcaattga   120
gcccaggagt tcaaagctgt agtgagctgt cattgtgcca ctatcctcca gt            172

<210> SEQ ID NO 579
<211> LENGTH: 269
<212> TYPE: DNA
<213> ORGANISM: Homo sapiens

<400> SEQUENCE: 579
ggagcagtgc ccaccaaggg tttgtcagat tcaagcctca ggcaagagaa aaatcaaaag     60
ccttctgcta ctctctccct ctgggcctct ggtctgccca gaggctggga ctccttcctc   120
taccttgctc tcaatctgga gggtgctggg gggtgcctcc atcttactgg gcccctggct   180
ggcttgtggg ctgaggtgct aatggggtct agtagctgct gtgctccctt cttcatgccc   240
agtctgaaac aggtgctccc ctaacccag                                      269

<210> SEQ ID NO 580
<211> LENGTH: 144
<212> TYPE: DNA
<213> ORGANISM: Homo sapiens

<400> SEQUENCE: 580
```

```
cagggaggcc tctctgcccc tatggggctc tgtcctgcac ccctcaggga tggcgacagc      60
aggccagaca cagtctgatg ccagctggga gtcttgctga ccctgccccg ggtccgaggg     120
tgtcaataaa gtgctgtcca gtga                                            144
```

<210> SEQ ID NO 581
<211> LENGTH: 204
<212> TYPE: DNA
<213> ORGANISM: Homo sapiens

<400> SEQUENCE: 581

```
aggatccgag tggtagtgtt tctgagagtc agggtctagg tgctggagtg cgcacggagg      60
ccgatgtaga ggaggaggcc ctgaggagga agctggagga gctgaccagc aacgtcagtg     120
accaggagac ctcgtccgag gaggaggagg ccaaggacga aaaggcagag cccaacaggg     180
acaaatcagt tgggcctcta gcgt                                            204
```

<210> SEQ ID NO 582
<211> LENGTH: 214
<212> TYPE: DNA
<213> ORGANISM: Homo sapiens

<400> SEQUENCE: 582

```
agtaacaata gccagaggtt gaagggcggg gtagaagagg ggggaatgtt gcagcgtaat      60
ccttcatacc acctggttct tgatattctg ccgcctgttc aagttcaaga ataaaagcga     120
cagcaggacc caaatgcagc tcccaaccca ctccccaggc tagacatgct tgtgtccaca     180
cagcacacca atgtgatact tccactgacc ggct                                 214
```

<210> SEQ ID NO 583
<211> LENGTH: 95
<212> TYPE: DNA
<213> ORGANISM: Homo sapiens

<400> SEQUENCE: 583

```
atgcagtgtg ttctgaggtc ctgtcacccc tgaggctgtg tgtgtccttt gccaaattaa      60
agagtcttac tgaatgcggt gcatccagga gacag                                95
```

<210> SEQ ID NO 584
<211> LENGTH: 244
<212> TYPE: DNA
<213> ORGANISM: Homo sapiens

<400> SEQUENCE: 584

```
acttttattt tctatgcaaa ggtgattcag agaatttata taaaggcggg cgaggggcag      60
ccgagcaggg agctttggga cagggctggg gcccccatat ccccccgggg ccacctgctt     120
tccctcctat ggctcccctg aacaggagg gagagccaag ggggcggccc agcctggaca     180
gcgcccgctc ctgcctgggt gcacacacgg cgggcctgag ctccagcatc tgagtttggg     240
ggta                                                                  244
```

<210> SEQ ID NO 585
<211> LENGTH: 170
<212> TYPE: DNA
<213> ORGANISM: Homo sapiens

<400> SEQUENCE: 585

```
tgcacattgt gacatgtaca ctaaaactta agtataata ataataaaat aaaaaaaaaa       60
```

```
gaaaagaacc tagtgtgtta aaccttaaat gcccttagaa ataacctaga ccagtgtttc      120
ttaaactgtg gtcatgagat cagttgaatg gattatgacc aacattgaaa                170
```

<210> SEQ ID NO 586
<211> LENGTH: 233
<212> TYPE: DNA
<213> ORGANISM: Homo sapiens
<220> FEATURE:
<221> NAME/KEY: misc_feature
<222> LOCATION: (160)..(183)
<223> OTHER INFORMATION: n is a, c, g, or t

<400> SEQUENCE: 586

```
cttgctttcc ctaggagttg aatccttctc cctgcctacc tgcagcatct cctttccctt      60
taaaatgacc atgtagtggc aagcagcctt ttactcttct gttagctctg gactcttaac     120
acttaagtta ctcttctgaa attgctagga ccattggggn nnnnnnnnnn nnnnnnnnnn     180
nnnatgtccg acctgtgatc gtggtacagc attagctgaa atttacccct gtt            233
```

<210> SEQ ID NO 587
<211> LENGTH: 240
<212> TYPE: DNA
<213> ORGANISM: Homo sapiens
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t

<400> SEQUENCE: 587

```
aaggaccctg aaaatgact tctcatttcc tgcctgcaga aaagagaaat attaggatag       60
tgttgtgtgc aaaaaaatgc aagcttgcaa tgagagatgc agagtgtgag ggagagaggc     120
acgaaggggg tggagaaaaa agacagagaa tttgaggttg actcacggct ttgaagggaa     180
aacaggaaga ngaagaaagt ctgtctncca tgggtcggca acccacactt tacacatttt     240
```

<210> SEQ ID NO 588
<211> LENGTH: 273
<212> TYPE: DNA
<213> ORGANISM: Homo sapiens

<400> SEQUENCE: 588

```
ataagtgtac caggactcta aaagaaactt gtttgtataa tgctatccaa ggtatgtagc      60
ccagggaata accaacctga tgtgtgttat gacccatttt aagcctcccg tgatcacagt     120
ttttaaaata aaattaagga ctggtcctat ttctaggtga cacaagtaag gtaatagcta     180
gaacgggaaa aagaggggc ccccaaaaat gtaaccttaa aatttggtgc ttgtgccgct      240
attgatagta agcagcatgg aataggatgt ggt                                  273
```

<210> SEQ ID NO 589
<211> LENGTH: 179
<212> TYPE: DNA
<213> ORGANISM: Homo sapiens

<400> SEQUENCE: 589

```
taacagtgca taaatcaatc caaatttaga ccctggcaac cagttcccca ttgctcatct      60
acgggactct gtcaacggta aataggcaat catctctctt gaaagtata catcctctct      120 cgcactggtg gaaagcaaat tgacttttg tttgctgtat aaaacccctta gcacttcaa     179
```

<210> SEQ ID NO 590
<211> LENGTH: 186
<212> TYPE: DNA
<213> ORGANISM: Homo sapiens

<400> SEQUENCE: 590
ggcaggaccg tgccacacca gctgtccaga gtcggaggac cccagctcct cagcttgcat      60
ggactctgcc ttcccagcgc ttgtcccccg aggaaagcgg ctgggcgggc ggggagctgg     120
gcctggagga tcctggagtc tcattaaatg cctgatttgt gaccatgtcc accagtatct     180
ggggtg                                                                186

<210> SEQ ID NO 591
<211> LENGTH: 238
<212> TYPE: DNA
<213> ORGANISM: Homo sapiens

<400> SEQUENCE: 591
ttcggcattc tccaagtcat ctagcccttc atcctcctcc acatcatcaa agtcgtcgcc      60
atcaaaattg tcctcgttgt ctgacatgac ccctcgcct cagcgacccc gctgcgcccc     120
ggtcccgcgc ggagacccgc aaacagcgac actacgactc gcgcggctcc tagcttatct     180
tgcgcctcgt gccgaattcg ccacccaggc ctcgctacaa ttacggaccg ttatagta       238

<210> SEQ ID NO 592
<211> LENGTH: 148
<212> TYPE: DNA
<213> ORGANISM: Homo sapiens

<400> SEQUENCE: 592 caaccttta gctatgatga cacataacaa aagatgttta tgtactaata gttgaaatct      60 gccttttct cattcaagaa ggcatacaaa tatctgagag tgactttgtt gtatggctac     120
ccttgtgatc tacagtaatt tattctttt                                       148

<210> SEQ ID NO 593
<211> LENGTH: 271
<212> TYPE: DNA
<213> ORGANISM: Homo sapiens

<400> SEQUENCE: 593
gtgggagaag ttggcgtcct aggctgggga ttggtcgggg gaccttaaag aaaaaggcca      60
gggctgaggg tcctgaggag agagagagag gccacgtgga tggaggactg tcacccctt     120 ctcggttctg tcaccccctt gagtctaact cactgttgag gggaggaaga aggggggatgg    180 acggaaggga gaccgaggaa aggctttcgg gagtggggac attatccacc cagaggtgtg    240
ctacccacaa ccaccgcgag atccttagag t                                    271

<210> SEQ ID NO 594
<211> LENGTH: 233
<212> TYPE: DNA
<213> ORGANISM: Homo sapiens

<400> SEQUENCE: 594
gaactgattt caaggaatgg gtccttccct tcagagccac atgtgtgcgg gacacccaga      60
cagaaaacac aaacacaaag tcgagtggag ggcatttgga aggagcagtg aagccgagcc     120
aggaaatacc aagatggcga gccagtgtgc ttgtagagat tgtagagagg gtagaattga    180
cactgtggac cctggcctcg atagagaaag gcatcagcta aggaagttgt tca            233

<210> SEQ ID NO 595
<211> LENGTH: 217
<212> TYPE: DNA
<213> ORGANISM: Homo sapiens

<400> SEQUENCE: 595
gaacattctg gatagcaagc ccactgcaaa caagaagtgc gacctgatca gcatccccaa      60
gaaaaccaca gacacggcca gtgtgcaaaa tgaagccaag ttggatgaga ttttaaaaga     120
gatcaaatct ataaaagaca caatctgcaa tcaagatgag ccgtatttcc aagttagaac    180
aagcagatgg caaagatagc agcctgaagg tcccacc                              217

<210> SEQ ID NO 596
<211> LENGTH: 267
<212> TYPE: DNA
<213> ORGANISM: Homo sapiens

<400> SEQUENCE: 596
tgataatctc aagactcctc ccttagctac tcaggaggcc gaggcggaaa aaccacccaa      60
acccaagagg tggagggtgg atgaggtgga acaatcaccg aaacccaaga ggcggagggc    120
ggatgaggtg gaacaatcgc ccaagcccaa gaggcagagg gaggccgagg cacaacaatt    180
acccaaaccc aagaggcgga ggttgagtaa gctgagaaca cgccattgca ctcaagcctg    240
ggcaataaga ataaatccgt gggtcga                                         267

<210> SEQ ID NO 597
<211> LENGTH: 275
<212> TYPE: DNA
<213> ORGANISM: Homo sapiens

<400> SEQUENCE: 597
aatttaccaa gccacatatt gggaatggta ccccaggcag aaggagtaga gtaagcaagc      60
cagaaaggaa atactatggt gcttttgagt aactgcagtg tggctgaaga atgtggaaaa     120
tgatgaggat aaagaggtgg acagggaact aggtaaggga gggccttcct ttaaataat    180 tagaccttgt cctgtgtaca tttaatggga ttttaatcag gccataatgc caaatttctt    240
tacttcggaa ggatctttat ggtgatggtt tcaga                                275

<210> SEQ ID NO 598
<211> LENGTH: 35
<212> TYPE: DNA
<213> ORGANISM: Homo sapiens

<400> SEQUENCE: 598
atttttcttg gcctagttgt gtgccatgga tattt                                 35

<210> SEQ ID NO 599
<211> LENGTH: 156
<212> TYPE: DNA
<213> ORGANISM: Homo sapiens

<400> SEQUENCE: 599
gagggatatt attttccata gccattacca tgatacatat gatactgcct aggtagagct      60
gggactgtag ggtggggaac caatgctgtc ctgcacactg aaactatgaa tgccaagata    120
tcactgccag atccttctgt ggatagctgg cggcat                               156

<210> SEQ ID NO 600
<211> LENGTH: 243
<212> TYPE: DNA
<213> ORGANISM: Homo sapiens

<400> SEQUENCE: 600
gaagcctgac cccaagtgtg tcttcaccta tgtgcagtcg ctctacaacc acctgcgacg      60
ccacgaactg cgcctgcgcg gcaagaatgt ctagcctgcc cgcccgcatg gccagccagt     120
ggcaagctgc cgcccccact ctccgggcac cgtctcctgc ctgtgcgtcc gcccaccgct     180
gccctgtctg ttgcgacacc ctcccccca catacacacg cagcgttttg ataaattatt     240
ggt                                                                   243

<210> SEQ ID NO 601
<211> LENGTH: 229
<212> TYPE: DNA
<213> ORGANISM: Homo sapiens

<400> SEQUENCE: 601
gcattattac tgatacttgc acacagtcaa aagcgcagac tggatggatg gtcttttata      60
aggcatttaa gggtacacta ctgtgtttca ctgaccatac attttttctta gcccctcaag    120 taatatagca cagagttatg aatgacaatt ccctaacca ttcctcttca tatctgcctc      180
ttccccttac catcgtaatt ctccaaactg gtcataaagg cactctgtg                 229

<210> SEQ ID NO 602
<211> LENGTH: 93
<212> TYPE: DNA
<213> ORGANISM: Homo sapiens
<220> FEATURE:
<221> NAME/KEY: misc_feature
<222> LOCATION: (33)..(48)
<223> OTHER INFORMATION: n is a, c, g, or t

<400> SEQUENCE: 602
cattaagtcc tctgtaaggt gtcaggcaag ccnnnnnnnn nnnnnnnntg ggtaagtcct      60
aaccccccac aaaggtgttc ccagtgacta cct                                  93

<210> SEQ ID NO 603
<211> LENGTH: 273
<212> TYPE: DNA
<213> ORGANISM: Homo sapiens

<400> SEQUENCE: 603
ttcgctggtt ctgaatgtca ttttctcctcc ctggtgtggt tttacatttt cagcttcttt    60
ccctttcctt ctctcccacc ctcaaaattc tgccttagca tttgtgtgct taattaaatc    120
cactctgtgc tttatagttg gagaatgtgg acaatacaaa gatttggggt ggggtcatac    180
agtgtataca aaacacagac actatgtgtt tggacaaatt cgcctagcgt gagaatcatc    240
agtagtgagt taaacgtttg aaatcagagc caa                                  273

<210> SEQ ID NO 604
<211> LENGTH: 164
<212> TYPE: DNA
<213> ORGANISM: Homo sapiens
<220> FEATURE:
<221> NAME/KEY: misc_feature
<222> LOCATION: (80)..(98)
<223> OTHER INFORMATION: n is a, c, g, or t

<400> SEQUENCE: 604

```
taattattgc tgtggatttc tctctagcat tttagctcat tccagtaaat gattttttc     60 tttatgaaat agaactaccn nnnnnnnnnn nnnnnnnngt tcaacaacaa caaactgaag    120
ggggagaaaa atacaccatt accacagcaa caaattagtt tatg                    164

<210> SEQ ID NO 605
<211> LENGTH: 275
<212> TYPE: DNA
<213> ORGANISM: Homo sapiens

<400> SEQUENCE: 605
ttctcccagt acctcatttg cacaagcctt cctgccattc ttcaaatatg cgaagcctgt     60
tctcacctca aagccattgt acttgctgtt tcctatgcct gaatgttctt cccacagatg    120
ttgacaagac ttgctccttc acttcaatga cattcagata tcttattctc agagagcatt    180
tgacaaccta tctaaaatag ctcccctca ctgttcctgc ccatgctctt tatacccat     240 tttactttca tctttcttcc tagtactgac attat                              275

<210> SEQ ID NO 606
<211> LENGTH: 271
<212> TYPE: DNA
<213> ORGANISM: Homo sapiens

<400> SEQUENCE: 606
agaactagca aaagccaagg ccctggggcg gggaggagcc tggtatgttc aaggggcaga     60
agggaggctg aagcagagtg atcaagcgga cagggcaggc agagcctcaa atcccagact    120
gaggaacatg gtgaacgagg acacttcggg ggtccacaca taaagacgga gacagagact    180
cagggcagga aagtcacatg ccctgggaca ccccagtaaa cagagccaaa ctcaaacctc    240
agcctgtctg cagctgacat aggatgaagt t                                   271

<210> SEQ ID NO 607
<211> LENGTH: 160
<212> TYPE: DNA
<213> ORGANISM: Homo sapiens

<400> SEQUENCE: 607
taagttatta actgaggctg accagagggg aggaccccc ctttaccacc ccatgcactt      60
tgcgagctgc cccttcttcc cccacatcag agagaaatgc ccccacacca gagccccaag    120
ggtagggctg ccgatcagag ctgtgagtta acacaacagg                          160

<210> SEQ ID NO 608
<211> LENGTH: 155
<212> TYPE: DNA
<213> ORGANISM: Homo sapiens

<400> SEQUENCE: 608
agcaccagta gtggttgggg ccctccctc aggctccatt tttaataagt ttttagtatt      60
tttgttaatg tgaggcattg agctgttggg ttttgtatat tatttatata gagacccag     120 agctgttgca cccaatacac agagcttctt tgcaa                               155

<210> SEQ ID NO 609
<211> LENGTH: 252
<212> TYPE: DNA
<213> ORGANISM: Homo sapiens

<400> SEQUENCE: 609
tacacacatg tgagtctggc tgggctggta ttttgtttga tcttcctgga aatgagcagt     60
```

```
gactaacgct cacataactg gttttttttt ttatctgggc tgatgaatac atttacctaa      120
gaaactcatt tcgttttact taagagggga agtgcagttt tcttttggca gttcagaatc      180
caagcacttg atttgctggg tttggaaaac tccttttttg gccttctatg tgcttagcca      240
taacaattcc at                                                          252

<210> SEQ ID NO 610
<211> LENGTH: 286
<212> TYPE: DNA
<213> ORGANISM: Homo sapiens

<400> SEQUENCE: 610
agaggggtca ccatactttt cttcagttcc atgttaactg aacaatcttt ttcttgctaa      60
tctgaacacc ctgtgcaata gagtctgact ccattttttg atgtttgact gcagacatct     120
tttcagccta acccttccat cttctctttc tgtccaacac tggggcaagc tgacaaaaat     180
cctcaggtgc tcctcttctg taaccagcag taagttcgaa tcatacactg ccaccctcac     240
cccaaccctg tcccttaacc acattaaaac ccaaagccag tctcct                    286

<210> SEQ ID NO 611
<211> LENGTH: 80
<212> TYPE: DNA
<213> ORGANISM: Homo sapiens

<400> SEQUENCE: 611
gggcctgttg aagatgcttg tattttactt ttcccttgta aatgctattc ccatcacagc      60
tgaacttgtt gagatccccg                                                  80

<210> SEQ ID NO 612
<211> LENGTH: 290
<212> TYPE: DNA
<213> ORGANISM: Homo sapiens

<400> SEQUENCE: 612
gaggagataa actaacagag gtcaagaaga tgaagagttg tttcaaacat ggtacagttg      60
agattcctag cattattcta gtcagacgtg tctgtcaagt aggccattgg atatcgggat     120
tgggatttga ggggaatcca tagatggaaa tataagttca agaggcatca gcatggatac     180
cctatttgga tctggatgaa attacctaaa ggagaaaatg caggaggacg tgatgctggg     240
tgattttaga ggagaaacca tgaaggattc caaggagcag cagttggtca                290

<210> SEQ ID NO 613
<211> LENGTH: 117
<212> TYPE: DNA
<213> ORGANISM: Homo sapiens

<400> SEQUENCE: 613
aaaaattcat cccatatcca gaaagtacca gttataaaga ttgctgacca agcaaagttt      60
tgcatcaaag tgtcacctca ttgctctgac caaagactga ctgttgtggt tttaact        117

<210> SEQ ID NO 614
<211> LENGTH: 214
<212> TYPE: DNA
<213> ORGANISM: Homo sapiens

<400> SEQUENCE: 614
acaccagtgt gctacagtgg cgggtggtct gatgcggcca gggaagagtc aggtgtcagg      60
```

```
gcaggaattc tattttcggg agatgtctat tgccgagtag agtaatatat acccagagta    120
tgtctatagc agaggggtt atggggcgg gagggtagac tgacatacag aagtctctat      180
ttatccgggt gggaagaggg agtcacatcg cttt                                 214

<210> SEQ ID NO 615
<211> LENGTH: 283
<212> TYPE: DNA
<213> ORGANISM: Homo sapiens

<400> SEQUENCE: 615
ccagctggag gtgacgaggg atgatgcgcg tcttcttgtt gtcccgagcc gcgttgcccg     60
ccagctccag gatctcggcg gtcagatact cgaggaccgc agccatgtag acgggcgcgc    120
cggcccccac tcgctccgcg tagttgcctt tgcgcagcaa gcgatgcact cgccctaccg    180
ggaactgaag gccagcgcgg gacgagcgcg acttggcctt ggcgcgggcc ttgcctcctt    240
gcttgccacg accagacatg acagcgatag tagtcaccga gag                      283

<210> SEQ ID NO 616
<211> LENGTH: 192
<212> TYPE: DNA
<213> ORGANISM: Homo sapiens

<400> SEQUENCE: 616
gaactatgat tgcactactg tgctccagct tgggcaacag agtgagatct tgtctccaaa     60
agtccttgaa ggattttagg aagttgttaa aagtcttgaa acgatgtttg ggggcatgtt    120
agggttcttg aatgtttaat tcctctaata actgcttatt caagagaagc atttctgact    180
gggtgcaggg ca                                                         192

<210> SEQ ID NO 617
<211> LENGTH: 234
<212> TYPE: DNA
<213> ORGANISM: Homo sapiens

<400> SEQUENCE: 617
atgaactttt gtgcttagtg agtgcaacga aatatttaaa caagttttgt atttttttgct    60 tttgtgtttt ggaatttgcc ttattttttct tggatgcgat gttcagaggc tgtttcctgc   120
agcatgtatt tccatggccc acacagctat gtgtttgagc agcgaagagt ctttgagctg    180
aatgagccag agtgataatt tcagtgcaac gaactttctg ctgaattaat ggta           234

<210> SEQ ID NO 618
<211> LENGTH: 146
<212> TYPE: DNA
<213> ORGANISM: Homo sapiens

<400> SEQUENCE: 618
ggaggatgaa gaaggttata acgatggaga ggtagatgac gaggaagatg aagaagagct     60
tggtgaagaa gaaagggtc agaagcgaaa acgagaacct gaagatgagg gagaagatga    120
tgactaagtg gataacctat tttgaa                                          146

<210> SEQ ID NO 619
<211> LENGTH: 63
<212> TYPE: DNA
<213> ORGANISM: Homo sapiens

<400> SEQUENCE: 619
gtgagctgtg atgttgccgc tacactccag gtgacagagc aagaccctaa gaccttatct     60
```

| | |
|---|---|
| ctt | 63 |

<210> SEQ ID NO 620
<211> LENGTH: 149
<212> TYPE: DNA
<213> ORGANISM: Homo sapiens

<400> SEQUENCE: 620

| | |
|---|---|
| atcaactgaa tccaatattt cctgtggcaa ataacacttt cctcatttca tacctttct | 60 |
| cctctcttcc atgccaacat ttctccaccc acaacgtaca ctttttattt ctccatcaat | 120 |
| atttgaaagc gagtgatttg tgaccagga | 149 |

<210> SEQ ID NO 621
<211> LENGTH: 151
<212> TYPE: DNA
<213> ORGANISM: Homo sapiens

<400> SEQUENCE: 621

| | |
|---|---|
| cagcaaccc tgcattcctt ttttttaccg ggctgacgag aatgatgagg tgaagatcac | 60 |
| tgtcatctaa aagccggcta ctgtcagcaa agcctgaaga agtggggctg atacccctgc | 120 |
| ccccaccata tccctaccat cccttctcag t | 151 |

<210> SEQ ID NO 622
<211> LENGTH: 258
<212> TYPE: DNA
<213> ORGANISM: Homo sapiens

<400> SEQUENCE: 622

| | |
|---|---|
| acaagcagac atgcactctc ttcttctcct ggcacacgcc gctggcctgc gagcaagcga | 60 |
| ccgaatgttc cgtgaggaat ggaagctcta ttgttgactt gtctcccctt attcatcgca | 120 |
| ctggtggtta tgaggcttat ggtaagagtg aggatgatgc ctccgatacc aaccctgatt | 180 |
| tctacatcaa tatttgtcag ccactaaatc ccatgcacgg agtgccctgt cctgccggag | 240 |
| ccgctgtgtg caaagttc | 258 |

<210> SEQ ID NO 623
<211> LENGTH: 278
<212> TYPE: DNA
<213> ORGANISM: Homo sapiens

<400> SEQUENCE: 623

| | |
|---|---|
| tctcctcttc agtcttcatc atgttttgt ccctcaaaca tcagccttac gtcctctttt | 60 |
| cttccctctg catcctctct ccttgagaga cctcatccag cccatgtttt caacaatcat | 120 |
| ctatacaaca atgatcttct acatacattc ctggcccaga tccctgccct gaattcccag | 180 |
| cctatagatc caacaaccct cctccaatac tgtcttcccc agccattctc caggcctctg | 240 |
| ctatggtctg aatgtttgtg tccaaaaaca tgatgaag | 278 |

<210> SEQ ID NO 624
<211> LENGTH: 290
<212> TYPE: DNA
<213> ORGANISM: Homo sapiens

<400> SEQUENCE: 624

| | |
|---|---|
| aagacagtcc tcagaaaacc caagctttca tacagatgcc aaaaaagtcc atggggttta | 60 |
| attctttgac cattttgagt gcagggactt attcatgctt acatcctcac aactcagctt | 120 |

```
ggggactgcc tcacacctgg cagctgatcc tttttgtttt ttaaatgtaa gaagccacac    180
tgagggctct ccaggcggaa aaagttagga cacaggacca gcatttcttt ccagccactt    240
gtggatccct gattgaatgt cacccttgac tgcctaactc atctctttcc               290
```

<210> SEQ ID NO 625
<211> LENGTH: 292
<212> TYPE: DNA
<213> ORGANISM: Homo sapiens

<400> SEQUENCE: 625

```
cgactaatca tcttacggca gagaacaaac accaccacca agtaaaaata tccctgcaac    60
aaacacaacg gattccaatt ccttccggcc aacccaatgt tccacggcgt ggacacatac    120
tggttgggcg caggcatcct cgcagtgacg tccctgtac tcgtggctgc agttgcagtg     180
ataggagccg tgcgtgttct cacagagggc cccgtgcagg caagggtttc cagagcactc    240
gtcgatatca ctctgacacc tttctcccct aaaacccgaa tcacactgac aa             292
```

<210> SEQ ID NO 626
<211> LENGTH: 249
<212> TYPE: DNA
<213> ORGANISM: Homo sapiens

<400> SEQUENCE: 626

```
actatccagg aaaggaaatt tacagtatat ctcattttgg ggtttggaag gatgtgtaca    60
aaatagtgta attgaaaatt gataaaataa aaatcttat atacttatat tgggtaaagg     120
aagataggag aagtgacaga gcgagagaga gagagagtgt ttatgtgtga aggaaataag    180
aaagctcagt cttataagaa gtctcagata atgtgtagac tttacagaaa agcagtttaa    240
gaatggtat                                                            249
```

<210> SEQ ID NO 627
<211> LENGTH: 262
<212> TYPE: DNA
<213> ORGANISM: Homo sapiens

<400> SEQUENCE: 627

```
gtatccaagt ccattgttac taggttggag gctggagatt ctaaatggct tccagaccat    60
ctctctgatt ctctttggga gatggggtct gaaagacaat gtcagtagtt ttggaaaatt    120
ctagaaagtg tgcttggaaa cgtgggaaga gctcttgcct agtgcctaaa tgctccattt    180
gcagctctag ccaagtagat acttggtagg tatagagccg ggtttgcgtt tatattagca    240
aaacctatgt cagagttgaa ga                                             262
```

<210> SEQ ID NO 628
<211> LENGTH: 147
<212> TYPE: DNA
<213> ORGANISM: Homo sapiens

<400> SEQUENCE: 628

```
ttctttatgg tggtgggatg attattgtaa tcatacttgg gaacagaagt gatgaaaaag    60
gtatgttact tgagatatgg gaaacgctat tttccatgtt tagttatggg gtattcaagt    120
ctaactagtg gaaagtatgg atacatt                                        147
```

<210> SEQ ID NO 629
<211> LENGTH: 97
<212> TYPE: DNA
<213> ORGANISM: Homo sapiens

<400> SEQUENCE: 629

```
tctgtgattc tctttgtcag ctcctttgcc tatatttgca tctcagttga caccoctgat    60
tctgacttgt ccttatcttc ctaccagtct ctgccga                              97
```

<210> SEQ ID NO 630
<211> LENGTH: 234
<212> TYPE: DNA
<213> ORGANISM: Homo sapiens

<400> SEQUENCE: 630

```
gttgtatcaa caatgattaa ctcctttatt atacatacac atgaatgtgc attttttggta    60
aatgcataaa tgagattcta taatgtttac tgatctttat attacagatt ttctcttctt   120
ttaggattag ctcagcttgc ccccccttc catctccacc atctatagtg agcctctcca    180
taattagtgc caaccattag tctcgttcat attttacac caggagtcaa caaa           234
```

<210> SEQ ID NO 631
<211> LENGTH: 115
<212> TYPE: DNA
<213> ORGANISM: Homo sapiens

<400> SEQUENCE: 631

```
ccccagccca agagatgaac atctggggac taatatcata gacccatctg gaggctccca    60
tgggctagga gccagtgtga ggctgtaact tatactaaag gttgtgttgc ctgct        115
```

<210> SEQ ID NO 632
<211> LENGTH: 56
<212> TYPE: DNA
<213> ORGANISM: Homo sapiens

<400> SEQUENCE: 632

```
gaagactaaa cagaaccag aactgaaaca ttcacctggt agcaaatgac actttg         56
```

<210> SEQ ID NO 633
<211> LENGTH: 251
<212> TYPE: DNA
<213> ORGANISM: Homo sapiens

<400> SEQUENCE: 633

```
ttctcgcccc acctagggac agattccccc tgctcttttt gtcctagaaa ccccgctagt    60
ttgggatggt agcgtctggg gtgggagg cttcccttc cccactcgag ggtgcgggtg     120
gggaagggg ggtgggtgga gacagccctg gggcagggag gatggtctct ccactgtaga   180
aagtagagta ggattgtggt cagacttaat ttgaggcatc tagtgaagac acgtacaaat   240
ccaccaagga a                                                         251
```

<210> SEQ ID NO 634
<211> LENGTH: 294
<212> TYPE: DNA
<213> ORGANISM: Homo sapiens

<400> SEQUENCE: 634

```
gctggtcatc tcaatggcag gtggtagggt actcagaagg gtggttgact ccgtgagagg    60
ggaagaggtg gaccgagagg tctgagggg tgaggactca ggcggaggat tggatgtggt   120
caactcagca atcggtgctg tgcttgtgtg gtgggggc ccgtgcttc cagtggtggg    180
tgttggggtt ggggtcaccg tagtggtggt gctgatgggt atcatggttg gggtctgtgt   240
```

```
gccggtgggt gttggggttg cggtcaccga tagttgtggt ggtgatgggt gtca          294

<210> SEQ ID NO 635
<211> LENGTH: 221
<212> TYPE: DNA
<213> ORGANISM: Homo sapiens

<400> SEQUENCE: 635
tttgaaaaat gtttacagct ccacaaagat agacaaattt ccttgatgta tgaaaaatgt    60
caacaaacca ataaaaagac taacaattca gtagaaaaat ggacaaagaa caaatatgga   120
gattcataga aatgagagat aaatgtcatg atgagaaggt gaggtgctca cttgatttat   180
aagagaaatg aaaattaaaa ctacaccaga tgccattttt t                       221

<210> SEQ ID NO 636
<211> LENGTH: 279
<212> TYPE: DNA
<213> ORGANISM: Homo sapiens

<400> SEQUENCE: 636
cgcggcgatt cttgaggtcg atgtcgcgga tagcgccgta tttgtagaac acgtcctcaa    60
tgtccttggt tcggatgtct ggaggtaagt tacccacgta gatgcggcaa tcgttgttcc   120
ctgcggggcc acgaatcaca ccacctcccg acatggcggt gacgaaaagc gcggactcga   180
gaacaggcct tcccaccaag cctagcgcac ggcagagcga gcccgcagcg gcaccacgtc   240
tcccgcggcc cctccaaaat ggcgccttta tcagctcgg                          279
```